US010738056B2

(12) United States Patent
Ndubaku et al.

(10) Patent No.: US 10,738,056 B2
(45) Date of Patent: Aug. 11, 2020

(54) PYRAZOLOPYRIMIDINONE COMPOUNDS AND USES THEREOF

(71) Applicant: Aduro BioTech, Inc., Berkeley, CA (US)

(72) Inventors: Chudi Obioma Ndubaku, Oakland, CA (US); George Edwin Katibah, Fremont, CA (US); Tucker Curran Roberts, Berkeley, CA (US); Leonard Sung, San Mateo, CA (US); Stephane Ciblat, Montreal (CA); Franck Raeppel, Montreal (CA); Vu Linh Ly, Montreal (CA); Yeeman K. Ramtohul, Pierrefonds (CA); Taras Rybak, Montreal (CA); Mariam Zaky, Boston, MA (US); Laura Gillard, Montreal (CA); Hossein Ismaili, Tres-Saint-Redempteur (CA)

(73) Assignee: Aduro BioTech Inc., Berkeley, CA (US)

( * ) Notice: Subject to any disclaimer, the term of this patent is extended or adjusted under 35 U.S.C. 154(b) by 0 days.

(21) Appl. No.: 16/131,221

(22) Filed: Sep. 14, 2018

(65) Prior Publication Data

US 2019/0119285 A1   Apr. 25, 2019

Related U.S. Application Data

(60) Provisional application No. 62/687,769, filed on Jun. 20, 2018, provisional application No. 62/633,248, filed on Feb. 21, 2018, provisional application No. 62/559,482, filed on Sep. 15, 2017.

(51) Int. Cl.

| | |
|---|---|
| *C07D 487/04* | (2006.01) |
| *C07D 517/00* | (2006.01) |
| *A61K 31/519* | (2006.01) |
| *A61K 45/06* | (2006.01) |
| *A61P 43/00* | (2006.01) |
| *C07D 519/00* | (2006.01) |
| *A61K 31/5377* | (2006.01) |

(52) U.S. Cl.
CPC .......... *C07D 487/04* (2013.01); *A61K 31/519* (2013.01); *A61K 31/5377* (2013.01); *A61K 45/06* (2013.01); *A61P 43/00* (2018.01); *C07D 519/00* (2013.01)

(58) Field of Classification Search
CPC ....... A61P 43/00; A61K 31/519; A61K 45/06; A61K 31/5377; C07D 519/00; C07D 487/04

See application file for complete search history.

(56) References Cited

U.S. PATENT DOCUMENTS

| | | |
|---|---|---|
| 4,522,811 A | 6/1985 | Eppstein et al. |
| 5,420,128 A | 5/1995 | Kiyokawa et al. |
| 5,763,263 A | 6/1998 | Dehlinger |
| 5,843,951 A | 12/1998 | Inoue et al. |
| 6,060,478 A | 5/2000 | Gilligan et al. |
| 6,197,774 B1 | 3/2001 | Yamada et al. |
| 6,245,759 B1 | 6/2001 | Bilodeau et al. |
| 6,379,395 B1 | 4/2002 | Vidal et al. |
| 7,196,111 B2 | 3/2007 | Shipps et al. |
| 7,776,864 B2 | 8/2010 | Holder et al. |
| 7,816,365 B2 | 10/2010 | Schiemann et al. |
| 8,426,595 B2 | 4/2013 | Huang et al. |
| 8,552,006 B2 | 10/2013 | Binch et al. |
| 8,796,285 B2 | 8/2014 | Zhang |
| 8,921,388 B2 | 12/2014 | Buschmann et al. |
| 9,505,767 B2 | 11/2016 | Albrecht et al. |
| 10,035,801 B2 | 7/2018 | Albrecht et al. |
| 10,329,298 B2 | 6/2019 | Konteatis et al. |
| 2003/0229065 A1 | 12/2003 | Levy et al. |
| 2005/0124678 A1 | 6/2005 | Levy et al. |
| 2006/0094706 A1 | 5/2006 | Paruch et al. |
| 2009/0163545 A1 | 6/2009 | Goldfarb |
| 2012/0178915 A1 | 7/2012 | Xu |
| 2012/0277224 A1* | 11/2012 | McCall ................ A61K 31/519 514/233.2 |
| 2014/0163033 A1 | 6/2014 | Anchuela et al. |

(Continued)

FOREIGN PATENT DOCUMENTS

| | | |
|---|---|---|
| JP | H02131235 A | 5/1990 |
| JP | 2005-008581 A | 1/2005 |
| JP | 3625362 | 3/2005 |

(Continued)

OTHER PUBLICATIONS

Gibson, Karl R.; Thomas, Steven R.; Rowley, Michael Corporate Source: The Neuroscience Research Centre, Merck Sharp and Dohme Research Laboratories, Essex, CM20 2QR, UK Source: Synlett (2001), (5), 712-714.*
Selleri, Silvia; Bruni, Fabrizio; Costanzo, Annarella; Guerrini, Gabriella; Casilli, Maria Lucia; Giusti, Laura; Lucacchini, Antonio; Martini, Claudia Dip. Sci. Farm., Univ. Firenze, Florence, 50121, Italy.*
CAS No. 701226-88-2 R, R'=H, Jun. 30, 2004.
CAS No. 924870-31-5, Mar. 5, 2007.
CAS No. 945188-34-1, R=H, Aug. 21, 2007.
CAS No. 1469778-85-5, Nov. 5, 2013.
CAS No. 1469778-83-3, Nov. 5, 2013.
CAS No. 1469778-81-1, Nov. 5, 2013.

(Continued)

*Primary Examiner* — Alexander R Pagano
*Assistant Examiner* — Ebenezer O Sackey
(74) *Attorney, Agent, or Firm* — Kyle W Grimshaw

(57) ABSTRACT

The present invention relates to pyrazolopyrimidinone compounds. The present invention also relates to pharmaceutical compositions containing these compounds and methods of treating autoimmune, inflammatory, and neurodegenerative diseases by administering these compounds and pharmaceutical compositions to subjects in need thereof. The present invention also relates to the use of such compounds for research or other non-therapeutic purposes.

35 Claims, 1 Drawing Sheet
Specification includes a Sequence Listing.

(56) References Cited

U.S. PATENT DOCUMENTS

| | | | |
|---|---|---|---|
| 2015/0065522 A1 | 3/2015 | Albrecht et al. | |
| 2018/0319819 A1 | 11/2018 | Yogo et al. | |

FOREIGN PATENT DOCUMENTS

| | | |
|---|---|---|
| WO | WO2004041209 | 5/2004 |
| WO | WO2006076009 | 7/2006 |
| WO | WO2009039323 | 3/2009 |
| WO | WO 2009/076593 A1 | 6/2009 |
| WO | WO2012041817 | 4/2012 |
| WO | WO 2012/149157 A2 | 11/2012 |
| WO | WO2013174930 | 11/2013 |
| WO | WO2013174931 | 11/2013 |
| WO | WO2014139326 | 9/2014 |
| WO | WO2015135094 | 9/2015 |
| WO | WO2015183989 | 12/2015 |
| WO | WO2017112678 | 6/2017 |
| WO | 2017/210678 A1 | 7/2017 |
| WO | WO2017178416 | 10/2017 |
| WO | WO2017210678 | 12/2017 |
| WO | WO2018039972 | 3/2018 |
| WO | WO2018045071 | 3/2018 |
| WO | WO2017069279 | 8/2018 |
| WO | 2018/229683 A1 | 12/2018 |
| WO | 2019/040499 A2 | 2/2019 |

OTHER PUBLICATIONS

CAS No. 173678-36-9, Feb. 29, 1996.
CAS No. 2166112-92-9, Dec. 27, 2017.
CAS No. 351350-33-9, Aug. 14, 2001.
CAS No. 1310262-92-0, Jun. 24, 2011.
CAS No. 1310260-35-5, Jun. 24, 2011.
CAS No. 1310281-86-7, Jun. 24, 2011.
CAS No. 1310083-35-2, Jun. 23, 2011.
CAS No. 1310262-95-3, Jun. 24, 2011.
CAS No. 1310140-17-0, Jun. 23, 2011.
CAS No. 1310091-63-4, Jun. 23, 2011.
CAS No. 842112-34-9, Mar. 4, 2005.
CAS No. 1040689-32-4, Aug. 13, 2008.
CAS No. 1310319-79-9, Jun. 24, 2011.
CAS No. 1310142-55-2, Jun. 23, 2011.
CAS No. 939898-95-0, Jun. 28, 2007.
CAS No. 2326220-66-8, Jul. 7, 2019.
CAS No. 896665-24-0, Jul. 28, 2006.
CAS No. 895830-26-9, Jul. 25, 2006.
CAS No. 879617-52-4, Apr. 7, 2006.
CAS No. 896665-30-8, Jul. 28, 2006.
CAS No. 896665-33-1, Jul. 28, 2006.
CAS No. 896665-27-3, Jul. 28, 2006.
CAS No. 896665-36-4, Jul. 28, 2006.
CAS No. 906762-15-0, Sep. 15, 2006.
CAS No. 896665-39-7, Jul. 28, 2006.
CAS No. 1040715-20-5, Aug. 13, 2008.
CAS No. 896665-42-2, Jul. 28, 2006.
CAS No. 894221-50-2, Jul. 19, 2006.
CAS No. 104691-75-5, Aug. 13, 2008.
CAS No. 708233-38-9, Jul. 12, 2004.
CAS No. 939894-43-6, Jun. 28, 2007.
CAS No. 1186694-47-2, Sep. 30, 2009.
CAS No. 895846-90-9, Jul. 25, 2006.
CAS No. 945169-97-1, Aug. 21, 2007.
CAS No. 1040698-13-2, Aug. 13, 2008.
CAS No. 945139-47-9, Aug. 21, 2007.
CAS No. 1040690-35-4, Aug. 13, 2008.
CAS No. 945118-21-8, Aug. 21, 2007.
CAS No. 1040712-88-6, Aug. 13, 2008.
CAS No. 879598-55-7, Apr. 7, 2006.
CAS No. 879479-35-3, Apr. 6, 2006.
CAS No. 879477-41-5, Apr. 6, 2006.
CAS No. 1040689-11-9, Aug. 13, 2008.
CAS No. 439128-53-7, Jul. 17, 2002.
CAS No. 1203342-18-0, Jan. 24, 2010.
CAS No. 1165948-24-2, Jul. 21, 2009.
Aggarwal et al., ARKIVOC 2014, 2:120-134. Synthesis of new bi(pyrazolo[1,5-a]pyrimidinyl)-7-one derivatives from dehydroacetic acid and its analogues as antibacterial agents.
Ananthan et al., "High Throughput screening for inhibitors of *Mycobacterium tuberculosis* H37Rv" Tuberculosis (Oxford, United Kingdom) (2009), 89(5), 334-353.
Barber, Immunol. Rev, Cytoplasmic DNA innate immune pathways, 243: 99-108, 2011.
Carré et al., Plos One, AutomiG, a Biosensor to Detect Alterations in miRNA Biogenesis and in Small RNA Silencing Guided by Perfect Target Complementarity, 2013, 8(9):e74296.
Chuvashlev et al., Izvestiya Vysshikh Uchebnykh Zavedenii, Khimiya i Khimicheskaya Tekhnologiya (2009), 52(11), 25-30. 5-Amino-3-Alkyl-4-Arylpyrazoles in Synthesis of Pyrazolo [1, 5-a] Pyrimidines.
Gibson et al., An intramolecular sulfoxide alkylation-elimination approach to the [1,2,3]triazolo[1,5-a]pyrimidine ring system, Synlett 2001, 5:712-714.
Ishikawa and Barber, STING an Endoplasmic Reticulum Adaptor that Facilitates Innate Immune Signaling, Nature 455: 674-79, 2008.
Jia et al., Pharmacology, Activation of KCNQ2/3 potassium channels by novel pyrazolo[1,5-a]pyrimidin-7(4H)-one derivatives, (2011), 87(5-6), 297-310.
Mao et al., Bioorganic & Medicinal Chemistry Letters, Structure-activity relationships of compounds targeting *Mycobacterium tuberculosis* 1-deoxy-xylulose 5-phosphate synthase, (2008), 18(19), 5320-5323.
Qi et al., European Journal of Medicinal Chemistry (2011), 46(3), 934-943. Design, synthesis and biological activity of pyrazolo[1,5-a]pyrimidin-7(4H)-ones as novel Kv7/KCNQ potassium channel activators.
Rayburn, E. R. et al., Anti-Inflammatory Agents for Cancer Therapy, Mol Cell Pharmacol. 2009, 1(1): 29-43.
Ablasser et al., "cGAS produces a 29-59-linked cyclic dinucleotide second messenger that activates STING", Nature 498: 380-84, 2013.
Ahn et al., "STING-Dependent Signaling Underlies IL-10 Controlled Inflammatory Colitis", Cell Reports 21:3873-3884, 2017.
Bai et al., "DsbA-L prevents obesity-induced inflammation and insulin resistance by suppressing the mtDNA release-activated cGAS-cGAMP-STING pathway", PNAS 114 (46): 12196-12201, 2017.
Bondeson, et al., "Catalytic in vivo protein knockdown by smallmolecule PROTACs", Nature Chemical Biology 11:611-617, 2015.
Bundgaard, H., "Design of prodrugs: Bioreversible derivatives for various functional groups and chemical entities", *Design of Prodrugs*, p. 1-92, 1985.
Collins et al., "Chemical approaches to targeted protein degradation through modulation of the ubiquitin-proteasome pathway", Biochemical Journal 474: 1127-1147, 2017.
Conlon et. al., "Mouse, but not Human STING, Binds and Signals in Response to the Vascular Disrupting Agent 5,6-Dimethylxanthenone-4-Acetic Acid", J Immunol 190:5216-5225, 2013.
Diner et al., "The Innate Immune DNA Sensor cGAS Produces a Noncanonical Cyclic Dinucleotide that Activates Human STING", Cell Reports 3:1355-1361, 2013.
Gao et al., "Activation of cyclic GMP-AMP synthase by self-DNA causes autoimmune diseases", PNAS 112(42):E5699-E5705, 2015.
Gao et al., "Structure-Function Analysis of STING Activation by c[G(2',5')pA(3',5')p] and Targeting by Antiviral DMXAA", Cell 154:748-762, 2013.
Gao et al., "Cyclic [G(2',5')pA(3',5')p] Is the Metazoan Second Messenger Produced by DNA-Activated Cyclic GMP-AMP Synthase", Cell 153:1094-1107, 2013.
Gray et al., "Cutting Edge: cGAS Is Required for Lethal Autoimmune Disease in the Trex1-Deficient Mouse Model of Aicardi-Goutières Syndrome", The Journal of Immunology 195:1939-1943, 2015.

(56) References Cited

OTHER PUBLICATIONS

Kerur et al., "cGAS drives noncanonical-inflammasome activation in age-related macular degeneration", Nature Medicine 24:50-61, 2018.
King et al., "IRF3 and type I interferons fuel a fatal response to myocardial infarction", Nature Medicine 23: 1481-1487, 2017.
Kranzusch et al., Structure of Human cGAS Reveals a Conserved Family of Second-Messenger Enzymes in Innate Immunity, Cell Reports 3: 1362-68, 2013.
Kreienkamp et al., "A Cell-Intrinsic Interferon-like Response Links Replication Stress to Cellular Aging Caused by Progerin", Cell Reports 22:2006-2015, 2018.
Li et al., "The cGAS-cGAMP-STI NG pathway connects DNA damage to inflammation, senescence, and cancer", Journal of Experimental Medicine, 215(5) 1287, 2018.
Nicolaou et al. "Total Synthesis of Viridicatumtoxin B and Analogues Thereof: Strategy Evolution, Structural Revision, and Biological Evaluation", JACS, 136(34), 12137-12160, 2014.
Sun et al., "Cyclic GMP-AMP Synthase Is a Cytosolic DNA Sensor That Activates the Type I Interferon Pathway", Science 339: 786-91, 2013.
Toure and Crews, "Small-Molecule PROTACS: New Approaches to Protein Degradation", Angew. Chem. Int. Ed. 55:1699-1973, 2016.
Vincent et al., "Small molecule inhibition of cGAS reduces interferon expression in primary macrophages from autoimmune mice", Nature Communications 8(1):750, 16 pages, 2017.
Wu et al., "Cyclic GMP-AMP Is an Endogenous Second Messenger in Innate Immune Signaling by Cytosolic DNA", Science 339: 826-30, 2013.
Yang et al., "cGAS is essential for cellular senescence", PNAS 114 (23): E4612-E4620, 2017.
Zhang et al., "Cyclic GMP-AMP Containing Mixed Phosphodiester Linkages Is an Endogenous High-Affinity Ligand for STING", Molecular Cell 51: 226-35, 2013.
Reynolds et al., Tuberculosis (Edinb). Jan. 2012; 92(1): 72-83. High Throughput Screening of a Library Based on Kinase Inhibitor Scaffolds Against *Mycobacterium* Tuberculosis H37Rv.
Selleri et al., Farmaco 1995, 50(10):679-687. New 2,3-substituted 4,7-dihydro-6-(1H-pyrazol-3-yl)pyrazolo[1,5-a]pyrimidin-7-ones and related compounds: synthesis and benzodiazepine receptor binding study.
Urbanska, A.M. et al., Cell Biochem Biophys. Jul. 2015;72(3):757-769.
Young et al., Cytometry, Part A (2009), 75A(3), 253-263. Duplex high-throughput flow cytometry screen identifies two novel formylpeptide receptor family probes.
CAS No. 1310131-19-1, Jun. 23, 2011.
CAS No. 634189-82-5, Jan. 5, 2004.
CAS No. 1310083-36-3, Jun. 23, 2011.
CAS No. 1310318-29-6, Jun. 24, 2011.
CAS No. 1310242-29-5, Jun. 24, 2011.
CAS No. 1310288-60-8, Jun. 24, 2011.
CAS No. 1310293-45-8, Jun. 24, 2011.
CAS No. 1310262-52-2, Jun. 24, 2011.
CAS No. 1310091-64-5, Jun. 23, 2011.
CAS No. 1310131-24-8, Jun. 23, 2011.
CAS No. 1310260-16-2, Jun. 24, 2011.
CAS No. 931936-12-8, Apr. 23, 2007.
CAS No. 890818-62-9, Jul. 6, 2006.
CAS No. 890818-70-9, Jul. 6, 2006.
CAS No. 890818-46-9, Jul. 6, 2006.
CAS No. 890818-54-9, Jul. 6, 2006.
CAS No. 890818-78-7, Jul. 6, 2006.
CAS No. 890818-86-7, Jul. 6, 2006.
CAS No. 331434-03-8, Apr. 16, 2001.
CAS No. 701972-85-2, Jul. 1, 2004.
CAS No. 701230-47-9, Jun. 30, 2004.
CAS No. 838890-78-1, Feb. 28, 2005.
CAS No. 767301-01-9, Oct. 22, 2004.
CAS No. 924866-49-9, Mar. 5, 2007.
CAS No. 1310318-28-5, Jun. 24, 2011.
CAS No. 2166113-04-6, Dec. 27, 2017.
CAS No. 1310199-18-8, Jun. 23, 2011.
CAS No. 1310083-34-1, Jun. 23, 2011.
CAS No. 1310140-15-8, Jun. 23, 2011.
CAS No. 2166113-29-5, Dec. 27, 2017.
CAS No. 1310319-80-2 R'=CN, R=H, Jun. 24, 2011.
CAS No. 1310199-16-6 R'=CN, R=H, Jun. 23, 2011.
CAS No. 1310281-98-1 R'=CN, R=H, Jun. 24, 2011.
CAS No. 1310142-52-9, Jun. 23, 2011.
CAS No. 1310281-60-7, Jun. 24, 2011.
CAS No. 924866-52-4, Mar. 5, 2007.
CAS No. 924866-51-3, Mar. 5, 2007.
CAS No. 924857-84-1, Mar. 5, 2007.
CAS No. 909378-43-4, Oct. 3, 2006.
CAS No. 2166112-95-2, Dec. 27, 2017.
CAS No. 2166112-94-1, Dec. 27, 2017.
CAS No. 879615-69-7, R2=Cl, R3=H, R4=H, Apr. 7, 2006.
CAS No. 896665-45-5, Jul. 28, 2006.
CAS No. 886185-64-4 R'=Cl, R=H, May 31, 2006.
Written Opinion of the International Searching Authority dated Jan. 9, 2019 for Application No. PCT/US2018/051014.
International Search Report dated Jan. 9, 2019 for Application No. PCT/US2018/051014.

* cited by examiner

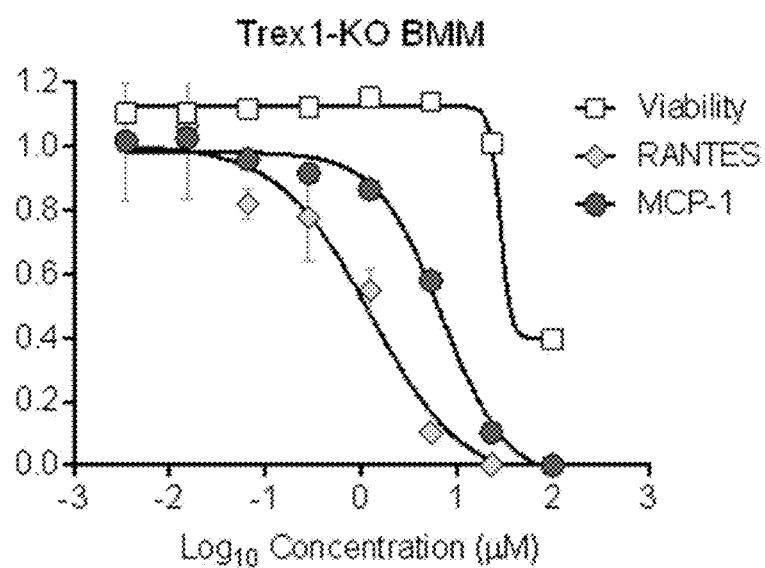

SEQUENCE LISTING

<160> NUMBER OF SEQ ID NOS: 3

<210> SEQ ID NO 1
<211> LENGTH: 366
<212> TYPE: PRT
<213> ORGANISM: Homo sapiens

<400> SEQUENCE: 1

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly

```
                20                  25                  30
        Val Val Asp His Leu Leu Arg Leu Lys Cys Asp Ser Ala Phe Arg
                    35                  40                  45
        Gly Val Gly Leu Leu Asn Thr Gly Ser Tyr Tyr Glu His Val Lys Ile
        50                  55                  60
        Ser Ala Pro Asn Glu Phe Asp Val Met Phe Lys Leu Glu Val Pro Arg
        65                  70                  75                  80
        Ile Gln Leu Glu Glu Tyr Ser Asn Thr Arg Ala Tyr Tyr Phe Val Lys
                        85                  90                  95
        Phe Lys Arg Asn Pro Lys Glu Asn Pro Leu Ser Gln Phe Leu Glu Gly
                    100                 105                 110
        Glu Ile Leu Ser Ala Ser Lys Met Leu Ser Lys Phe Arg Lys Ile Ile
                    115                 120                 125
        Lys Glu Glu Ile Asn Asp Ile Lys Asp Thr Asp Val Ile Met Lys Arg
                    130                 135                 140
        Lys Arg Gly Gly Ser Pro Ala Val Thr Leu Leu Ile Ser Glu Lys Ile
        145                 150                 155                 160
        Ser Val Asp Ile Thr Leu Ala Leu Glu Ser Lys Ser Ser Trp Pro Ala
                        165                 170                 175
        Ser Thr Gln Glu Gly Leu Arg Ile Gln Asn Trp Leu Ser Ala Lys Val
                    180                 185                 190
        Arg Lys Gln Leu Arg Leu Lys Pro Phe Tyr Leu Val Pro Lys His Ala
                    195                 200                 205
        Lys Glu Gly Asn Gly Phe Gln Glu Glu Thr Trp Arg Leu Ser Phe Ser
                    210                 215                 220
        His Ile Glu Lys Glu Ile Leu Asn Asn His Gly Lys Ser Lys Thr Cys
        225                 230                 235                 240
        Cys Glu Asn Lys Glu Glu Lys Cys Cys Arg Lys Asp Cys Leu Lys Leu
                        245                 250                 255
        Met Lys Tyr Leu Leu Glu Gln Leu Lys Glu Arg Phe Lys Asp Lys Lys
                    260                 265                 270
        His Leu Asp Lys Phe Ser Ser Tyr His Val Lys Thr Ala Phe Phe His
                    275                 280                 285
        Val Cys Thr Gln Asn Pro Gln Asp Ser Gln Trp Asp Arg Lys Asp Leu
                    290                 295                 300
        Gly Leu Cys Phe Asp Asn Cys Val Thr Tyr Phe Leu Gln Cys Leu Arg
        305                 310                 315                 320
        Thr Glu Lys Leu Glu Asn Tyr Phe Ile Pro Glu Phe Asn Leu Phe Ser
                        325                 330                 335
        Ser Asn Leu Ile Asp Lys Arg Ser Lys Glu Phe Leu Thr Lys Gln Ile
                    340                 345                 350
        Glu Tyr Glu Arg Asn Asn Glu Phe Pro Val Phe Asp Glu Phe
                    355                 360                 365

<210> SEQ ID NO 2
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 2
tacagatcta ctagtgatct atgactgatc tgtacatgat ctaca              45

<210> SEQ ID NO 3
```

```
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 3
tgtagatcat gtacagatca gtcatagatc actagtagat ctgta          45
```

PYRAZOLOPYRIMIDINONE COMPOUNDS AND USES THEREOF

RELATED APPLICATIONS

This application claims priority to, and the benefit of, U.S. Provisional Application No. 62/559,482, filed on Sep. 15, 2017; 62/633,248, filed on Feb. 21, 2018; 62/687,769, filed on Jun. 20, 2018, the contents of each of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ADRO_001_001US_SeqList_ST25.txt, date recorded: Oct. 18, 2018, file size 4 kilobytes).

BACKGROUND

The enzyme cyclic GMP-AMP Synthase (cGAS) catalyzes the synthesis of cyclic GMP-AMP (cGAMP) from ATP and GTP in the presence of DNA. This cGAMP then functions as a second messenger that binds to and activates STimulator of INterferon Genes (STING). The activation of IRF3 and the NF-κB signaling by this pathway results in the production of cytokines and type I interferons, which triggers an innate immune response to bacterial or viral infection. Genetic mutations that alter the balance of this pathway may result in an increased activation of the STING pathway, resulting in autoimmune and inflammatory diseases. For example, a loss of function mutation of TREX1 exonuclease, which digests DNA, can result in an accumulation of self-DNA in the cytosol, leading to excessive levels of cGAMP produced by cGAS and elevated expression of interferon induced genes in this pathway. Mutations in TREX1 are associated with systemic inflammatory diseases such as Aicardi-Goutieres Syndrome, familial chilblain lupus and systemic lupus erythematosus. Trex$^{-/-}$ mice were shown to exhibit autoimmune and inflammatory phenotypes which are eliminated with genetic deletion of cGas in these mice (Gao et al., PNAS 112(42):E5699-705, 2015; Gray et al., The Journal of Immunology 195:1939-1943, 2015). Thus there is a need for inhibitors of the cGAS/STING pathway for the treatment of a variety of diseases.

SUMMARY

The present invention provides the compounds of Formula (I):

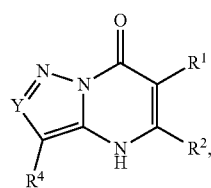

(I)

or a pharmaceutically acceptable salt, pharmaceutically acceptable solvate or pharmaceutically acceptable hydrate thereof. In this formula:

Y is —CR$^3$= or —N=;

R$^1$ is Q$^1$-T$^1$-(X$^1$)$_n$;

Q$^1$ is a bond or C$_{1-3}$alkylene, wherein the C$_{1-3}$alkylene group is optionally substituted with one or more substituents independently selected from the group consisting of halo, C$_{1-6}$alkyl, C$_{2-6}$alkenyl, C$_{2-6}$alkynyl, cyano, C$_{1-6}$haloalkyl, —OR$^{w2}$, and —NR$^{w2}$R$^{x2}$;

T$^1$ is C$_{3-8}$cycloalkyl, C$_{6-10}$aryl, 3- to 12-membered heterocycloalkyl, 5- to 10-membered heteroaryl, —C(=O)C$_{0-3}$alkylene-C$_{3-8}$cycloalkyl, —C(=O)—C$_{0-3}$alkylene-C$_{6-10}$aryl, —C(=O)—C$_{0-3}$alkylene-3 to 12-membered heterocycloalkyl, —C(=O)—C$_{0-3}$alkylene-5 to 10-membered heteroaryl, —NR$^a$R$^b$, —S(=O)$_2$R$^a$, —NR$^a$C(=O)R$^a$, —NR$^a$C(=O)NR$^a$R$^b$, —NR$^a$C(=O)OR$^a$, —NR$^a$S(=O)$_2$R$^a$, —C(=O)NR$^a$S(=O)$_2$R$^a$, —NR$^a$S(=O)$_2$NR$^a$R$^b$, —C(=O)NR$^a$R$^b$, or —S(=O)$_2$NR$^a$R$^b$;

each X$^1$ is independently selected from the group consisting of halo, cyano, oxo, C$_{0-3}$alkylene-C(=O)R$^c$, C$_{0-3}$alkylene-OR$^c$, C$_{0-3}$alkylene-C(=O)OR$^c$, C$_{0-3}$alkylene-OC(=O)R$^c$, C$_{0-3}$alkylene-NR$^c$R$^d$, C$_{0-3}$alkylene-N$^+$R$^c$R$^d$R$^{d'}$, C$_{0-3}$alkylene-S(=O)$_m$R$^c$, C$_{0-3}$alkylene-NR$^c$C(=O)R$^c$, C$_{0-3}$alkylene-NR$^c$C(=O)NR$^c$R$^d$, C$_{0-3}$alkylene-OC(=O)NR$^c$R$^d$, C$_{0-3}$alkylene-NR$^c$C(=O)OR$^c$, C$_{0-3}$alkylene-NR$^c$S(=O)$_2$R$^c$, C$_{0-3}$alkylene-C(=O)NR$^c$S(=O)$_2$R$^c$, C$_{0-3}$alkylene-NR$^c$S(=O)$_2$NR$^c$R$^d$, C$_{0-3}$alkylene-C(=O)NR$^c$R$^d$, C$_{0-3}$alkylene-S(=O)$_2$NR$^c$R$^d$, C$_{0-3}$alkylene-C(=NR$^c$)NR$^c$R$^d$, C$_{0-3}$alkylene-NR$^c$C(=NR)NR$^c$R$^d$, and R$^{S1}$, in which R$^{S1}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S1}$ is optionally substituted with one or more substituents independently selected from the group consisting of halo, cyano, nitro, oxo, C$_{1-6}$alkyl, C$_{2-6}$alkenyl, C$_{2-6}$alkynyl, C$_{1-6}$haloalkyl, C$_{0-3}$alkylene-NR$^e$R$^f$, C$_{0-3}$alkylene-OR$^e$, C$_{0-3}$alkylene-NR$^e$C(=O)R$^e$, C$_{0-3}$alkylene-NR$^e$C(=O)OR$^e$, C$_{0-3}$alkylene-NR$^e$C(=O)NR$^e$R$^f$, C$_{0-3}$alkylene-OC(=O)R$^e$, C$_{0-3}$alkylene-C(=O)OR$^e$, C$_{0-3}$alkylene-C(=O)NR$^e$R$^f$, C$_{0-3}$alkylene-C(=O)R$^e$, C$_{0-3}$alkylene-S(=O)$_m$R$^e$, C$_{0-3}$alkylene-S(=O)$_2$NR$^e$R$^f$, C$_{0-3}$alkylene-NR$^e$S(=O)$_2$R$^e$, C$_{0-3}$alkylene-C(=O)NR$^e$S(=O)$_2$R$^e$, C$_{0-3}$alkylene-NR$^e$S(=O)$_2$NR$^e$R$^f$, and R$^{S2}$, in which R$^{S2}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl, and each R$^{S2}$ is optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, —OR$^w$, and —NR$^w$R$^x$;

R$^2$ is Q$^2$-T$^2$-(X$^2$)$_p$;

Q$^2$ is a bond or C$_{1-3}$alkylene, wherein the C$_{1-3}$alkylene group is optionally substituted with one or more substituents independently selected from the group consisting of halo, C$_{1-6}$alkyl, C$_{2-6}$alkenyl, C$_{2-6}$alkynyl, cyano, C$_{2-6}$haloalkyl, —OR$^{w3}$, and —NR$^{w3}$R$^{x3}$;

T$^2$ is H, halo, cyano, C$_{1-6}$alkyl, C$_{2-6}$alkenyl, C$_{2-6}$alkynyl, C$_{3-8}$cycloalkyl, C$_{6-10}$aryl, 3- to 12-membered heterocycloalkyl, 5- to 10-membered heteroaryl, —C(=O)—C$_{0-3}$alkylene-C$_{3-8}$cycloalkyl, —C(=O)—C$_{0-3}$alkylene-C$_{6-10}$aryl, —C(=O)—C$_{0-3}$alkylene-3- to 12-membered heterocycloalkyl, —C(=O)—C$_{0-3}$alkylene-5- to 10-membered heteroaryl, —OR$^z$, —S(=O)$_m$R$^k$, —P(=O)R$^{kk}$R$^{mm}$, —NR$^k$R$^m$, —C(=O)OR$^k$, or —C(=O)NR$^k$R$^m$;

each X$^2$ is independently selected from the group consisting of halo, cyano, oxo, C$_{0-3}$alkylene-OR$^n$, C$_{0-3}$alkylene-S(=O)$_m$R$^n$, C$_{0-3}$alkylene-NR$^n$R$^o$, C$_{0-3}$alkylene-C(=O)NR$^n$R$^o$, C$_{0-3}$alkylene-C(=O)OR$^n$, and R$^{S3}$, in which R$^{S3}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and $R^{S3}$ is optionally substituted with one or more substituents independently selected from the group consisting of halo, oxo, cyano, $C_{0-3}$alkylene-$OR^p$, $C_{0-3}$alkylene-$S(=O)^m$ $R^p$, $C_{0-3}$alkylene-$NR^pR^q$, $C_{0-3}$alkylene-$C(=O)NR^pR^q$, $C_{0-3}$alkylene-$C_{0-3}$alkylene-$C(=O)OR^p$, $C_{1-6}$alkyl, $C_{2-6}$alkenyl, $C_{2-6}$alkynyl, $C_{1-6}$haloalkyl, and $R^{S4}$, in which $R^{S4}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S4}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w4}$, and —$NR^{w4}R^{x4}$;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —$C(=O)R^r$, —$S(=O)_mR^r$, $NR^rR^t$, or —$C(=O)OR^r$, wherein $C_{1-3}$alkyl, $C_{2-3}$alkenyl and $C_{2-3}$alkynyl are optionally substituted with one $C_{3-6}$cycloalkyl;

$R^4$ is $C_{1-6}$alkyl, $C_{1-6}$haloalkyl, $S(=O)_mR^u$, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, wherein $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl are optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, $OR^{w5}$, and $NR^{w5}R^{x5}$;

each of $R^a$ and $R^b$, independently, is H or $R^{S5}$, in which $R^{S5}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and $R^{S5}$ is optionally substituted with one or more substituents independently selected from the group consisting of halo, cyano, oxo, $C_{1-6}$haloalkyl, $C_{0-3}$alkylene-$OR^{c2}$, $C_{0-3}$alkylene-$C(=O)R^{c2}$, $C_{0-3}$alkylene-$C(=O)OR^{c2}$, $C_{0-3}$alkylene-$OC(=O)R^{c2}$, $C_{0-3}$alkylene-$C(=O)NR^{c2}R^{d2}$, $C_{0-3}$alkylene-$S(=O)_mR^2$, $C_{0-3}$alkylene-$S(=O)_2NR^{c2}R^{d2}$, $C_{0-3}$alkylene-$NR^{c2}R^{d2}$, $C_{0-3}$alkylene-$NR^2C(=O)R^{c2}$, $C_{0-3}$alkylene-$NR^2C(=O)OR^{c2}$, $C_{0-3}$alkylene-$NR^2C(=O)NR^{c2}R^{d2}$, $C_{0-3}$alkylene-$NR^2S(=O)_2R^{c2}$, $C_{0-3}$alkylene-$C(=O)NR^{c2}S(=O)_2R^{c2}$, $C_{0-3}$alkylene-$NR^{c2}S(=O)_2NR^{c2}R^{d2}$, $C_{0-3}$alkylene-$N(S(=O)_2R^2)_2$, and $R^{S6}$, in which $R^{S6}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S6}$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{e2}R^{f2}$, $C_{0-3}$alkylene-$OR^{e2}$, $C_{0-3}$alkylene-$NR^{e2}C(=O)R^{e2}$, $C_{0-3}$alkylene-$NR^{e2}C(=O)OR^{e2}$, $C_{0-3}$alkylene-$NR^{e2}C(=O)NR^{e2}R^{f2}$, $C_{0-3}$alkylene-$OC(=O)R^{e2}$, $C_{0-3}$alkylene-$C(=O)OR^{e2}$, $C_{0-3}$alkylene-$C(=O)NR^{e2}R^{f2}$, $C_{0-3}$alkylene-$C(=O)R^{e2}$, $C_{0-3}$alkylene-$S(=O)_mR^{e2}$, $C_{0-3}$alkylene-$S(=O)_2NR^{e2}R^{f2}$, $C_{0-3}$alkylene-$NR^{e2}S(=O)_2R^{e2}$, $C_{0-3}$alkylene-$C(=O)NR^{e2}S(=O)_2R^{e2}$, $C_{0-3}$alkylene-$NR^{e2}S(=O)_2NR^{e2}R^{f2}$, and $R^{S7}$, in which $R^{S7}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S7}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w6}$, and —$NR^{w6}R^{x6}$;

each of $R^c$, $R^{c2}$, $R^d$, $R^{d'}$, and $R^{d2}$, independently, is H or $R^{S8}$, in which $R^{S8}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S8}$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{e3}R^{f3}$, $C_{0-3}$alkylene-$OR^{e3}$, $C_{0-3}$alkylene-$C(=O)OR^{e3}$, $C_{0-3}$alkylene-$C(=O)NR^{e3}R^{f3}$, $C_{0-3}$alkylene-$C(=O)R^{e3}$, $C_{0-3}$alkylene-$S(=O)_mR^{e3}C_{0-3}$alkylene-$S(=O)_2NR^{e3}R^{f3}$, $C_{0-3}$alkylene-$NR^{f3}C(=O)R^{e3}$, $C_{0-3}$alkylene-$NR^{f3}S(=O)_mR^{e3}$, and $R^{S9}$, in which $R^{S9}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, $C_{0-3}$alkylene-5- to 10-membered heteroaryl;

and each $R^{S9}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w7}$, and —$NR^{w7}R^{x7}$;

each of $R^e$, $R^{e2}$, $R^{e3}$, $R^f$, $R^{f2}$, and $R^{f3}$, independently, is H or $R^{S10}$, in which $R^{S10}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S10}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w8}$, and —$NR^{w2}R^{x8}$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^z$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{n2}R^{o2}$, $C_{0-3}$alkylene-$OR^{n2}$, $C_{0-3}$alkylene-$C(=O)OR^{n2}$, $C_{0-3}$alkylene-$C(=O)NR^{n2}R^{o2}$, $C_{0-3}$alkylene-$C(=O)R^{n2}$, $C_{0-3}$alkylene-$S(=O)_mR^{n2}$, $C_{0-3}$alkylene-$S(=O)_2NR^{n2}R^{o2}$, and $R^{S11}$, in which $R^{S11}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, $C_{0-3}$alkylene-5- to 10-membered heteroaryl;

and each $R^{S11}$ is optionally substituted with one or more substituents independently selected from the group consisting of halo, oxo, cyano, $C_{0-3}$alkylene-$OR^{p2}$, $C_{0-3}$alkylene-$S(=O)_mR^{p2}$, $C_{0-3}$alkylene-$NR^{p2}R^{g2}$, $C_{0-3}$alkylene-$C(=O)NR^{p2}R^{g2}$, $C_{0-3}$alkylene-$C_{0-3}$alkylene-$C(=O)OR^{p2}$, $C_{1-6}$alkyl, $C_{2-6}$alkenyl, $C_{2-6}$alkynyl, $C_{1-6}$haloalkyl, and $R^{S12}$, in which $R^{S12}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S12}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w9}$, and —$NR^{w9}R^{x9}$;

each of $R^n$, $R^{n2}$, $R^o$, and $R^{o2}$, independently, is H or $R^{S13}$, in which $R^{S13}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S13}$ is optionally substituted with one or more substituents independently selected from the group consisting of halo, oxo, cyano, $C_{0-3}$alkylene-$OR^{p3}$, $C_{0-3}$alkylene-$S(=O)_mR^{p3}$, $C_{0-3}$alkylene-$NR^{p3}R^{q3}$, $C_{0-3}$alkylene-$C(=O)NR^{p3}R^{q3}$, $C_{0-3}$alkylene-$C(=O)OR^{p3}$, $C_{1-6}$alkyl, $C_{2-6}$alkenyl, $C_{2-6}$alkynyl, $C_{1-6}$haloalkyl, and $R^{S14}$, in which $R^{S14}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S14}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w10}$, and —$NR^{w10}R^{x10}$;

each of $R^p$, $R^{p2}$, $R^{p3}$, $R^q$, $R^{q2}$, and $R^{q3}$, independently, is H or $R^{S15}$, in which $R^{S15}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S15}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w11}$, and —$NR^{w11}R^{x11}$;

each of $R^r$, $R^t$, and $R^u$, independently, is H or $R^{S16}$, in which $R^{S16}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S16}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$C(=O)OR^{w12}$, —$OR^{w12}$, and —$NR^{w12}R^{x12}$;

each $R^w$, $R^{w2}$, $R^{w3}$, $R^{w4}$, $R^{w5}$, $R^{w6}$, $R^{w7}$, $R^{w8}$, $R^{w9}$, $R^{w10}$, $R^{w11}$, $R^{w12}$, $R^x$, $R^{x2}$, $R^{x3}$, $R^{x4}$, $R^{x5}$, $R^{x6}$, $R^{x7}$, $R^{x8}$, $R^{x9}$, $R^{x10}$, $R^{x11}$, and $R^{x12}$, independently, is H, $C_{1-6}$alkyl, $C_{2-6}$alkenyl, $C_{2-6}$alkynyl or $C_{1-6}$haloalkyl;

each of n and p independently is 0, 1, 2, 3, 4, or 5, wherein when $T^2$ is H, p is 0; and m is 0, 1, or 2;

with the proviso that, for compounds where Y is —$CR^3$=:

a) when $R^1$ is unsubstituted phenyl, $R^2$ is methyl and $R^3$ is methyl, $R^4$ is not ethyl, unsubstituted phenyl, or unsubstituted pyridine;

b) when $R^1$ is unsubstituted cyclohexyl, $R^2$ is methyl and $R^3$ is methyl, $R^4$ is not unsubstituted pyridine;

c) when $R^1$ is unsubstituted cyclopentyl, $R^2$ is methyl and $R^3$ is methyl, $R^4$ is not ethyl or unsubstituted pyridine, d) when $R^2$ is methyl, $R^3$ is methyl and $R^4$ is 3,4-diethoxy-phenyl, $R^1$ is not unsubstituted 1-pyrrolidine, unsubstituted 1-piperidine, 4-methyl-1-piperidine, 4-(phenylmethyl)-1-piperidine, unsubstituted 2-1,2,3,4-tetrahydroisoquinoline, unsubstituted morpholine, or NHCH$_2$CH$_2$-3-indole;

e) when $R^1$ is unsubstituted CH$_2$-phenyl, $R^2$ is methyl and $R^3$ is methyl, $R^4$ is not ethyl, trifluoromethyl, 1-methylpiperidin-4-yl, unsubstituted pyridine, unsubstituted phenyl, phenyl mono-substituted with 4-F, 4-Cl, 2-methoxy or 4-methoxy, or phenyl disubstituted with 3,4-methoxy;

f) when $R^2$ is methyl, $R^3$ is methyl and $R^4$ is unsubstituted pyridine, $R^1$ is not CH$_2$-phenyl wherein the phenyl is substituted with 4-CN, 4-NO$_2$, 4-F or 2-F;

g) when $R^2$ is methyl, $R^3$ is methyl and $R^4$ is ethyl, $R^1$ is not CH$_2$-phenyl wherein the phenyl is substituted with 4-CN or 4-NO$_2$;

h) when $R^2$ is methyl, $R^3$ is methyl and $R^4$ is 4-methoxyphenyl, $R^1$ is not CH$_2$-phenyl wherein the phenyl is substituted with 2-Cl, 3-Cl, 4-Br, 2-methyl or 4-methyl;

i) when $R^2$ is methyl, $R^3$ is methyl and $R^4$ is unsubstituted phenyl, $R^1$ is not CH$_2$-phenyl wherein the phenyl is substituted with 2-Cl, 3-Cl, 4-Cl, 4-Br, 2-methyl, 3-methyl, 4-methyl, 4-isopropyl or 4-tert-butyl; or $R^1$ is not unsubstituted CH$_2$-1-naphthylene or unsubstituted CH$_2$-pyridine;

j) when $R^2$ is methyl, $R^3$ is methyl and $R^4$ is 4-Cl-phenyl, $R^1$ is not CH$_2$-phenyl wherein the phenyl is substituted with 2-Cl, 4-Cl or 4-isopropyl;

k) when $R^1$ is unsubstituted CH$_2$-phenyl, $R^2$ is methyl and $R^3$ is trifluoromethyl, $R^4$ is not unsubstituted phenyl or phenyl substituted with 2-Cl or 4-Cl;

l) the compound is not wherein $R^1$ is CH$_2$-4-Br-phenyl, $R^2$ is methyl, $R^3$ is ethyl and $R^4$ is unsubstituted phenyl;

m) when $R^2$ is methyl, $R^3$ is methyl and $R^4$ is unsubstituted phenyl, $R^1$ is not CH$_2$CH$_2$C(=O)NH-phenyl wherein the phenyl ring is unsubstituted or is substituted at the 4-position with Cl, methyl or methoxy;

n) when $R^2$ is methyl or ethyl, $R^3$ is methyl and $R^4$ is unsubstituted phenyl, $R^1$ is not substituted pyrazolo[1,5-a]pyrimidin-7-yl;

o) when $R^2$ is H, $R^3$ is isopropyl and $R^4$ is methyl, $R^1$ is not unsubstituted pyrazole; and p) the compound is not wherein $R^1$ is unsubstituted CH$_2$-phenyl, $R^2$ is H, $R^3$ is methyl and $R^4$ is unsubstituted phenyl; and with the proviso that, for compounds where Y is —N=, the compound is not wherein $R^1$ is unsubstituted phenyl, $R^2$ is H and $R^4$ is 2-fluoro-phenyl.

For example, the compound can be of Formula (IA) or Formula (IA'):

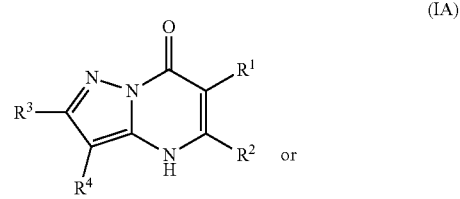

(IA)

or

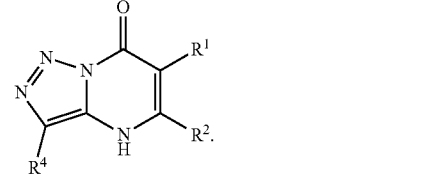

(IA').

For example, $Q^1$ is a bond or —CH$_2$— and $T^1$ is $C_{3-8}$cycloalkyl, $C_{6-10}$aryl, 3- to 12-membered heterocycloalkyl, 5- to 10-membered heteroaryl, or —C(=O)NR$^a$R$^b$.

For example, $Q^1$ is a bond and $T^1$ is $C_{3-8}$cycloalkyl, $C_{6-10}$aryl, 3- to 12-membered heterocycloalkyl, or 5- to 10-membered heteroaryl.

For example, $Q^1$ is a bond and $T^1$ is $C_{6-10}$aryl, 3- to 12-membered heterocycloalkyl, or 5- to 10-membered heteroaryl.

For example $Q^1$ is a bond and $T^1$ is phenyl, 5- or 6-membered monocyclic heteroaryl, or 9- or 10-membered bicyclic heteroaryl, preferably wherein $T^1$ is 9- or 10-membered bicyclic heteroaryl.

For example, $Q^1$ is a bond or —CH$_2$—, $T^1$ is —C(=O)NR$^a$R$^b$ and n is 0.

For example, one of $R^a$ and $R^b$ is H or methyl and the other of $R^a$ and $R^b$ is not H or methyl.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, $C_{2-6}$alkynyl, $C_{3-8}$cycloalkyl, $C_{6-10}$aryl, 3- to 12-membered heterocycloalkyl, or 5- to 10-membered heteroaryl, each $X^2$ independently is halo, cyano, oxo, $C_{0-3}$alkylene-$OR''$, $C_{0-3}$alkylene-$S(=O)_mR''$, $C_{0-3}$alkylene-$NR''R^o$, $C_{0-3}$alkylene-$C(=O)NR''R^o$, $C_{0-3}$alkylene-$C_{0-3}$alkylene-$C(=O)OR''$, and each $R''$ and $R^o$ is independently H, $C_{1-6}$alkyl, $C_{2-6}$alkenyl, $C_{2-6}$alkynyl or $C_{1-6}$haloalkyl.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, or $C_{2-6}$alkynyl, and each $X^2$ independently is halo or $OC_{1-6}$alkyl.

For example, $R^2$ is H, cyano, methyl or methoxymethyl.

For example, $R^2$ is H, methyl or methoxymethyl.

For example, $R^3$ is $C_{1-3}$alkyl, $C_{1-3}$haloalkyl, —CN, —$S(=O)_2C_{1-3}$alkyl or —$C(=O)OC_{1-3}$alkyl.

For example, $R^3$ is —CN, $C_{1-3}$alkyl, $C_{1-3}$haloalkyl or —$C(=O)OC_{1-3}$alkyl.

For example, $R^3$ is $C_{1-3}$alkyl, $C_{1-3}$haloalkyl or —$C(=O)OC_{1-3}$alkyl.

For example, $R^3$ is —$CF_3$, methyl or —$C(=O)OC_{1-3}$alkyl.

For example, $R^3$ is —$CF_3$ or —CN.

For example, $R^3$ is —$CF_3$

For example, $R^3$ is —CN.

For example, $R^4$ is $C_{1-3}$alkyl, $C_{1-3}$haloalkyl, —$S(=O)_2C_{1-3}$alkyl, $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$.

For example, $R^4$ is $C_{3-8}$cycloalkyl, $C_{6-10}$aryl, 3 to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is $C_{3-8}$cycloalkyl or $C_{6-10}$aryl, wherein $C_{3-8}$cycloalkyl and $C_{6-10}$aryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is phenyl optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is $C_{3-8}$cycloalkyl.

For example, $R^4$ is cyclopentyl.

For example, $R^4$ is phenyl.

For example, the compound can be of Formula (Ia) or Formula (Ia'):

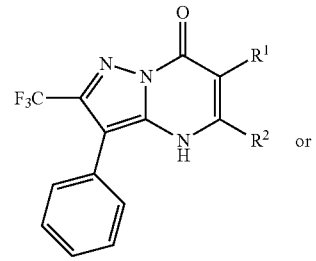

(Ia)

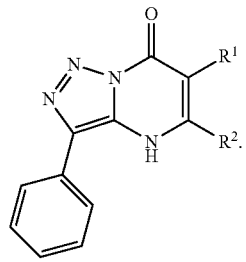

(Ia')

For example, $Q^1$ is a bond or —$CH_2$— and $T^1$ is $C_{3-8}$cycloalkyl, $C_{6-10}$aryl, 3- to 12-membered heterocycloalkyl, 5- to 10-membered heteroaryl, or —$C(=O)NR^aR^b$.

For example, $Q^1$ is a bond and $T^1$ is $C_{3-8}$cycloalkyl, $C_{6-10}$aryl, 3- to 12-membered heterocycloalkyl, or 5- to 10-membered heteroaryl.

For example, $Q^1$ is a bond and $T^1$ is $C_{6-10}$aryl, 3- to 12-membered heterocycloalkyl, or 5- to 10-membered heteroaryl.

For example $Q^1$ is a bond and $T^1$ is phenyl, 5- or 6-membered monocyclic heteroaryl, or 9- or 10-membered bicyclic heteroaryl, preferably wherein $T^1$ is 9- or 10-membered bicyclic heteroaryl.

For example, $Q^1$ is a bond or —$CH_2$—, $T^1$ is —$C(=O)NR^aR^b$ and n is 0.

For example, one of $R^a$ and $R^b$ is H or methyl and the other of $R^a$ and $R^b$ is not H or methyl.

For example, n is 0.

For example, $T^1$ is aryl or heteroaryl, preferably phenyl, 5- or 6-membered monocyclic heteroaryl, or 9- or 10-membered bicyclic heteroaryl.

For example, $T^1$ is 5- to 10-membered heteroaryl.

For example, $T^1$ is pyridinyl, pyrazinyl, pyridazinyl, pyrimidinyl, indolyl, indolinyl, isoindolyl, isoindolinyl, indazolyl, pyrazolopyridinyl, pyrazolopyrimidinyl, oxazolopyrimidinyl, oxazolopyridinyl, imidazopyridinyl, benzimidazolyl, tetrahydrobenzimidazolyl, benzofuranyl, dihydrobenzofuranyl, isobenzofuranyl, dihydroisobenzofuranyl, triazolopyridinyl, benzothiazolyl, azabenzimidazolyl, azabenzoxazolyl, azabenzothiazolyl, imidazopyridinyl, quinolinyl, isoquinolinyl, quinazolinyl, oxazolyl, isoxazolyl, thiazolyl, isothiazolyl, benzoxazolyl, benzodioxolyl, chromanyl, tetrahydrooxazoloazepinyl, tetrahydrobenzoxazolyl, oxadiazolyl, thiadiazolyl, pyrazolyl, triazolyl, imidazolyl, furanyl, or thiophenyl.

For example, $T^1$ is pyridinyl, pyrazinyl, pyridazinyl, pyrimidinyl, indolyl, indazolyl, pyrazolopyridinyl, benzimidazolyl, benzothiazolyl, azabenzimidazolyl, azabenzoxazolyl, azabenzothiazolyl, imidazopyridinyl, quinolinyl, isoquinolinyl, quinazolinyl, oxazolyl, isoxazolyl, thiazolyl, isothiazolyl, benzoxazolyl, oxadiazolyl, thiadiazolyl, triazolyl, imidazolyl, furanyl, or thiophenyl.

For example, T¹ is $C_{0-1}$alkylene-$C_{6-10}$aryl.

For example, T¹ is phenyl, benzyl, naphthyl, or CH₂naphthyl.

For example, T¹ is 3- to 12-membered heterocycloalkyl, preferably 4- to 10-membered heterocycloalkyl.

For example, T¹ is piperazine, piperidine, quinuclidine, or morpholine.

For example, the compound can be of Formula (Ib) or Formula (Ib'):

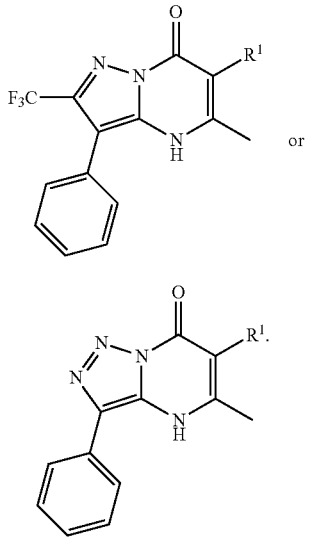

(Ib)

(Ib')

Subsets of compounds of Formula (I) includes those of Formula (IIa) or Formula (IIa'):

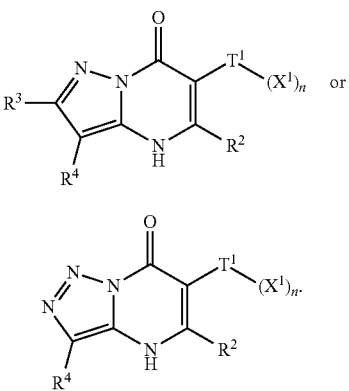

(IIa)

(IIa')

Subsets of compounds of Formula (I) includes those of Formula (IIb) or Formula (IIb'):

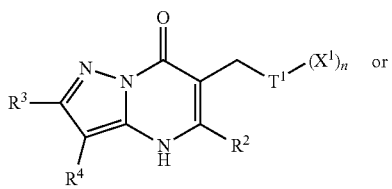

(IIb)

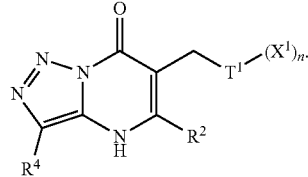

(IIb')

For example, T¹ is $C_{3-8}$cycloalkyl, $C_{6-10}$aryl, 3- to 12-membered heterocycloalkyl, 5- to 10-membered heteroaryl, —C(=O)—$C_{0-3}$alkylene-$C_{3-8}$cycloalkyl, —C(=O)—$C_{0-3}$alkylene-$C_{6-10}$aryl, —C(=O)—$C_{0-3}$alkylene-3- to 12-membered heterocycloalkyl, —C(=O)—$C_{0-3}$alkylene-5- to 10-membered heteroaryl, —NR$^a$R$^b$, —S(=O)$_2$R$^a$, —NR$^a$C(=O)R$^a$, —NR$^a$C(=O)NR$^a$R$^b$, —NR$^a$C(=O)OR$^a$, —NR$^a$S(=O)$_2$R$^a$, —C(=O)NR$^a$S(=O)$_2$R$^a$, —NR$^a$S(=O)$_2$NR$^a$R$^b$, —C(=O)NR$^a$R$^b$, or —S(=O)$_2$NR$^a$R$^b$; each X¹ independently is halo, cyano, oxo, $C_{0-3}$alkylene-C(=O)R$^c$, $C_{0-3}$alkylene-OR$^c$, $C_{0-3}$alkylene-NR$^c$R$^d$, $C_{0-3}$alkylene-OC(=O)NR$^c$R$^d$, $C_{0-3}$alkylene-C(=NR$^c$)NR$^c$R$^d$, $C_{0-3}$alkylene-NR$^c$(=NR)NR$^c$R$^d$, or R$^{S1}$, in which R$^{S1}$ is $C_{1-6}$alkyl, $C_{2-6}$alkenyl, $C_{2-6}$alkynyl, $C_{1-6}$haloalkyl, $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5 to 10-membered heteroaryl, and R$^{S1}$ is optionally substituted with one or more substituents independently selected from the group consisting of halo, oxo, $C_{1-6}$alkyl, $C_{2-6}$alkenyl, $C_{2-6}$alkynyl, $C_{1-6}$haloalkyl, $C_{0-3}$alkylene-NR$^e$R$^f$, $C_{0-3}$alkylene-OR$^e$, $C_{0-3}$alkylene-NR$^e$C(=O)R$^e$, $C_{0-3}$alkylene-NR$^e$C(=O)OR$^e$, $C_{0-3}$alkylene-NR$^e$C(=O)NR$^e$R$^f$, $C_{0-3}$alkylene-OC(=O)R$^e$, $C_{0-3}$alkylene-C(=O)OR$^e$, $C_{0-3}$alkylene-C(=O)R$^e$, $C_{0-3}$alkylene-S(=O)$_m$R$^e$, $C_{0-3}$alkylene-S(=O)$_2$NR$^e$R$^f$, $C_{0-3}$alkylene-NR$^e$S(=O)$_2$R$^e$, $C_{0-3}$alkylene-NR$^e$S(=O)$_2$NR$^e$R$^f$, and R$^{S2}$, in which R$^{S2}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, $C_{0-3}$alkylene-5- to 10-membered heteroaryl, and R$^{S2}$ is optionally substituted with one or more substituents independently selected from the group consisting of halo, $C_{1-6}$alkyl, $C_{2-6}$alkenyl, $C_{2-6}$alkynyl, cyano, $C_{1-6}$haloalkyl, —OR$^w$, and —NR$^w$R$^x$.

Subsets of compounds of Formula (I) includes those of Formula (IIc) or Formula (IIc'):

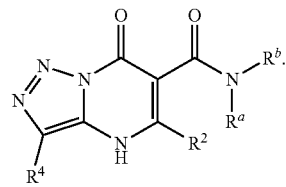

(IIc)

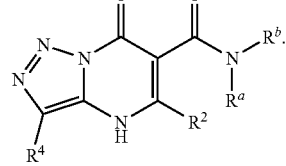

(IIc')

Subsets of compounds of Formula (I) includes those of Formula (IId) or Formula (IId'):

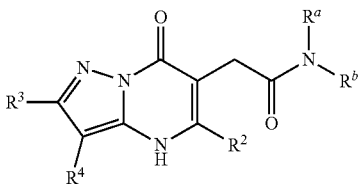

(IId)

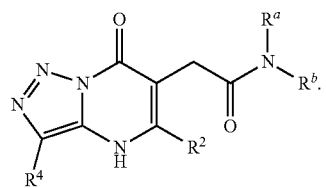

(IId')

Subsets of compounds of Formula (I) includes those of Formula (IIe) or Formula (IIe'):

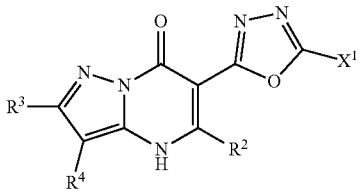

(IIe)

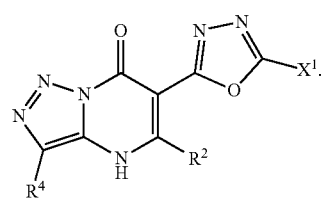

(IIe')

Subsets of compounds of Formula (I) includes those of Formula (IIf) or Formula (IIf'):

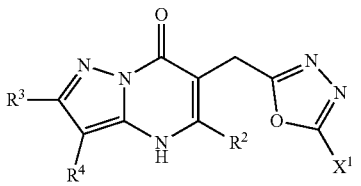

(IIf)

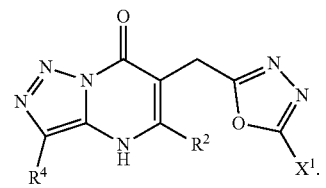

(IIf')

For example, one of $R^a$ and $R^b$ independently is 5 to 10-membered heteroaryl and the other is hydrogen.

For example, one of $R^a$ and $R^b$ independently is pyridinyl, pyrazinyl, pyridazinyl, pyrimidinyl, indolyl, indazolyl, benzimidazolyl, imidazopyridinyl, quinolinyl, isoquinolinyl, quinazolinyl, oxazolyl, isoxazolyl, thiazolyl, isothiazolyl, benzoxazolyl, oxadiazolyl, triazolyl, imidazolyl, furan, or thiophenyl, and the other of $R^a$ and $R^b$ is hydrogen.

For example, one of $R^a$ and $R^b$ is $C_{0-1}$alkylene-$C_{6-10}$aryl.

For example, one of $R^a$ and $R^b$ independently is phenyl, benzyl, naphthyl, or $CH_2$naphthyl.

For example, one of $R^a$ and $R^b$ independently is 5- to 9-membered heterocycloalkyl.

For example, one of $R^a$ and $R^b$ independently is dihydrobenzofuran, tetrahydrobenzimidazole, morpholine, tetrahydrofuran, piperidine, or piperazine.

For example, each of $R^a$ and $R^b$ independently is $C_{5-6}$cycloalkyl.

For example, each of $R^a$ and $R^b$ independently is cyclohexane or cyclopropane.

For example, $X^1$ is $C_{0-1}$alkylene-$C_{6-10}$aryl.

For example, $X^1$ is phenyl, benzyl, naphthyl, or $CH_2$naphthyl.

For example, $X^1$ is 5- to 10-membered heteroaryl.

For example, $X^1$ is benzoxazolyl, benzimidazolyl, pyridinyl, pyrazinyl, pyridazinyl, pyrimidinyl, indolyl, indazolyl, imidazopyridinyl, quinolinyl, isoquinolinyl, quinazolinyl, oxazolyl, isoxazolyl, thiazolyl, isothiazolyl, benzoxazolyl, oxadiazolyl, triazolyl, imidazolyl, furanyl, or thiophenyl.

For example, $X^1$ is 5- to 9-membered heterocycloalkyl.

For example, $X^1$ is tetrahydrobenzoxazole, tetrahydrobenzimidazole, morpholine, tetrahydrofuran, tetrahydropyran, piperidine, pyrrolidine, or piperazine.

For example, $X^1$ is $C_{3-6}$cycloalkyl.

For example, $X^1$ is $OR^a$ or $C(=O)C_{1-6}$alkyl.

For example, $X^1$ is $C_{1-3}$alkyl.

For example, $X^1$ is $OCF_3$, O $C_{1-3}$alkyl, $NH_2$, CN, OH or halo.

For example, $X^1$ is $C_{0-1}$alkylene-$C(=NR^c)NR^cR^d$.

For example, $X^1$ is $C_{0-1}$alkylene-$NR^cC(=NR^c)NR^cR^d$.

In one example, for a compound of Formula I, or a pharmaceutically acceptable salt, pharmaceutically acceptable solvate or pharmaceutically acceptable hydrate thereof:

$R^1$ is $Q^1$-$T^1$-$(X^1)_n$;

$Q^1$ is a bond, $-CH_2-$, or $-CH_2CH_2-$;

$T^1$ is $C_{6-10}$aryl, 3- to 12-membered heterocycloalkyl, 5- to 10-membered heteroaryl, $-C(=O)-C_{0-3}$alkylene-3- to 12-membered heterocycloalkyl, $-NR^aR^b$, $-NR^aC(=O)R^a$, $-C(=O)NR^aS(=O)_2R^a$, or $-C(=O)NR^aR^b$;

each $X^1$ independently is halo, cyano, oxo, $C_{0-3}$alkylene-$OR^c$, $C_{0-3}$alkylene-$C(=O)OR^c$, $C_{0-3}$alkylene-$NR^cR^d$, $C_{0-3}$alkylene-$N^+R^cR^dR^{d'}$, $C_{0-3}$alkylene-$S(=O)_mR^c$, $C_{0-3}$alkylene-$NR^cC(=O)R^c$, $C_{0-3}$alkylene-$OC(=O)NR^cR^d$, $C_{0-3}$alkylene-$C(=O)NR^cR^d$, $C_{0-3}$alkylene-$C(=NR^c)NR^cR^d$, $C_{0-3}$alkylene-$NR^cC(=NR^c)NR^cR^d$, or $R^{S1}$, in which $R^{S2}$ is $C_{1-6}$alkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, and each $R^{S1}$ is optionally substituted with one or more substituents independently selected from the group consisting of halo, cyano, nitro, oxo, $C_{1-6}$alkyl, $C_{1-6}$haloalkyl, $C_{0-3}$alkylene-$NR^eR^f$, $C_{0-3}$alkylene-$OR^e$, $C_{0-3}$alkylene-$NR^eC(=O)R^e$, $C_{0-3}$alkylene-$C(=O)OR^e$, $C_{0-3}$alkylene-$C(=O)R^e$, $C_{0-3}$alkylene-$S(=O)_mR^e$, $C_{0-3}$alkylene-$NR^eS(=O)_2R^e$, and $R^{S2}$, in which $R^{S2}$ is $C_{0-3}$alkylene-$C_{6-10}$aryl or $C_{0-3}$alkylene-3- to 12-membered heterocycloalkyl, and each $R^{S2}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, $-OR^w$, and $-NR^wR^x$;

each of $R^a$ and $R^b$, independently, is H or $R^{S5}$, in which $R^{S5}$ is $C_{1-6}$alkyl, $C_{0-3}$alkylene-$C_{3-8}$cycloalkyl, $C_{0-3}$alkylene- $C_{6-10}$aryl, $C_{0-3}$alkylene-3 to 12-membered heterocycloalkyl, or $C_{0-3}$alkylene-5- to 10-membered heteroaryl, and $R^{s5}$ is optionally substituted with one or more substituents independently selected from the group consisting of halo, cyano, oxo, $C_{1-6}$haloalkyl, $C_{0-3}$alkylene-$OR^{c2}$, $C_{0-3}$alkylene-$C(=O)R^{c2}$, $C_{0-3}$alkylene-$C(=O)OR^{c2}$, $C_{0-3}$alkylene-$S(=O)_mR^{c2}$, $C_{0-3}$alkylene-$NR^{c2}R^{d2}$, $C_{0-3}$alkylene-$NR^2C(=O)R^{c2}$, $C_{0-3}$alkylene-$NR^2C(=O)OR^{c2}$, $C_{0-3}$alkylene-$NR^{c2}S(=O)_2R^{c2}$, $C_{0-3}$alkylene-$N(S(=O)_2R^2)_2$, and $R^{s6}$, in which $R^{s6}$ is $C_{1-6}$alkyl, $C_{0-3}$alkylene-$C_{3-8}$cycloalkyl, or $C_{0-3}$alkylene-3- to 12-membered heterocycloalkyl, and each $R^{s6}$ is optionally substituted with one or more substituents independently selected from the group consisting of $C_{0-3}$alkylene-$C_{3-8}$cycloalkyl $C_{0-3}$alkylene-$NR^{e2}R^{f2}$, $C_{0-3}$alkylene-$OR^{e2}$;

$R^2$ is $Q^2$-$T^2$-$(X^2)_p$;

$Q^2$ is a bond, —$CH_2$—, or —$CH_2CH_2$—;

$T^2$ is H, halo, cyano, $C_{1-6}$alkyl, $C_{3-8}$cycloalkyl, 3- to 12-membered heterocycloalkyl, 5- to 10-membered heteroaryl, $C(=O)$— 3 to 12-membered heterocycloalkyl, —$OR^z$, —$S(=O)_mR^k$, —$P(=O)R^{kk}R^{mm}$, —$NR^kR^m$, —$C(=O)OR^k$ or —$C(=O)NR^kR^m$;

each $X^2$ independently is halo, cyano, oxo, $C_{0-3}$alkylene-$OR^n$, $C_{0-3}$alkylene-$C(=O)NR^nR^o$, $C_{0-3}$alkylene-$C(=O)OR^n$ or $R^{s3}$, in which $R^{s3}$ is $C_{1-6}$alkyl optionally substituted with $C_{0-3}$alkylene-$OR^p$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{0-3}$alkylene-$C_{3-8}$cycloalkyl, $C_{0-3}$alkylene-3 to 12-membered heterocycloalkyl, or $C_{0-3}$alkylene-5 to 10-membered heteroaryl:

and each $R^z$ is optionally substituted with one or more substituents independently selected from the group consisting of halo, $C_{0-3}$alkylene-$NR^{n2}R^{o2}$, $C_{0-3}$alkylene-$OR^{n2}$, $C_{0-3}$alkylene-$C(=O)OR^{n2}$, $C_{0-3}$alkylene-$C(=O)NR^{n2}R^{o2}$, and $R^{s11}$, in which $R^{s11}$ is $C_{0-3}$alkylene-3 to 12-membered heterocycloalkyl, and each $R^{s11}$ is optionally substituted with one or more substituents independently selected from the group consisting of halo, oxo, cyano, $C_{0-3}$alkylene-$OR^{p2}$, $C_{0-3}$alkylene-$S(=O)_mR^{p2}$, $C_{0-3}$alkylene-$NR^2R^{g2}$, $C_{0-3}$alkylene-$C(=O)NR^{p2}R^{g2}$, $C_{0-3}$alkylene-$C_{0-3}$alkylene-$C(=O)OR^{p2}$, $C_{1-6}$alkyl, $C_{2-6}$alkenyl, $C_{2-6}$alkynyl, and $C_{1-6}$haloalkyl;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —$C(=O)R^r$, —$S(=O)_mR^r$, —$NR^rR^t$, or —$C(=O)OR^r$, wherein $C_{1-3}$alkyl, $C_{2-3}$alkenyl and $C_{2-3}$alkynyl are optionally substituted with $C_{3-6}$cycloalkyl;

$R^4$ is $C_{1-3}$alkyl, $C_{1-3}$haloalkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, wherein $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5 to 10-membered heteroaryl are optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$;

each of $R^c$, $R^{c2}$, $R^d$, $R^{d'}$, and $R^{d2}$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each of $R^e$, $R^{e2}$, $R^f$, and $R^2$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5- to 10-membered heteroaryl;

each of $R^n$, $R^{n2}$, $R^o$, and $R^{o2}$, independently, is H or $R^{s13}$, in which $R^{s13}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl; and each $R^{s13}$ is optionally substituted with one or more substituents independently selected from the group consisting of halo, oxo, cyano, $C_{0-3}$alkylene-$OR^{p3}$, $C_{0-3}$alkylene-$S(=O)_mR^{p3}$, $C_{0-3}$alkylene-$NR^3R^{q3}$, $C_{0-3}$alkylene-$C(=O)NR^{p3}R^{q3}$, $C_{0-3}$alkylene-$C(=O)OR^3$, $C_{1-6}$alkyl, $C_{2-6}$alkenyl, $C_{2-6}$alkynyl, $C_{1-6}$haloalkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, and $C_{0-3}$alkylene-5- to 10-membered heteroaryl;

each of $R^p$, $R^{p2}$, $R^{p3}$, $R^{q2}$, and $R^{q3}$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each of $R^r$, and $R^t$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^w$, $R^{w5}$, $R^x$, and $R^{x5}$, independently, is H, $C_{1-6}$alkyl, $C_{2-6}$alkenyl, $C_{2-6}$alkynyl or $C_{1-6}$haloalkyl;

each of n and p independently is 0, 1, 2, 3, 4, or 5, wherein when $T^2$ is H, p is 0; and m is 0, 1, or 2.

In one example, for a compound of Formula I, or a pharmaceutically acceptable salt, pharmaceutically acceptable solvate or pharmaceutically acceptable hydrate thereof:

$R^1$ is —$(CH_2)_{0-1}$—$C(=O)NR^aR^b$; —$CH_2CH_2$—$NR^aR^b$; —$CH_2CH_2$—$NR^aC(=O)R^a$; —$C(=O)NR^aS(=O)_2R^a$; —$(CH_2)_{0-1}$—$C_{6-10}$aryl; —$(CH_2)_{0-1}$-5- to 6-membered monocyclic heteroaryl; —$(CH_2)_{0-1}$-9- to 10-membered bicyclic heteroaryl; a 4- to 6-membered monocyclic heterocycloalkyl; a 9- to 10-membered bicyclic heterocycloalkyl; —$C(=O)$-4- to 6-membered monocyclic heterocycloalkyl; —$C(=O)$-9- to 10-membered bicyclic heterocycloalkyl; wherein the aryl, 5heteroaryl, and heterocycloalkyl rings are optionally independently substituted with 1, 2, 3, 4, or 5 $X^1$;

each $X^1$ independently is halo; cyano; oxo; $C_{1-6}$alkyl optionally substituted with one or more substituents independently selected from the group consisting of halo, $C_{0-3}$alkylene-$NR^eR^f$, $C_{0-3}$alkylene-$OR^e$, $C_{0-3}$alkylene-$C(=O)OR^e$, $C_{0-3}$alkylene-$C_{3-6}$cycloalkyl, $C_{0-3}$alkylene-$C_{6-10}$aryl, and $C_{0-3}$alkylene-4 to 6-membered heterocycloalkyl, wherein heterocycloalkyl is optionally independently substituted with one or more $C_{1-6}$alkyl; $C_{0-3}$alkylene-$C_{3-6}$cycloalkyl optionally substituted with one or more substituents independently selected from the group consisting of $C_{1-6}$alkyl, $C_{1-6}$haloalkyl, $C_{0-3}$alkylene-$NR^eR^f$, and $C_{0-3}$alkylene-$OR^e$; $C_{0-3}$alkylene-$C_{6-10}$aryl, wherein $C_{6-10}$aryl is optionally substituted with one or more substituents selected from the group consisting of halo, cyano, nitro, $C_{1-6}$alkyl, $C_{1-6}$haloalkyl, $C_{0-3}$alkylene-$NR^eR^f$, $C_{0-3}$alkylene-$OR^e$, $C_{0-3}$alkylene-$C(=O)OR^e$, $C_{0-3}$alkylene-$C(=O)R^e$, $C_{0-3}$alkylene-$S(=O)_mR^e$, and $C_{0-3}$alkylene-$NR^eS(=O)_2R^e$; $C_{0-3}$alkylene-4- to 6-membered monocyclic heterocycloalkyl or 9- or 10-membered bicyclic heterocycloalkyl, wherein heterocycloalkyl is optionally substituted with one or more substituents independently selected from the group consisting of oxo, $C_{0-3}$alkylene-$NR^eR^f$, and $C_{0-3}$alkylene-$OR^e$; $C_{0-3}$alkylene-5- or 6-membered monocyclic heteroaryl or 9- or 10-membered bicyclic heteroaryl, wherein heteroaryl is independently optionally substituted with one or more $C_{0-3}$alkylene-$OR^e$; $C_{0-3}$alkylene-OR; $C_{0-3}$alkylene-C(=O)OR; $C_{0-3}$alkylene-$NR^cR^d$; $C_{0-3}$alkylene-$N^+R^cR^dR^{d'}$; $C_{0-3}$alkylene-S(=O)$_m$$R^c$; $C_{0-3}$alkylene-$NR^cC(=O)R^c$; $C_{0-3}$alkylene-OC(=O)$NR^cR^d$; $C_{1-3}$alkylene-C(=O)$NR^cR^d$; $C_{0-3}$alkylene-C(=NR)$NR^cR^d$; or $C_{0-3}$alkylene-$NR^cC(=NR)NR^cR^d$;

each of $R^a$ and $R^b$, independently, is H or $R^{S5}$, in which $R^{S5}$ is $C_{1-6}$alkyl, $C_{0-3}$alkylene-$C_{3-6}$cycloalkyl, $C_{0-3}$alkylene-$C_{6-10}$aryl, $C_{0-3}$alkylene-4- to 6-membered monocyclic heterocycloalkyl, $C_{0-3}$alkylene-9- or 10-membered bicyclic hetercycloalkyl, $C_{0-3}$alkylene-5- or 6-membered monocyclic heteroaryl, or $C_{0-3}$alkylene-9- or 10-membered bicyclic heteroaryl;

and $R^{S5}$ is optionally substituted with one or more substituents selected from the group consisting of halo, cyano, oxo, $C_{1-6}$haloalkyl, $C_{0-3}$alkylene-$OR^{c2}$, $C_{0-3}$alkylene-C(=O)$R^{c2}$, $C_{0-3}$alkylene-C(=O)$OR^{c2}$, $C_{0-3}$alkylene-S(=O)$_m$ $R^{c2}$, $C_{0-3}$alkylene-$NR^{c2}R^{d2}$, $C_{0-3}$alkylene-$NR^{c2}C(=O)R^{c2}$, $C_{0-3}$alkylene-$NR^{c2}C(=O)OR^{c2}$, $C_{0-3}$alkylene-$NR^{c2}S(=O)_2R^{c2}$, $C_{0-3}$alkylene-$N(S(=O)_2R^2)_2$, and $R^{S6}$, in which $R^{S6}$ is $C_{1-6}$alkyl, $C_{0-3}$alkylene-$C_{3-6}$cycloalkyl, or $C_{0-3}$alkylene-4- to 6-membered monocyclic heterocycloalkyl;

and each $R^{S6}$ is optionally substituted with one or more $C_{0-3}$alkylene-$C_{3-6}$cycloalkyl, $C_{0-3}$alkylene-$NR^{e2}R^{f2}$, $C_{0-3}$alkylene-$OR^{e2}$;

$R^2$ is $Q^2$-$T^2$-$(X^2)_p$;

$Q^2$ is a bond, —$CH_2$—, or —$CH_2CH_2$—;

$T^2$ is H, halo, cyano, $C_{1-6}$alkyl, $C_{3-6}$cycloalkyl, 4- to 6-membered monocyclic heterocycloalkyl, 9- or 10-membered bicyclic heterocycloalkyl, 5- or 6-membered monocyclic heteroaryl, 9- or 10-membered bicyclic heteroaryl, C(=O)— 4- to 6-membered monocyclic heterocycloalkyl, —$OR^z$, —S(=O)$_mR^k$, —P(=O)$R^kR^m$, —$NR^kR^m$, —C(=O)$OR^k$ or —C(=O)$NR^kR^m$;

each $X^2$ independently is halo, cyano, oxo, $C_{0-3}$alkylene-$OR^n$, $C_{0-3}$alkylene-C(=O)$NR^nR^o$, $C_{0-3}$alkylene-C(=O)$OR^n$ or $C_{1-6}$alkyl, wherein $C_{1-6}$alkyl is optionally substituted with one $C_{0-3}$alkylene-$OR^p$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{0-3}$alkylene-$C_{3-6}$cycloalkyl, $C_{0-3}$alkylene-4- to 6-membered monocyclic heterocycloalkyl, $C_{0-3}$alkylene-9- or 10-membered bicyclic heterocycloalkyl, $C_{0-3}$alkylene-5 or 6-membered monocyclic heteroaryl, or $C_{0-3}$alkylene-9- or 10-membered bicyclic heteroaryl:

and each $R^z$ is optionally substituted with one or more substituents selected from the group consisting of halo, $C_{1-6}$alkyl, $C_{0-3}$alkylene-$NR^{n2}R^{o2}$, $C_{0-3}$alkylene-$OR^{n2}$, $C_{0-3}$alkylene-C(=O)$OR^{n2}$, $C_{0-3}$alkylene-C(=O)$NR^{n2}R^{o2}$, and $R^{S11}$, in which $R^{S11}$ is $C_{0-3}$alkylene-4- to 6-membered monocyclic heterocycloalkyl, $C_{0-3}$alkylene-9- or 10-membered bicyclic heterocycloalkyl, $C_{0-3}$alkylene-5- or 6-membered monocyclic heteroaryl, or $C_{0-3}$alkylene-9- or 10-membered bicyclic heteroaryl;

and each $R^{S11}$ is optionally substituted with one or more substituents independently selected from the group consisting of halo, oxo, cyano, $C_{0-3}$alkylene-$OR^2$, $C_{0-3}$alkylene-S(=O)$_mR^{p2}$, $C_{0-3}$alkylene-$NR^{p2}R^{g2}$, $C_{0-3}$alkylene-C(=O)$NR^{p2}R^{g2}$, $C_{0-3}$alkylene-$C_{0-3}$alkylene-C(=O)$OR^{p2}$, $C_{1-6}$alkyl, $C_{2-6}$alkenyl, $C_{2-6}$alkynyl, and $C_{1-6}$haloalkyl;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —C(=O)$R^r$, —S(=O)$_mR^r$, $NR^rR^t$, or —C(=O)$OR^r$, wherein $C_{1-3}$alkyl, $C_{2-3}$alkenyl and $C_{2-3}$alkynyl are optionally substituted with $C_{3-6}$cycloalkyl;

$R^4$ is $C_{1-3}$alkyl, $C_{1-3}$haloalkyl, $C_{3-6}$cycloalkyl, phenyl, or 5- or 6-membered monocyclic heteroaryl, wherein cycloalkyl, phenyl and heteroaryl are optionally substituted with one or more substituents independently selected from the group consisting of halo, cyano, $C_{1-3}$alkyl, $C_{1-3}$haloalkyl, $C_{2-3}$alkenyl, $C_{2-3}$alkynyl, —$OR^{w5}$, and —$NR^{w5}R^{x5}$;

each of $R^r$, and $R^t$, independently, is H, $C_{1-3}$alkyl, $C_{1-3}$haloalkyl, $C_{2-3}$alkenyl, $C_{2-3}$alkynyl, $C_{3-6}$cycloalkyl, phenyl, 4- to 6-membered monocyclic heterocycloalkyl, or 5- or 6-membered monocyclic heteroaryl;

each of $R^c$, $R^{c2}$, $R^d$, $R^{d'}$, $R^{d2}$, $R^e$, $R^{e2}$, $R^f$, $R^{f2}$, $R^n$, $R^{n2}$, $R^o$, $R^{o2}$, $R^p$, $R^{p2}$, and $R^{q2}$, independently, is H, $C_{1-3}$alkyl, $C_{1-3}$haloalkyl, $C_{3-6}$cycloalkyl, phenyl, 4- to 6-membered monocyclic heterocycloalkyl, or 5- or 6-membered monocyclic heteroaryl;

each $R^w$, $R^{w5}$, $R^x$, and $R^{x5}$, independently, is H, $C_{1-3}$alkyl, or $C_{1-3}$haloalkyl;

p is 0, 1, 2, 3, 4, or 5; and m is 0, 1, or 2.

In another aspect, the present invention provides the compounds of Formula (III):

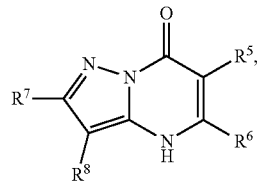

(III)

or a pharmaceutically acceptable salt, pharmaceutically acceptable solvate or pharmaceutically acceptable hydrate thereof. In this formula:

$R^5$ is selected from the group consisting of —C(=O)$NR^9R^{10}$; —$CH_2C(=O)NR^{11}R^{12}$; —$CH_2CH_2NR^{13}R^{14}$; —$CH_2$-phenyl; —$CH_2$-5-membered monocyclic heteroaryl optionally substituted with one $C_{1-3}$alkyl, monocyclic $C_{5-6}$cycloalkyl, or phenyl, wherein phenyl is optionally substituted with one —$OC_{1-3}$alkyl; phenyl optionally substituted with one halo or $C_{1-3}$alkyl; a 5- or 6-membered monocyclic heterocycloalkyl optionally substituted with 1, 2, or 3 $R^{15}$; a 5- or 6-membered monocylic heteroaryl optionally substituted with 1, 2, or 3 $R^{16}$; and 9- or 10-membered bicyclic heteroaryl optionally substituted with 1, 2, 3, or 4 $R^{17}$;

$R^9$ and $R^{10}$ are independently selected from the group consisting of H; $C_{1-3}$alkyl optionally substituted with 1 or 2 substituents independently selected from the group consisting of —OH and —$OC_{1-3}$alkyl; —$CH_2$phenyl; —S(=O)$_2$$R^{18}$; $C_{5-6}$cycloalkyl optionally substituted with one —$NH_2$, oxo, —OH, or —$OC_{1-3}$alkyl; phenyl optionally substituted with 1, 2, or 3 $R^{19}$; a 5- or 6-membered monocyclic heterocycloalkyl optionally substituted with one —$C_{1-3}$alkyl, —C(=O)$C_{1-3}$alkyl, or —C(=O)$OC_{1-6}$alkyl; a 5- or 6-membered monocyclic heteroaryl optionally substituted with 1, 2, or 3 $R^{20}$; and a 9- or 10-membered bicyclic heteroaryl optionally substituted with 1 or 2 halo; or $R^9$ and $R^{10}$ combine with the nitrogen to which they are bound to form an N-linked 5- or 6-membered monocyclic heterocycloalkyl optionally substituted with one phenyl;

$R^{11}$ and $R^{12}$ are independently selected from the group consisting of H; $C_{1-3}$alkyl optionally substituted with one —OH or —OC$_{1-3}$alkyl; phenyl optionally substituted with one —NH$_2$ or —OC$_{1-3}$alkyl; and a 5- or 6-membered monocyclic heteroaryl; or R$^{11}$ and R$^{12}$ combine with the nitrogen to which they are bound to form an N-linked 5- or 6-membered monocyclic heterocycloalkyl optionally substituted with one C$_{1-3}$alkyl, phenyl or —CH$_2$-phenyl, wherein the phenyl ring of phenyl or —CH$_2$-phenyl is optionally substituted with one C$_{1-3}$alkyl;

R$^{13}$ and R$^{14}$ are independently selected from the group consisting of H; —C(=O)C$_{1-3}$alkyl; —C(=O)phenyl; and phenyl optionally substituted with one —OC$_{1-3}$alkyl;

each R$^{15}$ is independently selected from the group consisting of oxo; —C(=O)OH; —C(=O)OC$_{1-3}$alkyl; and C$_{1-3}$alkyl optionally substituted with one —OH or —OC$_{1-3}$alkyl;

each R$^{16}$ is independently selected from the group consisting of —CN; —C(=O)OH; —C(=O)OC$_{1-3}$alkyl; —C(=O)NH$_2$; —C(=O)NHC$_{1-3}$alkyl; —C(=O)N(C$_{1-3}$alkyl)$_2$; —C(=NH)NH$_2$; —N HC(=NH)NH$_2$; —NH$_2$; —NHC$_{1-3}$alkyl; —N(C$_{1-3}$alkyl)$_2$; —NHC$_{3-6}$cycoalkyl; —N(C$_{1-3}$alkyl)C$_{3-6}$cycloalkyl; C$_{1-3}$alkyl optionally substituted with one —OH, —OC$_{1-3}$alkyl, or 5- or 6-membered monocyclic heterocycloalkyl, wherein the monocyclic heterocycloalkyl is optionally substituted with —C$_{1-3}$alkyl; C$_{1-3}$haloalkyl optionally substituted with 1 or 2 substituents independently selected from the group consisting of —OH and phenyl; —C$_{3-6}$cycloalkyl optionally substituted with one —NH$_2$, C$_{1-3}$alkyl, C$_{1-3}$haloalkyl, or —OC$_{1-3}$alkyl; phenyl optionally substituted with one —OH, —OC$_{1-3}$alkyl, —NO$_2$, —NH$_2$, —NHC$_{1-3}$alkyl, or —N(C$_{1-3}$alkyl)$_2$; 5- or 6-membered monocyclic heterocycloalkyl optionally substituted with 1 or 2 substituents independently selected from the group consisting of oxo, —OH, —NH$_2$, —OC$_{1-3}$alkyl, —C(=O)C$_{1-3}$alkyl, —S(=O)$_2$C$_{1-3}$alkyl, —C(=O)OC$_{1-6}$alkyl, —C(=O)OCH$_2$phenyl, and C$_{1-3}$alkyl, wherein C$_{1-3}$alkyl is optionally substituted with one —NH$_2$, —NHS(=O)$_2$C$_{1-3}$alkyl, —OH, or —OC$_{1-3}$alkyl; and 5- or 6-membered monocyclic heteroaryl optionally substituted with one —OH or —OC$_{1-3}$alkyl;

each R$^{17}$ is independently selected from the group consisting of oxo; halo; —OH; —CN; —NH$_2$; —NHC$_{1-3}$alkyl; —N(C$_{1-3}$alkyl)$_2$; —N+(C$_{1-3}$alkyl)$_3$; —NHC(=O)C$_{1-3}$alkyl; —C(=O)C$_{1-3}$alkyl; —S(=O)$_m$C$_{1-3}$alkyl; —C(=O)OH; —C(=O)OC$_{1-6}$alkyl; —C(=O)NH$_2$; —C(=O)NHC$_{1-3}$alkyl; —C(=O)N(C$_{1-3}$alkyl)$_2$; —OC(=O)NH$_2$; —OC(=O)NHC$_{1-3}$alkyl; —OC(=O)N(C$_{1-3}$alkyl)$_2$; —C(=NH)NH$_2$; —C(=NH)NHC$_{1-3}$alkyl; —C(=NH)N(C$_{1-3}$alkyl)$_2$; —OC$_{1-3}$haloalkyl; C$_{1-3}$haloalkyl; monocyclic C$_{3-6}$cycloalkyl; C$_{1-3}$alkyl optionally substituted with one monocyclic C$_{3-6}$cycloalkyl, —OH, —OC$_{1-3}$alkyl, —C(=O)OH, —C(=O)OC$_{1-3}$alkyl, —NH$_2$, —NHC$_{1-3}$alkyl, or —N(C$_{1-3}$alkyl)$_2$; —OC$_{1-3}$alkyl optionally substituted with one monocyclic C$_{3-6}$cycloalkyl, phenyl, —OH, —OC$_{1-3}$alkyl, —C(=O)OH, —C(=O)OC$_{1-3}$alkyl, —C(=O)NH$_2$, —C(=O)NHC$_{1-3}$alkyl, —C(=O)N(C$_{1-3}$alkyl)$_2$, —NH$_2$, —NHC$_{1-3}$alkyl, —N(C$_{1-3}$alkyl)$_2$, —NHC(=O)C$_{1-3}$alkyl, or —NHS(=O)$_2$C$_{1-3}$alkyl; and phenyl optionally substituted with one halo, —CN, C$_{1-3}$alkyl, C$_{1-3}$haloalkyl, —OC$_{1-3}$ alkyl, —NH$_2$, —NHC$_{1-3}$alkyl or —N(C$_{1-3}$alkyl)$_2$;

R$^{18}$ is selected from the group consisting of C$_{1-3}$alkyl; monocyclic C$_{3-6}$cycloalkyl; a 5- or 6-membered monocyclic heteroaryl; phenyl; and —CH$_2$phenyl; wherein the phenyl ring of phenyl or —CH$_2$phenyl is optionally substituted with one halo, —CN, or —OC$_{1-3}$alkyl;

each R$^{19}$ is independently selected from the group consisting of halo; —CN; —NH$_2$; —NHC$_{1-3}$alkyl; —N(C$_{1-3}$alkyl)$_2$; —NHC(=O)C$_{1-3}$alkyl; —NHS(=O)$_2$C$_{1-3}$alkyl; —N(S(=O)$_2$C$_{1-3}$alkyl)$_2$; —NHS(=O)$_2$C$_{3-6}$cycloalkyl; —NHS(=O)$_2$phenyl; —NHC(=O)OH; —NHC(=O)OC$_{1-3}$ alkyl; —S(=O)$_2$C$_{1-3}$alkyl; —OC$_{1-3}$alkyl optionally substituted with one phenyl; C$_{1-3}$haloalkyl; —OC$_{1-3}$haloalkyl; monocyclic C$_{3-6}$cycloalkyl; a 5- or 6-membered monocyclic heterocycloalkyl; and C$_{1-3}$alkyl optionally substituted with one monocyclic C$_{3-6}$cycloalkyl, —OH, —OC$_{1-3}$ alkyl, —NH$_2$, —NHC$_{1-3}$alkyl, or —N(C$_{1-3}$alkyl)$_2$;

each R$^{20}$ is independently selected from the group consisting of —CN; —OC$_{1-3}$alkyl; —S(=O)$_2$C$_{1-3}$alkyl; C$_{1-3}$haloalkyl; and C$_{1-3}$alkyl optionally substituted with one —OH or —OC$_{1-3}$alkyl; and monocyclic C$_{3-6}$cycloalkyl;

R$^6$ is selected from the group consisting of H; halo; —CN; —NH$_2$; —C(=O)OH; —C(=O)OC$_{1-3}$alkyl; —C(=O)C$_{1-3}$alkyl; —S(=O)$_m$C$_{1-3}$alkyl; —P(=O)(C$_{1-3}$alkyl)$_2$; —C(=O)NR$^{21}$R$^{22}$; C$_{1-3}$haloalkyl; —OC$_{1-3}$alkyl optionally substituted with one —OH, —OC$_{1-3}$alkyl, —NH$_2$, —NHC$_{1-3}$ alkyl, or —N(C$_{1-3}$alkyl)$_2$; C$_{1-3}$alkyl optionally substituted with one —NH$_2$, —NHC$_{1-3}$alkyl, —N(C$_{1-3}$alkyl)$_2$, —C(=O)OH, —C(=O)OC$_{1-3}$alkyl, —S(=O)$_m$C$_{1-3}$ alkyl, —C(=O)C$_{1-3}$alkyl, —OR$^{23}$, or 5- or 6-membered monocyclic heteroaryl, wherein monocyclic heteroaryl is optionally substituted with 1 or 2 C$_{1-3}$alkyl; monocyclic C$_{3-6}$cycloalkyl optionally substituted with one —C(=O)OH, —C(=O)OC$_{1-3}$alkyl or C$_{1-3}$alkyl, wherein C$_{1-3}$alkyl is optionally substituted with one —OH or —OC$_{1-3}$ alkyl; a 5- or 6-membered monocyclic heterocycloalkyl optionally substituted with one —C(=O)OH, or —C(=O)OC$_{1-3}$alkyl; and a 5- or 6-membered heteroaryl optionally substituted with 1 or 2 C$_{1-3}$alkyl;

R$^{21}$ and R$^{22}$ are independently selected from the group consisting of H; C$_{1-6}$alkyl optionally substituted with one —OH, —OC$_{1-3}$alkyl, —C(=O)OH, —C(=O)OC$_{1-3}$alkyl, —NH$_2$, —NHC$_{1-3}$alkyl, —N(C$_{1-3}$alkyl)$_2$, or 5- or 6-membered monocyclic heteroaryl; C$_{1-3}$haloalkyl optionally substituted with one —OH or —OC$_{1-3}$alkyl; a 5- or 6-membered monocyclic heteroaryl optionally substituted with 1 or 2 C$_{1-3}$alkyl; and a 4- to 6-membered monocyclic heterocycloalkyl; or R$^{21}$ and R$^{22}$ combine with the nitrogen to which they are bound to form an N-linked 5- or 6-membered monocyclic heterocycloalkyl optionally substituted with one —C(=O)OH, —C(=O)OC$_{1-3}$alkyl, or C$_{1-3}$alkyl, wherein C$_{1-3}$alkyl is optionally substituted with one —OH or —OC$_{1-3}$alkyl;

R$^{23}$ is selected from the group consisting of H; C$_{1-3}$haloalkyl; C$_{1-3}$alkyl optionally substituted with one —OH, —OC$_{1-3}$alkyl, —C(=O)OH, —C(=O)OC$_{1-3}$alkyl, —C(=O)NH$_2$, —C(=O)NHC$_{1-3}$alkyl, —C(=O)N(C$_{1-3}$alkyl)$_2$, phenyl, 5- or 6-membered monocyclic heteroaryl, or 5- or 6-membered monocyclic heterocycloalkyl, wherein monocyclic heterocycloalkyl is optionally substituted with 1 or 2 oxo or C$_{1-3}$alkyl; a 4-, 5-, or 6-membered monocyclic heterocycloalkyl optionally substituted with 1 or 2 substituents independently selected from the group consisting of oxo and C$_{1-3}$alkyl; and a 5- or 6-membered monocyclic heteroaryl;

R$^7$ is selected from the group consisting of —CN; —OH; —C(=O)OH; —C(=O)OC$_{1-3}$alkyl; —C(=O)C$_{1-3}$alkyl; —S(=O)$_m$C$_{1-3}$alkyl; —NH$_2$; —NHC$_{1-3}$alkyl; —N(C$_{1-3}$alkyl)$_2$; C$_{1-3}$alkyl optionally substituted with one monocyclic C$_{3-6}$cycloalkyl; C$_{1-3}$haloalkyl; C$_{2-3}$alkenyl optionally substituted with one monocyclic C$_{3-6}$cycloalkyl; C$_{2-3}$alkyny optionally substituted with one monocyclic C$_{3-6}$cycloalkyl; monocyclic C$_{3-6}$cycloalkyl; —O-5- or 6-membered monocyclic heterocycloalkyl; and —OC$_{1-3}$alkyl optionally substituted with one —OH, —OC$_{1-3}$alkyl, —C(=O)OH, or —C(=O)OC$_{1-3}$alkyl;

R$^8$ is selected from the group consisting of C$_{1-3}$alkyl; C$_{1-3}$haloalkyl; monocyclic C$_{3-6}$cycloalkyl; phenyl optionally substituted with 1, 2, or 3 substituents independently selected from the group consisting of —CN, halo, C$_{1-3}$alkyl, C$_{1-3}$haloalkyl, —OC$_{1-3}$alkyl and —OC$_{1-3}$haloalkyl; and pyridinyl optionally substituted with 1, 2, or 3 substituents independently selected from the group consisting of —CN, halo, C$_{1-3}$alkyl, C$_{1-3}$haloalkyl, —OC$_{1-3}$alkyl and —OC$_{1-3}$haloalkyl;

with the proviso that:

a) when R$^5$ is unsubstituted phenyl, R$^6$ is methyl and R$^7$ is methyl, R$^8$ is not ethyl, unsubstituted phenyl, or unsubstituted pyridine;

b) when R$^5$ is unsubstituted cyclohexyl, R$^6$ is methyl and R$^7$ is methyl, R$^8$ is not unsubstituted pyridine;

c) when R$^5$ is unsubstituted cyclopentyl, R$^6$ is methyl and R$^7$ is methyl, R$^8$ is not ethyl or unsubstituted pyridine, d) when R$^6$ is methyl, R$^7$ is methyl and R$^8$ is 3,4-di-ethoxy-phenyl, R$^5$ is not unsubstituted 1-pyrrolidine, unsubstituted 1-piperidine, 4-methyl-1-piperidine, unsubstituted 2-1,2,3,4-tetrahydro-isoquinoline, or unsubstituted morpholine;

e) when R$^5$ is unsubstituted CH$_2$-phenyl, R$^6$ is methyl and R$^7$ is methyl, R$^8$ is not ethyl, trifluoromethyl, unsubstituted pyridine, unsubstituted phenyl, phenyl mono-substituted with 4-F, 4-Cl, 2-methoxy or 4-methoxy, or phenyl disubstituted with 3,4-methoxy;

f) when R$^5$ is unsubstituted CH$_2$-phenyl, R$^6$ is methyl and R$^7$ is trifluoromethyl, R$^8$ is not unsubstituted phenyl or phenyl substituted with 2-Cl or 4-Cl;

g) when R$^6$ is methyl, R$^7$ is methyl and R$^8$ is unsubstituted phenyl, R$^5$ is not CH$_2$CH$_2$C(=O)NH-phenyl wherein the phenyl ring is unsubstituted or is substituted at the 4-position with Cl, methyl or methoxy;

h) when R$^6$ is methyl or ethyl, R$^7$ is methyl and R$^8$ is unsubstituted phenyl, R$^5$ is not substituted pyrazolo[1,5-a]pyrimidin-7-yl;

i) when R$^6$ is H, R$^7$ is isopropyl and R$^8$ is methyl, R$^5$ is not unsubstituted pyrazole; and j) the compound is not wherein R$^5$ is unsubstituted CH$_2$-phenyl, R$^6$ is H, R$^7$ is methyl and R$^8$ is unsubstituted phenyl.

In one embodiment of compounds of Formula (III), R$^5$ is a 9- or 10-membered bicyclic heteroaryl optionally substituted with 1, 2, 3, or 4 R$^{17}$.

In one embodiment, a subset of compounds of Formula (III) includes those of Formula (IIIa):

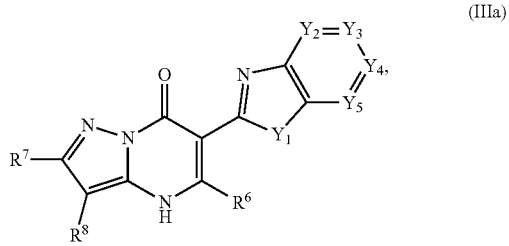

(IIIa)

or a pharmaceutically acceptable salt, pharmaceutically acceptable solvate or pharmaceutically acceptable hydrate thereof, wherein Y$_1$ is —O—, —NH—, —NR$^{24}$—, or —S—, and Y$_2$, Y$_3$, Y$_4$, and Y$_5$ are —N= or —CR$^{25}$=, provided that 0, 1 or 2 of Y$_2$, Y$_3$, Y$_4$, and Y$_5$ are —N=;

wherein R$^{24}$ is selected from the group consisting of C$_{1-3}$haloalkyl; monocyclic C$_{3-6}$cycloalkyl; C$_{1-3}$alkyl optionally substituted with one monocyclic C$_{3-6}$cycloalkyl, —OH, —OC$_{1-3}$alkyl, —C(=O)OH, —C(=O)OC$_{1-3}$alkyl, —NH$_2$, —NHC$_{1-3}$alkyl, or —N(C$_{1-3}$alkyl)$_2$; and phenyl optionally substituted with one halo, —CN, C$_{1-3}$alkyl, C$_{1-3}$haloalkyl, —OC$_{1-3}$alkyl, —NH$_2$, —NHC$_{1-3}$alkyl or —N(C$_{1-3}$alkyl)$_2$; and wherein R$^{25}$ is H or R$^{17}$, wherein R$^{17}$ is as defined for compounds of Formula (III), provided that 0, 1, 2 or 3 of Y$_2$, Y$_3$, Y$_4$, and Y$_5$ are —CR$^{25}$= wherein R$^{25}$ is R$^{17}$; and wherein R$^6$, R$^7$ and R$^8$ are as defined for compounds of Formula (III).

In one embodiment of compounds of Formula (IIIa), R$^6$ is —CN or C$_{1-3}$alkyl optionally substituted with one —NH$_2$, —NHC$_{1-3}$alkyl, —N(C$_{1-3}$alkyl)$_2$, —C(=O)OH, —C(=O)OC$_{1-3}$alkyl, —S(=O)$_m$C$_{1-3}$alkyl, —C(=O)C$_{1-3}$alkyl, —OR$^{23}$, or 5- or 6-membered monocyclic heteroaryl, wherein monocyclic heteroaryl is optionally substituted with 1 or 2 C$_{1-3}$alkyl; and R$^7$ is —CN or —CF$_3$, wherein R$^{23}$ is as defined for compounds of Formula (III).

In another aspect, the present invention provides the compounds of Formula (IV):

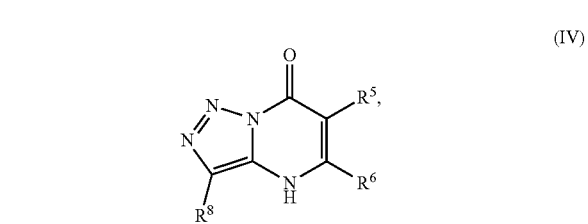

(IV)

or a pharmaceutically acceptable salt, pharmaceutically acceptable solvate or pharmaceutically acceptable hydrate thereof. In this formula R$^5$, R$^6$, and R$^8$ are as defined for compounds of Formula (III), and provided the compound is not wherein R$^5$ is unsubstituted phenyl, R$^6$ is H and R$^8$ is 2-fluoro-phenyl.

In another aspect, conjugates are provided comprising compounds of the invention linked to a suitable ligand. In one embodiment, compounds of Formula I can be modified by replacing or modifying the R$^3$ or R$^4$ substituent, e.g. in compounds of Formula IA, or by replacing or modifying the R$^4$ substituent in compounds of Formula IA', to provide a suitable substituent comprising a reactive group capable of binding to a suitable linker. In some embodiments, the reactive group comprises a suitable hydroxy or amine group (e.g. an R$^3$ or R$^4$ substituent or modification thereof comprising a terminal —OH, —NH$_2$, C(=O)NH$_2$, and the like) that is capable of reacting with a suitable linker. In one embodiment, compounds of Formula I can be modified by replacing or modifying the R$^3$ or R$^4$ substituent, e.g. in compounds of Formula IA, or by replacing or modifying the R$^4$ substituent in compounds of Formula IA', to provide a suitable substituent bound to a linker moiety, wherein said linker moiety comprises a reactive group capable of binding to a suitable ligand. In one embodiment, compounds of Formula I can be modified by replacing or modifying the R$^3$ or R$^4$ substituent, e.g. in compounds of Formula IA, or by replacing or modifying the R$^4$ substituent in compounds of Formula IA', to provide a suitable substituent bound to a linker moiety, wherein said linker moiety is bound to a suitable ligand. In one embodiment, the ligand binds to an E3 ubiquitin ligase. In some embodiments, the E3 ubiquitin ligase is MDM2, cIAP1, CRBN, or VHL. In one embodiment, a modified compound of the invention is a compound of Formula (Va), Formula (Vb), or Formula (Vc):

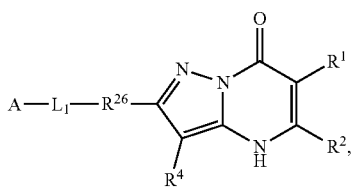

(Va)

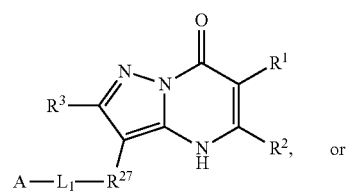

(Vb)

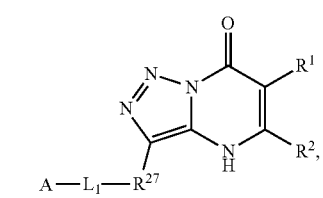

(Vc)

or a pharmaceutically acceptable salt, pharmaceutically acceptable solvate or pharmaceutically acceptable hydrate thereof. In these formulae, A is an E3 ubiquitin ligase ligand; Li is a suitable linker, $R^{26}$ is a suitable $R^3$ or modification or replacement of $R^3$ (as defined in Formula I), and $R^{27}$ is a suitable $R^4$ or modification or replacement of $R^4$ (as defined in Formula I); and $R^1$, $R^2$, $R^3$, and $R^4$ are as defined for compounds of Formula (I).

Representative compounds of the present invention include compounds listed in Table 1 (by name in Table 1A and structure in Table 1B).

In reference to the present invention comprising a compound as disclosed herein, the compound includes a compound of Formula I (including IA, IA', Ia, Ia', Ib and Ib'), Formula II (i.e. including IIa, IIa', IIb, IIb', IIc, IIc', IId, IId', IIe, IIe', IIf and IIf'), Formula III (including IIIa) or Formula IV and all embodiments thereof, including any pharmaceutically acceptable salt, pharmaceutically acceptable solvate or pharmaceutically acceptable hydrate thereof.

The present invention provides a pharmaceutical composition comprising a compound as disclosed herein, including any pharmaceutically acceptable salt, pharmaceutically acceptable solvate or pharmaceutically acceptable hydrate thereof together with a pharmaceutically acceptable diluent or carrier.

The present provides a kit comprising a compound as disclosed herein, or a pharmaceutically acceptable salt, pharmaceutically acceptable solvate or pharmaceutically acceptable hydrate thereof, including any container, pack, or dispenser together with instructions for administration.

The present invention provides a compound as disclosed herein, including any pharmaceutically acceptable salt, pharmaceutically acceptable solvate or pharmaceutically acceptable hydrate thereof, for use in the treatment of a cGAS/STING pathway-mediated condition.

The present invention provides a method of inhibiting the cGAS/STING pathway in a cell, comprising contacting the cell with one or more compounds or compositions of the present invention.

The present invention provides a method of inhibiting cytokine production in a cell, comprising contacting the cell with one or more compounds or compositions of the present invention, including any pharmaceutically acceptable salt, pharmaceutically acceptable solvate or pharmaceutically acceptable hydrate thereof.

The present invention provides a method of treating a cGAS/STING pathway-mediated condition, comprising administering to a subject in need thereof an effective amount of one or more compounds or compositions of the present invention, including any pharmaceutically acceptable salt, pharmaceutically acceptable solvate or pharmaceutically acceptable hydrate thereof.

For example, the cGAS/STING pathway-mediated condition is an autoimmune, inflammatory, or neurodegenerative condition. For example, wherein the disease is selected from the group consisting of systemic inflammatory response syndrome (SIRS), sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI (STING-associated vasculopathy with onset in infancy), CANDLE (Chronic Atypical Neutrophilic Dermatosis with Lipodystrophy and Elevated Temperature) syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease.

For example, wherein the disease is SIRS, sepsis, septic shock, atherosclerosis, celiac disease, interstitial cystitis, transplant rejection, Aicardi-Goutieres Syndrome, chilblain lupus erythematosus, systemic lupus erythematosus, idiopathic thrombocytopenic purpura, thrombotic thrombocytopenic purpura, autoimmune thrombocytopenia, spondyloenchondrodysplasia, psoriasis, Type 1 diabetes, Type 2 diabetes, or Sjogren's syndrome.

A method of treating an inflammatory disease in a subject, comprising administering to the subject in need thereof a therapeutically effective amount of one or more compounds or compositions of the present invention, including any pharmaceutically acceptable salt, pharmaceutically acceptable solvate or pharmaceutically acceptable hydrate thereof.

For example, wherein the disease is rheumatoid arthritis, juvenile rheumatoid arthritis, inflammatory bowel disease (ulcerative colitis, Crohn's disease), age-related macular degeneration, IgA nephropathy, glomerulonephritis, vasculitis, polymyositis, or Wegener's disease.

Another aspect of the invention provides a method of treating neurodegenerative diseases in a subject, comprising administering to the subject in need thereof a therapeutically effective amount of one or more compounds or compositions of the present invention, including any pharmaceutically acceptable salt, pharmaceutically acceptable solvate or pharmaceutically acceptable hydrate thereof.

For example, wherein the disease is Alzheimer's disease, Parkinson's disease, multiple sclerosis, IgM polyneuropathies, or myasthenia gravis.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DRAWINGS

FIG. 1 depicts the expression of cytokines RANTES or MCP-1 along with cell viability as a function of the $Log_{10}$ concentration (µM) of compound C1089 in Trex1-KO mice bone marrow-derived macrophages.

DETAILED DESCRIPTION

STING (STimulator of INterferon Genes) is a central mediator for a cytosolic pathway that triggers type I interferon, in response to sensing cytosolic double-stranded (ds) DNA from infectious pathogens or aberrant host cells (Danger Associated Molecular Patterns, DAMPS) (Barber, Immunol. Rev 243: 99-108, 2011). Alternatively known as TMEM173, MITA, ERIS, and MPYS, STING was discovered using cDNA expression cloning methods as a MyD88-independent host cell defense factor expressed in macrophages, dendritic cells (DCs) and fibroblasts was found to induce expression of IFN-β and NF-κB dependent pro-inflammatory cytokines in response to sensing cytoplasmic DNA, in response to infection with herpes simplex virus (Ishikawa and Barber, Nature 455: 674-79, 2008).

While STING was discovered as being the critical sensor for inducing the production of IFN-β in response to infection with herpes simplex virus, the mechanism for this sensing function initially remained elusive. This conundrum was solved with the discovery of cyclic GMP-AMP synthase (cGAS), a host cell nucleotidyl transferase that directly binds dsDNA, and in response synthesizes a second messenger, c[G(2',5')pA(3',5')p] (cyclic GMP-AMP or 2'3'-cGAMP), which activates the STING pathway and induces IFN-β expression (Sun et al., Science 339: 786-91, 2013; Wu et al., Science 339: 826-30, 2013). This 2'3'-cGAMP product differed from bacterial-derived canonical cyclic dinucleotides, which were shown to respond differently to single nucleotide polymorphisms in the hSTING gene (Diner et al., Cell Reports 3:1355-1361, 2013; Gao et al., Cell 154:748-762, 2013; Conlon et. al., J Immunol 190: 5216-5225, 2013). It was demonstrated that, while the bacterial-derived cyclic dinucleotides contained bis-3'-5' linkages, cGAS produces a non-canonical, i.e., mixed linkage, CDN represented as c[G(2',5')pA(3',5')p] (Diner et al., Cell Reports 3:1355-1361, 2013; Gao et al., Cell 153:1094-1107, 2013; Ablasser et al., Nature 498: 380-84, 2013; Kranzusch et al., Cell Reports 3: 1362-68, 2013; Zhang et al., Mol. Cell. 51: 226-35, 2013). Cells without a functional cGAS are unable to express IFN-β in response to stimulation with cytosolic DNA.

Given the role of cGAS in the STING pathway and the role of type I interferons in various diseases, treatment with a cGAS/STING pathway inhibitor may have therapeutic benefit in a number of inflammatory, autoimmune, and neurodegenerative diseases, including, but are not limited to, systemic inflammatory response syndrome (SIRS), sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI (STING-associated vasculopathy with onset in infancy), CANDLE (Chronic Atypical Neutrophilic Dermatosis with Lipodystrophy and Elevated Temperature) syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease. See, for example, Krienkamp et al., Cell Reports 22:2006-2015, 2018; Kerur et al., Nature Medicine 24:50-61, 2018; Yang et al., PNAS 114 (23): E4612-E4620, 2017; King et al., Nature Medicine 23:1481-1487, 2017; Bai et al., PNAS 114 (46):12196-12201, 2017; Ahn et al., Cell Reports 21:3873-3884, 2017; Li et al., J. Experimental Medicine, 215(5) 1287, 2018. In some embodiments, compounds of the invention are useful in treating Aicardi-Goutieres Syndrome, X-linked reticulate pigmentary disorder, dermatomyositis, systemic lupus erythematosus, rheumatoid arthritis, multiple sclerosis, or Type I or Type II diabetes.

The present invention provides novel pyrazolopyrimidinone or triazolopyrimidinone compounds, synthetic methods for making the compounds, pharmaceutical compositions containing them and various uses of the compounds. Pyrazolopyrimidinone and Triazolopyrimidinone Compounds The present invention provides the compounds of Formula (I), including Formula (IA) and Formula (IA'):

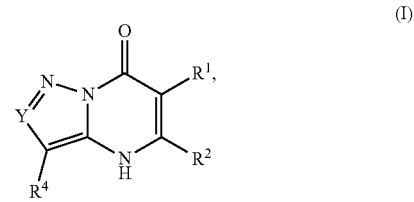

(I)

or a pharmaceutically acceptable salt, pharmaceutically acceptable solvate or pharmaceutically acceptable hydrate thereof. In this formula:

Y is —$CR^3$= or —N=;

$R^1$ is $Q^1$-$T^1$-$(X^1)_n$;

$Q^1$ is a bond or $C_{1-3}$alkylene, wherein the $C_{1-3}$alkylene group is optionally substituted with one or more substituents independently selected from the group consisting of halo, $C_{1-6}$alkyl, $C_{2-6}$alkenyl, $C_{2-6}$alkynyl, cyano, $C_{1-6}$haloalkyl, —$OR^{w2}$, and —$NR^{w2}R^{x2}$;

$T^1$ is $C_{3-8}$cycloalkyl, $C_{6-10}$aryl, 3- to 12-membered heterocycloalkyl, 5- to 10-membered heteroaryl, —C(=O)$C_{0-3}$alkylene-$C_{3-8}$cycloalkyl, —C(=O)—$C_{0-3}$alkylene-$C_{6-10}$aryl, —C(=O)—$C_{0-3}$alkylene-3 to 12-membered heterocycloalkyl, —C(=O)—$C_{0-3}$alkylene-5 to 10-membered heteroaryl, —$NR^aR^b$, —$S(=O)_2R^a$, —$NR^aC(=O)R^a$, —$NR^aC(=O)NR^aR^b$, —$NR^aC(=O)OR^a$, —$NR^aS(=O)_2R^a$, —C(=O)$NR^aS(=O)_2R^a$, —$NR^aS(=O)_2NR^aR^b$, —C(=O)$NR^aR^b$, or —$S(=O)_2NR^aR^b$;

each $X^1$ is independently selected from the group consisting of halo, cyano, oxo, $C_{0-3}$alkylene-C(=O)$R^c$, $C_{0-3}$alkylene-$OR^c$, $C_{0-3}$alkylene-C(=O)$OR^c$, $C_{0-3}$alkylene-OC(=O)$R^c$, $C_{0-3}$alkylene-$NR^cR^d$, $C_{0-3}$alkylene-$N^+R^cR^dR^{d'}$, $C_{0-3}$alkylene-$S(=O)_mR^c$, $C_{0-3}$alkylene-$NR^cC(=O)R^c$, $C_{0-3}$alkylene-$NR^cC(=O)NR^cR^d$, $C_{0-3}$alkylene-OC(=O)$NR^cR^d$, $C_{0-3}$alkylene-$NR^cC(=O)OR^c$, $C_{0-3}$alkylene-$NR^cS(=O)_2R^c$, $C_{0-3}$alkylene-C(=O)$NR^cS(=O)_2R^c$, $C_{0-3}$alkylene-$NR^cS(=O)_2NR^cR^d$, $C_{0-3}$alkylene-C(=O)$NR^cR^d$, $C_{0-3}$alkylene-$S(=O)_2NR^cR^d$, $C_{0-3}$alkylene-C(=$NR^c$)$NR^cR^d$, $C_{0-3}$alkylene-$NR^cC(=NR)NR^cR^d$, and $R^{S1}$, in which $R^{S2}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S1}$ is optionally substituted with one or more substituents independently selected from the group consisting of halo, cyano, nitro, oxo, $C_{1-6}$alkyl, $C_{2-6}$alkenyl, $C_{2-6}$alkynyl, $C_{1-6}$haloalkyl, $C_{0-3}$alkylene-$NR^eR^f$, $C_{0-3}$alkylene-$OR^e$, $C_{0-3}$alkylene-$NR^eC(=O)R^e$, $C_{0-3}$alkylene-$NR^eC(=O)OR^e$, $C_{0-3}$alkylene-$NR^eC(=O)NR^eR^f$, $C_{0-3}$alkylene-OC(=O)$R^e$, $C_{0-3}$alkylene-C(=O)$OR^e$, $C_{0-3}$alkylene-C(=O)$NR^eR^f$, $C_{0-3}$alkylene-C(=O)$R^e$, $C_{0-3}$alkylene-$S(=O)_mR^e$, $C_{0-3}$alkylene-$S(=O)_2NR^eR^f$ $C_{0-3}$alkylene-$NR^eS(=O)_2R^e$, $C_{0-3}$alkylene-C(=O)$NR^eS(=O)_2R^e$, $C_{0-3}$alkylene-$NR^eS(=O)_2NR^eR^f$, and $R^{S2}$, in which $R^{S2}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, and each $R^{S2}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^w$, and —$NR^wR^x$;

$R^2$ is $Q^2$-$T^2$-$(X^2)_p$;

$Q^2$ is a bond or $C_{1-3}$alkylene, wherein the $C_{1-3}$alkylene group is optionally substituted with one or more substituents independently selected from the group consisting of halo, $C_{1-6}$alkyl, $C_{2-6}$alkenyl, $C_{2-6}$alkynyl, cyano, $C_{1-6}$haloalkyl, —$OR^{w3}$, and —$NR^{w3}R^{x3}$;

$T^2$ is H, halo, cyano, $C_{1-6}$alkyl, $C_{2-6}$alkenyl, $C_{2-6}$alkynyl, $C_{3-8}$cycloalkyl, $C_{6-10}$aryl, 3- to 12-membered heterocycloalkyl, 5- to 10-membered heteroaryl, C(=O)—$C_{0-3}$alkylene-$C_{3-8}$cycloalkyl, C(=O)—$C_{0-3}$alkylene-$C_{6-10}$aryl, C(=O)—$C_{0-3}$alkylene-3- to 12-membered heterocycloalkyl, C(=O)—$C_{0-3}$alkylene-5- to 10-membered heteroaryl, —$OR^z$, —$S(=O)_mR^k$, —$P(=O)R^{kk}R^{mm}$, —$NR^kR^m$, —C(=O)$OR^k$, or —C(=O)$NR^kR^m$;

each $X^2$ is independently selected from the group consisting of halo, cyano, oxo, $C_{0-3}$alkylene-$OR^n$, $C_{0-3}$alkylene-$S(=O)_mR^n$, $C_{0-3}$alkylene-$NR^nR^o$, $C_{0-3}$alkylene-C(=O)$NR^nR^o$, $C_{0-3}$alkylene-C(=O)$OR^n$, and $R^{S3}$, in which $R^{S3}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and $R^{S3}$ is optionally substituted with one or more substituents independently selected from the group consisting of halo, oxo, cyano, $C_{0-3}$alkylene-$OR^p$, $C_{0-3}$alkylene-$S(=O)_mR^p$, $C_{0-3}$alkylene-$NR^pR^q$, $C_{0-3}$alkylene-C(=O)$NR^pR^q$, $C_{0-3}$alkylene-$C_{0-3}$alkylene-C(=O)$OR^p$, $C_{1-6}$alkyl, $C_{2-6}$alkenyl, $C_{2-6}$alkynyl, $C_{1-6}$haloalkyl, and $R^{S4}$, in which $R^{S4}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S4}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w4}$, and —$NR^{w4}R^{x4}$;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —C(=O)$R^r$, —$S(=O)_mR^r$, $NR^rR^t$, or —C(=O)$OR^r$, wherein $C_{1-3}$alkyl, $C_{2-3}$alkenyl and $C_{2-3}$alkynyl are optionally substituted with one $C_{3-6}$cycloalkyl;

$R^4$ is $C_{1-6}$alkyl, $C_{1-6}$haloalkyl, $S(=O)_mR^u$, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, wherein $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl are optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, $OR^{w5}$, and $NR^{w5}R^{x5}$;

each of $R^a$ and $R^b$, independently, is H or $R^{S5}$, in which $R^{S5}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and $R^{S5}$ is optionally substituted with one or more substituents independently selected from the group consisting of halo, cyano, oxo, $C_{1-6}$haloalkyl, $C_{0-3}$alkylene-$OR^{c2}$, $C_{0-3}$alkylene-C(=O)$R^{c2}$, $C_{0-3}$alkylene-C(=O)$OR^{c2}$, $C_{0-3}$alkylene-OC(=O)$R^{c2}$, $C_{0-3}$alkylene-C(=O)$NR^{c2}R^{d2}$, $C_{0-3}$alkylene-$S(=O)_mR^2$, $C_{0-3}$alkylene-$S(=O)_2NR^{c2}R^{d2}$, $C_{0-3}$alkylene-$NR^{c2}R^{d2}$, $C_{0-3}$alkylene-$NR^{c2}C(=O)R^{c2}$, $C_{0-3}$alkylene-$NR^{c2}C(=O)OR^{c2}$, $C_{0-3}$alkylene-$NR^{c2}C(=O)NR^{c2}R^{d2}$, $C_{0-3}$alkylene-$NR^{c2}S(=O)_2R^{c2}$, $C_{0-3}$alkylene-C(=O)$NR^{c2}S(=O)_2R^{c2}$, $C_{0-3}$alkylene-$NR^{c2}S(=O)_2NR^{c2}R^{d2}$, $C_{0-3}$alkylene-N$(S(=O)_2R^2)_2$, and $R^{S6}$, in which $R^{S6}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S6}$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{e2}R^{f2}$, $C_{0-3}$alkylene-$OR^{e2}$, $C_{0-3}$alkylene-$NR^{e2}C(=O)R^{e2}$, $C_{0-3}$alkylene-$NR^{e2}C(=O)OR^{e2}$, $C_{0-3}$alkylene-$NR^{e2}C(=O)NR^{e2}R^{f2}$, $C_{0-3}$alkylene-OC(=O)$R^{e2}$, $C_{0-3}$alkylene-C(=O)$OR^{e2}$, $C_{0-3}$alkylene-C(=O)$NR^{e2}R^{f2}$, $C_{0-3}$alkylene-C(=O)$R^{e2}$, $C_{0-3}$alkylene-$S(=O)_mR^{e2}$, $C_{0-3}$alkylene-$S(=O)_2NR^{e2}R^{f2}$, $C_{0-3}$alkylene-$NR^{e2}S(=O)_2R^{e2}$, $C_{0-3}$alkylene-C(=O)$NR^{e2}S(=O)_2R^{e2}$, $C_{0-3}$alkylene-$NR^{e2}S(=O)_2NR^{e2}R^{f2}$, and $R^{S7}$, in which $R^{S7}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S7}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w6}$, and —$NR^{w6}R^{x6}$;

each of $R^c$, $R^{c2}$, $R^d$, $R^{d'}$, and $R^{d2}$, independently, is H or $R^{S8}$, in which $R^{S8}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S8}$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{e3}R^{f3}$, $C_{0-3}$alkylene-$OR^{e3}$, $C_{0-3}$alkylene-C(=O)$OR^{e3}$, $C_{0-3}$alkylene-C(=O)$NR^{e3}R^{f3}$, $C_{0-3}$alkylene-C(=O)$R^{e3}$, $C_{0-3}$alkylene-S(=O)$_m R^{e3}$, $C_{0-3}$alkylene-S(=O)$_2 NR^{e3}R^{f3}$, $C_{0-3}$alkylene-$NR^{f3}$C(=O)$R^{e3}$, $C_{0-3}$alkylene-$NR^{f3}$S(=O)$_m R^{e3}$, and $R^{S9}$, in which $R^{S9}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S9}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w7}$, and —$NR^{w7}R^{x7}$;

each of $R^e$, $R^{e2}$, $R^{e3}$, $R^f$, $R^{f2}$, and $R^{f3}$, independently, is H or $R^{S10}$, in which $R^{S10}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S10}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w8}$, and —$NR^{w2}R^{x8}$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^z$ is optionally substituted with one or more substituents independently selected from the group consisting of halo, cyano, oxo, $C_{1-6}$alkyl, $C_{2-6}$alkenyl, $C_{2-6}$alkynyl, $C_{1-6}$haloalkyl, $C_{0-3}$alkylene-$NR^{n2}R^{o2}$, $C_{0-3}$alkylene-$OR^{n2}$, $C_{0-3}$alkylene-C(=O)$OR^{n2}$, $C_{0-3}$alkylene-C(=O)$NR^{n2}R^{o2}$, $C_{0-3}$alkylene-C(=O)$R^{n2}$, $C_{0-3}$alkylene-S(=O)$_m R^{n2}$, $C_{0-3}$alkylene-S(=O)$_2 NR^{n2}R^{o2}$, and $R^{S11}$, in which $R^{S11}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, $C_{0-3}$alkylene-5- to 10-membered heteroaryl;

and each $R^{S11}$ is optionally substituted with one or more substituents independently selected from the group consisting of halo, oxo, cyano, $C_{0-3}$alkylene-$OR^2$, $C_{0-3}$alkylene-S(=O)$_m R^{p2}$, $C_{0-3}$alkylene-$NR^{p2}R^{q2}$, $C_{0-3}$alkylene-C(=O)$NR^{p2}R^{q2}$, $C_{0-3}$alkylene-$C_{0-3}$alkylene-C(=O)$OR^{p2}$, $C_{1-6}$alkyl, $C_{2-6}$alkenyl, $C_{2-6}$alkynyl, $C_{1-6}$haloalkyl, and $R^{S12}$, in which $R^{S12}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S12}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w9}$, and —$NR^{w9}R^{x9}$;

each of $R^n$, $R^{n2}$, $R^o$, and $R^{o2}$, independently, is H or $R^{S13}$, in which $R^{S13}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S13}$ is optionally substituted with one or more substituents independently selected from the group consisting of halo, oxo, cyano, $C_{0-3}$alkylene-$OR^3$, $C_{0-3}$alkylene-S(=O)$_m R^{p3}$, $C_{0-3}$alkylene-$NR^{p3}R^{q3}$, $C_{0-3}$alkylene-C(=O)$NR^{p3}R^{q3}$, $C_{0-3}$alkylene-C(=O)$OR^{p3}$, $C_{1-6}$alkyl, $C_{2-6}$alkenyl, $C_{2-6}$alkynyl, $C_{1-6}$haloalkyl, and $R^{S14}$, in which $R^{S14}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S14}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w10}$, and —$NR^{w10}R^{x10}$;

each of $R^p$, $R^{p2}$, $R^{p3}$, $R^q$, $R^{q2}$, and $R^{q3}$, independently, is H or $R^{S15}$, in which $R^{S15}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S15}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w1}$, and —$NR^{w11}R^{x11}$;

each of $R^r$, $R^t$, and $R^u$, independently, is H or $R^{S16}$, in which $R^{S16}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S16}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —C(=O)$OR^{w12}$, —$OR^{w12}$, and —$NR^{w12}R^{x12}$;

each $R^w$, $R^{w2}$, $R^{w3}$, $R^{w4}$, $R^{w5}$, $R^{w6}$, $R^{w7}$, $R^{w8}$, $R^{w9}$, $R^{w10}$, $R^{w11}$, $R^{w12}$, $R^x$, $R^{x2}$, $R^{x3}$, $R^{x4}$, $R^{x5}$, $R^{x6}$, $R^{x7}$, $R^{x8}$, $R^{x9}$, $R^{x10}$, $R^{x11}$, and $R^{x12}$, independently, is H, $C_{1-6}$alkyl, $C_{2-6}$alkenyl, $C_{2-6}$alkynyl or $C_{1-6}$haloalkyl;

each of n and p independently is 0, 1, 2, 3, 4, or 5, wherein when $T^2$ is H, p is 0; and m is 0, 1, or 2;

with the proviso that, for compounds where Y is —$CR^3$=:

a) when $R^1$ is unsubstituted phenyl, $R^2$ is methyl and $R^3$ is methyl, $R^4$ is not ethyl, unsubstituted phenyl, or unsubstituted pyridine;

b) when $R^1$ is unsubstituted cyclohexyl, $R^2$ is methyl and $R^3$ is methyl, $R^4$ is not unsubstituted pyridine;

c) when $R^1$ is unsubstituted cyclopentyl, $R^2$ is methyl and $R^3$ is methyl, $R^4$ is not ethyl or unsubstituted pyridine, d) when $R^2$ is methyl, $R^3$ is methyl and $R^4$ is 3,4-diethoxy-phenyl, $R^1$ is not unsubstituted 1-pyrrolidine, unsubstituted 1-piperidine, 4-methyl-1-piperidine, 4-(phenylmethyl)-1-piperidine, unsubstituted 2-1,2,3,4-tetrahydro-isoquinoline, unsubstituted morpholine, or NHCH$_2$CH$_2$-3-indole;

e) when $R^1$ is unsubstituted CH$_2$-phenyl, $R^2$ is methyl and $R^3$ is methyl, $R^4$ is not ethyl, trifluoromethyl, 1-methyl-piperidin-4-yl, unsubstituted pyridine, unsubstituted phenyl, phenyl mono-substituted with 4-F, 4-Cl, 2-methoxy or 4-methoxy, or phenyl disubstituted with 3,4-methoxy;

f) when $R^2$ is methyl, $R^3$ is methyl and $R^4$ is unsubstituted pyridine, $R^1$ is not CH$_2$— phenyl wherein the phenyl is substituted with 4-CN, 4-NO$_2$, 4-F or 2-F;

g) when $R^2$ is methyl, $R^3$ is methyl and $R^4$ is ethyl, $R^1$ is not CH$_2$-phenyl wherein the phenyl is substituted with 4-CN or 4-NO$_2$;

h) when $R^2$ is methyl, $R^3$ is methyl and $R^4$ is 4-methoxy-phenyl, $R^1$ is not CH$_2$-phenyl wherein the phenyl is substituted with 2-Cl, 3-Cl, 4-Br, 2-methyl or 4-methyl;

i) when $R^2$ is methyl, $R^3$ is methyl and $R^4$ is unsubstituted phenyl, $R^1$ is not CH$_2$— phenyl wherein the phenyl is substituted with 2-Cl, 3-Cl, 4-Cl, 4-Br, 2-methyl, 3-methyl, 4-methyl, 4-isopropyl or 4-tert-butyl; or $R^1$ is not unsubstituted $CH_{2-1}$-naphthylene or unsubstituted $CH_2$-pyridine;

j) when $R^2$ is methyl, $R^3$ is methyl and $R^4$ is 4-Cl-phenyl, $R^1$ is not $CH_2$-phenyl wherein the phenyl is substituted with 2-Cl, 4-Cl or 4-isopropyl;

k) when $R^1$ is unsubstituted $CH_2$-phenyl, $R^2$ is methyl and $R^3$ is trifluoromethyl, $R^4$ is not unsubstituted phenyl or phenyl substituted with 2-Cl or 4-Cl;

l) the compound is not wherein $R^1$ is $CH_2$-4-Br-phenyl, $R^2$ is methyl, $R^3$ is ethyl and $R^4$ is unsubstituted phenyl;

m) when $R^2$ is methyl, $R^3$ is methyl and $R^4$ is unsubstituted phenyl, $R^1$ is not $CH_2CH_2C(=O)NH$-phenyl wherein the phenyl ring is unsubstituted or is substituted at the 4-position with Cl, methyl or methoxy;

n) when $R^2$ is methyl or ethyl, $R^3$ is methyl and $R^4$ is unsubstituted phenyl, $R^1$ is not substituted pyrazolo[1,5-a]pyrimidin-7-yl;

o) when $R^2$ is H, $R^3$ is isopropyl and $R^4$ is methyl, $R^1$ is not unsubstituted pyrazole; and p) the compound is not wherein $R^1$ is unsubstituted $CH_2$-phenyl, $R^2$ is H, $R^3$ is methyl and $R^4$ is unsubstituted phenyl; and with the proviso that, for compounds where Y is —N=, the compound is not wherein $R^1$ is unsubstituted phenyl, $R^2$ is H and $R^4$ is 2-fluoro-phenyl.

For example, the compound can be of Formula (IA) or Formula (IA'):

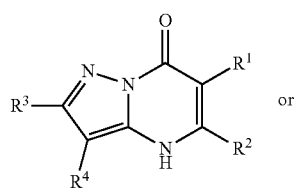

(IA)

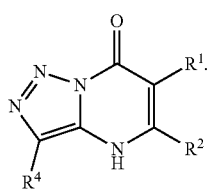

(IA')

For example, $Q^1$ is a bond or —$CH_2$— and $T^1$ is $C_{3-8}$cycloalkyl, $C_{6-10}$aryl, 3- to 12-membered heterocycloalkyl, 5- to 10-membered heteroaryl, or —C(=O)$NR^aR^b$.

For example, $Q^1$ is a bond and $T^1$ is $C_{3-8}$cycloalkyl, $C_{6-10}$aryl, 3- to 12-membered heterocycloalkyl, or 5- to 10-membered heteroaryl.

For example, $Q^1$ is a bond and $T^1$ is $C_{6-10}$aryl, 3- to 12-membered heterocycloalkyl, or 5- to 10-membered heteroaryl.

For example $Q^1$ is a bond and $T^1$ is phenyl, 5- or 6-membered monocyclic heteroaryl, or 9- or 10-membered bicyclic heteroaryl, preferably wherein $T^1$ is 9- or 10-membered bicyclic heteroaryl.

For example, $Q^1$ is a bond or —$CH_2$—, $T^1$ is —C(=O)$NR^aR^b$ and n is 0.

For example, one of $R^a$ and $R^b$ is H or methyl and the other of $R^a$ and $R^b$ is not H or methyl.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, $C_{2-6}$alkynyl, $C_{3-8}$cycloalkyl, $C_{6-10}$aryl, 3- to 12-membered heterocycloalkyl, or 5- to 10-membered heteroaryl, each $X^2$ independently is halo, cyano, oxo, $C_{0-3}$alkylene-OR'', $C_{0-3}$alkylene-S(=O)$_m$R'', $C_{0-3}$alkylene-NR''R°, $C_{0-3}$alkylene-C(=O)NR''R°, $C_{0-3}$alkylene-$C_{0-3}$alkylene-C(=O)OR'', and each R'' and R° is independently H, $C_{1-6}$alkyl, $C_{2-6}$alkenyl, $C_{2-6}$alkynyl or $C_{1-6}$haloalkyl.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, or $C_{2-6}$alkynyl, and each $X^2$ independently is halo or —$OC_{1-6}$alkyl.

For example, $R^2$ is H, cyano, methyl or methoxymethyl.

For example, $R^2$ is H, methyl or methoxymethyl.

For example, $R^3$ is $C_{1-3}$alkyl, $C_{1-3}$haloalkyl, —CN, —S(=O)$_2C_{1-3}$alkyl or —C(=O)$OC_{1-3}$alkyl.

For example, $R^3$ is —CN, $C_{1-3}$alkyl, $C_{1-3}$haloalkyl or —C(=O)$OC_{1-3}$alkyl.

For example, $R^3$ is $C_{1-3}$alkyl, $C_{1-3}$haloalkyl or —C(=O)$OC_{1-3}$alkyl.

For example, $R^3$ is —$CF_3$, methyl or —C(=O)$OC_{1-3}$alkyl.

For example, $R^3$ is —$CF_3$ or —CN.

For example, $R^3$ is —$CF_3$

For example, $R^3$ is —CN.

For example, $R^4$ is $C_{1-3}$alkyl, $C_{1-3}$haloalkyl, —S(=O)$_2C_{1-3}$alkyl, $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$.

For example, $R^4$ is $C_{3-8}$cycloalkyl, $C_{6-10}$aryl, 3 to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is $C_{3-8}$cycloalkyl or $C_{6-10}$aryl, wherein $C_{3-8}$cycloalkyl and $C_{6-10}$aryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is phenyl optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

For example, $R^4$ is $C_{3-8}$cycloalkyl.

For example, $R^4$ is cyclopentyl.

For example, $R^4$ is $C_{6-10}$aryl.

For example, $R^4$ is phenyl.

For example, the compound can be of Formula (Ia) or Formula (Ia'):

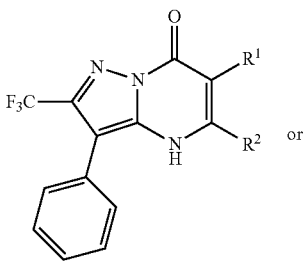

(Ia)

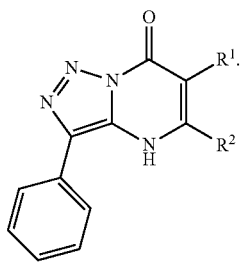

(Ia')

For example, Q¹ is a bond or —CH₂—.

For example, T¹ is —C(=O)—C$_{0-1}$alkylene-C$_{6-10}$aryl or —C(=O)—C$_{0-1}$alkylene-5 to 10-membered heteroaryl.

For example, Q¹ is a bond or —CH₂— and T¹ is C$_{3-8}$cycloalkyl, C$_{6-10}$aryl, 3- to 12-membered heterocycloalkyl, 5- to 10-membered heteroaryl, or —C(=O)NR$^a$R$^b$.

For example, Q¹ is a bond and T¹ is C$_{3-8}$cycloalkyl, C$_{6-10}$aryl, 3- to 12-membered heterocycloalkyl, or 5- to 10-membered heteroaryl.

For example, Q¹ is a bond and T¹ is C$_{6-10}$aryl, 3- to 12-membered heterocycloalkyl, or 5- to 10-membered heteroaryl.

For example Q¹ is a bond and T¹ is phenyl, 5- or 6-membered monocyclic heteroaryl, or 9- or 10-membered bicyclic heteroaryl, preferably wherein T¹ is 9- or 10-membered bicyclic heteroaryl.

For example, T¹ is C(=O)NR$^a$R$^b$ and n is 0.

For example, one of R$^a$ and R$^b$ is H or methyl and the other of R$^a$ and R$^b$ is not H or methyl.

For example, n is 0.

For example, T¹ is aryl or heteroaryl, preferably phenyl, 5- or 6-membered monocyclic heteroaryl, or 9- or 10-membered bicyclic heteroaryl.

For example, T¹ is 5- to 10-membered heteroaryl.

For example, T¹ is pyridinyl, pyrazinyl, pyridazinyl, pyrimidinyl, indolyl, indolinyl, isoindolyl, isoindolinyl, indazolyl, pyrazolopyridinyl, pyrazolopyrimidinyl, oxazolopyrimidinyl, oxazolopyridinyl, imidazopyridinyl, benzimidazolyl, tetrahydrobenzimidazolyl, benzofuranyl, dihydrobenzofuranyl, isobenzofuranyl, dihydroisobenzofuranyl, triazolopyridinyl, benzothiazolyl, azabenzimidazolyl, azabenzoxazolyl, azabenzothiazolyl, quinolinyl, isoquinolinyl, quinazolinyl, oxazolyl, isoxazolyl, thiazolyl, isothiazolyl, benzoxazolyl, benzodioxolyl, chromanyl, tetrahydrooxazoloazepinyl, tetrahydrobenzoxazolyl, oxadiazolyl, thiadiazolyl, pyrazolyl, triazolyl, imidazolyl, furanyl, or thiophenyl.

For example, T¹ is pyridinyl, pyrazinyl, pyridazinyl, pyrimidinyl, indolyl, indazolyl, pyrazolopyridinyl, benzimidazolyl, benzothiazolyl, azabenzimidazolyl, azabenzoxazolyl, azabenzothiazolyl, imidazopyridinyl, quinolinyl, isoquinolinyl, quinazolinyl, oxazolyl, isoxazolyl, thiazolyl, isothiazolyl, benzoxazolyl, tetrahydrobenzoxazolyl, tetrahydrobenzimidazolyl, oxadiazolyl, thiadiazolyl, triazolyl, imidazolyl, furanyl, or thiophenyl.

For example, T¹ is pyridinyl, pyrazinyl, pyridazinyl, pyrimidinyl, indolyl, indazolyl, pyrazolopyridinyl, benzimidazolyl, benzothiazolyl, azabenzimidazolyl, azabenzoxazolyl, azabenzothiazolyl, imidazopyridinyl, quinolinyl, isoquinolinyl, quinazolinyl, oxazolyl, isoxazolyl, thiazolyl, isothiazolyl, benzoxazolyl, tetrahydrobenzoxazolyl, tetrahydrobenzimidazolyl, oxadiazolyl, thiadiazolyl, triazolyl, imidazolyl, furanyl, or thiophenyl, and X¹ is halo, C$_{0-3}$alkylene-OR$^c$, C$_{0-3}$alkylene-NR$^c$R$^d$, or R$^{S1}$, in which R$^{S1}$ is C$_{1-6}$alkyl or C$_{0-3}$alkylene-C$_{3-8}$cycloalkyl.

For example, T¹ is C$_{0-1}$alkylene-C$_{6-10}$aryl.

For example, T¹ is phenyl, benzyl, naphthyl, or CH₂naphthyl.

For example, T¹ is 3- to 12-membered heterocycloalkyl, preferably 4- to 10-membered heterocycloalkyl.

For example, T¹ is piperazine, piperidine, quinuclidine, or morpholine.

For example, R² is Q²-T²-(X²)$_p$, Q² is a bond, T² is H, halo, cyano, C$_{1-6}$alkyl, C$_{1-6}$haloalkyl, C$_{2-6}$alkenyl, C$_{2-6}$alkynyl, C$_{3-8}$cycloalkyl, C$_{6-10}$aryl, 3- to 12-membered heterocycloalkyl, or 5 to 10-membered heteroaryl, each X² independently is halo, cyano, oxo, C$_{0-3}$alkylene-OR″, C$_{0-3}$alkylene-S(=O)$_m$R″, C$_{0-3}$alkylene-NR″R°, C$_{0-3}$alkylene-C(=O)NR″R°, C$_{0-3}$alkylene-C$_{0-3}$alkylene-C(=O)OR″, and each R″ and R° is independently H, C$_{1-6}$alkyl, C$_{2-6}$alkenyl, C$_{2-6}$alkynyl or C$_{1-6}$haloalkyl.

For example, R² is Q²-T²-(X²)$_p$, Q² is a bond, T² is H, halo, cyano, C$_{1-6}$alkyl, C$_{1-6}$haloalkyl, C$_{2-6}$alkenyl, or C$_{2-6}$alkynyl, and each X² independently is halo or OC$_{1-6}$alkyl.

For example, R² is H, cyano, methyl or methoxymethyl.

For example, R² is H, methyl or methoxymethyl.

The present invention provides the compounds of Formula (Ib) or Formula (Ib'):

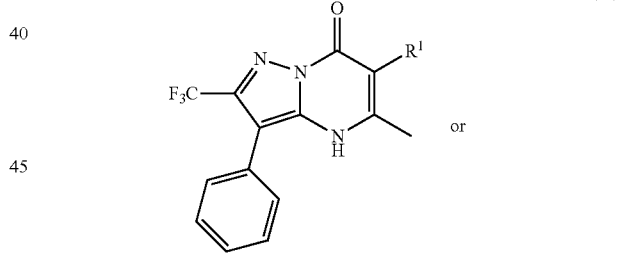

(Ib)

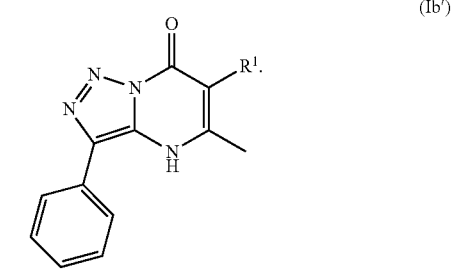

(Ib')

In some embodiments of Formula Ib or Ib', Q¹ is a bond or —CH₂— and T¹ is C$_{3-8}$cycloalkyl, C$_{6-10}$aryl, 3- to 12-membered heterocycloalkyl, 5- to 10-membered heteroaryl, or —C(=O)NR$^a$R$^b$.

In some embodiments of Formula Ib or Ib', Q¹ is a bond and T¹ is C$_{3-8}$cycloalkyl, C$_{6-10}$aryl, 3- to 12-membered heterocycloalkyl, or 5- to 10-membered heteroaryl.

In some embodiments of Formula Ib or Ib', $Q^1$ is a bond or —$CH_2$— and $T^1$ is —C(=O)$NR^aR^b$ and n is 0.

Another subset of the compounds of Formula (I) includes those of Formula (IIa), Formula (IIa'), Formula (IIb) or Formula (IIb'):

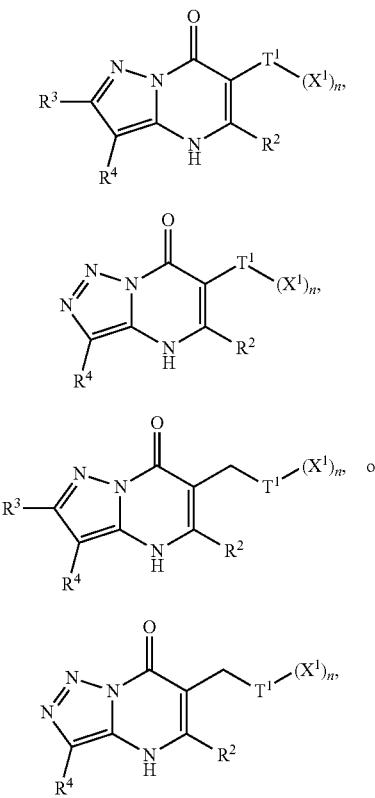

(IIa)

(IIa')

(IIb)

(IIb')

$R^2$, $R^3$, $R^4$, $T^1$, $X^1$ and n are as defined for Formula I.

In some embodiments of Formula IIa, IIa', IIb, or IIb', $T^1$ is $C_{3-8}$cycloalkyl, $C_{6-10}$aryl, 3- to 12-membered heterocycloalkyl, 5- to 10-membered heteroaryl, or C(=O)$NR^aR^b$.

In some embodiments of Formula IIa, or IIa', $T^1$ is $C_{3-8}$cycloalkyl, $C_{6-10}$aryl, 3- to 12-membered heterocycloalkyl, or 5 to 10-membered heteroaryl.

In some embodiments of Formula IIa, IIa', IIb, or IIb', $T^1$ is —C(=O)$NR^aR^b$ and n is 0.

In some embodiments of Formula IIa, IIa', IIb or IIb', $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, $C_{2-6}$alkynyl, $C_{3-8}$cycloalkyl, $C_{6-10}$aryl, 3- to 12-membered heterocycloalkyl, or 5- to 10-membered heteroaryl, each $X^2$ independently is halo, cyano, oxo, $C_{0-3}$alkylene-$OR''$, $C_{0-3}$alkylene-$S(=O)_mR''$, $C_{0-3}$alkylene-$NR''R^o$, $C_{0-3}$alkylene-$C(=O)NR''R^o$, $C_{0-3}$alkylene-$C_{0-3}$alkylene-$C(=O)OR''$, and each $R''$ and $R^o$ is independently H, $C_{1-6}$alkyl, $C_{2-6}$alkenyl, $C_{2-6}$alkynyl or $C_{1-6}$haloalkyl.

In some embodiments of Formula IIa, IIa', IIb, or IIb', $R^2$ is $Q^2$-$T^2$-$(X^2)_p$, $Q^2$ is a bond, $T^2$ is H, halo, cyano, $C_{1-6}$alkyl, $C_1$ haloalkyl, $C_{2-6}$alkenyl, or $C_{2-6}$alkynyl, and each $X^2$ independently is halo or —$OC_{1-6}$alkyl.

In some embodiments of Formula IIa, IIa', IIb, or IIb', $R^2$ is H, cyano, methyl or methoxymethyl.

In some embodiments of Formula IIa, IIa', IIb, or IIb', $R^2$ is H, methyl or methoxymethyl.

In some embodiments of Formula IIa or IIb, $R^3$ is $C_{1-3}$alkyl, $C_{1-3}$haloalkyl, —CN, —S(=O)$_2C_{1-3}$alkyl or —C(=O)$OC_{1-3}$alkyl.

In some embodiments of Formula IIa or IIb, $R^3$ is $C_{1-3}$alkyl, $C_{1-3}$haloalkyl or —C(=O)$OC_{1-3}$alkyl.

In some embodiments of Formula IIa or IIb, $R^3$ is —CN, —$CF_3$, methyl or —C(=O)$OC_{1-3}$alkyl.

In some embodiments of Formula IIa or IIb, $R^3$ is —CN or —$CF_3$.

In some embodiments of Formula IIa, IIa', IIb, or IIb', $R^4$ is $C_{1-3}$alkyl, $C_{1-3}$haloalkyl, —S(=O)$_2C_{1-3}$alkyl, $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$.

In some embodiments of Formula IIa, IIa', IIb, or IIb', $R^4$ is $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$ wherein $R^{w5}$ and $R^{x5}$ are independently H, $C_{1-6}$alkyl or $C_{1-6}$haloalkyl.

In some embodiments of Formula IIa, IIa', IIb, or IIb', $R^4$ is $C_{3-8}$cycloalkyl or $C_{6-10}$aryl, wherein $C_{3-8}$cycloalkyl and $C_{6-10}$aryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$, wherein $R^{w5}$ and $R^{x5}$ are independently H, $C_{1-6}$alkyl or $C_{1-6}$haloalkyl.

In some embodiments of Formula IIa, IIa', IIb, or IIb', $R^4$ is $C_{3-8}$cycloalkyl.

In some embodiments of Formula IIa, IIa', IIb, or IIb', $R^4$ is cyclopentyl.

In some embodiments of Formula IIa, IIa', IIb, or IIb', $R^4$ is $C_{6-10}$aryl.

In some embodiments of Formula IIa, IIa', IIb, or IIb', $R^4$ is phenyl.

In some embodiments of Formula IIa, IIa', IIb, or IIb', $T^1$ is $C_{3-8}$cycloalkyl, $C_{6-10}$aryl, 3- to 12-membered heterocycloalkyl, 5- to 10-membered heteroaryl, —C(=O)—$C_{0-3}$alkylene-$C_{3-8}$cycloalkyl, —C(=O)—$C_{0-3}$alkylene-$C_{6-10}$aryl, —C(=O)—$C_{0-3}$alkylene-3- to 12-membered heterocycloalkyl, —C(=O)—$C_{0-3}$alkylene-5- to 10-membered heteroaryl, —$NR^aR^b$, —S(=O)$_2R^a$, —$NR^aC(=O)R^a$, —$NR^aC(=O)NR^aR^b$, —$NR^aC(=O)OR^a$, —$NR^aS(=O)_2R^a$, —C(=O)$NR^aS(=O)_2R^a$, —$NR^aS(=O)_2NR^aR^b$, —C(=O)$NR^aR^b$, or —S(=O)$_2NR^aR^b$; each $X^1$ independently is halo, cyano, oxo, $C_{0-3}$alkylene-C(=O)$R^c$, $C_{0-3}$alkylene-$OR^c$, $C_{0-3}$alkylene-$NR^cR^d$, $C_{0-3}$alkylene-OC(=O)$NR^cR^d$, $C_{0-3}$alkylene-C(=$NR^c$)$NR^cR^d$, $C_{0-3}$alkylene-$NR^c$(=NR)$NR^cR^d$, or $R^{S1}$, in which $R^{S1}$ is $C_{1-6}$alkyl, $C_{2-6}$alkenyl, $C_{2-6}$alkynyl, $C_{1-6}$haloalkyl, $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5 to 10-membered heteroaryl, and $R^{S1}$ is optionally substituted with one or more substituents independently selected from the group consisting of halo, oxo, $C_{1-6}$alkyl, $C_{2-6}$alkenyl, $C_{2-6}$alkynyl, $C_{1-6}$haloalkyl, $C_{0-3}$alkylene-$NR^eR^f$, $C_{0-3}$alkylene-$OR^e$, $C_{0-3}$alkylene-$NR^eC(=O)R^e$, $C_{0-3}$alkylene-C(=O)$OR^e$, $C_{0-3}$alkylene-$NR^eC(=O)NR^eR^f$, $C_{0-3}$alkylene-OC(=O)$R^e$, $C_{0-3}$alkylene-C(=O)$OR^e$, $C_{0-3}$alkylene-C(=O)$R^e$, $C_{0-3}$alkylene-S(=O)$_mR^e$, $C_{0-3}$alkylene-S(=O)$_2$ NR$^e$R$^f$, C$_{0-3}$alkylene-NR$^e$S(=O)$_2$R$^e$, C$_{0-3}$alkylene-NR$^e$S(=O)$_2$NR$^e$R$^f$, and R$^{S2}$, in which R$^{S2}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, C$_{0-3}$alkylene-5- to 10-membered heteroaryl, and R$^{S2}$ is optionally substituted with one or more substituents independently selected from the group consisting of halo, C$_{1-6}$alkyl, C$_{2-6}$alkenyl, C$_{2-6}$alkynyl, cyano, C$_{1-6}$haloalkyl, —OR$^w$, and —NR$^w$R$^x$.

Yet another subset of the compounds of Formula I includes those of Formula (IIc), Formula (IIc'), Formula (IId), or Formula (IId'):

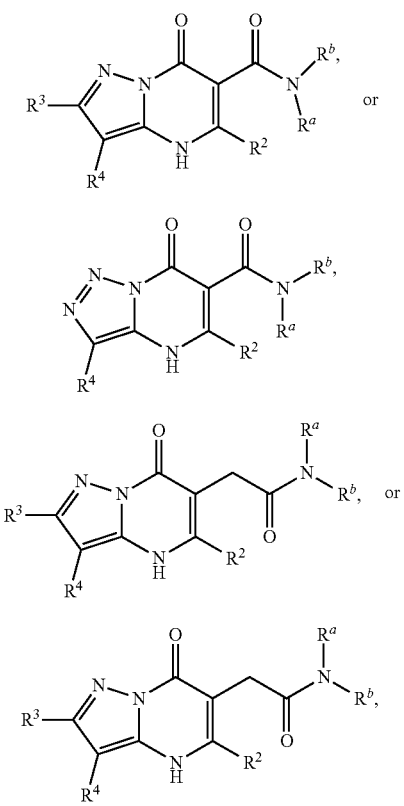

R$^2$, R$^3$, R$^4$, R$^a$ and R$^b$ are as defined for Formula I.

In some embodiments of Formula IIc, IIc', IId, or IId', R$^2$ is Q$^2$-T$^2$-(X$^2$)$_p$, Q$^2$ is a bond, T$^2$ is H, halo, cyano, C$_{1-6}$alkyl, C$_{1-6}$haloalkyl, C$_{2-6}$alkenyl, C$_{2-6}$alkynyl, C$_{3-8}$cycloalkyl, C$_{6-10}$aryl, 3 to 12-membered heterocycloalkyl, or 5 to 10-membered heteroaryl, each X$^2$ independently is halo, cyano, oxo, C$_{0-3}$alkylene-OR$^n$, C$_{0-3}$alkylene-S(=O)$_m$R$^n$, C$_{0-3}$alkylene-NR$^n$R$^o$, C$_{0-3}$alkylene-C(=O)NR$^n$R$^o$, C$_{0-3}$alkylene-C$_{0-3}$alkylene-C(=O)OR$^n$, and each R$^n$ and R$^o$ is independently H, C$_{1-6}$alkyl, C$_{2-6}$alkenyl, C$_{2-6}$alkynyl or C$_{1-6}$haloalkyl.

In some embodiments of Formula IIc, IIc', IId, or IId', R$^2$ is Q$^2$-T$^2$-(X$^2$)$_p$, Q$^2$ is a bond, T$^2$ is H, halo, cyano, C$_{1-6}$alkyl, C$_{1-6}$haloalkyl, C$_{2-6}$alkenyl, or C$_{2-6}$alkynyl, and each X$^2$ independently is halo or OC$_{1-6}$alkyl.

In some embodiments of Formula IIc, IIc', IId, or IId', R$^2$ is H, cyano, methyl or methoxymethyl.

In some embodiments of Formula IIc, IIc', IId, or IId', R$^2$ is H, methyl or methoxymethyl.

In some embodiments of Formula IIc or IId, R$^3$ is C$_{1-3}$alkyl, C$_{1-3}$haloalkyl, —CN, —S(=O)$_2$C$_{1-3}$alkyl or —C(=O)OC$_{1-3}$alkyl In some embodiments of Formula IIc or IId, R$^3$ is —CN, C$_{1-3}$alkyl, C$_{1-3}$haloalkyl or —C(=O)OC$_{1-3}$alkyl.

In some embodiments of Formula IIc or IId, R$^3$ is C$_{1-3}$alkyl, C$_{1-3}$haloalkyl or —C(=O)OC$_{1-3}$alkyl.

In some embodiments of Formula IIc or IId, R$^3$ is —CN, —CF$_3$, methyl or —C(=O)OC$_{1-3}$alkyl.

In some embodiments of Formula IIc or IId, R$^3$ is —CN or —CF$_3$.

In some embodiments of Formula IIc, IIc', IId, or IId', R$^4$ is C$_{1-3}$alkyl, C$_{1-3}$haloalkyl, —S(=O)$_2$C$_{1-3}$alkyl, C$_{3-8}$cycloalkyl, C$_{6-10}$aryl, 3- to 12-membered heterocycloalkyl, or 5- to 10-membered heteroaryl, wherein C$_{3-8}$cycloalkyl, C$_{6-10}$aryl, 3- to 12-membered heterocycloalkyl, or 5- to 10-membered heteroaryl are optionally substituted with 1-3 substituents selected from the group consisting of halo, oxo, C$_{1-6}$alkyl, C$_{2-6}$alkenyl, C$_{2-6}$alkynyl, cyano, C$_{1-6}$haloalkyl, —OR$^{w5}$, and —NR$^{w5}$R$^{x5}$.

In some embodiments of Formula IIc, IIc', IId, or IId', R$^4$ is C$_{3-8}$cycloalkyl, C$_{6-10}$aryl, 3- to 12-membered heterocycloalkyl, or 5 to 10-membered heteroaryl, wherein C$_{3-8}$cycloalkyl, C$_{6-10}$aryl, 3 to 12-membered heterocycloalkyl, or 5- to 10-membered heteroaryl are optionally substituted with 1-3 substituents selected from the group consisting of halo, oxo, C$_{1-6}$alkyl, C$_{2-6}$alkenyl, C$_{2-6}$alkynyl, cyano, C$_{1-6}$haloalkyl, —OR$^{w5}$, and —NR$^{w5}$R$^{x5}$, wherein R$^{w5}$ and R$^{x5}$ are independently H, C$_{1-6}$alkyl or C$_{1-6}$haloalkyl.

In some embodiments of Formula IIc, IIc', IId, or IId', R$^4$ is C$_{3-8}$cycloalkyl or C$_{6-10}$aryl, wherein C$_{3-8}$cycloalkyl and C$_{6-10}$aryl are optionally substituted with 1-3 substituents selected from the group consisting of halo, oxo, C$_{1-6}$alkyl, C$_{2-6}$alkenyl, C$_{2-6}$alkynyl, cyano, C$_{1-6}$haloalkyl, —OR$^{w5}$, and —NR$^{w5}$R$^{x5}$, wherein R$^{w5}$ and R$^{x5}$ are independently H, C$_{1-6}$alkyl or C$_{1-6}$haloalkyl.

In some embodiments of Formula IIc, IIc', IId, or IId', R$^4$ is C$_{3-8}$cycloalkyl.

In some embodiments of Formula IIc, IIc', IId, or IId', R$^4$ is cyclopentyl.

In some embodiments of Formula IIc or IId IIc, IIc', IId, or IId', R$^4$ is C$_{6-10}$aryl.

In some embodiments of Formula IIc, IIc', IId, or IId', R$^4$ is phenyl.

Still another subset of the compounds of Formula (I) includes those of Formula (IIe), Formula (IIe'), Formula (IIf), or Formula (IIf'):

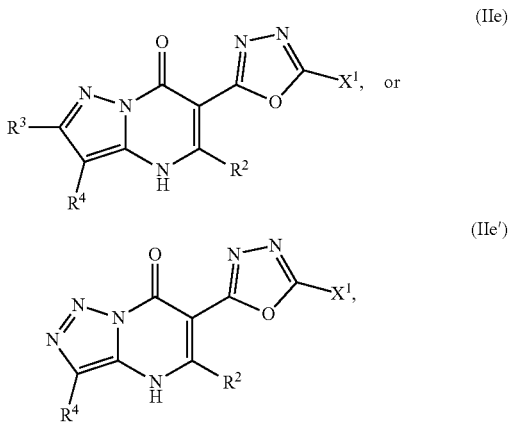

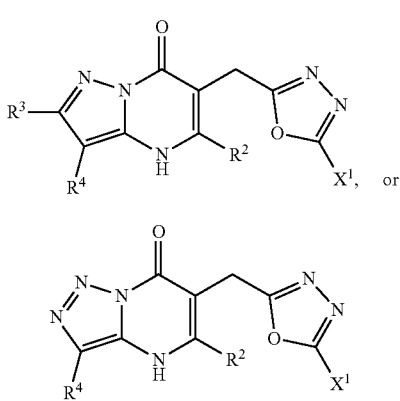

(IIf)

(IIf')

wherein each $X^1$ independently is halo, cyano, $C_{0-3}$alkylene-C(=O)$R^c$, $C_{0-3}$alkylene-O$R^c$, $C_{0-3}$alkylene-C(=O)O$R^c$, $C_{0-3}$alkylene-OC(=O)$R^c$, $C_{0-3}$alkylene-N$R^cR^d$, $C_{0-3}$alkylene-S(=O)$_mR^c$, $C_{0-3}$alkylene-N$R^c$C(=O)$R^c$, $C_{0-3}$alkylene-N$R^c$C(=O)N$R^cR^d$, $C_{0-3}$alkylene-OC(=O)N$R^cR^d$, $C_{0-3}$alkylene-N$R^c$C(=O)O$R^c$, $C_{0-3}$alkylene-N$R^c$S(=O)$_2R^c$, $C_{0-3}$alkylene-C(=O)N$R^c$S(=O)$_2R^c$, $C_{0-3}$alkylene-N$R^c$S(=O)$_2$N$R^cR^d$, $C_{0-3}$alkylene-C(=O)N$R^cR^d$, $C_{0-3}$alkylene-S(=O)$_2$N$R^cR^d$, $C_{0-3}$alkylene-C(=NR)N$R^cR^d$, $C_{0-3}$alkylene-N$R^c$C(=NR)N$R^cR^d$, or $R^{S1}$, in which $R^{S1}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, $R^2$, $R^3$, $R^4$, $R^c$, $R^d$ and $R^{S1}$ are as defined for Formula I.

In some embodiments of Formula IIe, IIe', IIf or IIf', $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, $C_{2-6}$alkynyl, $C_{3-8}$cycloalkyl, $C_{6-10}$aryl, 3 to 12-membered heterocycloalkyl, or 5 to 10-membered heteroaryl, each $X^2$ independently is halo, cyano, oxo, $C_{0-3}$alkylene-O$R^n$, $C_{0-3}$alkylene-S(=O)$_mR^n$, $C_{0-3}$alkylene-N$R^nR^o$, $C_{0-3}$alkylene-C(=O)N$R^nR^o$, $C_{0-3}$alkylene-$C_{0-3}$alkylene-C(=O)O$R^n$, and each $R^n$ and $R^o$ is independently H, $C_{1-6}$alkyl, $C_{2-6}$alkenyl, $C_{2-6}$alkynyl or $C_{1-6}$haloalkyl.

In some embodiments of Formula IIe, IIe', IIf or IIf', $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, or $C_{2-6}$alkynyl, and each $X^2$ independently is halo or —O$C_{1-6}$alkyl.

In some embodiments of Formula IIe, IIe', IIf or IIf', $R^2$ is H, cyano, methyl or methoxymethyl.

In some embodiments of Formula IIe, IIe', IIf or IIf', $R^2$ is H, methyl or methoxymethyl.

In some embodiments of Formula IIe or IIf, $R^3$ is $C_{1-3}$alkyl, $C_{1-3}$haloalkyl, —CN, S(=O)$_2C_{1-3}$alkyl or —C(=O)O$C_{1-3}$alkyl In some embodiments of Formula IIe or IIf, $R^3$ is —CN, $C_{1-3}$alkyl, $C_{1-3}$haloalkyl or —C(=O)O$C_{1-3}$alkyl.

In some embodiments of Formula IIe or IIf, $R^3$ is $C_{1-3}$alkyl, $C_{1-3}$haloalkyl or —C(=O)O$C_{1-3}$alkyl.

In some embodiments of Formula IIe or IIf, $R^3$ is —CN, —CF$_3$, methyl or —C(=O)O$C_{1-3}$alkyl.

In some embodiments of Formula IIe or IIf, $R^3$ is —CN or —CF$_3$.

In some embodiments of Formula IIe, IIe', IIf or IIf', $R^4$ is $C_{1-3}$alkyl, $C_{1-3}$haloalkyl, S(=O)$_2C_{1-3}$alkyl, $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —OR$^{w5}$, and —NR$^{w5}$R$^{x5}$.

In some embodiments of Formula IIe, IIe', IIf or IIf', $R^4$ is $C_{3-8}$cycloalkyl, $C_{6-10}$aryl, 3 to 12-membered heterocycloalkyl, or 5 to 10-membered heteroaryl, wherein $C_{3-8}$cycloalkyl, $C_{6-10}$aryl, 3 to 12-membered heterocycloalkyl, or 5 to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —OR$^{w5}$, and —NR$^{w5}$R$^{x5}$, wherein Rw5 and Rx5 are independently H, $C_{1-6}$alkyl or $C_{1-6}$haloalkyl.

In some embodiments of Formula IIe, IIe', IIf or IIf', $R^4$ is $C_{3-8}$cycloalkyl or $C_{6-10}$aryl, wherein $C_{3-8}$cycloalkyl and $C_{6-10}$aryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, OR$^{w5}$, and NR$^{w5}R^{x5}$, wherein $R^{w5}$ and $R^{x5}$ are independently H, $C_{1-6}$alkyl or $C_{1-6}$haloalkyl.

In some embodiments of Formula IIe, IIe', IIf or IIf', $R^4$ is $C_{3-8}$cycloalkyl.

In some embodiments of Formula IIe, IIe', IIf or IIf', $R^4$ is cyclopentyl.

In some embodiments of Formula IIe, IIe', IIf or IIf', $R^4$ is $C_{6-10}$aryl.

In some embodiments of Formula IIe, IIe', IIf or IIf', $R^4$ is phenyl.

Any of the substituents described herein for any of $R^1$, $R^2$, $R^3$, $R^4$, $R^a$, $R^b$, $R^c$, $R^d$, $R^e$, $R^f$, $R^g$, $R^h$, $R^i$, $R^j$, $R^k$, $R^m$, $R^n$, $R^p$, $R^r$, $R^t$, $R^u$, $R^w$, $R^{w2}$, $R^x$, $R^z$, $R^{x2}$, $R^1$, $R^2$, $R^{S3}$, $R^{S4}$, $Q^1$, $Q^2$, $T^1$, $T^2$, $X^1$, and $X^2$ can be combined with any of the substituents described herein for one or more of the remainder of $R^1$, $R^2$, $R^3$, $R^4$, $R^a$, $R^b$, $R^c$, $R^d$, $R^e$, $R^f$, $R^g$, $R^h$, $R^i$, $R^j$, $R^k$, $R^m$, $R^n$, $R^p$, $R^r$, $R^t$, $R^u$, $R^w$, $R^{w2}$, $R^x$, $R^z$, $R^{x2}$, $R^{S1}$, $R^{S2}$, $R^{S3}$, $R^{S4}$, $Q^1$, $Q^2$, $T^1$, $T^2$, $X^1$, and $X^2$.

In one embodiment, $R^1$, $Q^1$, $T^1$, $X^1$, $R^a$, $R^b$, $R^c$, $R^d$, $R^e$, $R^f$, $R^g$, $R^h$, $R^{S1}$, $R^{S2}$, $R^w$, $R^{w2}$, $R^x$, $R^z$, and $R^{x2}$ are each as defined, where applicable, in any of Formula I (including IA, IA', Ia, Ia', Ib and Ib'), Formula II (i.e. including IIa, IIa', IIb, IIb', IIc, IIc', IId, IId', IIe, IIe', IIf and IIf').

For example, $T^1$ is C(=O)N$R^aR^b$ and n is 0.

For example, one of $R^a$ and $R^b$ independently is 5- to 10-membered heteroaryl and the other is hydrogen.

For example, one of $R^a$ and $R^b$ independently is pyridinyl, pyrazinyl, pyridazinyl, pyrimidinyl, indolyl, indazolyl, benzimidazolyl, imidazopyridinyl, quinolinyl, isoquinolinyl, quinazolinyl, oxazolyl, isoxazolyl, thiazolyl, isothiazolyl, benzoxazolyl, oxadiazolyl, pyrazolyl, benzodioxolyl, dihydrobenzofuranyl, triazolyl, imidazolyl, furanyl, or thiophenyl, each of which is optionally substituted with one or more groups independently selected from cyano, $C_{1-6}$haloalkyl, $C_{0-3}$alkylene-S(=O)$_mR^2$, $C_{0-3}$alkylene-OR$^{c2}$, $C_{0-3}$alkylene-NR$^{c2}R^{d2}$, and $R^{S6}$, in which $R^{S6}$ is $C_{1-6}$alkyl, $C_{0-3}$alkylene-$C_{3-8}$cycloalkyl, or $C_{0-3}$alkylene-$C_{610}$aryl.

For example, one of $R^a$ and $R^b$ independently is pyridinyl, pyrazinyl, pyridazinyl, pyrimidinyl, indolyl, indazolyl, benzimidazolyl, imidazopyridinyl, quinolinyl, isoquinolinyl, quinazolinyl, oxazolyl, isoxazolyl, thiazolyl, isothiazolyl, benzoxazolyl, oxadiazolyl, pyrazolyl, benzodioxolyl, dihydrobenzofuranyl, triazolyl, imidazolyl, furanyl, or thiophenyl, each of which is optionally substituted with one or more groups independently selected from cyano, —CF$_3$, —S(=O)$_2$CH$_3$, —OCH$_3$, —NH$_2$, and $R^{S6}$, in which $R^{S6}$ is CH$_3$, i-propyl, cyclopropyl, cyclopentyl, cyclohexyl, or phenyl.

For example, one of $R^a$ and $R^b$ is $C_{0-1}$alkylene-$C_{6-10}$aryl.

For example, one of $R^a$ and $R^b$ independently is phenyl, benzyl, naphthyl, or $CH_2$naphthyl, each of which is optionally substituted with one or more groups independently selected from halo, cyano, $CF_3$, $C_{0-3}$alkylene-S(=O)$_m$R$^{c2}$, $C_{0-3}$alkylene-NR$^{c2}$S(=O)$_2$R$^{c2}$, $C_{0-3}$alkylene-N(S(=O)$_2$R$^{c2}$)$_2$, $C_{0-3}$alkylene-NR$^{c2}$C(=O)R$^{c2}$, $C_{0-3}$alkylene-NR$^{c2}$C(=O)OR$^{c2}$, $C_{0-3}$alkylene-OR$^{c2}$, $C_{0-3}$alkylene-NR$^{c2}$R$^{d2}$, and R$^{S6}$, in which R$^{S6}$ is $C_{1-6}$alkyl, $C_{0-3}$alkylene-OR$^{e2}$, or R$^{S7}$, in which R$^{S7}$ is $C_{0-3}$alkylene-$C_{3-8}$cycloalkyl, $C_{0-3}$alkylene-$C_{6-10}$aryl, or $C_{0-3}$alkylene-3- to 12-membered heterocycloalkyl.

For example, one of $R^a$ and $R^b$ independently is phenyl, —CH$_2$phenyl, naphthyl, or —CH$_2$naphthyl, each of which is optionally substituted with one or more groups independently selected from F, Cl, cyano, —CF$_3$, —S(=O)$_2$CH$_3$, —S(=O)$_2$i-propyl, —NHS(=O)$_2$CH$_3$, —NHS(=O)$_2$phenyl, —N(S(=O)$_2$CH$_3$)$_2$, —NHC(=O)CH$_3$, —NHC(=O)OCH$_3$, —OCH$_3$, —OCF$_3$, —Oi-propyl, —Ocyclopentyl, —OCH$_2$phenyl, —NH$_2$, —N(CH$_3$)$_2$, and R$^{S6}$, in which R$^{S6}$ is —CH$_3$, —CH$_2$OCH$_3$, i-propyl, or R$^{S7}$, in which R$^{S7}$ is cyclopropyl, cyclopentyl, cyclohexyl, phenyl, pyrrolidinyl, or piperidinyl.

For example, one of $R^a$ and $R^b$ independently is optionally substituted 5- to 9-membered heterocycloalkyl.

For example, one of $R^a$ and $R^b$ independently is, tetrahydrobenzimidazole, morpholine, tetrahydrofuran, tetrahydropyran, pyrrolidine, piperidine, or piperazine, each of which is optionally substituted with $C_{0-3}$alkylene-C(=O)R$^{c2}$, $C_{0-3}$alkylene-C(=O)OR$^{c2}$, or R$^{S6}$, in which R$^{S6}$ is $C_{1-6}$alkyl.

For example, one of $R^a$ and $R^b$ independently is, tetrahydrobenzimidazole, morpholine, tetrahydrofuran, tetrahydropyran, pyrrolidine, piperidine, or piperazine, each of which is optionally substituted with —CH$_3$, —C(=O)CH$_3$, or —C(=O)Ot-butyl.

For example, one of $R^a$ and $R^b$ independently is $C_{5-6}$cycloalkyl and the other is hydrogen.

For example, each of $R^a$ and $R^b$ independently is cyclohexane or cyclopropane, each of which is optionally substituted with $C_{0-3}$alkylene-OR$^{c2}$ or $C_{0-3}$alkylene-NR$^{c2}$R$^{d2}$.

For example, each of $R^a$ and $R^b$ independently is cyclohexane or cyclopropane, each of which is optionally substituted with —OH, —OCH$_3$, or —NH$_2$.

For example, $X^1$ is optionally substituted $C_{0-1}$alkylene-$C_{6-10}$aryl.

For example, $X^1$ is phenyl, benzyl, naphthyl, or CH$_2$naphthyl.

For example, $X^1$ is optionally substituted 5 to 10-membered heteroaryl.

For example, $X^1$ is benzoxazolyl, benzimidazolyl, pyridinyl, pyrazinyl, pyridazinyl, pyrimidinyl, indolyl, indazolyl, imidazopyridinyl, quinolinyl, isoquinolinyl, quinazolinyl, oxazolyl, isoxazolyl, thiazolyl, isothiazolyl, benzoxazolyl, oxadiazolyl, triazolyl, imidazolyl, furanyl, or thiophenyl, each of which can be optionally substituted with one or more substituents selected from oxo.

For example, $X^1$ is optionally substituted 5- to 9-membered heterocycloalkyl.

For example, $X^1$ is tetrahydrobenzoxazole, tetrahydrobenzimidazole, morpholine, tetrahydrofuran, tetrahydropyran, piperidine, pyrrolidine, or piperazine, each of which can be optionally substituted with one or more substituents independently selected from $C_{1-6}$alkyl, $C_{1-6}$haloalkyl, $C_{0-3}$alkylene-OR$^e$, $C_{0-3}$alkylene-C(=O)OR$^e$, or R$^{S2}$, in which R$^{S2}$ is $C_{0-3}$alkylene-$C_{6-10}$aryl.

For example, $X^1$ is optionally substituted $C_{3-6}$cycloalkyl.

For example, $X^1$ is —OR$^c$ or —C(=O)$C_{1-6}$alkyl.

For example, $X^1$ is $C_{1-3}$alkyl.

For example, $X^1$ is —OCF$_3$, —O$C_{1-3}$alkyl, —NH$_2$, —CN, —OH or halo.

For example, $X^1$ is $C_{0-1}$alkylene-C(=NR)NR$^c$R$^d$. For example, $X^1$ is —C(=NH)NH$_2$.

For example, $X^1$ is $C_{0-1}$alkylene-NR$^c$C(=NR)NR$^c$R$^d$. For example, $X^1$ is —NHC(=NH)NH$_2$.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, $C_{2-6}$alkynyl, $C_{3-8}$cycloalkyl, $C_{6-10}$aryl, 3- to 12-membered heterocycloalkyl, or 5- to 10-membered heteroaryl, each $X^2$ independently is halo, cyano, oxo, $C_{0-3}$alkylene-OR$''$, $C_{0-3}$alkylene-S(=O)$_m$R$''$, $C_{0-3}$alkylene-NR$''$R$^o$, $C_{0-3}$alkylene-C(=O)NR$''$R$^o$, $C_{0-3}$alkylene-$C_{0-3}$alkylene-C(=O)OR$''$, and each R$''$ and R$^o$ is independently H, $C_{1-6}$alkyl, $C_{2-6}$alkenyl, $C_{2-6}$alkynyl or $C_{1-6}$haloalkyl.

For example, $R^2$ is $Q^2$-$T^2$-$(X^2)_p$, $Q^2$ is a bond, $T^2$ is H, halo, cyano, $C_{1-6}$alkyl, $C_{1-6}$haloalkyl, $C_{2-6}$alkenyl, or $C_{2-6}$alkynyl, and each $X^2$ independently is halo or —O$C_{1-6}$alkyl.

For example, $R^2$ is H, cyano, methyl or methoxymethyl.

For example, $R^2$ is H, methyl or methoxymethyl.

For example, $R^3$ is $C_{1-3}$alkyl, $C_{1-3}$haloalkyl, —CN, —S(=O)$_2C_{1-3}$alkyl or C(=O)O$C_{1-3}$alkyl.

For example, $R^3$ is —CN, $C_{1-3}$alkyl, $C_{1-3}$haloalkyl or —C(=O)O$C_{1-3}$alkyl.

For example, $R^3$ is $C_{1-3}$alkyl, $C_{1-3}$haloalkyl or —C(=O)O$C_{1-3}$alkyl.

For example, $R^3$ is CN, CF$_3$, methyl or —C(=O)O$C_{1-3}$alkyl.

For example, $R^3$ is —CN or —CF$_3$.

For example, $R^4$ is $C_{1-3}$alkyl, $C_{1-3}$haloalkyl, —S(=O)$_2C_{1-3}$alkyl, $C_{3-8}$cycloalkyl, $C_{6-10}$aryl, 3- to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —OR$^{w5}$, and —NR$^{w5}$R$^{x5}$.

For example, $R^4$ is $C_{3-8}$cycloalkyl, $C_{6-10}$aryl, 3 to 12-membered heterocycloalkyl, or 5- to 10-membered heteroaryl, wherein $C_{3-8}$cycloalkyl, $C_{6-10}$aryl, 3- to 12-membered heterocycloalkyl, or 5- to 10-membered heteroaryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —OR$^{w5}$, and —NR$^{w5}$R$^{x5}$, wherein R$^{w5}$ and R$^{x5}$ are independently H, $C_{1-6}$alkyl or $C_{1-6}$haloalkyl.

For example, $R^4$ is $C_{3-8}$cycloalkyl or $C_{6-10}$aryl, wherein $C_{3-8}$cycloalkyl and $C_{6-10}$aryl are optionally substituted with 1-3 substituents selected from the group consisting of halo, oxo, $C_{1-6}$alkyl, $C_{2-6}$alkenyl, $C_{2-6}$alkynyl, cyano, $C_{1-6}$haloalkyl, —OR$^{w5}$, and —NR$^{w5}$R$^{x5}$, wherein R$^{w5}$ and R$^{x5}$ are independently H, $C_{1-6}$alkyl or $C_{1-6}$haloalkyl.

For example, $R^4$ is $C_{3-8}$cycloalkyl.

For example, $R^4$ is cyclopentyl.

For example, $R^4$ is $C_{6-10}$aryl.

For example, $R^4$ is phenyl.

In some embodiments, for a compound of Formula I, or a pharmaceutically acceptable salt, pharmaceutically acceptable solvate or pharmaceutically acceptable hydrate thereof:

Y is —CR$^3$= or —N=;

$R^1$ is $Q^1$-$T^1$-$(X^1)_n$;

$Q^1$ is a bond, —CH$_2$—, or —CH$_2$CH$_2$—;

$T^1$ is $C_{6-10}$aryl, 3- to 12-membered heterocycloalkyl, 5- to 10-membered heteroaryl, —C(=O)—$C_{0-3}$alkylene-3- to 12-membered heterocycloalkyl, —NR$^a$R$^b$, —NR$^a$C(=O)R$^a$, —C(=O)NR$^a$S(=O)$_2$R$^a$, or —C(=O)NR$^a$R$^b$;

each $X^1$ independently is halo, cyano, oxo, $C_{0-3}$alkylene-$OR^c$, $C_{0-3}$alkylene-$C(=O)OR^e$, $C_{0-3}$alkylene-$NR^cR^d$, $C_{0-3}$alkylene-$N^+R^cR^dR^{d'}$, $C_{0-3}$alkylene-$S(=O)_mR^c$, $C_{0-3}$alkylene-$NR^cC(=O)R^c$, $C_{0-3}$alkylene-$OC(=O)NR^cR^d$, $C_{0-3}$alkylene-$C(=O)NR^cR^d$, $C_{0-3}$alkylene-$C(=NR^c)NR^cR^d$, $C_{0-3}$alkylene-$NR^cC(=NR)NR^cR^d$, or $R^{S1}$, in which $R^{S2}$ is $C_{1-6}$alkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, and each $R^{S1}$ is optionally substituted with one or more substituents independently selected from the group consisting of halo, cyano, nitro, oxo, $C_{1-6}$alkyl, $C_{1-6}$haloalkyl, $C_{0-3}$alkylene-$NR^eR^f$, $C_{0-3}$alkylene-$OR^e$, $C_{0-3}$alkylene-$NR^eC(=O)R^e$, $C_{0-3}$alkylene-$C(=O)OR^e$, $C_{0-3}$alkylene-$C(=O)R^e$, $C_{0-3}$alkylene-$S(=O)_mR^e$, $C_{0-3}$alkylene-$NR^eS(=O)_2R^e$, and $R^{S2}$, in which $R^{S2}$ is $C_{0-3}$alkylene-$C_{6-10}$aryl or $C_{0-3}$alkylene-3- to 12-membered heterocycloalkyl, and each $R^{S2}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^w$, and —$NR^wR^x$;

each of $R^a$ and $R^b$, independently, is H or $R^{S5}$, in which $R^{S5}$ is $C_{1-6}$alkyl, $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5- to 10-membered heteroaryl, and $R^{S5}$ is optionally substituted with one or more substituents independently selected from the group consisting of halo, cyano, oxo, $C_{1-6}$haloalkyl, $C_{0-3}$alkylene-$OR^{c2}$, $C_{0-3}$alkylene-$C(=O)R^{c2}$, $C_{0-3}$alkylene-$C(=O)OR^{c2}$, $C_{0-3}$alkylene-$S(=O)_mR^{c2}$, $C_{0-3}$alkylene-$NR^{c2}R^{d2}$, $C_{0-3}$alkylene-$NR^2C(=O)R^{c2}$, $C_{0-3}$alkylene-$NR^2C(=O)OR^{c2}$, $C_{0-3}$alkylene-$NR^{c2}S(=O)_2R^{c2}$, $C_{0-3}$alkylene-$N(S(=O)_2R^2)_2$, and $R^{S6}$, in which $R^{S6}$ is $C_{1-6}$alkyl, $C_{0-3}$alkylene-$C_{3-8}$cycloalkyl, or $C_{0-3}$alkylene-3- to 12-membered heterocycloalkyl, and each $R^{S6}$ is optionally substituted with one or more substituents independently selected from the group consisting of $C_{0-3}$alkylene-$C_{3-8}$cycloalkyl $C_{0-3}$alkylene-$NR^{e2}R^{f2}$, $C_{0-3}$alkylene-$OR^{e2}$;

$R^2$ is $Q^2$-$T^2$-$(X^2)_p$;

$Q^2$ is a bond, —$CH_2$—, or —$CH_2CH_2$—;

$T^2$ is H, halo, cyano, $C_{1-6}$alkyl, $C_{3-8}$cycloalkyl, 3- to 12-membered heterocycloalkyl, 5- to 10-membered heteroaryl, $C(=O)$— 3 to 12-membered heterocycloalkyl, —$OR^z$, —$S(=O)_mR^k$, —$P(=O)R^{kk}R^{mm}$, —$NR^kR^m$, —$C(=O)OR^k$ or —$C(=O)NR^kR^m$;

each $X^2$ independently is halo, cyano, oxo, $C_{0-3}$alkylene-$OR^n$, $C_{0-3}$alkylene-$C(=O)NR^nR^o$, $C_{0-3}$alkylene-$C(=O)OR^n$ or $R^{S3}$, in which $R^{S3}$ is $C_{1-6}$alkyl optionally substituted with $C_{0-3}$alkylene-$OR^p$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{0-3}$alkylene-$C_{3-8}$cycloalkyl, $C_{0-3}$alkylene-3 to 12-membered heterocycloalkyl, or $C_{0-3}$alkylene-5 to 10-membered heteroaryl:

and each $R^z$ is optionally substituted with one or more substituents independently selected from the group consisting of halo, $C_{0-3}$alkylene-$NR^{n2}R^{o2}$, $C_{0-3}$alkylene-$OR^{n2}$, $C_{0-3}$alkylene-$C(=O)OR^{n2}$, $C_{0-3}$alkylene-$C(=O)NR^{n2}R^{o2}$, and $R^{S11}$, in which $R^{S11}$ is $C_{0-3}$alkylene-3 to 12-membered heterocycloalkyl, and each $R^{S11}$ is optionally substituted with one or more substituents independently selected from the group consisting of halo, oxo, cyano, $C_{0-3}$alkylene-$OR^2$, $C_{0-3}$alkylene-$S(=O)_mR^{p2}$, $C_{0-3}$alkylene-$NR^{p2}R^{q2}$, $C_{0-3}$alkylene-$C(=O)$ $NR^{p2}R^{q2}$, $C_{0-3}$alkylene-$C_{0-3}$alkylene-$C(=O)OR^{p2}$, $C_{1-6}$alkyl, $C_{2-6}$alkenyl, $C_{2-6}$alkynyl, and $C_{1-6}$haloalkyl;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —$C(=O)R^r$, —$S(=O)_mR^r$, —$NR^rR^t$, or —$C(=O)OR^r$, wherein $C_{1-3}$alkyl, $C_{2-3}$alkenyl and $C_{2-3}$alkynyl are optionally substituted with $C_{3-6}$cycloalkyl;

$R^4$ is $C_{1-3}$alkyl, $C_{1-3}$haloalkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, wherein $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5 to 10-membered heteroaryl are optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w5}$, and —$NR^{w5}R^{x5}$;

each of $R^c$, $R^{c2}$, $R^d$, $R^{d'}$, and $R^{d2}$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$-cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each of $R^e$, $R^{e2}$, $R^f$, and $R^2$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3 to 12-membered heterocycloalkyl, or $C_{0-3}$alkylene-5- to 10-membered heteroaryl;

each of $R^n$, $R^{n2}$, $R^o$, and $R^{o2}$, independently, is H or $R^{S13}$, in which $R^{S13}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl; and each $R^{S13}$ is optionally substituted with one or more substituents independently selected from the group consisting of halo, oxo, cyano, $C_{0-3}$alkylene-$OR^{p3}$, $C_{0-3}$alkylene-$S(=O)_mR^{p3}$, $C_{0-3}$alkylene-$NR^3R^{g3}$, $C_{0-3}$alkylene-$C(=O)NR^{p3}R^{q3}$, $C_{0-3}$alkylene-$C(=O)OR^3$, $C_{1-6}$alkyl, $C_{2-6}$alkenyl, $C_{2-6}$alkynyl, $C_{1-6}$haloalkyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, and $C_{0-3}$alkylene-5- to 10-membered heteroaryl;

each of $R^p$, $R^{p2}$, $R^{p3}$, $R^{q2}$, and $R^{q3}$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each of $R^r$, and $R^t$, independently, is H, $C_{1-6}$alkyl, $C_{1-6}$haloalkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^w$, $R^{w5}$, $R^x$, and $R^{x5}$, independently, is H, $C_{1-6}$alkyl, $C_{2-6}$alkenyl, $C_{2-6}$alkynyl or $C_{1-6}$haloalkyl;

each of n and p independently is 0, 1, 2, 3, 4, or 5, wherein when $T^2$ is H, p is 0; and m is 0, 1, or 2.

In one embodiment, for a compound of Formula I, or a pharmaceutically acceptable salt, pharmaceutically acceptable solvate or pharmaceutically acceptable hydrate thereof:

$R^1$ is —$(CH_2)_{0-1}$—$C(=O)NR^aR^b$; —$CH_2CH_2$—$NR^aR^b$; —$CH_2CH_2$—$NR^aC(=O)R^a$; —$C(=O)NR^aS(=O)_2R^a$; —$(CH_2)_{0-1}$—$C_{6-10}$aryl; —$(CH_2)_{0-1}$-5- to 6-membered monocyclic heteroaryl; —$(CH_2)_{0-1}$-9- to 10-membered bicyclic heteroaryl; a 4- to 6-membered monocyclic heterocycloalkyl; a 9- to 10-membered bicyclic heterocycloalkyl; —$C(=O)$-4- to 6-membered monocyclic heterocycloalkyl; —$C(=O)$-9- to 10-membered bicyclic heterocycloalkyl;

wherein the aryl, 5heteroaryl, and heterocycloalkyl rings are optionally independently substituted with 1, 2, 3, 4, or 5 $X^1$;

each $X^1$ independently is halo; cyano; oxo; $C_{1-6}$alkyl optionally substituted with one or more substituents independently selected from the group consisting of halo, $C_{0-3}$alkylene-$NR^eR^f$, $C_{0-3}$alkylene-$OR^e$, $C_{0-3}$alkylene-C(=O)$OR^e$, $C_{0-3}$alkylene-$C_{3-6}$cycloalkyl, $C_{0-3}$alkylene-$C_{6-10}$aryl, and $C_{0-3}$alkylene-4 to 6-membered heterocycloalkyl, wherein heterocycloalkyl is optionally independently substituted with one or more $C_{1-6}$alkyl; $C_{0-3}$alkylene-$C_{3-6}$cycloalkyl optionally substituted with one or more substituents independently selected from the group consisting of $C_{1-6}$alkyl, $C_{1-6}$haloalkyl, $C_{0-3}$alkylene-$NR^eR^f$, and $C_{0-3}$alkylene-$OR^e$; $C_{0-3}$alkylene-$C_{6-10}$aryl, wherein $C_{6-10}$aryl is optionally substituted with one or more substituents selected from the group consisting of halo, cyano, nitro, $C_{1-6}$alkyl, $C_{1-6}$haloalkyl, $C_{0-3}$alkylene-$NR^eR^f$, $C_{0-3}$alkylene-$OR^e$, $C_{0-3}$alkylene-C(=O)$OR^e$, $C_{0-3}$alkylene-C(=O)$R^e$, $C_{0-3}$alkylene-S(=O)$_mR^e$, and $C_{0-3}$alkylene-$NR^eS$(=O)$_2R^e$; $C_{0-3}$alkylene-4- to 6-membered monocyclic heterocycloalkyl or 9- or 10-membered bicyclic heterocycloalkyl, wherein heterocycloalkyl is optionally substituted with one or more substituents independently selected from the group consisting of oxo, $C_{0-3}$alkylene-$NR^eR^f$, and $C_{0-3}$alkylene-$OR^e$; $C_{0-3}$alkylene-5- or 6-membered monocyclic heteroaryl or 9- or 10-membered bicyclic heteroaryl, wherein heteroaryl is independently optionally substituted with one or more $C_{0-3}$alkylene-$OR^e$; $C_{0-3}$alkylene-$OR^c$; $C_{0-3}$alkylene-C(=O)$R^c$; $C_{0-3}$alkylene-$NR^cR^d$; $C_{0-3}$alkylene-$N^+R^cR^dR^{d'}$; $C_{0-3}$alkylene-S(=O)$_mR^c$; $C_{0-3}$alkylene-$NR^cC$(=O)$R^c$; $C_{0-3}$alkylene-OC(=O)$NR^cR^d$; $C_{0-3}$alkylene-C(=O)$NR^cR^d$; $C_{0-3}$alkylene-C(=NR)$NR^cR^d$; or $C_{0-3}$alkylene-$NR^cC$(=NR)$NR^cR^d$;

each of $R^a$ and $R^b$, independently, is H or $R^{S5}$, in which $R^{S5}$ is $C_{1-6}$alkyl, $C_{0-3}$alkylene-$C_{3-6}$cycloalkyl, $C_{0-3}$alkylene-$C_{6-10}$aryl, $C_{0-3}$alkylene-4- to 6-membered monocyclic heterocycloalkyl, $C_{0-3}$alkylene-9- or 10-membered bicyclic hetercycloalkyl, $C_{0-3}$alkylene-5- or 6-membered monocyclic heteroaryl, or $C_{0-3}$alkylene-9- or 10-membered bicyclic heteroaryl;

and $R^{S5}$ is optionally substituted with one or more substituents selected from the group consisting of halo, cyano, oxo, $C_{1-6}$haloalkyl, $C_{0-3}$alkylene-$OR^{c2}$, $C_{0-3}$alkylene-C(=O)$R^{c2}$, $C_{0-3}$alkylene-C(=O)$OR^{c2}$, $C_{0-3}$alkylene-S(=O)$_m$ $R^{c2}$, $C_{0-3}$alkylene-$NR^{c2}R^{d2}$, $C_{0-3}$alkylene-$NR^2C$(=O)$R^{c2}$, $C_{0-3}$alkylene-$NR^2C$(=O)$OR^{c2}$, $C_{0-3}$alkylene-$NR^2S$(=O)$_2R^{c2}$, $C_{0-3}$alkylene-N(S(=O)$_2R^2$)$_2$, and $R^{S6}$, in which $R^{S6}$ is $C_{1-6}$alkyl, $C_{0-3}$alkylene-$C_{3-6}$cycloalkyl, or $C_{0-3}$alkylene-4- to 6-membered monocyclic heterocycloalkyl;

and each $R^{S6}$ is optionally substituted with one or more $C_{0-3}$alkylene-$C_{3-6}$cycloalkyl, $C_{0-3}$alkylene-$NR^{e2}R^{f2}$, $C_{0-3}$alkylene-$OR^{e2}$;

$R^2$ is $Q^2$-$T^2$-$(X^2)_p$;

$Q^2$ is a bond, —$CH_2$—, or —$CH_2CH_2$—;

$T^2$ is H, halo, cyano, $C_{1-6}$alkyl, $C_{3-6}$cycloalkyl, 4- to 6-membered monocyclic heterocycloalkyl, 9- or 10-membered bicyclic heterocycloalkyl, 5- or 6-membered monocyclic heteroaryl, 9- or 10-membered bicyclic heteroaryl, C(=O)— 4- to 6-membered monocyclic heterocycloalkyl, —$OR^z$, —S(=O)$_mR^k$, —P(=O)$R^kR^m$, —$NR^kR^m$, —C(=O)$OR^k$ or —C(=O)$NR^kR^m$;

each $X^2$ independently is halo, cyano, oxo, $C_{0-3}$alkylene-$OR^n$, $C_{0-3}$alkylene-C(=O)$NR^nR^o$, $C_{0-3}$alkylene-C(=O)$OR^n$ or $C_{1-6}$alkyl, wherein $C_{1-6}$alkyl is optionally substituted with one $C_{0-3}$alkylene-$OR^p$;

each of $R^{kk}$, and $R^{mm}$, is independently selected from the group consisting of $R^k$, —$OR^k$, and —$NR^kR^m$;

each of $R^k$, and $R^m$, independently, is H or $R^z$, in which $R^z$ is $C_{1-6}$alkyl, $C_{0-3}$alkylene-$C_{3-6}$cycloalkyl, $C_{0-3}$alkylene-4- to 6-membered monocyclic heterocycloalkyl, $C_{0-3}$alkylene-9- or 10-membered bicyclic heterocycloalkyl, $C_{0-3}$alkylene-5 or 6-membered monocyclic heteroaryl, or $C_{0-3}$alkylene-9- or 10-membered bicyclic heteroaryl;

and each $R^z$ is optionally substituted with one or more substituents selected from the group consisting of halo, $C_{1-6}$alkyl, $C_{0-3}$alkylene-$NR^{n2}R^{o2}$, $C_{0-3}$alkylene-$OR^{n2}$, $C_{0-3}$alkylene-C(=O)$OR^{n2}$, $C_{0-3}$alkylene-C(=O)$NR^{n2}R^{o2}$, and $R^{S11}$, in which $R^{S11}$ is $C_{0-3}$alkylene-4- to 6-membered monocyclic heterocycloalkyl, $C_{0-3}$alkylene-9- or 10-membered bicyclic heterocycloalkyl, $C_{0-3}$alkylene-5- or 6-membered monocyclic heteroaryl, or $C_{0-3}$alkylene-9- or 10-membered bicyclic heteroaryl;

and each $R^{S11}$ is optionally substituted with one or more substituents independently selected from the group consisting of halo, oxo, cyano, $C_{0-3}$alkylene-$OR^{p2}$, $C_{0-3}$alkylene-S(=O)$_mR^{p2}$, $C_{0-3}$alkylene-$NR^{p2}R^{q2}$, $C_{0-3}$alkylene-C(=O)$NR^{p2}R^{q2}$, $C_{0-3}$alkylene-$C_{0-3}$alkylene-C(=O)$OR^{p2}$, $C_{1-6}$alkyl, $C_{2-6}$alkenyl, $C_{2-6}$alkynyl, and $C_{1-6}$haloalkyl;

$R^3$ is $C_{1-3}$alkyl, $C_{1-3}$haloalkyl, $C_{2-3}$alkenyl, $C_{2-3}$alkynyl, $C_{3-6}$cycloalkyl, —CN, —$OR^r$, —C(=O)$R^r$, —S(=O)$_mR^r$, $NR^rR^t$, or —C(=O)$OR^r$, wherein $C_{1-3}$alkyl, $C_{2-3}$alkenyl and $C_{2-3}$alkynyl are optionally substituted with $C_{3-6}$cycloalkyl;

$R^4$ is $C_{1-3}$alkyl, $C_{1-3}$haloalkyl, $C_{3-6}$cycloalkyl, phenyl, or 5- or 6-membered monocyclic heteroaryl, wherein cycloalkyl, phenyl and heteroaryl are optionally substituted with one or more substituents independently selected from the group consisting of halo, cyano, $C_{1-3}$alkyl, $C_{1-3}$haloalkyl, $C_{2-3}$alkenyl, $C_{2-3}$alkynyl, —$OR^{w5}$, and —$NR^{w5}R^{x5}$;

each of $R^r$, and $R^t$, independently, is H, $C_{1-3}$alkyl, $C_{1-3}$haloalkyl, $C_{2-3}$alkenyl, $C_{2-3}$alkynyl, $C_{3-6}$cycloalkyl, phenyl, 4- to 6-membered monocyclic heterocycloalkyl, or 5- or 6-membered monocyclic heteroaryl;

each of $R^c$, $R^{c2}$, $R^d$, $R^{d'}$, $R^{d2}$, $R^e$, $R^{e2}$, $R^f$, $R^{f2}$, $R^n$, $R^{n2}$, $R^o$, $R^{o2}$, $R^p$, $R^{p2}$, and $R^{q2}$, independently, is H, $C_{1-3}$alkyl, $C_{1-3}$haloalkyl, $C_{3-6}$cycloalkyl, phenyl, 4- to 6-membered monocyclic heterocycloalkyl, or 5- or 6-membered monocyclic heteroaryl;

each $R^w$, $R^{w5}$, $R^x$, and $R^{x5}$, independently, is H, $C_{1-3}$alkyl, or $C_{1-3}$haloalkyl;

p is 0, 1, 2, 3, 4, or 5; and m is 0, 1, or 2.

In another aspect, the present invention provides the compounds of Formula (III):

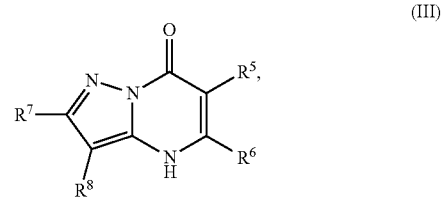

or a pharmaceutically acceptable salt, pharmaceutically acceptable solvate or pharmaceutically acceptable hydrate thereof. In this formula:

$R^5$ is selected from the group consisting of —C(=O)$NR^9R^{10}$; —$CH_2C$(=O)$NR^{11}R^{12}$; —$CH_2CH_2NR^{13}R^{14}$; —$CH_2$-phenyl; —$CH_2$-5-membered monocyclic heteroaryl optionally substituted with one $C_{1-3}$alkyl, monocyclic $C_{5-6}$cycloalkyl, or phenyl, wherein phenyl is optionally substituted with one —$OC_{1-3}$alkyl; phenyl optionally substituted with one halo or $C_{1-3}$alkyl; a 5- or 6-membered monocylic heterocycloalkyl optionally substituted with 1, 2, or 3 $R^{15}$; a 5- or 6-membered monocylic heteroaryl optionally substituted with 1, 2, or 3 $R^{16}$; and 9- or 10-membered bicyclic heteroaryl optionally substituted with 1, 2, 3, or 4 $R^{17}$;

$R^9$ and $R^{10}$ are independently selected from the group consisting of H; $C_{1-3}$alkyl optionally substituted with 1 or 2 substituents independently selected from the group consisting of —OH and —$OC_{1-3}$alkyl; —$CH_2$phenyl; —S(=O)$_2$ $R^{18}$; $C_{5-6}$cycloalkyl optionally substituted with one —$NH_2$, oxo, —OH, or —$OC_{1-3}$alkyl; phenyl optionally substituted with 1, 2, or 3 $R^{19}$; a 5- or 6-membered monocyclic heterocycloalkyl optionally substituted with one —$C_{1-3}$alkyl, —C(=O)$C_{1-3}$alkyl, or —C(=O)$OC_{1-6}$alkyl; a 5- or 6-membered monocyclic heteroaryl optionally substituted with 1, 2, or 3 $R^{20}$; and a 9- or 10-membered bicyclic heteroaryl optionally substituted with 1 or 2 halo; or $R^9$ and $R^{10}$ combine with the nitrogen to which they are bound to form an N-linked 5- or 6-membered monocyclic heterocycloalkyl optionally substituted with one phenyl;

$R^{11}$ and $R^{12}$ are independently selected from the group consisting of H; $C_{1-3}$alkyl optionally substituted with one —OH or —$OC_{1-3}$alkyl; phenyl optionally substituted with one —$NH_2$ or —$OC_{1-3}$alkyl; and a 5- or 6-membered monocyclic heteroaryl; or $R^{11}$ and $R^{12}$ combine with the nitrogen to which they are bound to form an N-linked 5- or 6-membered monocyclic heterocycloalkyl optionally substituted with one $C_{1-3}$alkyl, phenyl or —$CH_2$-phenyl, wherein the phenyl ring of phenyl or —$CH_2$-phenyl is optionally substituted with one $C_{1-3}$alkyl;

$R^{13}$ and $R^{14}$ are independently selected from the group consisting of H; —C(=O)$C_{1-3}$alkyl; —C(=O)phenyl; and phenyl optionally substituted with one —$OC_{1-3}$alkyl;

each $R^{15}$ is independently selected from the group consisting of oxo; —C(=O)OH; —C(=O)$OC_{1-3}$alkyl; and $C_{1-3}$alkyl optionally substituted with one —OH or —$OC_{1-3}$alkyl;

each $R^{16}$ is independently selected from the group consisting of —CN; —C(=O)OH; —C(=O)$OC_{1-3}$alkyl; —C(=O)$NH_2$; —C(=O)$NHC_{1-3}$alkyl; —C(=O)N($C_{1-3}$alkyl)$_2$; —C(=NH)$NH_2$; —N HC(=NH)$NH_2$; —$NH_2$; —$NHC_{1-3}$alkyl; —N($C_{1-3}$alkyl)$_2$; —$NHC_{3-6}$cycoalkyl; —N($C_{1-3}$alkyl)$C_{3-6}$cycoalkyl; $C_{1-3}$alkyl optionally substituted with one —OH, —$OC_{1-3}$alkyl, or 5- or 6-membered monocyclic heterocycloalkyl, wherein the monocyclic heterocycloalkyl is optionally substituted with —$C_{1-3}$alkyl; $C_{1-3}$haloalkyl optionally substituted with 1 or 2 substituents independently selected from the group consisting of —OH and phenyl; —$C_{3-6}$cycloalkyl optionally substituted with one —$NH_2$, $C_{1-3}$alkyl, $C_{1-3}$haloalkyl, or —$OC_{1-3}$alkyl; phenyl optionally substituted with one —OH, —$OC_{1-3}$alkyl, —$NO_2$, —$NH_2$, —$NHC_{1-3}$alkyl, or —N($C_{1-3}$alkyl)$_2$; 5- or 6-membered monocyclic heterocycloalkyl optionally substituted with 1 or 2 substituents independently selected from the group consisting of oxo, —OH, —$NH_2$, —$OC_{1-3}$alkyl, —C(=O)$C_{1-3}$alkyl, —S(=O)$_2C_{1-3}$alkyl, —C(=O)$OC_{1-6}$alkyl, —C(=O)$OCH_2$phenyl, and $C_{1-3}$alkyl, wherein $C_{1-3}$alkyl is optionally substituted with one —$NH_2$, —NHS(=O)$_2C_{1-3}$alkyl, —OH, or —$OC_{1-3}$alkyl; and 5- or 6-membered monocyclic heteroaryl optionally substituted with one —OH or —$OC_{1-3}$alkyl;

each $R^{17}$ is independently selected from the group consisting of oxo; halo; —OH; —CN; —$NH_2$; —$NHC_{1-3}$alkyl; —N($C_{1-3}$alkyl)$_2$; —N+($C_{1-3}$alkyl)$_3$; —$NHC(=O)C_{1-3}$alkyl; —C(=O)$C_{1-3}$alkyl; —S(=O)$_mC_{1-3}$alkyl; —C(=O)OH;  —C(=O)$OC_{1-6}$alkyl; —C(=O)$NH_2$; —C(=O)$NHC_{1-3}$alkyl; —C(=O)N($C_{1-3}$alkyl)$_2$; —OC(=O)$NH_2$; —OC(=O)$NHC_{1-3}$alkyl; —OC(=O)N($C_{1-3}$alkyl)$_2$; —C(=NH)$NH_2$; —C(=NH)$NHC_{1-3}$alkyl; —C(=NH)N($C_{1-3}$alkyl)$_2$; —$OC_{1-3}$haloalkyl; $C_{1-3}$haloalkyl; monocyclic $C_{3-6}$cycloalkyl; $C_{1-3}$alkyl optionally substituted with one monocyclic $C_{3-6}$cycloalkyl, —OH, —$OC_{1-3}$alkyl, —C(=O)OH, —C(=O)$OC_{1-3}$alkyl, —$NH_2$, —$NHC_{1-3}$alkyl, or —N($C_{1-3}$alkyl)$_2$; —$OC_{1-3}$alkyl optionally substituted with one monocyclic $C_{3-6}$cycloalkyl, phenyl, —OH, —$OC_{1-3}$alkyl, —C(=O)OH, —C(=O)$OC_{1-3}$alkyl, —C(=O)$NH_2$, —C(=O)$NHC_{1-3}$alkyl, —C(=O)N($C_{1-3}$alkyl)$_2$, —$NH_2$, —$NHC_{1-3}$alkyl, —N($C_{1-3}$alkyl)$_2$, —NHC(=O)$C_{1-3}$alkyl, or —NHS(=O)$_2C_{1-3}$alkyl; and phenyl optionally substituted with one halo, —CN, $C_{1-3}$alkyl, $C_{1-3}$haloalkyl, —$OC_{1-3}$ alkyl, —$NH_2$, —$NHC_{1-3}$alkyl or —N($C_{1-3}$alkyl)$_2$;

$R^{18}$ is selected from the group consisting of $C_{1-3}$alkyl; monocyclic $C_{3-6}$cycloalkyl; a 5- or 6-membered monocyclic heteroaryl; phenyl; and —$CH_2$phenyl; wherein the phenyl ring of phenyl or —$CH_2$phenyl is optionally substituted with one halo, —CN, or —$OC_{1-3}$alkyl;

each $R^{19}$ is independently selected from the group consisting of halo; —CN; —$NH_2$; —$NHC_{1-3}$alkyl; —N($C_{1-3}$alkyl)$_2$; —$NHC(=O)C_{1-3}$alkyl; —NHS(=O)$_2C_{1-3}$alkyl; —N(S(=O)$_2C_{1-3}$alkyl)$_2$; —NHS(=O)$_2C_{3-6}$cycloalkyl; —NHS(=O)$_2$phenyl; —NHC(=O)OH; —NHC(=O)$OC_{1-3}$ alkyl; —S(=O)$_2C_{1-3}$alkyl; —$OC_{1-3}$alkyl optionally substituted with one phenyl; $C_{1-3}$haloalkyl; —$OC_{1-3}$haloalkyl; monocyclic $C_{3-6}$cycloalkyl; a 5- or 6-membered monocyclic heterocycloalkyl; and $C_{1-3}$alkyl optionally substituted with one monocyclic $C_{3-6}$cycloalkyl, —OH, —$OC_{1-3}$ alkyl, —$NH_2$, —$NHC_{1-3}$alkyl, or —N($C_{1-3}$alkyl)$_2$;

each $R^{20}$ is independently selected from the group consisting of —CN; —$OC_{1-3}$alkyl; —S(=O)$_2C_{1-3}$alkyl; $C_{1-3}$haloalkyl; and $C_{1-3}$alkyl optionally substituted with one —OH or —$OC_{1-3}$alkyl; and monocyclic $C_{3-6}$cycloalkyl;

$R^6$ is selected from the group consisting of H; halo; —CN; —$NH_2$; —C(=O)OH; —C(=O)$OC_{1-3}$alkyl; —C(=O)$C_{1-3}$alkyl; —S(=O)$_mC_{1-3}$alkyl; —P(=O)($C_{1-3}$alkyl)$_2$; —C(=O)$NR^{21}R^{22}$; $C_{1-3}$haloalkyl; —$OC_{1-3}$alkyl optionally substituted with one —OH, —$OC_{1-3}$alkyl, —$NH_2$, —$NHC_{1-3}$ alkyl, or —N($C_{1-3}$alkyl)$_2$; $C_{1-3}$alkyl optionally substituted with one —$NH_2$, —$NHC_{1-3}$alkyl, —N($C_{1-3}$alkyl)$_2$, —C(=O)OH, —C(=O)$OC_{1-3}$alkyl, —S(=O)$_mC_{1-3}$ alkyl, —C(=O)$C_{1-3}$alkyl, —$OR^{23}$, or 5- or 6-membered monocyclic heteroaryl, wherein monocyclic heteroaryl is optionally substituted with 1 or 2 $C_{1-3}$alkyl; monocyclic $C_{3-6}$cycloalkyl optionally substituted with one —C(=O)OH, —C(=O)$OC_{1-3}$alkyl or $C_{1-3}$alkyl, wherein $C_{1-3}$alkyl is optionally substituted with one —OH or —$OC_{1-3}$ alkyl; a 5- or 6-membered monocyclic heterocycloalkyl optionally substituted with one —C(=O)OH, or —C(=O)$OC_{1-3}$alkyl; and a 5- or 6-membered heteroaryl optionally substituted with 1 or 2 $C_{1-3}$alkyl;

$R^{21}$ and $R^{22}$ are independently selected from the group consisting of H; $C_{1-6}$alkyl optionally substituted with one —OH, —$OC_{1-3}$alkyl, —C(=O)OH, —C(=O)$OC_{1-3}$alkyl, —$NH_2$, —$NHC_{1-3}$alkyl, —N($C_{1-3}$alkyl)$_2$, or 5- or 6-membered monocyclic heteroaryl; $C_{1-3}$haloalkyl optionally substituted with one —OH or —$OC_{1-3}$alkyl; a 5- or 6-membered monocyclic heteroaryl optionally substituted with 1 or 2 $C_{1-3}$alkyl; and a 4- to 6-membered monocyclic heterocycloalkyl; or $R^{21}$ and $R^{22}$ combine with the nitrogen to which they are bound to form an N-linked 5- or 6-membered monocyclic heterocycloalkyl optionally substituted with one —C(=O)

OH, —C(=O)OC$_{1-3}$alkyl, or C$_{1-3}$alkyl, wherein C$_{1-3}$alkyl is optionally substituted with one —OH or —OC$_{1-3}$alkyl;

R$^{23}$ is selected from the group consisting of H; C$_{1-3}$haloalkyl; C$_{1-3}$alkyl optionally substituted with one —OH, —OC$_{1-3}$alkyl, —C(=O)OH, —C(=O)OC$_{1-3}$alkyl, —C(=O)NH$_2$, —C(=O)NHC$_{1-3}$alkyl, —C(=O)N(C$_{1-3}$alkyl)$_2$, phenyl, 5- or 6-membered monocyclic heteroaryl, or 5- or 6-membered monocyclic heterocycloalkyl, wherein monocyclic heterocycloalkyl is optionally substituted with 1 or 2 oxo or C$_{1-3}$alkyl; a 4-, 5-, or 6-membered monocyclic heterocycloalkyl optionally substituted with 1 or 2 substituents independently selected from the group consisting of oxo and C$_{1-3}$alkyl; and a 5- or 6-membered monocyclic heteroaryl;

R$^7$ is selected from the group consisting of —CN; —OH; —C(=O)OH; —C(=O)OC$_{1-3}$alkyl; —C(=O)C$_{1-3}$alkyl; —S(=O)$_m$C$_{1-3}$alkyl; —NH$_2$; —NHC$_{1-3}$alkyl; —N(C$_{1-3}$alkyl)$_2$; C$_{1-3}$alkyl optionally substituted with one monocyclic C$_{3-6}$cycloalkyl; C$_{1-3}$haloalkyl; C$_{2-3}$alkenyl optionally substituted with one monocyclic C$_{3-6}$cycloalkyl; C$_{2-3}$alkynyl optionally substituted with one monocyclic C$_{3-6}$cycloalkyl; monocyclic C$_{3-6}$cycloalkyl; —O-5- or 6-membered monocyclic heterocycloalkyl; and —OC$_{1-3}$alkyl optionally substituted with one —OH, —OC$_{1-3}$alkyl, —C(=O)OH, or —C(=O)OC$_{1-3}$alkyl;

R$^8$ is selected from the group consisting of C$_{1-3}$alkyl; C$_{1-3}$haloalkyl; monocyclic C$_{3-6}$cycloalkyl; phenyl optionally substituted with 1, 2, or 3 substituents independently selected from the group consisting of —CN, halo, C$_{1-3}$alkyl, C$_{1-3}$haloalkyl, —OC$_{1-3}$alkyl and —OC$_{1-3}$haloalkyl; and pyridinyl optionally substituted with 1, 2, or 3 substituents independently selected from the group consisting of —CN, halo, C$_{1-3}$alkyl, C$_{1-3}$haloalkyl, —OC$_{1-3}$alkyl and —OC$_{1-3}$haloalkyl;

with the proviso that:

a) when R$^5$ is unsubstituted phenyl, R$^6$ is methyl and R$^7$ is methyl, R$^8$ is not ethyl, unsubstituted phenyl, or unsubstituted pyridine;

b) when R$^5$ is unsubstituted cyclohexyl, R$^6$ is methyl and R$^7$ is methyl, R$^8$ is not unsubstituted pyridine;

c) when R$^5$ is unsubstituted cyclopentyl, R$^6$ is methyl and R$^7$ is methyl, R$^8$ is not ethyl or unsubstituted pyridine, d) when R$^6$ is methyl, R$^7$ is methyl and R$^8$ is 3,4-diethoxy-phenyl, R$^5$ is not unsubstituted 1-pyrrolidine, unsubstituted 1-piperidine, 4-methyl-1-piperidine, unsubstituted 2-1,2,3,4-tetrahydro-isoquinoline, or unsubstituted morpholine;

e) when R$^5$ is unsubstituted CH$_2$-phenyl, R$^6$ is methyl and R$^7$ is methyl, R$^8$ is not ethyl, trifluoromethyl, unsubstituted pyridine, unsubstituted phenyl, phenyl mono-substituted with 4-F, 4-Cl, 2-methoxy or 4-methoxy, or phenyl disubstituted with 3,4-methoxy;

f) when R$^5$ is unsubstituted CH$_2$-phenyl, R$^6$ is methyl and R$^7$ is trifluoromethyl, R$^8$ is not unsubstituted phenyl or phenyl substituted with 2-Cl or 4-Cl;

g) when R$^6$ is methyl, R$^7$ is methyl and R$^8$ is unsubstituted phenyl, R$^5$ is not CH$_2$CH$_2$C(=O)NH-phenyl wherein the phenyl ring is unsubstituted or is substituted at the 4-position with Cl, methyl or methoxy;

h) when R$^6$ is methyl or ethyl, R$^7$ is methyl and R$^8$ is unsubstituted phenyl, R$^5$ is not substituted pyrazolo[1,5-a]pyrimidin-7-yl;

i) when R$^6$ is H, R$^7$ is isopropyl and R$^8$ is methyl, R$^5$ is not unsubstituted pyrazole; and j) the compound is not wherein R$^5$ is unsubstituted CH$_2$-phenyl, R$^6$ is H, R$^7$ is methyl and R$^8$ is unsubstituted phenyl.

In one embodiment of compounds of Formula (III), R$^5$ is a 9- or 10-membered bicyclic heteroaryl optionally substituted with 1, 2, 3, or 4 R$^{17}$.

In one embodiment, a subset of compounds of Formula (III) includes those of Formula (IIIa):

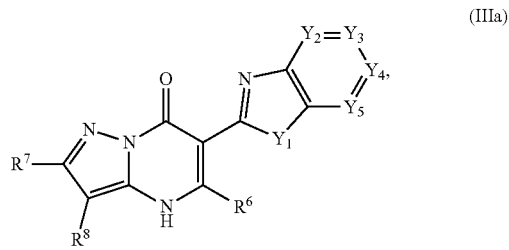

(IIIa)

or a pharmaceutically acceptable salt, pharmaceutically acceptable solvate or pharmaceutically acceptable hydrate thereof, wherein Y$_1$ is —O—, —NH—, —NR$^{24}$—, or —S—, and Y$_2$, Y$_3$, Y$_4$, and Y$_5$ are —N= or —CR$^{25}$=, provided that 0, 1 or 2 of Y$_2$, Y$_3$, Y$_4$, and Y$_5$ are —N=; wherein R$^{24}$ is selected from the group consisting of C$_{1-3}$haloalkyl; monocyclic C$_{3-6}$cycloalkyl; C$_{1-3}$alkyl optionally substituted with one monocyclic C$_{3-6}$cycloalkyl, —OH, —OC$_{1-3}$alkyl, —C(=O)OH, —C(=O)OC$_{1-3}$alkyl, —NH$_2$, —NHC$_{1-3}$alkyl, or —N(C$_{1-3}$alkyl)$_2$; and phenyl optionally substituted with one halo, —CN, C$_{1-3}$alkyl, C$_{1-3}$haloalkyl, —OC$_{1-3}$alkyl, —NH$_2$, —NHC$_{1-3}$alkyl or —N(C$_{1-3}$alkyl)$_2$; and wherein R$^{25}$ is H or R$^{17}$, wherein R$^{17}$ is as defined for compounds of Formula (III), provided that 0, 1, 2 or 3 of Y$_2$, Y$_3$, Y$_4$, and Y$_5$ are —CR$^{25}$= wherein R$^{25}$ is R$^{17}$; and wherein R$^6$, R$^7$ and R$^8$ are as defined for compounds of Formula (III).

In one embodiment of compounds of Formula (IIIa), R$^6$ is —CN or C$_{1-3}$alkyl optionally substituted with one —NH$_2$, —NHC$_{1-3}$alkyl, —N(C$_{1-3}$alkyl)$_2$, —C(=O)OH, —C(=O)OC$_{1-3}$alkyl, —S(=O)$_m$C$_{1-3}$alkyl, —C(=O)C$_{1-3}$alkyl, —OR$^{23}$, or 5- or 6-membered monocyclic heteroaryl, wherein monocyclic heteroaryl is optionally substituted with 1 or 2 C$_{1-3}$alkyl; and R$^7$ is —CN or —CF$_3$, wherein R$^{23}$ is as defined for compounds of Formula (III).

In another aspect, the present invention provides the compounds of Formula (IV):

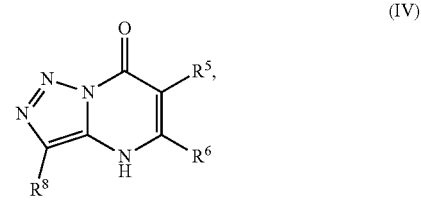

(IV)

or a pharmaceutically acceptable salt, pharmaceutically acceptable solvate or pharmaceutically acceptable hydrate thereof. In this formula R$^5$, R$^6$, and R$^8$ are as defined for compounds of Formula (III), and provided the compound is not wherein R$^5$ is unsubstituted phenyl, R$^6$ is H and R$^8$ is 2-fluoro-phenyl.

Representative compounds of the present invention are listed in Table 1A below followed by their compound number:

TABLE 1A

N-(4-methoxyphenyl)-5-methyl-7-oxo-3-phenyl-2-(trifluoromethyl)-4,7-dihydropyrazolo[1,5-a]pyrimidine-6-carboxamide (A1001);
5-methyl-7-oxo-N,3-diphenyl-2-(trifluoromethyl)-4,7-dihydropyrazolo[1,5-a]pyrimidine-6-carboxamide (A1002);
5-methyl-3-phenyl-6-(4-phenylpiperazine-1-carbonyl)-2-(trifluoromethyl)pyrazolo[1,5-a]pyrimidin-7(4H)-one (A1003);
5-methyl-6-(morpholine-4-carbonyl)-3-phenyl-2-(trifluoromethyl)pyrazolo[1,5-a]pyrimidin-7(4H)-one (A1004);
5-methyl-7-oxo-3-phenyl-N-(pyridin-3-yl)-2-(trifluoromethyl)-4,7-dihydropyrazolo[1,5-a]pyrimidine-6-carboxamide (A1005);
N-(2-aminophenyl)-5-methyl-7-oxo-3-phenyl-2-(trifluoromethyl)-4,7-dihydropyrazolo[1,5-a]pyrimidine-6-carboxamide (A1006);
5-methyl-7-oxo-3-phenyl-2-(trifluoromethyl)-N-(4-(trifluoromethyl)phenyl)-4,7-dihydropyrazolo[1,5-a]pyrimidine-6-carboxamide (A1007);
N-cyclopentyl-5-methyl-7-oxo-3-phenyl-2-(trifluoromethyl)-4,7-dihydropyrazolo[1,5-a]pyrimidine-6-carboxamide (A1008);
5-methyl-3-phenyl-6-(pyrrolidine-1-carbonyl)-2-(trifluoromethyl)pyrazolo[1,5-a]pyrimidin-7(4H)-one (A1009);
N-cyclohexyl-5-methyl-7-oxo-3-phenyl-2-(trifluoromethyl)-4,7-dihydropyrazolo[1,5-a]pyrimidine-6-carboxamide (A1010);
5-methyl-3-phenyl-6-(piperidine-1-carbonyl)-2-(trifluoromethyl)pyrazolo[1,5-a]pyrimidin-7(4H)-one (A1011);
5-methyl-7-oxo-3-phenyl-N-(p-tolyl)-2-(trifluoromethyl)-4,7-dihydropyrazolo[1,5-a]pyrimidine-6-carboxamide (A1012);
N-benzyl-N-methyl-7-oxo-3-phenyl-2-(trifluoromethyl)-4,7-dihydropyrazolo[1,5-a]pyrimidine-6-carboxamide (A1013);
N-((1R,2R)-2-aminocyclohexyl)-5-methyl-7-oxo-3-phenyl-2-(trifluoromethyl)-4,7-dihydropyrazolo[1,5-a]pyrimidine-6-carboxamide (A1014);
N-(4-cyanophenyl)-5-methyl-7-oxo-3-phenyl-2-(trifluoromethyl)-4,7-dihydropyrazolo[1,5-a]pyrimidine-6-carboxamide (A1015);
N-(4-chlorophenyl)-5-methyl-7-oxo-3-phenyl-2-(trifluoromethyl)-4,7-dihydropyrazolo[1,5-a]pyrimidine-6-carboxamide (A1016);
5-methyl-7-oxo-3-phenyl-N-(pyridin-2-yl)-2-(trifluoromethyl)-4,7-dihydropyrazolo[1,5-a]pyrimidine-6-carboxamide (A1017);
5-methyl-7-oxo-3-phenyl-N-(pyridazin-4-yl)-2-(trifluoromethyl)-4,7-dihydropyrazolo[1,5-a]pyrimidine-6-carboxamide (A1018);
N-(3,5-dimethylisoxazol-4-yl)-5-methyl-7-oxo-3-phenyl-2-(trifluoromethyl)-4,7-dihydropyrazolo[1,5-a]pyrimidine-6-carboxamide (A1019);
N-(isoxazol-3-yl)-5-methyl-7-oxo-3-phenyl-2-(trifluoromethyl)-4,7-dihydropyrazolo[1,5-a]pyrimidine-6-carboxamide (A1020);
N-(2-acetamidophenyl)-5-methyl-7-oxo-3-phenyl-2-(trifluoromethyl)-4,7-dihydropyrazolo[1,5-a]pyrimidine-6-carboxamide (A1021);
5-methyl-N-(2-(methylsulfonamido)phenyl)-7-oxo-3-phenyl-2-(trifluoromethyl)-4,7-dihydropyrazolo[1,5-a]pyrimidine-6-carboxamide (A1022);
N-benzyl-5-methyl-7-oxo-3-phenyl-2-(trifluoromethyl)-4,7-dihydropyrazolo[1,5-a]pyrimidine-6-carboxamide (A1023);
5-methyl-7-oxo-3-phenyl-N-(pyrazin-2-yl)-2-(trifluoromethyl)-4,7-dihydropyrazolo[1,5-a]pyrimidine-6-carboxamide (A1024);
5-methyl-7-oxo-3-phenyl-N-(tetrahydro-2H-pyran-4-yl)-2-(trifluoromethyl)-4,7-dihydropyrazolo[1,5-a]pyrimidine-6-carboxamide (A1025);
5-methyl-N-(1-methylpiperidin-4-yl)-7-oxo-3-phenyl-2-(trifluoromethyl)-4,7-dihydropyrazolo[1,5-a]pyrimidine-6-carboxamide (A1026);
N-(1-acetylpiperidin-4-yl)-5-methyl-7-oxo-3-phenyl-2-(trifluoromethyl)-4,7-dihydropyrazolo[1,5-a]pyrimidine-6-carboxamide (A1027);
5-methyl-7-oxo-3-phenyl-N-(thiazol-2-yl)-2-(trifluoromethyl)-4,7-dihydropyrazolo[1,5-a]pyrimidine-6-carboxamide (A1028);
5-methyl-N-(1-methyl-1H-pyrazol-3-yl)-7-oxo-3-phenyl-2-(trifluoromethyl)-4,7-dihydropyrazolo[1,5-a]pyrimidine-6-carboxamide (A1029);
N-(3-chlorophenyl)-5-methyl-7-oxo-3-phenyl-2-(trifluoromethyl)-4,7-dihydropyrazolo[1,5-a]pyrimidine-6-carboxamide (A1030);
N-(2-methoxyphenyl)-5-methyl-7-oxo-3-phenyl-2-(trifluoromethyl)-4,7-dihydropyrazolo[1,5-a]pyrimidine-6-carboxamide (A1031);
N-(3-methoxyphenyl)-5-methyl-7-oxo-3-phenyl-2-(trifluoromethyl)-4,7-dihydropyrazolo[1,5-a]pyrimidine-6-carboxamide (A1032);
N-(2-chlorophenyl)-5-methyl-7-oxo-3-phenyl-2-(trifluoromethyl)-4,7-dihydropyrazolo[1,5-a]pyrimidine-6-carboxamide (A1033);
tert-butyl (S)-3-(5-methyl-7-oxo-3-phenyl-2-(trifluoromethyl)-4,7-dihydropyrazolo[1,5-a]pyrimidine-6-carboxamido)pyrrolidine-1-carboxylate (A1034);
(S)-5-methyl-7-oxo-3-phenyl-N-(pyrrolidin-3-yl)-2-(trifluoromethyl)-4,7-dihydropyrazolo[1,5-a]pyrimidine-6-carboxamide (A1035);
N-(2-cyanophenyl)-5-methyl-7-oxo-3-phenyl-2-(trifluoromethyl)-4,7-dihydropyrazolo[1,5-a]pyrimidine-6-carboxamide (A1036);
5-methyl-7-oxo-3-phenyl-N-(o-tolyl)-2-(trifluoromethyl)-4,7-dihydropyrazolo[1,5-a]pyrimidine-6-carboxamide (A1037);
methyl (2-(5-methyl-7-oxo-3-phenyl-2-(trifluoromethyl)-4,7-dihydropyrazolo[1,5-a]pyrimidine-6-carboxamido)phenyl)carbamate (A1038);
N-(3-acetamidophenyl)-5-methyl-7-oxo-3-phenyl-2-(trifluoromethyl)-4,7-dihydropyrazolo[1,5-a]pyrimidine-6-carboxamide (A1039);
5-methyl-7-oxo-3-phenyl-N-(1H-1,2,4-triazol-3-yl)-2-(trifluoromethyl)-4,7-dihydropyrazolo[1,5-a]pyrimidine-6-carboxamide (A1040);

TABLE 1A-continued

N-(1-cyclohexyl-1H-pyrazol-3-yl)-5-methyl-7-oxo-3-phenyl-2-(trifluoromethyl)-4,7-dihydropyrazolo[1,5-a]pyrimidine-6-carboxamide (A1041);
5-(methoxymethyl)-N-(2-methoxyphenyl)-7-oxo-3-phenyl-2-(trifluoromethyl)-4,7-dihydropyrazolo[1,5-a]pyrimidine-6-carboxamide (A1042);
N-(2,3-dimethoxyphenyl)-5-methyl-7-oxo-3-phenyl-2-(trifluoromethyl)-4,7-dihydropyrazolo[1,5-a]pyrimidine-6-carboxamide (A1043);
N-(2-(cyclopentyloxy)phenyl)-5-methyl-7-oxo-3-phenyl-2-(trifluoromethyl)-4,7-dihydropyrazolo[1,5-a]pyrimidine-6-carboxamide (A1044);
5-methyl-N-(3-(methylsulfonamido)phenyl)-7-oxo-3-phenyl-2-(trifluoromethyl)-4,7-dihydropyrazolo[1,5-a]pyrimidine-6-carboxamide (A1045);
5-methyl-N-(3-(N-(methylsulfonyl)methylsulfonamido)phenyl)-7-oxo-3-phenyl-2-(trifluoromethyl)-4,7-dihydropyrazolo[1,5-a]pyrimidine-6-carboxamide (A1046);
5-methyl-7-oxo-3-phenyl-N-(pyridin-4-yl)-2-(trifluoromethyl)-4,7-dihydropyrazolo[1,5-a]pyrimidine-6-carboxamide (A1047);
N-(4-isopropyloxazol-2-yl)-5-methyl-7-oxo-3-phenyl-2-(trifluoromethyl)-4,7-dihydropyrazolo[1,5-a]pyrimidine-6-carboxamide (A1048);
5-methyl-7-oxo-3-phenyl-N-(2-(trifluoromethoxy)phenyl)-2-(trifluoromethyl)-4,7-dihydropyrazolo[1,5-a]pyrimidine-6-carboxamide (A1049);
5-methyl-7-oxo-3-phenyl-N-(3-(trifluoromethoxy)phenyl)-2-(trifluoromethyl)-4,7-dihydropyrazolo[1,5-a]pyrimidine-6-carboxamide (A1050);
N-(2-(isopropylsulfonyl)phenyl)-5-methyl-7-oxo-3-phenyl-2-(trifluoromethyl)-4,7-dihydropyrazolo[1,5-a]pyrimidine-6-carboxamide (A1051);
3-cyclopentyl-N-(2-methoxyphenyl)-5-methyl-7-oxo-2-(trifluoromethyl)-4,7-dihydropyrazolo[1,5-a]pyrimidine-6-carboxamide (A1052);
N-(2-(dimethylamino)phenyl)-5-methyl-7-oxo-3-phenyl-2-(trifluoromethyl)-4,7-dihydropyrazolo[1,5-a]pyrimidine-6-carboxamide (A1053);
5-methyl-7-oxo-3-phenyl-N-(2-(pyrrolidin-1-yl)phenyl)-2-(trifluoromethyl)-4,7-dihydropyrazolo[1,5-a]pyrimidine-6-carboxamide (A1054);
5-methyl-7-oxo-3-phenyl-N-(2-(piperidin-1-yl)phenyl)-2-(trifluoromethyl)-4,7-dihydropyrazolo[1,5-a]pyrimidine-6-carboxamide (A1055);
N-(4,5-dimethyloxazol-2-yl)-5-methyl-7-oxo-3-phenyl-2-(trifluoromethyl)-4,7-dihydropyrazolo[1,5-a]pyrimidine-6-carboxamide (A1056);
N-(2-methoxyphenyl)-7-oxo-3-phenyl-2-(trifluoromethyl)-4,7-dihydropyrazolo[1,5-a]pyrimidine-6-carboxamide (A1057);
N-(4-isopropyl-3-(trifluoromethyl)-1H-pyrazol-5-yl)-5-methyl-7-oxo-3-phenyl-2-(trifluoromethyl)-4,7-dihydropyrazolo[1,5-a]pyrimidine-6-carboxamide (A1058);
5-methyl-7-oxo-3-phenyl-N-(2-(phenylsulfonamido)phenyl)-2-(trifluoromethyl)-4,7-dihydropyrazolo[1,5-a]pyrimidine-6-carboxamide (A1059);
N-(2-isopropoxyphenyl)-5-methyl-7-oxo-3-phenyl-2-(trifluoromethyl)-4,7-dihydropyrazolo[1,5-a]pyrimidine-6-carboxamide (A1060);
N-(4-cyclopentyl-3-(trifluoromethyl)-1H-pyrazol-5-yl)-5-methyl-7-oxo-3-phenyl-2-(trifluoromethyl)-4,7-dihydropyrazolo[1,5-a]pyrimidine-6-carboxamide (A1061);
N-(2,2-difluorobenzo[d][1,3]dioxol-4-yl)-5-methyl-7-oxo-3-phenyl-2-(trifluoromethyl)-4,7-dihydropyrazolo[1,5-a]pyrimidine-6-carboxamide (A1062);
N-(4-methoxypyridin-2-yl)-5-methyl-7-oxo-3-phenyl-2-(trifluoromethyl)-4,7-dihydropyrazolo[1,5-a]pyrimidine-6-carboxamide (A1063);
N-(6-methoxypyridin-2-yl)-5-methyl-7-oxo-3-phenyl-2-(trifluoromethyl)-4,7-dihydropyrazolo[1,5-a]pyrimidine-6-carboxamide (A1064);
N-(1-isopropyl-1H-pyrazol-3-yl)-5-methyl-7-oxo-3-phenyl-2-(trifluoromethyl)-4,7-dihydropyrazolo[1,5-a]pyrimidine-6-carboxamide (A1065);
N-(3-isopropoxyphenyl)-5-methyl-7-oxo-3-phenyl-2-(trifluoromethyl)-4,7-dihydropyrazolo[1,5-a]pyrimidine-6-carboxamide (A1066);
N-(3,5-dimethoxyphenyl)-5-methyl-7-oxo-3-phenyl-2-(trifluoromethyl)-4,7-dihydropyrazolo[1,5-a]pyrimidine-6-carboxamide (A1067);
5-methyl-7-oxo-3-phenyl-N-(1H-pyrazol-4-yl)-2-(trifluoromethyl)-4,7-dihydropyrazolo[1,5-a]pyrimidine-6-carboxamide (A1068);
N-(3-aminophenyl)-5-methyl-7-oxo-3-phenyl-2-(trifluoromethyl)-4,7-dihydropyrazolo[1,5-a]pyrimidine-6-carboxamide (A1069);
N-(3-cyanophenyl)-5-methyl-7-oxo-3-phenyl-2-(trifluoromethyl)-4,7-dihydropyrazolo[1,5-a]pyrimidine-6-carboxamide (A1070);
N-(5-fluoro-2-methoxyphenyl)-5-methyl-7-oxo-3-phenyl-2-(trifluoromethyl)-4,7-dihydropyrazolo[1,5-a]pyrimidine-6-carboxamide (A1071);
N-(2-(methoxymethyl)phenyl)-5-methyl-7-oxo-3-phenyl-2-(trifluoromethyl)-4,7-dihydropyrazolo[1,5-a]pyrimidine-6-carboxamide (A1072);
N-(1,3-dimethyl-1H-pyrazol-5-yl)-5-methyl-7-oxo-3-phenyl-2-(trifluoromethyl)-4,7-dihydropyrazolo[1,5-a]pyrimidine-6-carboxamide (A1073);
5-methyl-N-(oxazol-2-yl)-7-oxo-3-phenyl-2-(trifluoromethyl)-4,7-dihydropyrazolo[1,5-a]pyrimidine-6-carboxamide (A1074);
5-methyl-N-(5-methyloxazol-2-yl)-7-oxo-3-phenyl-2-(trifluoromethyl)-4,7-dihydropyrazolo[1,5-a]pyrimidine-6-carboxamide (A1075);
5-methyl-7-oxo-3-phenyl-N-(1H-pyrazol-3-yl)-2-(trifluoromethyl)-4,7-dihydropyrazolo[1,5-a]pyrimidine-6-carboxamide (A1076);
5-methyl-N-(1-methyl-1H-pyrazol-4-yl)-7-oxo-3-phenyl-2-(trifluoromethyl)-4,7-dihydropyrazolo[1,5-a]pyrimidine-6-carboxamide (A1077);
5-methyl-N-(1-methyl-1H-pyrazol-5-yl)-7-oxo-3-phenyl-2-(trifluoromethyl)-4,7-dihydropyrazolo[1,5-a]pyrimidine-6-carboxamide (A1078);
N-(1,5-dimethyl-1H-pyrazol-3-yl)-5-methyl-7-oxo-3-phenyl-2-(trifluoromethyl)-4,7-dihydropyrazolo[1,5-a]pyrimidine-6-carboxamide (A1079);
N-(4,5-difluoro-2-methoxyphenyl)-5-methyl-7-oxo-3-phenyl-2-(trifluoromethyl)-4,7-dihydropyrazolo[1,5-a]pyrimidine-6-carboxamide (A1080);

TABLE 1A-continued 5-methyl-N-(3-methyl-1H-pyrazol-5-yl)-7-oxo-3-phenyl-2-(trifluoromethyl)-4,7-dihydropyrazolo[1,5-a]pyrimidine-6-carboxamide (A1081);
N-(3-(cyclopentyloxy)phenyl)-5-methyl-7-oxo-3-phenyl-2-(trifluoromethyl)-4,7-dihydropyrazolo[1,5-a]pyrimidine-6-carboxamide (A1082);
5-methyl-N-(2-(methylsulfonyl)phenyl)-7-oxo-3-phenyl-2-(trifluoromethyl)-4,7-dihydropyrazolo[1,5-a]pyrimidine-6-carboxamide (A1083);
5-methyl-N-(3-(methylsulfonyl)phenyl)-7-oxo-3-phenyl-2-(trifluoromethyl)-4,7-dihydropyrazolo[1,5-a]pyrimidine-6-carboxamide (A1084);
N-(2-methoxycyclohexyl)-5-methyl-7-oxo-3-phenyl-2-(trifluoromethyl)-4,7-dihydropyrazolo[1,5-a]pyrimidine-6-carboxamide (diastereomer 1) (A1085);
N-(3-(benzyloxy)phenyl)-5-methyl-7-oxo-3-phenyl-2-(trifluoromethyl)-4,7-dihydropyrazolo[1,5-a]pyrimidine-6-carboxamide (A1086);
N-(2-methoxypyridin-4-yl)-5-methyl-7-oxo-3-phenyl-2-(trifluoromethyl)-4,7-dihydropyrazolo[1,5-a]pyrimidine-6-carboxamide (A1087);
N-(6-methoxypyridin-3-yl)-5-methyl-7-oxo-3-phenyl-2-(trifluoromethyl)-4,7-dihydropyrazolo[1,5-a]pyrimidine-6-carboxamide (A1088);
N-(2-methoxycyclohexyl)-5-methyl-7-oxo-3-phenyl-2-(trifluoromethyl)-4,7-dihydropyrazolo[1,5-a]pyrimidine-6-carboxamide (diastereomer 2) (A1089);
N-(4-cyano-1-methyl-1H-pyrazol-3-yl)-5-methyl-7-oxo-3-phenyl-2-(trifluoromethyl)-4,7-dihydropyrazolo[1,5-a]pyrimidine-6-carboxamide (A1090);
N-((1S,2S)-2-hydroxycyclohexyl)-5-methyl-7-oxo-3-phenyl-2-(trifluoromethyl)-4,7-dihydropyrazolo[1,5-a]pyrimidine-6-carboxamide (A1091);
N-((1S,2R)-2-hydroxycyclohexyl)-5-methyl-7-oxo-3-phenyl-2-(trifluoromethyl)-4,7-dihydropyrazolo[1,5-a]pyrimidine-6-carboxamide (A1092);
N-(2-methoxypyridin-3-yl)-5-methyl-7-oxo-3-phenyl-2-(trifluoromethyl)-4,7-dihydropyrazolo[1,5-a]pyrimidine-6-carboxamide (A1093);
N-(5-methoxypyridin-3-yl)-5-methyl-7-oxo-3-phenyl-2-(trifluoromethyl)-4,7-dihydropyrazolo[1,5-a]pyrimidine-6-carboxamide (A1094);
N-(4-cyclopropylthiazol-2-yl)-5-methyl-7-oxo-3-phenyl-2-(trifluoromethyl)-4,7-dihydropyrazolo[1,5-a]pyrimidine-6-carboxamide (A1095);
5-methyl-N-(2-(methylsulfonyl)pyridin-3-yl)-7-oxo-3-phenyl-2-(trifluoromethyl)-4,7-dihydropyrazolo[1,5-a]pyrimidine-6-carboxamide (A1096);
N-(3-methoxypyrazin-2-yl)-5-methyl-7-oxo-3-phenyl-2-(trifluoromethyl)-4,7-dihydropyrazolo[1,5-a]pyrimidine-6-carboxamide (A1097);
N-(6-methoxypyrazin-2-yl)-5-methyl-7-oxo-3-phenyl-2-(trifluoromethyl)-4,7-dihydropyrazolo[1,5-a]pyrimidine-6-carboxamide (A1098);
N-(3-methoxypyridin-4-yl)-5-methyl-7-oxo-3-phenyl-2-(trifluoromethyl)-4,7-dihydropyrazolo[1,5-a]pyrimidine-6-carboxamide (A1099);
N-(3-methoxypyridin-2-yl)-5-methyl-7-oxo-3-phenyl-2-(trifluoromethyl)-4,7-dihydropyrazolo[1,5-a]pyrimidine-6-carboxamide (A1100);
N-(2,3-dihydrobenzofuran-7-yl)-5-methyl-7-oxo-3-phenyl-2-(trifluoromethyl)-4,7-dihydropyrazolo[1,5-a]pyrimidine-6-carboxamide (A1101);
N-(2,3-dihydrobenzofuran-4-yl)-5-methyl-7-oxo-3-phenyl-2-(trifluoromethyl)-4,7-dihydropyrazolo[1,5-a]pyrimidine-6-carboxamide (A1102);
N-(4-methoxypyridin-3-yl)-5-methyl-7-oxo-3-phenyl-2-(trifluoromethyl)-4,7-dihydropyrazolo[1,5-a]pyrimidine-6-carboxamide (A1103);
N-(4-methoxypyrimidin-2-yl)-5-methyl-7-oxo-3-phenyl-2-(trifluoromethyl)-4,7-dihydropyrazolo[1,5-a]pyrimidine-6-carboxamide (A1104);
N-(4-methoxypyridin-2-yl)-2,5-dimethyl-7-oxo-3-phenyl-4,7-dihydropyrazolo[1,5-a]pyrimidine-6-carboxamide (A1105);
2,5-dimethyl-N-(2-(methylsulfonyl)phenyl)-7-oxo-3-phenyl-4,7-dihydropyrazolo[1,5-a]pyrimidine-6-carboxamide (A1106);
N-(chroman-8-yl)-5-methyl-7-oxo-3-phenyl-2-(trifluoromethyl)-4,7-dihydropyrazolo[1,5-a]pyrimidine-6-carboxamide (A1107);
5-methyl-N-(5-(methylsulfonyl)pyridin-2-yl)-7-oxo-3-phenyl-2-(trifluoromethyl)-4,7-dihydropyrazolo[1,5-a]pyrimidine-6-carboxamide (A1108);
5-methyl-N-(4-(methylsulfonyl)pyridin-3-yl)-7-oxo-3-phenyl-2-(trifluoromethyl)-4,7-dihydropyrazolo[1,5-a]pyrimidine-6-carboxamide (A1109);
N-(6-methoxypyridazin-3-yl)-5-methyl-7-oxo-3-phenyl-2-(trifluoromethyl)-4,7-dihydropyrazolo[1,5-a]pyrimidine-6-carboxamide (A1110);
5-methyl-7-oxo-3-phenyl-N-(propylsulfonyl)-2-(trifluoromethyl)-4,7-dihydropyrazolo[1,5-a]pyrimidine-6-carboxamide (A1111);
N-(benzylsulfonyl)-5-methyl-7-oxo-3-phenyl-2-(trifluoromethyl)-4,7-dihydropyrazolo[1,5-a]pyrimidine-6-carboxamide (A1112);
5-methyl-N-(6-(methylsulfonyl)pyridin-3-yl)-7-oxo-3-phenyl-2-(trifluoromethyl)-4,7-dihydropyrazolo[1,5-a]pyrimidine-6-carboxamide (A1113);
N-(3-methoxyphenyl)-N,5-dimethyl-7-oxo-3-phenyl-2-(trifluoromethyl)-4,7-dihydropyrazolo[1,5-a]pyrimidine-6-carboxamide (A1114);
N-(1-(2-methoxyethyl)-1H-pyrazol-3-yl)-5-methyl-7-oxo-3-phenyl-2-(trifluoromethyl)-4,7-dihydropyrazolo[1,5-a]pyrimidine-6-carboxamide (A1115);
5-methyl-7-oxo-3-phenyl-N-(phenylsulfonyl)-2-(trifluoromethyl)-4,7-dihydropyrazolo[1,5-a]pyrimidine-6-carboxamide (A1116);
5-methyl-N-(methylsulfonyl)-7-oxo-3-phenyl-2-(trifluoromethyl)-4,7-dihydropyrazolo[1,5-a]pyrimidine-6-carboxamide (A1117);
N-(1-(2-hydroxyethyl)-1H-pyrazol-3-yl)-5-methyl-7-oxo-3-phenyl-2-(trifluoromethyl)-4,7-dihydropyrazolo[1,5-a]pyrimidine-6-carboxamide (A1118);
N-(2-(cyclohexanesulfonamido)phenyl)-5-methyl-7-oxo-3-phenyl-2-(trifluoromethyl)-4,7-dihydropyrazolo[1,5-a]pyrimidine-6-carboxamide (A1119);
5-methyl-7-oxo-3-phenyl-N-(pyridin-2-ylsulfonyl)-2-(trifluoromethyl)-4,7-dihydropyrazolo[1,5-a]pyrimidine-6-carboxamide (A1120);

TABLE 1A-continued

N-((2-methoxyphenyl)sulfonyl)-5-methyl-7-oxo-3-phenyl-2-(trifluoromethyl)-4,7-dihydropyrazolo[1,5-a]pyrimidine-6-carboxamide (A1121);
N-(3-methoxyphenyl)-5-methyl-2-(methylthio)-7-oxo-3-phenyl-4,7-dihydropyrazolo[1,5-a]pyrimidine-6-carboxamide (A1122);
2-cyclopropyl-N-(3-methoxyphenyl)-5-methyl-7-oxo-3-phenyl-4,7-dihydropyrazolo[1,5-a]pyrimidine-6-carboxamide (A1123);
N-(cyclohexylsulfonyl)-5-methyl-7-oxo-3-phenyl-2-(trifluoromethyl)-4,7-dihydropyrazolo[1,5-a]pyrimidine-6-carboxamide (A1124);
N-((3-methoxyphenyl)sulfonyl)-5-methyl-7-oxo-3-phenyl-2-(trifluoromethyl)-4,7-dihydropyrazolo[1,5-a]pyrimidine-6-carboxamide (A1125);
N-(3-methoxyphenyl)-5-methyl-2-(methylsulfonyl)-7-oxo-3-phenyl-4,7-dihydropyrazolo[1,5-a]pyrimidine-6-carboxamide (A1126);
N-((2-chlorophenyl)sulfonyl)-5-methyl-7-oxo-3-phenyl-2-(trifluoromethyl)-4,7-dihydropyrazolo[1,5-a]pyrimidine-6-carboxamide (A1127);
N-((3-cyanophenyl)sulfonyl)-5-methyl-7-oxo-3-phenyl-2-(trifluoromethyl)-4,7-dihydropyrazolo[1,5-a]pyrimidine-6-carboxamide (A1128);
N-(3-bromo-5-methoxyphenyl)-5-methyl-7-oxo-3-phenyl-2-(trifluoromethyl)-4,7-dihydropyrazolo[1,5-a]pyrimidine-6-carboxamide (A1129);
N-(3-bromo-2-methoxyphenyl)-5-methyl-7-oxo-3-phenyl-2-(trifluoromethyl)-4,7-dihydropyrazolo[1,5-a]pyrimidine-6-carboxamide (A1130);
N-(2-bromo-3-methoxyphenyl)-5-methyl-7-oxo-3-phenyl-2-(trifluoromethyl)-4,7-dihydropyrazolo[1,5-a]pyrimidine-6-carboxamide (A1131);
N-((3-methoxybenzyl)sulfonyl)-5-methyl-7-oxo-3-phenyl-2-(trifluoromethyl)-4,7-dihydropyrazolo[1,5-a]pyrimidine-6-carboxamide (A1132);
N-(3-fluoro-5-methoxyphenyl)-5-methyl-7-oxo-3-phenyl-2-(trifluoromethyl)-4,7-dihydropyrazolo[1,5-a]pyrimidine-6-carboxamide (A1133);
N-(3-chloro-5-methoxyphenyl)-5-methyl-7-oxo-3-phenyl-2-(trifluoromethyl)-4,7-dihydropyrazolo[1,5-a]pyrimidine-6-carboxamide (A1134);
N-(2-chloro-3-methoxyphenyl)-5-methyl-7-oxo-3-phenyl-2-(trifluoromethyl)-4,7-dihydropyrazolo[1,5-a]pyrimidine-6-carboxamide (A1135);
N-(2-fluoro-3-methoxyphenyl)-5-methyl-7-oxo-3-phenyl-2-(trifluoromethyl)-4,7-dihydropyrazolo[1,5-a]pyrimidine-6-carboxamide (A1136);
N-(3-fluoro-2-methoxyphenyl)-5-methyl-7-oxo-3-phenyl-2-(trifluoromethyl)-4,7-dihydropyrazolo[1,5-a]pyrimidine-6-carboxamide (A1137);
N-(3-chloro-2-methoxyphenyl)-5-methyl-7-oxo-3-phenyl-2-(trifluoromethyl)-4,7-dihydropyrazolo[1,5-a]pyrimidine-6-carboxamide (A1138);
N-(3-bromo-5-((dimethylamino)methyl)phenyl)-5-methyl-7-oxo-3-phenyl-2-(trifluoromethyl)-4,7-dihydropyrazolo[1,5-a]pyrimidine-6-carboxamide (A1139);
5-methyl-7-oxo-3-phenyl-2-(trifluoromethyl)-4,7-dihydropyrazolo[1,5-a]pyrimidine-6-carboxamide (A1140);
N-(2-hydroxycyclohexyl)-5-methyl-7-oxo-3-phenyl-2-(trifluoromethyl)-4,7-dihydropyrazolo[1,5-a]pyrimidine-6-carboxamide (A1141);
5-methyl-7-oxo-N-(2-oxocyclohexyl)-3-phenyl-2-(trifluoromethyl)-4,7-dihydropyrazolo[1,5-a]pyrimidine-6-carboxamide (A1142);
(S)-N-(1-hydroxy-3-methoxypropan-2-yl)-5-methyl-7-oxo-3-phenyl-2-(trifluoromethyl)-4,7-dihydropyrazolo[1,5-a]pyrimidine-6-carboxamide (A1143);
2-cyano-N-(6-methoxypyridin-2-yl)-5-methyl-7-oxo-3-phenyl-4,7-dihydropyrazolo[1,5-a]pyrimidine-6-carboxamide (A1144);
N-(2-aminophenyl)-2-(5-methyl-7-oxo-3-phenyl-2-(trifluoromethyl)-4,7-dihydropyrazolo[1,5-a]pyrimidin-6-yl)acetamide (B1001);
5-methyl-6-(2-morpholino-2-oxoethyl)-3-phenyl-2-(trifluoromethyl)pyrazolo[1,5-a]pyrimidin-7(4H)-one (B1002);
N-(2-methoxyethyl)-2-(5-methyl-7-oxo-3-phenyl-2-(trifluoromethyl)-4,7-dihydropyrazolo[1,5-a]pyrimidin-6-yl)acetamide (B1003);
2-(5-methyl-7-oxo-3-phenyl-2-(trifluoromethyl)-4,7-dihydropyrazolo[1,5-a]pyrimidin-6-yl)-N-(pyridin-4-yl)acetamide (B1004);
2-(5-methyl-7-oxo-3-phenyl-2-(trifluoromethyl)-4,7-dihydropyrazolo[1,5-a]pyrimidin-6-yl)-N-phenylacetamide (B1005);
N-(4-methoxyphenyl)-2-(5-methyl-7-oxo-3-phenyl-2-(trifluoromethyl)-4,7-dihydropyrazolo[1,5-a]pyrimidin-6-yl)acetamide (B1006);
5-methyl-6-(2-oxo-2-(4-phenylpiperazin-1-yl)ethyl)-3-phenyl-2-(trifluoromethyl)pyrazolo[1,5-a]pyrimidin-7(4H)-one (B1007);
2-(5-methyl-7-oxo-3-phenyl-2-(trifluoromethyl)-4,7-dihydropyrazolo[1,5-a]pyrimidin-6-yl)-N-(pyridin-3-yl)acetamide (B1008);
5-methyl-6-(2-(4-(4-methylbenzyl)piperazin-1-yl)-2-oxoethyl)-3-phenyl-2-(trifluoromethyl)pyrazolo[1,5-a]pyrimidin-7(4H)-one (B1009);
N-(2-methoxyphenyl)-2-(5-methyl-7-oxo-3-phenyl-2-(trifluoromethyl)-4,7-dihydropyrazolo[1,5-a]pyrimidin-6-yl)acetamide (B1010);
N-(3-methoxyphenyl)-2-(5-methyl-7-oxo-3-phenyl-2-(trifluoromethyl)-4,7-dihydropyrazolo[1,5-a]pyrimidin-6-yl)acetamide (B1011);
6-(2-aminoethyl)-5-methyl-3-phenyl-2-(trifluoromethyl)pyrazolo[1,5-a]pyrimidin-7(4H)-one (B1012);
N-(2-(5-methyl-7-oxo-3-phenyl-2-(trifluoromethyl)-4,7-dihydropyrazolo[1,5-a]pyrimidin-6-yl)ethyl)acetamide (B1013);
N-(2-(5-methyl-7-oxo-3-phenyl-2-(trifluoromethyl)-4,7-dihydropyrazolo[1,5-a]pyrimidin-6-yl)ethyl)benzamide (B1014);
6-(2-((3-methoxyphenyl)amino)ethyl)-5-methyl-3-phenyl-2-(trifluoromethyl)pyrazolo[1,5-a]pyrimidin-7(4H)-one (B1015);
5-methyl-3-phenyl-6-(pyridin-4-yl)-2-(trifluoromethyl)pyrazolo[1,5-a]pyrimidin-7(4H)-one (C1001);

TABLE 1A-continued 5-methyl-3-phenyl-6-(m-tolyl)-2-(trifluoromethyl)pyrazolo[1,5-a]pyrimidin-7(4H)-one (C1002);
5-methyl-3-phenyl-6-(pyridin-3-yl)-2-(trifluoromethyl)pyrazolo[1,5-a]pyrimidin-7(4H)-one (C1003);
6-(3-chlorophenyl)-5-methyl-3-phenyl-2-(trifluoromethyl)pyrazolo[1,5-a]pyrimidin-7(4H)-one (C1004);
6-(1H-benzo[d]imidazol-2-yl)-5-methyl-3-phenyl-2-(trifluoromethyl)pyrazolo[1,5-a]pyrimidin-7(4H)-one (C1005);
6-(imidazo[1,2-a]pyridin-6-yl)-5-methyl-3-phenyl-2-(trifluoromethyl)pyrazolo[1,5-a]pyrimidin-7(4H)-one (C1006);
5-methyl-3-phenyl-6-(quinolin-3-yl)-2-(trifluoromethyl)pyrazolo[1,5-a]pyrimidin-7(4H)-one (C1007);
6-(7-amino-1H-benzo[d]imidazol-2-yl)-5-methyl-3-phenyl-2-(trifluoromethyl)pyrazolo[1,5-a]pyrimidin-7(4H)-one (C1008);
N-(2-(5-methyl-7-oxo-3-phenyl-2-(trifluoromethyl)-4,7-dihydropyrazolo[1,5-a]pyrimidin-6-yl)-1H-benzo[d]imidazol-7-yl)acetamide (C1009);
6-(5-cyclopentyloxazol-2-yl)-5-methyl-3-phenyl-2-(trifluoromethyl)pyrazolo[1,5-a]pyrimidin-7(4H)-one (C1010);
6-(benzo[d]oxazol-2-yl)-5-methyl-3-phenyl-2-(trifluoromethyl)pyrazolo[1,5-a]pyrimidin-7(4H)-one (C1011);
6-(5-methoxybenzo[d]oxazol-2-yl)-5-methyl-3-phenyl-2-(trifluoromethyl)pyrazolo[1,5-a]pyrimidin-7(4H)-one (C1012);
6-(5-cyclopentyloxazol-2-yl)-5-(methoxymethyl)-3-phenyl-2-(trifluoromethyl)pyrazolo[1,5-a]pyrimidin-7(4H)-one (C1013);
6-(4-methoxybenzo[d]oxazol-2-yl)-5-methyl-3-phenyl-2-(trifluoromethyl)pyrazolo[1,5-a]pyrimidin-7(4H)-one (C1014);
5-methyl-3-phenyl-6-(4,5,6,7-tetrahydrobenzo[d]oxazol-2-yl)-2-(trifluoromethyl)pyrazolo[1,5-a]pyrimidin-7(4H)-one (C1015);
6-(5-methoxy-1H-benzo[d]imidazol-2-yl)-5-methyl-3-phenyl-2-(trifluoromethyl)pyrazolo[1,5-a]pyrimidin-7(4H)-one (C1016);
5-methyl-3-phenyl-6-(4,5,6,7-tetrahydro-1H-benzo[d]imidazol-2-yl)-2-(trifluoromethyl)pyrazolo[1,5-a]pyrimidin-7(4H)-one (C1017);
6-(4-methoxy-1H-benzo[d]imidazol-2-yl)-5-methyl-3-phenyl-2-(trifluoromethyl)pyrazolo[1,5-a]pyrimidin-7(4H)-one (C1018);
2-(5-methyl-7-oxo-3-phenyl-2-(trifluoromethyl)-4,7-dihydropyrazolo[1,5-a]pyrimidin-6-yl)quinazolin-4(3H)-one (C1019);
5-methyl-6-(5-methyl-4H-1,2,4-triazol-3-yl)-3-phenyl-2-(trifluoromethyl)pyrazolo[1,5-a]pyrimidin-7(4H)-one (C1020);
6-(4,5-dimethyl-1H-imidazol-2-yl)-5-methyl-3-phenyl-2-(trifluoromethyl)pyrazolo[1,5-a]pyrimidin-7(4H)-one (C1021);
6-(7-methoxybenzo[d]oxazol-2-yl)-5-methyl-3-phenyl-2-(trifluoromethyl)pyrazolo[1,5-a]pyrimidin-7(4H)-one (C1022);
3-isopropyl-5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1023);
5-methoxy-2-(5-methyl-7-oxo-3-phenyl-2-(trifluoromethyl)-4,7-dihydropyrazolo[1,5-a]pyrimidin-6-yl)quinazolin-4(3H)-one (C1024);
8-methoxy-2-(5-methyl-7-oxo-3-phenyl-2-(trifluoromethyl)-4,7-dihydropyrazolo[1,5-a]pyrimidin-6-yl)quinazolin-4(3H)-one (C1025);
6-(7-methoxy-1H-indazol-3-yl)-5-methyl-3-phenyl-2-(trifluoromethyl)pyrazolo[1,5-a]pyrimidin-7(4H)-one (C1026);
5-methyl-3-phenyl-6-(5-(tetrahydro-2H-pyran-3-yl)oxazol-2-yl)-2-(trifluoromethyl)pyrazolo[1,5-a]pyrimidin-7(4H)-one (C1027);
6-(5-chlorobenzo[d]oxazol-2-yl)-5-methyl-3-phenyl-2-(trifluoromethyl)pyrazolo[1,5-a]pyrimidin-7(4H)-one (C1028);
5,5'-bis(methoxymethyl)-3,3'-diphenyl-2,2'-bis(trifluoromethyl)-[6,6'-bipyrazolo[1,5-a]pyrimidine]-7,7'(4H,4'H)-dione (C1029);
5-methyl-6-(oxazolo[4,5-b]pyridin-2-yl)-3-phenyl-2-(trifluoromethyl)pyrazolo[1,5-a]pyrimidin-7(4H)-one (C1030);
2,5-dimethyl-3-phenyl-6-(4,5,6,7-tetrahydrobenzo[d]oxazol-2-yl)pyrazolo[1,5-a]pyrimidin-7(4H)-one (C1032);
2-(5-methyl-7-oxo-3-phenyl-2-(trifluoromethyl)-4,7-dihydropyrazolo[1,5-a]pyrimidin-6-yl)-6,7-dihydrobenzo[d]oxazol-4(5H)-one (C1033);
5-methyl-6-(4,5,6,7-tetrahydrobenzo[d]oxazol-2-yl)-3-(m-tolyl)-2-(trifluoromethyl)pyrazolo[1,5-a]pyrimidin-7(4H)-one (C1034);
3-(3-fluorophenyl)-5-methyl-6-(4,5,6,7-tetrahydrobenzo[d]oxazol-2-yl)-2-(trifluoromethyl)pyrazolo[1,5-a]pyrimidin-7(4H)-one (C1035);
5-methyl-3-(pyridin-3-yl)-6-(4,5,6,7-tetrahydrobenzo[d]oxazol-2-yl)-2-(trifluoromethyl)pyrazolo[1,5-a]pyrimidin-7(4H)-one (C1036);
6-(4-methoxyoxazolo[4,5-c]pyridin-2-yl)-5-methyl-3-phenyl-2-(trifluoromethyl)pyrazolo[1,5-a]pyrimidin-7(4H)-one (C1037);
6-(4-ethoxybenzo[d]oxazol-2-yl)-5-methyl-3-phenyl-2-(trifluoromethyl)pyrazolo[1,5-a]pyrimidin-7(4H)-one (C1038);
6-(4-isopropoxybenzo[d]oxazol-2-yl)-5-methyl-3-phenyl-2-(trifluoromethyl)pyrazolo[1,5-a]pyrimidin-7(4H)-one (C1039);
6-(4-bromobenzo[d]oxazol-2-yl)-5-methyl-3-phenyl-2-(trifluoromethyl)pyrazolo[1,5-a]pyrimidin-7(4H)-one (C1040);
6-(4-(2-methoxyethoxy)benzo[d]oxazol-2-yl)-5-methyl-3-phenyl-2-(trifluoromethyl)pyrazolo[1,5-a]pyrimidin-7(4H)-one (C1041);
6-(4-methoxybenzo[d]oxazol-2-yl)-2,5-dimethyl-3-phenylpyrazolo[1,5-a]pyrimidin-7(4H)-one (C1042);

TABLE 1A-continued 6-(4-methoxybenzo[d]oxazol-2-yl)-5-methyl-7-oxo-3-phenyl-4,7-dihydropyrazolo[1,5-a]pyrimidine-2-carboxylic acid (C1043);
6-(8-methoxyimidazo[1,2-a]pyridin-2-yl)-5-methyl-3-phenyl-2-(trifluoromethyl)pyrazolo[1,5-a]pyrimidin-7(4H)-one (C1044);
6-(4-(cyclopropylmethoxy)benzo[d]oxazol-2-yl)-5-methyl-3-phenyl-2-(trifluoromethyl)pyrazolo[1,5-a]pyrimidin-7(4H)-one (C1045);
6-(4-ethylbenzo[d]oxazol-2-yl)-5-methyl-3-phenyl-2-(trifluoromethyl)pyrazolo[1,5-a]pyrimidin-7(4H)-one (C1046);
5-methyl-6-(4-(methylthio)benzo[d]oxazol-2-yl)-3-phenyl-2-(trifluoromethyl)pyrazolo[1,5-a]pyrimidin-7(4H)-one (C1047);
6-(4-methoxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1048);
6-(4-methoxybenzo[d]oxazol-2-yl)-5-methyl-3-phenylpyrazolo[1,5-a]pyrimidine-2,7(1H,4H)-dione (C1049);
2-(difluoromethyl)-6-(4-methoxybenzo[d]oxazol-2-yl)-5-methyl-3-phenylpyrazolo[1,5-a]pyrimidin-7(4H)-one (C1050);
6-(4-methoxybenzo[d]oxazol-2-yl)-5-methyl-7-oxo-3-phenyl-4,7-dihydropyrazolo[1,5-a]pyrimidine-2-carbonitrile (C1051);
6-(4-hydroxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1052);
6-(4-hydroxybenzo[d]oxazol-2-yl)-5-methyl-3-phenyl-2-(trifluoromethyl)pyrazolo[1,5-a]pyrimidin-7(4H)-one (C1053);
5-methyl-6-(4-(methylsulfonyl)benzo[d]oxazol-2-yl)-3-phenyl-2-(trifluoromethyl)pyrazolo[1,5-a]pyrimidin-7(4H)-one (C1054);
6-(4-chlorobenzo[d]oxazol-2-yl)-5-methyl-3-phenyl-2-(trifluoromethyl)pyrazolo[1,5-a]pyrimidin-7(4H)-one (C1055);
6-(4-methoxybenzo[d]oxazol-2-yl)-5-(methoxymethyl)-3-phenyl-2-(trifluoromethyl)pyrazolo[1,5-a]pyrimidin-7(4H)-one (C1056);
6-(5-methoxyimidazo[1,2-a]pyridin-2-yl)-5-methyl-3-phenyl-2-(trifluoromethyl)pyrazolo[1,5-a]pyrimidin-7(4H)-one (C1057);
6-(7-methoxyoxazolo[5,4-b]pyridin-2-yl)-5-methyl-3-phenyl-2-(trifluoromethyl)pyrazolo[1,5-a]pyrimidin-7(4H)-one (C1058);
2-(5-methyl-7-oxo-3-phenyl-2-(trifluoromethyl)-4,7-dihydropyrazolo[1,5-a]pyrimidin-6-yl)-5,6,7,8-tetrahydro-4H-oxazolo[4,5-c]azepin-4-one (C1059);
5-methyl-6-(4-methylbenzo[d]oxazol-2-yl)-3-phenyl-2-(trifluoromethyl)pyrazolo[1,5-a]pyrimidin-7(4H)-one (C1060);
6-(4-(2-aminoethoxy)benzo[d]oxazol-2-yl)-5-methyl-3-phenyl-2-(trifluoromethyl)pyrazolo[1,5-a]pyrimidin-7(4H)-one (C1061);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)acetamide (C1062);
2-amino-6-(4-methoxybenzo[d]oxazol-2-yl)-5-methyl-3-phenylpyrazolo[1,5-a]pyrimidin-7(4H)-one (C1063);
2-methoxy-6-(4-methoxybenzo[d]oxazol-2-yl)-5-methyl-3-phenylpyrazolo[1,5-a]pyrimidin-7(4H)-one (C1064);
6-(7-methoxy-1-methyl-1H-benzo[d]imidazol-2-yl)-5-methyl-3-phenyl-2-(trifluoromethyl)pyrazolo[1,5-a]pyrimidin-7(4H)-one (C1065);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)methanesulfonamide (C1066);
5-(2-(dimethylamino)ethoxy)-6-(4-methoxybenzo[d]oxazol-2-yl)-3-phenyl-2-(trifluoromethyl)pyrazolo[1,5-a]pyrimidin-7(4H)-one (C1067);
6-(4-methoxybenzo[d]oxazol-2-yl)-5-methyl-2-(methylsulfonyl)-3-phenylpyrazolo[1,5-a]pyrimidin-7(4H)-one (C1068);
6-(4-methoxybenzo[d]thiazol-2-yl)-5-methyl-3-phenyl-2-(trifluoromethyl)pyrazolo[1,5-a]pyrimidin-7(4H)-one (C1070);
5-chloro-6-(4-methoxybenzo[d]oxazol-2-yl)-3-phenyl-2-(trifluoromethyl)pyrazolo[1,5-a]pyrimidin-7(4H)-one (C1071);
2-((6-(4-methoxybenzo[d]oxazol-2-yl)-5-methyl-7-oxo-3-phenyl-4,7-dihydropyrazolo[1,5-a]pyrimidin-2-yl)oxy)acetic acid (C1072);
6-(4-(benzyloxy)benzo[d]oxazol-2-yl)-5-methyl-3-phenyl-2-(trifluoromethyl)pyrazolo[1,5-a]pyrimidin-7(4H)-one (C1073);
2-(5-methyl-7-oxo-3-phenyl-2-(trifluoromethyl)-4,7-dihydropyrazolo[1,5-a]pyrimidin-6-yl)benzo[d]oxazole-4-carboxamide (C1074);
2-(5-methyl-7-oxo-3-phenyl-2-(trifluoromethyl)-4,7-dihydropyrazolo[1,5-a]pyrimidin-6-yl)benzo[d]oxazole-4-carbonitrile (C1075);
6-(4-fluorobenzo[d]oxazol-2-yl)-5-methyl-3-phenyl-2-(trifluoromethyl)pyrazolo[1,5-a]pyrimidin-7(4H)-one (C1076);
6-(4-methoxybenzo[d]oxazol-2-yl)-3-phenyl-2,5-bis(trifluoromethyl)pyrazolo[1,5-a]pyrimidin-7(4H)-one (C1077);
6-(4-(dimethylamino)benzo[d]oxazol-2-yl)-5-methyl-3-phenyl-2-(trifluoromethyl)pyrazolo[1,5-a]pyrimidin-7(4H)-one (C1078);
6-(4-methoxybenzo[d]oxazol-2-yl)-3-phenyl-2-(trifluoromethyl)pyrazolo[1,5-a]pyrimidin-7(4H)-one (C1079);
6-(4-methoxybenzo[d]oxazol-2-yl)-5-methyl-3-phenyl-2-((tetrahydro-2H-pyran-4-yl)oxy)pyrazolo[1,5-a]pyrimidin-7(4H)-one (C1080);
6-(7-bromo-4-methoxybenzo[d]oxazol-2-yl)-5-methyl-3-phenyl-2-(trifluoromethyl)pyrazolo[1,5-a]pyrimidin-7(4H)-one (C1081);
6-(5-bromo-4-methoxybenzo[d]oxazol-2-yl)-5-methyl-3-phenyl-2-(trifluoromethyl)pyrazolo[1,5-a]pyrimidin-7(4H)-one (C1082);
6-(4-methoxybenzo[d]oxazol-2-yl)-2-(2-methoxyethoxy)-5-methyl-3-phenylpyrazolo[1,5-a]pyrimidin-7(4H)-one (C1083);

TABLE 1A-continued 5-methoxy-6-(4-methoxybenzo[d]oxazol-2-yl)-3-phenyl-2-(trifluoromethyl)pyrazolo[1,5-a]pyrimidin-7(4H)-one (C1084);
5-amino-6-(4-methoxybenzo[d]oxazol-2-yl)-3-phenyl-2-(trifluoromethyl)pyrazolo[1,5-a]pyrimidin-7(4H)-one (C1085);
6-(4-methoxybenzo[d]oxazol-2-yl)-3-(2-methoxyphenyl)-5-methyl-2-(trifluoromethyl)pyrazolo[1,5-a]pyrimidin-7(4H)-one (C1086);
6-(4-methoxy-1-methyl-1H-benzo[d]imidazol-2-yl)-5-methyl-3-phenyl-2-(trifluoromethyl)pyrazolo[1,5-a]pyrimidin-7(4H)-one (C1087);
2-(5-methyl-7-oxo-3-phenyl-2-(trifluoromethyl)-4,7-dihydropyrazolo[1,5-a]pyrimidin-6-yl)benzo[d]oxazol-4-yl dimethylcarbamate (C1088);
6-(4-methoxybenzo[d]oxazol-2-yl)-7-oxo-3-phenyl-2-(trifluoromethyl)-4,7-dihydropyrazolo[1,5-a]pyrimidine-5-carbonitrile (C1089);
6-(4-methoxybenzo[d]oxazol-2-yl)-5-(methoxymethyl)-7-oxo-3-phenyl-4,7-dihydropyrazolo[1,5-a]pyrimidine-2-carboxylic acid (C1090);
3-(2-fluorophenyl)-6-(4-methoxybenzo[d]oxazol-2-yl)-5-methyl-2-(trifluoromethyl)pyrazolo[1,5-a]pyrimidin-7(4H)-one (C1091);
6-(4-methoxy-7-methylbenzo[d]oxazol-2-yl)-5-methyl-3-phenyl-2-(trifluoromethyl)pyrazolo[1,5-a]pyrimidin-7(4H)-one (C1092);
6-(4-methoxy-5-methylbenzo[d]oxazol-2-yl)-5-methyl-3-phenyl-2-(trifluoromethyl)pyrazolo[1,5-a]pyrimidin-7(4H)-one (C1093);
6-(7-chloro-4-methoxybenzo[d]oxazol-2-yl)-5-methyl-3-phenyl-2-(trifluoromethyl)pyrazolo[1,5-a]pyrimidin-7(4H)-one (C1094);
6-(5-chloro-4-methoxybenzo[d]oxazol-2-yl)-5-methyl-3-phenyl-2-(trifluoromethyl)pyrazolo[1,5-a]pyrimidin-7(4H)-one (C1095);
6-(7-methoxyoxazolo[5,4-c]pyridin-2-yl)-5-methyl-3-phenyl-2-(trifluoromethyl)pyrazolo[1,5-a]pyrimidin-7(4H)-one (C1096);
5-methyl-6-(4-(methylsulfinyl)benzo[d]oxazol-2-yl)-3-phenyl-2-(trifluoromethyl)pyrazolo[1,5-a]pyrimidin-7(4H)-one (C1097);
6-(4-methoxy-6-methylbenzo[d]oxazol-2-yl)-5-methyl-3-phenyl-2-(trifluoromethyl)pyrazolo[1,5-a]pyrimidin-7(4H)-one (C1098);
5-((benzyloxy)methyl)-6-(4-methoxybenzo[d]oxazol-2-yl)-3-phenyl-2-(trifluoromethyl)pyrazolo[1,5-a]pyrimidin-7(4H)-one (C1099);
4-methoxy-2-(5-methyl-7-oxo-3-phenyl-2-(trifluoromethyl)-4,7-dihydropyrazolo[1,5-a]pyrimidin-6-yl)benzo[d]oxazole-7-carbonitrile (C1100);
ethyl 2-(5-methyl-7-oxo-3-phenyl-2-(trifluoromethyl)-4,7-dihydropyrazolo[1,5-a]pyrimidin-6-yl)oxazole-4-carboxylate (C1101);
2-(5-methyl-7-oxo-3-phenyl-2-(trifluoromethyl)-4,7-dihydropyrazolo[1,5-a]pyrimidin-6-yl)oxazole-4-carboxamide (C1102);
5-(hydroxymethyl)-6-(4-methoxybenzo[d]oxazol-2-yl)-3-phenyl-2-(trifluoromethyl)pyrazolo[1,5-a]pyrimidin-7(4H)-one (C1103);
6-(4-(hydroxymethyl)oxazol-2-yl)-5-methyl-3-phenyl-2-(trifluoromethyl)pyrazolo[1,5-a]pyrimidin-7(4H)-one (C1104);
6-(6-chloro-4-methoxybenzo[d]oxazol-2-yl)-5-methyl-3-phenyl-2-(trifluoromethyl)pyrazolo[1,5-a]pyrimidin-7(4H)-one (C1105);
5-methyl-2-(5-methyl-7-oxo-3-phenyl-2-(trifluoromethyl)-4,7-dihydropyrazolo[1,5-a]pyrimidin-6-yl)oxazolo[4,5-c]pyridin-4(5H)-one (C1106);
3-(4-fluorophenyl)-6-(4-methoxybenzo[d]oxazol-2-yl)-5-methyl-2-(trifluoromethyl)pyrazolo[1,5-a]pyrimidin-7(4H)-one (C1107);
6-(4-(methoxymethyl)oxazol-2-yl)-5-methyl-3-phenyl-2-(trifluoromethyl)pyrazolo[1,5-a]pyrimidin-7(4H)-one (C1108);
5-((dimethylamino)methyl)-6-(4-methoxybenzo[d]oxazol-2-yl)-3-phenyl-2-(trifluoromethyl)pyrazolo[1,5-a]pyrimidin-7(4H)-one (C1109);
6-(8-methoxy-[1,2,4]triazolo[1,5-a]pyridin-2-yl)-5-methyl-3-phenyl-2-(trifluoromethyl)pyrazolo[1,5-a]pyrimidin-7(4H)-one (C1110);
6-(7-acetyl-4-methoxybenzo[d]oxazol-2-yl)-5-methyl-3-phenyl-2-(trifluoromethyl)pyrazolo[1,5-a]pyrimidin-7(4H)-one (C1111);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carbonitrile (C1112);
4-methoxy-2-(5-methyl-7-oxo-3-phenyl-2-(trifluoromethyl)-4,7-dihydropyrazolo[1,5-a]pyrimidin-6-yl)benzo[d]oxazole-7-carboxamide (C1113);
3-(3-fluorophenyl)-6-(4-methoxybenzo[d]oxazol-2-yl)-5-methyl-2-(trifluoromethyl)pyrazolo[1,5-a]pyrimidin-7(4H)-one (C1114);
6-(4-methoxybenzo[d]oxazol-2-yl)-3-(4-methoxyphenyl)-5-methyl-2-(trifluoromethyl)pyrazolo[1,5-a]pyrimidin-7(4H)-one (C1115);
2-(5-methyl-7-oxo-3-phenyl-2-(trifluoromethyl)-4,7-dihydropyrazolo[1,5-a]pyrimidin-6-yl)oxazolo[4,5-c]pyridin-4(5H)-one (C1116);
2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)acetic acid (C1117);
6-(4-methoxybenzo[d]oxazol-2-yl)-7-oxo-3-phenyl-5-(trifluoromethyl)-4,7-dihydropyrazolo[1,5-a]pyrimidine-2-carbonitrile (C1118);
3-(3,5-difluorophenyl)-6-(4-methoxybenzo[d]oxazol-2-yl)-5-methyl-2-(trifluoromethyl)pyrazolo[1,5-a]pyrimidin-7(4H)-one (C1119);
6-(4-methoxybenzo[d]oxazol-2-yl)-3-(3-methoxyphenyl)-5-methyl-2-(trifluoromethyl)pyrazolo[1,5-a]pyrimidin-7(4H)-one (C1120);
6-(4-methoxybenzo[d]oxazol-2-yl)-5-(methylthio)-3-phenyl-2-(trifluoromethyl)pyrazolo[1,5-a]pyrimidin-7(4H)-one (C1121);
2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)acetamide (C1122);
6-(6-amino-4-methoxybenzo[d]oxazol-2-yl)-5-methyl-3-phenyl-2-(trifluoromethyl)pyrazolo[1,5-a]pyrimidin-7(4H)-one (C1123);

TABLE 1A-continued 6-(4-methoxy-7-(methylsulfonyl)benzo[d]oxazol-2-yl)-5-methyl-3-phenyl-2-(trifluoromethyl)pyrazolo[1,5-a]pyrimidin-7(4H)-one (C1125);
4-methoxy-2-(5-methyl-7-oxo-3-phenyl-2-(trifluoromethyl)-4,7-dihydropyrazolo[1,5-a]pyrimidin-6-yl)benzo[d]oxazole-5-carbonitrile (C1126);
6-(4-methoxybenzo[d]oxazol-2-yl)-5-methyl-3-(pyridin-2-yl)-2-(trifluoromethyl)pyrazolo[1,5-a]pyrimidin-7(4H)-one (C1127);
6-(6-(aminomethyl)-4-methoxybenzo[d]oxazol-2-yl)-5-methyl-3-phenyl-2-(trifluoromethyl)pyrazolo[1,5-a]pyrimidin-7(4H)-one (C1128);
6-(4-methoxybenzo[d]oxazol-2-yl)-5-methyl-3-(pyridin-3-yl)-2-(trifluoromethyl)pyrazolo[1,5-a]pyrimidin-7(4H)-one (C1129);
6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1130);
6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1131);
6-(4-methoxybenzo[d]oxazol-2-yl)-7-oxo-3-phenyl-2-(trifluoromethyl)-4,7-dihydropyrazolo[1,5-a]pyrimidine-5-carboxamide (C1132);
3-(2,6-difluorophenyl)-6-(4-methoxybenzo[d]oxazol-2-yl)-5-methyl-2-(trifluoromethyl)pyrazolo[1,5-a]pyrimidin-7(4H)-one (C1133);
6-(4-methoxybenzo[d]oxazol-2-yl)-3-phenyl-5-(((tetrahydro-2H-pyran-2-yl)oxy)methyl)-2-(trifluoromethyl)pyrazolo[1,5-a]pyrimidin-7(4H)-one (C1134);
6-(6-(aminomethyl)-4-methoxybenzo[d]oxazol-2-yl)-5-methyl-3-phenyl-2-(trifluoromethyl)pyrazolo[1,5-a]pyrimidin-7(4H)-one (HCl salt) (C1135);
6-(4-methoxybenzo[d]oxazol-2-yl)-5-((methylthio)methyl)-3-phenyl-2-(trifluoromethyl)pyrazolo[1,5-a]pyrimidin-7(4H)-one (C1136);
6-(4-methoxybenzo[d]oxazol-2-yl)-5-((methylsulfinyl)methyl)-3-phenyl-2-(trifluoromethyl)pyrazolo[1,5-a]pyrimidin-7(4H)-one (C1137);
6-(4-methoxybenzo[d]oxazol-2-yl)-5-((methylsulfonyl)methyl)-3-phenyl-2-(trifluoromethyl)pyrazolo[1,5-a]pyrimidin-7(4H)-one (C1138);
6-(4-methoxybenzo[d]oxazol-2-yl)-5-(methoxymethyl)-7-oxo-3-phenyl-4,7-dihydropyrazolo[1,5-a]pyrimidine-2-carbonitrile (C1139);
ethyl 2-(6-(4-methoxybenzo[d]oxazol-2-yl)-7-oxo-3-phenyl-2-(trifluoromethyl)-4,7-dihydropyrazolo[1,5-a]pyrimidin-5-yl)acetate (C1140);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboximidamide (C1141);
6-(4-methoxybenzo[d]oxazol-2-yl)-N-(2-methoxyethyl)-7-oxo-3-phenyl-2-(trifluoromethyl)-4,7-dihydropyrazolo[1,5-a]pyrimidine-5-carboxamide (C1142);
6-(4-(hydroxymethyl)-5-isopropyloxazol-2-yl)-5-methyl-3-phenyl-2-(trifluoromethyl)pyrazolo[1,5-a]pyrimidin-7(4H)-one (C1143);
5-acetyl-6-(4-methoxybenzo[d]oxazol-2-yl)-3-phenyl-2-(trifluoromethyl)pyrazolo[1,5-a]pyrimidin-7(4H)-one (C1144);
6-(6-chloro-4-methoxybenzo[d]oxazol-2-yl)-5-(methoxymethyl)-7-oxo-3-phenyl-4,7-dihydropyrazolo[1,5-a]pyrimidine-2-carbonitrile (C1145);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)acetic acid (C1146);
2-(6-(4-methoxybenzo[d]oxazol-2-yl)-7-oxo-3-phenyl-2-(trifluoromethyl)-4,7-dihydropyrazolo[1,5-a]pyrimidin-5-yl)acetic acid (C1147);
2-(6-(4-methoxybenzo[d]oxazol-2-yl)-5-methyl-7-oxo-2-(trifluoromethyl)-4,7-dihydropyrazolo[1,5-a]pyrimidin-3-yl)benzonitrile (C1148);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboxamide (C1149);
N-(7-methoxy-2-(5-methyl-7-oxo-3-phenyl-2-(trifluoromethyl)-4,7-dihydropyrazolo[1,5-a]pyrimidin-6-yl)oxazolo[5,4-d]pyrimidin-5-yl)acetamide (C1150);
6-(4-methoxybenzo[d]oxazol-2-yl)-5-((2-methoxyethoxy)methyl)-3-phenyl-2-(trifluoromethyl)pyrazolo[1,5-a]pyrimidin-7(4H)-one (C1151);
6-(4-methoxybenzo[d]oxazol-2-yl)-5-((oxetan-3-yloxy)methyl)-3-phenyl-2-(trifluoromethyl)pyrazolo[1,5-a]pyrimidin-7(4H)-one (C1152);
6-(5-isopropyl-4-(methoxymethyl)oxazol-2-yl)-5-methyl-3-phenyl-2-(trifluoromethyl)pyrazolo[1,5-a]pyrimidin-7(4H)-one (C1153);
6-(7-amino-4-methoxybenzo[d]oxazol-2-yl)-5-methyl-3-phenyl-2-(trifluoromethyl)pyrazolo[1,5-a]pyrimidin-7(4H)-one (C1154);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboxylic acid (C1155);
6-(6-aminobenzo[d]oxazol-2-yl)-5-methyl-3-phenyl-2-(trifluoromethyl)pyrazolo[1,5-a]pyrimidin-7(4H)-one (C1156);
6-(5-cyclohexyl-4-(hydroxymethyl)oxazol-2-yl)-5-methyl-3-phenyl-2-(trifluoromethyl)pyrazolo[1,5-a]pyrimidin-7(4H)-one (C1157);
6-(5-cyclohexyl-4-(methoxymethyl)oxazol-2-yl)-5-methyl-3-phenyl-2-(trifluoromethyl)pyrazolo[1,5-a]pyrimidin-7(4H)-one (C1158);
6-(4-methoxybenzo[d]oxazol-2-yl)-5-(((2-oxopyrrolidin-3-yl)oxy)methyl)-3-phenyl-2-(trifluoromethyl)pyrazolo[1,5-a]pyrimidin-7(4H)-one (C1159);
6-(6-chloro-4-methoxybenzo[d]oxazol-2-yl)-5-methyl-7-oxo-3-phenyl-4,7-dihydropyrazolo[1,5-a]pyrimidine-2-carbonitrile (C1160);
6-(4-methoxy-6-(methylamino)benzo[d]oxazol-2-yl)-5-methyl-3-phenyl-2-(trifluoromethyl)pyrazolo[1,5-a]pyrimidin-7(4H)-one (C1161);
6-(6-(dimethylamino)-4-methoxybenzo[d]oxazol-2-yl)-5-methyl-3-phenyl-2-(trifluoromethyl)pyrazolo[1,5-a]pyrimidin-7(4H)-one (C1162);
4-methoxy-N,N,N-trimethyl-2-(5-methyl-7-oxo-3-phenyl-2-(trifluoromethyl)-4,7-dihydropyrazolo[1,5-a]pyrimidin-6-yl)benzo[d]oxazol-6-aminium (C1163);
4-(6-(4-methoxybenzo[d]oxazol-2-yl)-5-methyl-7-oxo-2-(trifluoromethyl)-4,7-dihydropyrazolo[1,5-a]pyrimidin-3-yl)benzonitrile (C1164);

TABLE 1A-continued 2-(5-methyl-7-oxo-3-phenyl-2-(trifluoromethyl)-4,7-dihydropyrazolo[1,5-a]pyrimidin-6-yl)oxazole-4-carboxylic acid (C1165);
6-(6-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1166);
6-(4-methoxyoxazolo[4,5-c]pyridin-2-yl)-5-methyl-7-oxo-3-phenyl-4,7-dihydropyrazolo[1,5-a]pyrimidine-2-carbonitrile (C1167);
5-methyl-6-(3-oxo-1,3-dihydroisobenzofuran-1-yl)-3-phenyl-2-(trifluoromethyl)pyrazolo[1,5-a]pyrimidin-7(4H)-one (C1168);
5-cyclohexyl-2-(5-methyl-7-oxo-3-phenyl-2-(trifluoromethyl)-4,7-dihydropyrazolo[1,5-a]pyrimidin-6-yl)oxazole-4-carboxylic acid (C1169);
5-methyl-6-(oxazol-2-yl)-3-phenyl-2-(trifluoromethyl)pyrazolo[1,5-a]pyrimidin-7(4H)-one (C1170);
6-(4-methoxybenzo[d]oxazol-2-yl)-5-methyl-4-(m-tolyl)-2-(trifluoromethyl)pyrazolo[1,5-a]pyrimidin-7(4H)-one (C1171);
6-(4-methoxybenzo[d]oxazol-2-yl)-5-methyl-3-(m-tolyl)-2-(trifluoromethyl)pyrazolo[1,5-a]pyrimidin-7(4H)-one (C1172);
3-(6-(4-methoxybenzo[d]oxazol-2-yl)-7-oxo-3-phenyl-2-(trifluoromethyl)-4,7-dihydropyrazolo[1,5-a]pyrimidin-5-yl)propanoic acid (C1173);
6-(5-amino-7-methoxyoxazolo[5,4-d]pyrimidin-2-yl)-5-methyl-3-phenyl-2-(trifluoromethyl)pyrazolo[1,5-a]pyrimidin-7(4H)-one (C1174);
6-(6-amino-4-methoxybenzo[d]oxazol-2-yl)-5-methyl-7-oxo-3-phenyl-4,7-dihydropyrazolo[1,5-a]pyrimidine-2-carbonitrile (C1175);
6-(1-cyclohexyl-4-methoxy-1H-benzo[d]imidazol-2-yl)-5-methyl-3-phenyl-2-(trifluoromethyl)pyrazolo[1,5-a]pyrimidin-7(4H)-one (C1176);
5-(((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)methyl)oxazolidin-2-one (C1177);
N-(2-hydroxyethyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1178);
6-(4-methoxybenzo[d]oxazol-2-yl)-N-(2-methoxyethyl)-N-methyl-7-oxo-3-phenyl-2-(trifluoromethyl)-4,7-dihydropyrazolo[1,5-a]pyrimidine-5-carboxamide (C1179);
5-((1H-imidazol-1-yl)methyl)-6-(4-methoxybenzo[d]oxazol-2-yl)-3-phenyl-2-(trifluoromethyl)pyrazolo[1,5-a]pyrimidin-7(4H)-one (C1180);
6-(5-aminobenzo[d]oxazol-2-yl)-5-methyl-7-oxo-3-phenyl-4,7-dihydropyrazolo[1,5-a]pyrimidine-2-carbonitrile (C1181);
5-(((1H-imidazol-5-yl)methoxy)methyl)-6-(4-methoxybenzo[d]oxazol-2-yl)-3-phenyl-2-(trifluoromethyl)pyrazolo[1,5-a]pyrimidin-7(4H)-one (C1182);
5-ethyl-6-(4-methoxybenzo[d]oxazol-2-yl)-3-phenyl-2-(trifluoromethyl)pyrazolo[1,5-a]pyrimidin-7(4H)-one (C1183);
(R)-6-(4-(methoxymethyl)-4,5-dihydrooxazol-2-yl)-5-methyl-3-phenyl-2-(trifluoromethyl)pyrazolo[1,5-a]pyrimidin-7(4H)-one (C1184);
6-(4-methoxybenzo[d]oxazol-2-yl)-N-(oxetan-3-yl)-7-oxo-3-phenyl-2-(trifluoromethyl)-4,7-dihydropyrazolo[1,5-a]pyrimidine-5-carboxamide (C1185);
6-(4-methoxybenzo[d]oxazol-2-yl)-3-phenyl-5-(piperidine-1-carbonyl)-2-(trifluoromethyl)pyrazolo[1,5-a]pyrimidin-7(4H)-one (C1186);
methyl (S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylate (C1187);
6-(4-ethylbenzo[d]oxazol-2-yl)-5-methyl-7-oxo-3-phenyl-4,7-dihydropyrazolo[1,5-a]pyrimidine-2-carbonitrile (C1188);
6-(1-(cyclopropylmethyl)-4-methoxy-1H-benzo[d]imidazol-2-yl)-5-methyl-3-phenyl-2-(trifluoromethyl)pyrazolo[1,5-a]pyrimidin-7(4H)-one (C1189);
6-(1-cyclohexyl-1H-benzo[d]imidazol-2-yl)-5-methyl-3-phenyl-2-(trifluoromethyl)pyrazolo[1,5-a]pyrimidin-7(4H)-one (C1190);
6-(7-(aminomethyl)-4-methoxybenzo[d]oxazol-2-yl)-5-methyl-3-phenyl-2-(trifluoromethyl)pyrazolo[1,5-a]pyrimidin-7(4H)-one (C1191);
(S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1192);
6-(6-aminobenzo[d]oxazol-2-yl)-5-methyl-7-oxo-3-phenyl-4,7-dihydropyrazolo[1,5-a]pyrimidine-2-carbonitrile (C1193);
6-(4-methoxybenzo[d]oxazol-2-yl)-7-oxo-3-phenyl-N-(tetrahydro-2H-pyran-4-yl)-2-(trifluoromethyl)-4,7-dihydropyrazolo[1,5-a]pyrimidine-5-carboxamide (C1194);
(6-(4-methoxybenzo[d]oxazol-2-yl)-7-oxo-3-phenyl-2-(trifluoromethyl)-4,7-dihydropyrazolo[1,5-a]pyrimidine-5-carbonyl)glycine (C1195);
(S)-N-(1-hydroxypropan-2-yl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1196);
N-(6-(4-methoxybenzo[d]oxazol-2-yl)-7-oxo-3-phenyl-2-(trifluoromethyl)-4,7-dihydropyrazolo[1,5-a]pyrimidine-5-carbonyl)-N-methylglycine (C1197);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)acetamide (C1198);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)-N-methylacetamide (C1199);
6-(4-methoxy-1-(2-methoxyethyl)-1H-benzo[d]imidazol-2-yl)-5-methyl-3-phenyl-2-(trifluoromethyl)pyrazolo[1,5-a]pyrimidin-7(4H)-one (C1200);
6-(1-(2-hydroxyethyl)-4-methoxy-1H-benzo[d]imidazol-2-yl)-5-methyl-3-phenyl-2-(trifluoromethyl)pyrazolo[1,5-a]pyrimidin-7(4H)-one (C1201);
6-(6-amino-7-chloro-4-methoxybenzo[d]oxazol-2-yl)-5-methyl-7-oxo-3-phenyl-4,7-dihydropyrazolo[1,5-a]pyrimidine-2-carbonitrile (C1202);
6-(6-(hydroxymethyl)-4-methoxybenzo[d]oxazol-2-yl)-5-methyl-7-oxo-3-phenyl-4,7-dihydropyrazolo[1,5-a]pyrimidine-2-carbonitrile (C1203);
5-methyl-6-(4-(methylthio)benzo[d]oxazol-2-yl)-7-oxo-3-phenyl-4,7-dihydropyrazolo[1,5-a]pyrimidine-2-carbonitrile (C1204);

TABLE 1A-continued 6-(7-chloro-4-methoxybenzo[d]oxazol-2-yl)-5-methyl-7-oxo-3-phenyl-4,7-dihydropyrazolo[1,5-a]pyrimidine-2-carbonitrile (C1205);
6-(5-chloro-4-methoxybenzo[d]oxazol-2-yl)-5-methyl-7-oxo-3-phenyl-4,7-dihydropyrazolo[1,5-a]pyrimidine-2-carbonitrile (C1206);
(R)-5-(2-(hydroxymethyl)pyrrolidine-1-carbonyl)-6-(4-methoxybenzo[d]oxazol-2-yl)-3-phenyl-2-(trifluoromethyl)pyrazolo[1,5-a]pyrimidin-7(4H)-one (C1207);
(S)-N-(1-hydroxy-3-methylbutan-2-yl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1208);
6-(4-methoxybenzo[d]oxazol-2-yl)-7-oxo-3-phenyl-N-(3,3,3-trifluoro-2-hydroxypropyl)-2-(trifluoromethyl)-4,7-dihydropyrazolo[1,5-a]pyrimidine-5-carboxamide (C1209);
2-acetyl-6-(4-methoxybenzo[d]oxazol-2-yl)-5-methyl-3-phenylpyrazolo[1,5-a]pyrimidin-7(4H)-one (C1210);
2-ethynyl-6-(4-methoxybenzo[d]oxazol-2-yl)-5-methyl-3-phenylpyrazolo[1,5-a]pyrimidin-7(4H)-one (C1211);
N-(2-(dimethylamino)ethyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1212);
(4R,5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1213);
5-methyl-6-(1-oxoisoindolin-2-yl)-3-phenyl-2-(trifluoromethyl)pyrazolo[1,5-a]pyrimidin-7(4H)-one (C1214);
6-(3-(hydroxymethyl)-8-methoxyimidazo[1,2-a]pyridin-2-yl)-5-methyl-3-phenyl-2-(trifluoromethyl)pyrazolo[1,5-a]pyrimidin-7(4H)-one (C1215);
(5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1216);
6-(6-amino-1-oxoisoindolin-2-yl)-5-methyl-3-phenyl-2-(trifluoromethyl)pyrazolo[1,5-a]pyrimidin-7(4H)-one (C1217);
6-(6-amino-4-methoxyoxazolo[4,5-c]pyridin-2-yl)-5-methyl-7-oxo-3-phenyl-4,7-dihydropyrazolo[1,5-a]pyrimidine-2-carbonitrile (C1218);
N-(2-hydroxy-2-methylpropyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1219);
6-(4-methoxy-1-oxoisoindolin-2-yl)-5-methyl-3-phenyl-2-(trifluoromethyl)pyrazolo[1,5-a]pyrimidin-7(4H)-one (C1220);
2-(4-methoxy-2-(5-methyl-7-oxo-3-phenyl-2-(trifluoromethyl)-4,7-dihydropyrazolo[1,5-a]pyrimidin-6-yl)-1H-benzo[d]imidazol-1-yl)acetic acid (C1221);
6-(benzo[d]oxazol-2-yl)-5-methyl-7-oxo-3-phenyl-4,7-dihydropyrazolo[1,5-a]pyrimidine-2-carbonitrile (C1222);
6-(4-aminobenzo[d]oxazol-2-yl)-5-methyl-7-oxo-3-phenyl-4,7-dihydropyrazolo[1,5-a]pyrimidine-2-carbonitrile (C1223);
6-(7-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1224);
6-(4-methoxybenzo[d]oxazol-2-yl)-5-(((1-methyl-2-oxopyrrolidin-3-yl)oxy)methyl)-3-phenyl-2-(trifluoromethyl)pyrazolo[1,5-a]pyrimidin-7(4H)-one (C1225);
5-((2-hydroxyethoxy)methyl)-6-(4-methoxybenzo[d]oxazol-2-yl)-3-phenyl-2-(trifluoromethyl)pyrazolo[1,5-a]pyrimidin-7(4H)-one (C1226);
6-(6-amino-4-methoxyoxazolo[4,5-c]pyridin-2-yl)-5-(methoxymethyl)-7-oxo-3-phenyl-4,7-dihydropyrazolo[1,5-a]pyrimidine-2-carbonitrile (C1227);
2-(cyclopropylethynyl)-6-(4-methoxybenzo[d]oxazol-2-yl)-5-methyl-3-phenylpyrazolo[1,5-a]pyrimidin-7(4H)-one (C1228);
5-methyl-3-phenyl-6-(1-phenyl-1H-benzo[d]imidazol-2-yl)-2-(trifluoromethyl)pyrazolo[1,5-a]pyrimidin-7(4H)-one (C1229);
6-(7-aminobenzo[d]oxazol-2-yl)-5-methyl-7-oxo-3-phenyl-4,7-dihydropyrazolo[1,5-a]pyrimidine-2-carbonitrile (C1230);
5-methyl-3-phenyl-6-(1-(2,2,2-trifluoroethyl)-1H-benzo[d]imidazol-2-yl)-2-(trifluoromethyl)pyrazolo[1,5-a]pyrimidin-7(4H)-one (C1231);
5-((2,2-difluoroethoxy)methyl)-6-(4-methoxybenzo[d]oxazol-2-yl)-3-phenyl-2-(trifluoromethyl)pyrazolo[1,5-a]pyrimidin-7(4H)-one (C1232);
ethyl 4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylate (C1233);
4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylic acid (C1234);
6-(1-(cyclopentylmethyl)-1H-benzo[d]imidazol-2-yl)-5-methyl-3-phenyl-2-(trifluoromethyl)pyrazolo[1,5-a]pyrimidin-7(4H)-one (C1235);
5-(3-(hydroxymethyl)cyclopentyl)-6-(4-methoxybenzo[d]oxazol-2-yl)-3-phenyl-2-(trifluoromethyl)pyrazolo[1,5-a]pyrimidin-7(4H)-one (C1236);
4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohexane-1-carboxylic acid (Isomer 1) (C1237);
4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohexane-1-carboxylic acid (Isomer 2) (C1238);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclopentane-1-carboxylic acid (C1239);
6-(6-(1-hydroxyethyl)-4-methoxybenzo[d]oxazol-2-yl)-5-methyl-7-oxo-3-phenyl-4,7-dihydropyrazolo[1,5-a]pyrimidine-2-carbonitrile (C1240);
6-(4-methoxybenzo[d]oxazol-2-yl)-5-methyl-3-phenyl-2-vinylpyrazolo[1,5-a]pyrimidin-7(4H)-one (C1241);
2-cyclopropyl-6-(4-methoxybenzo[d]oxazol-2-yl)-5-methyl-3-phenylpyrazolo[1,5-a]pyrimidin-7(4H)-one (C1242);
6-(4-methoxybenzo[d]oxazol-2-yl)-5-((2-methoxyethoxy)methyl)-7-oxo-3-phenyl-4,7-dihydropyrazolo[1,5-a]pyrimidine-2-carbonitrile (C1243);
6-(4-methoxybenzo[d]oxazol-2-yl)-7-oxo-3-phenyl-N-(1H-pyrazol-4-yl)-2-(trifluoromethyl)-4,7-dihydropyrazolo[1,5-a]pyrimidine-5-carboxamide (C1244);

TABLE 1A-continued

N-((1H-pyrazol-3-yl)methyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1245);
5-(methoxymethyl)-6-(4-methoxyoxazolo[4,5-c]pyridin-2-yl)-7-oxo-3-phenyl-4,7-dihydropyrazolo[1,5-a]pyrimidine-2-carbonitrile (C1246);
5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1247);
5-((2-hydroxyethoxy)methyl)-6-(4-methoxybenzo[d]oxazol-2-yl)-7-oxo-3-phenyl-4,7-dihydropyrazolo[1,5-a]pyrimidine-2-carbonitrile (C1248);
2-cyano-6-(4-methoxybenzo[d]oxazol-2-yl)-7-oxo-3-phenyl-4,7-dihydropyrazolo[1,5-a]pyrimidine-5-carboxylic acid (C1249);
6-(5-amino-4-methoxybenzo[d]oxazol-2-yl)-5-methyl-7-oxo-3-phenyl-4,7-dihydropyrazolo[1,5-a]pyrimidine-2-carbonitrile (C1250);
6-(4-methoxybenzo[d]oxazol-2-yl)-7-oxo-5-(((2-oxooxazolidin-5-yl)methoxy)methyl)-3-phenyl-4,7-dihydropyrazolo[1,5-a]pyrimidine-2-carbonitrile (C1251);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclobutane-1-carboxylic acid (C1252);
6-(4-methoxybenzo[d]oxazol-2-yl)-5-(3-methylisoxazol-4-yl)-3-phenyl-2-(trifluoromethyl)pyrazolo[1,5-a]pyrimidin-7(4H)-one (C1253);
6-(4-methoxybenzo[d]oxazol-2-yl)-3-phenyl-5-(1H-pyrazol-4-yl)-2-(trifluoromethyl)pyrazolo[1,5-a]pyrimidin-7(4H)-one (C1254);
6-(4-methoxybenzo[d]oxazol-2-yl)-5-(1-methyl-1H-pyrazol-4-yl)-3-phenyl-2-(trifluoromethyl)pyrazolo[1,5-a]pyrimidin-7(4H)-one (C1255);
6-(4-methoxybenzo[d]oxazol-2-yl)-N-(1-methyl-1H-pyrazol-3-yl)-7-oxo-3-phenyl-2-(trifluoromethyl)-4,7-dihydropyrazolo[1,5-a]pyrimidine-5-carboxamide (C1256);
1-(6-(4-methoxybenzo[d]oxazol-2-yl)-7-oxo-3-phenyl-2-(trifluoromethyl)-4,7-dihydropyrazolo[1,5-a]pyrimidin-5-yl)piperidine-3-carboxylic acid (C1257);
6-(4-methoxybenzo[d]oxazol-2-yl)-5-morpholino-3-phenyl-2-(trifluoromethyl)pyrazolo[1,5-a]pyrimidin-7(4H)-one (C1258);
6-(4-methoxybenzo[d]oxazol-2-yl)-5-((oxetan-3-yloxy)methyl)-7-oxo-3-phenyl-4,7-dihydropyrazolo[1,5-a]pyrimidine-2-carbonitrile (C1259);
6-(5-isopropyloxazol-2-yl)-5-methyl-7-oxo-3-phenyl-4,7-dihydropyrazolo[1,5-a]pyrimidine-2-carbonitrile (C1260);
6-(4-(difluoromethoxy)benzo[d]oxazol-2-yl)-5-(methoxymethyl)-7-oxo-3-phenyl-4,7-dihydropyrazolo[1,5-a]pyrimidine-2-carbonitrile (C1261);
5-(methoxymethyl)-7-oxo-3-phenyl-6-(4-(2,2,2-trifluoroethoxy)benzo[d]oxazol-2-yl)-4,7-dihydropyrazolo[1,5-a]pyrimidine-2-carbonitrile (C1262);
5-((2-methoxyethoxy)methyl)-7-oxo-3-phenyl-6-(4-(2,2,2-trifluoroethyl)oxazolo[4,5-c]pyridin-2-yl)-4,7-dihydropyrazolo[1,5-a]pyrimidine-2-carbonitrile (C1263);
6-benzyl-3-cyclopropyl-5-methyl-2-(trifluoromethyl)pyrazolo[1,5-a]pyrimidin-7(4H)-one (C1264);
3-cyclopropyl-5-methyl-6-phenyl-2-(trifluoromethyl)pyrazolo[1,5-a]pyrimidin-7(4H)-one (C1265);
3-cyclopentyl-5-methyl-6-phenyl-2-(trifluoromethyl)pyrazolo[1,5-a]pyrimidin-7(4H)-one (C1266);
6-benzyl-3-cyclopentyl-5-methyl-2-(trifluoromethyl)pyrazolo[1,5-a]pyrimidin-7(4H)-one (C1267);
6-benzyl-3-isopropyl-5-methyl-2-(trifluoromethyl)pyrazolo[1,5-a]pyrimidin-7(4H)-one (C1268);
3-isopropyl-5-methyl-6-phenyl-2-(trifluoromethyl)pyrazolo[1,5-a]pyrimidin-7(4H)-one (C1269);
5-methyl-6-(oxazol-2-yl)-7-oxo-3-phenyl-4,7-dihydropyrazolo[1,5-a]pyrimidine-2-carbonitrile (C1270);
6-(6-amino-7-chlorobenzo[d]oxazol-2-yl)-5-methyl-7-oxo-3-phenyl-4,7-dihydropyrazolo[1,5-a]pyrimidine-2-carbonitrile (C1271);
6-(4-(dimethylamino)benzo[d]oxazol-2-yl)-5-methyl-7-oxo-3-phenyl-4,7-dihydropyrazolo[1,5-a]pyrimidine-2-carbonitrile (C1272);
5-methyl-7-oxo-3,6-diphenyl-4,7-dihydropyrazolo[1,5-a]pyrimidine-2-carbonitrile (C1273);
5-methyl-6-(4-(methylamino)benzo[d]oxazol-2-yl)-7-oxo-3-phenyl-4,7-dihydropyrazolo[1,5-a]pyrimidine-2-carbonitrile (C1274);
5-methyl-6-(oxazolo[4,5-c]pyridin-2-yl)-7-oxo-3-phenyl-4,7-dihydropyrazolo[1,5-a]pyrimidine-2-carbonitrile (C1275);
6-(1-cyclohexyl-1H-benzo[d]imidazol-2-yl)-5-methyl-7-oxo-3-phenyl-4,7-dihydropyrazolo[1,5-a]pyrimidine-2-carbonitrile (C1276);
6-(4-cyclopropoxybenzo[d]oxazol-2-yl)-5-methyl-7-oxo-3-phenyl-4,7-dihydropyrazolo[1,5-a]pyrimidine-2-carbonitrile (C1277);
5-methyl-3-phenyl-6-(5-(pyridin-3-yl)-4H-1,2,4-triazol-3-yl)-2-(trifluoromethyl)pyrazolo[1,5-a]pyrimidin-7(4H)-one (C1278);
6-(6-amino-1-cyclohexyl-1H-benzo[d]imidazol-2-yl)-5-methyl-7-oxo-3-phenyl-4,7-dihydropyrazolo[1,5-a]pyrimidine-2-carbonitrile (C1279);
5-methyl-7-oxo-3-phenyl-6-(piperidin-1-yl)-4,7-dihydropyrazolo[1,5-a]pyrimidine-2-carbonitrile (C1280);
6-(isoxazol-4-yl)-5-methyl-7-oxo-3-phenyl-4,7-dihydropyrazolo[1,5-a]pyrimidine-2-carbonitrile (C1281);
5-methyl-6-(1-methyl-1H-pyrazol-4-yl)-7-oxo-3-phenyl-4,7-dihydropyrazolo[1,5-a]pyrimidine-2-carbonitrile (C1282);
3-(3-fluorophenyl)-6-(4-methoxybenzo[d]oxazol-2-yl)-5-methyl-7-oxo-4,7-dihydropyrazolo[1,5-a]pyrimidine-2-carbonitrile (C1283);
5-(dimethylphosphoryl)-6-(4-methoxybenzo[d]oxazol-2-yl)-3-phenyl-2-(trifluoromethyl)pyrazolo[1,5-a]pyrimidin-7(4H)-one (C1284);

TABLE 1A-continued 5-methyl-6-(5-methyl-1,3,4-oxadiazol-2-yl)-3-phenyl-2-(trifluoromethyl)pyrazolo[1,5-a]pyrimidin-7(4H)-one (D1001);
6-(5-(4-methoxyphenyl)-1,3,4-oxadiazol-2-yl)-5-methyl-3-phenyl-2-(trifluoromethyl)pyrazolo[1,5-a]pyrimidin-7(4H)-one (D1002);
6-(5-cyclopentyl-1,3,4-oxadiazol-2-yl)-5-methyl-3-phenyl-2-(trifluoromethyl)pyrazolo[1,5-a]pyrimidin-7(4H)-one (D1003);
6-(5-cyclohexyl-1,3,4-oxadiazol-2-yl)-5-methyl-3-phenyl-2-(trifluoromethyl)pyrazolo[1,5-a]pyrimidin-7(4H)-one (D1004);
6-(5-isopropyl-1,3,4-oxadiazol-2-yl)-5-methyl-3-phenyl-2-(trifluoromethyl)pyrazolo[1,5-a]pyrimidin-7(4H)-one (D1005);
6-(5-cyclohexyl-1,3,4-thiadiazol-2-yl)-5-methyl-3-phenyl-2-(trifluoromethyl)pyrazolo[1,5-a]pyrimidin-7(4H)-one (D1006);
6-(5-(furan-2-yl)-1,3,4-oxadiazol-2-yl)-5-methyl-3-phenyl-2-(trifluoromethyl)pyrazolo[1,5-a]pyrimidin-7(4H)-one (D1007);
5-methyl-3-phenyl-6-(5-(1,1,1-trifluoro-2-hydroxypropan-2-yl)-1,3,4-oxadiazol-2-yl)-2-(trifluoromethyl)pyrazolo[1,5-a]pyrimidin-7(4H)-one (D1008);
5-methyl-6-(5-morpholino-1,3,4-oxadiazol-2-yl)-3-phenyl-2-(trifluoromethyl)pyrazolo[1,5-a]pyrimidin-7(4H)-one (D1009);
5-methyl-3-phenyl-6-(5-phenyl-1,3,4-oxadiazol-2-yl)-2-(trifluoromethyl)pyrazolo[1,5-a]pyrimidin-7(4H)-one (D1011);
5-methyl-3-phenyl-6-(5-(tetrahydrofuran-2-yl)-1,3,4-oxadiazol-2-yl)-2-(trifluoromethyl)pyrazolo[1,5-a]pyrimidin-7(4H)-one (D1012);
5-methyl-3-phenyl-6-(5-(tetrahydrofuran-3-yl)-1,3,4-oxadiazol-2-yl)-2-(trifluoromethyl)pyrazolo[1,5-a]pyrimidin-7(4H)-one (D1013);
5-methyl-3-phenyl-6-(5-(pyrrolidin-1-yl)-1,3,4-oxadiazol-2-yl)-2-(trifluoromethyl)pyrazolo[1,5-a]pyrimidin-7(4H)-one (D1014);
5-methyl-3-phenyl-6-(5-(tetrahydro-2H-pyran-3-yl)-1,3,4-oxadiazol-2-yl)-2-(trifluoromethyl)pyrazolo[1,5-a]pyrimidin-7(4H)-one (D1015);
5-methyl-3-phenyl-6-(5-(tetrahydro-2H-pyran-4-yl)-1,3,4-oxadiazol-2-yl)-2-(trifluoromethyl)pyrazolo[1,5-a]pyrimidin-7(4H)-one (D1016);
6-(5-cyclohexyl-1,3,4-oxadiazol-2-yl)-3-cyclopentyl-5-methyl-2-(trifluoromethyl)pyrazolo[1,5-a]pyrimidin-7(4H)-one (D1017);
6-(5-cyclopentyl-1,3,4-oxadiazol-2-yl)-5-(methoxymethyl)-3-phenyl-2-(trifluoromethyl)pyrazolo[1,5-a]pyrimidin-7(4H)-one (D1018);
6-(5-(methoxymethyl)-1,3,4-oxadiazol-2-yl)-5-methyl-3-phenyl-2-(trifluoromethyl)pyrazolo[1,5-a]pyrimidin-7(4H)-one (D1019);
5-methyl-3-phenyl-6-(5-(piperidin-1-yl)-1,3,4-oxadiazol-2-yl)-2-(trifluoromethyl)pyrazolo[1,5-a]pyrimidin-7(4H)-one (D1020);
6-(5-(3-methoxycyclohexyl)-1,3,4-oxadiazol-2-yl)-5-methyl-3-phenyl-2-(trifluoromethyl)pyrazolo[1,5-a]pyrimidin-7(4H)-one (D1021);
5-methyl-6-(5-(2-methylpyrrolidin-1-yl)-1,3,4-oxadiazol-2-yl)-3-phenyl-2-(trifluoromethyl)pyrazolo[1,5-a]pyrimidin-7(4H)-one (D1022);
5-methyl-6-(5-(1-methylcyclopentyl)-1,3,4-oxadiazol-2-yl)-3-phenyl-2-(trifluoromethyl)pyrazolo[1,5-a]pyrimidin-7(4H)-one (D1023);
5-methyl-3-phenyl-6-(5-(tetrahydro-2H-pyran-2-yl)-1,3,4-oxadiazol-2-yl)-2-(trifluoromethyl)pyrazolo[1,5-a]pyrimidin-7(4H)-one (D1024);
(S)-5-methyl-3-phenyl-6-(5-(tetrahydro-2H-pyran-3-yl)-1,3,4-oxadiazol-2-yl)-2-(trifluoromethyl)pyrazolo[1,5-a]pyrimidin-7(4H)-one (D1025);
(R)-5-methyl-3-phenyl-6-(5-(tetrahydro-2H-pyran-3-yl)-1,3,4-oxadiazol-2-yl)-2-(trifluoromethyl)pyrazolo[1,5-a]pyrimidin-7(4H)-one (D1026);
6-(5-(3-methoxypiperidin-1-yl)-1,3,4-oxadiazol-2-yl)-5-methyl-3-phenyl-2-(trifluoromethyl)pyrazolo[1,5-a]pyrimidin-7(4H)-one (D1027);
(S)-5-methyl-3-phenyl-6-(5-(2,2,2-trifluoro-1-methoxy-1-phenylethyl)-1,3,4-oxadiazol-2-yl)-2-(trifluoromethyl)pyrazolo[1,5-a]pyrimidin-7(4H)-one (D1028);
(R)-5-methyl-3-phenyl-6-(5-(2,2,2-trifluoro-1-methoxy-1-phenylethyl)-1,3,4-oxadiazol-2-yl)-2-(trifluoromethyl)pyrazolo[1,5-a]pyrimidin-7(4H)-one (D1029);
2,5-dimethyl-3-phenyl-6-(5-(tetrahydro-2H-pyran-3-yl)-1,3,4-oxadiazol-2-yl)pyrazolo[1,5-a]pyrimidin-7(4H)-one (D1030);
tert-butyl 3-(5-(5-methyl-7-oxo-3-phenyl-2-(trifluoromethyl)-4,7-dihydropyrazolo[1,5-a]pyrimidin-6-yl)-1,3,4-oxadiazol-2-yl)piperidine-1-carboxylate (D1031);
5-methyl-6-((5-methyl-1,3,4-oxadiazol-2-yl)methyl)-3-phenyl-2-(trifluoromethyl)pyrazolo[1,5-a]pyrimidin-7(4H)-one (D1032);
6-((5-(4-methoxyphenyl)-1,3,4-oxadiazol-2-yl)methyl)-5-methyl-3-phenyl-2-(trifluoromethyl)pyrazolo[1,5-a]pyrimidin-7(4H)-one (D1033);
6-((5-cyclopentyl-1,3,4-oxadiazol-2-yl)methyl)-5-methyl-3-phenyl-2-(trifluoromethyl)pyrazolo[1,5-a]pyrimidin-7(4H)-one (D1034);
6-((5-cyclohexyl-1,3,4-oxadiazol-2-yl)methyl)-5-methyl-3-phenyl-2-(trifluoromethyl)pyrazolo[1,5-a]pyrimidin-7(4H)-one (D1035);
5-methyl-3-phenyl-6-(5-(piperidin-3-yl)-1,3,4-oxadiazol-2-yl)-2-(trifluoromethyl)pyrazolo[1,5-a]pyrimidin-7(4H)-one (D1036);
6-(5-(3-methoxypyrrolidin-1-yl)-1,3,4-oxadiazol-2-yl)-5-methyl-3-phenyl-2-(trifluoromethyl)pyrazolo[1,5-a]pyrimidin-7(4H)-one (D1037);
5-methyl-3-phenyl-2-(trifluoromethyl)-6-(5-(1-(trifluoromethyl)cyclopropyl)-1,3,4-oxadiazol-2-yl)pyrazolo[1,5-a]pyrimidin-7(4H)-one (D1038);
benzyl 3-(5-(5-methyl-7-oxo-3-phenyl-2-(trifluoromethyl)-4,7-dihydropyrazolo[1,5-a]pyrimidin-6-yl)-1,3,4-oxadiazol-2-yl)morpholine-4-carboxylate (D1039);
5-methyl-6-(5-(1-(methylsulfonyl)piperidin-3-yl)-1,3,4-oxadiazol-2-yl)-3-phenyl-2-(trifluoromethyl)pyrazolo[1,5-a]pyrimidin-7(4H)-one (D1040);
6-(5-(1-acetylpiperidin-3-yl)-1,3,4-oxadiazol-2-yl)-5-methyl-3-phenyl-2-(trifluoromethyl)pyrazolo[1,5-a]pyrimidin-7(4H)-one (D1041);

TABLE 1A-continued 5-methyl-6-(5-(morpholin-3-yl)-1,3,4-oxadiazol-2-yl)-3-phenyl-2-
(trifluoromethyl)pyrazolo[1,5-a]pyrimidin-7(4H)-one (D1042);
6-(5-(cyclohexyl(methyl)amino)-1,3,4-oxadiazol-2-yl)-5-methyl-3-phenyl-2-
(trifluoromethyl)pyrazolo[1,5-a]pyrimidin-7(4H)-one (D1043);
tert-butyl 4-(5-(5-methyl-7-oxo-3-phenyl-2-(trifluoromethyl)-4,7-dihydropyrazolo[1,5-
a]pyrimidin-6-yl)-1,3,4-oxadiazol-2-yl)piperidine-1-carboxylate (D1044);
tert-butyl 2-(5-(5-methyl-7-oxo-3-phenyl-2-(trifluoromethyl)-4,7-dihydropyrazolo[1,5-
a]pyrimidin-6-yl)-1,3,4-oxadiazol-2-yl)piperidine-1-carboxylate (D1045);
6-(5-(2-methoxycyclohexyl)-1,3,4-oxadiazol-2-yl)-5-methyl-3-phenyl-2-
(trifluoromethyl)pyrazolo[1,5-a]pyrimidin-7(4H)-one (Isomers 1, 2 and 3) (D1046);
5-methyl-6-(5-(4-(methylsulfonyl)morpholin-3-yl)-1,3,4-oxadiazol-2-yl)-3-phenyl-2-
(trifluoromethyl)pyrazolo[1,5-a]pyrimidin-7(4H)-one (D1047);
6-(5-(2-methoxypropan-2-yl)-1,3,4-oxadiazol-2-yl)-5-methyl-3-phenyl-2-
(trifluoromethyl)pyrazolo[1,5-a]pyrimidin-7(4H)-one (D1048);
6-(5-(2-methoxycyclopentyl)-1,3,4-oxadiazol-2-yl)-5-methyl-3-phenyl-2-
(trifluoromethyl)pyrazolo[1,5-a]pyrimidin-7(4H)-one (Isomers 1 and 2) (D1049);
6-(5-(4-acetylmorpholin-3-yl)-1,3,4-oxadiazol-2-yl)-5-methyl-3-phenyl-2-
(trifluoromethyl)pyrazolo[1,5-a]pyrimidin-7(4H)-one (D1050);
5-methyl-6-(5-(3-methyltetrahydro-2H-pyran-3-yl)-1,3,4-oxadiazol-2-yl)-3-phenyl-2-
(trifluoromethyl)pyrazolo[1,5-a]pyrimidin-7(4H)-one (D1051);
5-methyl-3-phenyl-6-(5-(piperidin-4-yl)-1,3,4-oxadiazol-2-yl)-2-
(trifluoromethyl)pyrazolo[1,5-a]pyrimidin-7(4H)-one (D1052);
5-methyl-6-(5-(1-(methylsulfonyl)piperidin-4-yl)-1,3,4-oxadiazol-2-yl)-3-phenyl-2-
(trifluoromethyl)pyrazolo[1,5-a]pyrimidin-7(4H)-one (D1053);
6-(5-(1-acetylpiperidin-4-yl)-1,3,4-oxadiazol-2-yl)-5-methyl-3-phenyl-2-
(trifluoromethyl)pyrazolo[1,5-a]pyrimidin-7(4H)-one (D1054);
6-(5-(1-methoxycyclopentyl)-1,3,4-oxadiazol-2-yl)-5-methyl-3-phenyl-2-
(trifluoromethyl)pyrazolo[1,5-a]pyrimidin-7(4H)-one (D1055);
5-methyl-6-(5-(1-(methylsulfonyl)piperidin-2-yl)-1,3,4-oxadiazol-2-yl)-3-phenyl-2-
(trifluoromethyl)pyrazolo[1,5-a]pyrimidin-7(4H)-one (D1056);
6-(5-(1-acetylpiperidin-2-yl)-1,3,4-oxadiazol-2-yl)-5-methyl-3-phenyl-2-
(trifluoromethyl)pyrazolo[1,5-a]pyrimidin-7(4H)-one (D1057);
5-methyl-6-(5-(4-methylpiperazin-1-yl)-1,3,4-oxadiazol-2-yl)-3-phenyl-2-
(trifluoromethyl)pyrazolo[1,5-a]pyrimidin-7(4H)-one (D1058);
6-(5-(2-(methoxymethyl)pyrrolidin-1-yl)-1,3,4-oxadiazol-2-yl)-5-methyl-3-phenyl-2-
(trifluoromethyl)pyrazolo[1,5-a]pyrimidin-7(4H)-one (D1059);
6-(5-(2-(methoxymethyl)piperidin-1-yl)-1,3,4-oxadiazol-2-yl)-5-methyl-3-phenyl-2-
(trifluoromethyl)pyrazolo[1,5-a]pyrimidin-7(4H)-one (D1060);
5-methyl-6-(5-(4-nitrophenyl)-1,3,4-oxadiazol-2-yl)-3-phenyl-2-
(trifluoromethyl)pyrazolo[1,5-a]pyrimidin-7(4H)-one (D1061);
6-(5-(1-aminocyclopentyl)-1,3,4-oxadiazol-2-yl)-5-methyl-3-phenyl-2-
(trifluoromethyl)pyrazolo[1,5-a]pyrimidin-7(4H)-one (D1062);
5-methyl-3-phenyl-6-(5-(pyridin-3-yl)-1,3,4-oxadiazol-2-yl)-2-
(trifluoromethyl)pyrazolo[1,5-a]pyrimidin-7(4H)-one (D1063);
6-(5-(2-methoxypyridin-3-yl)-1,3,4-oxadiazol-2-yl)-5-methyl-3-phenyl-2-
(trifluoromethyl)pyrazolo[1,5-a]pyrimidin-7(4H)-one (D1064);
5-methyl-6-(5-((1-methylpiperidin-4-yl)methyl)-1,3,4-oxadiazol-2-yl)-3-phenyl-2-
(trifluoromethyl)pyrazolo[1,5-a]pyrimidin-7(4H)-one (D1065);
5-(5-methyl-7-oxo-3-phenyl-2-(trifluoromethyl)-4,7-dihydropyrazolo[1,5-a]pyrimidin-6-
yl)-1,3,4-oxadiazole-2-carboxamide (D1066);
6-(5-(2-hydroxypyridin-3-yl)-1,3,4-oxadiazol-2-yl)-5-methyl-3-phenyl-2-
(trifluoromethyl)pyrazolo[1,5-a]pyrimidin-7(4H)-one (D1067);
6-(5-(1,1-dioxidothiomorpholino)-1,3,4-oxadiazol-2-yl)-5-methyl-3-phenyl-2-
(trifluoromethyl)pyrazolo[1,5-a]pyrimidin-7(4H)-one (D1068);
6-(5-(2-(2-aminoethyl)piperidin-1-yl)-1,3,4-oxadiazol-2-yl)-5-methyl-3-phenyl-2-
(trifluoromethyl)pyrazolo[1,5-a]pyrimidin-7(4H)-one (D1069);
6-(5-(2-(aminomethyl)piperidin-1-yl)-1,3,4-oxadiazol-2-yl)-5-methyl-3-phenyl-2-
(trifluoromethyl)pyrazolo[1,5-a]pyrimidin-7(4H)-one (D1070);
5-(5-methyl-7-oxo-3-phenyl-2-(trifluoromethyl)-4,7-dihydropyrazolo[1,5-a]pyrimidin-6-
yl)-1,3,4-oxadiazole-2-carbonitrile (D1071);
5-methyl-3-phenyl-6-(5-(1,4,5,6-tetrahydropyrimidin-2-yl)-1,3,4-oxadiazol-2-yl)-2-
(trifluoromethyl)pyrazolo[1,5-a]pyrimidin-7(4H)-one (D1072);
N-(2-(1-(5-(5-methyl-7-oxo-3-phenyl-2-(trifluoromethyl)-4,7-dihydropyrazolo[1,5-
a]pyrimidin-6-yl)-1,3,4-oxadiazol-2-yl)piperidin-2-yl)ethyl)methanesulfonamide (D1073);
5-(5-methyl-7-oxo-3-phenyl-2-(trifluoromethyl)-4,7-dihydropyrazolo[1,5-a]pyrimidin-6-
yl)-1,3,4-oxadiazole-2-carboximidamide (D1074);
6-(5-amino-1,3,4-oxadiazol-2-yl)-5-methyl-3-phenyl-2-(trifluoromethyl)pyrazolo[1,5-
a]pyrimidin-7(4H)-one (D1075);
6-(5-(4-methoxypyrimidin-2-yl)-1,3,4-oxadiazol-2-yl)-5-methyl-3-phenyl-2-
(trifluoromethyl)pyrazolo[1,5-a]pyrimidin-7(4H)-one (D1076);
1-(5-(5-methyl-7-oxo-3-phenyl-2-(trifluoromethyl)-4,7-dihydropyrazolo[1,5-a]pyrimidin-
6-yl)-1,3,4-oxadiazol-2-yl)guanidine (D1077);
6-(5-(4-hydroxypyrimidin-2-yl)-1,3,4-oxadiazol-2-yl)-5-methyl-3-phenyl-2-
(trifluoromethyl)pyrazolo[1,5-a]pyrimidin-7(4H)-one (D1078);
6-(5-(3-aminophenyl)-1,3,4-oxadiazol-2-yl)-5-methyl-3-phenyl-2-
(trifluoromethyl)pyrazolo[1,5-a]pyrimidin-7(4H)-one (D1079);
6-(5-(2-aminocyclohexyl)-1,3,4-oxadiazol-2-yl)-5-methyl-3-phenyl-2-
(trifluoromethyl)pyrazolo[1,5-a]pyrimidin-7(4H)-one (D1080);
6-(5-(4-aminophenyl)-1,3,4-oxadiazol-2-yl)-5-methyl-3-phenyl-2-
(trifluoromethyl)pyrazolo[1,5-a]pyrimidin-7(4H)-one (D1081);

TABLE 1A-continued 6-(5-(2-aminophenyl)-1,3,4-oxadiazol-2-yl)-5-methyl-3-phenyl-2-(trifluoromethyl)pyrazolo[1,5-a]pyrimidin-7(4H)-one (D1082);
6-(5-(3-(aminomethyl)piperidin-1-yl)-1,3,4-oxadiazol-2-yl)-5-methyl-3-phenyl-2-(trifluoromethyl)pyrazolo[1,5-a]pyrimidin-7(4H)-one (D1083);
6-(5-(3-aminopiperidin-1-yl)-1,3,4-oxadiazol-2-yl)-5-methyl-3-phenyl-2-(trifluoromethyl)pyrazolo[1,5-a]pyrimidin-7(4H)-one (D1084);
6-(5-(2-hydroxypyridin-4-yl)-1,3,4-oxadiazol-2-yl)-5-methyl-3-phenyl-2-(trifluoromethyl)pyrazolo[1,5-a]pyrimidin-7(4H)-one (D1085);
6-(5-(6-hydroxypyridin-2-yl)-1,3,4-oxadiazol-2-yl)-5-methyl-3-phenyl-2-(trifluoromethyl)pyrazolo[1,5-a]pyrimidin-7(4H)-one (D1086);
6-(5-(3-hydroxypiperidin-1-yl)-1,3,4-oxadiazol-2-yl)-5-methyl-3-phenyl-2-(trifluoromethyl)pyrazolo[1,5-a]pyrimidin-7(4H)-one (D1087);
5-(methoxymethyl)-7-oxo-3-phenyl-6-(5-(piperidin-1-yl)-1,3,4-oxadiazol-2-yl)-4,7-dihydropyrazolo[1,5-a]pyrimidine-2-carbonitrile (D1088);
6-(5-cyclohexyl-1,3,4-oxadiazol-2-yl)-5-methyl-7-oxo-3-phenyl-4,7-dihydropyrazolo[1,5-a]pyrimidine-2-carbonitrile (D1089); and
6-(4-methoxybenzo[d]oxazol-2-yl)-5-methyl-3-phenyl-[1,2,3]triazolo[1,5-a]pyrimidin-7(4H)-one (E1001);

or a pharmaceutically acceptable salt, solvate or hydrate thereof.

The representative compounds have the following structures as shown in Table 1B below:

TABLE 1B

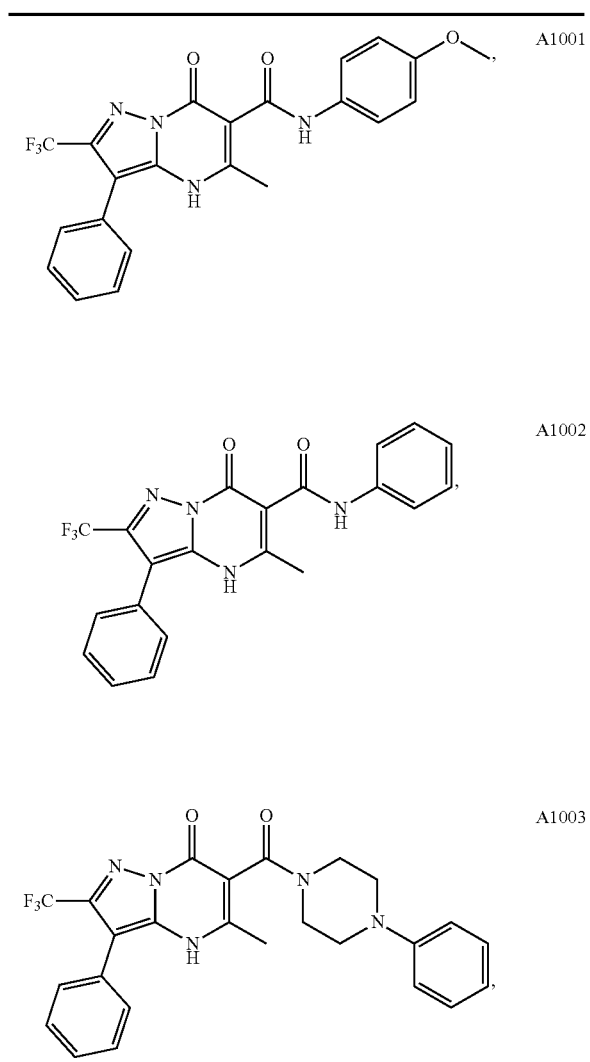

TABLE 1B-continued

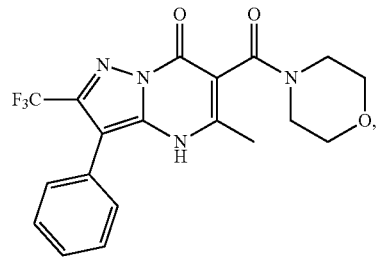 [SMILES: Cc1[nH]c2c(-c3ccccc3)c(C(F)(F)F)nn2c(=O)c1C(=O)N1CCOCC1]

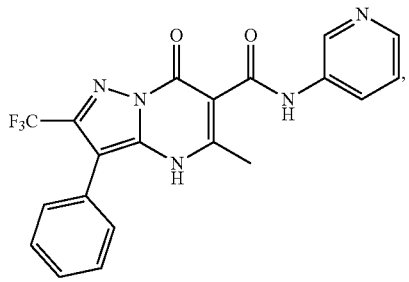 [SMILES: Cc1[nH]c2c(-c3ccccc3)c(C(F)(F)F)nn2c(=O)c1C(=O)Nc1cccnc1]

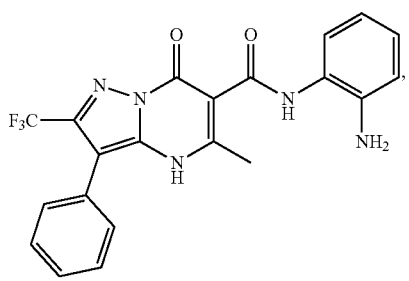 [SMILES: Cc1[nH]c2c(-c3ccccc3)c(C(F)(F)F)nn2c(=O)c1C(=O)Nc1ccccc1N]

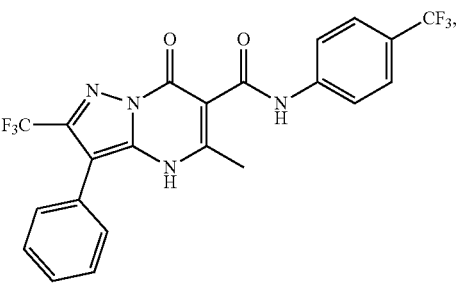 [SMILES: Cc1[nH]c2c(-c3ccccc3)c(C(F)(F)F)nn2c(=O)c1C(=O)Nc1ccc(C(F)(F)F)cc1]

TABLE 1B-continued
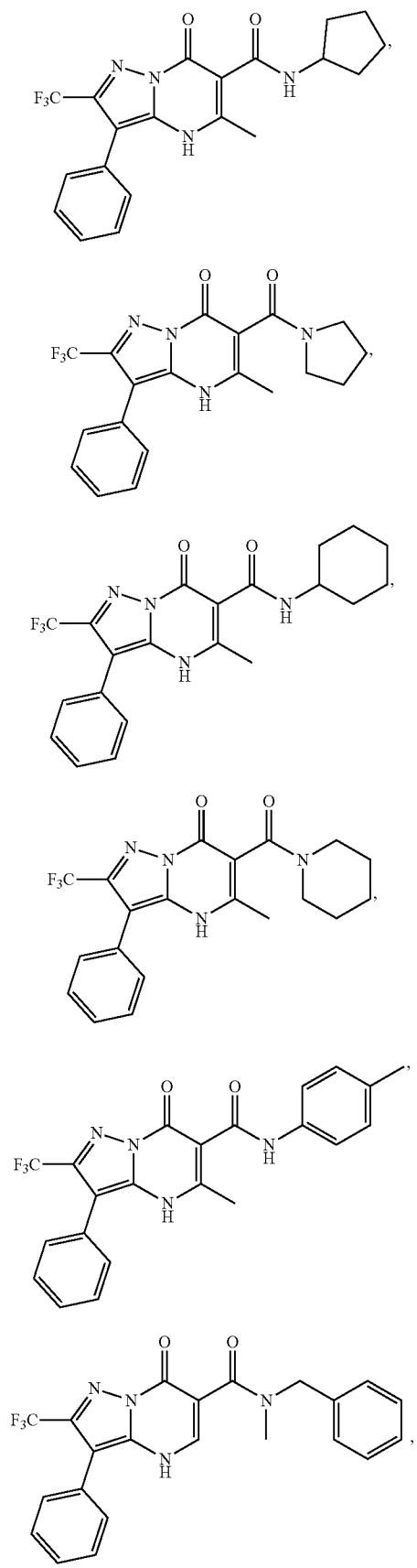
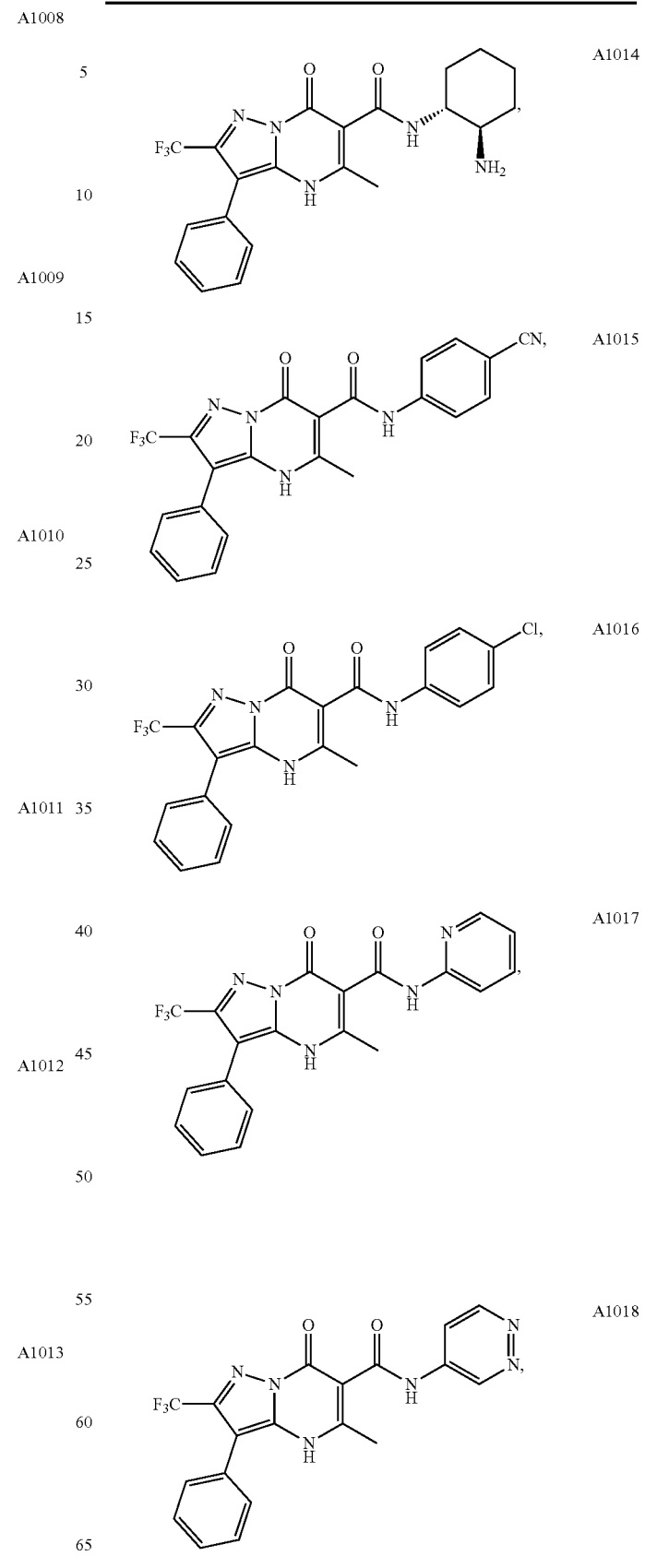

TABLE 1B-continued
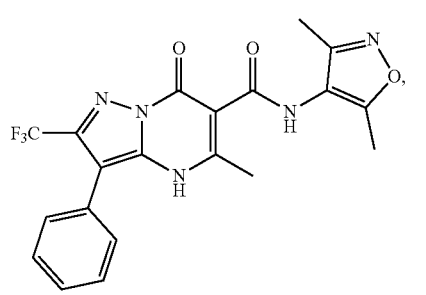 [SMILES: Cc1noc(C)c1NC(=O)c1c(C)[nH]c2c(-c3ccccc3)c(C(F)(F)F)nn2c1=O] A1019
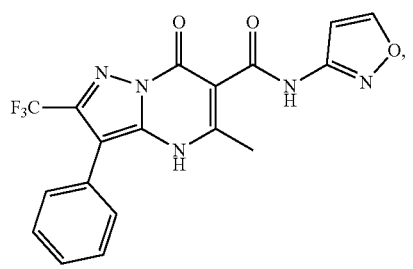 [SMILES: Cc1[nH]c2c(-c3ccccc3)c(C(F)(F)F)nn2c(=O)c1C(=O)Nc1ccon1] A1020
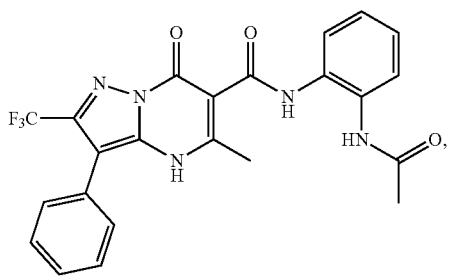 [SMILES: CC(=O)Nc1ccccc1NC(=O)c1c(C)[nH]c2c(-c3ccccc3)c(C(F)(F)F)nn2c1=O] A1021
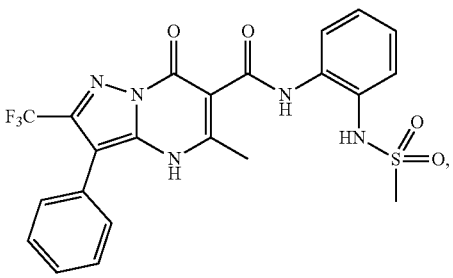 [SMILES: Cc1[nH]c2c(-c3ccccc3)c(C(F)(F)F)nn2c(=O)c1C(=O)Nc1ccccc1NS(C)(=O)=O] A1022
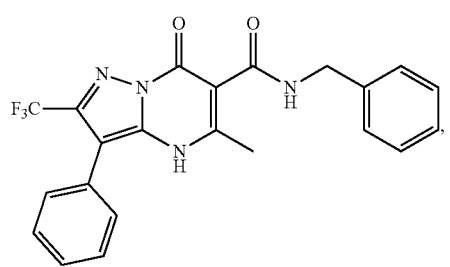 [SMILES: Cc1[nH]c2c(-c3ccccc3)c(C(F)(F)F)nn2c(=O)c1C(=O)NCc1ccccc1] A1023
TABLE 1B-continued
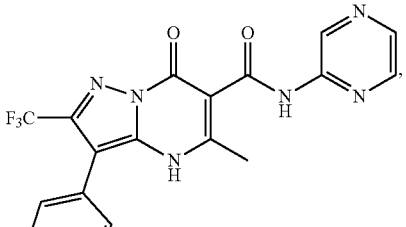 A1024
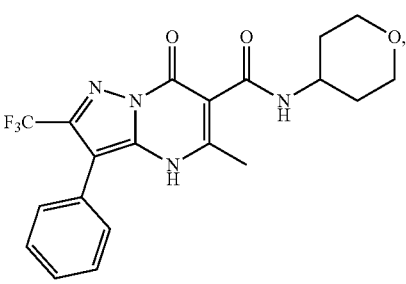 [SMILES: Cc1[nH]c2c(-c3ccccc3)c(C(F)(F)F)nn2c(=O)c1C(=O)NC1CCOCC1] A1025
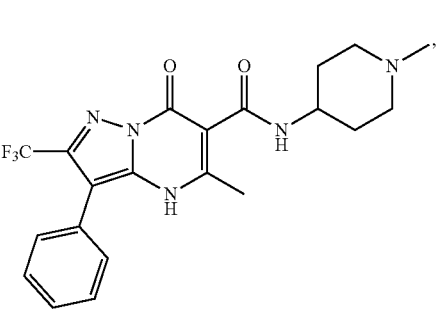 [SMILES: Cc1[nH]c2c(-c3ccccc3)c(C(F)(F)F)nn2c(=O)c1C(=O)NC1CCN(C)CC1] A1026
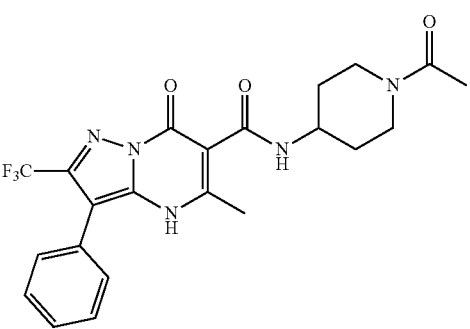 [SMILES: CC(=O)N1CCC(NC(=O)c2c(C)[nH]c3c(-c4ccccc4)c(C(F)(F)F)nn3c2=O)CC1] A1027
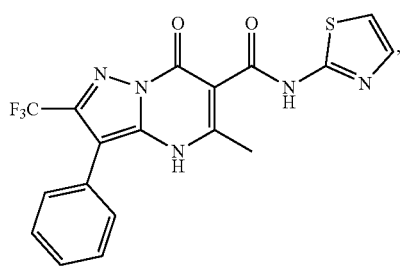 [SMILES: Cc1[nH]c2c(-c3ccccc3)c(C(F)(F)F)nn2c(=O)c1C(=O)Nc1nccs1] A1028

TABLE 1B-continued
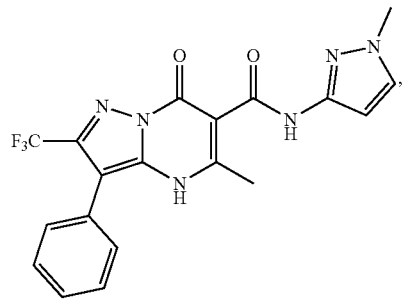 [SMILES: Cc1[nH]c2c(-c3ccccc3)c(C(F)(F)F)nn2c(=O)c1C(=O)Nc1ccn(C)n1]
A1029
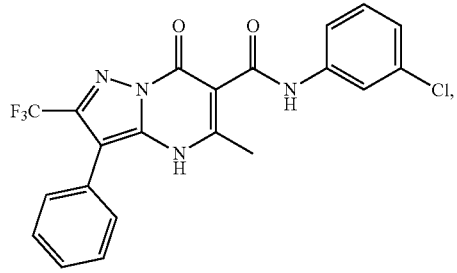 [SMILES: Cc1[nH]c2c(-c3ccccc3)c(C(F)(F)F)nn2c(=O)c1C(=O)Nc1cccc(Cl)c1]
A1030
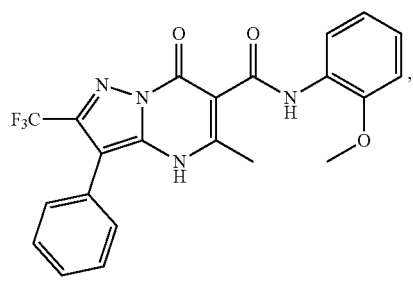 [SMILES: COc1ccccc1NC(=O)c1c(C)[nH]c2c(-c3ccccc3)c(C(F)(F)F)nn2c1=O]
A1031
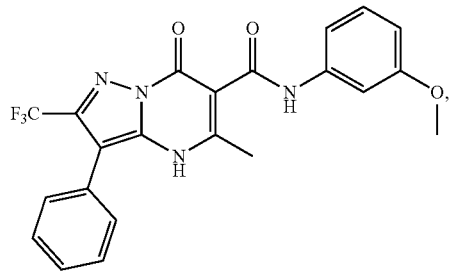 [SMILES: COc1cccc(NC(=O)c2c(C)[nH]c3c(-c4ccccc4)c(C(F)(F)F)nn3c2=O)c1]
A1032
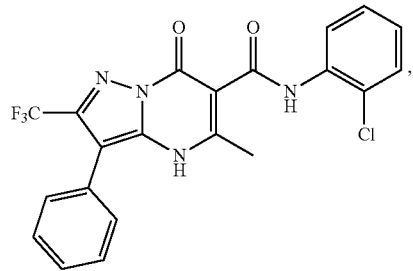
A1033
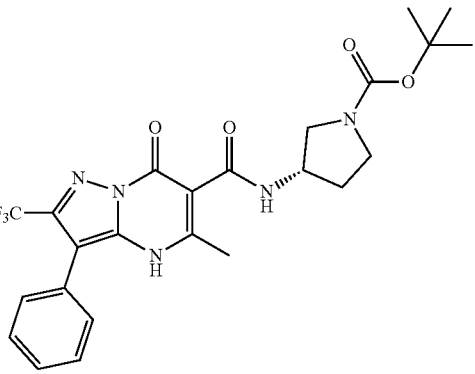
A1034
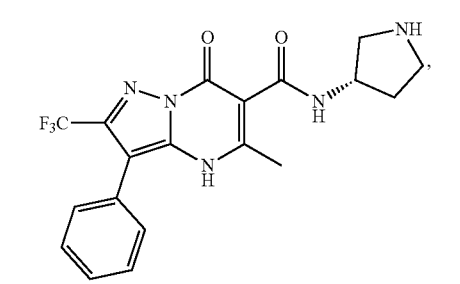 [SMILES: Cc1[nH]c2c(-c3ccccc3)c(C(F)(F)F)nn2c(=O)c1C(=O)N[C@H]1CCNC1]
A1035
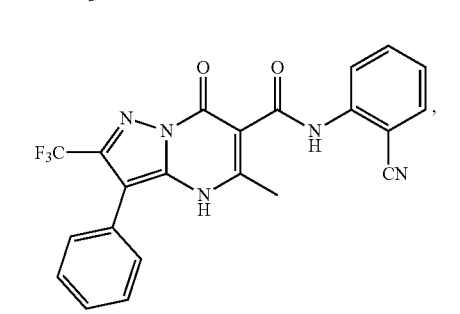
A1036
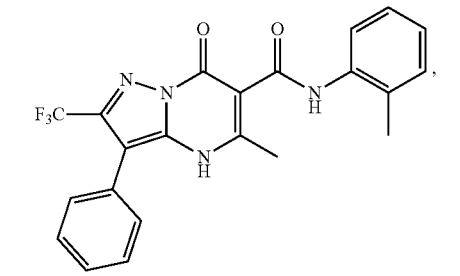
A1037
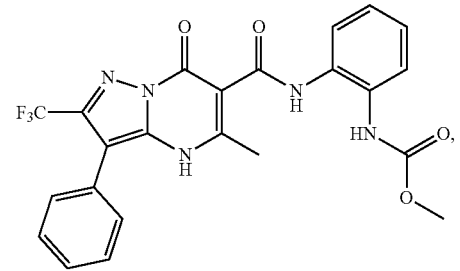 [SMILES: COC(=O)Nc1ccccc1NC(=O)c1c(C)[nH]c2c(-c3ccccc3)c(C(F)(F)F)nn2c1=O]
A1038

TABLE 1B-continued
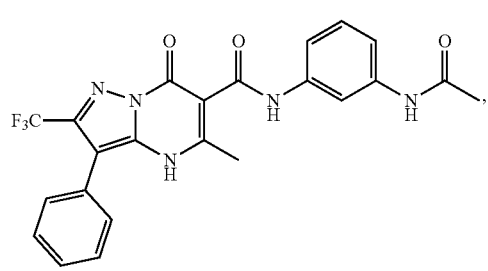 [SMILES: CC(=O)Nc1cccc(NC(=O)c2c(C)[nH]c3c(-c4ccccc4)c(C(F)(F)F)nn3c2=O)c1]
A1039
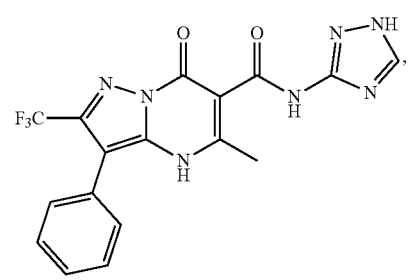 [SMILES: Cc1[nH]c2c(-c3ccccc3)c(C(F)(F)F)nn2c(=O)c1C(=O)Nc1nc[nH]n1]
A1040
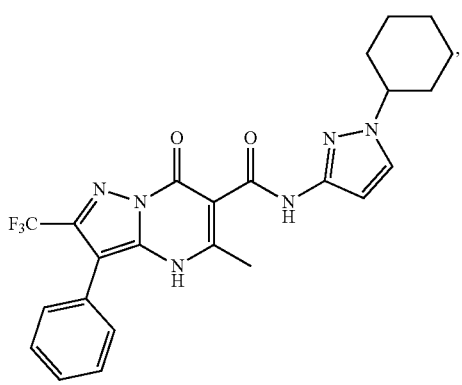 [SMILES: Cc1[nH]c2c(-c3ccccc3)c(C(F)(F)F)nn2c(=O)c1C(=O)Nc1ccn(C2CCCCC2)n1]
A1041
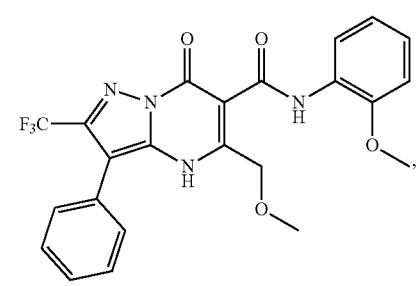 [SMILES: COCc1[nH]c2c(-c3ccccc3)c(C(F)(F)F)nn2c(=O)c1C(=O)Nc1ccccc1OC]
A1042
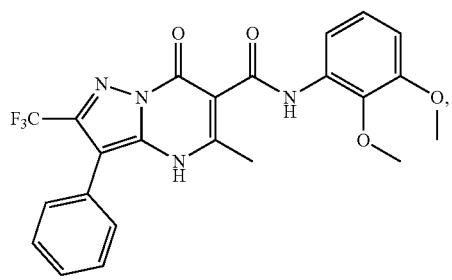 [SMILES: COc1cccc(NC(=O)c2c(C)[nH]c3c(-c4ccccc4)c(C(F)(F)F)nn3c2=O)c1OC]
A1043
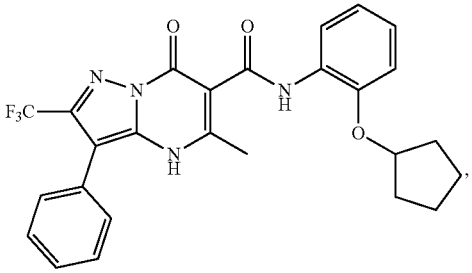 [SMILES: Cc1[nH]c2c(-c3ccccc3)c(C(F)(F)F)nn2c(=O)c1C(=O)Nc1ccccc1OC1CCCC1]
A1044
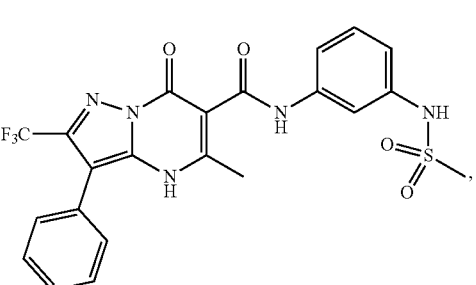
A1045
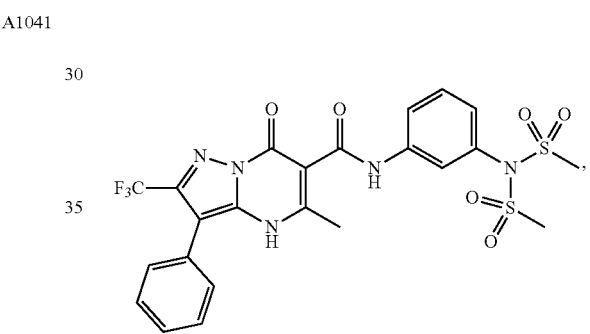
A1046
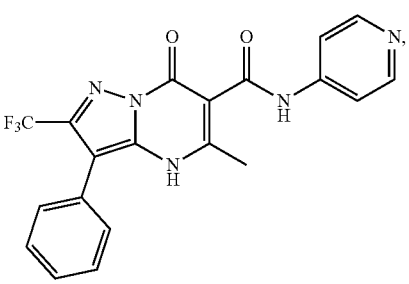 [SMILES: Cc1[nH]c2c(-c3ccccc3)c(C(F)(F)F)nn2c(=O)c1C(=O)Nc1ccncc1]
A1047
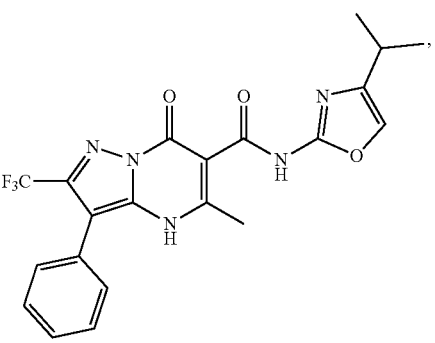 [SMILES: Cc1[nH]c2c(-c3ccccc3)c(C(F)(F)F)nn2c(=O)c1C(=O)Nc1nc(C(C)C)co1]
A1048

TABLE 1B-continued
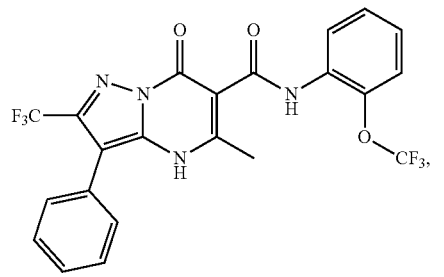 [SMILES: Cc1[nH]c2c(-c3ccccc3)c(C(F)(F)F)nn2c(=O)c1C(=O)Nc1ccccc1OC(F)(F)F]
A1049
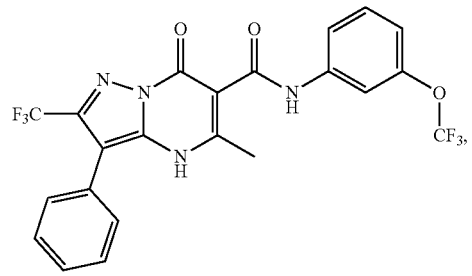 [SMILES: Cc1[nH]c2c(-c3ccccc3)c(C(F)(F)F)nn2c(=O)c1C(=O)Nc1cccc(OC(F)(F)F)c1]
A1050
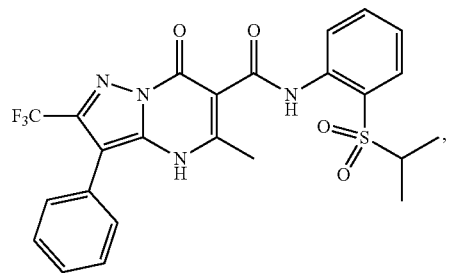 [SMILES: Cc1[nH]c2c(-c3ccccc3)c(C(F)(F)F)nn2c(=O)c1C(=O)Nc1ccccc1S(=O)(=O)C(C)C]
A1051
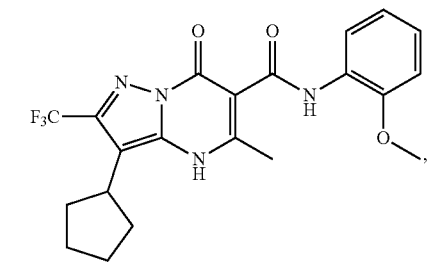 [SMILES: COc1ccccc1NC(=O)c1c(C)[nH]c2c(C3CCCC3)c(C(F)(F)F)nn2c1=O]
A1052
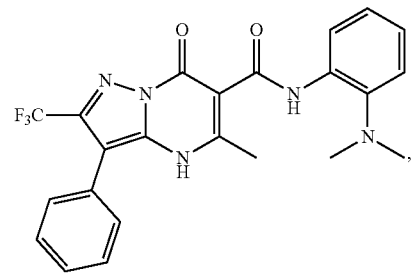 [SMILES: Cc1[nH]c2c(-c3ccccc3)c(C(F)(F)F)nn2c(=O)c1C(=O)Nc1ccccc1N(C)C]
A1053
TABLE 1B-continued
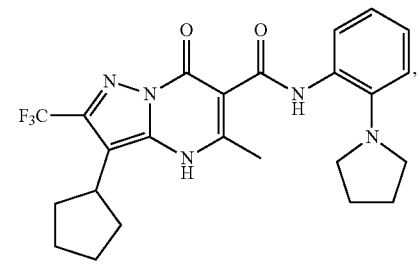 [SMILES: Cc1[nH]c2c(C3CCCC3)c(C(F)(F)F)nn2c(=O)c1C(=O)Nc1ccccc1N1CCCC1]
A1054
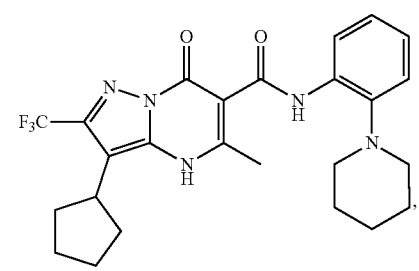 [SMILES: Cc1[nH]c2c(C3CCCC3)c(C(F)(F)F)nn2c(=O)c1C(=O)Nc1ccccc1N1CCCCC1]
A1055
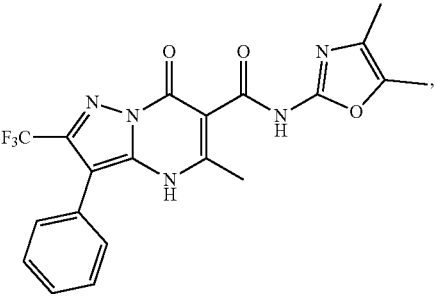 [SMILES: Cc1nc(NC(=O)c2c(C)[nH]c3c(-c4ccccc4)c(C(F)(F)F)nn3c2=O)oc1C]
A1056
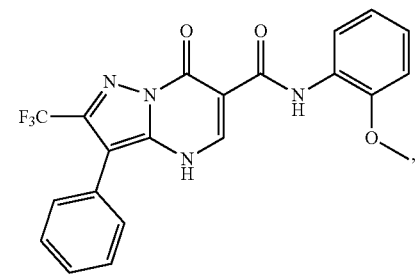 [SMILES: COc1ccccc1NC(=O)c1c[nH]c2c(-c3ccccc3)c(C(F)(F)F)nn2c1=O]
A1057
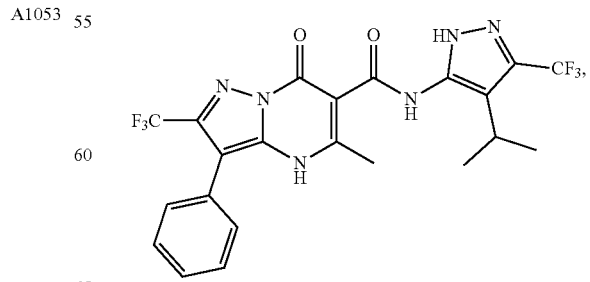
A1058

TABLE 1B-continued
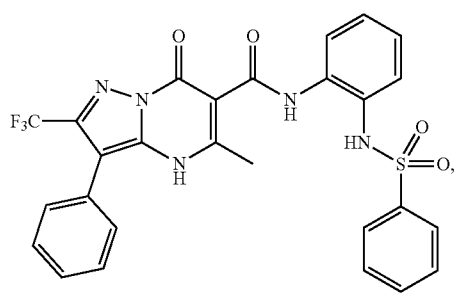 [SMILES: Cc1[nH]c2c(-c3ccccc3)c(C(F)(F)F)nn2c(=O)c1C(=O)Nc1ccccc1NS(=O)(=O)c1ccccc1] A1059
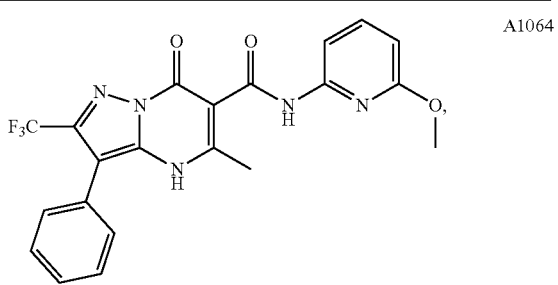 A1064
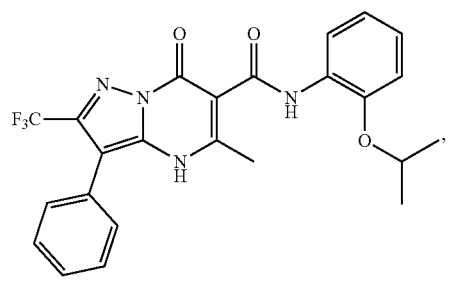 [SMILES: Cc1[nH]c2c(-c3ccccc3)c(C(F)(F)F)nn2c(=O)c1C(=O)Nc1ccccc1OC(C)C] A1060
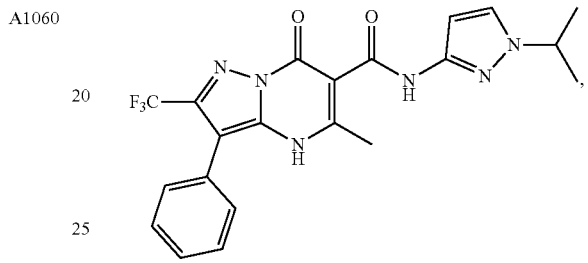 A1065
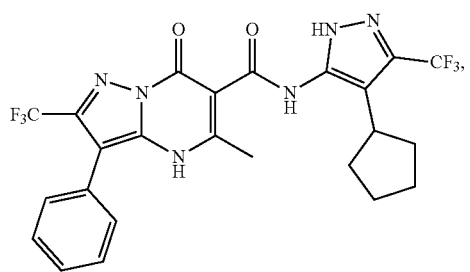 [SMILES: Cc1[nH]c2c(-c3ccccc3)c(C(F)(F)F)nn2c(=O)c1C(=O)Nc1[nH]nc(C(F)(F)F)c1C1CCCC1] A1061
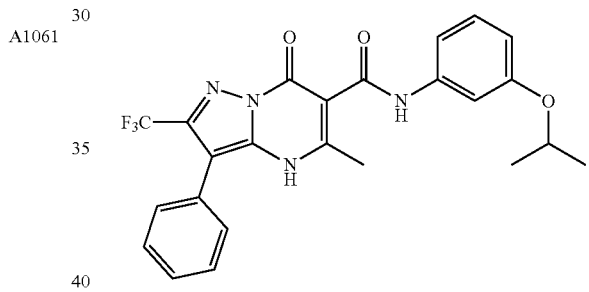 A1066
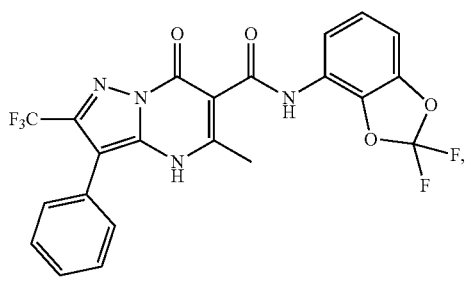 [SMILES: Cc1[nH]c2c(-c3ccccc3)c(C(F)(F)F)nn2c(=O)c1C(=O)Nc1cccc2c1OC(F)(F)O2] A1062
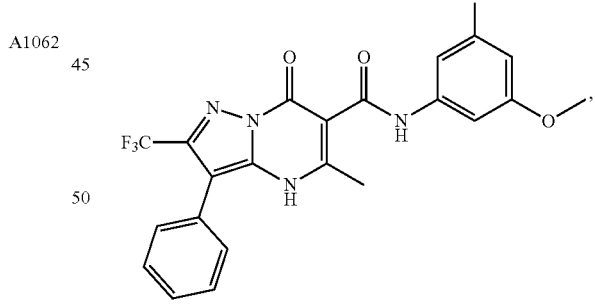 A1067
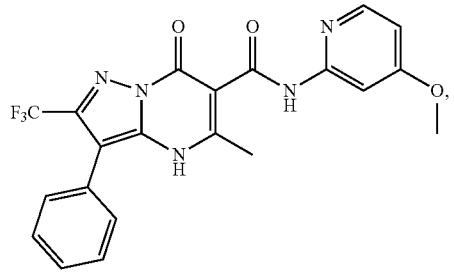 [SMILES: COc1ccnc(NC(=O)c2c(C)[nH]c3c(-c4ccccc4)c(C(F)(F)F)nn3c2=O)c1] A1063
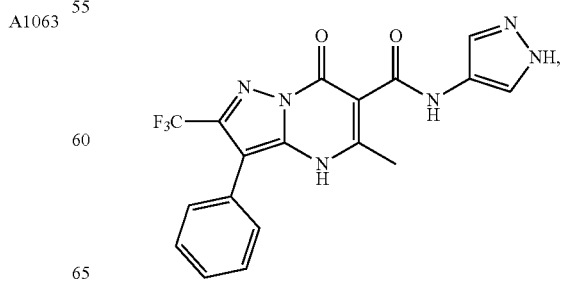 A1068

TABLE 1B-continued
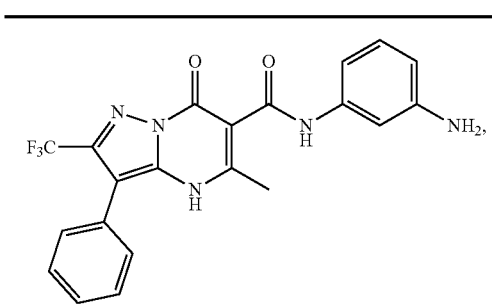 A1069
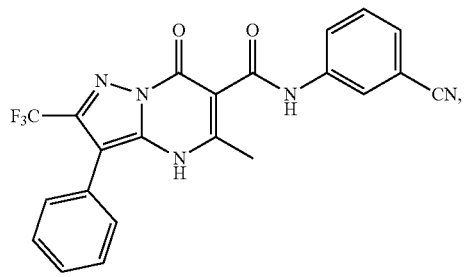 [SMILES: Cc1[nH]c2c(-c3ccccc3)c(C(F)(F)F)nn2c(=O)c1C(=O)Nc1cccc(C#N)c1] A1070
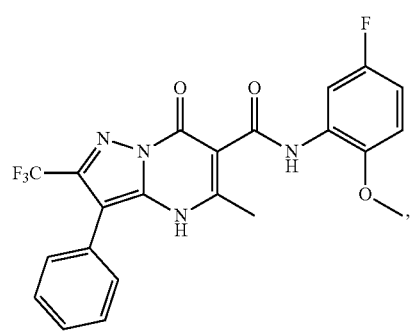 [SMILES: COc1ccc(F)cc1NC(=O)c1c(C)[nH]c2c(-c3ccccc3)c(C(F)(F)F)nn2c1=O] A1071
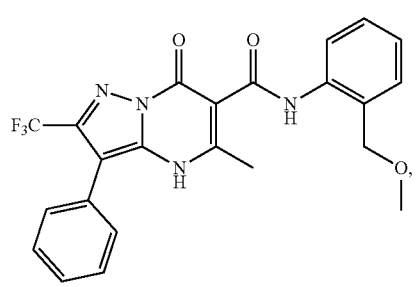 [SMILES: COCc1ccccc1NC(=O)c1c(C)[nH]c2c(-c3ccccc3)c(C(F)(F)F)nn2c1=O] A1072
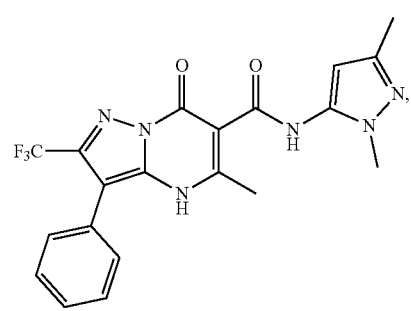 [SMILES: Cc1cc(NC(=O)c2c(C)[nH]c3c(-c4ccccc4)c(C(F)(F)F)nn3c2=O)n(C)n1] A1073
TABLE 1B-continued
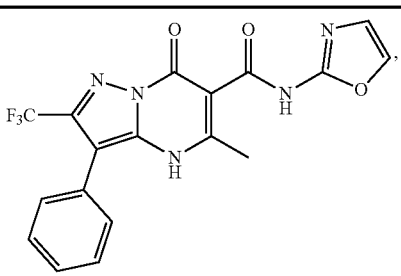 A1074
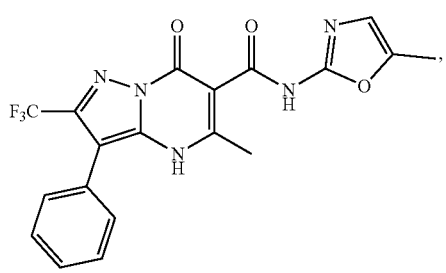 [SMILES: Cc1cnc(NC(=O)c2c(C)[nH]c3c(-c4ccccc4)c(C(F)(F)F)nn3c2=O)o1] A1075
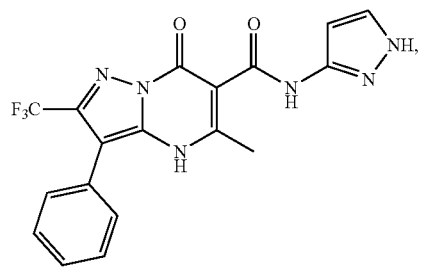 [SMILES: Cc1[nH]c2c(-c3ccccc3)c(C(F)(F)F)nn2c(=O)c1C(=O)Nc1cc[nH]n1] A1076
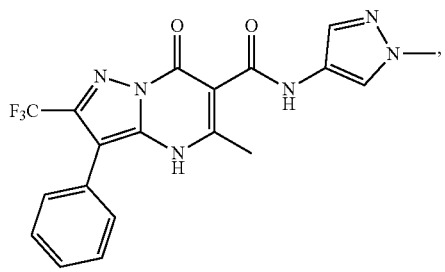 [SMILES: Cc1[nH]c2c(-c3ccccc3)c(C(F)(F)F)nn2c(=O)c1C(=O)Nc1cnn(C)c1] A1077
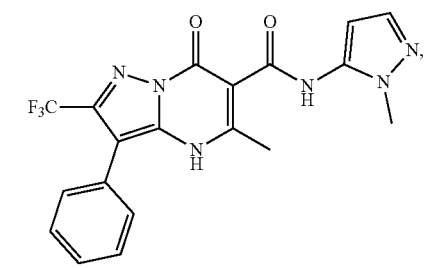 [SMILES: Cc1[nH]c2c(-c3ccccc3)c(C(F)(F)F)nn2c(=O)c1C(=O)Nc1ccnn1C] A1078
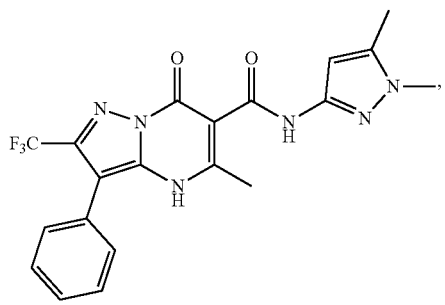 [SMILES: Cc1[nH]c2c(-c3ccccc3)c(C(F)(F)F)nn2c(=O)c1C(=O)Nc1cc(C)n(C)n1] A1079

TABLE 1B-continued
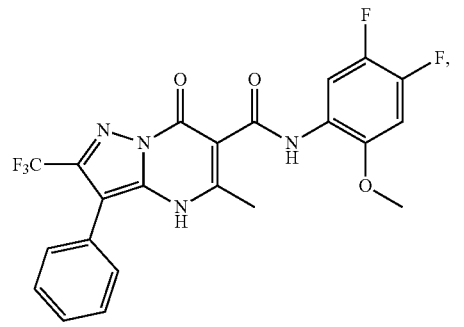 [SMILES: COc1cc(F)c(F)cc1NC(=O)c1c(C)[nH]c2c(-c3ccccc3)c(C(F)(F)F)nn2c1=O]
A1080
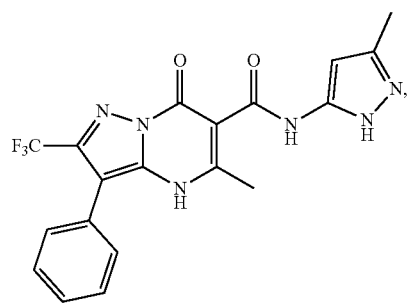 [SMILES: Cc1cc(NC(=O)c2c(C)[nH]c3c(-c4ccccc4)c(C(F)(F)F)nn3c2=O)[nH]n1]
A1081
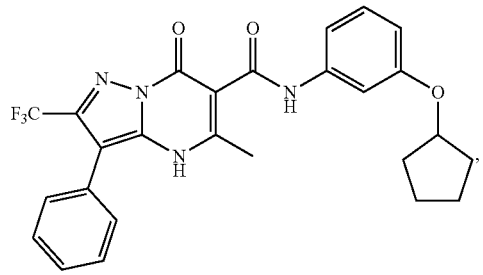 [SMILES: Cc1[nH]c2c(-c3ccccc3)c(C(F)(F)F)nn2c(=O)c1C(=O)Nc1cccc(OC2CCCC2)c1]
A1082
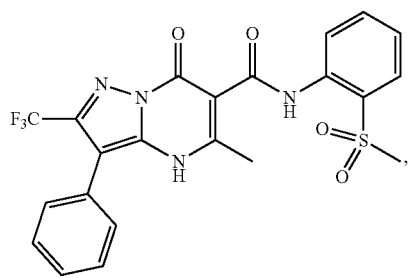 [SMILES: Cc1[nH]c2c(-c3ccccc3)c(C(F)(F)F)nn2c(=O)c1C(=O)Nc1ccccc1S(C)(=O)=O]
A1083
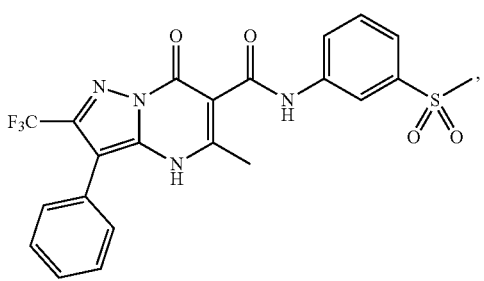 [SMILES: Cc1[nH]c2c(-c3ccccc3)c(C(F)(F)F)nn2c(=O)c1C(=O)Nc1cccc(S(C)(=O)=O)c1]
A1084
TABLE 1B-continued
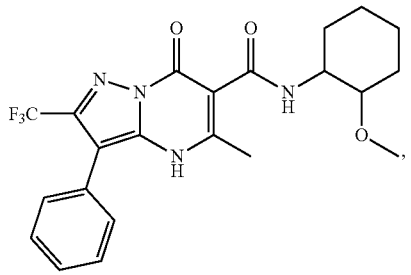 [SMILES: COC1CCCCC1NC(=O)c1c(C)[nH]c2c(-c3ccccc3)c(C(F)(F)F)nn2c1=O]
A1085
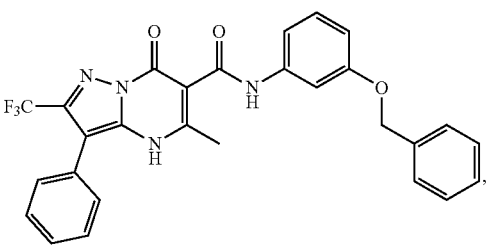 [SMILES: Cc1[nH]c2c(-c3ccccc3)c(C(F)(F)F)nn2c(=O)c1C(=O)Nc1cccc(OCc2ccccc2)c1]
A1086
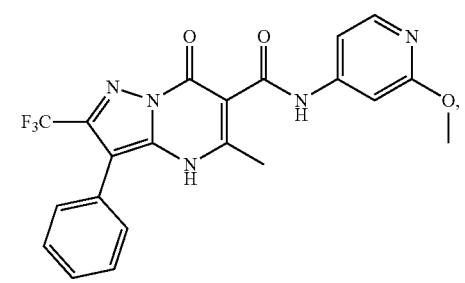 [SMILES: COc1cc(NC(=O)c2c(C)[nH]c3c(-c4ccccc4)c(C(F)(F)F)nn3c2=O)ccn1]
A1087
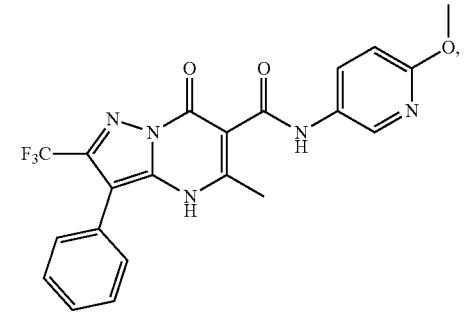 [SMILES: COc1ccc(NC(=O)c2c(C)[nH]c3c(-c4ccccc4)c(C(F)(F)F)nn3c2=O)cn1]
A1088
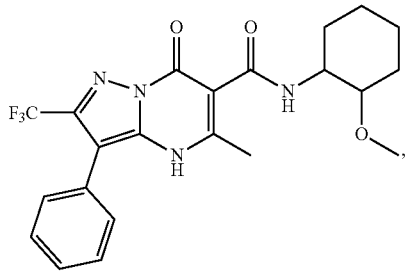 [SMILES: COC1CCCCC1NC(=O)c1c(C)[nH]c2c(-c3ccccc3)c(C(F)(F)F)nn2c1=O]
A1089

TABLE 1B-continued
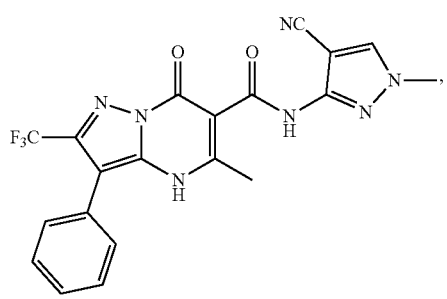 [SMILES: Cc1[nH]c2c(-c3ccccc3)c(C(F)(F)F)nn2c(=O)c1C(=O)Nc1nn(C)cc1C#N] A1090
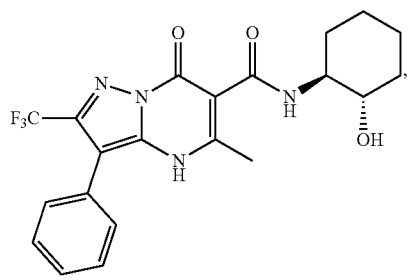 [SMILES: Cc1[nH]c2c(-c3ccccc3)c(C(F)(F)F)nn2c(=O)c1C(=O)N[C@H]1CCCC[C@@H]1O] A1091
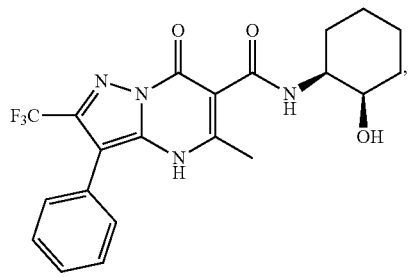 [SMILES: Cc1[nH]c2c(-c3ccccc3)c(C(F)(F)F)nn2c(=O)c1C(=O)N[C@H]1CCCC[C@H]1O] A1092
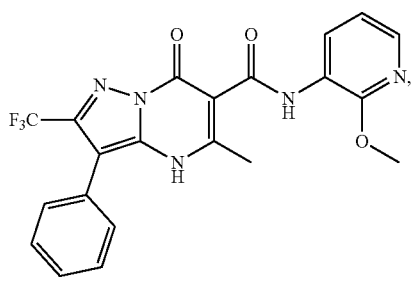 A1093
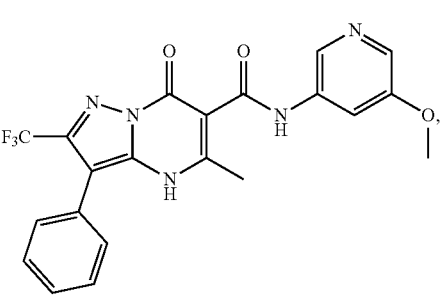 [SMILES: COc1cncc(NC(=O)c2c(C)[nH]c3c(-c4ccccc4)c(C(F)(F)F)nn3c2=O)c1] A1094
TABLE 1B-continued
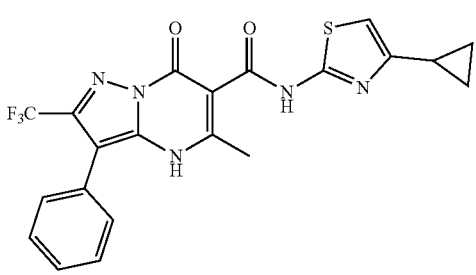 [SMILES: Cc1[nH]c2c(-c3ccccc3)c(C(F)(F)F)nn2c(=O)c1C(=O)Nc1nc(C2CC2)cs1] A1095
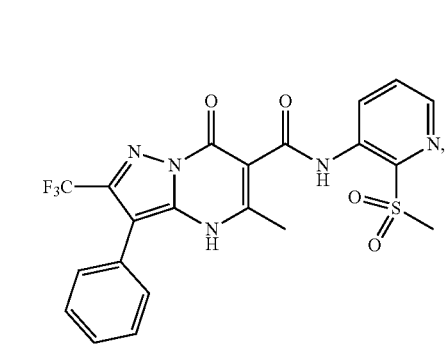 [SMILES: Cc1[nH]c2c(-c3ccccc3)c(C(F)(F)F)nn2c(=O)c1C(=O)Nc1cccnc1S(C)(=O)=O] A1096
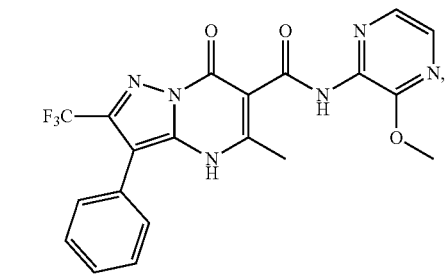 [SMILES: COc1nccnc1NC(=O)c1c(C)[nH]c2c(-c3ccccc3)c(C(F)(F)F)nn2c1=O] A1097
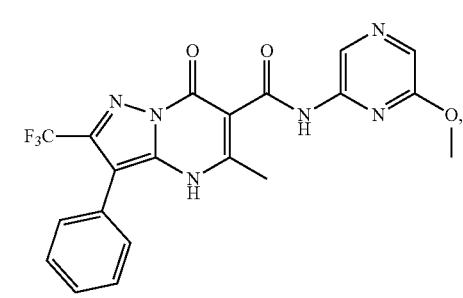 [SMILES: COc1cncc(NC(=O)c2c(C)[nH]c3c(-c4ccccc4)c(C(F)(F)F)nn3c2=O)n1] A1098
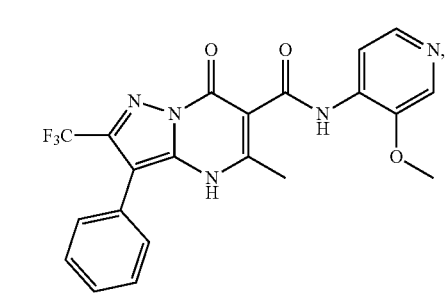 [SMILES: COc1cnccc1NC(=O)c1c(C)[nH]c2c(-c3ccccc3)c(C(F)(F)F)nn2c1=O] A1099

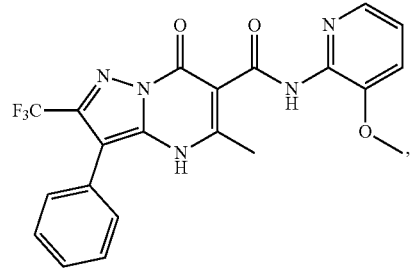 [SMILES: COc1cccnc1NC(=O)c1c(C)[nH]c2c(-c3ccccc3)c(C(F)(F)F)nn2c1=O]
A1100
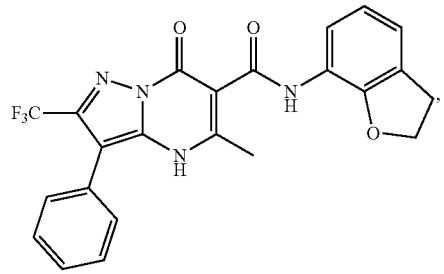
A1101
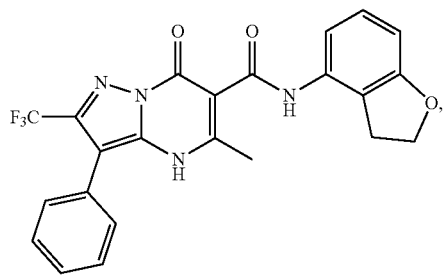 [SMILES: Cc1[nH]c2c(-c3ccccc3)c(C(F)(F)F)nn2c(=O)c1C(=O)Nc1cccc2c1CCO2]
A1102
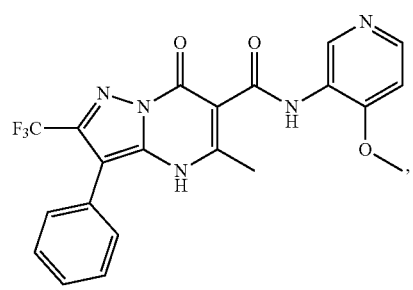 [SMILES: COc1ccncc1NC(=O)c1c(C)[nH]c2c(-c3ccccc3)c(C(F)(F)F)nn2c1=O]
A1103
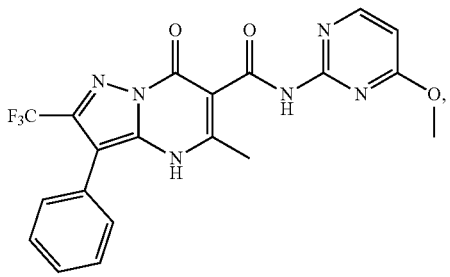
A1104
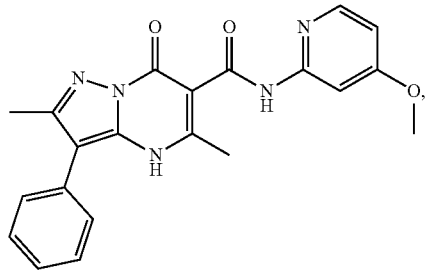 [SMILES: COc1ccnc(NC(=O)c2c(C)[nH]c3c(-c4ccccc4)c(C)nn3c2=O)c1]
A1105
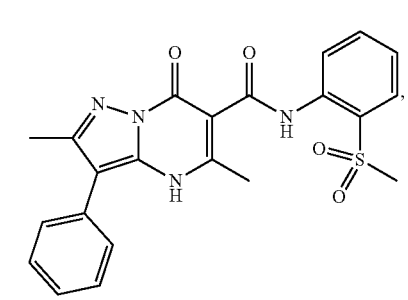 [SMILES: Cc1nn2c(=O)c(C(=O)Nc3ccccc3S(C)(=O)=O)c(C)[nH]c2c1-c1ccccc1]
A1106
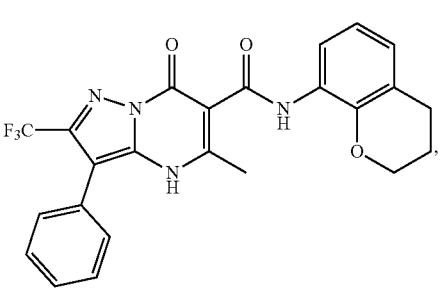 [SMILES: Cc1[nH]c2c(-c3ccccc3)c(C(F)(F)F)nn2c(=O)c1C(=O)Nc1cccc2c1OCCC2]
A1107
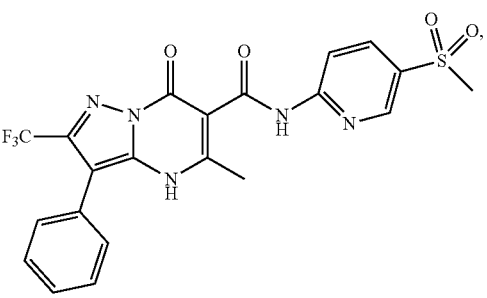 [SMILES: Cc1[nH]c2c(-c3ccccc3)c(C(F)(F)F)nn2c(=O)c1C(=O)Nc1ccc(S(C)(=O)=O)cn1]
A1108
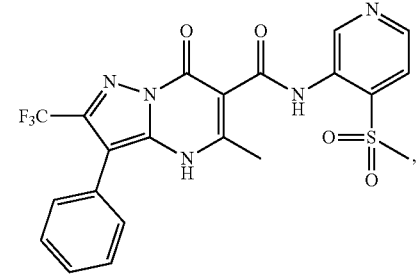 [SMILES: Cc1[nH]c2c(-c3ccccc3)c(C(F)(F)F)nn2c(=O)c1C(=O)Nc1cnccc1S(C)(=O)=O]
A1109

TABLE 1B-continued
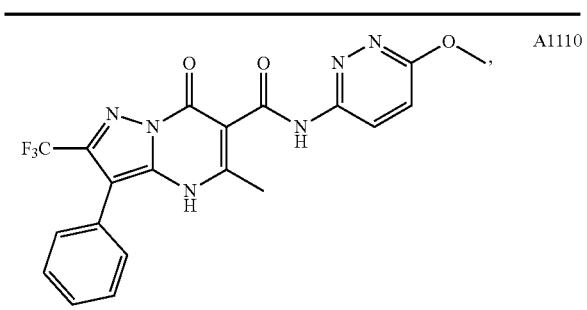
A1110
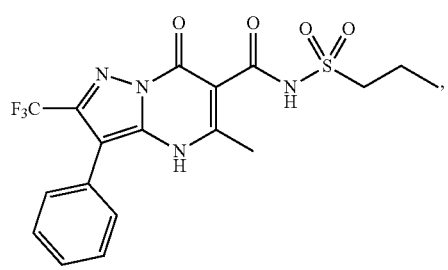 [SMILES: CCCS(=O)(=O)NC(=O)c1c(C)[nH]c2c(-c3ccccc3)c(C(F)(F)F)nn2c1=O]
A1111
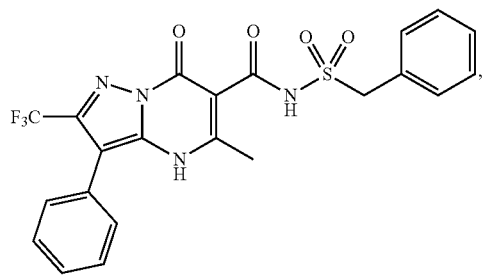 [SMILES: Cc1[nH]c2c(-c3ccccc3)c(C(F)(F)F)nn2c(=O)c1C(=O)NS(=O)(=O)Cc1ccccc1]
A1112
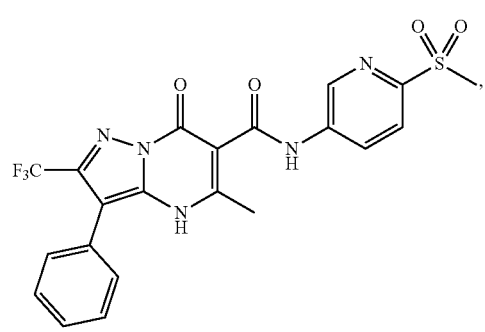 [SMILES: Cc1[nH]c2c(-c3ccccc3)c(C(F)(F)F)nn2c(=O)c1C(=O)Nc1ccc(S(C)(=O)=O)nc1]
A1113
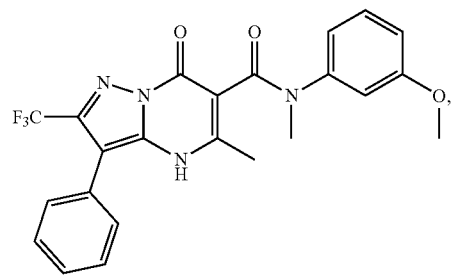
A1114
TABLE 1B-continued
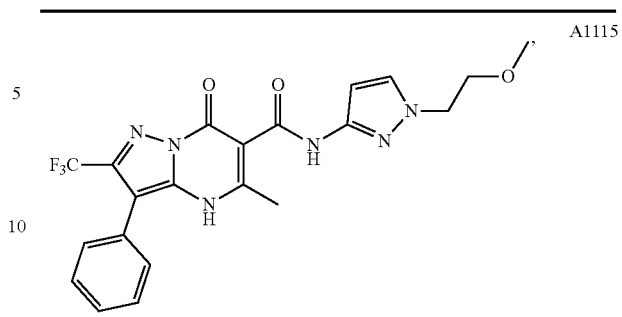
A1115
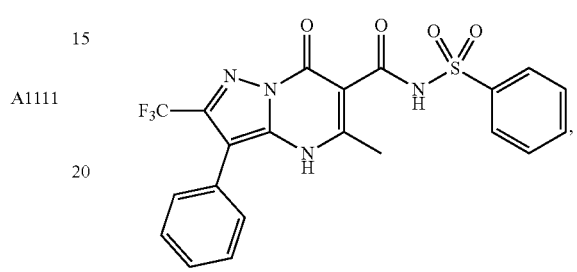
A1116
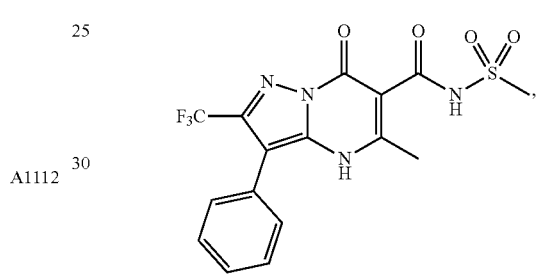
A1117
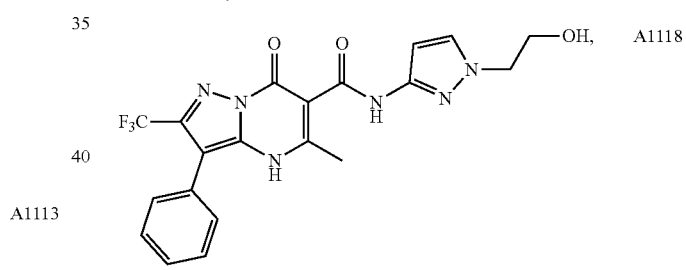
A1118
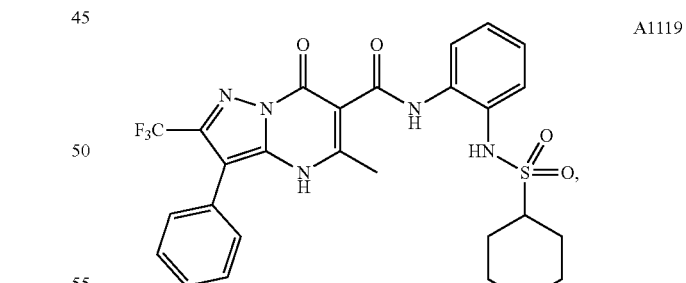
A1119
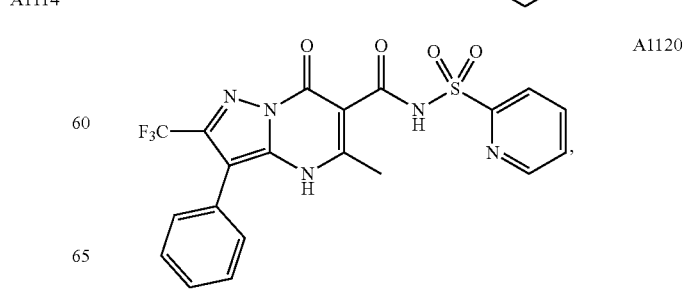
A1120

TABLE 1B-continued
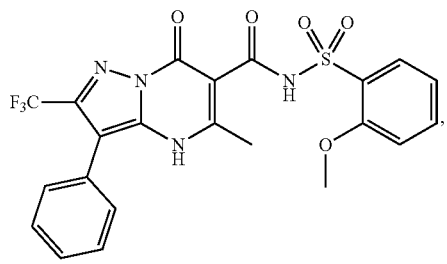 [SMILES: COc1ccccc1S(=O)(=O)NC(=O)c1c(C)[nH]c2c(-c3ccccc3)c(C(F)(F)F)nn2c1=O]
A1121
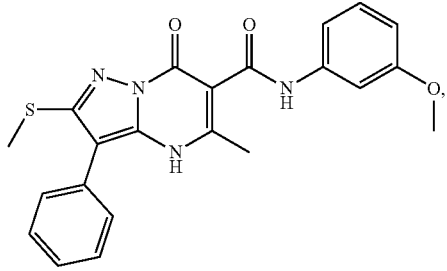
A1122
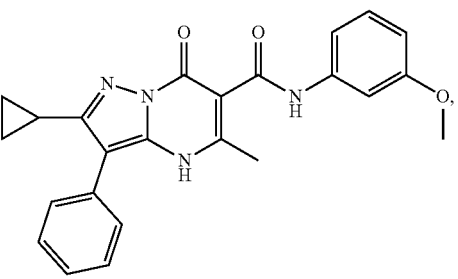 [SMILES: COc1cccc(NC(=O)c2c(C)[nH]c3c(-c4ccccc4)c(C4CC4)nn3c2=O)c1]
A1123
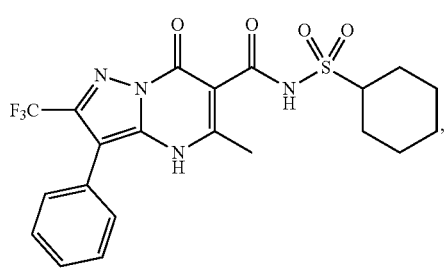 [SMILES: Cc1[nH]c2c(-c3ccccc3)c(C(F)(F)F)nn2c(=O)c1C(=O)NS(=O)(=O)C1CCCCC1]
A1124
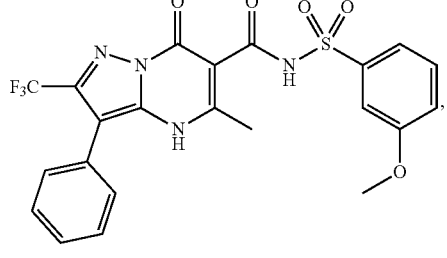
A1125
TABLE 1B-continued
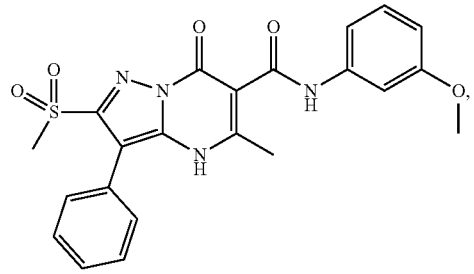 [SMILES: COc1cccc(NC(=O)c2c(C)[nH]c3c(-c4ccccc4)c(S(C)(=O)=O)nn3c2=O)c1]
A1126
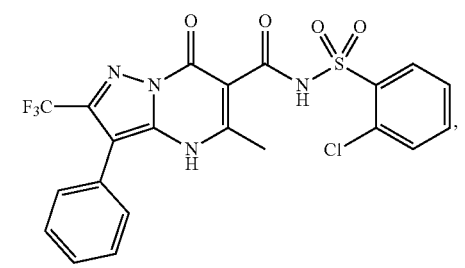 [SMILES: Cc1[nH]c2c(-c3ccccc3)c(C(F)(F)F)nn2c(=O)c1C(=O)NS(=O)(=O)c1ccccc1Cl]
A1127
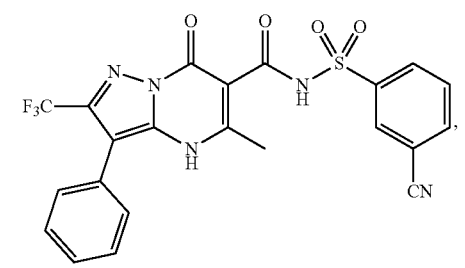 [SMILES: Cc1[nH]c2c(-c3ccccc3)c(C(F)(F)F)nn2c(=O)c1C(=O)NS(=O)(=O)c1cccc(C#N)c1]
A1128
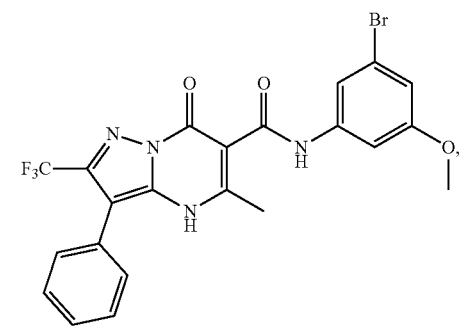 [SMILES: COc1cc(Br)cc(NC(=O)c2c(C)[nH]c3c(-c4ccccc4)c(C(F)(F)F)nn3c2=O)c1]
A1129
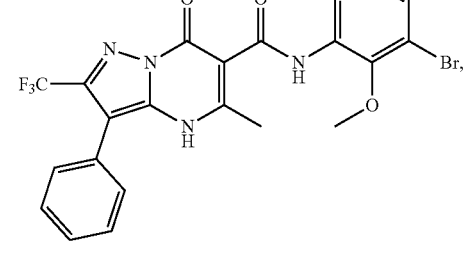
A1130

TABLE 1B-continued
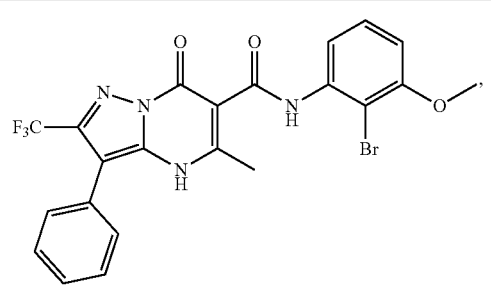 A1131
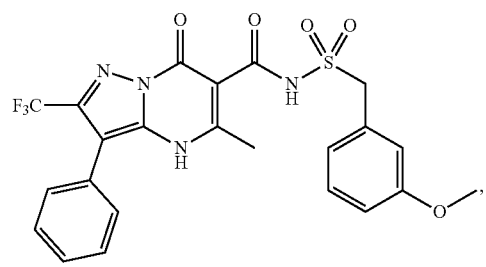 [SMILES: COc1cccc(CS(=O)(=O)NC(=O)c2c(C)[nH]c3c(-c4ccccc4)c(C(F)(F)F)nn3c2=O)c1] A1132
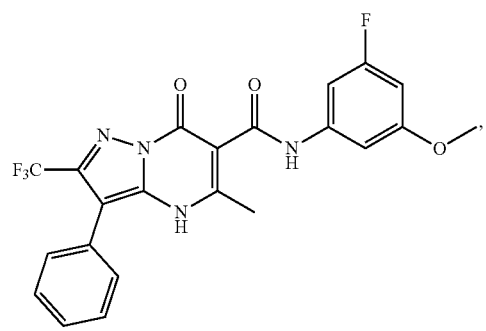 A1133
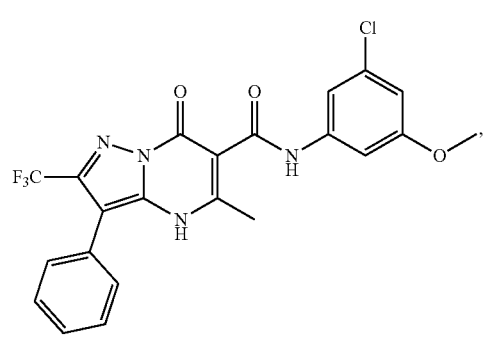 [SMILES: COc1cc(Cl)cc(NC(=O)c2c(C)[nH]c3c(-c4ccccc4)c(C(F)(F)F)nn3c2=O)c1] A1134
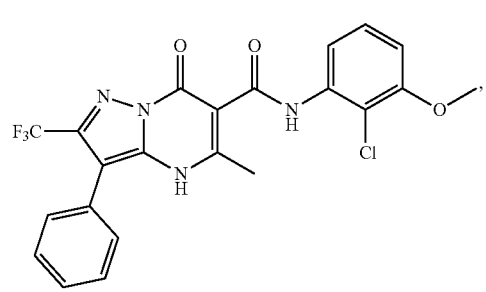 [SMILES: COc1cccc(NC(=O)c2c(C)[nH]c3c(-c4ccccc4)c(C(F)(F)F)nn3c2=O)c1Cl] A1135
TABLE 1B-continued
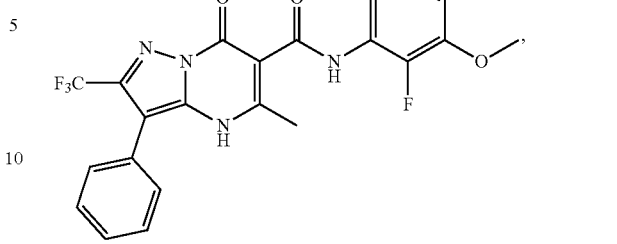 A1136
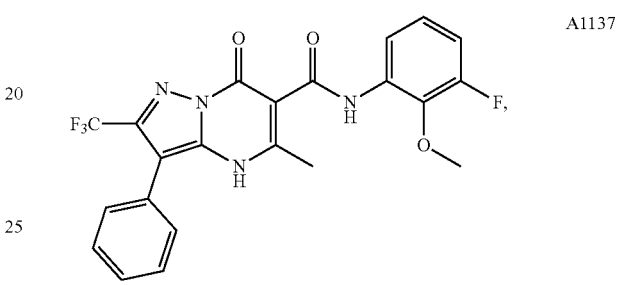 A1137
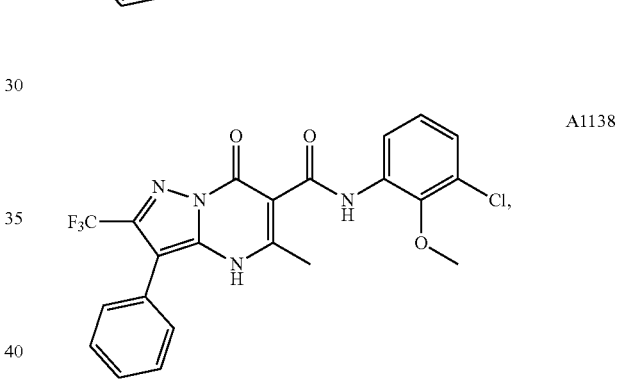 A1138
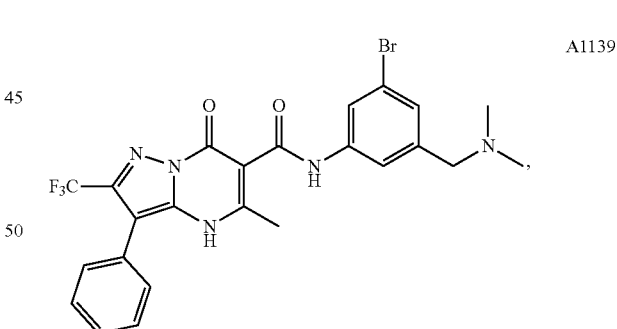 A1139
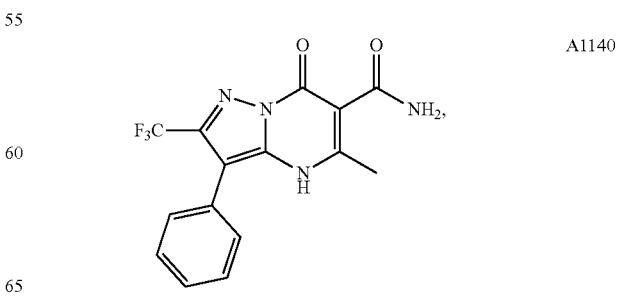 A1140

TABLE 1B-continued
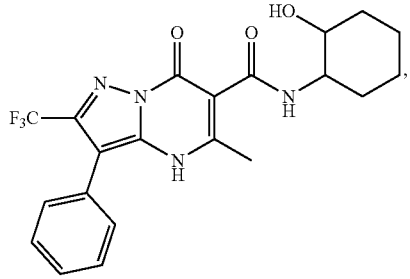 [SMILES: Cc1[nH]c2c(-c3ccccc3)c(C(F)(F)F)nn2c(=O)c1C(=O)NC1CCCCC1O] A1141
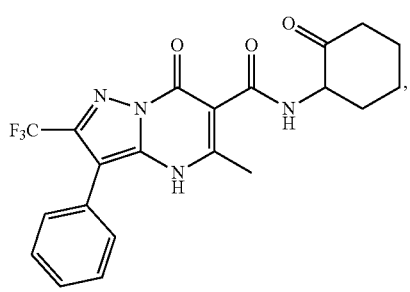 [SMILES: Cc1[nH]c2c(-c3ccccc3)c(C(F)(F)F)nn2c(=O)c1C(=O)NC1CCCCC1=O] A1142
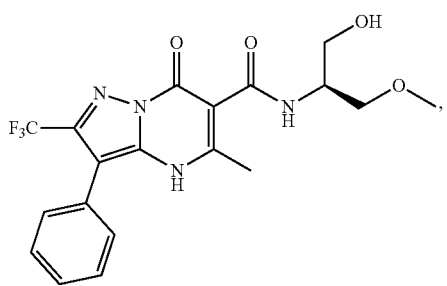 [SMILES: COC[C@H](CO)NC(=O)c1c(C)[nH]c2c(-c3ccccc3)c(C(F)(F)F)nn2c1=O] A1143
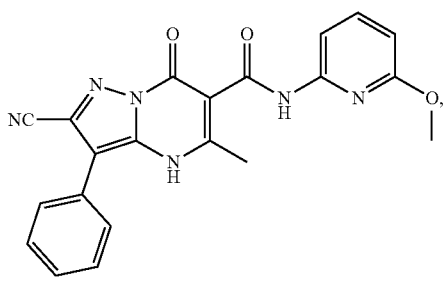 [SMILES: COc1cccc(NC(=O)c2c(C)[nH]c3c(-c4ccccc4)c(C#N)nn3c2=O)n1] A1144
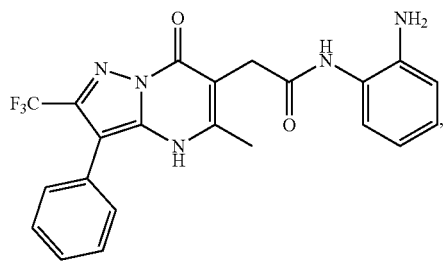 [SMILES: Cc1[nH]c2c(-c3ccccc3)c(C(F)(F)F)nn2c(=O)c1CC(=O)Nc1ccccc1N] B1001
TABLE 1B-continued
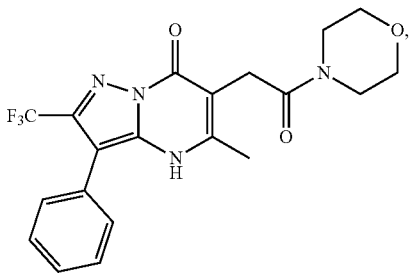 [SMILES: Cc1[nH]c2c(-c3ccccc3)c(C(F)(F)F)nn2c(=O)c1CC(=O)N1CCOCC1] B1002
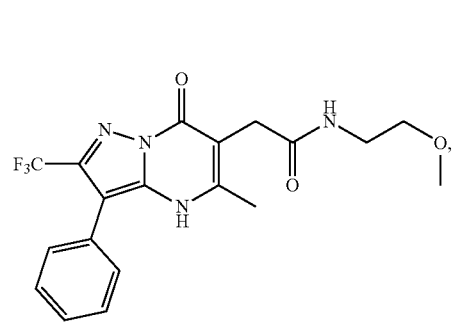 [SMILES: COCCNC(=O)Cc1c(C)[nH]c2c(-c3ccccc3)c(C(F)(F)F)nn2c1=O] B1003
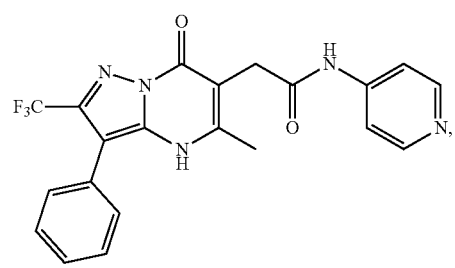 [SMILES: Cc1[nH]c2c(-c3ccccc3)c(C(F)(F)F)nn2c(=O)c1CC(=O)Nc1ccncc1] B1004
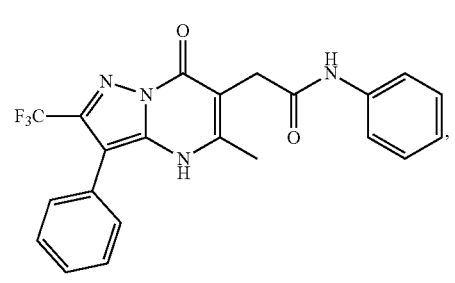 [SMILES: Cc1[nH]c2c(-c3ccccc3)c(C(F)(F)F)nn2c(=O)c1CC(=O)Nc1ccccc1] B1005
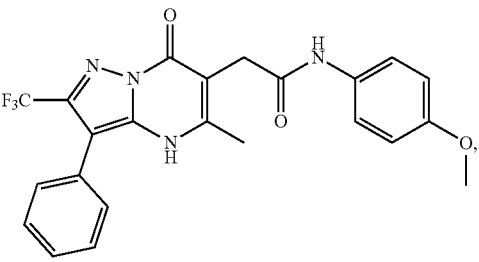 [SMILES: COc1ccc(NC(=O)Cc2c(C)[nH]c3c(-c4ccccc4)c(C(F)(F)F)nn3c2=O)cc1] B1006

TABLE 1B-continued
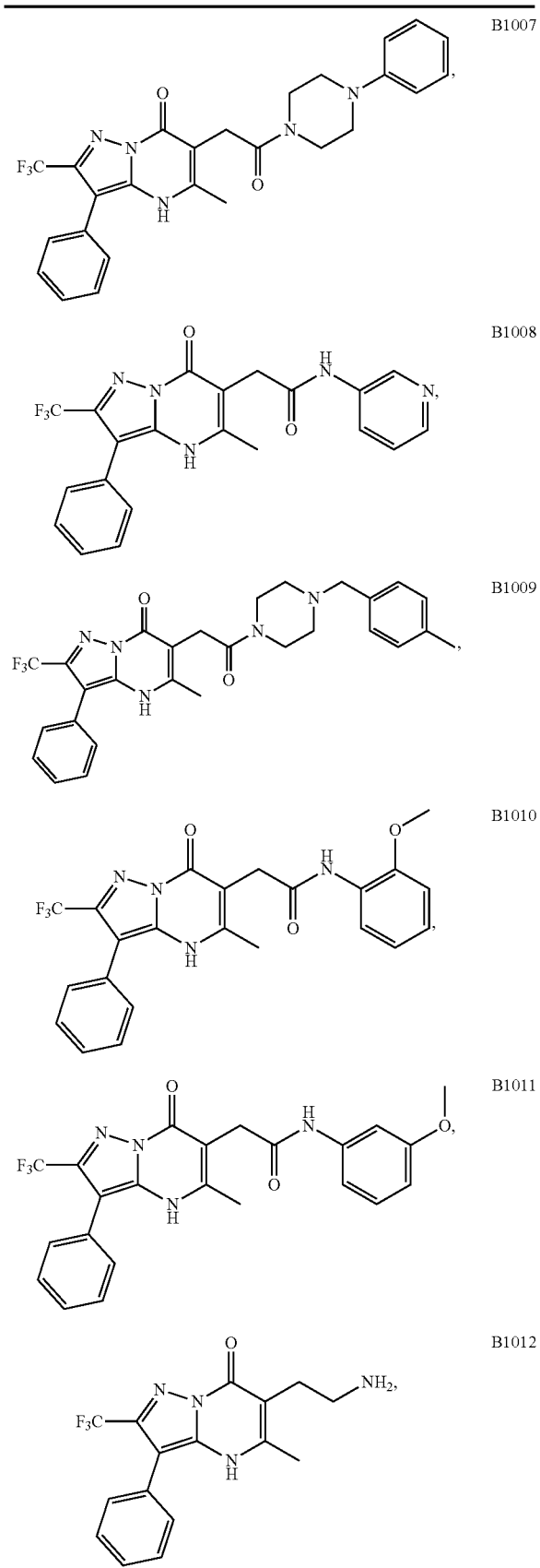
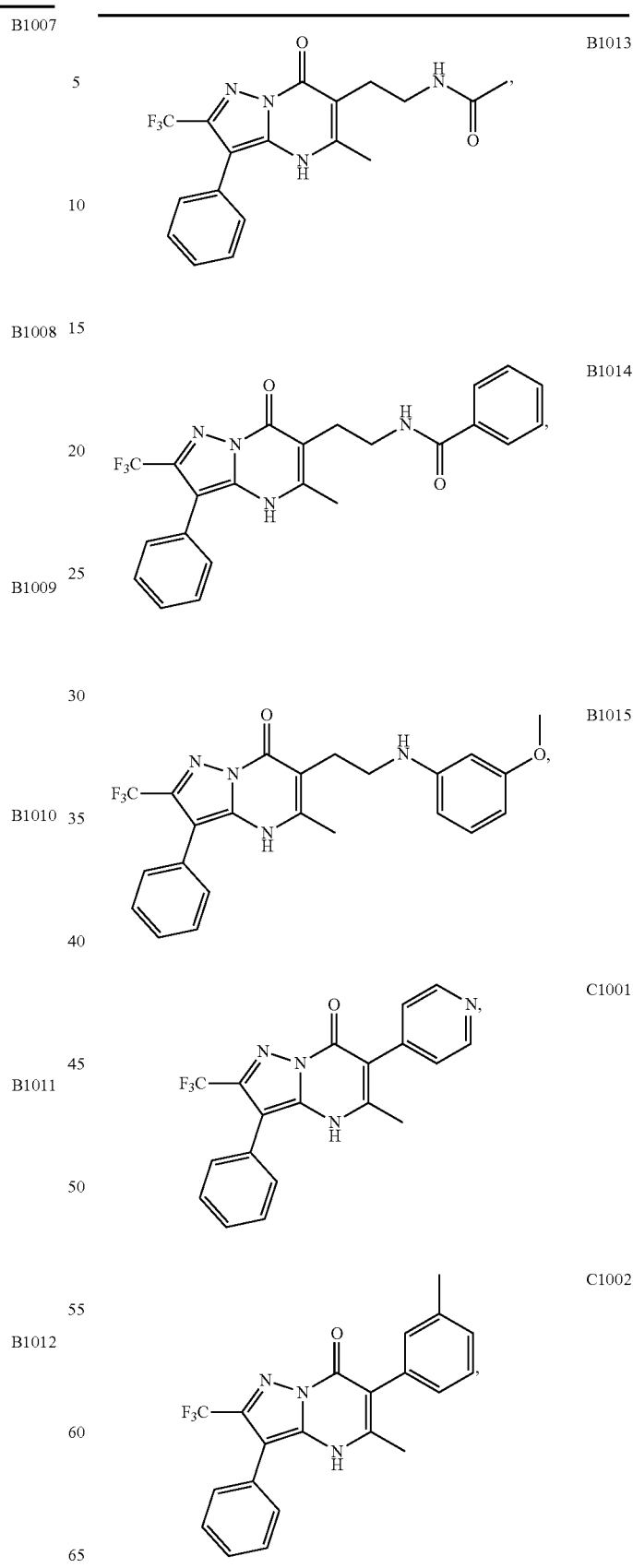

TABLE 1B-continued
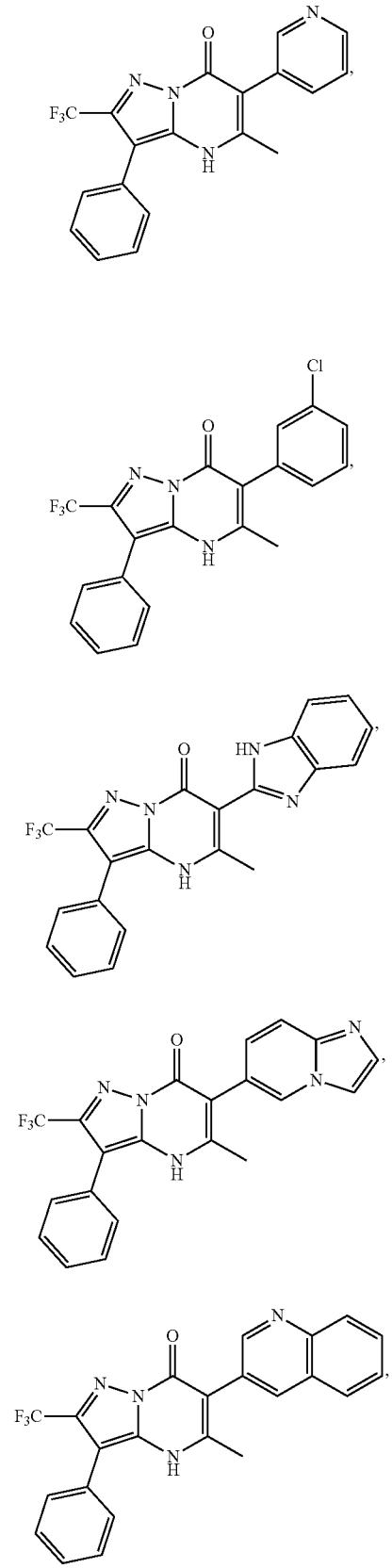
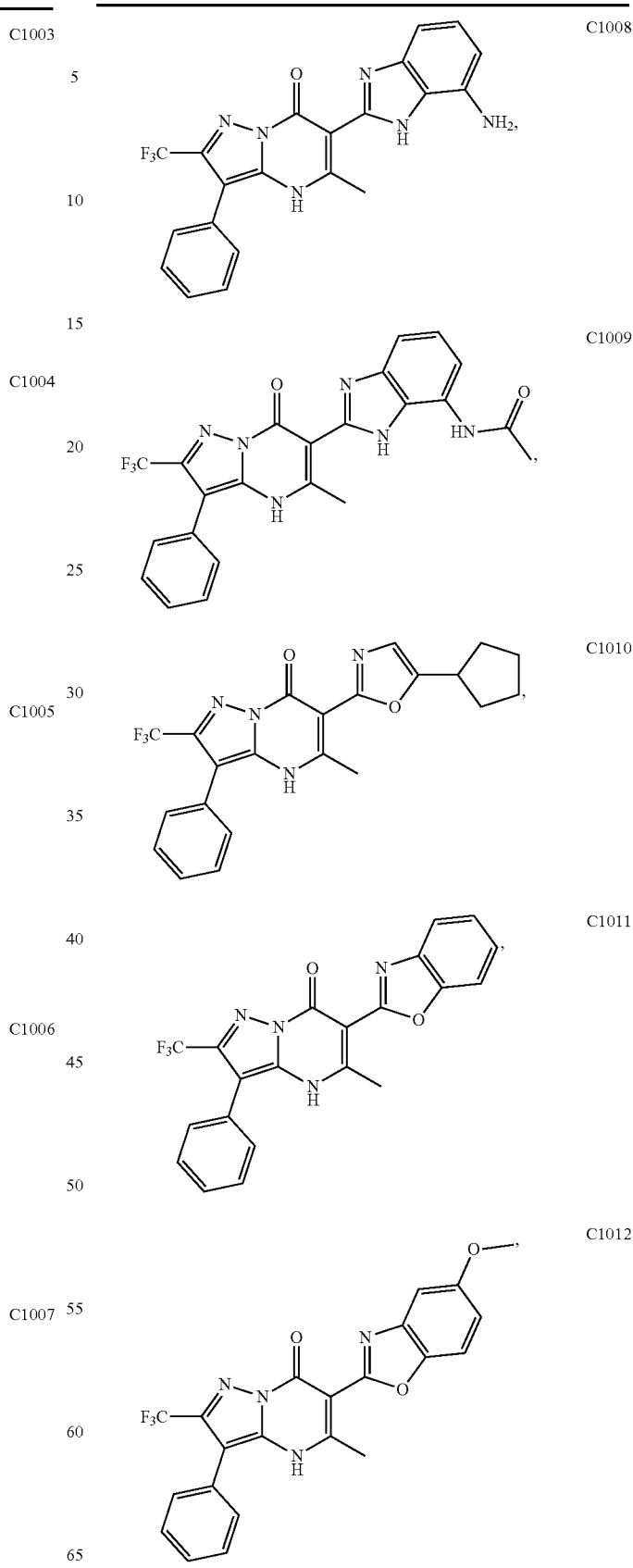

TABLE 1B-continued
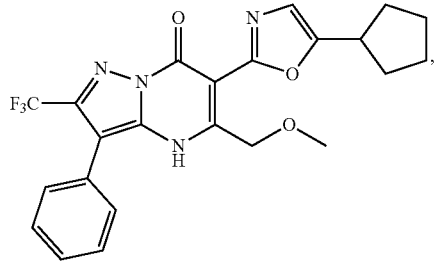 [SMILES: COCc1[nH]c2c(-c3ccccc3)c(C(F)(F)F)nn2c(=O)c1-c1ncc(C2CCCC2)o1] C1013
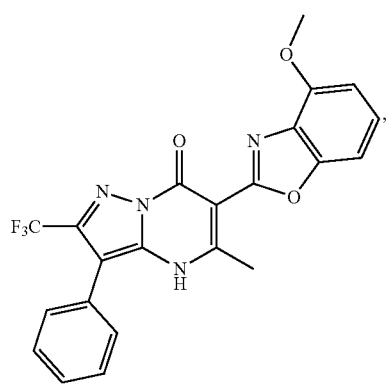 [SMILES: COc1cccc2oc(-c3c(C)[nH]c4c(-c5ccccc5)c(C(F)(F)F)nn4c3=O)nc12] C1014
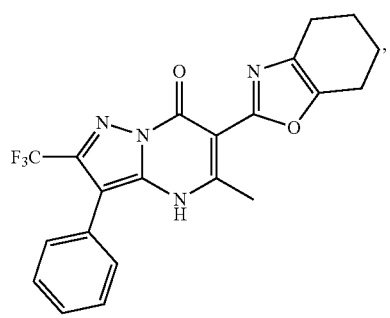 C1015
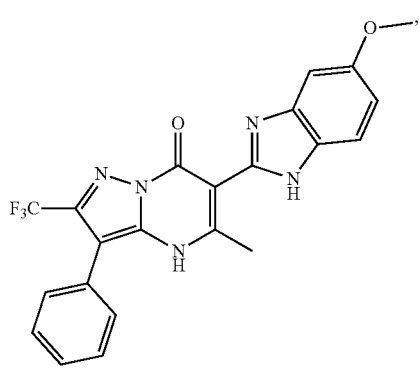 [SMILES: COc1ccc2[nH]c(-c3c(C)[nH]c4c(-c5ccccc5)c(C(F)(F)F)nn4c3=O)nc2c1] C1016
TABLE 1B-continued
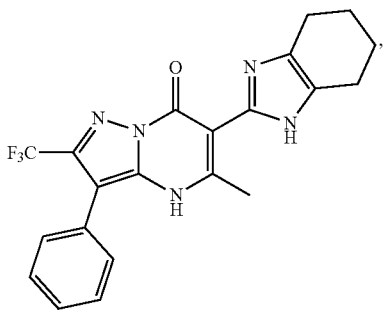 [SMILES: Cc1[nH]c2c(-c3ccccc3)c(C(F)(F)F)nn2c(=O)c1-c1nc2c([nH]1)CCCC2] C1017
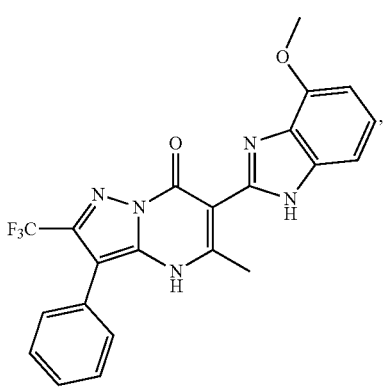 [SMILES: COc1cccc2[nH]c(-c3c(C)[nH]c4c(-c5ccccc5)c(C(F)(F)F)nn4c3=O)nc12] C1018
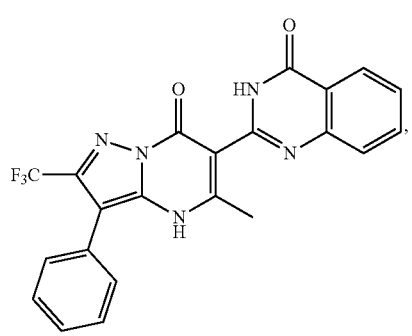 [SMILES: Cc1[nH]c2c(-c3ccccc3)c(C(F)(F)F)nn2c(=O)c1-c1nc2ccccc2c(=O)[nH]1] C1019
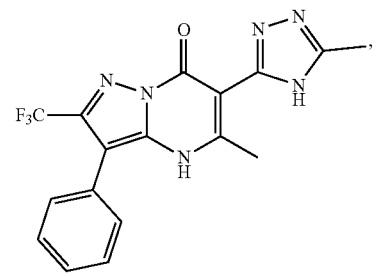 [SMILES: Cc1nnc(-c2c(C)[nH]c3c(-c4ccccc4)c(C(F)(F)F)nn3c2=O)[nH]1] C1020
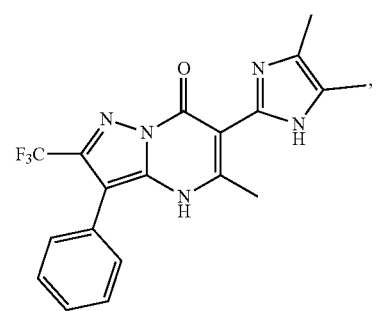 [SMILES: Cc1nc(-c2c(C)[nH]c3c(-c4ccccc4)c(C(F)(F)F)nn3c2=O)[nH]c1C] C1021

TABLE 1B-continued
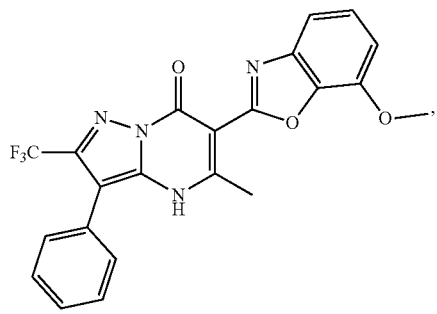 [SMILES: COc1cccc2nc(-c3c(C)[nH]c4c(-c5ccccc5)c(C(F)(F)F)nn4c3=O)oc12]
C1022
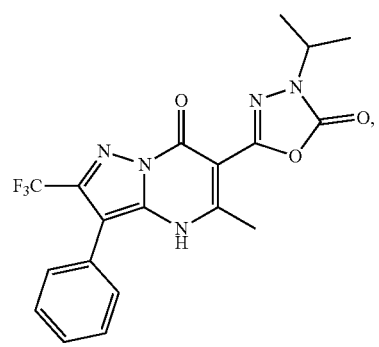 [SMILES: Cc1[nH]c2c(-c3ccccc3)c(C(F)(F)F)nn2c(=O)c1-c1nn(C(C)C)c(=O)o1]
C1023
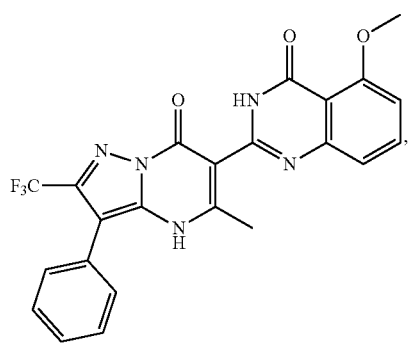 [SMILES: COc1cccc2nc(-c3c(C)[nH]c4c(-c5ccccc5)c(C(F)(F)F)nn4c3=O)[nH]c(=O)c12]
C1024
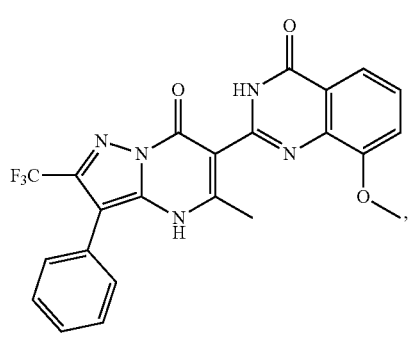 [SMILES: COc1cccc2c(=O)[nH]c(-c3c(C)[nH]c4c(-c5ccccc5)c(C(F)(F)F)nn4c3=O)nc12]
C1025
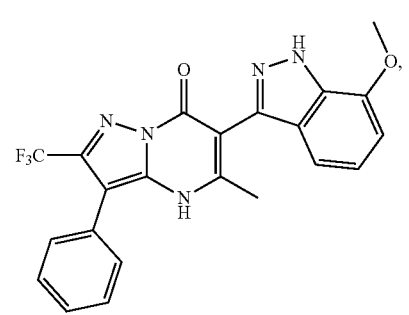 [SMILES: COc1cccc2c(-c3c(C)[nH]c4c(-c5ccccc5)c(C(F)(F)F)nn4c3=O)n[nH]c12]
C1026
TABLE 1B-continued
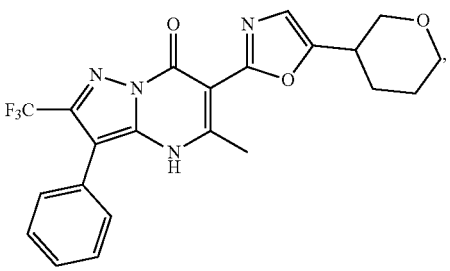 [SMILES: Cc1[nH]c2c(-c3ccccc3)c(C(F)(F)F)nn2c(=O)c1-c1ncc(C2CCCOC2)o1]
C1027
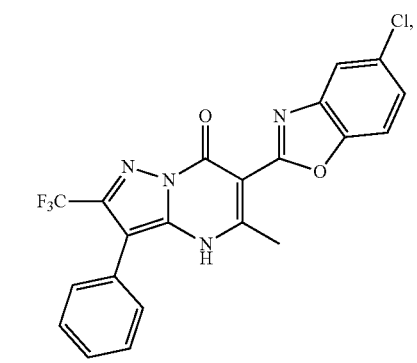 [SMILES: Cc1[nH]c2c(-c3ccccc3)c(C(F)(F)F)nn2c(=O)c1-c1nc2cc(Cl)ccc2o1]
C1028
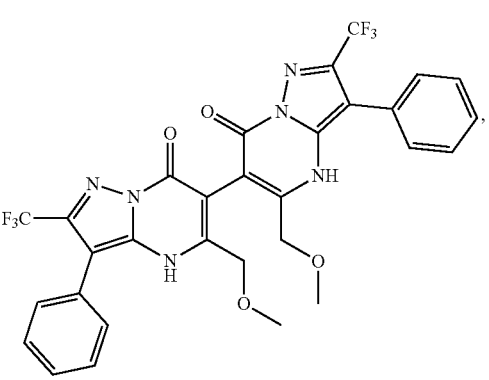 [SMILES: COCc1[nH]c2c(-c3ccccc3)c(C(F)(F)F)nn2c(=O)c1-c1c(COC)[nH]c2c(-c3ccccc3)c(C(F)(F)F)nn2c1=O]
C1029
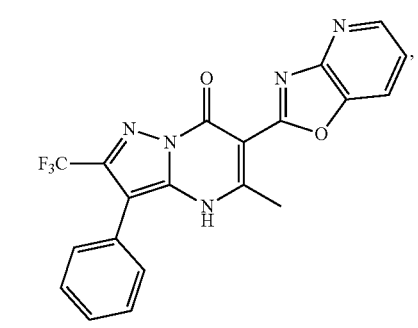 [SMILES: Cc1[nH]c2c(-c3ccccc3)c(C(F)(F)F)nn2c(=O)c1-c1nc2ncccc2o1]
C1030
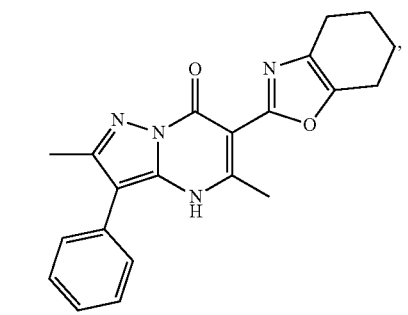 [SMILES: Cc1nn2c(=O)c(-c3nc4c(o3)CCCC4)c(C)[nH]c2c1-c1ccccc1]
C1032

TABLE 1B-continued
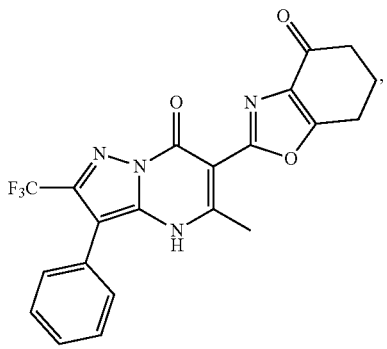 [SMILES: Cc1[nH]c2c(-c3ccccc3)c(C(F)(F)F)nn2c(=O)c1-c1nc2c(o1)CCCC2=O] C1033
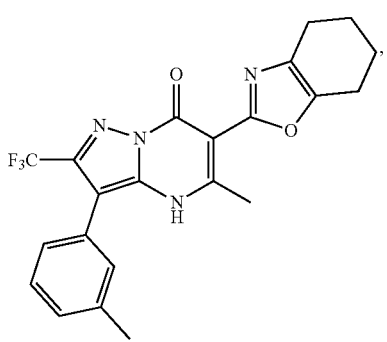 [SMILES: Cc1cccc(-c2c(C(F)(F)F)nn3c(=O)c(-c4nc5c(o4)CCCC5)c(C)[nH]c23)c1] C1034
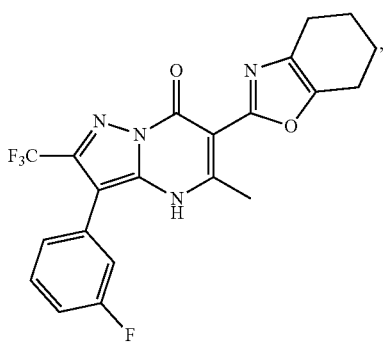 [SMILES: Cc1[nH]c2c(-c3cccc(F)c3)c(C(F)(F)F)nn2c(=O)c1-c1nc2c(o1)CCCC2] C1035
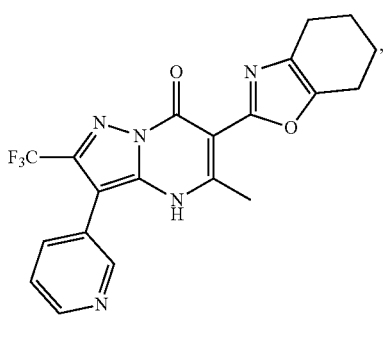 [SMILES: Cc1[nH]c2c(-c3cccnc3)c(C(F)(F)F)nn2c(=O)c1-c1nc2c(o1)CCCC2] C1036
TABLE 1B-continued
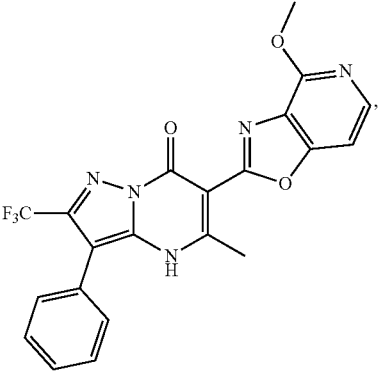 C1037
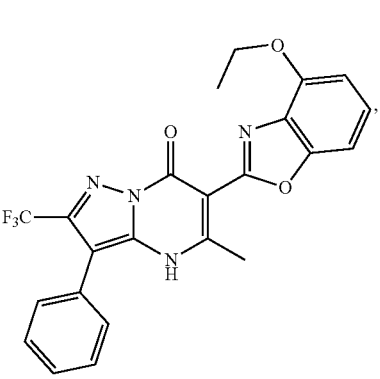 [SMILES: CCOc1cccc2oc(-c3c(C)[nH]c4c(-c5ccccc5)c(C(F)(F)F)nn4c3=O)nc12] C1038
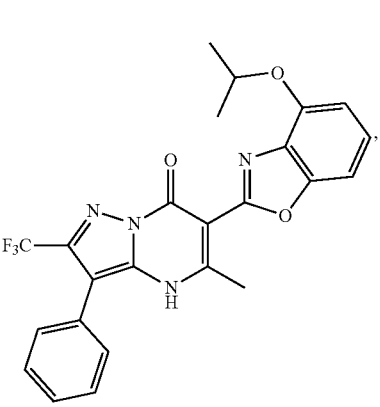 [SMILES: Cc1[nH]c2c(-c3ccccc3)c(C(F)(F)F)nn2c(=O)c1-c1nc2c(OC(C)C)cccc2o1] C1039
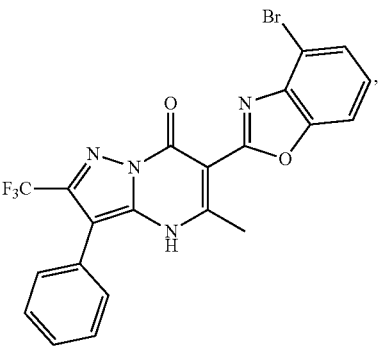 [SMILES: Cc1[nH]c2c(-c3ccccc3)c(C(F)(F)F)nn2c(=O)c1-c1nc2c(Br)cccc2o1] C1040

TABLE 1B-continued
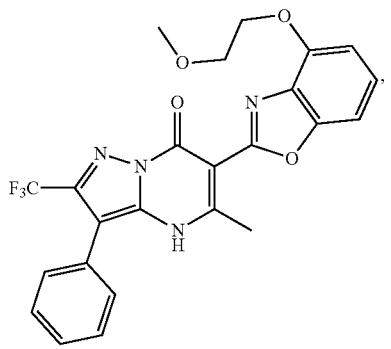 [SMILES: COCCOc1cccc2oc(-c3c(C)[nH]c4c(-c5ccccc5)c(C(F)(F)F)nn4c3=O)nc12]
C1041
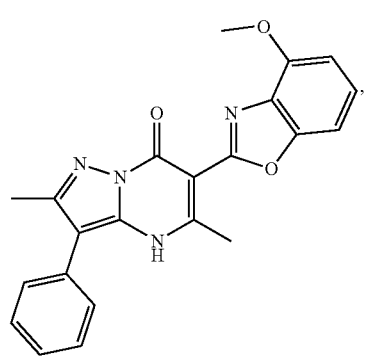 [SMILES: COc1cccc2oc(-c3c(C)[nH]c4c(-c5ccccc5)c(C)nn4c3=O)nc12]
C1042
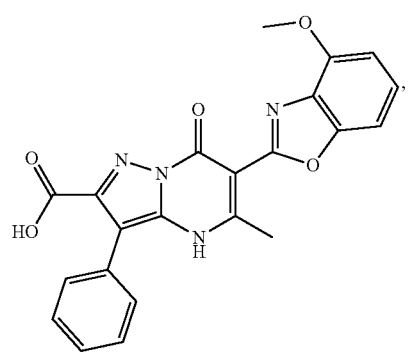 [SMILES: COc1cccc2oc(-c3c(C)[nH]c4c(-c5ccccc5)c(C(=O)O)nn4c3=O)nc12]
C1043
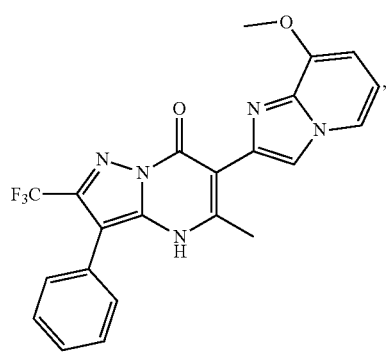 [SMILES: COc1cccn2cc(-c3c(C)[nH]c4c(-c5ccccc5)c(C(F)(F)F)nn4c3=O)nc12]
C1044
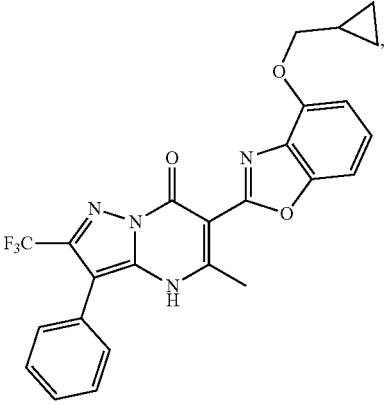 [SMILES: Cc1[nH]c2c(-c3ccccc3)c(C(F)(F)F)nn2c(=O)c1-c1nc2c(OCC3CC3)cccc2o1]
C1045
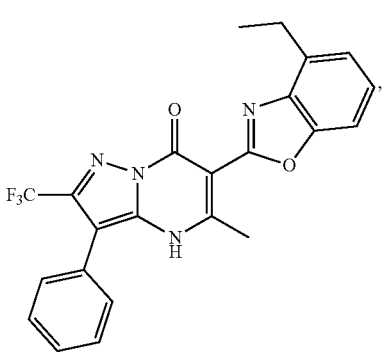 [SMILES: CCc1cccc2oc(-c3c(C)[nH]c4c(-c5ccccc5)c(C(F)(F)F)nn4c3=O)nc12]
C1046
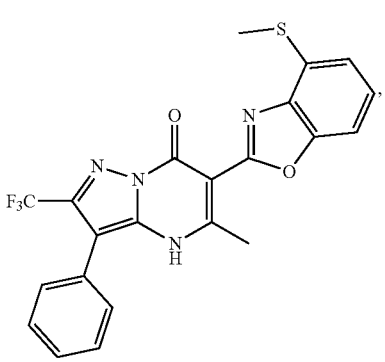
C1047
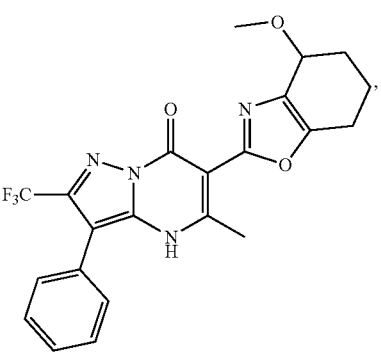 [SMILES: COC1CCCc2oc(-c3c(C)[nH]c4c(-c5ccccc5)c(C(F)(F)F)nn4c3=O)nc21]
C1048

TABLE 1B-continued
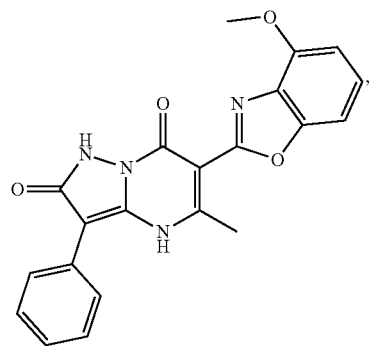 [SMILES: COc1cccc2oc(-c3c(C)[nH]c4c(-c5ccccc5)c(=O)[nH]n4c3=O)nc12] C1049
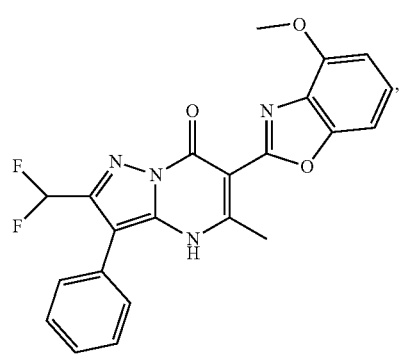 [SMILES: COc1cccc2oc(-c3c(C)[nH]c4c(-c5ccccc5)c(C(F)F)nn4c3=O)nc12] C1050
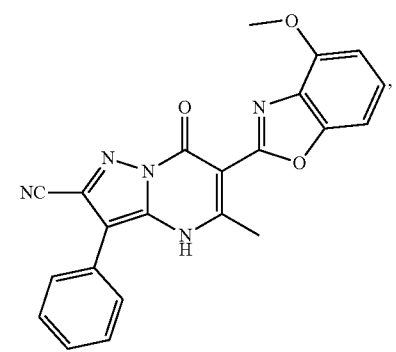 [SMILES: COc1cccc2oc(-c3c(C)[nH]c4c(-c5ccccc5)c(C#N)nn4c3=O)nc12] C1051
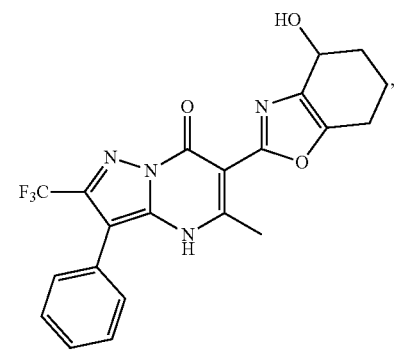 [SMILES: Cc1[nH]c2c(-c3ccccc3)c(C(F)(F)F)nn2c(=O)c1-c1nc2c(o1)CCCC2O] C1052
TABLE 1B-continued
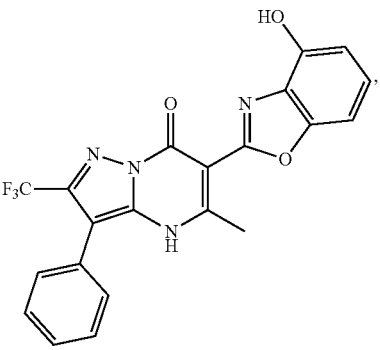 C1053
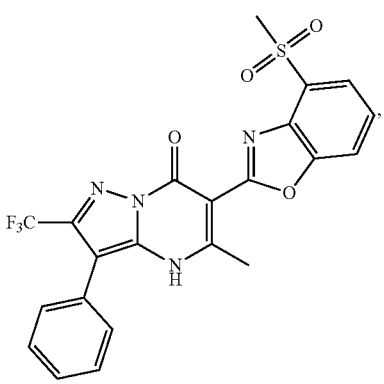 [SMILES: Cc1[nH]c2c(-c3ccccc3)c(C(F)(F)F)nn2c(=O)c1-c1nc2c(S(C)(=O)=O)cccc2o1] C1054
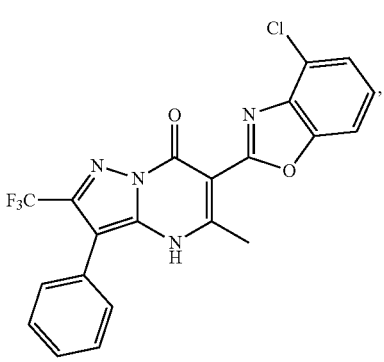 C1055
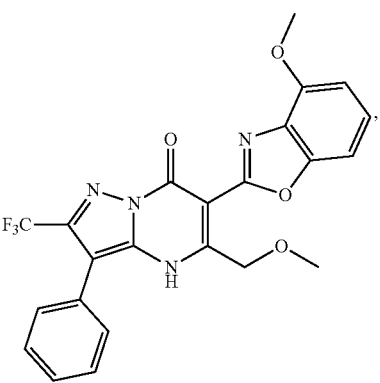 [SMILES: COCc1[nH]c2c(-c3ccccc3)c(C(F)(F)F)nn2c(=O)c1-c1nc2c(OC)cccc2o1] C1056

TABLE 1B-continued
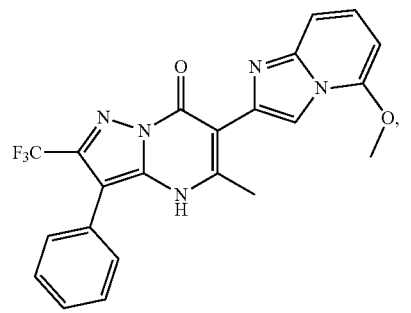 [SMILES: COc1cccc2nc(-c3c(C)[nH]c4c(-c5ccccc5)c(C(F)(F)F)nn4c3=O)cn12]
C1057
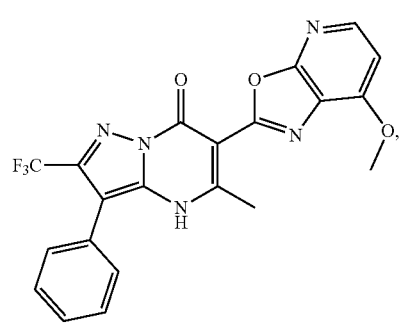 [SMILES: COc1ccnc2oc(-c3c(C)[nH]c4c(-c5ccccc5)c(C(F)(F)F)nn4c3=O)nc12]
C1058
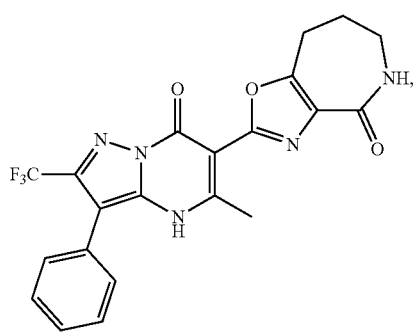 [SMILES: Cc1[nH]c2c(-c3ccccc3)c(C(F)(F)F)nn2c(=O)c1-c1nc2c(o1)CCCNC2=O]
C1059
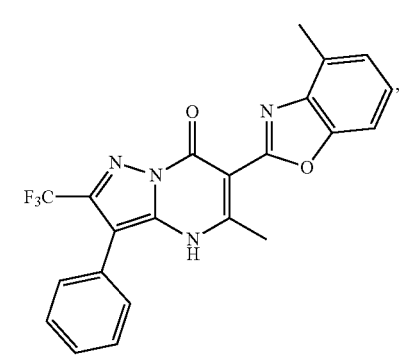 [SMILES: Cc1[nH]c2c(-c3ccccc3)c(C(F)(F)F)nn2c(=O)c1-c1nc2c(C)cccc2o1]
C1060
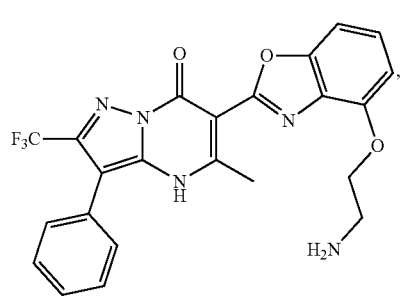 [SMILES: Cc1[nH]c2c(-c3ccccc3)c(C(F)(F)F)nn2c(=O)c1-c1nc2c(OCCN)cccc2o1]
C1061
TABLE 1B-continued
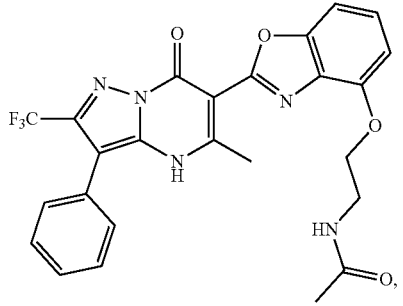 [SMILES: CC(=O)NCCOc1cccc2oc(-c3c(C)[nH]c4c(-c5ccccc5)c(C(F)(F)F)nn4c3=O)nc12]
C1062
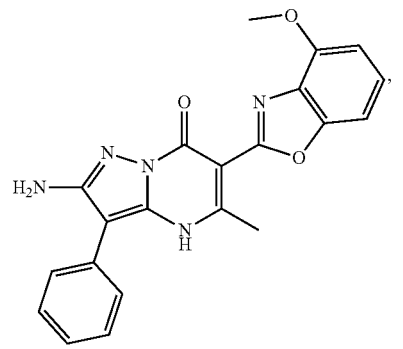
C1063
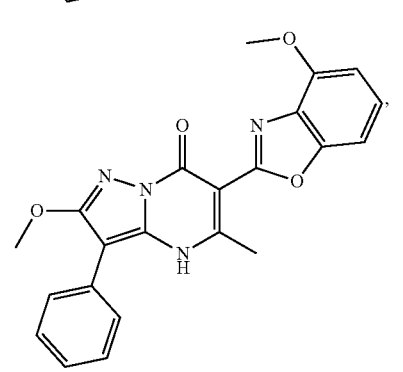
C1064
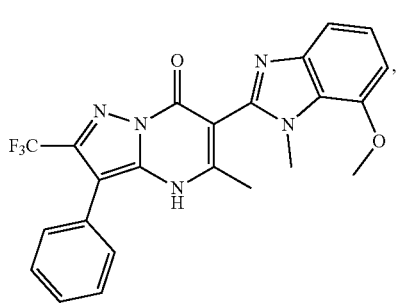 [SMILES: COc1cccc2nc(-c3c(C)[nH]c4c(-c5ccccc5)c(C(F)(F)F)nn4c3=O)n(C)c12]
C1065
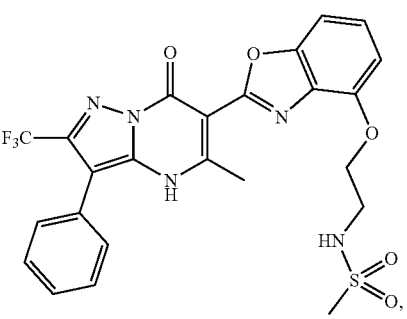 [SMILES: Cc1[nH]c2c(-c3ccccc3)c(C(F)(F)F)nn2c(=O)c1-c1nc2c(OCCNS(C)(=O)=O)cccc2o1]
C1066

TABLE 1B-continued
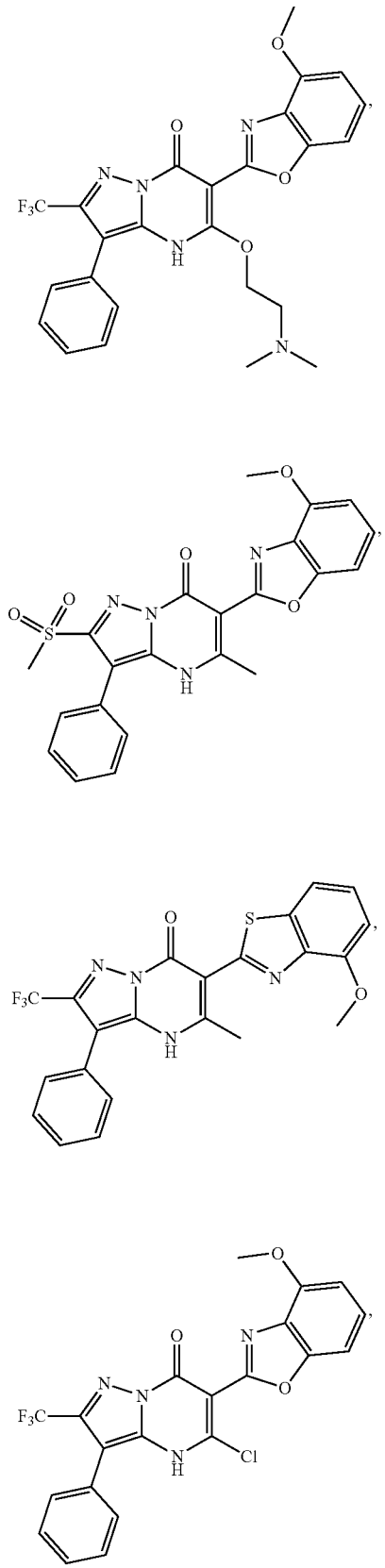
C1067
C1068
C1070
C1071
TABLE 1B-continued
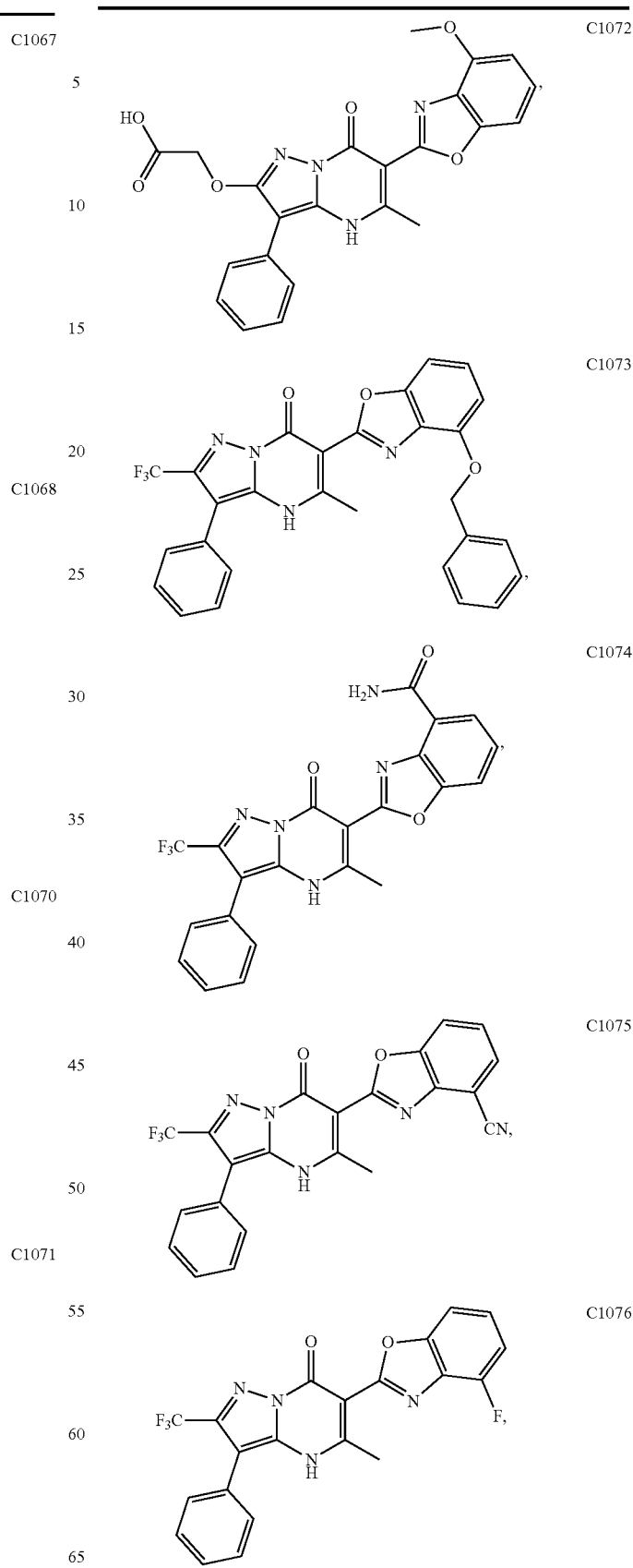
C1072
C1073
C1074
C1075
C1076

TABLE 1B-continued
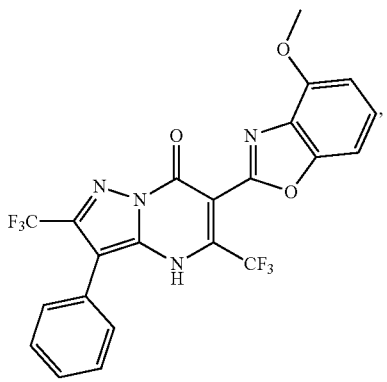 [SMILES: COc1cccc2oc(-c3c(C(F)(F)F)[nH]c4c(-c5ccccc5)c(C(F)(F)F)nn4c3=O)nc12]
C1077
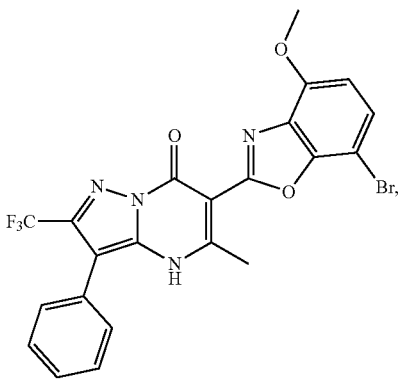
C1081
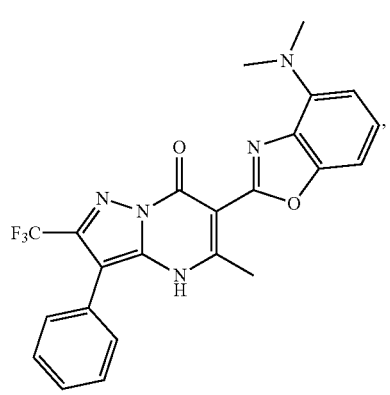 [SMILES: Cc1[nH]c2c(-c3ccccc3)c(C(F)(F)F)nn2c(=O)c1-c1nc2c(N(C)C)cccc2o1]
C1078
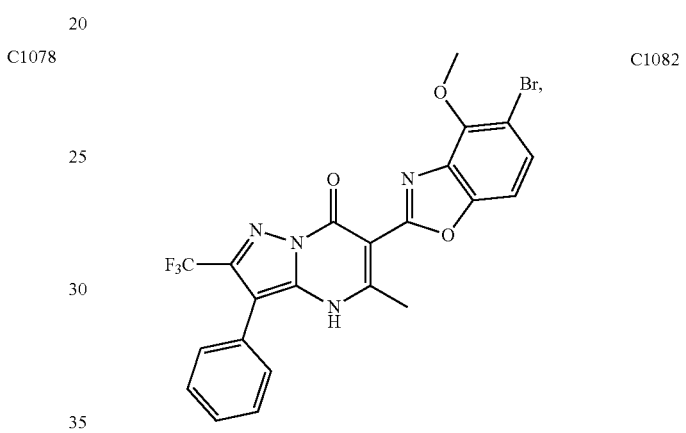
C1082
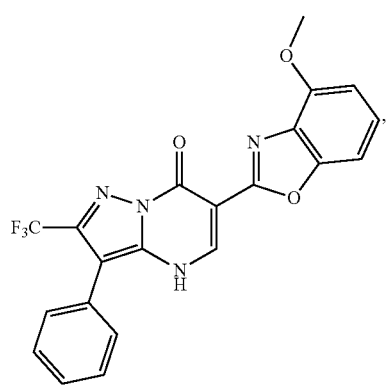 [SMILES: COc1cccc2oc(-c3c[nH]c4c(-c5ccccc5)c(C(F)(F)F)nn4c3=O)nc12]
C1079
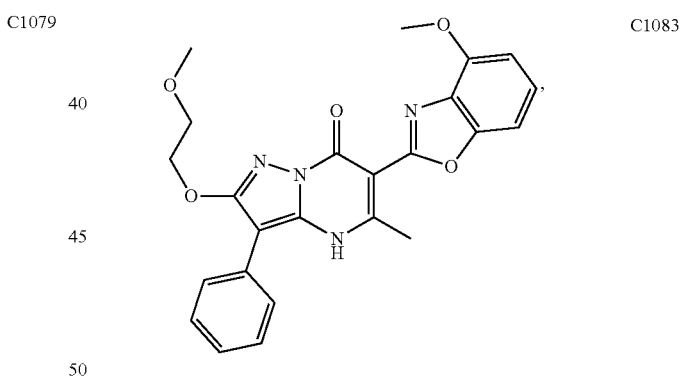
C1083
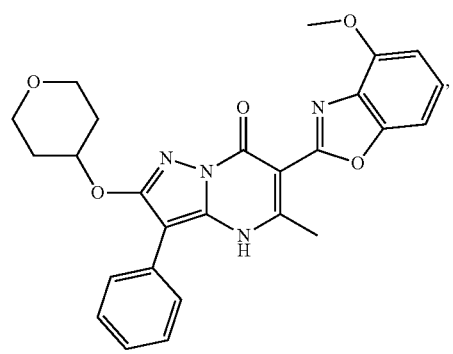 [SMILES: COc1cccc2oc(-c3c(C)[nH]c4c(-c5ccccc5)c(OC5CCOCC5)nn4c3=O)nc12]
C1080
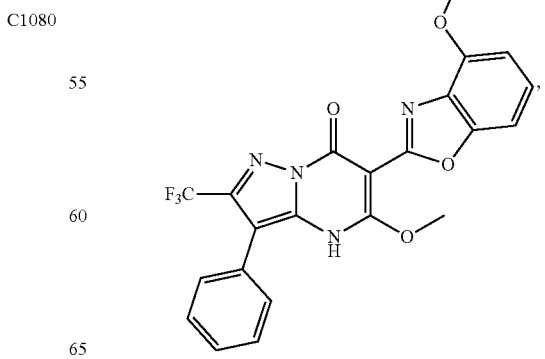
C1084

TABLE 1B-continued
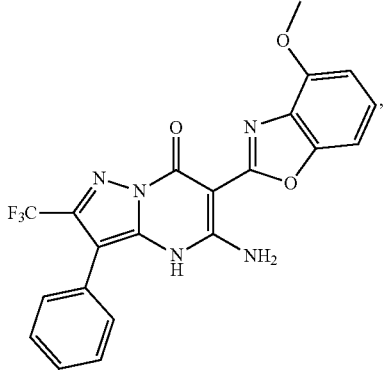 [SMILES: COc1cccc2oc(-c3c(N)[nH]c4c(-c5ccccc5)c(C(F)(F)F)nn4c3=O)nc12]
C1085
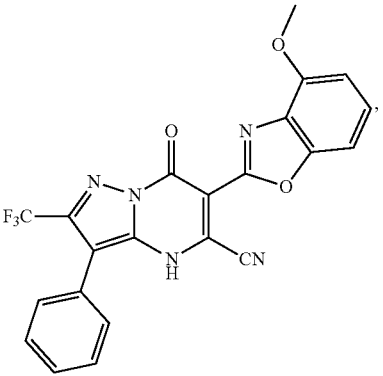
C1086
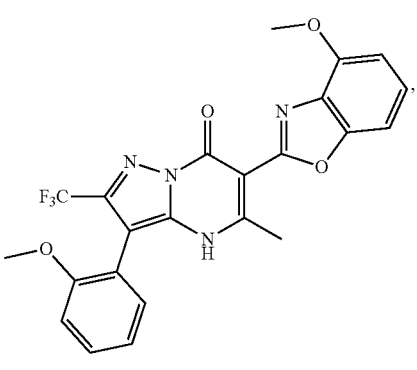 [SMILES: COc1ccccc1-c1c(C(F)(F)F)nn2c(=O)c(-c3nc4c(OC)cccc4o3)c(C)[nH]c12]
C1087
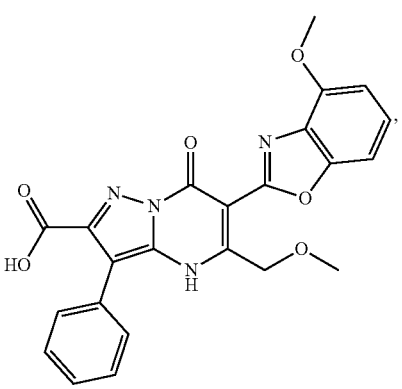
C1088
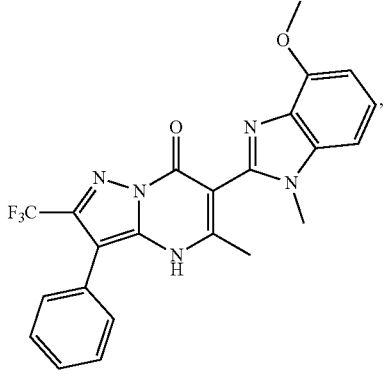 [SMILES: COc1cccc2c1nc(-c1c(C)[nH]c3c(-c4ccccc4)c(C(F)(F)F)nn3c1=O)n2C]
C1089
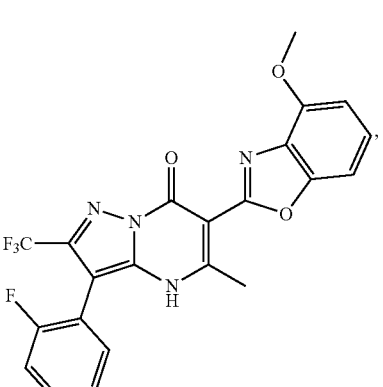
C1090
C1091
C1092

TABLE 1B-continued
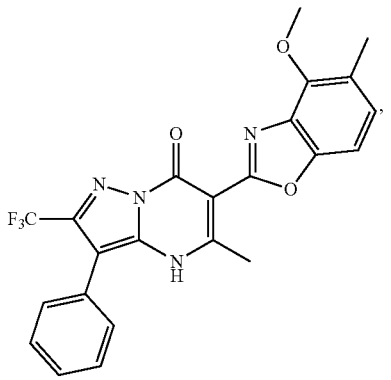
C1093
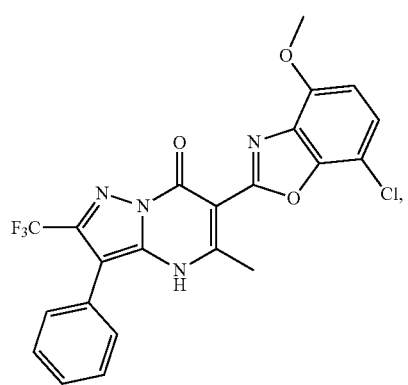
C1094
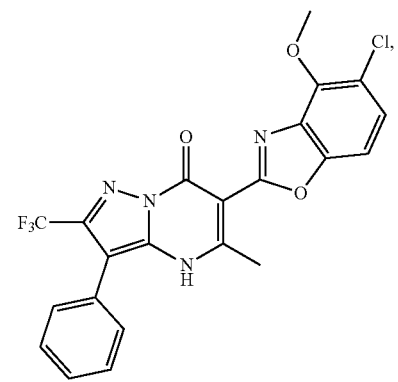
C1095
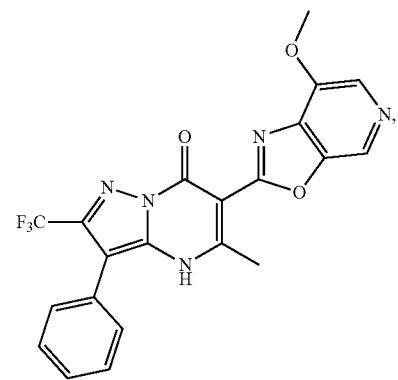 [SMILES: COc1cncc2oc(-c3c(C)[nH]c4c(-c5ccccc5)c(C(F)(F)F)nn4c3=O)nc12]
C1096
TABLE 1B-continued
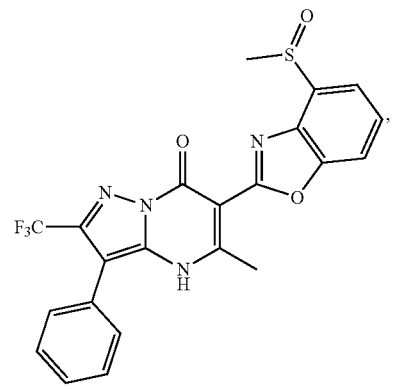 [SMILES: Cc1[nH]c2c(-c3ccccc3)c(C(F)(F)F)nn2c(=O)c1-c1nc2c(S(C)=O)cccc2o1]
C1097
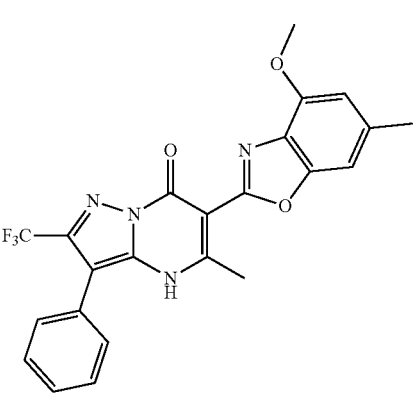 [SMILES: COc1cc(C)cc2oc(-c3c(C)[nH]c4c(-c5ccccc5)c(C(F)(F)F)nn4c3=O)nc12]
C1098
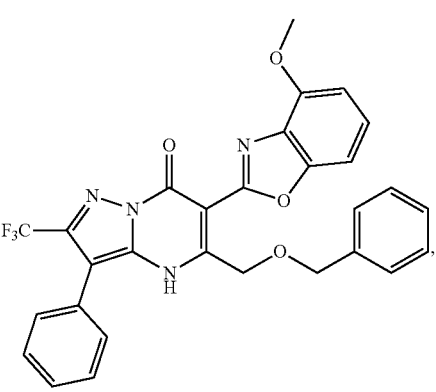 [SMILES: COc1cccc2oc(-c3c(COCc4ccccc4)[nH]c4c(-c5ccccc5)c(C(F)(F)F)nn4c3=O)nc12]
C1099
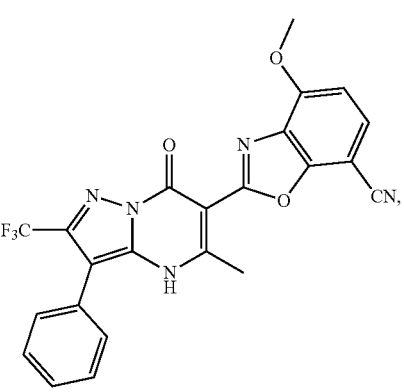 [SMILES: COc1ccc(C#N)c2oc(-c3c(C)[nH]c4c(-c5ccccc5)c(C(F)(F)F)nn4c3=O)nc12]
C1100

TABLE 1B-continued
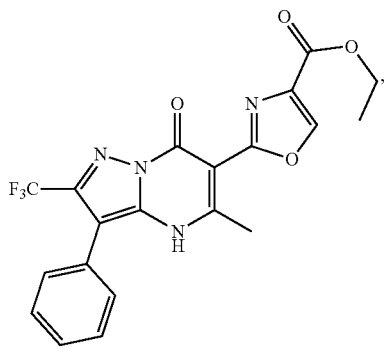 [SMILES: CCOC(=O)c1coc(-c2c(C)[nH]c3c(-c4ccccc4)c(C(F)(F)F)nn3c2=O)n1]
C1101
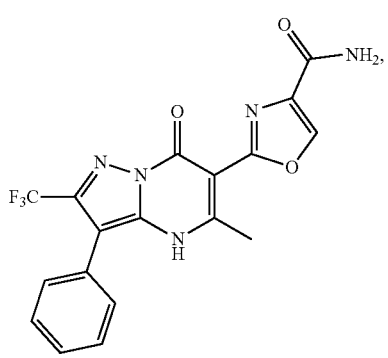 [SMILES: Cc1[nH]c2c(-c3ccccc3)c(C(F)(F)F)nn2c(=O)c1-c1nc(C(N)=O)co1]
C1102
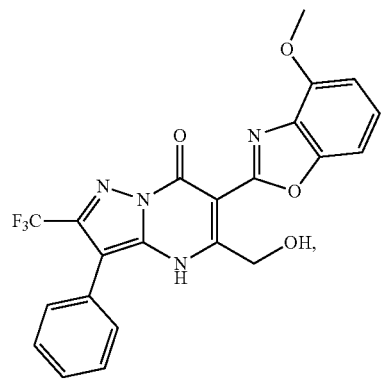 [SMILES: COc1cccc2oc(-c3c(CO)[nH]c4c(-c5ccccc5)c(C(F)(F)F)nn4c3=O)nc12]
C1103
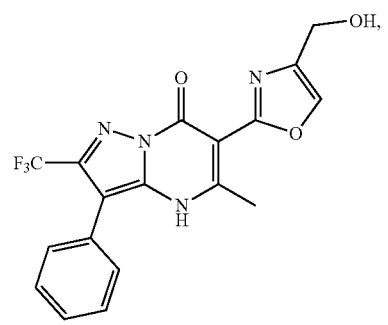 [SMILES: Cc1[nH]c2c(-c3ccccc3)c(C(F)(F)F)nn2c(=O)c1-c1nc(CO)co1]
C1104
TABLE 1B-continued
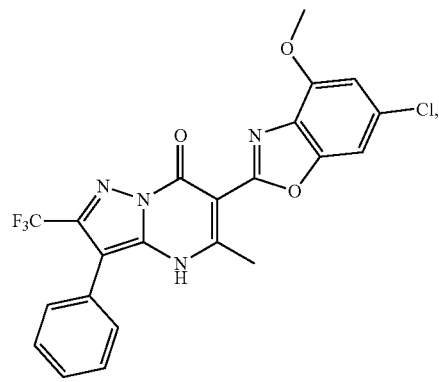 [SMILES: COc1cc(Cl)cc2oc(-c3c(C)[nH]c4c(-c5ccccc5)c(C(F)(F)F)nn4c3=O)nc12]
C1105
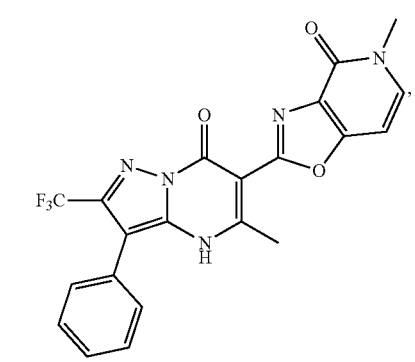 [SMILES: Cc1[nH]c2c(-c3ccccc3)c(C(F)(F)F)nn2c(=O)c1-c1nc2c(=O)n(C)ccc2o1]
C1106
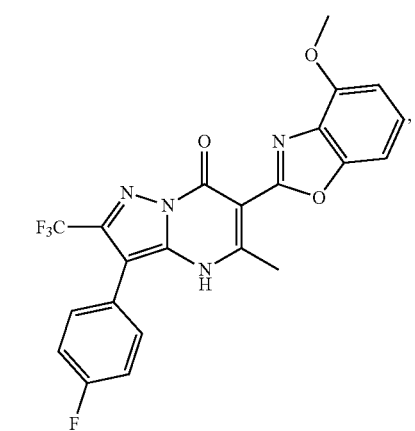 [SMILES: COc1cccc2oc(-c3c(C)[nH]c4c(-c5ccc(F)cc5)c(C(F)(F)F)nn4c3=O)nc12]
C1107
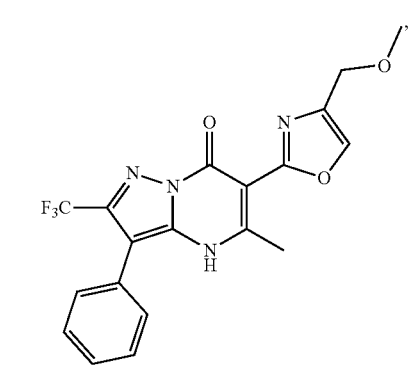 [SMILES: COCc1coc(-c2c(C)[nH]c3c(-c4ccccc4)c(C(F)(F)F)nn3c2=O)n1]
C1108

TABLE 1B-continued
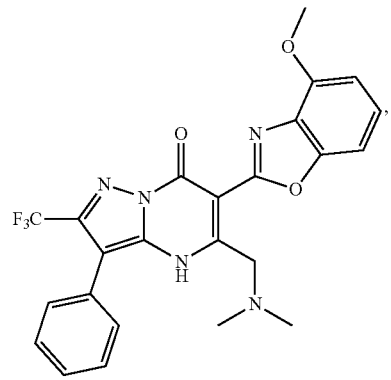 [SMILES: COc1cccc2oc(-c3c(CN(C)C)[nH]c4c(-c5ccccc5)c(C(F)(F)F)nn4c3=O)nc12]
C1109
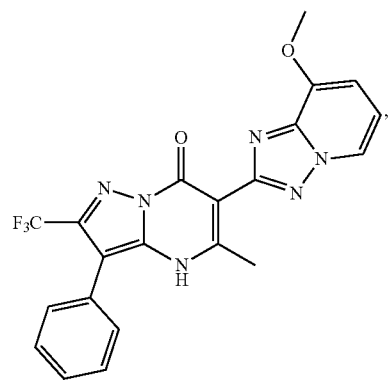 [SMILES: COc1cccn2nc(-c3c(C)[nH]c4c(-c5ccccc5)c(C(F)(F)F)nn4c3=O)nc12]
C1110
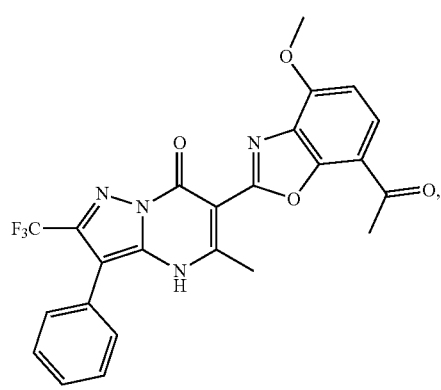 [SMILES: COc1ccc(C(C)=O)c2oc(-c3c(C)[nH]c4c(-c5ccccc5)c(C(F)(F)F)nn4c3=O)nc12]
C1111
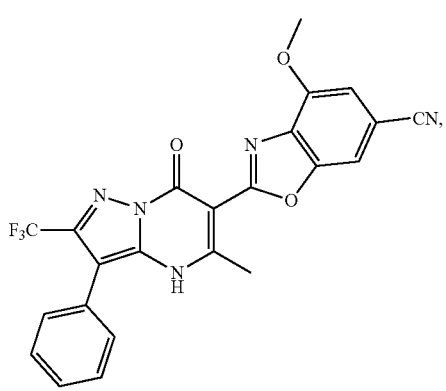 [SMILES: COc1cc(C#N)cc2oc(-c3c(C)[nH]c4c(-c5ccccc5)c(C(F)(F)F)nn4c3=O)nc12]
C1112
TABLE 1B-continued
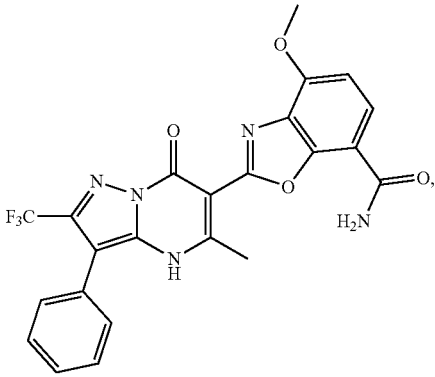
C1113
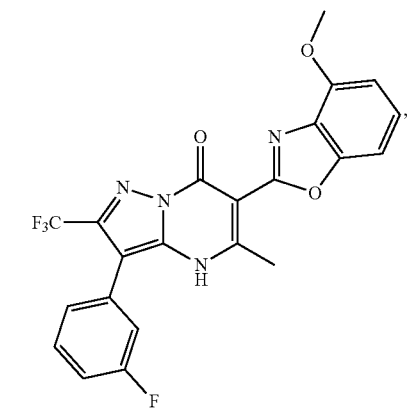 [SMILES: COc1cccc2oc(-c3c(C)[nH]c4c(-c5cccc(F)c5)c(C(F)(F)F)nn4c3=O)nc12]
C1114
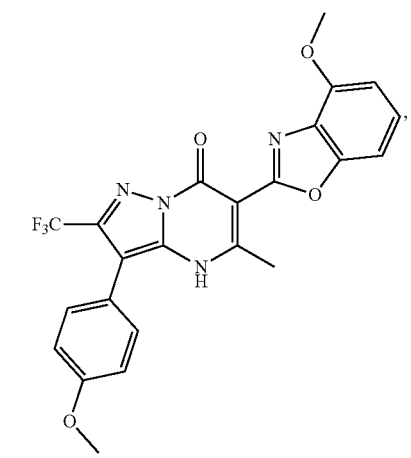 [SMILES: COc1ccc(-c2c(C(F)(F)F)nn3c(=O)c(-c4nc5c(OC)cccc5o4)c(C)[nH]c23)cc1]
C1115
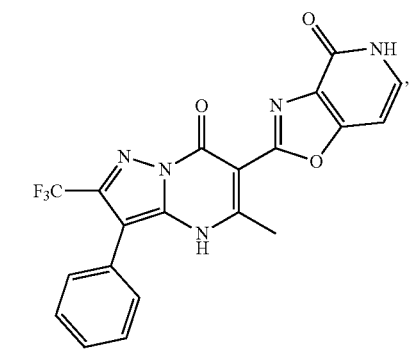 [SMILES: Cc1[nH]c2c(-c3ccccc3)c(C(F)(F)F)nn2c(=O)c1-c1nc2c(=O)[nH]ccc2o1]
C1116

TABLE 1B-continued
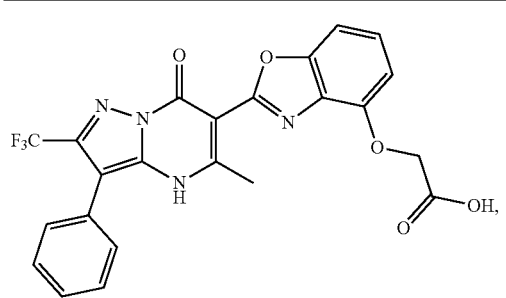
C1117
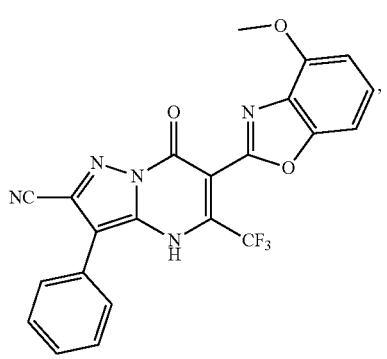
C1118
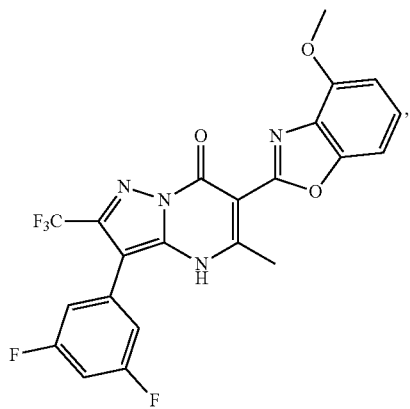 [SMILES: COc1cccc2oc(-c3c(C)[nH]c4c(-c5cc(F)cc(F)c5)c(C(F)(F)F)nn4c3=O)nc12]
C1119
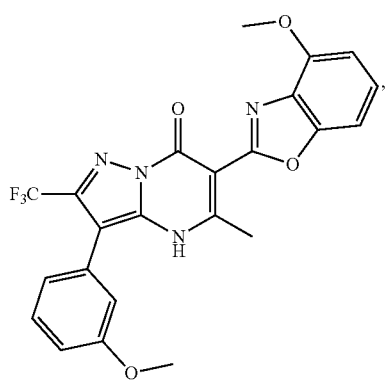 [SMILES: COc1cccc(-c2c(C(F)(F)F)nn3c(=O)c(-c4nc5c(OC)cccc5o4)c(C)[nH]c23)c1]
C1120
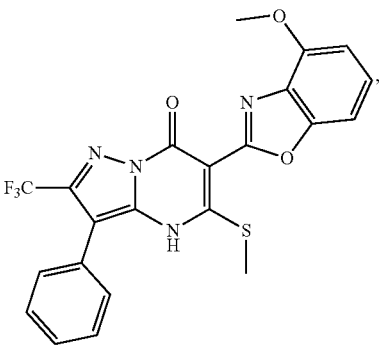 [SMILES: COc1cccc2oc(-c3c(SC)[nH]c4c(-c5ccccc5)c(C(F)(F)F)nn4c3=O)nc12]
C1121
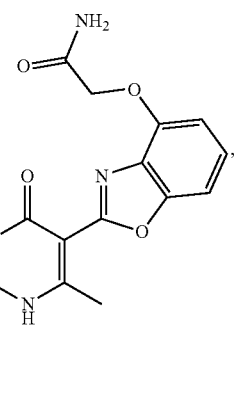
C1122
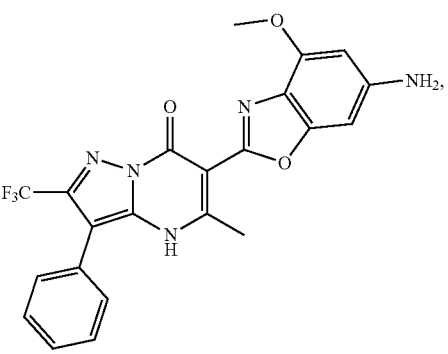 [SMILES: COc1cc(N)cc2oc(-c3c(C)[nH]c4c(-c5ccccc5)c(C(F)(F)F)nn4c3=O)nc12]
C1123
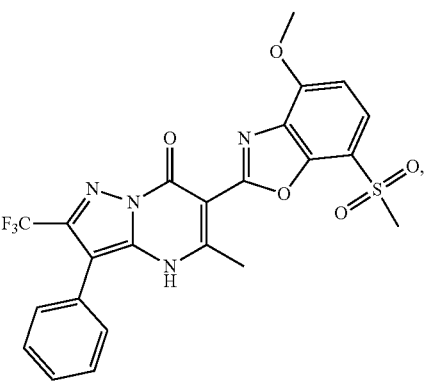 [SMILES: COc1ccc(S(C)(=O)=O)c2oc(-c3c(C)[nH]c4c(-c5ccccc5)c(C(F)(F)F)nn4c3=O)nc12]
C1125

TABLE 1B-continued
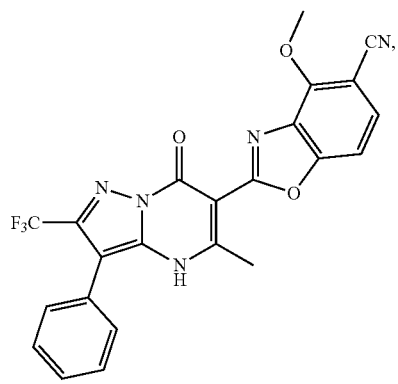 [SMILES: COc1c(C#N)ccc2oc(-c3c(C)[nH]c4c(-c5ccccc5)c(C(F)(F)F)nn4c3=O)nc12] C1126
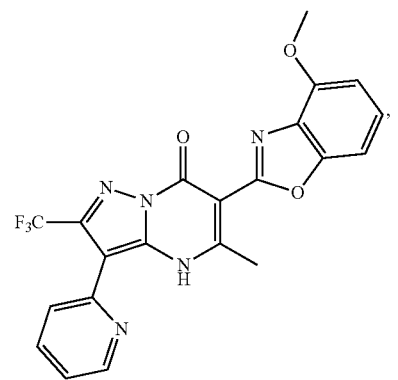 C1127
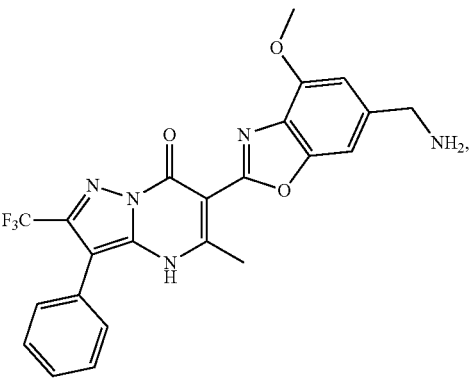 [SMILES: COc1cc(CN)cc2oc(-c3c(C)[nH]c4c(-c5ccccc5)c(C(F)(F)F)nn4c3=O)nc12] C1128
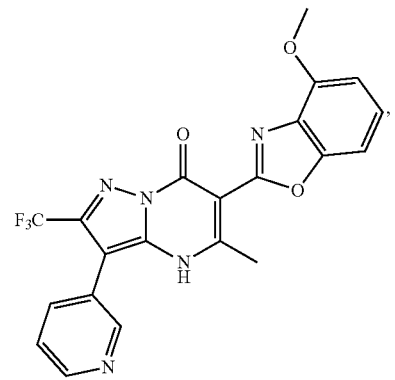 C1129
TABLE 1B-continued
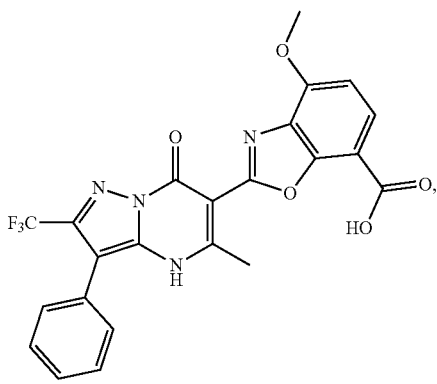 [SMILES: COc1ccc(C(=O)O)c2oc(-c3c(C)[nH]c4c(-c5ccccc5)c(C(F)(F)F)nn4c3=O)nc12] C1130
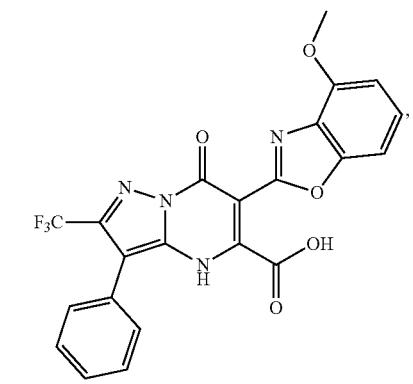 [SMILES: COc1cccc2oc(-c3c(C(=O)O)[nH]c4c(-c5ccccc5)c(C(F)(F)F)nn4c3=O)nc12] C1131
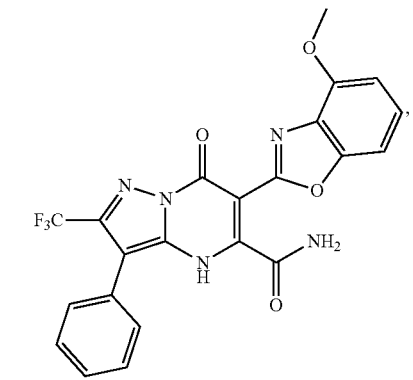 [SMILES: COc1cccc2oc(-c3c(C(N)=O)[nH]c4c(-c5ccccc5)c(C(F)(F)F)nn4c3=O)nc12] C1132
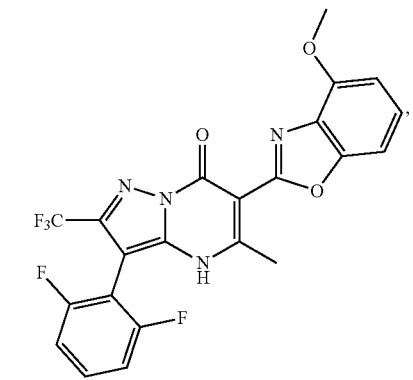 [SMILES: COc1cccc2oc(-c3c(C)[nH]c4c(-c5c(F)cccc5F)c(C(F)(F)F)nn4c3=O)nc12] C1133

TABLE 1B-continued
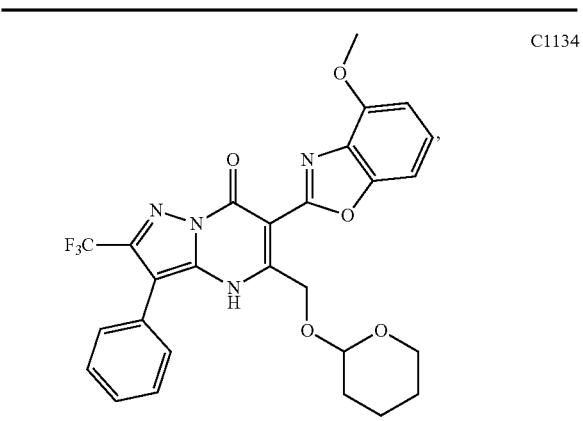
C1134
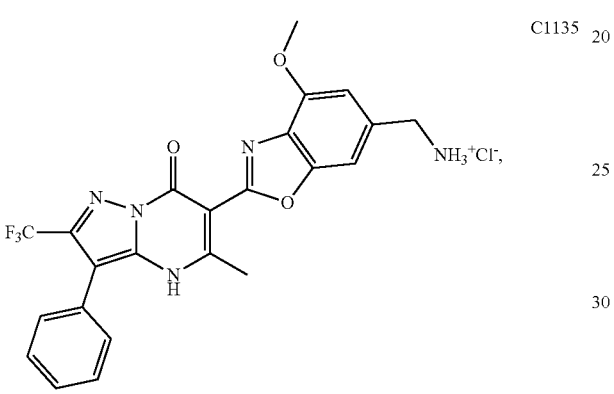
C1135
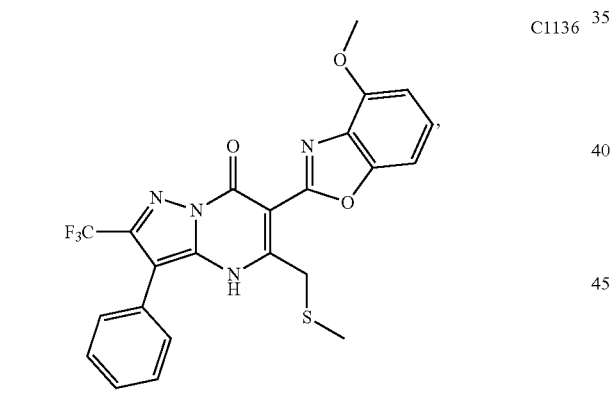
C1136
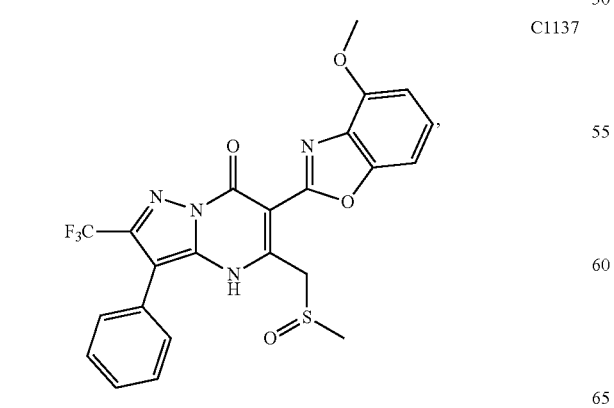
C1137
TABLE 1B-continued
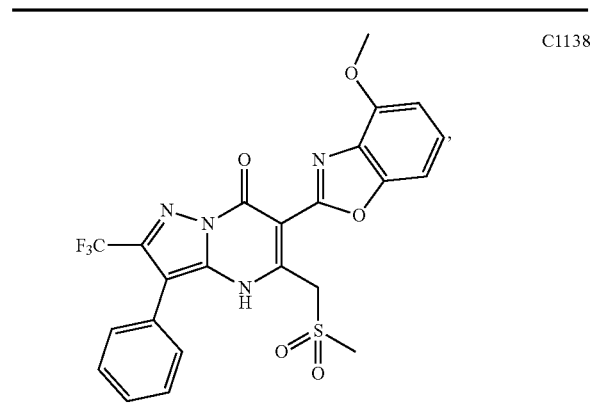
C1138
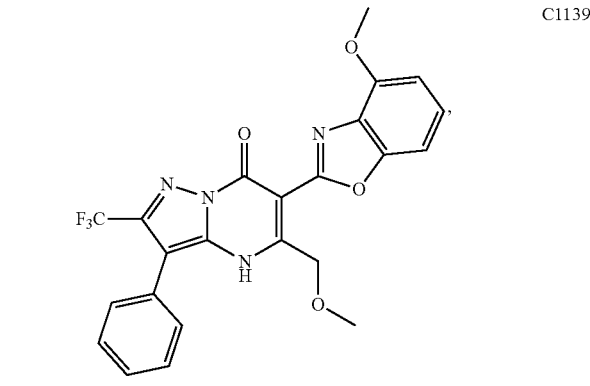
C1139
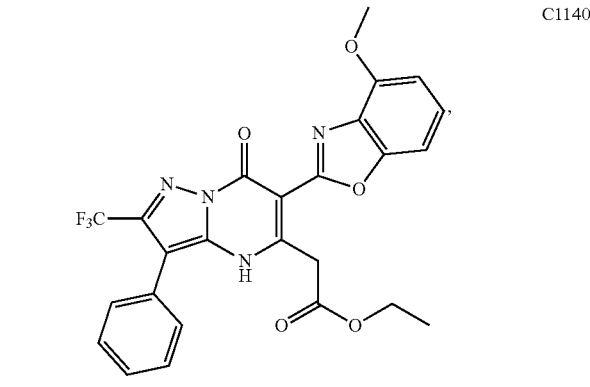
C1140
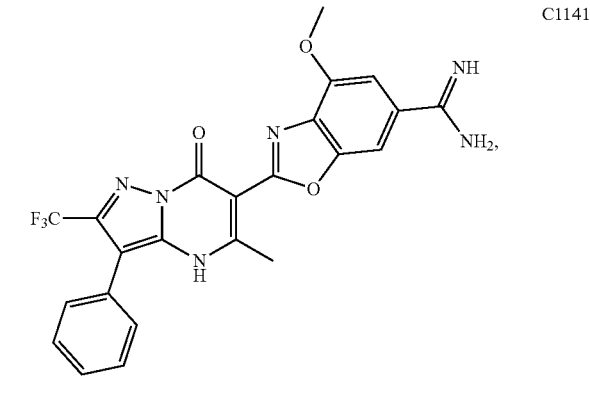
C1141

TABLE 1B-continued
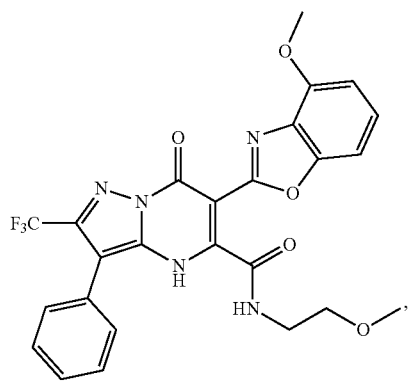 [SMILES: COCCNC(=O)c1[nH]c2c(-c3ccccc3)c(C(F)(F)F)nn2c(=O)c1-c1nc2c(OC)cccc2o1] C1142
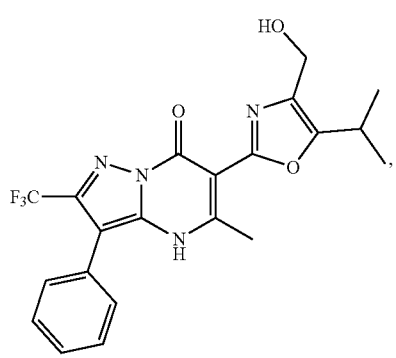 [SMILES: Cc1[nH]c2c(-c3ccccc3)c(C(F)(F)F)nn2c(=O)c1-c1nc(CO)c(C(C)C)o1] C1143
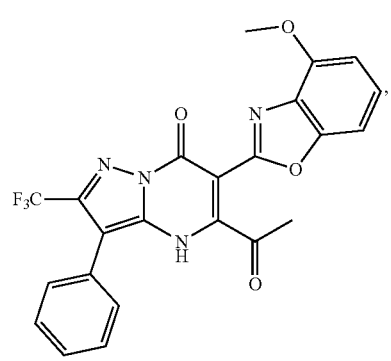 [SMILES: COc1cccc2oc(-c3c(C(C)=O)[nH]c4c(-c5ccccc5)c(C(F)(F)F)nn4c3=O)nc12] C1144
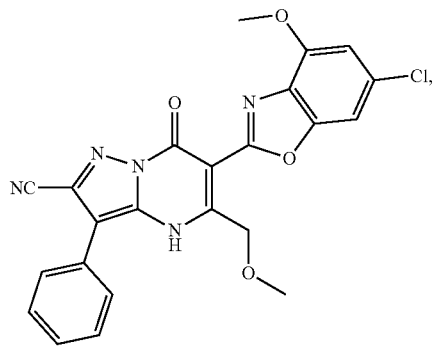 [SMILES: COCc1[nH]c2c(-c3ccccc3)c(C#N)nn2c(=O)c1-c1nc2c(OC)cc(Cl)cc2o1] C1145
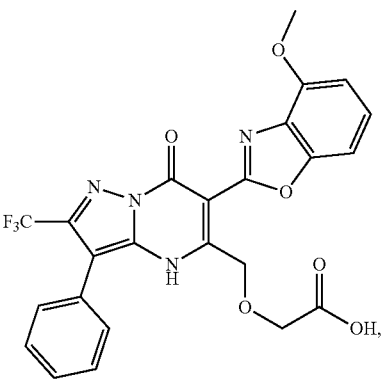 [SMILES: COc1cccc2oc(-c3c(COCC(=O)O)[nH]c4c(-c5ccccc5)c(C(F)(F)F)nn4c3=O)nc12] C1146
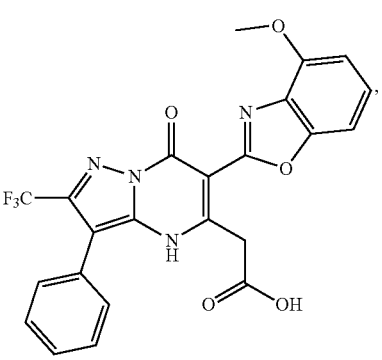 [SMILES: COc1cccc2oc(-c3c(CC(=O)O)[nH]c4c(-c5ccccc5)c(C(F)(F)F)nn4c3=O)nc12] C1147
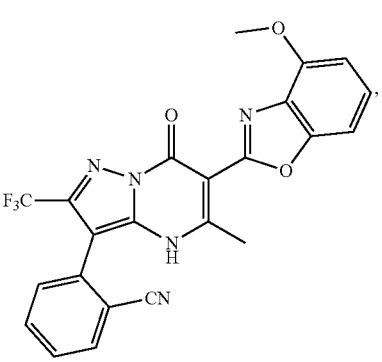 [SMILES: COc1cccc2oc(-c3c(C)[nH]c4c(-c5ccccc5C#N)c(C(F)(F)F)nn4c3=O)nc12] C1148
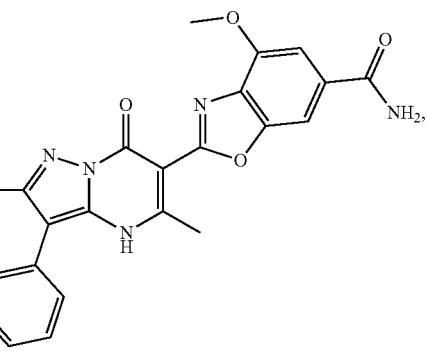 C1149

TABLE 1B-continued
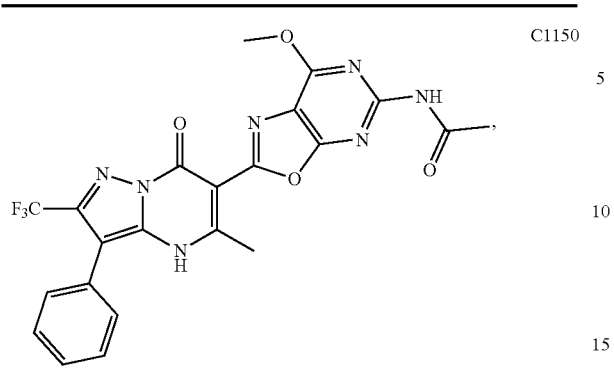 C1150
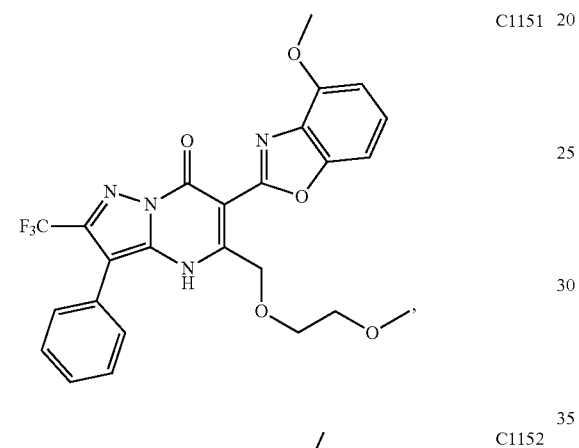 C1151
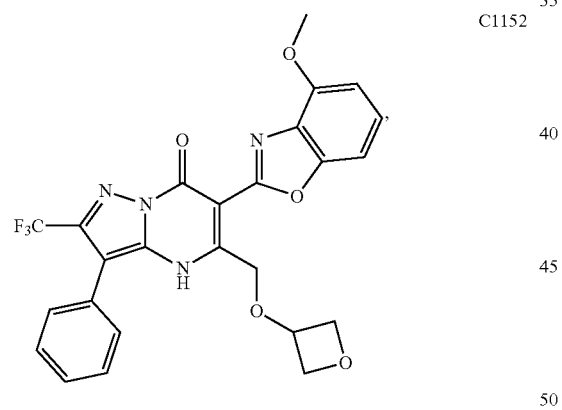 C1152
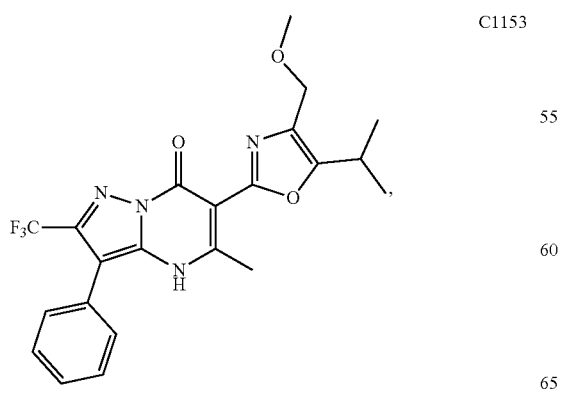 C1153
TABLE 1B-continued
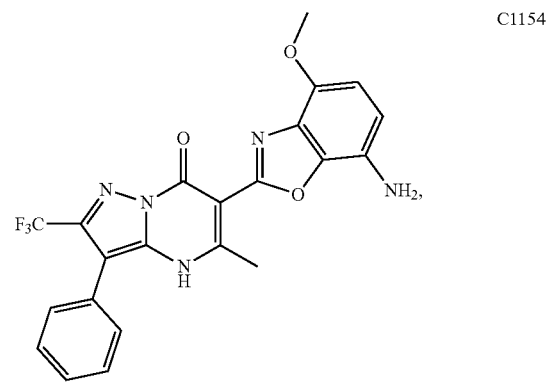 C1154
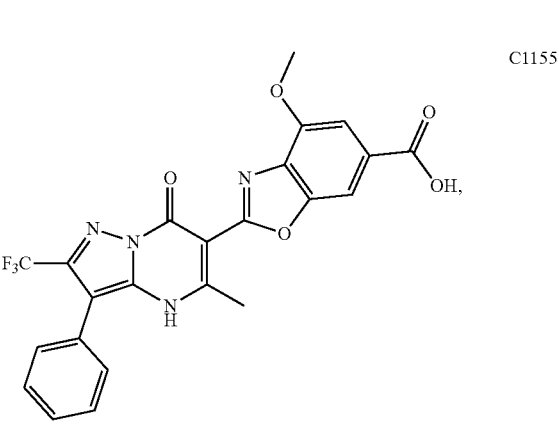 C1155
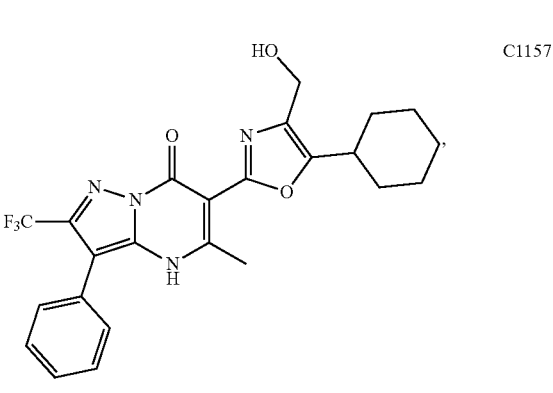 C1156
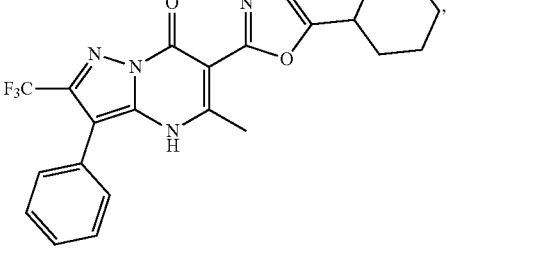 C1157

TABLE 1B-continued
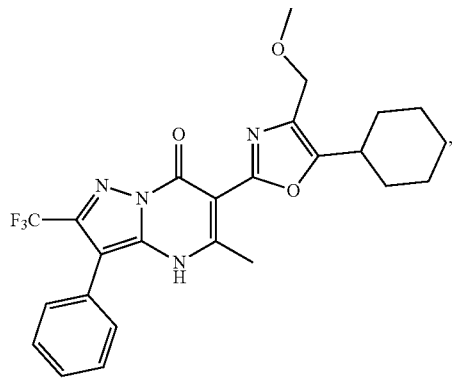 [SMILES: COCc1nc(-c2c(C)[nH]c3c(-c4ccccc4)c(C(F)(F)F)nn3c2=O)oc1C1CCCCC1]
C1158
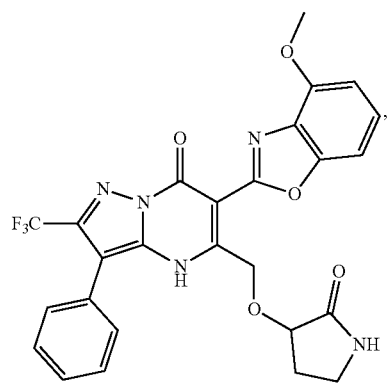 [SMILES: COc1cccc2oc(-c3c(COC4CCNC4=O)[nH]c4c(-c5ccccc5)c(C(F)(F)F)nn4c3=O)nc12]
C1159
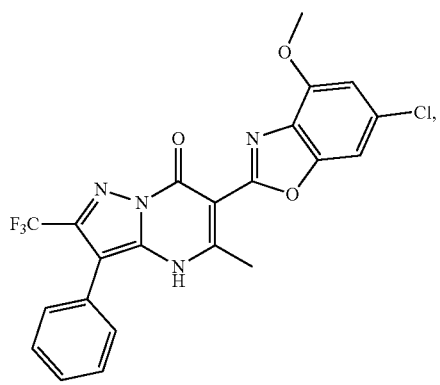 [SMILES: COc1cc(Cl)cc2oc(-c3c(C)[nH]c4c(-c5ccccc5)c(C(F)(F)F)nn4c3=O)nc12]
C1160
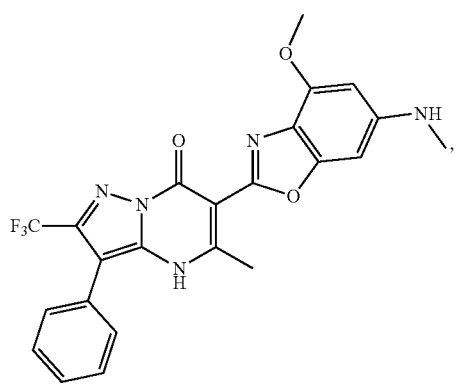 [SMILES: CNc1cc(OC)c2nc(-c3c(C)[nH]c4c(-c5ccccc5)c(C(F)(F)F)nn4c3=O)oc2c1]
C1161
TABLE 1B-continued
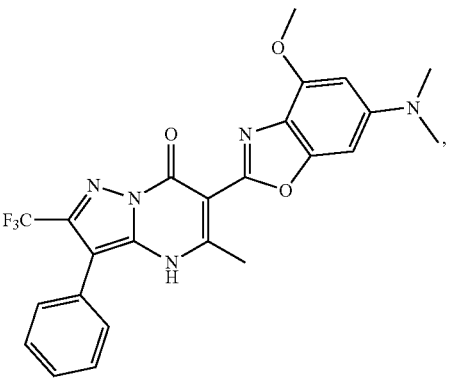 [SMILES: COc1cc(N(C)C)cc2oc(-c3c(C)[nH]c4c(-c5ccccc5)c(C(F)(F)F)nn4c3=O)nc12]
C1162
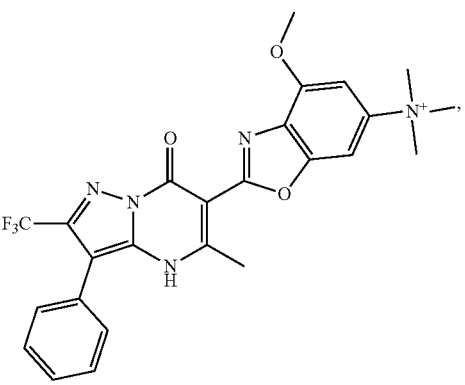 [SMILES: COc1cc([N+](C)(C)C)cc2oc(-c3c(C)[nH]c4c(-c5ccccc5)c(C(F)(F)F)nn4c3=O)nc12]
C1163
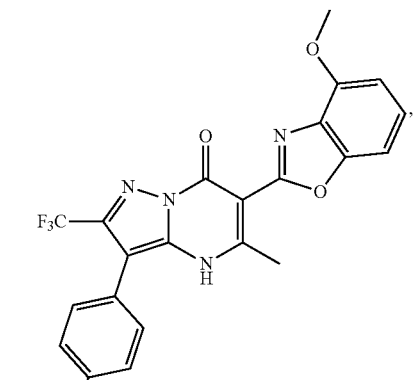
C1164
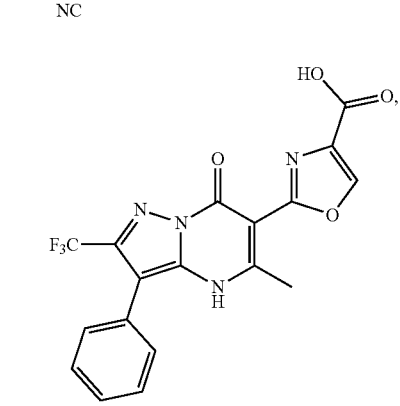
C1165

TABLE 1B-continued
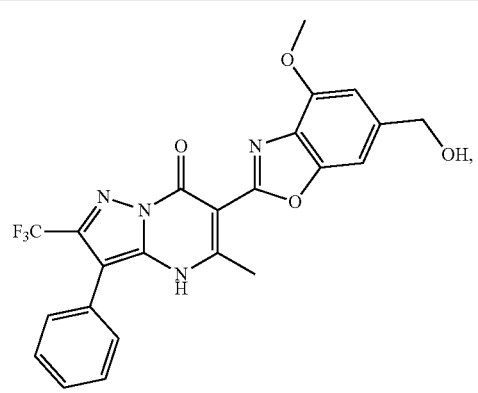 C1166
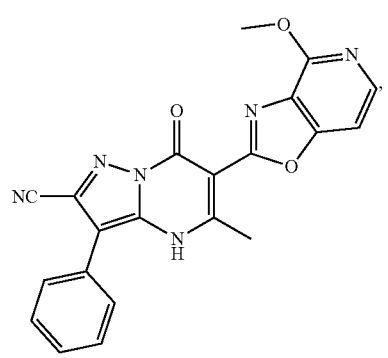 C1167
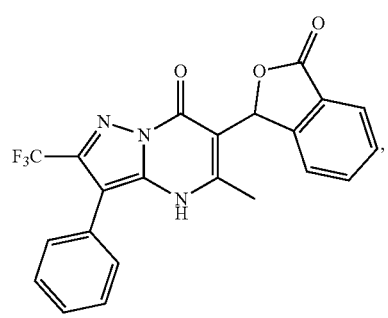 [SMILES: Cc1[nH]c2c(-c3ccccc3)c(C(F)(F)F)nn2c(=O)c1C1OC(=O)c2ccccc21] C1168
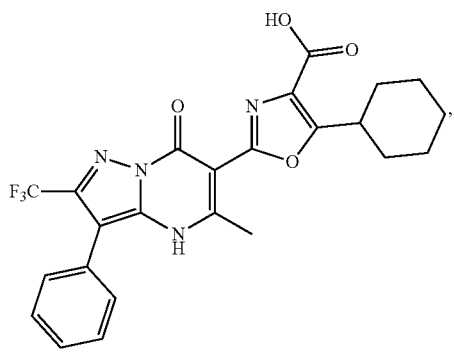 [SMILES: Cc1[nH]c2c(-c3ccccc3)c(C(F)(F)F)nn2c(=O)c1-c1nc(C(=O)O)c(C2CCCCC2)o1] C1169
TABLE 1B-continued
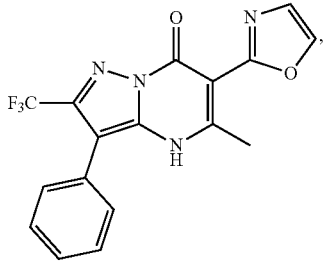 [SMILES: Cc1[nH]c2c(-c3ccccc3)c(C(F)(F)F)nn2c(=O)c1-c1ncco1] C1170
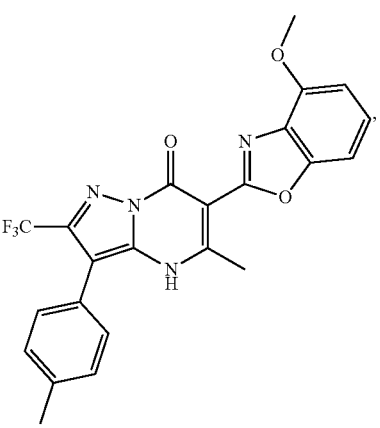 [SMILES: COc1cccc2oc(-c3c(C)[nH]c4c(-c5ccc(C)cc5)c(C(F)(F)F)nn4c3=O)nc12] C1171
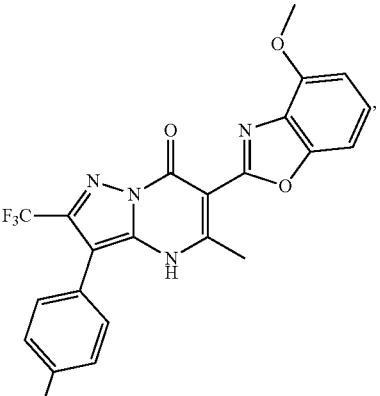 C1172
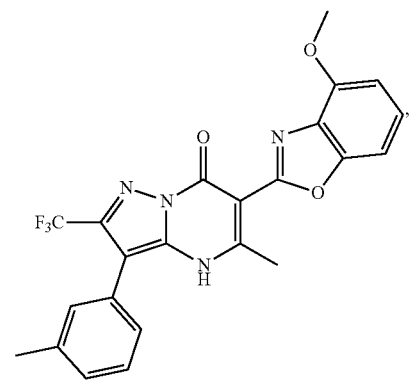 [SMILES: COc1cccc2oc(-c3c(C)[nH]c4c(-c5cccc(C)c5)c(C(F)(F)F)nn4c3=O)nc12] C1173

TABLE 1B-continued
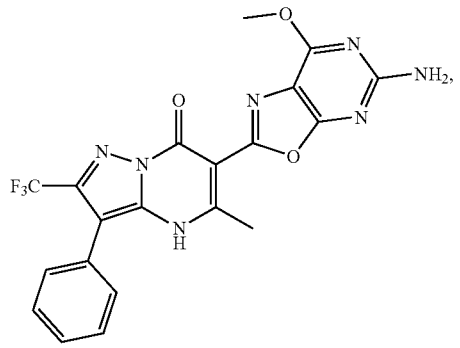
C1174
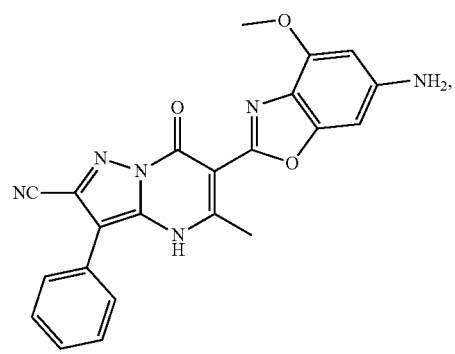 [SMILES: COc1cc(N)cc2oc(-c3c(C)[nH]c4c(-c5ccccc5)c(C#N)nn4c3=O)nc12]
C1175
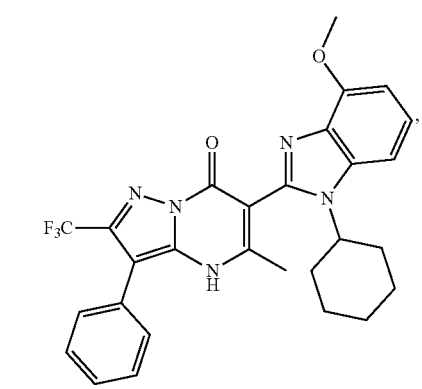 [SMILES: COc1cccc2c1nc(-c1c(C)[nH]c3c(-c4ccccc4)c(C(F)(F)F)nn3c1=O)n2C1CCCCC1]
C1176
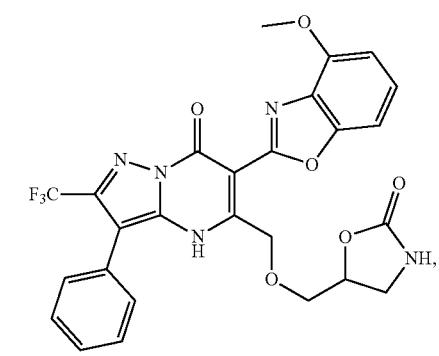 [SMILES: COc1cccc2oc(-c3c(COCC4CNC(=O)O4)[nH]c4c(-c5ccccc5)c(C(F)(F)F)nn4c3=O)nc12]
C1177
TABLE 1B-continued
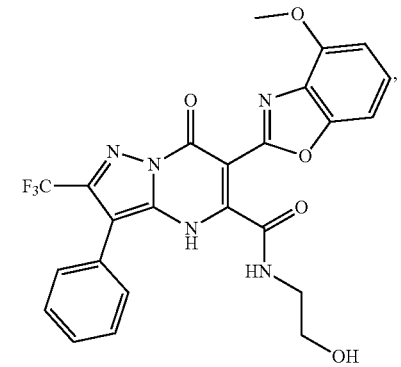 [SMILES: COc1cccc2oc(-c3c(C(=O)NCCO)[nH]c4c(-c5ccccc5)c(C(F)(F)F)nn4c3=O)nc12]
C1178
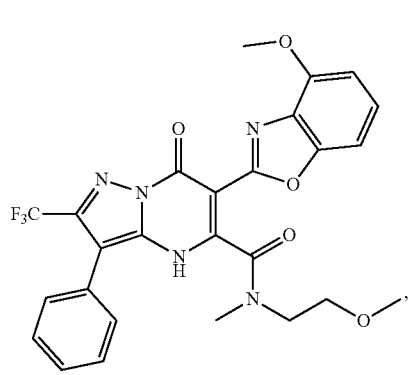 [SMILES: COCCN(C)C(=O)c1[nH]c2c(-c3ccccc3)c(C(F)(F)F)nn2c(=O)c1-c1nc2c(OC)cccc2o1]
C1179
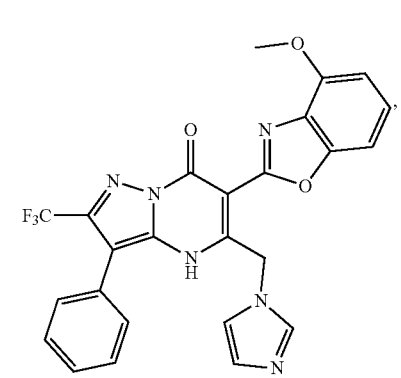 [SMILES: COc1cccc2oc(-c3c(Cn4ccnc4)[nH]c4c(-c5ccccc5)c(C(F)(F)F)nn4c3=O)nc12]
C1180
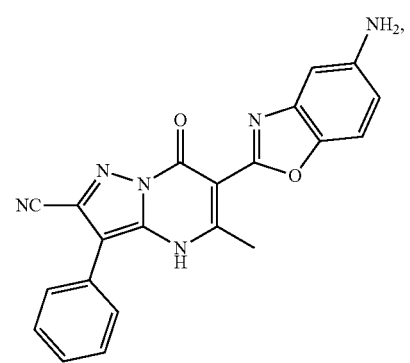 [SMILES: Cc1[nH]c2c(-c3ccccc3)c(C#N)nn2c(=O)c1-c1nc2cc(N)ccc2o1]
C1181

TABLE 1B-continued
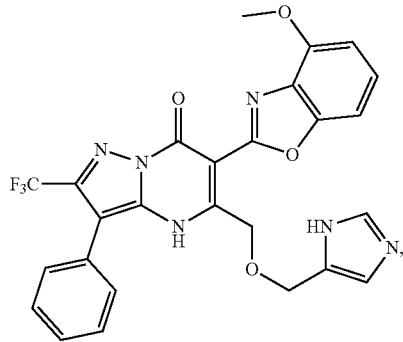 [SMILES: COc1cccc2oc(-c3c(COCc4cnc[nH]4)[nH]c4c(-c5ccccc5)c(C(F)(F)F)nn4c3=O)nc12]
C1182
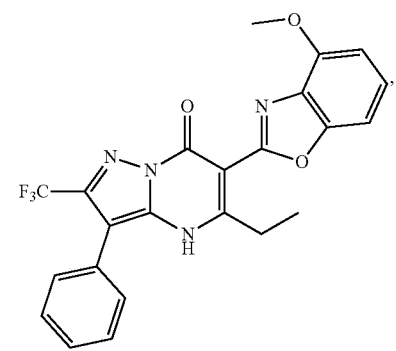 [SMILES: CCc1[nH]c2c(-c3ccccc3)c(C(F)(F)F)nn2c(=O)c1-c1nc2c(OC)cccc2o1]
C1183
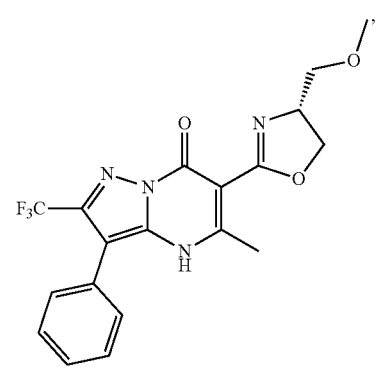 [SMILES: COC[C@@H]1COC(c2c(C)[nH]c3c(-c4ccccc4)c(C(F)(F)F)nn3c2=O)=N1]
C1184
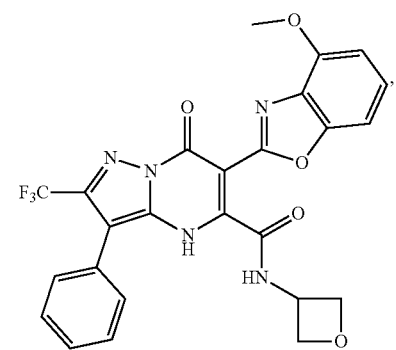 [SMILES: COc1cccc2oc(-c3c(C(=O)NC4COC4)[nH]c4c(-c5ccccc5)c(C(F)(F)F)nn4c3=O)nc12]
C1185
TABLE 1B-continued
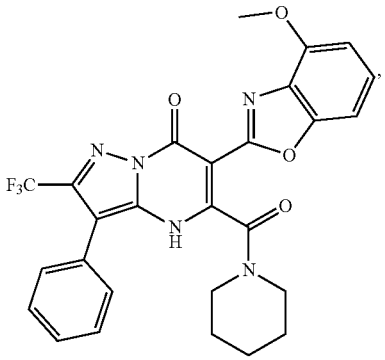 [SMILES: COc1cccc2oc(-c3c(C(=O)N4CCCCC4)[nH]c4c(-c5ccccc5)c(C(F)(F)F)nn4c3=O)nc12]
C1186
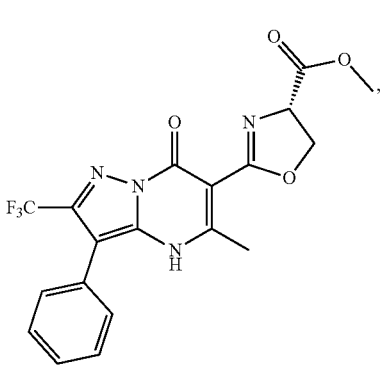 [SMILES: COC(=O)[C@@H]1COC(c2c(C)[nH]c3c(-c4ccccc4)c(C(F)(F)F)nn3c2=O)=N1]
C1187
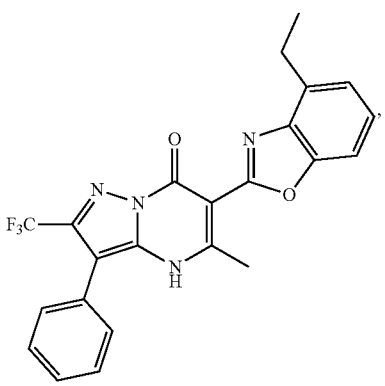
C1188
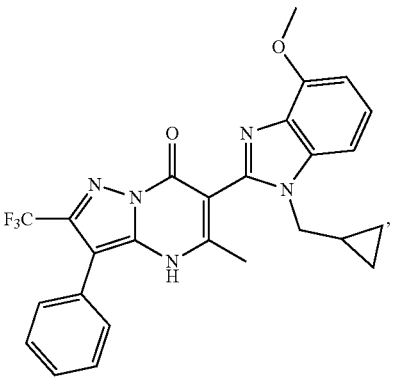 [SMILES: COc1cccc2c1nc(-c1c(C)[nH]c3c(-c4ccccc4)c(C(F)(F)F)nn3c1=O)n2CC1CC1]
C1189

TABLE 1B-continued
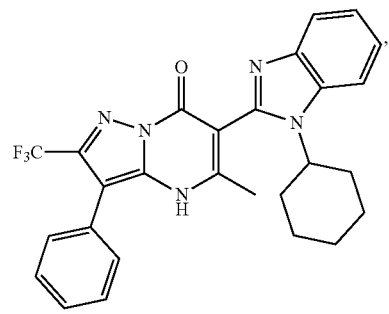 [SMILES: Cc1[nH]c2c(-c3ccccc3)c(C(F)(F)F)nn2c(=O)c1-c1nc2ccccc2n1C1CCCCC1] C1190
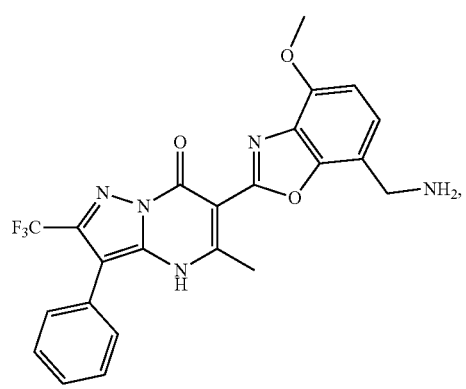 [SMILES: COc1ccc(CN)c2oc(-c3c(C)[nH]c4c(-c5ccccc5)c(C(F)(F)F)nn4c3=O)nc12] C1191
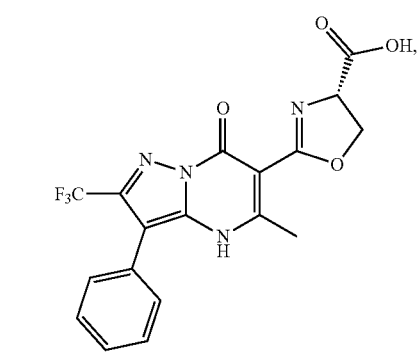 [SMILES: Cc1[nH]c2c(-c3ccccc3)c(C(F)(F)F)nn2c(=O)c1C1=N[C@H](C(=O)O)CO1] C1192
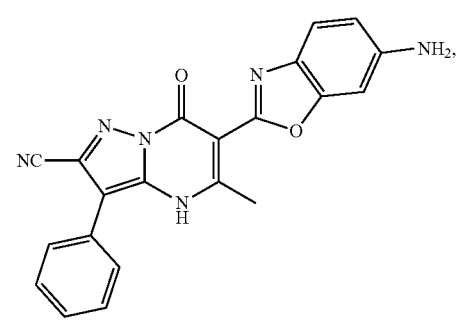 [SMILES: Cc1[nH]c2c(-c3ccccc3)c(C#N)nn2c(=O)c1-c1nc2ccc(N)cc2o1] C1193
TABLE 1B-continued
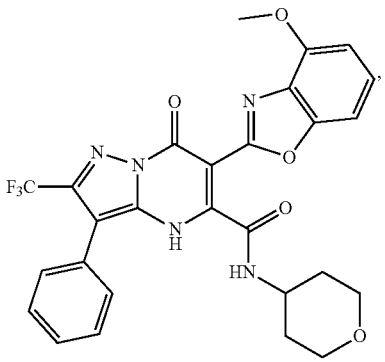 [SMILES: COc1cccc2oc(-c3c(C(=O)NC4CCOCC4)[nH]c4c(-c5ccccc5)c(C(F)(F)F)nn4c3=O)nc12] C1194
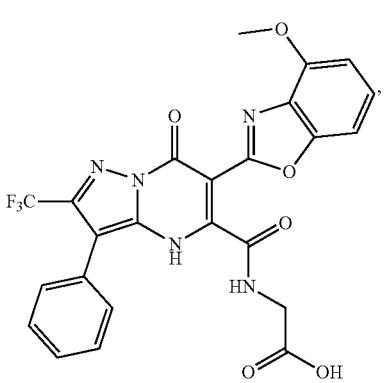 [SMILES: COc1cccc2oc(-c3c(C(=O)NCC(=O)O)[nH]c4c(-c5ccccc5)c(C(F)(F)F)nn4c3=O)nc12] C1195
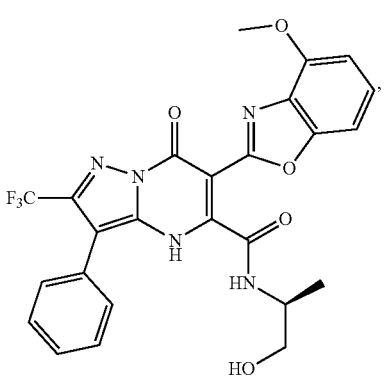 [SMILES: COc1cccc2oc(-c3c(C(=O)N[C@@H](C)CO)[nH]c4c(-c5ccccc5)c(C(F)(F)F)nn4c3=O)nc12] C1196
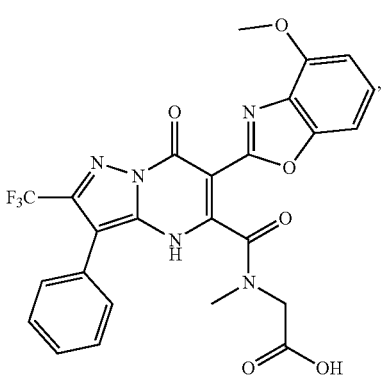 [SMILES: COc1cccc2oc(-c3c(C(=O)N(C)CC(=O)O)[nH]c4c(-c5ccccc5)c(C(F)(F)F)nn4c3=O)nc12] C1197

TABLE 1B-continued
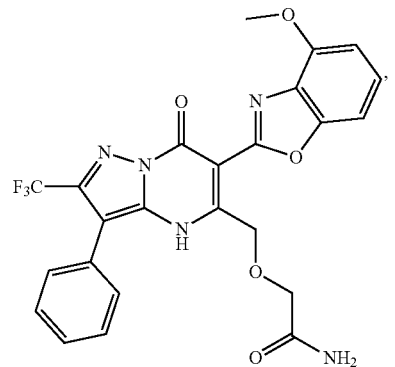 [SMILES: COc1cccc2oc(-c3c(COCC(N)=O)[nH]c4c(-c5ccccc5)c(C(F)(F)F)nn4c3=O)nc12]
C1198
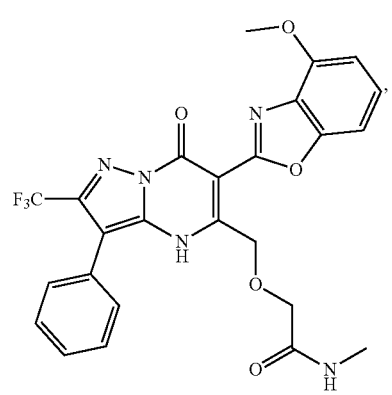 [SMILES: CNC(=O)COCc1[nH]c2c(-c3ccccc3)c(C(F)(F)F)nn2c(=O)c1-c1nc2c(OC)cccc2o1]
C1199
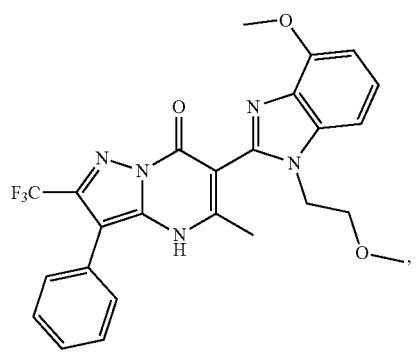 [SMILES: COCCn1c(-c2c(C)[nH]c3c(-c4ccccc4)c(C(F)(F)F)nn3c2=O)nc2c(OC)cccc21]
C1200
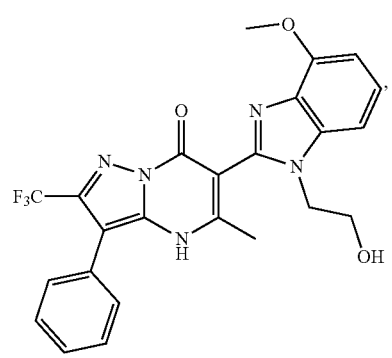 [SMILES: COc1cccc2c1nc(-c1c(C)[nH]c3c(-c4ccccc4)c(C(F)(F)F)nn3c1=O)n2CCO]
C1201
TABLE 1B-continued
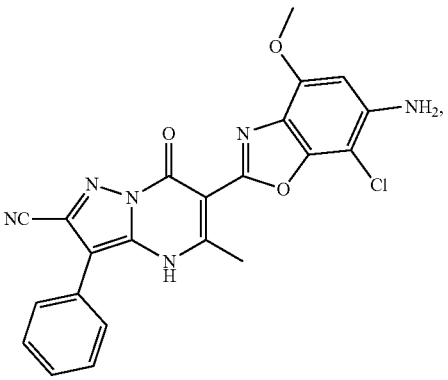 [SMILES: COc1cc(N)c(Cl)c2oc(-c3c(C)[nH]c4c(-c5ccccc5)c(C#N)nn4c3=O)nc12]
1202
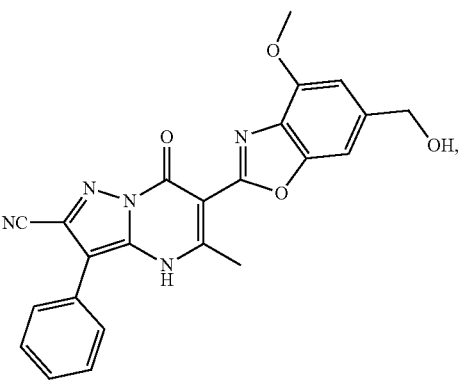 [SMILES: COc1cc(CO)cc2oc(-c3c(C)[nH]c4c(-c5ccccc5)c(C#N)nn4c3=O)nc12]
C1203
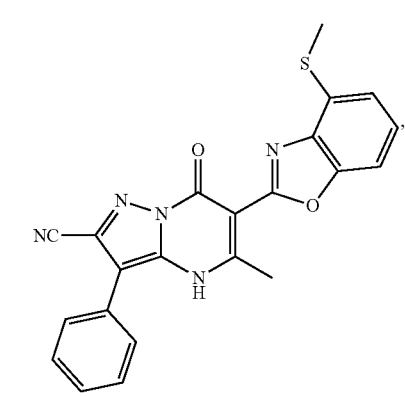 [SMILES: CSc1cccc2oc(-c3c(C)[nH]c4c(-c5ccccc5)c(C#N)nn4c3=O)nc12]
C1204
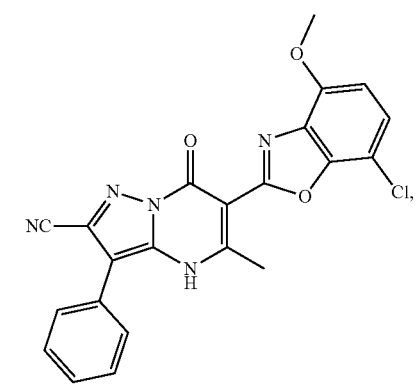 [SMILES: COc1ccc(Cl)c2oc(-c3c(C)[nH]c4c(-c5ccccc5)c(C#N)nn4c3=O)nc12]
C1205

TABLE 1B-continued
C1206 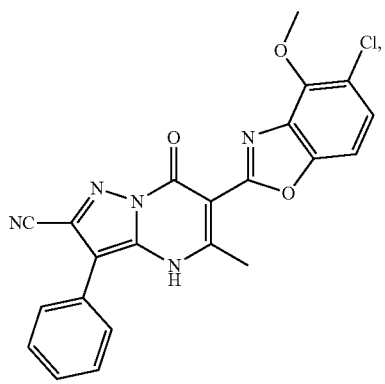 [SMILES: COc1c(Cl)ccc2oc(-c3c(C)[nH]c4c(-c5ccccc5)c(C#N)nn4c3=O)nc12]
C1207 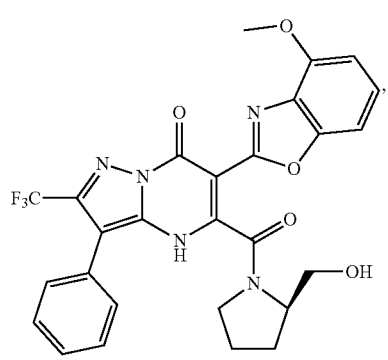 [SMILES: COc1cccc2oc(-c3c(C(=O)N4CCC[C@@H]4CO)[nH]c4c(-c5ccccc5)c(C(F)(F)F)nn4c3=O)nc12]
C1208 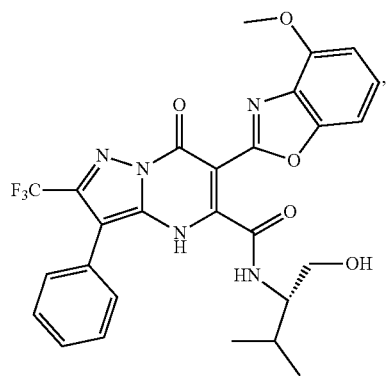 [SMILES: COc1cccc2oc(-c3c(C(=O)N[C@H](CO)C(C)C)[nH]c4c(-c5ccccc5)c(C(F)(F)F)nn4c3=O)nc12]
C1209 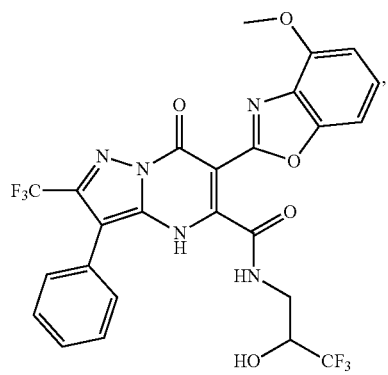 [SMILES: COc1cccc2oc(-c3c(C(=O)NCC(O)C(F)(F)F)[nH]c4c(-c5ccccc5)c(C(F)(F)F)nn4c3=O)nc12]
TABLE 1B-continued
C1210 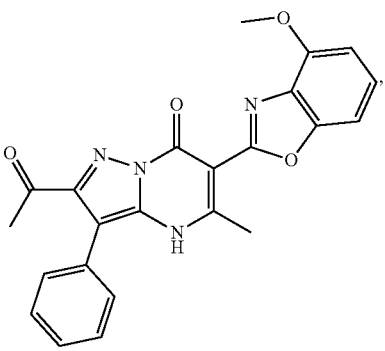 [SMILES: COc1cccc2oc(-c3c(C)[nH]c4c(-c5ccccc5)c(C(C)=O)nn4c3=O)nc12]
C1211 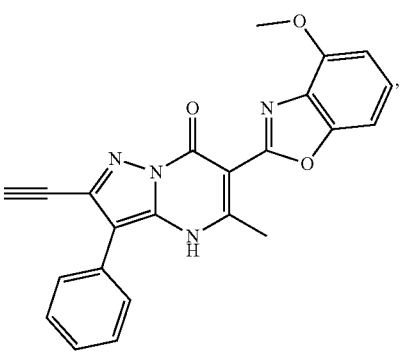 [SMILES: C#Cc1nn2c(=O)c(-c3nc4c(OC)cccc4o3)c(C)[nH]c2c1-c1ccccc1]
C1212 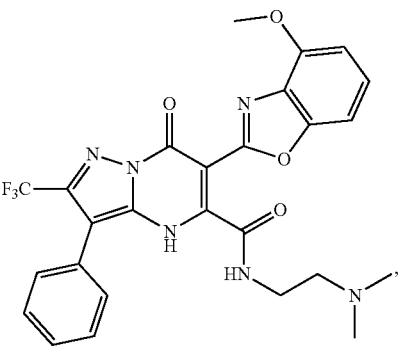
C1213 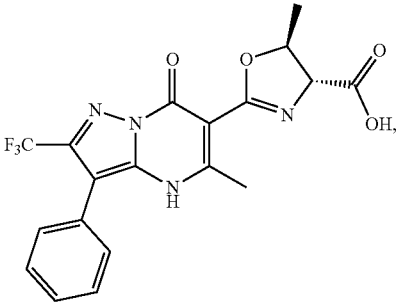 [SMILES: Cc1[nH]c2c(-c3ccccc3)c(C(F)(F)F)nn2c(=O)c1C1=N[C@@H](C(=O)O)[C@H](C)O1]

TABLE 1B-continued
C1214
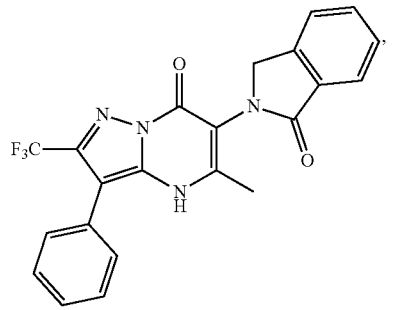 [SMILES: Cc1[nH]c2c(-c3ccccc3)c(C(F)(F)F)nn2c(=O)c1N1Cc2ccccc2C1=O]
C1215
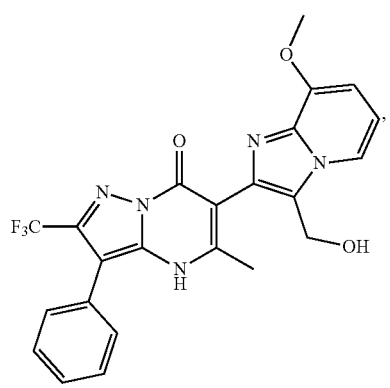 [SMILES: COc1cccn2c(CO)c(-c3c(C)[nH]c4c(-c5ccccc5)c(C(F)(F)F)nn4c3=O)nc12]
C1216
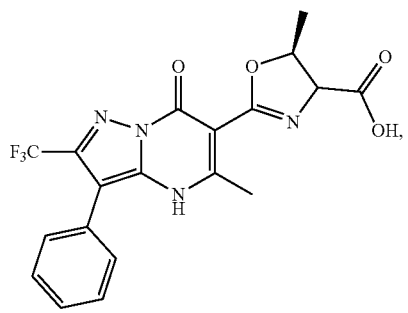 [SMILES: Cc1[nH]c2c(-c3ccccc3)c(C(F)(F)F)nn2c(=O)c1C1=NC(C(=O)O)[C@H](C)O1]
C1217
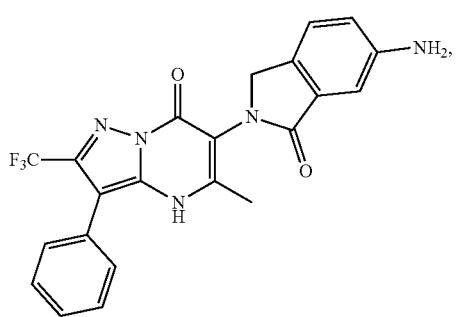 [SMILES: Cc1[nH]c2c(-c3ccccc3)c(C(F)(F)F)nn2c(=O)c1N1Cc2ccc(N)cc2C1=O]
TABLE 1B-continued
C1218
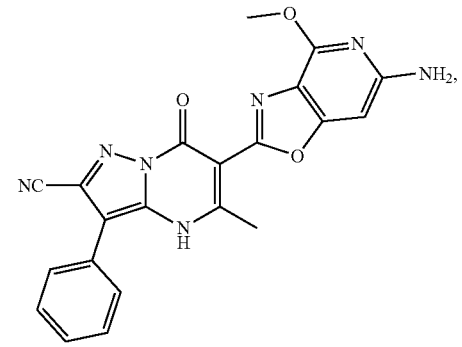 [SMILES: COc1nc(N)cc2oc(-c3c(C)[nH]c4c(-c5ccccc5)c(C#N)nn4c3=O)nc12]
C1219
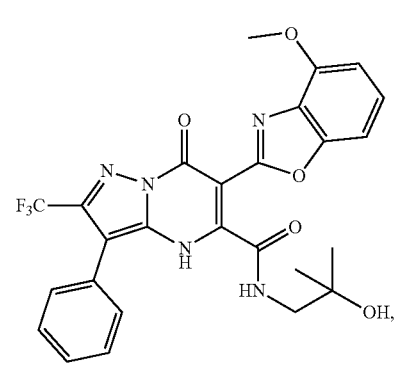 [SMILES: COc1cccc2oc(-c3c(C(=O)NCC(C)(C)O)[nH]c4c(-c5ccccc5)c(C(F)(F)F)nn4c3=O)nc12]
C1220
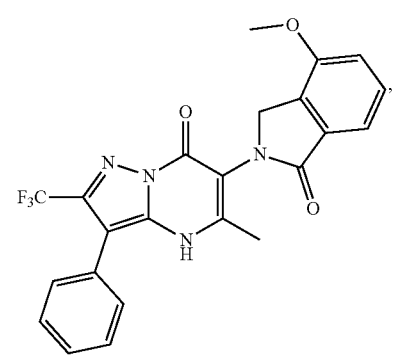 [SMILES: COc1cccc2c1CN(c1c(C)[nH]c3c(-c4ccccc4)c(C(F)(F)F)nn3c1=O)C2=O]
C1221
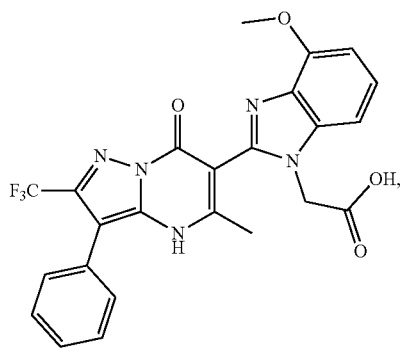 [SMILES: COc1cccc2c1nc(-c1c(C)[nH]c3c(-c4ccccc4)c(C(F)(F)F)nn3c1=O)n2CC(=O)O]

TABLE 1B-continued
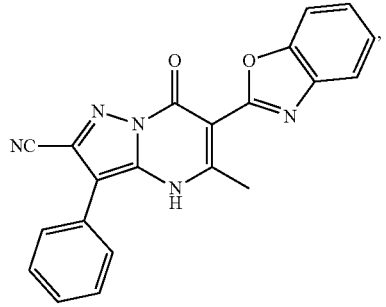 [SMILES: Cc1[nH]c2c(-c3ccccc3)c(C#N)nn2c(=O)c1-c1nc2ccccc2o1]
C1222
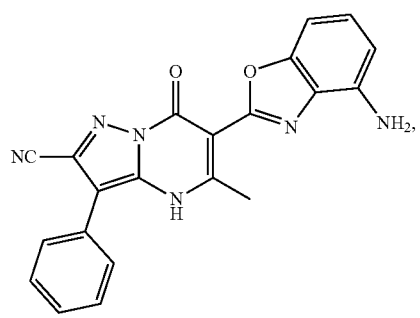 [SMILES: Cc1[nH]c2c(-c3ccccc3)c(C#N)nn2c(=O)c1-c1nc2c(N)cccc2o1]
C1223
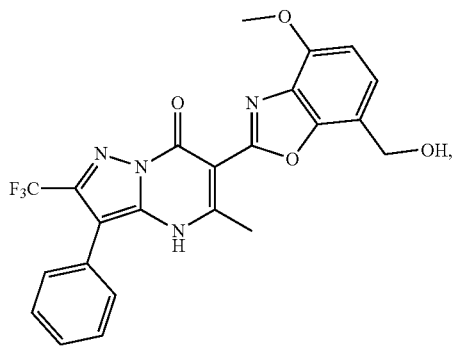 [SMILES: COc1ccc(CO)c2oc(-c3c(C)[nH]c4c(-c5ccccc5)c(C(F)(F)F)nn4c3=O)nc12]
C1224
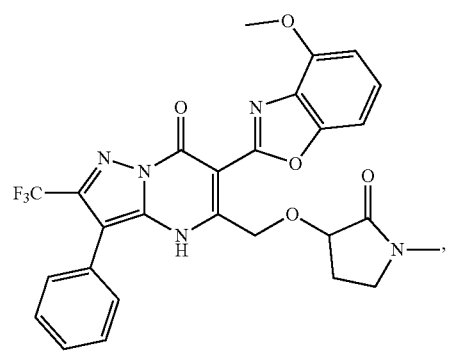 [SMILES: COc1cccc2oc(-c3c(COC4CCN(C)C4=O)[nH]c4c(-c5ccccc5)c(C(F)(F)F)nn4c3=O)nc12]
C1225
TABLE 1B-continued
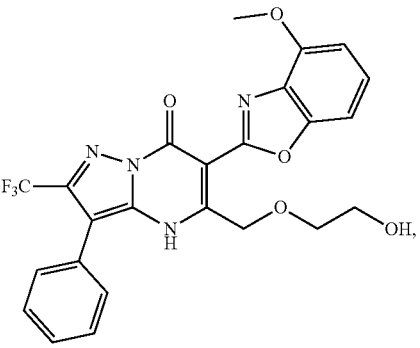 [SMILES: COc1cccc2oc(-c3c(COCCO)[nH]c4c(-c5ccccc5)c(C(F)(F)F)nn4c3=O)nc12]
C1226
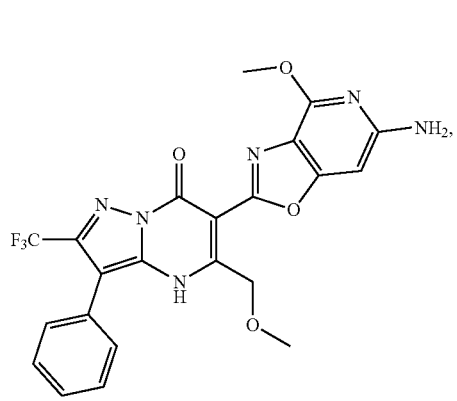 [SMILES: COCc1[nH]c2c(-c3ccccc3)c(C(F)(F)F)nn2c(=O)c1-c1nc2c(OC)nc(N)cc2o1]
C1227
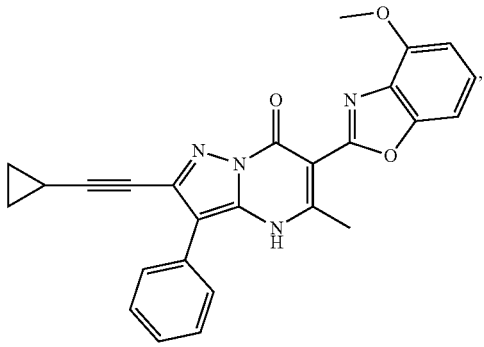 [SMILES: COc1cccc2oc(-c3c(C)[nH]c4c(-c5ccccc5)c(C#CC5CC5)nn4c3=O)nc12]
C1228
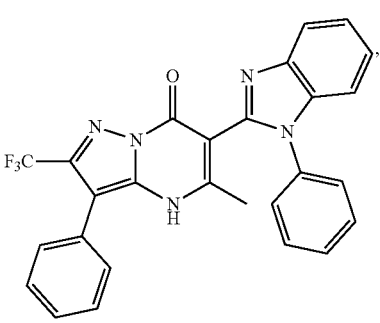
C1229

TABLE 1B-continued
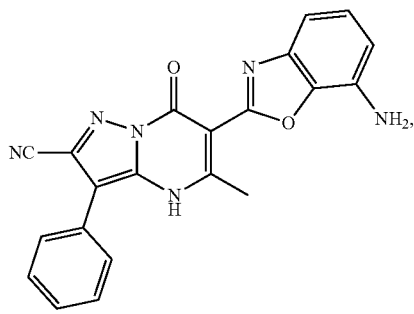 [SMILES: Cc1[nH]c2c(-c3ccccc3)c(C#N)nn2c(=O)c1-c1nc2cccc(N)c2o1]
C1230
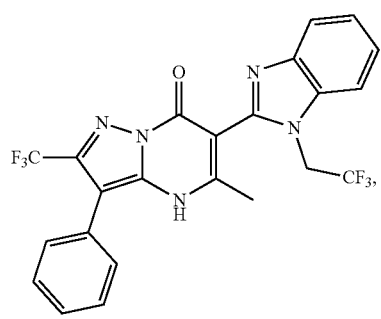 [SMILES: Cc1[nH]c2c(-c3ccccc3)c(C(F)(F)F)nn2c(=O)c1-c1nc2ccccc2n1CC(F)(F)F]
C1231
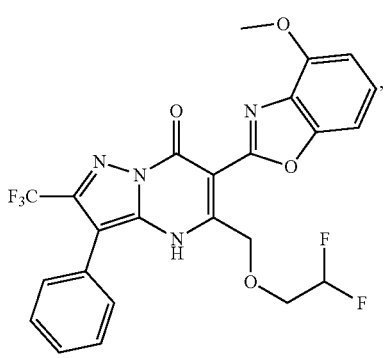 [SMILES: COc1cccc2oc(-c3c(COCC(F)F)[nH]c4c(-c5ccccc5)c(C(F)(F)F)nn4c3=O)nc12]
C1232
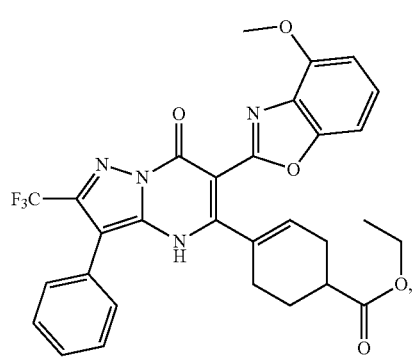 [SMILES: CCOC(=O)C1CC=C(c2[nH]c3c(-c4ccccc4)c(C(F)(F)F)nn3c(=O)c2-c2nc3c(OC)cccc3o2)CC1]
C1233
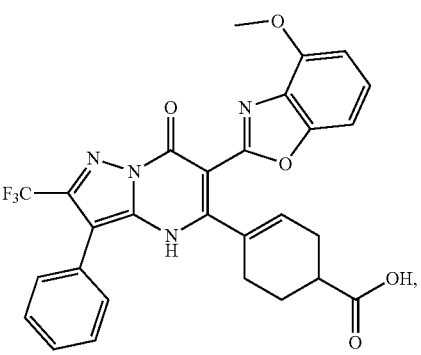 [SMILES: COc1cccc2oc(-c3c(C4=CCC(C(=O)O)CC4)[nH]c4c(-c5ccccc5)c(C(F)(F)F)nn4c3=O)nc12]
C1234
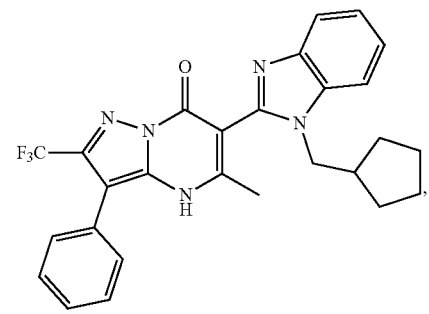 [SMILES: Cc1[nH]c2c(-c3ccccc3)c(C(F)(F)F)nn2c(=O)c1-c1nc2ccccc2n1CC1CCCC1]
C1235
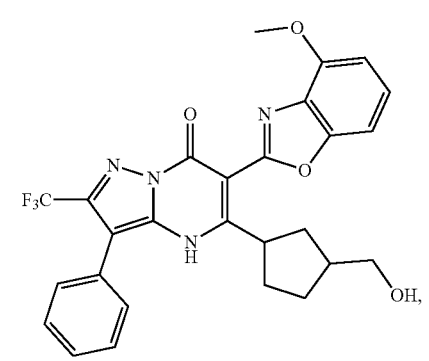 [SMILES: COc1cccc2oc(-c3c(C4CCC(CO)C4)[nH]c4c(-c5ccccc5)c(C(F)(F)F)nn4c3=O)nc12]
C1236
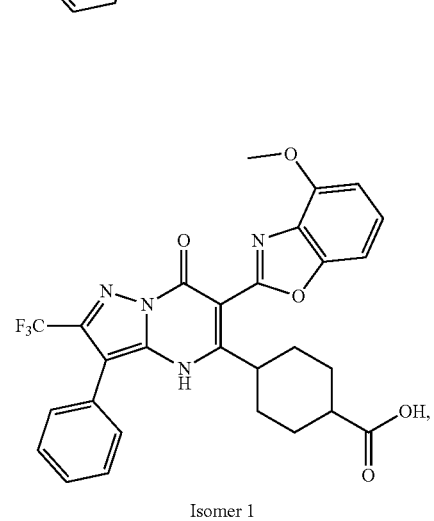
C1237
Isomer 1

TABLE 1B-continued
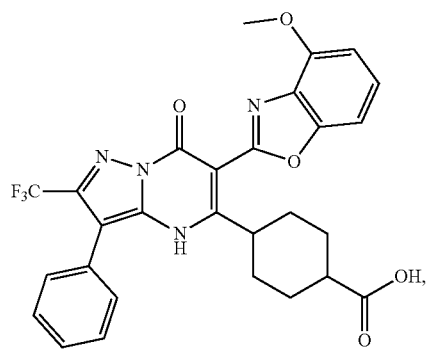
C1238
Isomer 2
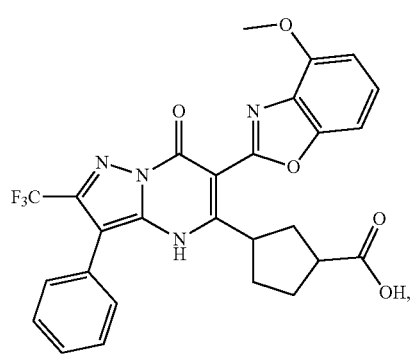 [SMILES: COc1cccc2oc(-c3c(C4CCC(C(=O)O)C4)[nH]c4c(-c5ccccc5)c(C(F)(F)F)nn4c3=O)nc12]
C1239
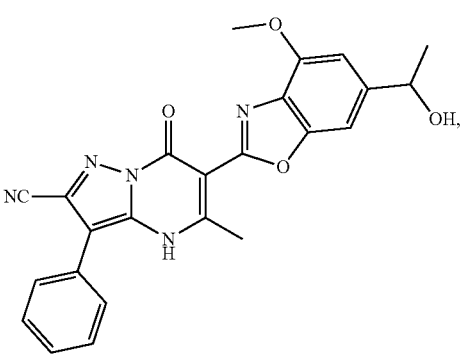 [SMILES: COc1cc(C(C)O)cc2oc(-c3c(C)[nH]c4c(-c5ccccc5)c(C#N)nn4c3=O)nc12]
C1240
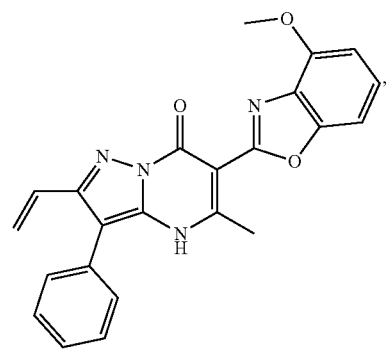 [SMILES: C=Cc1nn2c(=O)c(-c3nc4c(OC)cccc4o3)c(C)[nH]c2c1-c1ccccc1]
C1241
TABLE 1B-continued
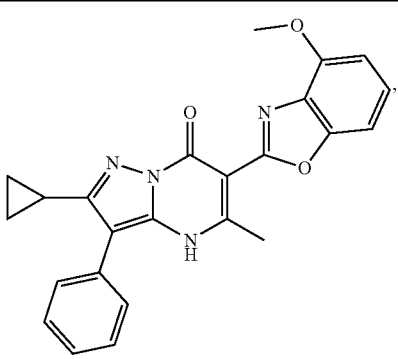
C1242
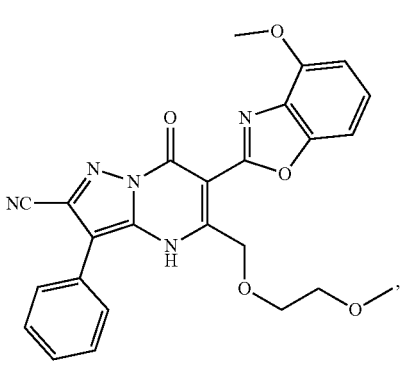 [SMILES: COCCOCc1[nH]c2c(-c3ccccc3)c(C#N)nn2c(=O)c1-c1nc2c(OC)cccc2o1]
C1243
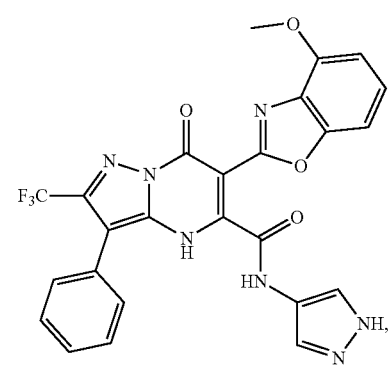 [SMILES: COc1cccc2oc(-c3c(C(=O)Nc4cn[nH]c4)[nH]c4c(-c5ccccc5)c(C(F)(F)F)nn4c3=O)nc12]
C1244
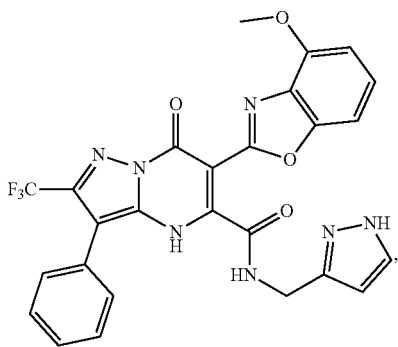 [SMILES: COc1cccc2oc(-c3c(C(=O)NCc4cc[nH]n4)[nH]c4c(-c5ccccc5)c(C(F)(F)F)nn4c3=O)nc12]
C1245

TABLE 1B-continued
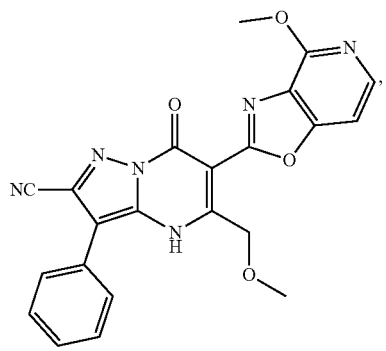 [SMILES: COCc1[nH]c2c(-c3ccccc3)c(C#N)nn2c(=O)c1-c1nc2c(OC)nccc2o1]
C1246
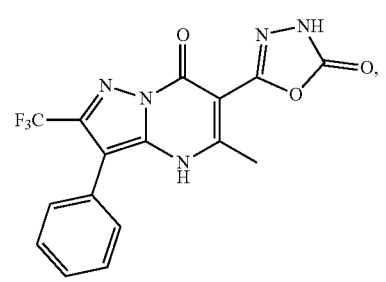 [SMILES: Cc1[nH]c2c(-c3ccccc3)c(C(F)(F)F)nn2c(=O)c1-c1n[nH]c(=O)o1]
C1247
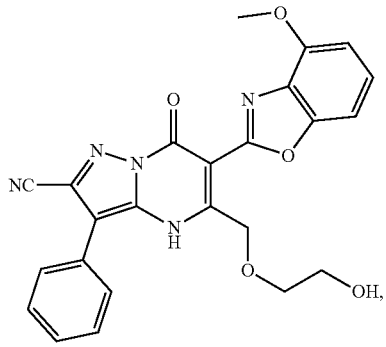 [SMILES: COc1cccc2oc(-c3c(COCCO)[nH]c4c(-c5ccccc5)c(C#N)nn4c3=O)nc12]
C1248
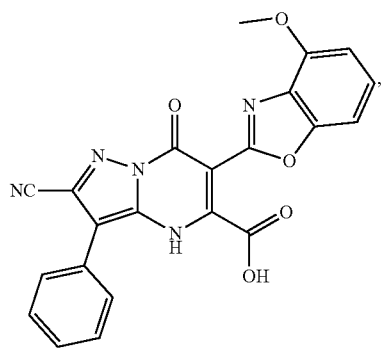 [SMILES: COc1cccc2oc(-c3c(C(=O)O)[nH]c4c(-c5ccccc5)c(C#N)nn4c3=O)nc12]
C1249
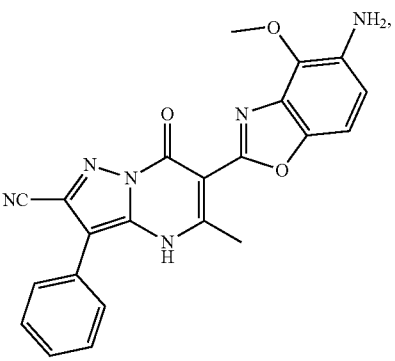 [SMILES: COc1c(N)ccc2oc(-c3c(C)[nH]c4c(-c5ccccc5)c(C#N)nn4c3=O)nc12]
C1250
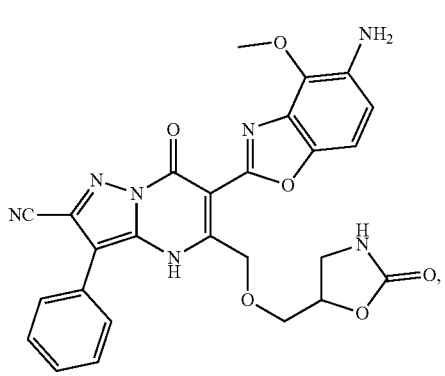 [SMILES: COc1c(N)ccc2oc(-c3c(COCC4CNC(=O)O4)[nH]c4c(-c5ccccc5)c(C#N)nn4c3=O)nc12]
C1251
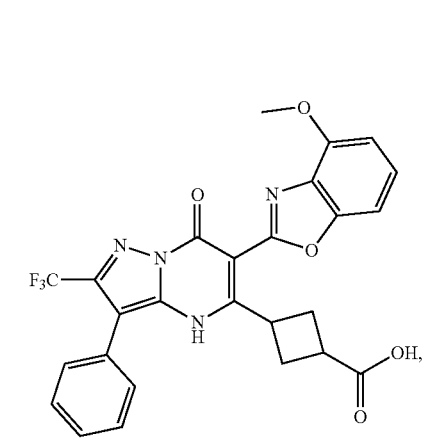 [SMILES: COc1cccc2oc(-c3c(C4CC(C(=O)O)C4)[nH]c4c(-c5ccccc5)c(C(F)(F)F)nn4c3=O)nc12]
C1252
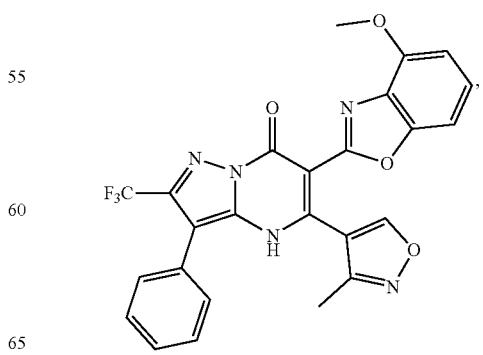
C1253

TABLE 1B-continued
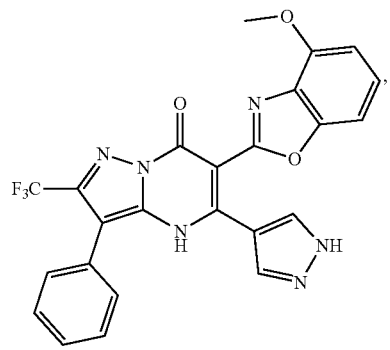 [SMILES: COc1cccc2oc(-c3c(-c4cn[nH]c4)[nH]c4c(-c5ccccc5)c(C(F)(F)F)nn4c3=O)nc12] C1254
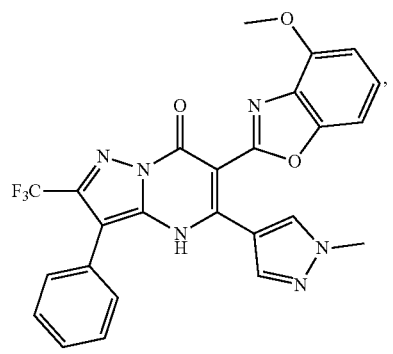 [SMILES: COc1cccc2oc(-c3c(-c4cnn(C)c4)[nH]c4c(-c5ccccc5)c(C(F)(F)F)nn4c3=O)nc12] C1255
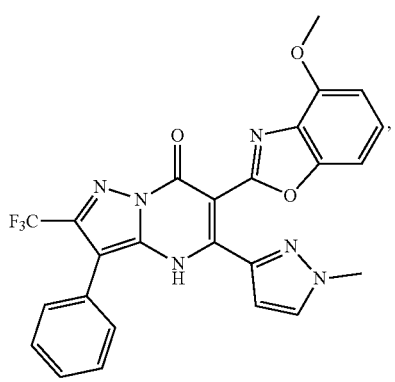 [SMILES: COc1cccc2oc(-c3c(-c4ccn(C)n4)[nH]c4c(-c5ccccc5)c(C(F)(F)F)nn4c3=O)nc12] C1256
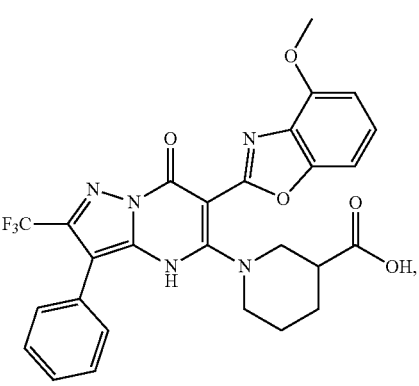 [SMILES: COc1cccc2oc(-c3c(N4CCCC(C(=O)O)C4)[nH]c4c(-c5ccccc5)c(C(F)(F)F)nn4c3=O)nc12] C1257
TABLE 1B-continued
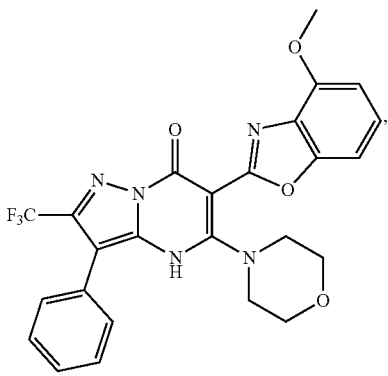 [SMILES: COc1cccc2oc(-c3c(N4CCOCC4)[nH]c4c(-c5ccccc5)c(C(F)(F)F)nn4c3=O)nc12] C1258
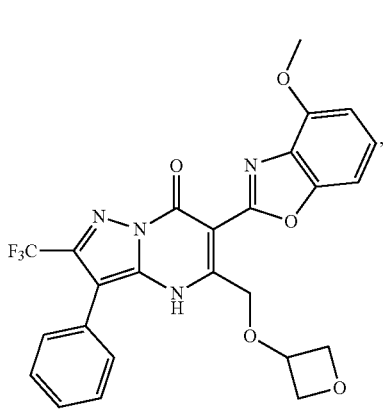 [SMILES: COc1cccc2oc(-c3c(COC4COC4)[nH]c4c(-c5ccccc5)c(C(F)(F)F)nn4c3=O)nc12] C1259
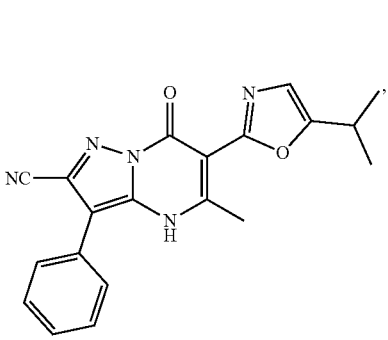 [SMILES: Cc1[nH]c2c(-c3ccccc3)c(C#N)nn2c(=O)c1-c1ncc(C(C)C)o1] C1260
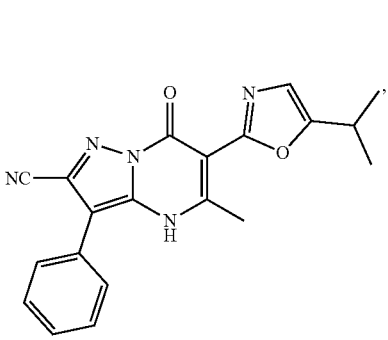 [SMILES: Cc1[nH]c2c(-c3ccccc3)c(C#N)nn2c(=O)c1-c1ncc(C(C)C)o1] C1261

TABLE 1B-continued
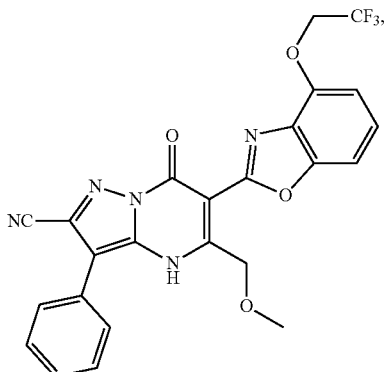 C1262
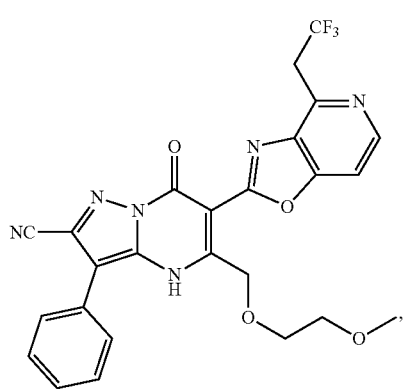 [SMILES: COCCOCc1[nH]c2c(-c3ccccc3)c(C#N)nn2c(=O)c1-c1nc2c(CC(F)(F)F)nccc2o1] C1263
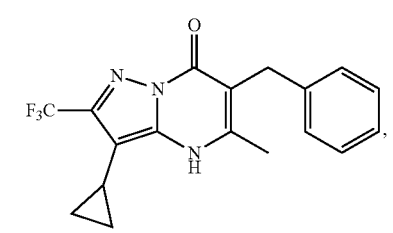 [SMILES: Cc1[nH]c2c(C3CC3)c(C(F)(F)F)nn2c(=O)c1Cc1ccccc1] C1264
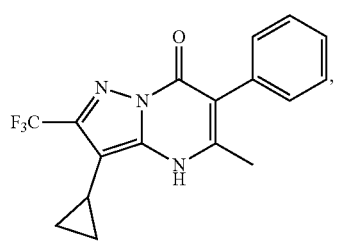 [SMILES: Cc1[nH]c2c(C3CC3)c(C(F)(F)F)nn2c(=O)c1-c1ccccc1] C1265
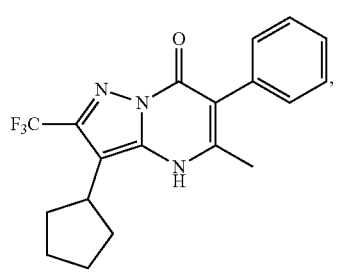 [SMILES: Cc1[nH]c2c(C3CCCC3)c(C(F)(F)F)nn2c(=O)c1-c1ccccc1] C1266
TABLE 1B-continued
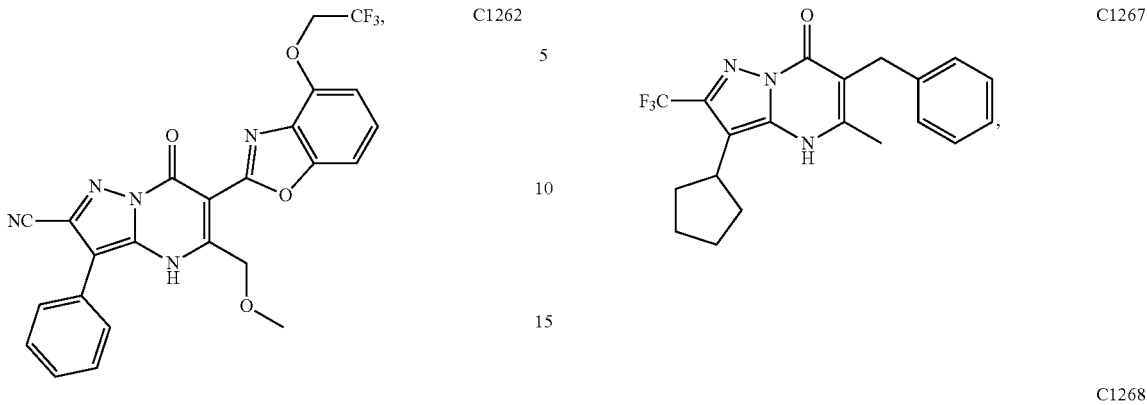 C1267
 C1268
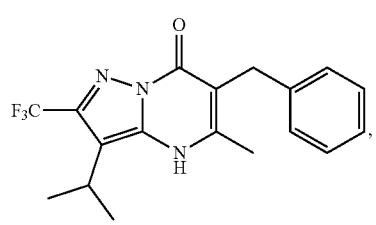 [SMILES: Cc1[nH]c2c(C(C)C)c(C(F)(F)F)nn2c(=O)c1Cc1ccccc1] C1268
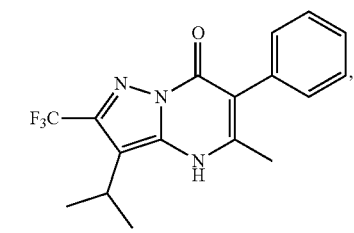 [SMILES: Cc1[nH]c2c(C(C)C)c(C(F)(F)F)nn2c(=O)c1-c1ccccc1] C1269
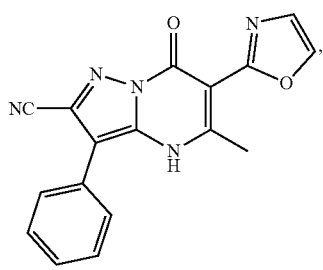 [SMILES: Cc1[nH]c2c(-c3ccccc3)c(C#N)nn2c(=O)c1-c1ncco1] C1270
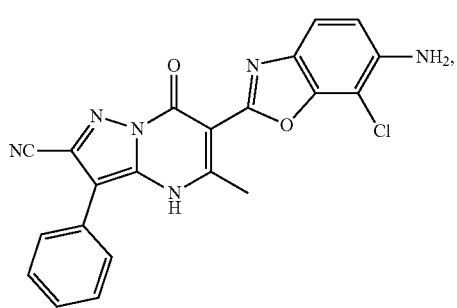 [SMILES: Cc1[nH]c2c(-c3ccccc3)c(C#N)nn2c(=O)c1-c1nc2ccc(N)c(Cl)c2o1] C1271

TABLE 1B-continued
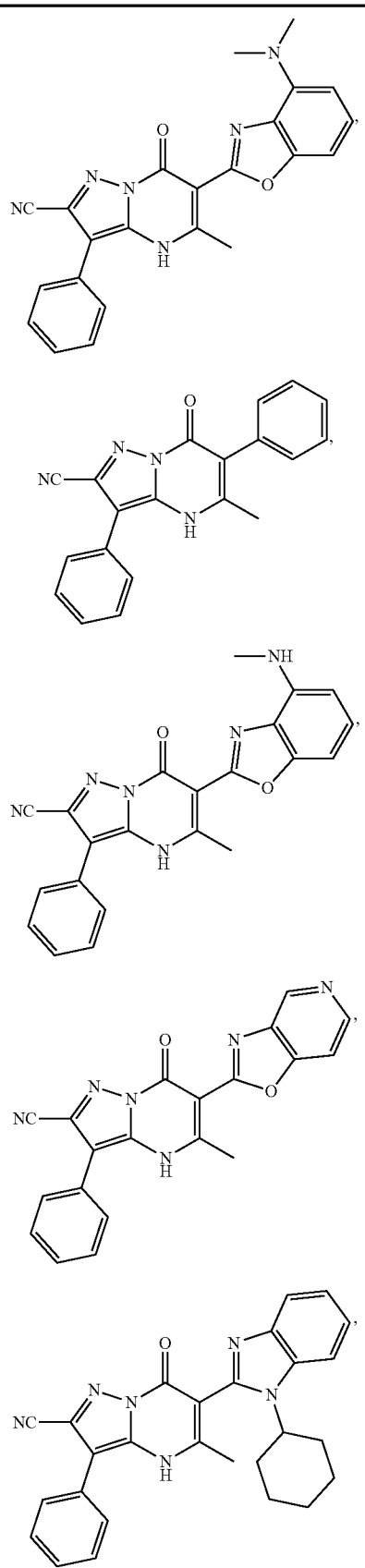
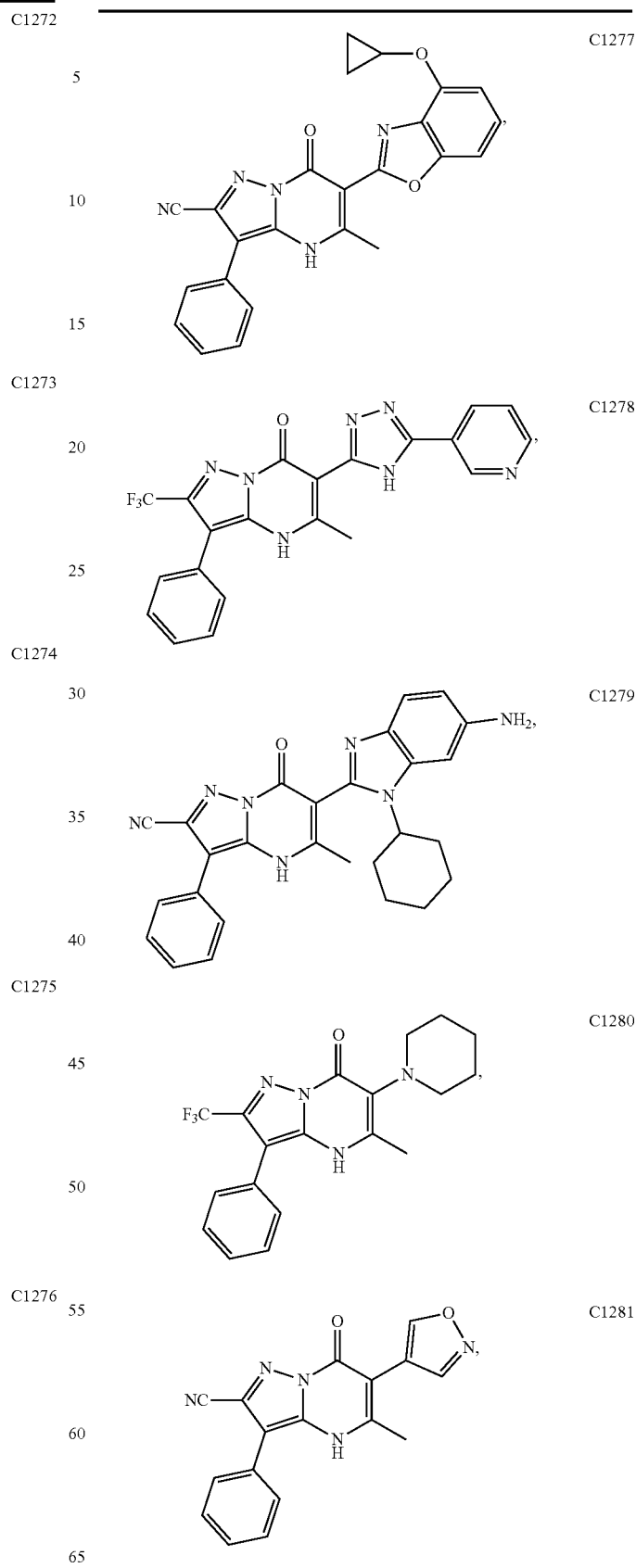

TABLE 1B-continued
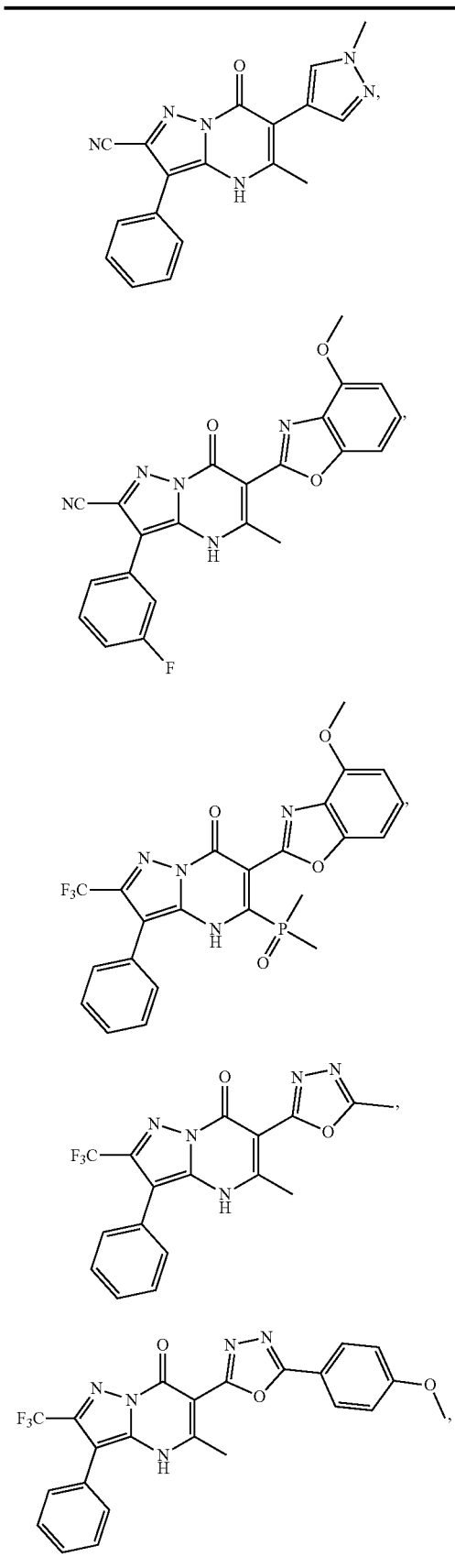
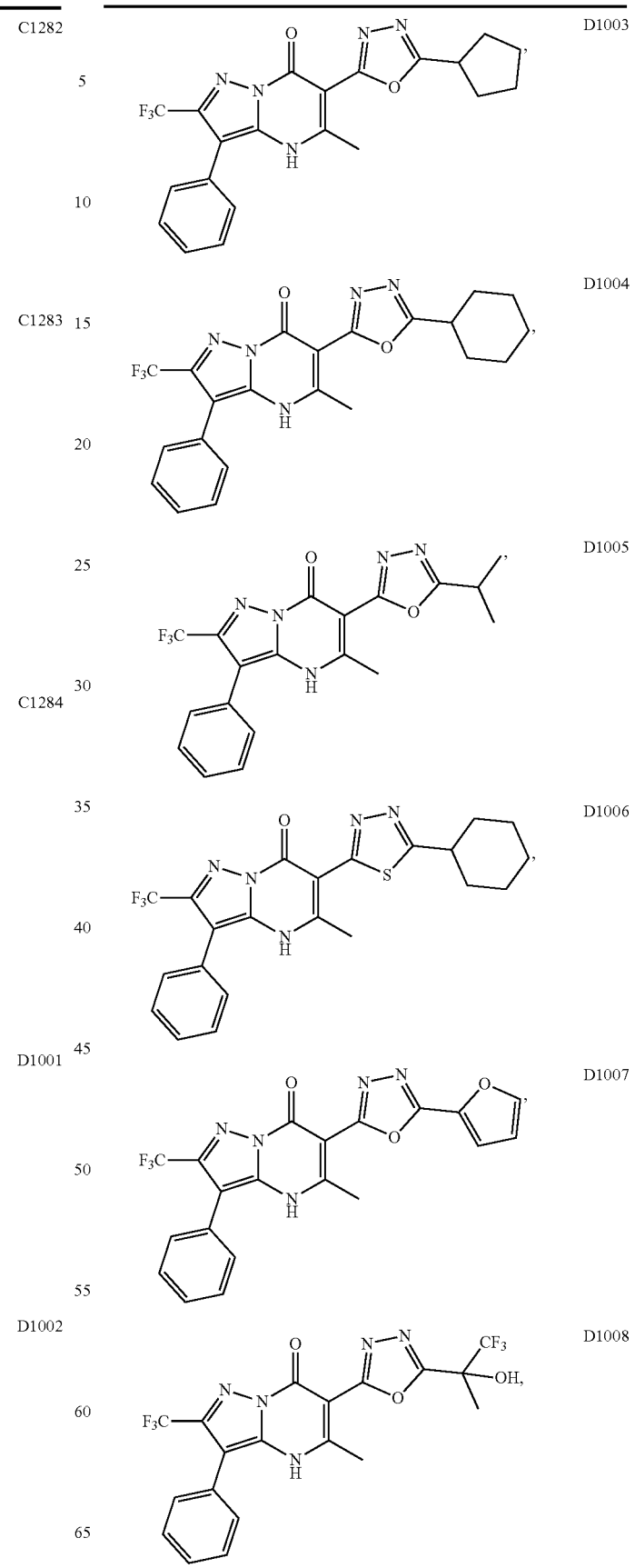

TABLE 1B-continued
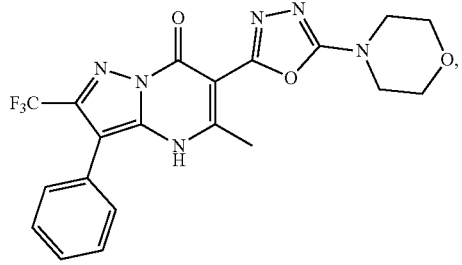 D1009
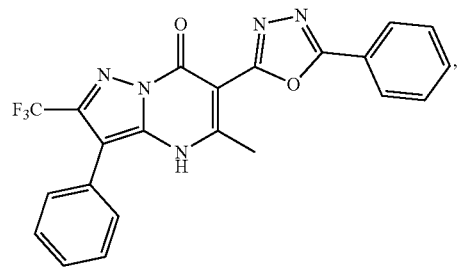 D1011
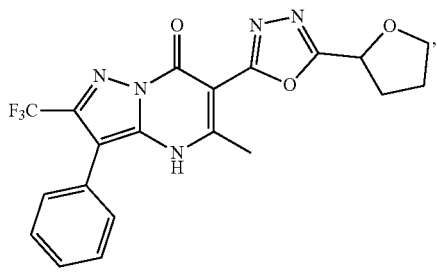 D1012
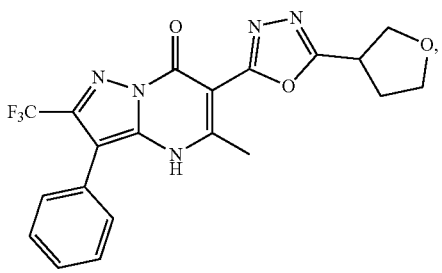 D1013
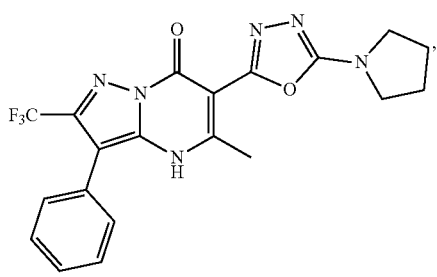 D1014
TABLE 1B-continued
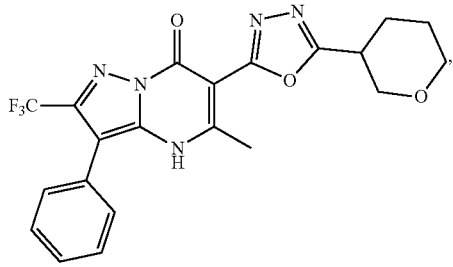 [SMILES: Cc1[nH]c2c(-c3ccccc3)c(C(F)(F)F)nn2c(=O)c1-c1nnc(C2CCCCC2)o1] D1015
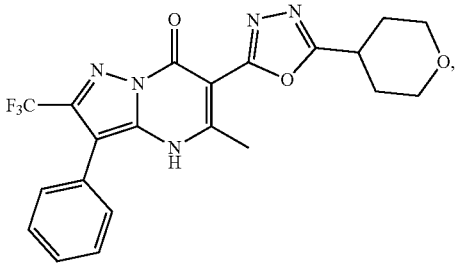 [SMILES: Cc1[nH]c2c(-c3ccccc3)c(C(F)(F)F)nn2c(=O)c1-c1nnc(C2CCOCC2)o1] D1016
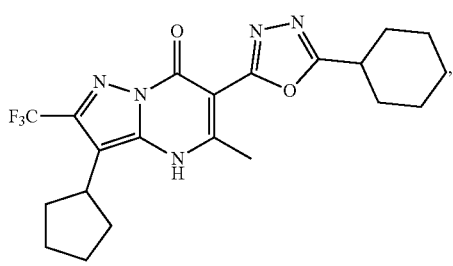 [SMILES: Cc1[nH]c2c(C3CCCC3)c(C(F)(F)F)nn2c(=O)c1-c1nnc(C2CCCCC2)o1] D1017
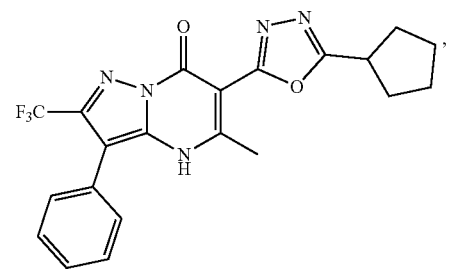 D1018
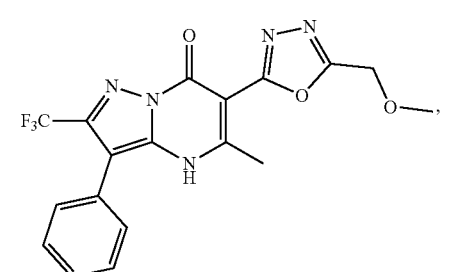 D1019
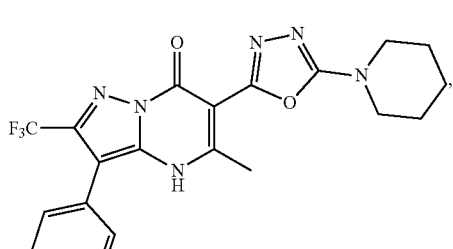 D1020

TABLE 1B-continued
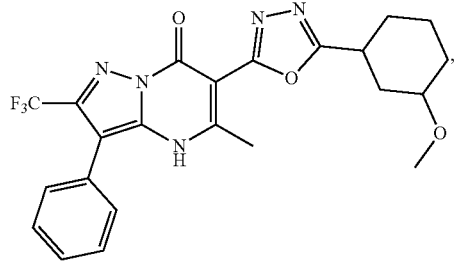 D1021
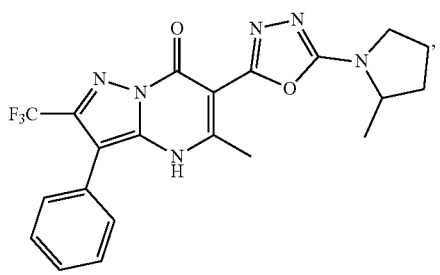 [SMILES: Cc1[nH]c2c(-c3ccccc3)c(C(F)(F)F)nn2c(=O)c1-c1nnc(C2CCCC2)o1] D1022
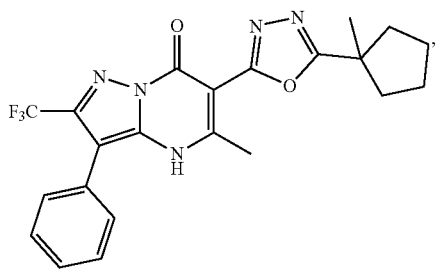 D1023
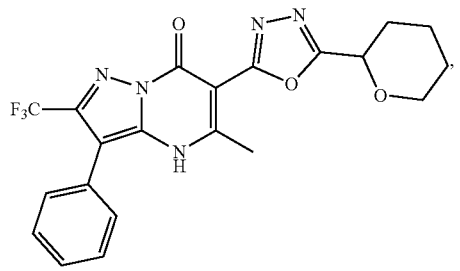 D1024
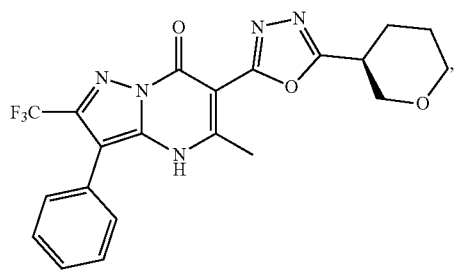 [SMILES: Cc1[nH]c2c(-c3ccccc3)c(C(F)(F)F)nn2c(=O)c1-c1nnc([C@H]2CCCOC2)o1] D1025
TABLE 1B-continued
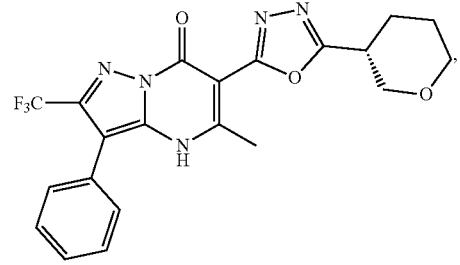 D1026
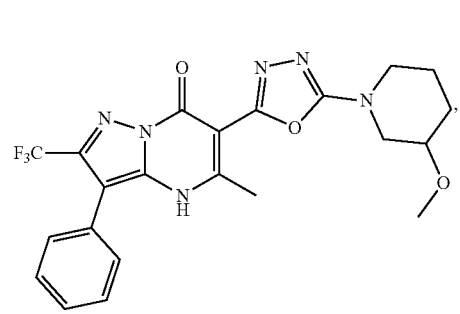 [SMILES: COC1CCCN(c2nnc(-c3c(C)[nH]c4c(-c5ccccc5)c(C(F)(F)F)nn4c3=O)o2)C1] D1027
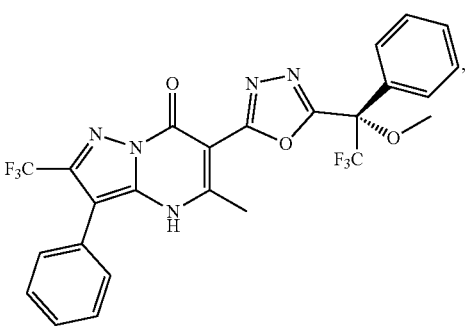 [SMILES: CO[C@@](c1ccccc1)(c1nnc(-c2c(C)[nH]c3c(-c4ccccc4)c(C(F)(F)F)nn3c2=O)o1)C(F)(F)F] D1028
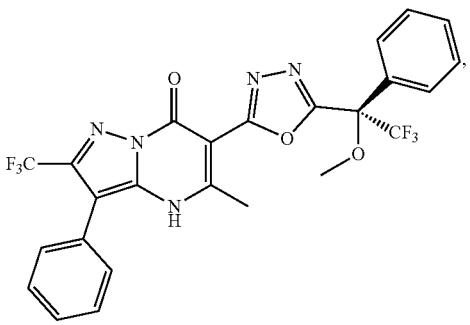 D1029
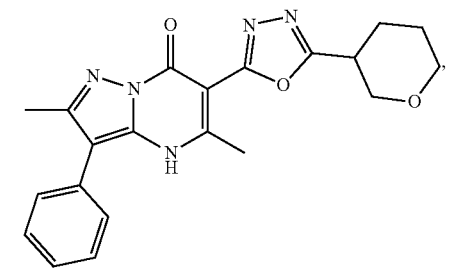 [SMILES: Cc1nn2c(=O)c(-c3nnc(C4CCCOC4)o3)c(C)[nH]c2c1-c1ccccc1] D1030

TABLE 1B-continued
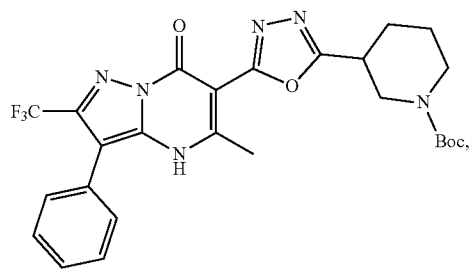 [SMILES: Cc1[nH]c2c(-c3ccccc3)c(C(F)(F)F)nn2c(=O)c1-c1nnc(C2CCCN(C(=O)OC(C)(C)C)C2)o1] D1031
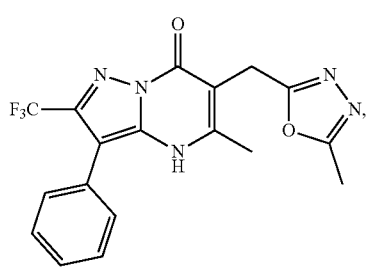 [SMILES: Cc1nnc(Cc2c(C)[nH]c3c(-c4ccccc4)c(C(F)(F)F)nn3c2=O)o1] D1032
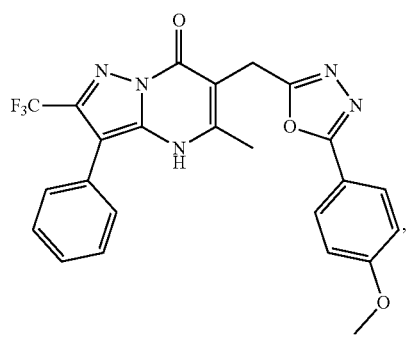 [SMILES: COc1ccc(-c2nnc(Cc3c(C)[nH]c4c(-c5ccccc5)c(C(F)(F)F)nn4c3=O)o2)cc1] D1033
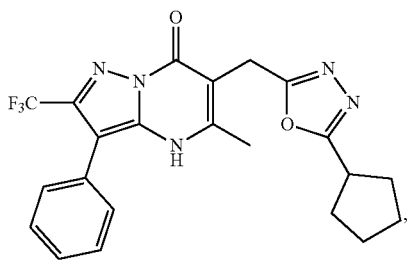 [SMILES: Cc1[nH]c2c(-c3ccccc3)c(C(F)(F)F)nn2c(=O)c1Cc1nnc(C2CCCC2)o1] D1034
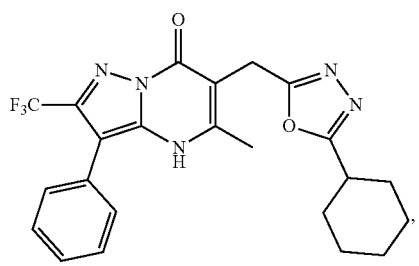 [SMILES: Cc1[nH]c2c(-c3ccccc3)c(C(F)(F)F)nn2c(=O)c1Cc1nnc(C2CCCCC2)o1] D1035
TABLE 1B-continued
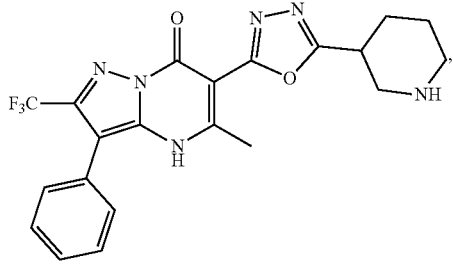 [SMILES: Cc1[nH]c2c(-c3ccccc3)c(C(F)(F)F)nn2c(=O)c1-c1nnc(C2CCCNC2)o1] D1036
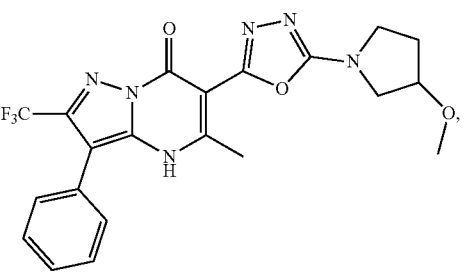 [SMILES: COC1CCN(c2nnc(-c3c(C)[nH]c4c(-c5ccccc5)c(C(F)(F)F)nn4c3=O)o2)C1] D1037
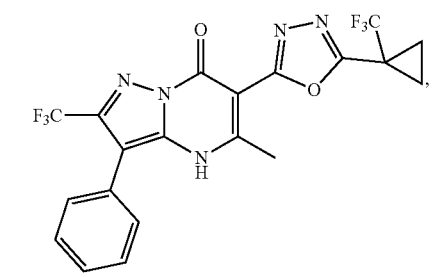 [SMILES: Cc1[nH]c2c(-c3ccccc3)c(C(F)(F)F)nn2c(=O)c1-c1nnc(C2(C(F)(F)F)CC2)o1] D1038
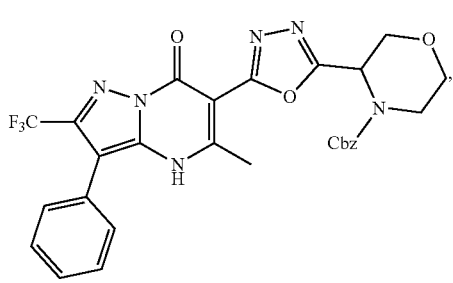 D1039
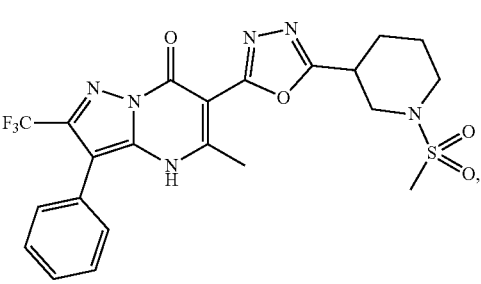 [SMILES: Cc1[nH]c2c(-c3ccccc3)c(C(F)(F)F)nn2c(=O)c1-c1nnc(C2CCCN(S(C)(=O)=O)C2)o1] D1040
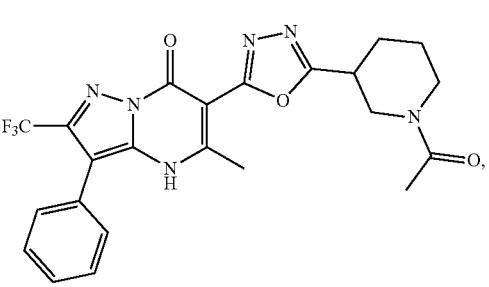 [SMILES: CC(=O)N1CCCC(c2nnc(-c3c(C)[nH]c4c(-c5ccccc5)c(C(F)(F)F)nn4c3=O)o2)C1] D1041

TABLE 1B-continued
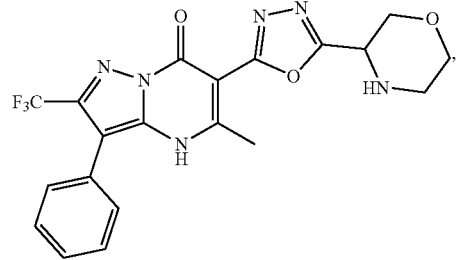 [SMILES: Cc1[nH]c2c(-c3ccccc3)c(C(F)(F)F)nn2c(=O)c1-c1nnc(C2COCCN2)o1]
D1042
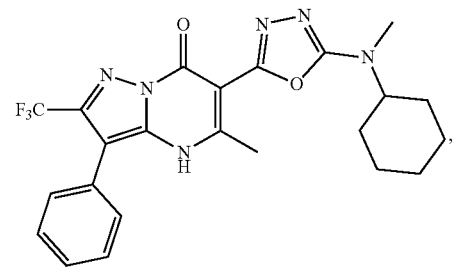 [SMILES: Cc1[nH]c2c(-c3ccccc3)c(C(F)(F)F)nn2c(=O)c1-c1nnc(N(C)C2CCCCC2)o1]
D1043
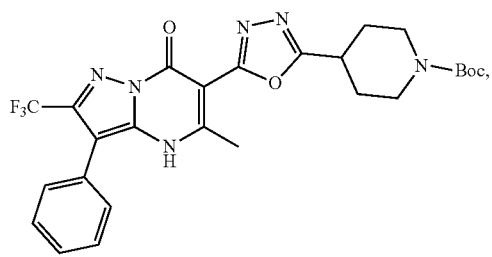 [SMILES: Cc1[nH]c2c(-c3ccccc3)c(C(F)(F)F)nn2c(=O)c1-c1nnc(C2CCN(C(=O)OC(C)(C)C)CC2)o1]
D1044
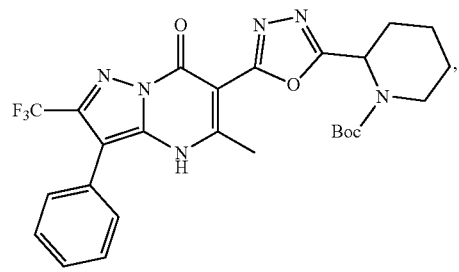
D1045
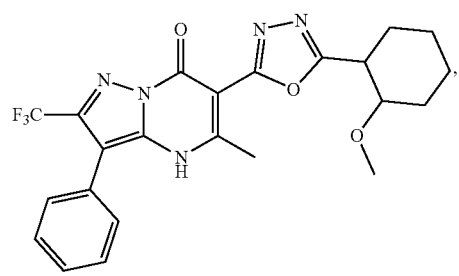 [SMILES: COC1CCCCC1c1nnc(-c2c(C)[nH]c3c(-c4ccccc4)c(C(F)(F)F)nn3c2=O)o1]
D1046
TABLE 1B-continued
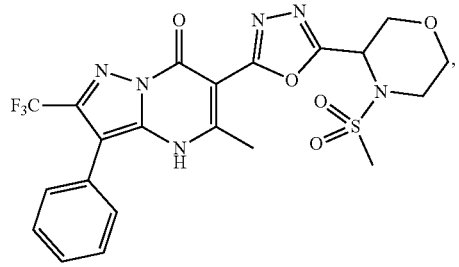 [SMILES: Cc1[nH]c2c(-c3ccccc3)c(C(F)(F)F)nn2c(=O)c1-c1nnc(C2COCCN2S(C)(=O)=O)o1]
D1047
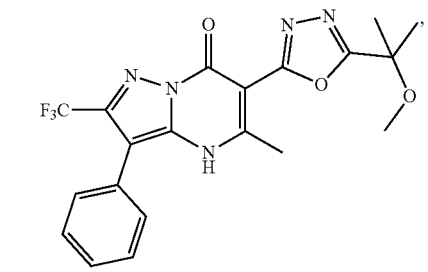 [SMILES: COC(C)(C)c1nnc(-c2c(C)[nH]c3c(-c4ccccc4)c(C(F)(F)F)nn3c2=O)o1]
D1048
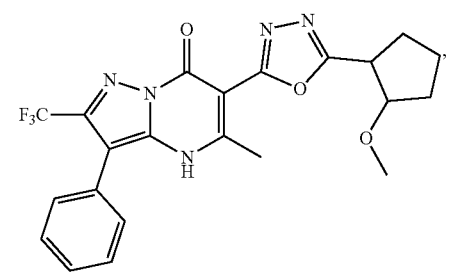 [SMILES: COC1CCCC1c1nnc(-c2c(C)[nH]c3c(-c4ccccc4)c(C(F)(F)F)nn3c2=O)o1]
D1049
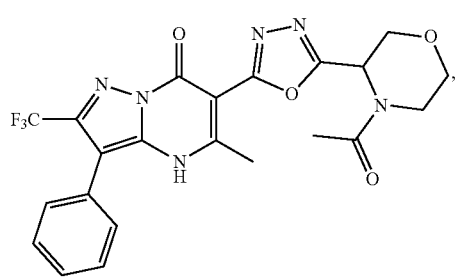 [SMILES: CC(=O)N1CCOCC1c1nnc(-c2c(C)[nH]c3c(-c4ccccc4)c(C(F)(F)F)nn3c2=O)o1]
D1050
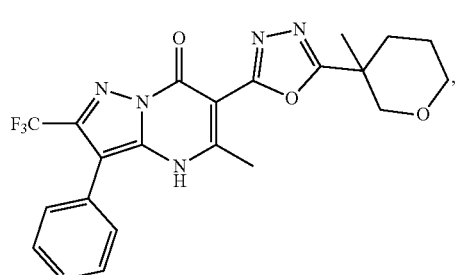
D1051
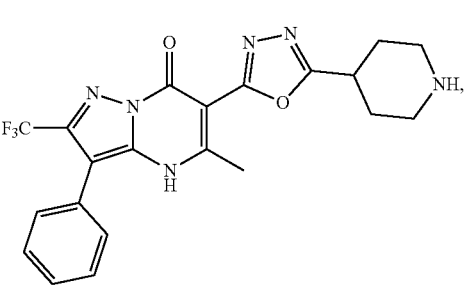 [SMILES: Cc1[nH]c2c(-c3ccccc3)c(C(F)(F)F)nn2c(=O)c1-c1nnc(C2CCNCC2)o1]
D1052

TABLE 1B-continued
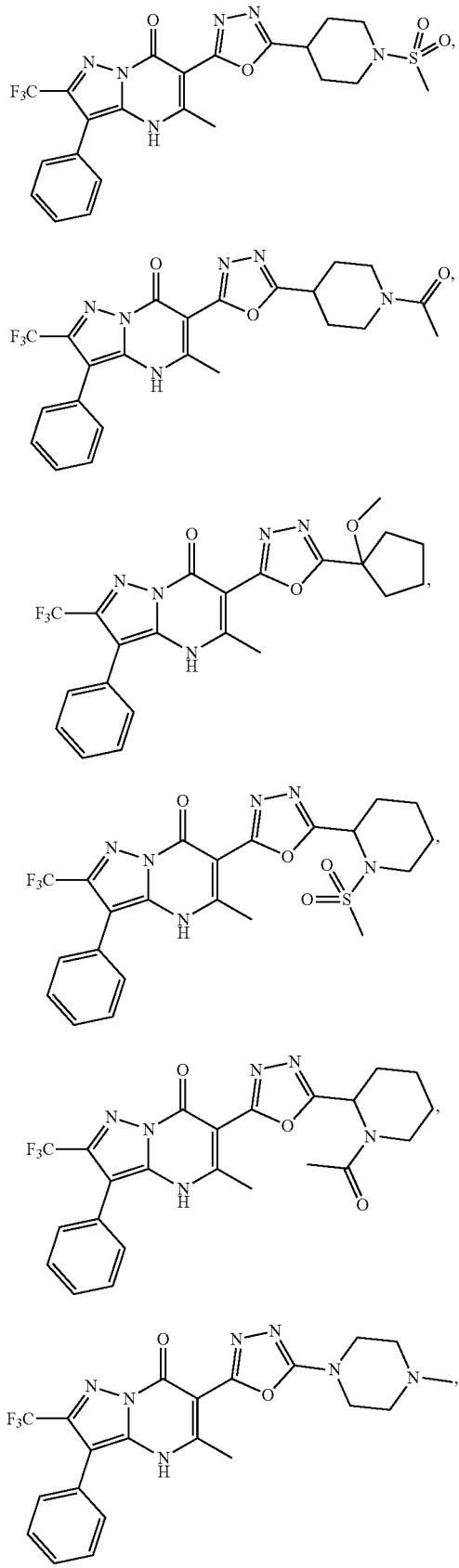
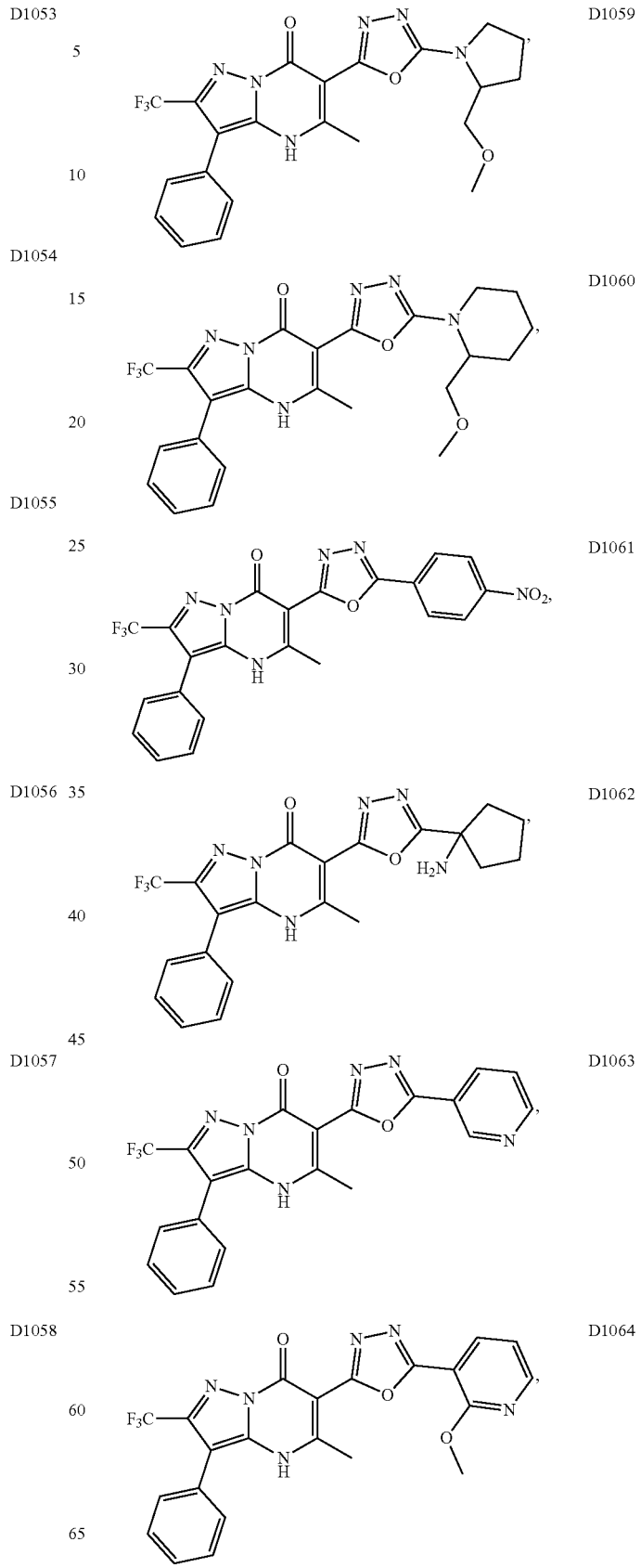

TABLE 1B-continued
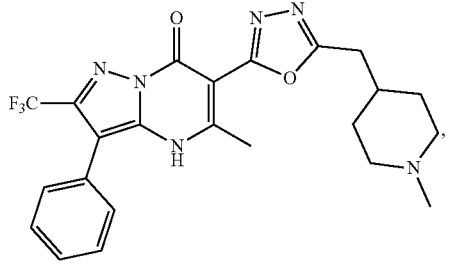 [SMILES: Cc1[nH]c2c(-c3ccccc3)c(C(F)(F)F)nn2c(=O)c1-c1nnc(CC2CCN(C)CC2)o1] D1065
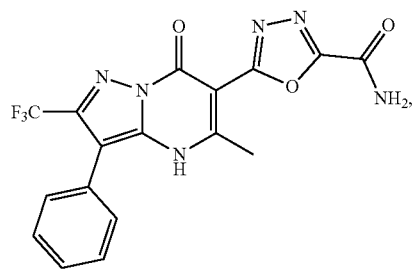 D1066
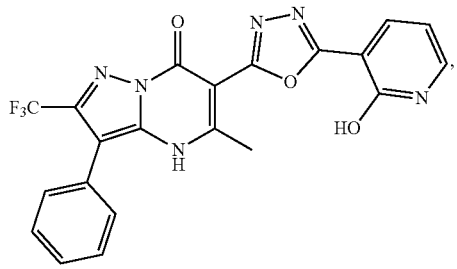 [SMILES: Cc1[nH]c2c(-c3ccccc3)c(C(F)(F)F)nn2c(=O)c1-c1nnc(-c2cccnc2O)o1] D1067
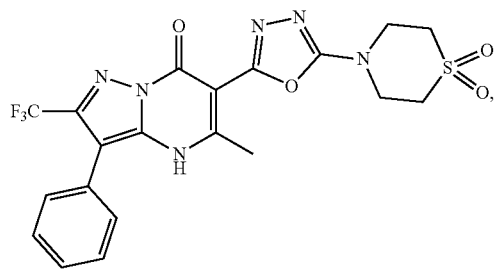 [SMILES: Cc1[nH]c2c(-c3ccccc3)c(C(F)(F)F)nn2c(=O)c1-c1nnc(N2CCS(=O)(=O)CC2)o1] D1068
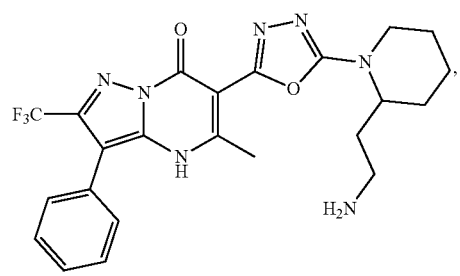 [SMILES: Cc1[nH]c2c(-c3ccccc3)c(C(F)(F)F)nn2c(=O)c1-c1nnc(N2CCCCC2CCN)o1] D1069
TABLE 1B-continued
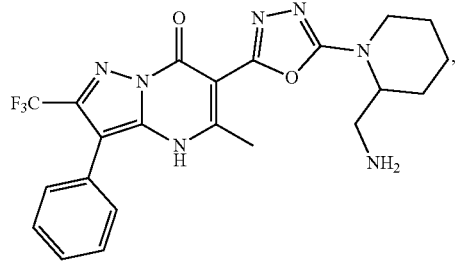 [SMILES: Cc1[nH]c2c(-c3ccccc3)c(C(F)(F)F)nn2c(=O)c1-c1nnc(N2CCCCC2CN)o1] D1070
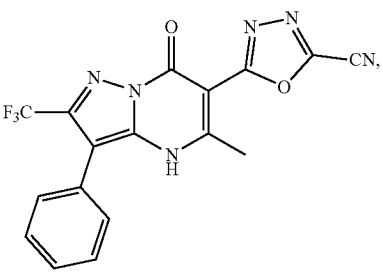 [SMILES: Cc1[nH]c2c(-c3ccccc3)c(C(F)(F)F)nn2c(=O)c1-c1nnc(C#N)o1] D1071
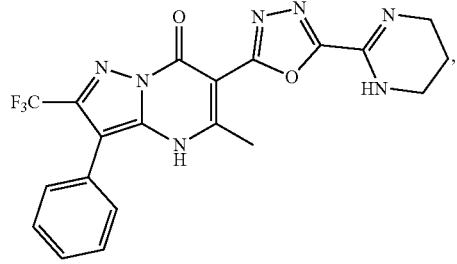 [SMILES: Cc1[nH]c2c(-c3ccccc3)c(C(F)(F)F)nn2c(=O)c1-c1nnc(C2=NCCCN2)o1] D1072
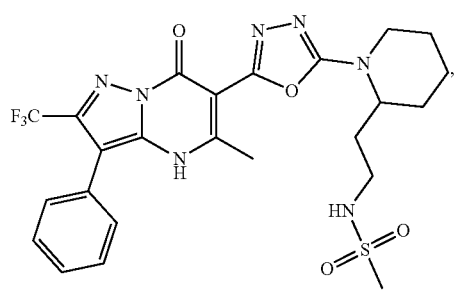 [SMILES: Cc1[nH]c2c(-c3ccccc3)c(C(F)(F)F)nn2c(=O)c1-c1nnc(N2CCCCC2CCNS(C)(=O)=O)o1] D1073
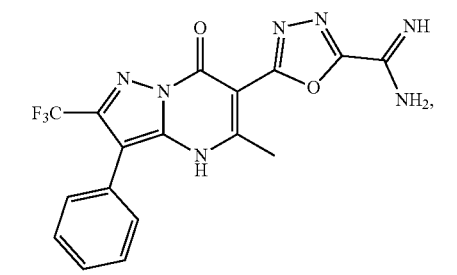 [SMILES: Cc1[nH]c2c(-c3ccccc3)c(C(F)(F)F)nn2c(=O)c1-c1nnc(C(=N)N)o1] D1074

TABLE 1B-continued
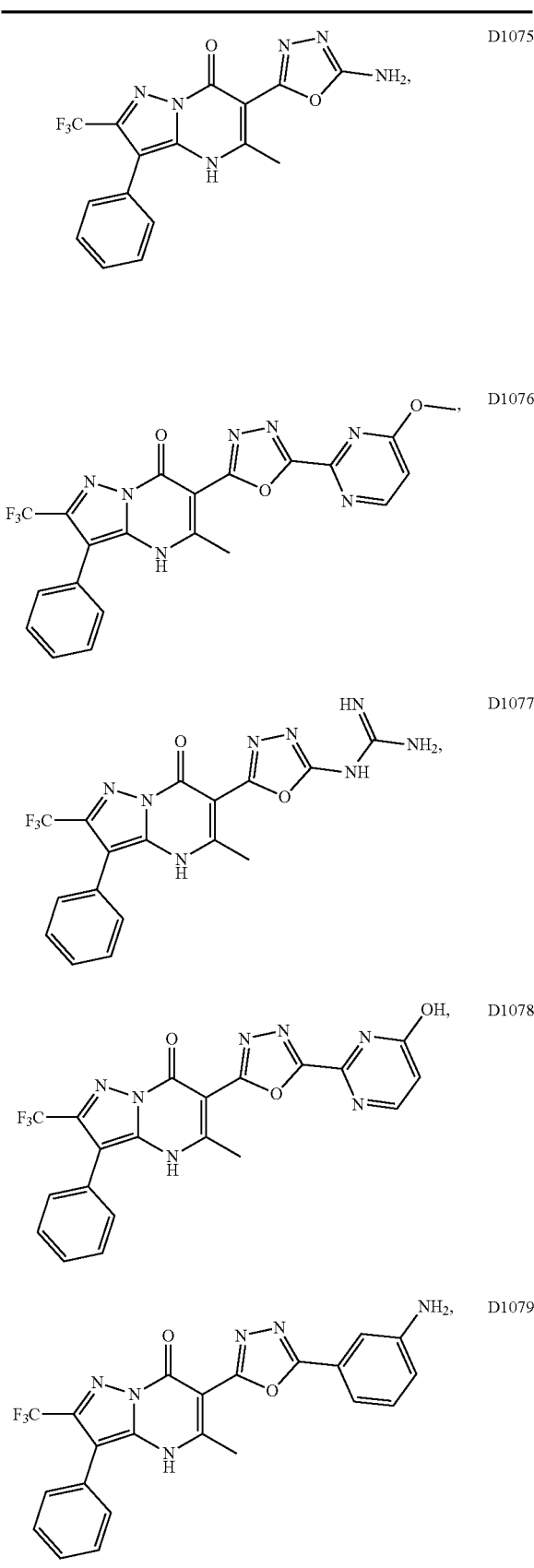
D1075
D1076
D1077
D1078
D1079
TABLE 1B-continued
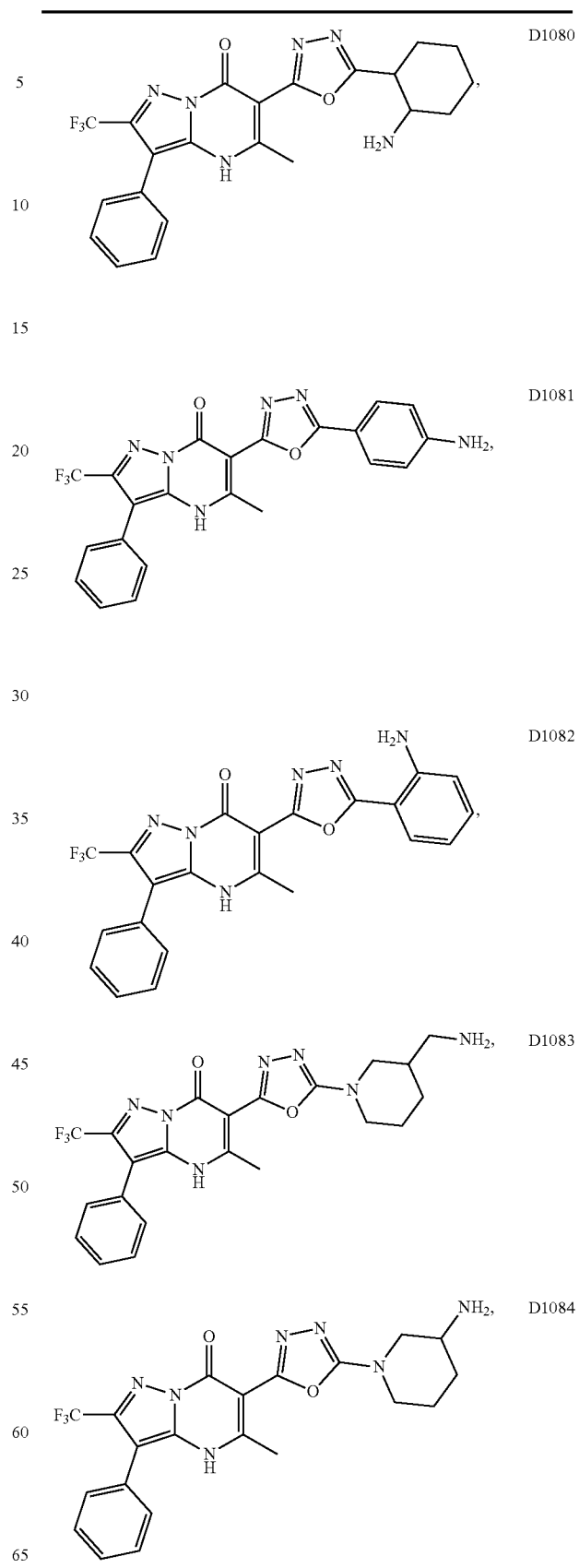
D1080
D1081
D1082
D1083
D1084

TABLE 1B-continued

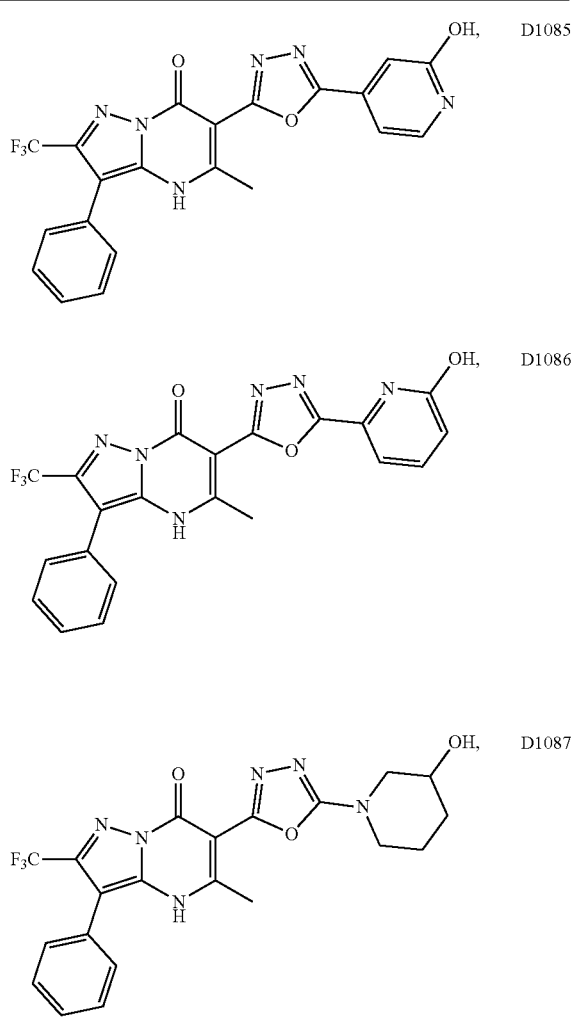

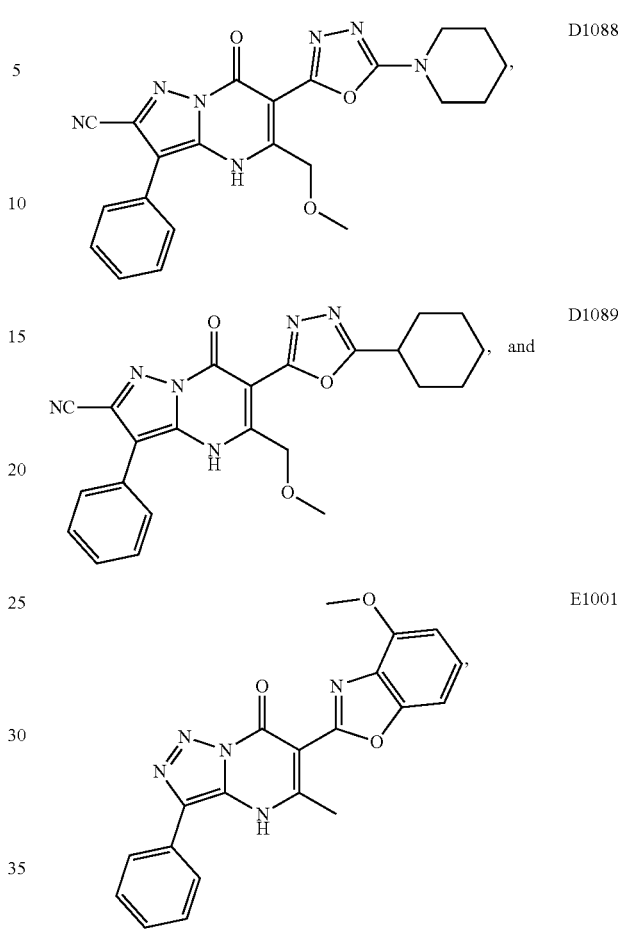

or a pharmaceutically acceptable salt, solvate or hydrate thereof.

In one embodiment, the compound is selected from the group consisting of 5-methyl-7-oxo-N,3-diphenyl-2-(trifluoromethyl)-4,7-dihydropyrazolo[1,5-a]pyrimidine-6-carboxamide (A1002);
N-(2-aminophenyl)-5-methyl-7-oxo-3-phenyl-2-(trifluoromethyl)-4,7-dihydropyrazolo[1,5-a]pyrimidine-6-carboxamide (A1006);
5-methyl-7-oxo-3-phenyl-N-(pyridin-2-yl)-2-(trifluoromethyl)-4,7-dihydropyrazolo[1,5-a]pyrimidine-6-carboxamide (A1017);
5-methyl-N-(2-(methylsulfonamido)phenyl)-7-oxo-3-phenyl-2-(trifluoromethyl)-4,7-dihydropyrazolo[1,5-a]pyrimidine-6-carboxamide (A1022);
5-methyl-7-oxo-3-phenyl-N-(pyrazin-2-yl)-2-(trifluoromethyl)-4,7-dihydropyrazolo[1,5-a]pyrimidine-6-carboxamide (A1024);
5-methyl-7-oxo-3-phenyl-N-(thiazol-2-yl)-2-(trifluoromethyl)-4,7-dihydropyrazolo[1,5-a]pyrimidine-6-carboxamide (A1028);
5-methyl-N-(1-methyl-1H-pyrazol-3-yl)-7-oxo-3-phenyl-2-(trifluoromethyl)-4,7-dihydropyrazolo[1,5-a]pyrimidine-6-carboxamide (A1029);
N-(3-chlorophenyl)-5-methyl-7-oxo-3-phenyl-2-(trifluoromethyl)-4,7-dihydropyrazolo[1,5-a]pyrimidine-6-carboxamide (A1030);
N-(2-methoxyphenyl)-5-methyl-7-oxo-3-phenyl-2-(trifluoromethyl)-4,7-dihydropyrazolo[1,5-a]pyrimidine-6-carboxamide (A1031);
N-(3-methoxyphenyl)-5-methyl-7-oxo-3-phenyl-2-(trifluoromethyl)-4,7-dihydropyrazolo[1,5-a]pyrimidine-6-carboxamide (A1032);
5-methyl-N-(3-(methylsulfonamido)phenyl)-7-oxo-3-phenyl-2-(trifluoromethyl)-4,7-dihydropyrazolo[1,5-a]pyrimidine-6-carboxamide (A1045);
N-(2-(isopropylsulfonyl)phenyl)-5-methyl-7-oxo-3-phenyl-2-(trifluoromethyl)-4,7-dihydropyrazolo[1,5-a]pyrimidine-6-carboxamide (A1051);
N-(4,5-dimethyloxazol-2-yl)-5-methyl-7-oxo-3-phenyl-2-(trifluoromethyl)-4,7-dihydropyrazolo[1,5-a]pyrimidine-6-carboxamide (A1056);
5-methyl-7-oxo-3-phenyl-N-(2-(phenylsulfonamido)phenyl)-2-(trifluoromethyl)-4,7- dihydropyrazolo[1,5-a]pyrimidine-6-carboxamide (A1059);
N-(2,2-difluorobenzo[d][1,3]dioxol-4-yl)-5-methyl-7-oxo-3-phenyl-2-(trifluoromethyl)-
4,7-dihydropyrazolo[1,5-a]pyrimidine-6-carboxamide (A1062);
N-(6-methoxypyridin-2-yl)-5-methyl-7-oxo-3-phenyl-2-(trifluoromethyl)-4,7-
dihydropyrazolo[1,5-a]pyrimidine-6-carboxamide (A1064);
N-(1-isopropyl-1H-pyrazol-3-yl)-5-methyl-7-oxo-3-phenyl-2-(trifluoromethyl)-4,7-
dihydropyrazolo[1,5-a]pyrimidine-6-carboxamide (A1065);
N-(3-isopropoxyphenyl)-5-methyl-7-oxo-3-phenyl-2-(trifluoromethyl)-4,7-
dihydropyrazolo[1,5-a]pyrimidine-6-carboxamide (A1066);
N-(3,5-dimethoxyphenyl)-5-methyl-7-oxo-3-phenyl-2-(trifluoromethyl)-4,7-
dihydropyrazolo[1,5-a]pyrimidine-6-carboxamide (A1067);
N-(3-aminophenyl)-5-methyl-7-oxo-3-phenyl-2-(trifluoromethyl)-4,7-dihydropyrazolo[1,5-
a]pyrimidine-6-carboxamide (A1069);
N-(3-cyanophenyl)-5-methyl-7-oxo-3-phenyl-2-(trifluoromethyl)-4,7-dihydropyrazolo[1,5-
a]pyrimidine-6-carboxamide (A1070);
5-methyl-N-(oxazol-2-yl)-7-oxo-3-phenyl-2-(trifluoromethyl)-4,7-dihydropyrazolo[1,5-
a]pyrimidine-6-carboxamide (A1074);
5-methyl-N-(5-methyloxazol-2-yl)-7-oxo-3-phenyl-2-(trifluoromethyl)-4,7-
dihydropyrazolo[1,5-a]pyrimidine-6-carboxamide (A1075);
5-methyl-7-oxo-3-phenyl-N-(1H-pyrazol-3-yl)-2-(trifluoromethyl)-4,7-
dihydropyrazolo[1,5-a]pyrimidine-6-carboxamide (A1076);
5-methyl-N-(1-methyl-1H-pyrazol-4-yl)-7-oxo-3-phenyl-2-(trifluoromethyl)-4,7-
dihydropyrazolo[1,5-a]pyrimidine-6-carboxamide (A1077);
N-(1,5-dimethyl-1H-pyrazol-3-yl)-5-methyl-7-oxo-3-phenyl-2-(trifluoromethyl)-4,7-
dihydropyrazolo[1,5-a]pyrimidine-6-carboxamide (A1079);
5-methyl-N-(3-methyl-1H-pyrazol-5-yl)-7-oxo-3-phenyl-2-(trifluoromethyl)-4,7-
dihydropyrazolo[1,5-a]pyrimidine-6-carboxamide (A1081);
N-(3-(cyclopentyloxy)phenyl)-5-methyl-7-oxo-3-phenyl-2-(trifluoromethyl)-4,7-
dihydropyrazolo[1,5-a]pyrimidine-6-carboxamide (A1082);
5-methyl-N-(2-(methylsulfonyl)phenyl)-7-oxo-3-phenyl-2-(trifluoromethyl)-4,7-
dihydropyrazolo[1,5-a]pyrimidine-6-carboxamide (A1083);
5-methyl-N-(3-(methylsulfonyl)phenyl)-7-oxo-3-phenyl-2-(trifluoromethyl)-4,7-
dihydropyrazolo[1,5-a]pyrimidine-6-carboxamide (A1084);
N-(3-(benzyloxy)phenyl)-5-methyl-7-oxo-3-phenyl-2-(trifluoromethyl)-4,7-
dihydropyrazolo[1,5-a]pyrimidine-6-carboxamide (A1086);
N-(2-methoxypyridin-4-yl)-5-methyl-7-oxo-3-phenyl-2-(trifluoromethyl)-4,7-
dihydropyrazolo[1,5-a]pyrimidine-6-carboxamide (A1087);
N-(2-methoxycyclohexyl)-5-methyl-7-oxo-3-phenyl-2-(trifluoromethyl)-4,7-
dihydropyrazolo[1,5-a]pyrimidine-6-carboxamide (diastereomer 2) (A1089);
N-(4-cyano-1-methyl-1H-pyrazol-3-yl)-5-methyl-7-oxo-3-phenyl-2-(trifluoromethyl)-4,7-
dihydropyrazolo[1,5-a]pyrimidine-6-carboxamide (A1090);
N-((1S,2S)-2-hydroxycyclohexyl)-5-methyl-7-oxo-3-phenyl-2-(trifluoromethyl)-4,7-
dihydropyrazolo[1,5-a]pyrimidine-6-carboxamide (A1091);
N-(5-methoxypyridin-3-yl)-5-methyl-7-oxo-3-phenyl-2-(trifluoromethyl)-4,7-
dihydropyrazolo[1,5-a]pyrimidine-6-carboxamide (A1094);
N-(4-cyclopropylthiazol-2-yl)-5-methyl-7-oxo-3-phenyl-2-(trifluoromethyl)-4,7-
dihydropyrazolo[1,5-a]pyrimidine-6-carboxamide (A1095);
5-methyl-N-(2-(methylsulfonyl)pyridin-3-yl)-7-oxo-3-phenyl-2-(trifluoromethyl)-4,7-
dihydropyrazolo[1,5-a]pyrimidine-6-carboxamide (A1096);
N-(3-methoxypyridin-2-yl)-5-methyl-7-oxo-3-phenyl-2-(trifluoromethyl)-4,7-
dihydropyrazolo[1,5-a]pyrimidine-6-carboxamide (A1100);
N-(2,3-dihydrobenzofuran-7-yl)-5-methyl-7-oxo-3-phenyl-2-(trifluoromethyl)-4,7-
dihydropyrazolo[1,5-a]pyrimidine-6-carboxamide (A1101);
N-(2,3-dihydrobenzofuran-4-yl)-5-methyl-7-oxo-3-phenyl-2-(trifluoromethyl)-4,7-
dihydropyrazolo[1,5-a]pyrimidine-6-carboxamide (A1102);
N-(4-methoxypyrimidin-2-yl)-5-methyl-7-oxo-3-phenyl-2-(trifluoromethyl)-4,7-
dihydropyrazolo[1,5-a]pyrimidine-6-carboxamide (A1104);
N-(4-methoxypyridin-2-yl)-2,5-dimethyl-7-oxo-3-phenyl-4,7-dihydropyrazolo[1,5-
a]pyrimidine-6-carboxamide (A1105);
2,5-dimethyl-N-(2-(methylsulfonyl)phenyl)-7-oxo-3-phenyl-4,7-dihydropyrazolo[1,5-
a]pyrimidine-6-carboxamide (A1106);
N-(chroman-8-yl)-5-methyl-7-oxo-3-phenyl-2-(trifluoromethyl)-4,7-dihydropyrazolo[1,5-
a]pyrimidine-6-carboxamide (A1107);
N-(6-methoxypyridazin-3-yl)-5-methyl-7-oxo-3-phenyl-2-(trifluoromethyl)-4,7-
dihydropyrazolo[1,5-a]pyrimidine-6-carboxamide (A1110);
5-methyl-7-oxo-3-phenyl-N-(propylsulfonyl)-2-(trifluoromethyl)-4,7-dihydropyrazolo[1,5-
a]pyrimidine-6-carboxamide (A1111);
N-(benzylsulfonyl)-5-methyl-7-oxo-3-phenyl-2-(trifluoromethyl)-4,7-dihydropyrazolo[1,5-
a]pyrimidine-6-carboxamide (A1112);
5-methyl-7-oxo-3-phenyl-N-(phenylsulfonyl)-2-(trifluoromethyl)-4,7-dihydropyrazolo[1,5-
a]pyrimidine-6-carboxamide (A1116);
5-methyl-7-oxo-3-phenyl-N-(pyridin-2-ylsulfonyl)-2-(trifluoromethyl)-4,7-
dihydropyrazolo[1,5-a]pyrimidine-6-carboxamide (A1120);
N-((2-methoxyphenyl)sulfonyl)-5-methyl-7-oxo-3-phenyl-2-(trifluoromethyl)-4,7-
dihydropyrazolo[1,5-a]pyrimidine-6-carboxamide (A1121);
N-(cyclohexylsulfonyl)-5-methyl-7-oxo-3-phenyl-2-(trifluoromethyl)-4,7-
dihydropyrazolo[1,5-a]pyrimidine-6-carboxamide (A1124);
N-((3-methoxyphenyl)sulfonyl)-5-methyl-7-oxo-3-phenyl-2-(trifluoromethyl)-4,7-
dihydropyrazolo[1,5-a]pyrimidine-6-carboxamide (A1125);

N-((2-chlorophenyl)sulfonyl)-5-methyl-7-oxo-3-phenyl-2-(trifluoromethyl)-4,7-dihydropyrazolo[1,5-a]pyrimidine-6-carboxamide (A1127);
N-((3-cyanophenyl)sulfonyl)-5-methyl-7-oxo-3-phenyl-2-(trifluoromethyl)-4,7-dihydropyrazolo[1,5-a]pyrimidine-6-carboxamide (A1128);
N-(3-bromo-5-methoxyphenyl)-5-methyl-7-oxo-3-phenyl-2-(trifluoromethyl)-4,7-dihydropyrazolo[1,5-a]pyrimidine-6-carboxamide (A1129);
N-((3-methoxybenzyl)sulfonyl)-5-methyl-7-oxo-3-phenyl-2-(trifluoromethyl)-4,7-dihydropyrazolo[1,5-a]pyrimidine-6-carboxamide (A1132);
N-(3-fluoro-5-methoxyphenyl)-5-methyl-7-oxo-3-phenyl-2-(trifluoromethyl)-4,7-dihydropyrazolo[1,5-a]pyrimidine-6-carboxamide (A1133);
N-(3-chloro-5-methoxyphenyl)-5-methyl-7-oxo-3-phenyl-2-(trifluoromethyl)-4,7-dihydropyrazolo[1,5-a]pyrimidine-6-carboxamide (A1134);
N-(2-chloro-3-methoxyphenyl)-5-methyl-7-oxo-3-phenyl-2-(trifluoromethyl)-4,7-dihydropyrazolo[1,5-a]pyrimidine-6-carboxamide (A1135);
N-(2-fluoro-3-methoxyphenyl)-5-methyl-7-oxo-3-phenyl-2-(trifluoromethyl)-4,7-dihydropyrazolo[1,5-a]pyrimidine-6-carboxamide (A1136);
N-(3-bromo-5-((dimethylamino)methyl)phenyl)-5-methyl-7-oxo-3-phenyl-2-(trifluoromethyl)-4,7-dihydropyrazolo[1,5-a]pyrimidine-6-carboxamide (A1139);
2-cyano-N-(6-methoxypyridin-2-yl)-5-methyl-7-oxo-3-phenyl-4,7-dihydropyrazolo[1,5-a]pyrimidine-6-carboxamide (A1144);
6-(2-((3-methoxyphenyl)amino)ethyl)-5-methyl-3-phenyl-2-(trifluoromethyl)pyrazolo[1,5-a]pyrimidin-7(4H)-one (B1015);
N-(2-(5-methyl-7-oxo-3-phenyl-2-(trifluoromethyl)-4,7-dihydropyrazolo[1,5-a]pyrimidin-6-yl)-1H-benzo[d]imidazol-7-yl)acetamide (C1009);
6-(4-methoxybenzo[d]oxazol-2-yl)-5-methyl-3-phenyl-2-(trifluoromethyl)pyrazolo[1,5-a]pyrimidin-7(4H)-one (C1014);
6-(5-methoxy-1H-benzo[d]imidazol-2-yl)-5-methyl-3-phenyl-2-(trifluoromethyl)pyrazolo[1,5-a]pyrimidin-7(4H)-one (C1016);
5-methyl-3-phenyl-6-(4,5,6,7-tetrahydro-1H-benzo[d]imidazol-2-yl)-2-(trifluoromethyl)pyrazolo[1,5-a]pyrimidin-7(4H)-one (C1017);
6-(4-methoxy-1H-benzo[d]imidazol-2-yl)-5-methyl-3-phenyl-2-(trifluoromethyl)pyrazolo[1,5-a]pyrimidin-7(4H)-one (C1018);
2-(5-methyl-7-oxo-3-phenyl-2-(trifluoromethyl)-4,7-dihydropyrazolo[1,5-a]pyrimidin-6-yl)quinazolin-4(3H)-one (C1019);
6-(7-methoxybenzo[d]oxazol-2-yl)-5-methyl-3-phenyl-2-(trifluoromethyl)pyrazolo[1,5-a]pyrimidin-7(4H)-one (C1022);
3-isopropyl-5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1023);
5-methoxy-2-(5-methyl-7-oxo-3-phenyl-2-(trifluoromethyl)-4,7-dihydropyrazolo[1,5-a]pyrimidin-6-yl)quinazolin-4(3H)-one (C1024);
8-methoxy-2-(5-methyl-7-oxo-3-phenyl-2-(trifluoromethyl)-4,7-dihydropyrazolo[1,5-a]pyrimidin-6-yl)quinazolin-4(3H)-one (C1025);
5-methyl-3-phenyl-6-(5-(tetrahydro-2H-pyran-3-yl)oxazol-2-yl)-2-(trifluoromethyl)pyrazolo[1,5-a]pyrimidin-7(4H)-one (C1027);
5-methyl-6-(oxazolo[4,5-b]pyridin-2-yl)-3-phenyl-2-(trifluoromethyl)pyrazolo[1,5-a]pyrimidin-7(4H)-one (C1030);
2,5-dimethyl-3-phenyl-6-(4,5,6,7-tetrahydrobenzo[d]oxazol-2-yl)pyrazolo[1,5-a]pyrimidin-7(4H)-one (C1032);
2-(5-methyl-7-oxo-3-phenyl-2-(trifluoromethyl)-4,7-dihydropyrazolo[1,5-a]pyrimidin-6-yl)-6,7-dihydrobenzo[d]oxazol-4(5H)-one (C1033);
6-(4-methoxyoxazolo[4,5-c]pyridin-2-yl)-5-methyl-3-phenyl-2-(trifluoromethyl)pyrazolo[1,5-a]pyrimidin-7(4H)-one (C1037);
6-(4-ethoxybenzo[d]oxazol-2-yl)-5-methyl-3-phenyl-2-(trifluoromethyl)pyrazolo[1,5-a]pyrimidin-7(4H)-one (C1038);
6-(4-isopropoxybenzo[d]oxazol-2-yl)-5-methyl-3-phenyl-2-(trifluoromethyl)pyrazolo[1,5-a]pyrimidin-7(4H)-one (C1039);
6-(4-bromobenzo[d]oxazol-2-yl)-5-methyl-3-phenyl-2-(trifluoromethyl)pyrazolo[1,5-a]pyrimidin-7(4H)-one (C1040);
6-(4-(2-methoxyethoxy)benzo[d]oxazol-2-yl)-5-methyl-3-phenyl-2-(trifluoromethyl)pyrazolo[1,5-a]pyrimidin-7(4H)-one (C1041);
6-(4-methoxybenzo[d]oxazol-2-yl)-2,5-dimethyl-3-phenylpyrazolo[1,5-a]pyrimidin-7(4H)-one (C1042);
6-(8-methoxyimidazo[1,2-a]pyridin-2-yl)-5-methyl-3-phenyl-2-(trifluoromethyl)pyrazolo[1,5-a]pyrimidin-7(4H)-one (C1044);
6-(4-(cyclopropylmethoxy)benzo[d]oxazol-2-yl)-5-methyl-3-phenyl-2-(trifluoromethyl)pyrazolo[1,5-a]pyrimidin-7(4H)-one (C1045);
6-(4-ethylbenzo[d]oxazol-2-yl)-5-methyl-3-phenyl-2-(trifluoromethyl)pyrazolo[1,5-a]pyrimidin-7(4H)-one (C1046);
5-methyl-6-(4-(methylthio)benzo[d]oxazol-2-yl)-3-phenyl-2-(trifluoromethyl)pyrazolo[1,5-a]pyrimidin-7(4H)-one (C1047);
6-(4-methoxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1048);
2-(difluoromethyl)-6-(4-methoxybenzo[d]oxazol-2-yl)-5-methyl-3-phenylpyrazolo[1,5-a]pyrimidin-7(4H)-one (C1050);
6-(4-methoxybenzo[d]oxazol-2-yl)-5-methyl-7-oxo-3-phenyl-4,7-dihydropyrazolo[1,5-a]pyrimidine-2-carbonitrile (C1051);
6-(4-hydroxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1052);
6-(4-hydroxybenzo[d]oxazol-2-yl)-5-methyl-3-phenyl-2-(trifluoromethyl)pyrazolo[1,5- a]pyrimidin-7(4H)-one (C1053);
6-(4-chlorobenzo[d]oxazol-2-yl)-5-methyl-3-phenyl-2-(trifluoromethyl)pyrazolo[1,5-a]pyrimidin-7(4H)-one (C1055);
6-(4-methoxybenzo[d]oxazol-2-yl)-5-(methoxymethyl)-3-phenyl-2-(trifluoromethyl)pyrazolo[1,5-a]pyrimidin-7(4H)-one (C1056);
6-(5-methoxyimidazo[1,2-a]pyridin-2-yl)-5-methyl-3-phenyl-2-(trifluoromethyl)pyrazolo[1,5-a]pyrimidin-7(4H)-one (C1057);
6-(7-methoxyoxazolo[5,4-b]pyridin-2-yl)-5-methyl-3-phenyl-2-(trifluoromethyl)pyrazolo[1,5-a]pyrimidin-7(4H)-one (C1058);
2-(5-methyl-7-oxo-3-phenyl-2-(trifluoromethyl)-4,7-dihydropyrazolo[1,5-a]pyrimidin-6-yl)-5,6,7,8-tetrahydro-4H-oxazolo[4,5-c]azepin-4-one (C1059);
5-methyl-6-(4-methylbenzo[d]oxazol-2-yl)-3-phenyl-2-(trifluoromethyl)pyrazolo[1,5-a]pyrimidin-7(4H)-one (C1060);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)acetamide (C1062);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)methanesulfonamide (C1066);
6-(4-methoxybenzo[d]thiazol-2-yl)-5-methyl-3-phenyl-2-(trifluoromethyl)pyrazolo[1,5-a]pyrimidin-7(4H)-one (C1070);
5-chloro-6-(4-methoxybenzo[d]oxazol-2-yl)-3-phenyl-2-(trifluoromethyl)pyrazolo[1,5-a]pyrimidin-7(4H)-one (C1071);
6-(4-(benzyloxy)benzo[d]oxazol-2-yl)-5-methyl-3-phenyl-2-(trifluoromethyl)pyrazolo[1,5-a]pyrimidin-7(4H)-one (C1073);
2-(5-methyl-7-oxo-3-phenyl-2-(trifluoromethyl)-4,7-dihydropyrazolo[1,5-a]pyrimidin-6-yl)benzo[d]oxazole-4-carbonitrile (C1075);
6-(4-fluorobenzo[d]oxazol-2-yl)-5-methyl-3-phenyl-2-(trifluoromethyl)pyrazolo[1,5-a]pyrimidin-7(4H)-one (C1076);
6-(4-methoxybenzo[d]oxazol-2-yl)-3-phenyl-2,5-bis(trifluoromethyl)pyrazolo[1,5-a]pyrimidin-7(4H)-one (C1077);
6-(4-(dimethylamino)benzo[d]oxazol-2-yl)-5-methyl-3-phenyl-2-(trifluoromethyl)pyrazolo[1,5-a]pyrimidin-7(4H)-one (C1078);
6-(7-bromo-4-methoxybenzo[d]oxazol-2-yl)-5-methyl-3-phenyl-2-(trifluoromethyl)pyrazolo[1,5-a]pyrimidin-7(4H)-one (C1081);
6-(5-bromo-4-methoxybenzo[d]oxazol-2-yl)-5-methyl-3-phenyl-2-(trifluoromethyl)pyrazolo[1,5-a]pyrimidin-7(4H)-one (C1082);
5-methoxy-6-(4-methoxybenzo[d]oxazol-2-yl)-3-phenyl-2-(trifluoromethyl)pyrazolo[1,5-a]pyrimidin-7(4H)-one (C1084);
5-amino-6-(4-methoxybenzo[d]oxazol-2-yl)-3-phenyl-2-(trifluoromethyl)pyrazolo[1,5-a]pyrimidin-7(4H)-one (C1085);
2-(5-methyl-7-oxo-3-phenyl-2-(trifluoromethyl)-4,7-dihydropyrazolo[1,5-a]pyrimidin-6-yl)benzo[d]oxazol-4-yl dimethylcarbamate (C1088);
6-(4-methoxybenzo[d]oxazol-2-yl)-7-oxo-3-phenyl-2-(trifluoromethyl)-4,7-dihydropyrazolo[1,5-a]pyrimidine-5-carbonitrile (C1089);
3-(2-fluorophenyl)-6-(4-methoxybenzo[d]oxazol-2-yl)-5-methyl-2-(trifluoromethyl)pyrazolo[1,5-a]pyrimidin-7(4H)-one (C1091);
6-(4-methoxy-7-methylbenzo[d]oxazol-2-yl)-5-methyl-3-phenyl-2-(trifluoromethyl)pyrazolo[1,5-a]pyrimidin-7(4H)-one (C1092);
6-(4-methoxy-5-methylbenzo[d]oxazol-2-yl)-5-methyl-3-phenyl-2-(trifluoromethyl)pyrazolo[1,5-a]pyrimidin-7(4H)-one (C1093);
6-(7-chloro-4-methoxybenzo[d]oxazol-2-yl)-5-methyl-3-phenyl-2-(trifluoromethyl)pyrazolo[1,5-a]pyrimidin-7(4H)-one (C1094);
6-(5-chloro-4-methoxybenzo[d]oxazol-2-yl)-5-methyl-3-phenyl-2-(trifluoromethyl)pyrazolo[1,5-a]pyrimidin-7(4H)-one (C1095);
6-(7-methoxyoxazolo[5,4-c]pyridin-2-yl)-5-methyl-3-phenyl-2-(trifluoromethyl)pyrazolo[1,5-a]pyrimidin-7(4H)-one (C1096);
5-methyl-6-(4-(methylsulfinyl)benzo[d]oxazol-2-yl)-3-phenyl-2-(trifluoromethyl)pyrazolo[1,5-a]pyrimidin-7(4H)-one (C1097);
6-(4-methoxy-6-methylbenzo[d]oxazol-2-yl)-5-methyl-3-phenyl-2-(trifluoromethyl)pyrazolo[1,5-a]pyrimidin-7(4H)-one (C1098);
5-((benzyloxy)methyl)-6-(4-methoxybenzo[d]oxazol-2-yl)-3-phenyl-2-(trifluoromethyl)pyrazolo[1,5-a]pyrimidin-7(4H)-one (C1099);
4-methoxy-2-(5-methyl-7-oxo-3-phenyl-2-(trifluoromethyl)-4,7-dihydropyrazolo[1,5-a]pyrimidin-6-yl)benzo[d]oxazole-7-carbonitrile (C1100);
ethyl 2-(5-methyl-7-oxo-3-phenyl-2-(trifluoromethyl)-4,7-dihydropyrazolo[1,5-a]pyrimidin-6-yl)oxazole-4-carboxylate (C1101);
2-(5-methyl-7-oxo-3-phenyl-2-(trifluoromethyl)-4,7-dihydropyrazolo[1,5-a]pyrimidin-6-yl)oxazole-4-carboxamide (C1102);
5-(hydroxymethyl)-6-(4-methoxybenzo[d]oxazol-2-yl)-3-phenyl-2-(trifluoromethyl)pyrazolo[1,5-a]pyrimidin-7(4H)-one (C1103);
6-(4-(hydroxymethyl)oxazol-2-yl)-5-methyl-3-phenyl-2-(trifluoromethyl)pyrazolo[1,5-a]pyrimidin-7(4H)-one (C1104);
6-(6-chloro-4-methoxybenzo[d]oxazol-2-yl)-5-methyl-3-phenyl-2-(trifluoromethyl)pyrazolo[1,5-a]pyrimidin-7(4H)-one (C1105);
5-methyl-2-(5-methyl-7-oxo-3-phenyl-2-(trifluoromethyl)-4,7-dihydropyrazolo[1,5-a]pyrimidin-6-yl)oxazolo[4,5-c]pyridin-4(5H)-one (C1106);
6-(4-(methoxymethyl)oxazol-2-yl)-5-methyl-3-phenyl-2-(trifluoromethyl)pyrazolo[1,5-a]pyrimidin-7(4H)-one (C1108);
5-((dimethylamino)methyl)-6-(4-methoxybenzo[d]oxazol-2-yl)-3-phenyl-2-(trifluoromethyl)pyrazolo[1,5-a]pyrimidin-7(4H)-one (C1109);

6-(7-acetyl-4-methoxybenzo[d]oxazol-2-yl)-5-methyl-3-phenyl-2-
(trifluoromethyl)pyrazolo[1,5-a]pyrimidin-7(4H)-one (C1111);
4-methoxy-2-(5-methyl-7-oxo-3-phenyl-2-(trifluoromethyl)-4,7-dihydropyrazolo[1,5-
a]pyrimidin-6-yl)benzo[d]oxazole-7-carboxamide (C1113);
3-(3-fluorophenyl)-6-(4-methoxybenzo[d]oxazol-2-yl)-5-methyl-2-
(trifluoromethyl)pyrazolo[1,5-a]pyrimidin-7(4H)-one (C1114);
2-(5-methyl-7-oxo-3-phenyl-2-(trifluoromethyl)-4,7-dihydropyrazolo[1,5-a]pyrimidin-6-
yl)oxazolo[4,5-c]pyridin-4(5H)-one (C1116);
2-((2-(5-methyl-7-oxo-3-phenyl-2-(trifluoromethyl)-4,7-dihydropyrazolo[1,5-a]pyrimidin-
6-yl)benzo[d]oxazol-4-yl)oxy)acetic acid (C1117);
6-(4-methoxybenzo[d]oxazol-2-yl)-7-oxo-3-phenyl-5-(trifluoromethyl)-4,7-
dihydropyrazolo[1,5-a]pyrimidine-2-carbonitrile (C1118);
3-(3,5-difluorophenyl)-6-(4-methoxybenzo[d]oxazol-2-yl)-5-methyl-2-
(trifluoromethyl)pyrazolo[1,5-a]pyrimidin-7(4H)-one (C1119);
6-(4-methoxybenzo[d]oxazol-2-yl)-5-(methylthio)-3-phenyl-2-
(trifluoromethyl)pyrazolo[1,5-a]pyrimidin-7(4H)-one (C1121);
2-((2-(5-methyl-7-oxo-3-phenyl-2-(trifluoromethyl)-4,7-dihydropyrazolo[1,5-a]pyrimidin-
6-yl)benzo[d]oxazol-4-yl)oxy)acetamide (C1122);
6-(6-amino-4-methoxybenzo[d]oxazol-2-yl)-5-methyl-3-phenyl-2-
(trifluoromethyl)pyrazolo[1,5-a]pyrimidin-7(4H)-one (C1123);
6-(4-methoxy-7-(methylsulfonyl)benzo[d]oxazol-2-yl)-5-methyl-3-phenyl-2-
(trifluoromethyl)pyrazolo[1,5-a]pyrimidin-7(4H)-one (C1125);
4-methoxy-2-(5-methyl-7-oxo-3-phenyl-2-(trifluoromethyl)-4,7-dihydropyrazolo[1,5-
a]pyrimidin-6-yl)benzo[d]oxazole-5-carbonitrile (C1126);
6-(6-(aminomethyl)-4-methoxybenzo[d]oxazol-2-yl)-5-methyl-3-phenyl-2-
(trifluoromethyl)pyrazolo[1,5-a]pyrimidin-7(4H)-one (C1128);
6-(4-methoxybenzo[d]oxazol-2-yl)-7-oxo-3-phenyl-2-(trifluoromethyl)-4,7-
dihydropyrazolo[1,5-a]pyrimidine-5-carboxylic acid (C1130);
6-(4-methoxybenzo[d]oxazol-2-yl)-7-oxo-3-phenyl-2-(trifluoromethyl)-4,7-
dihydropyrazolo[1,5-a]pyrimidine-5-carboxylic acid (C1131);
6-(4-methoxybenzo[d]oxazol-2-yl)-7-oxo-3-phenyl-2-(trifluoromethyl)-4,7-
dihydropyrazolo[1,5-a]pyrimidine-5-carboxamide (C1132);
6-(4-methoxybenzo[d]oxazol-2-yl)-3-phenyl-5-((((tetrahydro-2H-pyran-2-yl)oxy)methyl)-
2-(trifluoromethyl)pyrazolo[1,5-a]pyrimidin-7(4H)-one (C1134);
6-(6-(aminomethyl)-4-methoxybenzo[d]oxazol-2-yl)-5-methyl-3-phenyl-2-
(trifluoromethyl)pyrazolo[1,5-a]pyrimidin-7(4H)-one (HCl salt) (C1135);
6-(4-methoxybenzo[d]oxazol-2-yl)-5-((methylthio)methyl)-3-phenyl-2-
(trifluoromethyl)pyrazolo[1,5-a]pyrimidin-7(4H)-one (C1136);
6-(4-methoxybenzo[d]oxazol-2-yl)-5-((methylsulfinyl)methyl)-3-phenyl-2-
(trifluoromethyl)pyrazolo[1,5-a]pyrimidin-7(4H)-one (C1137);
6-(4-methoxybenzo[d]oxazol-2-yl)-5-((methylsulfonyl)methyl)-3-phenyl-2-
(trifluoromethyl)pyrazolo[1,5-a]pyrimidin-7(4H)-one (C1138);
6-(4-methoxybenzo[d]oxazol-2-yl)-5-(methoxymethyl)-7-oxo-3-phenyl-4,7-
dihydropyrazolo[1,5-a]pyrimidine-2-carbonitrile (C1139);
4-methoxy-2-(5-methyl-7-oxo-3-phenyl-2-(trifluoromethyl)-4,7-dihydropyrazolo[1,5-
a]pyrimidin-6-yl)benzo[d]oxazole-6-carboximidamide (C1141);
6-(4-methoxybenzo[d]oxazol-2-yl)-N-(2-methoxyethyl)-7-oxo-3-phenyl-2-
(trifluoromethyl)-4,7-dihydropyrazolo[1,5-a]pyrimidine-5-carboxamide (C1142);
6-(4-(hydroxymethyl)-5-isopropyloxazol-2-yl)-5-methyl-3-phenyl-2-
(trifluoromethyl)pyrazolo[1,5-a]pyrimidin-7(4H)-one (C1143);
6-(6-chloro-4-methoxybenzo[d]oxazol-2-yl)-5-(methoxymethyl)-7-oxo-3-phenyl-4,7-
dihydropyrazolo[1,5-a]pyrimidine-2-carbonitrile (C1145);
2-((6-(4-methoxybenzo[d]oxazol-2-yl)-7-oxo-3-phenyl-2-(trifluoromethyl)-4,7-
dihydropyrazolo[1,5-a]pyrimidin-5-yl)methoxy)acetic acid (C1146);
4-methoxy-2-(5-methyl-7-oxo-3-phenyl-2-(trifluoromethyl)-4,7-dihydropyrazolo[1,5-
a]pyrimidin-6-yl)benzo[d]oxazole-6-carboxamide (C1149);
6-(4-methoxybenzo[d]oxazol-2-yl)-5-((2-methoxyethoxy)methyl)-3-phenyl-2-
(trifluoromethyl)pyrazolo[1,5-a]pyrimidin-7(4H)-one (C1151);
6-(4-methoxybenzo[d]oxazol-2-yl)-5-((oxetan-3-yloxy)methyl)-3-phenyl-2-
(trifluoromethyl)pyrazolo[1,5-a]pyrimidin-7(4H)-one (C1152);
6-(5-isopropyl-4-(methoxymethyl)oxazol-2-yl)-5-methyl-3-phenyl-2-
(trifluoromethyl)pyrazolo[1,5-a]pyrimidin-7(4H)-one (C1153);
6-(7-amino-4-methoxybenzo[d]oxazol-2-yl)-5-methyl-3-phenyl-2-
(trifluoromethyl)pyrazolo[1,5-a]pyrimidin-7(4H)-one (C1154);
4-methoxy-2-(5-methyl-7-oxo-3-phenyl-2-(trifluoromethyl)-4,7-dihydropyrazolo[1,5-
a]pyrimidin-6-yl)benzo[d]oxazole-6-carboxylic acid (C1155);
6-(6-aminobenzo[d]oxazol-2-yl)-5-methyl-3-phenyl-2-(trifluoromethyl)pyrazolo[1,5-
a]pyrimidin-7(4H)-one (C1156);
6-(5-cyclohexyl-4-(hydroxymethyl)oxazol-2-yl)-5-methyl-3-phenyl-2-
(trifluoromethyl)pyrazolo[1,5-a]pyrimidin-7(4H)-one (C1157);
6-(4-methoxybenzo[d]oxazol-2-yl)-5-(((2-oxopyrrolidin-3-yl)oxy)methyl)-3-phenyl-2-
(trifluoromethyl)pyrazolo[1,5-a]pyrimidin-7(4H)-one (C1159);
6-(6-chloro-4-methoxybenzo[d]oxazol-2-yl)-5-methyl-7-oxo-3-phenyl-4,7-
dihydropyrazolo[1,5-a]pyrimidine-2-carbonitrile (C1160);
6-(4-methoxy-6-(methylamino)benzo[d]oxazol-2-yl)-5-methyl-3-phenyl-2-
(trifluoromethyl)pyrazolo[1,5-a]pyrimidin-7(4H)-one (C1161);
6-(6-(dimethylamino)-4-methoxybenzo[d]oxazol-2-yl)-5-methyl-3-phenyl-2-
(trifluoromethyl)pyrazolo[1,5-a]pyrimidin-7(4H)-one (C1162);
4-methoxy-N,N,N-trimethyl-2-(5-methyl-7-oxo-3-phenyl-2-(trifluoromethyl)-4,7- dihydropyrazolo[1,5-a]pyrimidin-6-yl)benzo[d]oxazol-6-aminium (C1163);
2-(5-methyl-7-oxo-3-phenyl-2-(trifluoromethyl)-4,7-dihydropyrazolo[1,5-a]pyrimidin-6-yl)oxazole-4-carboxylic acid (C1165);
6-(6-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1166);
6-(4-methoxyoxazolo[4,5-c]pyridin-2-yl)-5-methyl-7-oxo-3-phenyl-4,7-dihydropyrazolo[1,5-a]pyrimidine-2-carbonitrile (C1167);
5-cyclohexyl-2-(5-methyl-7-oxo-3-phenyl-2-(trifluoromethyl)-4,7-dihydropyrazolo[1,5-a]pyrimidin-6-yl)oxazole-4-carboxylic acid (C1169);
5-methyl-6-(oxazol-2-yl)-3-phenyl-2-(trifluoromethyl)pyrazolo[1,5-a]pyrimidin-7(4H)-one (C1170);
6-(4-methoxybenzo[d]oxazol-2-yl)-5-methyl-3-(m-tolyl)-2-(trifluoromethyl)pyrazolo[1,5-a]pyrimidin-7(4H)-one (C1172);
3-(6-(4-methoxybenzo[d]oxazol-2-yl)-7-oxo-3-phenyl-2-(trifluoromethyl)-4,7-dihydropyrazolo[1,5-a]pyrimidin-5-yl)propanoic acid (C1173);
6-(5-amino-7-methoxyoxazolo[5,4-d]pyrimidin-2-yl)-5-methyl-3-phenyl-2-(trifluoromethyl)pyrazolo[1,5-a]pyrimidin-7(4H)-one (C1174);
6-(6-amino-4-methoxybenzo[d]oxazol-2-yl)-5-methyl-7-oxo-3-phenyl-4,7-dihydropyrazolo[1,5-a]pyrimidine-2-carbonitrile (C1175);
5-(((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)methyl)oxazolidin-2-one (C1177);
N-(2-hydroxyethyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1178);
5-((1H-imidazol-1-yl)methyl)-6-(4-methoxybenzo[d]oxazol-2-yl)-3-phenyl-2-(trifluoromethyl)pyrazolo[1,5-a]pyrimidin-7(4H)-one (C1180);
6-(5-aminobenzo[d]oxazol-2-yl)-5-methyl-7-oxo-3-phenyl-4,7-dihydropyrazolo[1,5-a]pyrimidine-2-carbonitrile (C1181);
5-(((1H-imidazol-5-yl)methoxy)methyl)-6-(4-methoxybenzo[d]oxazol-2-yl)-3-phenyl-2-(trifluoromethyl)pyrazolo[1,5-a]pyrimidin-7(4H)-one (C1182);
5-ethyl-6-(4-methoxybenzo[d]oxazol-2-yl)-3-phenyl-2-(trifluoromethyl)pyrazolo[1,5-a]pyrimidin-7(4H)-one (C1183);
(R)-6-(4-(methoxymethyl)-4,5-dihydrooxazol-2-yl)-5-methyl-3-phenyl-2-(trifluoromethyl)pyrazolo[1,5-a]pyrimidin-7(4H)-one (C1184);
6-(4-methoxybenzo[d]oxazol-2-yl)-N-(oxetan-3-yl)-7-oxo-3-phenyl-2-(trifluoromethyl)-4,7-dihydropyrazolo[1,5-a]pyrimidine-5-carboxamide (C1185);
methyl (S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylate (C1187);
6-(4-ethylbenzo[d]oxazol-2-yl)-5-methyl-7-oxo-3-phenyl-4,7-dihydropyrazolo[1,5-a]pyrimidine-2-carbonitrile (C1188);
(S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1192);
6-(6-aminobenzo[d]oxazol-2-yl)-5-methyl-7-oxo-3-phenyl-4,7-dihydropyrazolo[1,5-a]pyrimidine-2-carbonitrile (C1193);
6-(4-methoxybenzo[d]oxazol-2-yl)-7-oxo-3-phenyl-N-(tetrahydro-2H-pyran-4-yl)-2-(trifluoromethyl)-4,7-dihydropyrazolo[1,5-a]pyrimidine-5-carboxamide (C1194);
(6-(4-methoxybenzo[d]oxazol-2-yl)-7-oxo-3-phenyl-2-(trifluoromethyl)-4,7-dihydropyrazolo[1,5-a]pyrimidine-5-carbonyl)glycine (C1195);
(S)-N-(1-hydroxypropan-2-yl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1196);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)acetamide (C1198);
6-(6-amino-7-chloro-4-methoxybenzo[d]oxazol-2-yl)-5-methyl-7-oxo-3-phenyl-4,7-dihydropyrazolo[1,5-a]pyrimidine-2-carbonitrile (C1202);
6-(6-(hydroxymethyl)-4-methoxybenzo[d]oxazol-2-yl)-5-methyl-7-oxo-3-phenyl-4,7-dihydropyrazolo[1,5-a]pyrimidine-2-carbonitrile (C1203);
5-methyl-6-(4-(methylthio)benzo[d]oxazol-2-yl)-7-oxo-3-phenyl-4,7-dihydropyrazolo[1,5-a]pyrimidine-2-carbonitrile (C1204);
6-(7-chloro-4-methoxybenzo[d]oxazol-2-yl)-5-methyl-7-oxo-3-phenyl-4,7-dihydropyrazolo[1,5-a]pyrimidine-2-carbonitrile (C1205);
6-(5-chloro-4-methoxybenzo[d]oxazol-2-yl)-5-methyl-7-oxo-3-phenyl-4,7-dihydropyrazolo[1,5-a]pyrimidine-2-carbonitrile (C1206);
6-(4-methoxybenzo[d]oxazol-2-yl)-7-oxo-3-phenyl-N-(3,3,3-trifluoro-2-hydroxypropyl)-2-(trifluoromethyl)-4,7-dihydropyrazolo[1,5-a]pyrimidine-5-carboxamide (C1209);
2-acetyl-6-(4-methoxybenzo[d]oxazol-2-yl)-5-methyl-3-phenylpyrazolo[1,5-a]pyrimidin-7(4H)-one (C1210);
2-ethynyl-6-(4-methoxybenzo[d]oxazol-2-yl)-5-methyl-3-phenylpyrazolo[1,5-a]pyrimidin-7(4H)-one (C1211);
(4R,5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1213);
(5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1216);
6-(6-amino-4-methoxyoxazolo[4,5-c]pyridin-2-yl)-5-methyl-7-oxo-3-phenyl-4,7-dihydropyrazolo[1,5-a]pyrimidine-2-carbonitrile (C1218);
N-(2-hydroxy-2-methylpropyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1219);
6-(benzo[d]oxazol-2-yl)-5-methyl-7-oxo-3-phenyl-4,7-dihydropyrazolo[1,5-a]pyrimidine-2-carbonitrile (C1222);
6-(4-aminobenzo[d]oxazol-2-yl)-5-methyl-7-oxo-3-phenyl-4,7-dihydropyrazolo[1,5-a]pyrimidine-2-carbonitrile (C1223);

-continued 6-(7-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1224);
6-(4-methoxybenzo[d]oxazol-2-yl)-5-(((1-methyl-2-oxopyrrolidin-3-yl)oxy)methyl)-3-phenyl-2-(trifluoromethyl)pyrazolo[1,5-a]pyrimidin-7(4H)-one (C1225);
5-((2-hydroxyethoxy)methyl)-6-(4-methoxybenzo[d]oxazol-2-yl)-3-phenyl-2-(trifluoromethyl)pyrazolo[1,5-a]pyrimidin-7(4H)-one (C1226);
6-(6-amino-4-methoxyoxazolo[4,5-c]pyridin-2-yl)-5-(methoxymethyl)-7-oxo-3-phenyl-4,7-dihydropyrazolo[1,5-a]pyrimidine-2-carbonitrile (C1227);
6-(7-aminobenzo[d]oxazol-2-yl)-5-methyl-7-oxo-3-phenyl-4,7-dihydropyrazolo[1,5-a]pyrimidine-2-carbonitrile (C1230);
5-((2,2-difluoroethoxy)methyl)-6-(4-methoxybenzo[d]oxazol-2-yl)-3-phenyl-2-(trifluoromethyl)pyrazolo[1,5-a]pyrimidin-7(4H)-one (C1232);
ethyl 4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylate (C1233);
4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylic acid (C1234);
5-(3-(hydroxymethyl)cyclopentyl)-6-(4-methoxybenzo[d]oxazol-2-yl)-3-phenyl-2-(trifluoromethyl)pyrazolo[1,5-a]pyrimidin-7(4H)-one (C1236);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclopentane-1-carboxylic acid (C1239);
6-(6-(1-hydroxyethyl)-4-methoxybenzo[d]oxazol-2-yl)-5-methyl-7-oxo-3-phenyl-4,7-dihydropyrazolo[1,5-a]pyrimidine-2-carbonitrile (C1240);
6-(4-methoxybenzo[d]oxazol-2-yl)-5-methyl-3-phenyl-2-vinylpyrazolo[1,5-a]pyrimidin-7(4H)-one (C1241);
6-(4-methoxybenzo[d]oxazol-2-yl)-5-((2-methoxyethoxy)methyl)-7-oxo-3-phenyl-4,7-dihydropyrazolo[1,5-a]pyrimidine-2-carbonitrile (C1243);
6-(4-methoxybenzo[d]oxazol-2-yl)-7-oxo-3-phenyl-N-(1H-pyrazol-4-yl)-2-(trifluoromethyl)-4,7-dihydropyrazolo[1,5-a]pyrimidine-5-carboxamide (C1244);
N-((1H-pyrazol-3-yl)methyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1245);
5-(methoxymethyl)-6-(4-methoxyoxazolo[4,5-c]pyridin-2-yl)-7-oxo-3-phenyl-4,7-dihydropyrazolo[1,5-a]pyrimidine-2-carbonitrile (C1246);
5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1247);
5-((2-hydroxyethoxy)methyl)-6-(4-methoxybenzo[d]oxazol-2-yl)-7-oxo-3-phenyl-4,7-dihydropyrazolo[1,5-a]pyrimidine-2-carbonitrile (C1248);
2-cyano-6-(4-methoxybenzo[d]oxazol-2-yl)-7-oxo-3-phenyl-4,7-dihydropyrazolo[1,5-a]pyrimidine-5-carboxylic acid (C1249);
6-(5-amino-4-methoxybenzo[d]oxazol-2-yl)-5-methyl-7-oxo-3-phenyl-4,7-dihydropyrazolo[1,5-a]pyrimidine-2-carbonitrile (C1250);
6-(4-methoxybenzo[d]oxazol-2-yl)-7-oxo-5-(((2-oxooxazolidin-5-yl)methoxy)methyl)-3-phenyl-4,7-dihydropyrazolo[1,5-a]pyrimidine-2-carbonitrile (C1251);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclobutane-1-carboxylic acid (C1252);
6-(4-methoxybenzo[d]oxazol-2-yl)-5-(3-methylisoxazol-4-yl)-3-phenyl-2-(trifluoromethyl)pyrazolo[1,5-a]pyrimidin-7(4H)-one (C1253);
6-(4-methoxybenzo[d]oxazol-2-yl)-3-phenyl-5-(1H-pyrazol-4-yl)-2-(trifluoromethyl)pyrazolo[1,5-a]pyrimidin-7(4H)-one (C1254);
6-(4-methoxybenzo[d]oxazol-2-yl)-5-(1-methyl-1H-pyrazol-4-yl)-3-phenyl-2-(trifluoromethyl)pyrazolo[1,5-a]pyrimidin-7(4H)-one (C1255);
6-(4-methoxybenzo[d]oxazol-2-yl)-N-(1-methyl-1H-pyrazol-3-yl)-7-oxo-3-phenyl-2-(trifluoromethyl)-4,7-dihydropyrazolo[1,5-a]pyrimidine-5-carboxamide (C1256);
1-(6-(4-methoxybenzo[d]oxazol-2-yl)-7-oxo-3-phenyl-2-(trifluoromethyl)-4,7-dihydropyrazolo[1,5-a]pyrimidin-5-yl)piperidine-3-carboxylic acid (C1257);
6-(4-methoxybenzo[d]oxazol-2-yl)-5-morpholino-3-phenyl-2-(trifluoromethyl)pyrazolo[1,5-a]pyrimidin-7(4H)-one (C1258);
6-(4-methoxybenzo[d]oxazol-2-yl)-5-((oxetan-3-yloxy)methyl)-7-oxo-3-phenyl-4,7-dihydropyrazolo[1,5-a]pyrimidine-2-carbonitrile (C1259);
5-methyl-6-(oxazol-2-yl)-7-oxo-3-phenyl-4,7-dihydropyrazolo[1,5-a]pyrimidine-2-carbonitrile (C1270);
6-(6-amino-7-chlorobenzo[d]oxazol-2-yl)-5-methyl-7-oxo-3-phenyl-4,7-dihydropyrazolo[1,5-a]pyrimidine-2-carbonitrile (C1271);
6-(4-(dimethylamino)benzo[d]oxazol-2-yl)-5-methyl-7-oxo-3-phenyl-4,7-dihydropyrazolo[1,5-a]pyrimidine-2-carbonitrile (C1272);
5-methyl-7-oxo-3,6-diphenyl-4,7-dihydropyrazolo[1,5-a]pyrimidine-2-carbonitrile (C1273);
5-methyl-6-(4-(methylamino)benzo[d]oxazol-2-yl)-7-oxo-3-phenyl-4,7-dihydropyrazolo[1,5-a]pyrimidine-2-carbonitrile (C1274);
5-methyl-6-(oxazolo[4,5-c]pyridin-2-yl)-7-oxo-3-phenyl-4,7-dihydropyrazolo[1,5-a]pyrimidine-2-carbonitrile (C1275);
6-(1-cyclohexyl-1H-benzo[d]imidazol-2-yl)-5-methyl-7-oxo-3-phenyl-4,7-dihydropyrazolo[1,5-a]pyrimidine-2-carbonitrile (C1276);
6-(4-cyclopropoxybenzo[d]oxazol-2-yl)-5-methyl-7-oxo-3-phenyl-4,7-dihydropyrazolo[1,5-a]pyrimidine-2-carbonitrile (C1277);
5-(dimethylphosphoryl)-6-(4-methoxybenzo[d]oxazol-2-yl)-3-phenyl-2-(trifluoromethyl)pyrazolo[1,5-a]pyrimidin-7(4H)-one (C1284);
6-(5-cyclopentyl-1,3,4-oxadiazol-2-yl)-5-methyl-3-phenyl-2-(trifluoromethyl)pyrazolo[1,5-a]pyrimidin-7(4H)-one (D1003);
6-(5-cyclohexyl-1,3,4-oxadiazol-2-yl)-5-methyl-3-phenyl-2-(trifluoromethyl)pyrazolo[1,5- a]pyrimidin-7(4H)-one (D1004);
6-(5-cyclohexyl-1,3,4-thiadiazol-2-yl)-5-methyl-3-phenyl-2-(trifluoromethyl)pyrazolo[1,5-a]pyrimidin-7(4H)-one (D1006);
5-methyl-3-phenyl-6-(5-(tetrahydrofuran-2-yl)-1,3,4-oxadiazol-2-yl)-2-(trifluoromethyl)pyrazolo[1,5-a]pyrimidin-7(4H)-one (D1012);
5-methyl-3-phenyl-6-(5-(pyrrolidin-1-yl)-1,3,4-oxadiazol-2-yl)-2-(trifluoromethyl)pyrazolo[1,5-a]pyrimidin-7(4H)-one (D1014);
5-methyl-3-phenyl-6-(5-(tetrahydro-2H-pyran-4-yl)-1,3,4-oxadiazol-2-yl)-2-(trifluoromethyl)pyrazolo[1,5-a]pyrimidin-7(4H)-one (D1016);
6-(5-cyclopentyl-1,3,4-oxadiazol-2-yl)-5-(methoxymethyl)-3-phenyl-2-(trifluoromethyl)pyrazolo[1,5-a]pyrimidin-7(4H)-one (D1018);
6-(5-(methoxymethyl)-1,3,4-oxadiazol-2-yl)-5-methyl-3-phenyl-2-(trifluoromethyl)pyrazolo[1,5-a]pyrimidin-7(4H)-one (D1019);
5-methyl-3-phenyl-6-(5-(piperidin-1-yl)-1,3,4-oxadiazol-2-yl)-2-(trifluoromethyl)pyrazolo[1,5-a]pyrimidin-7(4H)-one (D1020);
6-(5-(3-methoxycyclohexyl)-1,3,4-oxadiazol-2-yl)-5-methyl-3-phenyl-2-(trifluoromethyl)pyrazolo[1,5-a]pyrimidin-7(4H)-one (isomers 1 and 2) (D1021);
5-methyl-6-(5-(2-methylpyrrolidin-1-yl)-1,3,4-oxadiazol-2-yl)-3-phenyl-2-(trifluoromethyl)pyrazolo[1,5-a]pyrimidin-7(4H)-one (D1022);
5-methyl-6-(5-(1-methylcyclopentyl)-1,3,4-oxadiazol-2-yl)-3-phenyl-2-(trifluoromethyl)pyrazolo[1,5-a]pyrimidin-7(4H)-one (D1023);
5-methyl-3-phenyl-6-(5-(tetrahydro-2H-pyran-2-yl)-1,3,4-oxadiazol-2-yl)-2-(trifluoromethyl)pyrazolo[1,5-a]pyrimidin-7(4H)-one (D1024);
(S)-5-methyl-3-phenyl-6-(5-(tetrahydro-2H-pyran-3-yl)-1,3,4-oxadiazol-2-yl)-2-(trifluoromethyl)pyrazolo[1,5-a]pyrimidin-7(4H)-one (D1025);
(R)-5-methyl-3-phenyl-6-(5-(tetrahydro-2H-pyran-3-yl)-1,3,4-oxadiazol-2-yl)-2-(trifluoromethyl)pyrazolo[1,5-a]pyrimidin-7(4H)-one (D1026);
6-(5-(3-methoxypiperidin-1-yl)-1,3,4-oxadiazol-2-yl)-5-methyl-3-phenyl-2-(trifluoromethyl)pyrazolo[1,5-a]pyrimidin-7(4H)-one (D1027);
(S)-5-methyl-3-phenyl-6-(5-(2,2,2-trifluoro-1-methoxy-1-phenylethyl)-1,3,4-oxadiazol-2-yl)-2-(trifluoromethyl)pyrazolo[1,5-a]pyrimidin-7(4H)-one (D1028);
(R)-5-methyl-3-phenyl-6-(5-(2,2,2-trifluoro-1-methoxy-1-phenylethyl)-1,3,4-oxadiazol-2-yl)-2-(trifluoromethyl)pyrazolo[1,5-a]pyrimidin-7(4H)-one (D1029);
2,5-dimethyl-3-phenyl-6-(5-(tetrahydro-2H-pyran-3-yl)-1,3,4-oxadiazol-2-yl)pyrazolo[1,5-a]pyrimidin-7(4H)-one (D1030);
5-methyl-6-((5-methyl-1,3,4-oxadiazol-2-yl)methyl)-3-phenyl-2-(trifluoromethyl)pyrazolo[1,5-a]pyrimidin-7(4H)-one (D1032);
6-(5-(3-methoxypyrrolidin-1-yl)-1,3,4-oxadiazol-2-yl)-5-methyl-3-phenyl-2-(trifluoromethyl)pyrazolo[1,5-a]pyrimidin-7(4H)-one (D1037);
5-methyl-3-phenyl-2-(trifluoromethyl)-6-(5-(1-(trifluoromethyl)cyclopropyl)-1,3,4-oxadiazol-2-yl)pyrazolo[1,5-a]pyrimidin-7(4H)-one (D1038);
5-methyl-6-(5-(1-(methylsulfonyl)piperidin-3-yl)-1,3,4-oxadiazol-2-yl)-3-phenyl-2-(trifluoromethyl)pyrazolo[1,5-a]pyrimidin-7(4H)-one (D1040);
6-(5-(2-methoxycyclohexyl)-1,3,4-oxadiazol-2-yl)-5-methyl-3-phenyl-2-(trifluoromethyl)pyrazolo[1,5-a]pyrimidin-7(4H)-one (Isomers 1, 2 and 3) (D1046);
5-methyl-6-(5-(4-(methylsulfonyl)morpholin-3-yl)-1,3,4-oxadiazol-2-yl)-3-phenyl-2-(trifluoromethyl)pyrazolo[1,5-a]pyrimidin-7(4H)-one (D1047);
6-(5-(2-methoxycyclopentyl)-1,3,4-oxadiazol-2-yl)-5-methyl-3-phenyl-2-(trifluoromethyl)pyrazolo[1,5-a]pyrimidin-7(4H)-one (Isomers 1 and 2) (D1049);
5-methyl-6-(5-(3-methyltetrahydro-2H-pyran-3-yl)-1,3,4-oxadiazol-2-yl)-3-phenyl-2-(trifluoromethyl)pyrazolo[1,5-a]pyrimidin-7(4H)-one (D1051);
6-(5-(1-methoxycyclopentyl)-1,3,4-oxadiazol-2-yl)-5-methyl-3-phenyl-2-(trifluoromethyl)pyrazolo[1,5-a]pyrimidin-7(4H)-one (D1055);
5-methyl-6-(5-(1-(methylsulfonyl)piperidin-2-yl)-1,3,4-oxadiazol-2-yl)-3-phenyl-2-(trifluoromethyl)pyrazolo[1,5-a]pyrimidin-7(4H)-one (D1056);
6-(5-(1-acetylpiperidin-2-yl)-1,3,4-oxadiazol-2-yl)-5-methyl-3-phenyl-2-(trifluoromethyl)pyrazolo[1,5-a]pyrimidin-7(4H)-one (D1057);
6-(5-(1-aminocyclopentyl)-1,3,4-oxadiazol-2-yl)-5-methyl-3-phenyl-2-(trifluoromethyl)pyrazolo[1,5-a]pyrimidin-7(4H)-one (D1062);
5-(5-methyl-7-oxo-3-phenyl-2-(trifluoromethyl)-4,7-dihydropyrazolo[1,5-a]pyrimidin-6-yl)-1,3,4-oxadiazole-2-carboxamide (D1066);
6-(5-(2-hydroxypyridin-3-yl)-1,3,4-oxadiazol-2-yl)-5-methyl-3-phenyl-2-(trifluoromethyl)pyrazolo[1,5-a]pyrimidin-7(4H)-one (D1067);
6-(5-(2-(aminomethyl)piperidin-1-yl)-1,3,4-oxadiazol-2-yl)-5-methyl-3-phenyl-2-(trifluoromethyl)pyrazolo[1,5-a]pyrimidin-7(4H)-one (D1070);
5-(5-methyl-7-oxo-3-phenyl-2-(trifluoromethyl)-4,7-dihydropyrazolo[1,5-a]pyrimidin-6-yl)-1,3,4-oxadiazole-2-carbonitrile (D1071);
5-methyl-3-phenyl-6-(5-(1,4,5,6-tetrahydropyrimidin-2-yl)-1,3,4-oxadiazol-2-yl)-2-(trifluoromethyl)pyrazolo[1,5-a]pyrimidin-7(4H)-one (D1072);
N-(2-(1-(5-(5-methyl-7-oxo-3-phenyl-2-(trifluoromethyl)-4,7-dihydropyrazolo[1,5-a]pyrimidin-6-yl)-1,3,4-oxadiazol-2-yl)piperidin-2-yl)ethyl)methanesulfonamide (D1073);
5-(5-methyl-7-oxo-3-phenyl-2-(trifluoromethyl)-4,7-dihydropyrazolo[1,5-a]pyrimidin-6-yl)-1,3,4-oxadiazole-2-carboximidamide (D1074);
1-(5-(5-methyl-7-oxo-3-phenyl-2-(trifluoromethyl)-4,7-dihydropyrazolo[1,5-a]pyrimidin-6-yl)-1,3,4-oxadiazol-2-yl)guanidine (D1077);
6-(5-(4-hydroxypyrimidin-2-yl)-1,3,4-oxadiazol-2-yl)-5-methyl-3-phenyl-2-(trifluoromethyl)pyrazolo[1,5-a]pyrimidin-7(4H)-one (D1078);
6-(5-(3-aminopiperidin-1-yl)-1,3,4-oxadiazol-2-yl)-5-methyl-3-phenyl-2-(trifluoromethyl)pyrazolo[1,5-a]pyrimidin-7(4H)-one (D1084);

-continued 6-(5-(2-hydroxypyridin-4-yl)-1,3,4-oxadiazol-2-yl)-5-methyl-3-phenyl-2-(trifluoromethyl)pyrazolo[1,5-a]pyrimidin-7(4H)-one (D1085);
6-(5-(6-hydroxypyridin-2-yl)-1,3,4-oxadiazol-2-yl)-5-methyl-3-phenyl-2-(trifluoromethyl)pyrazolo[1,5-a]pyrimidin-7(4H)-one (D1086);
6-(5-cyclohexyl-1,3,4-oxadiazol-2-yl)-5-methyl-7-oxo-3-phenyl-4,7-dihydropyrazolo[1,5-a]pyrimidine-2-carbonitrile (D1089); and
6-(4-methoxybenzo[d]oxazol-2-yl)-5-methyl-3-phenyl-[1,2,3]triazolo[1,5-a]pyrimidin-7(4H)-one (E1001);

or a pharmaceutically acceptable salt, solvate or hydrate thereof.

In one embodiment, the compound is selected from the group consisting of

N-(2-(5-methyl-7-oxo-3-phenyl-2-(trifluoromethyl)-4,7-dihydropyrazolo[1,5-a]pyrimidin-6-yl)-1H-benzo[d]imidazol-7-yl)acetamide (C1009);
6-(4-methoxybenzo[d]oxazol-2-yl)-5-methyl-3-phenyl-2-(trifluoromethyl)pyrazolo[1,5-a]pyrimidin-7(4H)-one (C1014);
6-(5-methoxy-1H-benzo[d]imidazol-2-yl)-5-methyl-3-phenyl-2-(trifluoromethyl)pyrazolo[1,5-a]pyrimidin-7(4H)-one (C1016);
5-methyl-3-phenyl-6-(4,5,6,7-tetrahydro-1H-benzo[d]imidazol-2-yl)-2-(trifluoromethyl)pyrazolo[1,5-a]pyrimidin-7(4H)-one (C1017);
6-(4-methoxy-1H-benzo[d]imidazol-2-yl)-5-methyl-3-phenyl-2-(trifluoromethyl)pyrazolo[1,5-a]pyrimidin-7(4H)-one (C1018);
2-(5-methyl-7-oxo-3-phenyl-2-(trifluoromethyl)-4,7-dihydropyrazolo[1,5-a]pyrimidin-6-yl)quinazolin-4(3H)-one (C1019);
6-(7-methoxybenzo[d]oxazol-2-yl)-5-methyl-3-phenyl-2-(trifluoromethyl)pyrazolo[1,5-a]pyrimidin-7(4H)-one (C1022);
3-isopropyl-5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1023);
5-methoxy-2-(5-methyl-7-oxo-3-phenyl-2-(trifluoromethyl)-4,7-dihydropyrazolo[1,5-a]pyrimidin-6-yl)quinazolin-4(3H)-one (C1024);
8-methoxy-2-(5-methyl-7-oxo-3-phenyl-2-(trifluoromethyl)-4,7-dihydropyrazolo[1,5-a]pyrimidin-6-yl)quinazolin-4(3H)-one (C1025);
5-methyl-3-phenyl-6-(5-(tetrahydro-2H-pyran-3-yl)oxazol-2-yl)-2-(trifluoromethyl)pyrazolo[1,5-a]pyrimidin-7(4H)-one (C1027);
5-methyl-6-(oxazolo[4,5-b]pyridin-2-yl)-3-phenyl-2-(trifluoromethyl)pyrazolo[1,5-a]pyrimidin-7(4H)-one (C1030);
2,5-dimethyl-3-phenyl-6-(4,5,6,7-tetrahydrobenzo[d]oxazol-2-yl)pyrazolo[1,5-a]pyrimidin-7(4H)-one (C1032);
2-(5-methyl-7-oxo-3-phenyl-2-(trifluoromethyl)-4,7-dihydropyrazolo[1,5-a]pyrimidin-6-yl)-6,7-dihydrobenzo[d]oxazol-4(5H)-one (C1033);
6-(4-methoxyoxazolo[4,5-c]pyridin-2-yl)-5-methyl-3-phenyl-2-(trifluoromethyl)pyrazolo[1,5-a]pyrimidin-7(4H)-one (C1037);
6-(4-ethoxybenzo[d]oxazol-2-yl)-5-methyl-3-phenyl-2-(trifluoromethyl)pyrazolo[1,5-a]pyrimidin-7(4H)-one (C1038);
6-(4-isopropoxybenzo[d]oxazol-2-yl)-5-methyl-3-phenyl-2-(trifluoromethyl)pyrazolo[1,5-a]pyrimidin-7(4H)-one (C1039);
6-(4-bromobenzo[d]oxazol-2-yl)-5-methyl-3-phenyl-2-(trifluoromethyl)pyrazolo[1,5-a]pyrimidin-7(4H)-one (C1040);
6-(4-(2-methoxyethoxy)benzo[d]oxazol-2-yl)-5-methyl-3-phenyl-2-(trifluoromethyl)pyrazolo[1,5-a]pyrimidin-7(4H)-one (C1041);
6-(4-methoxybenzo[d]oxazol-2-yl)-2,5-dimethyl-3-phenylpyrazolo[1,5-a]pyrimidin-7(4H)-one (C1042);
6-(8-methoxyimidazo[1,2-a]pyridin-2-yl)-5-methyl-3-phenyl-2-(trifluoromethyl)pyrazolo[1,5-a]pyrimidin-7(4H)-one (C1044);
6-(4-(cyclopropylmethoxy)benzo[d]oxazol-2-yl)-5-methyl-3-phenyl-2-(trifluoromethyl)pyrazolo[1,5-a]pyrimidin-7(4H)-one (C1045);
6-(4-ethylbenzo[d]oxazol-2-yl)-5-methyl-3-phenyl-2-(trifluoromethyl)pyrazolo[1,5-a]pyrimidin-7(4H)-one (C1046);
5-methyl-6-(4-(methylthio)benzo[d]oxazol-2-yl)-3-phenyl-2-(trifluoromethyl)pyrazolo[1,5-a]pyrimidin-7(4H)-one (C1047);
6-(4-methoxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1048);
2-(difluoromethyl)-6-(4-methoxybenzo[d]oxazol-2-yl)-5-methyl-3-phenylpyrazolo[1,5-a]pyrimidin-7(4H)-one (C1050);
6-(4-methoxybenzo[d]oxazol-2-yl)-5-methyl-7-oxo-3-phenyl-4,7-dihydropyrazolo[1,5-a]pyrimidine-2-carbonitrile (C1051);
6-(4-hydroxy-4,5,6,7-tetrahydrobenzo[d]oxazol-2-yl)-5-methyl-3-phenyl-2-(trifluoromethyl)pyrazolo[1,5-a]pyrimidin-7(4H)-one (C1052);
6-(4-hydroxybenzo[d]oxazol-2-yl)-5-methyl-3-phenyl-2-(trifluoromethyl)pyrazolo[1,5-a]pyrimidin-7(4H)-one (C1053);
6-(4-chlorobenzo[d]oxazol-2-yl)-5-methyl-3-phenyl-2-(trifluoromethyl)pyrazolo[1,5-a]pyrimidin-7(4H)-one (C1055);
6-(4-methoxybenzo[d]oxazol-2-yl)-5-(methoxymethyl)-3-phenyl-2-(trifluoromethyl)pyrazolo[1,5-a]pyrimidin-7(4H)-one (C1056);
6-(5-methoxyimidazo[1,2-a]pyridin-2-yl)-5-methyl-3-phenyl-2-(trifluoromethyl)pyrazolo[1,5-a]pyrimidin-7(4H)-one (C1057);

-continued 6-(7-methoxyoxazolo[5,4-b]pyridin-2-yl)-5-methyl-3-phenyl-2-(trifluoromethyl)pyrazolo[1,5-a]pyrimidin-7(4H)-one (C1058);
2-(5-methyl-7-oxo-3-phenyl-2-(trifluoromethyl)-4,7-dihydropyrazolo[1,5-a]pyrimidin-6-yl)-5,6,7,8-tetrahydro-4H-oxazolo[4,5-c]azepin-4-one (C1059);
5-methyl-6-(4-methylbenzo[d]oxazol-2-yl)-3-phenyl-2-(trifluoromethyl)pyrazolo[1,5-a]pyrimidin-7(4H)-one (C1060);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)acetamide (C1062);
N-(2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)ethyl)methanesulfonamide (C1066);
6-(4-methoxybenzo[d]thiazol-2-yl)-5-methyl-3-phenyl-2-(trifluoromethyl)pyrazolo[1,5-a]pyrimidin-7(4H)-one (C1070);
5-chloro-6-(4-methoxybenzo[d]oxazol-2-yl)-3-phenyl-2-(trifluoromethyl)pyrazolo[1,5-a]pyrimidin-7(4H)-one (C1071);
6-(4-(benzyloxy)benzo[d]oxazol-2-yl)-5-methyl-3-phenyl-2-(trifluoromethyl)pyrazolo[1,5-a]pyrimidin-7(4H)-one (C1073);
2-(5-methyl-7-oxo-3-phenyl-2-(trifluoromethyl)-4,7-dihydropyrazolo[1,5-a]pyrimidin-6-yl)benzo[d]oxazole-4-carbonitrile (C1075);
6-(4-fluorobenzo[d]oxazol-2-yl)-5-methyl-3-phenyl-2-(trifluoromethyl)pyrazolo[1,5-a]pyrimidin-7(4H)-one (C1076);
6-(4-methoxybenzo[d]oxazol-2-yl)-3-phenyl-2,5-bis(trifluoromethyl)pyrazolo[1,5-a]pyrimidin-7(4H)-one (C1077);
6-(4-(dimethylamino)benzo[d]oxazol-2-yl)-5-methyl-3-phenyl-2-(trifluoromethyl)pyrazolo[1,5-a]pyrimidin-7(4H)-one (C1078);
6-(7-bromo-4-methoxybenzo[d]oxazol-2-yl)-5-methyl-3-phenyl-2-(trifluoromethyl)pyrazolo[1,5-a]pyrimidin-7(4H)-one (C1081);
6-(5-bromo-4-methoxybenzo[d]oxazol-2-yl)-5-methyl-3-phenyl-2-(trifluoromethyl)pyrazolo[1,5-a]pyrimidin-7(4H)-one (C1082);
5-methoxy-6-(4-methoxybenzo[d]oxazol-2-yl)-3-phenyl-2-(trifluoromethyl)pyrazolo[1,5-a]pyrimidin-7(4H)-one (C1084);
5-amino-6-(4-methoxybenzo[d]oxazol-2-yl)-3-phenyl-2-(trifluoromethyl)pyrazolo[1,5-a]pyrimidin-7(4H)-one (C1085);
2-(5-methyl-7-oxo-3-phenyl-2-(trifluoromethyl)-4,7-dihydropyrazolo[1,5-a]pyrimidin-6-yl)benzo[d]oxazol-4-yl dimethylcarbamate (C1088);
6-(4-methoxybenzo[d]oxazol-2-yl)-7-oxo-3-phenyl-2-(trifluoromethyl)-4,7-dihydropyrazolo[1,5-a]pyrimidine-5-carbonitrile (C1089);
3-(2-fluorophenyl)-6-(4-methoxybenzo[d]oxazol-2-yl)-5-methyl-2-(trifluoromethyl)pyrazolo[1,5-a]pyrimidin-7(4H)-one (C1091);
6-(4-methoxy-7-methylbenzo[d]oxazol-2-yl)-5-methyl-3-phenyl-2-(trifluoromethyl)pyrazolo[1,5-a]pyrimidin-7(4H)-one (C1092);
6-(4-methoxy-5-methylbenzo[d]oxazol-2-yl)-5-methyl-3-phenyl-2-(trifluoromethyl)pyrazolo[1,5-a]pyrimidin-7(4H)-one (C1093);
6-(7-chloro-4-methoxybenzo[d]oxazol-2-yl)-5-methyl-3-phenyl-2-(trifluoromethyl)pyrazolo[1,5-a]pyrimidin-7(4H)-one (C1094);
6-(5-chloro-4-methoxybenzo[d]oxazol-2-yl)-5-methyl-3-phenyl-2-(trifluoromethyl)pyrazolo[1,5-a]pyrimidin-7(4H)-one (C1095);
6-(7-methoxyoxazolo[5,4-c]pyridin-2-yl)-5-methyl-3-phenyl-2-(trifluoromethyl)pyrazolo[1,5-a]pyrimidin-7(4H)-one (C1096);
5-methyl-6-(4-(methylsulfinyl)benzo[d]oxazol-2-yl)-3-phenyl-2-(trifluoromethyl)pyrazolo[1,5-a]pyrimidin-7(4H)-one (C1097);
6-(4-methoxy-6-methylbenzo[d]oxazol-2-yl)-5-methyl-3-phenyl-2-(trifluoromethyl)pyrazolo[1,5-a]pyrimidin-7(4H)-one (C1098);
5-((benzyloxy)methyl)-6-(4-methoxybenzo[d]oxazol-2-yl)-3-phenyl-2-(trifluoromethyl)pyrazolo[1,5-a]pyrimidin-7(4H)-one (C1099);
4-methoxy-2-(5-methyl-7-oxo-3-phenyl-2-(trifluoromethyl)-4,7-dihydropyrazolo[1,5-a]pyrimidin-6-yl)benzo[d]oxazole-7-carbonitrile (C1100);
ethyl 2-(5-methyl-7-oxo-3-phenyl-2-(trifluoromethyl)-4,7-dihydropyrazolo[1,5-a]pyrimidin-6-yl)oxazole-4-carboxylate (C1101);
2-(5-methyl-7-oxo-3-phenyl-2-(trifluoromethyl)-4,7-dihydropyrazolo[1,5-a]pyrimidin-6-yl)oxazole-4-carboxamide (C1102);
5-(hydroxymethyl)-6-(4-methoxybenzo[d]oxazol-2-yl)-3-phenyl-2-(trifluoromethyl)pyrazolo[1,5-a]pyrimidin-7(4H)-one (C1103);
6-(4-(hydroxymethyl)oxazol-2-yl)-5-methyl-3-phenyl-2-(trifluoromethyl)pyrazolo[1,5-a]pyrimidin-7(4H)-one (C1104);
6-(6-chloro-4-methoxybenzo[d]oxazol-2-yl)-5-methyl-3-phenyl-2-(trifluoromethyl)pyrazolo[1,5-a]pyrimidin-7(4H)-one (C1105);
5-methyl-2-(5-methyl-7-oxo-3-phenyl-2-(trifluoromethyl)-4,7-dihydropyrazolo[1,5-a]pyrimidin-6-yl)oxazolo[4,5-c]pyridin-4(5H)-one (C1106);
6-(4-(methoxymethyl)oxazol-2-yl)-5-methyl-3-phenyl-2-(trifluoromethyl)pyrazolo[1,5-a]pyrimidin-7(4H)-one (C1108);
5-((dimethylamino)methyl)-6-(4-methoxybenzo[d]oxazol-2-yl)-3-phenyl-2-(trifluoromethyl)pyrazolo[1,5-a]pyrimidin-7(4H)-one (C1109);
6-(7-acetyl-4-methoxybenzo[d]oxazol-2-yl)-5-methyl-3-phenyl-2-(trifluoromethyl)pyrazolo[1,5-a]pyrimidin-7(4H)-one (C1111);
4-methoxy-2-(5-methyl-7-oxo-3-phenyl-2-(trifluoromethyl)-4,7-dihydropyrazolo[1,5-a]pyrimidin-6-yl)benzo[d]oxazole-7-carboxamide (C1113);
3-(3-fluorophenyl)-6-(4-methoxybenzo[d]oxazol-2-yl)-5-methyl-2-(trifluoromethyl)pyrazolo[1,5-a]pyrimidin-7(4H)-one (C1114);
2-(5-methyl-7-oxo-3-phenyl-2-(trifluoromethyl)-4,7-dihydropyrazolo[1,5-a]pyrimidin-6- yl)oxazolo[4,5-c]pyridin-4(5H)-one (C1116);
2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)acetic acid (C1117);
6-(4-methoxybenzo[d]oxazol-2-yl)-7-oxo-3-phenyl-5-(trifluoromethyl)-4,7-dihydropyrazolo[1,5-a]pyrimidine-2-carbonitrile (C1118);
3-(3,5-difluorophenyl)-6-(4-methoxybenzo[d]oxazol-2-yl)-5-methyl-2-(trifluoromethyl)pyrazolo[1,5-a]pyrimidin-7(4H)-one (C1119);
6-(4-methoxybenzo[d]oxazol-2-yl)-5-(methylthio)-3-phenyl-2-(trifluoromethyl)pyrazolo[1,5-a]pyrimidin-7(4H)-one (C1121);
2-((2-(5-methyl-7-oxo-3-phenyl-2-(trifluoromethyl)-4,7-dihydropyrazolo[1,5-a]pyrimidin-6-yl)benzo[d]oxazol-4-yl)oxy)acetamide (C1122);
6-(6-amino-4-methoxybenzo[d]oxazol-2-yl)-5-methyl-3-phenyl-2-(trifluoromethyl)pyrazolo[1,5-a]pyrimidin-7(4H)-one (C1123);
6-(4-methoxy-7-(methylsulfonyl)benzo[d]oxazol-2-yl)-5-methyl-3-phenyl-2-(trifluoromethyl)pyrazolo[1,5-a]pyrimidin-7(4H)-one (C1125);
4-methoxy-2-(5-methyl-7-oxo-3-phenyl-2-(trifluoromethyl)-4,7-dihydropyrazolo[1,5-a]pyrimidin-6-yl)benzo[d]oxazole-5-carbonitrile (C1126);
6-(6-(aminomethyl)-4-methoxybenzo[d]oxazol-2-yl)-5-methyl-3-phenyl-2-(trifluoromethyl)pyrazolo[1,5-a]pyrimidin-7(4H)-one (C1128);
6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1130);
6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1131);
6-(4-methoxybenzo[d]oxazol-2-yl)-7-oxo-3-phenyl-2-(trifluoromethyl)-4,7-dihydropyrazolo[1,5-a]pyrimidine-5-carboxamide (C1132);
6-(4-methoxybenzo[d]oxazol-2-yl)-3-phenyl-5-(((tetrahydro-2H-pyran-2-yl)oxy)methyl)-2-(trifluoromethyl)pyrazolo[1,5-a]pyrimidin-7(4H)-one (C1134);
6-(6-(aminomethyl)-4-methoxybenzo[d]oxazol-2-yl)-5-methyl-3-phenyl-2-(trifluoromethyl)pyrazolo[1,5-a]pyrimidin-7(4H)-one (HCl salt) (C1135);
6-(4-methoxybenzo[d]oxazol-2-yl)-5-((methylthio)methyl)-3-phenyl-2-(trifluoromethyl)pyrazolo[1,5-a]pyrimidin-7(4H)-one (C1136);
6-(4-methoxybenzo[d]oxazol-2-yl)-5-((methylsulfinyl)methyl)-3-phenyl-2-(trifluoromethyl)pyrazolo[1,5-a]pyrimidin-7(4H)-one (C1137);
6-(4-methoxybenzo[d]oxazol-2-yl)-5-((methylsulfonyl)methyl)-3-phenyl-2-(trifluoromethyl)pyrazolo[1,5-a]pyrimidin-7(4H)-one (C1138);
6-(4-methoxybenzo[d]oxazol-2-yl)-5-(methoxymethyl)-7-oxo-3-phenyl-4,7-dihydropyrazolo[1,5-a]pyrimidine-2-carbonitrile (C1139);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboximidamide (C1141);
6-(4-methoxybenzo[d]oxazol-2-yl)-N-(2-methoxyethyl)-7-oxo-3-phenyl-2-(trifluoromethyl)-4,7-dihydropyrazolo[1,5-a]pyrimidine-5-carboxamide (C1142);
6-(4-(hydroxymethyl)-5-isopropyloxazol-2-yl)-5-methyl-3-phenyl-2-(trifluoromethyl)pyrazolo[1,5-a]pyrimidin-7(4H)-one (C1143);
6-(6-chloro-4-methoxybenzo[d]oxazol-2-yl)-5-(methoxymethyl)-7-oxo-3-phenyl-4,7-dihydropyrazolo[1,5-a]pyrimidine-2-carbonitrile (C1145);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)acetic acid (C1146);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboxamide (C1149);
6-(4-methoxybenzo[d]oxazol-2-yl)-5-((2-methoxyethoxy)methyl)-3-phenyl-2-(trifluoromethyl)pyrazolo[1,5-a]pyrimidin-7(4H)-one (C1151);
6-(4-methoxybenzo[d]oxazol-2-yl)-5-((oxetan-3-yloxy)methyl)-3-phenyl-2-(trifluoromethyl)pyrazolo[1,5-a]pyrimidin-7(4H)-one (C1152);
6-(5-isopropyl-4-(methoxymethyl)oxazol-2-yl)-5-methyl-3-phenyl-2-(trifluoromethyl)pyrazolo[1,5-a]pyrimidin-7(4H)-one (C1153);
6-(7-amino-4-methoxybenzo[d]oxazol-2-yl)-5-methyl-3-phenyl-2-(trifluoromethyl)pyrazolo[1,5-a]pyrimidin-7(4H)-one (C1154);
4-methoxy-2-(5-methyl-7-oxo-3-phenyl-2-(trifluoromethyl)-4,7-dihydropyrazolo[1,5-a]pyrimidin-6-yl)benzo[d]oxazole-6-carboxylic acid (C1155);
6-(6-aminobenzo[d]oxazol-2-yl)-5-methyl-3-phenyl-2-(trifluoromethyl)pyrazolo[1,5-a]pyrimidin-7(4H)-one (C1156);
6-(5-cyclohexyl-4-(hydroxymethyl)oxazol-2-yl)-5-methyl-3-phenyl-2-(trifluoromethyl)pyrazolo[1,5-a]pyrimidin-7(4H)-one (C1157);
6-(4-methoxybenzo[d]oxazol-2-yl)-5-(((2-oxopyrrolidin-3-yl)oxy)methyl)-3-phenyl-2-(trifluoromethyl)pyrazolo[1,5-a]pyrimidin-7(4H)-one (C1159);
6-(6-chloro-4-methoxybenzo[d]oxazol-2-yl)-5-methyl-7-oxo-3-phenyl-4,7-dihydropyrazolo[1,5-a]pyrimidine-2-carbonitrile (C1160);
6-(4-methoxy-6-(methylamino)benzo[d]oxazol-2-yl)-5-methyl-3-phenyl-2-(trifluoromethyl)pyrazolo[1,5-a]pyrimidin-7(4H)-one (C1161);
6-(6-(dimethylamino)-4-methoxybenzo[d]oxazol-2-yl)-5-methyl-3-phenyl-2-(trifluoromethyl)pyrazolo[1,5-a]pyrimidin-7(4H)-one (C1162);
4-methoxy-N,N,N-trimethyl-2-(5-methyl-7-oxo-3-phenyl-2-(trifluoromethyl)-4,7-dihydropyrazolo[1,5-a]pyrimidin-6-yl)benzo[d]oxazol-6-aminium (C1163);
2-(5-methyl-7-oxo-3-phenyl-2-(trifluoromethyl)-4,7-dihydropyrazolo[1,5-a]pyrimidin-6-yl)oxazole-4-carboxylic acid (C1165);
6-(6-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1166);
6-(4-methoxyoxazolo[4,5-c]pyridin-2-yl)-5-methyl-7-oxo-3-phenyl-4,7-dihydropyrazolo[1,5-a]pyrimidine-2-carbonitrile (C1167);

-continued 5-cyclohexyl-2-(5-methyl-7-oxo-3-phenyl-2-(trifluoromethyl)-4,7-dihydropyrazolo[1,5-a]pyrimidin-6-yl)oxazole-4-carboxylic acid (C1169);
5-methyl-6-(oxazol-2-yl)-3-phenyl-2-(trifluoromethyl)pyrazolo[1,5-a]pyrimidin-7(4H)-one (C1170);
6-(4-methoxybenzo[d]oxazol-2-yl)-5-methyl-3-(m-tolyl)-2-(trifluoromethyl)pyrazolo[1,5-a]pyrimidin-7(4H)-one (C1172);
3-(6-(4-methoxybenzo[d]oxazol-2-yl)-7-oxo-3-phenyl-2-(trifluoromethyl)-4,7-dihydropyrazolo[1,5-a]pyrimidin-5-yl)propanoic acid (C1173);
6-(5-amino-7-methoxyoxazolo[5,4-d]pyrimidin-2-yl)-5-methyl-3-phenyl-2-(trifluoromethyl)pyrazolo[1,5-a]pyrimidin-7(4H)-one (C1174);
6-(6-amino-4-methoxybenzo[d]oxazol-2-yl)-5-methyl-7-oxo-3-phenyl-4,7-dihydropyrazolo[1,5-a]pyrimidine-2-carbonitrile (C1175);
5-(((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)methyl)oxazolidin-2-one (C1177);
N-(2-hydroxyethyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1178);
5-((1H-imidazol-1-yl)methyl)-6-(4-methoxybenzo[d]oxazol-2-yl)-3-phenyl-2-(trifluoromethyl)pyrazolo[1,5-a]pyrimidin-7(4H)-one (C1180);
6-(5-aminobenzo[d]oxazol-2-yl)-5-methyl-7-oxo-3-phenyl-4,7-dihydropyrazolo[1,5-a]pyrimidine-2-carbonitrile (C1181);
5-(((1H-imidazol-5-yl)methoxy)methyl)-6-(4-methoxybenzo[d]oxazol-2-yl)-3-phenyl-2-(trifluoromethyl)pyrazolo[1,5-a]pyrimidin-7(4H)-one (C1182);
5-ethyl-6-(4-methoxybenzo[d]oxazol-2-yl)-3-phenyl-2-(trifluoromethyl)pyrazolo[1,5-a]pyrimidin-7(4H)-one (C1183);
(R)-6-(4-(methoxymethyl)-4,5-dihydrooxazol-2-yl)-5-methyl-3-phenyl-2-(trifluoromethyl)pyrazolo[1,5-a]pyrimidin-7(4H)-one (C1184);
6-(4-methoxybenzo[d]oxazol-2-yl)-N-(oxetan-3-yl)-7-oxo-3-phenyl-2-(trifluoromethyl)-4,7-dihydropyrazolo[1,5-a]pyrimidine-5-carboxamide (C1185);
methyl (S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylate (C1187);
6-(4-ethylbenzo[d]oxazol-2-yl)-5-methyl-7-oxo-3-phenyl-4,7-dihydropyrazolo[1,5-a]pyrimidine-2-carbonitrile (C1188);
(S)-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1192);
6-(6-aminobenzo[d]oxazol-2-yl)-5-methyl-7-oxo-3-phenyl-4,7-dihydropyrazolo[1,5-a]pyrimidine-2-carbonitrile (C1193);
6-(4-methoxybenzo[d]oxazol-2-yl)-7-oxo-3-phenyl-N-(tetrahydro-2H-pyran-4-yl)-2-(trifluoromethyl)-4,7-dihydropyrazolo[1,5-a]pyrimidine-5-carboxamide (C1194);
(6-(4-methoxybenzo[d]oxazol-2-yl)-7-oxo-3-phenyl-2-(trifluoromethyl)-4,7-dihydropyrazolo[1,5-a]pyrimidine-5-carbonyl)glycine (C1195);
(S)-N-(1-hydroxypropan-2-yl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1196);
2-((6-(4-methoxybenzo[d]oxazol-2-yl)-7-oxo-3-phenyl-2-(trifluoromethyl)-4,7-dihydropyrazolo[1,5-a]pyrimidin-5-yl)methoxy)acetamide (C1198);
6-(6-amino-7-chloro-4-methoxybenzo[d]oxazol-2-yl)-5-methyl-7-oxo-3-phenyl-4,7-dihydropyrazolo[1,5-a]pyrimidine-2-carbonitrile (C1202);
6-(6-(hydroxymethyl)-4-methoxybenzo[d]oxazol-2-yl)-5-methyl-7-oxo-3-phenyl-4,7-dihydropyrazolo[1,5-a]pyrimidine-2-carbonitrile (C1203);
5-methyl-6-(4-(methylthio)benzo[d]oxazol-2-yl)-7-oxo-3-phenyl-4,7-dihydropyrazolo[1,5-a]pyrimidine-2-carbonitrile (C1204);
6-(7-chloro-4-methoxybenzo[d]oxazol-2-yl)-5-methyl-7-oxo-3-phenyl-4,7-dihydropyrazolo[1,5-a]pyrimidine-2-carbonitrile (C1205);
6-(5-chloro-4-methoxybenzo[d]oxazol-2-yl)-5-methyl-7-oxo-3-phenyl-4,7-dihydropyrazolo[1,5-a]pyrimidine-2-carbonitrile (C1206);
6-(4-methoxybenzo[d]oxazol-2-yl)-7-oxo-3-phenyl-N-(3,3,3-trifluoro-2-hydroxypropyl)-2-(trifluoromethyl)-4,7-dihydropyrazolo[1,5-a]pyrimidine-5-carboxamide (C1209);
2-acetyl-6-(4-methoxybenzo[d]oxazol-2-yl)-5-methyl-3-phenylpyrazolo[1,5-a]pyrimidin-7(4H)-one (C1210);
2-ethynyl-6-(4-methoxybenzo[d]oxazol-2-yl)-5-methyl-3-phenylpyrazolo[1,5-a]pyrimidin-7(4H)-one (C1211);
(4R,5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1213);
(5S)-5-methyl-2-(5-methyl-7-oxo-3-phenyl-2-(trifluoromethyl)-4,7-dihydropyrazolo[1,5-a]pyrimidin-6-yl)-4,5-dihydrooxazole-4-carboxylic acid (C1216);
6-(6-amino-4-methoxyoxazolo[4,5-c]pyridin-2-yl)-5-methyl-7-oxo-3-phenyl-4,7-dihydropyrazolo[1,5-a]pyrimidine-2-carbonitrile (C1218);
N-(2-hydroxy-2-methylpropyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1219);
6-(benzo[d]oxazol-2-yl)-5-methyl-7-oxo-3-phenyl-4,7-dihydropyrazolo[1,5-a]pyrimidine-2-carbonitrile (C1222);
6-(4-aminobenzo[d]oxazol-2-yl)-5-methyl-7-oxo-3-phenyl-4,7-dihydropyrazolo[1,5-a]pyrimidine-2-carbonitrile (C1223);
6-(7-(hydroxymethyl)-4-methoxybenzo[d]oxazol-2-yl)-5-methyl-3-phenyl-2-(trifluoromethyl)pyrazolo[1,5-a]pyrimidin-7(4H)-one (C1224);
6-(4-methoxybenzo[d]oxazol-2-yl)-5-(((1-methyl-2-oxopyrrolidin-3-yl)oxy)methyl)-3-phenyl-2-(trifluoromethyl)pyrazolo[1,5-a]pyrimidin-7(4H)-one (C1225);
5-((2-hydroxyethoxy)methyl)-6-(4-methoxybenzo[d]oxazol-2-yl)-3-phenyl-2-(trifluoromethyl)pyrazolo[1,5-a]pyrimidin-7(4H)-one (C1226);
6-(6-amino-4-methoxyoxazolo[4,5-c]pyridin-2-yl)-5-(methoxymethyl)-7-oxo-3-phenyl- -continued 4,7-dihydropyrazolo[1,5-a]pyrimidine-2-carbonitrile (C1227);
6-(7-aminobenzo[d]oxazol-2-yl)-5-methyl-7-oxo-3-phenyl-4,7-dihydropyrazolo[1,5-a]pyrimidine-2-carbonitrile (C1230);
5-((2,2-difluoroethoxy)methyl)-6-(4-methoxybenzo[d]oxazol-2-yl)-3-phenyl-2-(trifluoromethyl)pyrazolo[1,5-a]pyrimidin-7(4H)-one (C1232);
ethyl 4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylate (C1233);
4-(6-(4-methoxybenzo[d]oxazol-2-yl)-7-oxo-3-phenyl-2-(trifluoromethyl)-4,7-dihydropyrazolo[1,5-a]pyrimidin-5-yl)cyclohex-3-ene-1-carboxylic acid (C1234);
5-(3-(hydroxymethyl)cyclopentyl)-6-(4-methoxybenzo[d]oxazol-2-yl)-3-phenyl-2-(trifluoromethyl)pyrazolo[1,5-a]pyrimidin-7(4H)-one (C1236);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclopentane-1-carboxylic acid (C1239);
6-(6-(1-hydroxyethyl)-4-methoxybenzo[d]oxazol-2-yl)-5-methyl-7-oxo-3-phenyl-4,7-dihydropyrazolo[1,5-a]pyrimidine-2-carbonitrile (C1240);
6-(4-methoxybenzo[d]oxazol-2-yl)-5-methyl-3-phenyl-2-vinylpyrazolo[1,5-a]pyrimidin-7(4H)-one (C1241);
6-(4-methoxybenzo[d]oxazol-2-yl)-5-((2-methoxyethoxy)methyl)-7-oxo-3-phenyl-4,7-dihydropyrazolo[1,5-a]pyrimidine-2-carbonitrile (C1243);
6-(4-methoxybenzo[d]oxazol-2-yl)-7-oxo-3-phenyl-N-(1H-pyrazol-4-yl)-2-(trifluoromethyl)-4,7-dihydropyrazolo[1,5-a]pyrimidine-5-carboxamide (C1244);
N-((1H-pyrazol-3-yl)methyl)-6-(4-methoxybenzo[d]oxazol-2-yl)-7-oxo-3-phenyl-2-(trifluoromethyl)-4,7-dihydropyrazolo[1,5-a]pyrimidine-5-carboxamide (C1245);
5-(methoxymethyl)-6-(4-methoxyoxazolo[4,5-c]pyridin-2-yl)-7-oxo-3-phenyl-4,7-dihydropyrazolo[1,5-a]pyrimidine-2-carbonitrile (C1246);
5-(5-methyl-7-oxo-3-phenyl-2-(trifluoromethyl)-4,7-dihydropyrazolo[1,5-a]pyrimidin-6-yl)-1,3,4-oxadiazol-2(3H)-one (C1247);
5-((2-hydroxyethoxy)methyl)-6-(4-methoxybenzo[d]oxazol-2-yl)-7-oxo-3-phenyl-4,7-dihydropyrazolo[1,5-a]pyrimidine-2-carbonitrile (C1248);
2-cyano-6-(4-methoxybenzo[d]oxazol-2-yl)-7-oxo-3-phenyl-4,7-dihydropyrazolo[1,5-a]pyrimidine-5-carboxylic acid (C1249);
6-(5-amino-4-methoxybenzo[d]oxazol-2-yl)-5-methyl-7-oxo-3-phenyl-4,7-dihydropyrazolo[1,5-a]pyrimidine-2-carbonitrile (C1250);
6-(4-methoxybenzo[d]oxazol-2-yl)-7-oxo-5-(((2-oxooxazolidin-5-yl)methoxy)methyl)-3-phenyl-4,7-dihydropyrazolo[1,5-a]pyrimidine-2-carbonitrile (C1251);
3-(6-(4-methoxybenzo[d]oxazol-2-yl)-7-oxo-3-phenyl-2-(trifluoromethyl)-4,7-dihydropyrazolo[1,5-a]pyrimidin-5-yl)cyclobutane-1-carboxylic acid (C1252);
6-(4-methoxybenzo[d]oxazol-2-yl)-5-(3-methylisoxazol-4-yl)-3-phenyl-2-(trifluoromethyl)pyrazolo[1,5-a]pyrimidin-7(4H)-one (C1253);
6-(4-methoxybenzo[d]oxazol-2-yl)-3-phenyl-5-(1H-pyrazol-4-yl)-2-(trifluoromethyl)pyrazolo[1,5-a]pyrimidin-7(4H)-one (C1254);
6-(4-methoxybenzo[d]oxazol-2-yl)-5-(1-methyl-1H-pyrazol-4-yl)-3-phenyl-2-(trifluoromethyl)pyrazolo[1,5-a]pyrimidin-7(4H)-one (C1255);
6-(4-methoxybenzo[d]oxazol-2-yl)-N-(1-methyl-1H-pyrazol-3-yl)-7-oxo-3-phenyl-2-(trifluoromethyl)-4,7-dihydropyrazolo[1,5-a]pyrimidine-5-carboxamide (C1256);
1-(6-(4-methoxybenzo[d]oxazol-2-yl)-7-oxo-3-phenyl-2-(trifluoromethyl)-4,7-dihydropyrazolo[1,5-a]pyrimidin-5-yl)piperidine-3-carboxylic acid (C1257);
6-(4-methoxybenzo[d]oxazol-2-yl)-5-morpholino-3-phenyl-2-(trifluoromethyl)pyrazolo[1,5-a]pyrimidin-7(4H)-one (C1258);
6-(4-methoxybenzo[d]oxazol-2-yl)-5-((oxetan-3-yloxy)methyl)-7-oxo-3-phenyl-4,7-dihydropyrazolo[1,5-a]pyrimidine-2-carbonitrile (C1259);
5-methyl-6-(oxazol-2-yl)-7-oxo-3-phenyl-4,7-dihydropyrazolo[1,5-a]pyrimidine-2-carbonitrile (C1270);
6-(6-amino-7-chlorobenzo[d]oxazol-2-yl)-5-methyl-7-oxo-3-phenyl-4,7-dihydropyrazolo[1,5-a]pyrimidine-2-carbonitrile (C1271);
6-(4-(dimethylamino)benzo[d]oxazol-2-yl)-5-methyl-7-oxo-3-phenyl-4,7-dihydropyrazolo[1,5-a]pyrimidine-2-carbonitrile (C1272);
5-methyl-7-oxo-3,6-diphenyl-4,7-dihydropyrazolo[1,5-a]pyrimidine-2-carbonitrile (C1273);
5-methyl-6-(4-(methylamino)benzo[d]oxazol-2-yl)-7-oxo-3-phenyl-4,7-dihydropyrazolo[1,5-a]pyrimidine-2-carbonitrile (C1274);
5-methyl-6-(oxazolo[4,5-c]pyridin-2-yl)-7-oxo-3-phenyl-4,7-dihydropyrazolo[1,5-a]pyrimidine-2-carbonitrile (C1275);
6-(1-cyclohexyl-1H-benzo[d]imidazol-2-yl)-5-methyl-7-oxo-3-phenyl-4,7-dihydropyrazolo[1,5-a]pyrimidine-2-carbonitrile (C1276);
6-(4-cyclopropoxybenzo[d]oxazol-2-yl)-5-methyl-7-oxo-3-phenyl-4,7-dihydropyrazolo[1,5-a]pyrimidine-2-carbonitrile (C1277);
5-(dimethylphosphoryl)-6-(4-methoxybenzo[d]oxazol-2-yl)-3-phenyl-2-(trifluoromethyl)pyrazolo[1,5-a]pyrimidin-7(4H)-one (C1284); and
6-(4-methoxybenzo[d]oxazol-2-yl)-5-methyl-3-phenyl-[1,2,3]triazolo[1,5-a]pyrimidin-7(4H)-one (E1001);

or a pharmaceutically acceptable salt, solvate or hydrate thereof.

As used herein, "alkyl", "$C_1$, $C_2$, $C_3$, $C_4$, $C_5$ or $C_6$ alkyl" or "$C_{1-6}$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl. The term Cm n means the alkyl group has "m" to "n" carbon atoms. The term "alkylene" refers to an alkyl group having a substituent, i.e. as used here in it is a bivalent alkyl moiety. For example $C_{0-3}$alkylene, as used herein as part of a substituent of another group includes a direct bond, a linear group —$CH_2$—, —$CH_2CH_2$—, or —$CH_2CH_2CH_2$—, or a branched group —$CH(CH_3)$—, —$CH_2CH(CH_3)$—, or —$CH(CH_3)CH_2$—, where $C_2$ or $C_3$ alkylene is preferably linear. For groups described as having more than one alkyl component, for example —$N(C_{1-3}alkyl)_2$, —$C(=O)N(C_{1-3}alkyl)_2$, —$P(=O)(C_{1-3}alkyl)_2$, or the like, the alkyl components may be the same or different. For example dialkylamino represents as —$N(C_{1-3}alkyl)_2$ includes N,N-dimethylamino, N,N-diethylamino, N-isopropyl-N-methylamino, and the like.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_{3-10}$). For example, a $C_{3-8}$ cycloalkyl is intended to include a monocyclic, bicyclic or tricyclic ring having 3, 4, 5, 6, 7, or 8 carbon atoms. Examples of cycloalkyl rings include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of cycloalkyl, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included. In the case of multicyclic rings, none of the rings is aromatic.

The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. For example, a 3 to 12-membered heterocycloalkyl ring is intended to include a monocyclic, bicyclic, or tricyclic ring having 3, 4, 5, 6, 7, 8, 9, 10, 11, 12 atoms selected from C, O, N, S, and Se. In the case of multicyclic rings, none of the rings is aromatic. Examples of heterocycloalkyl groups include, but are not limited to, piperidinyl, piperazinyl, pyrrolidinyl, dioxanyl, tetrahydrofuranyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, decahydroquinolinyl, 2H,6H-1,5,2-dithiazinyl, dihydrofuro[2,3-b]tetrahydrofuran, imidazolinyl, morpholinyl, octahydroisoquinolinyl, oxazolidinyl (dihydrooxazolyl), oxazolidinyl, piperidonyl, 4-piperidonyl, piperonyl, pyranyl, pyrazolidinyl, pyrazolinyl, pyrrolinyl, 2H-pyrrolyl, quinuclidinyl, 6H-1,2,5-thiadiazinyl, and the like.

Substituted alkyl is alkyl in which the designated substituents replace one or more hydrogen atoms on one or more carbons of the hydrocarbon backbone. Such substituents can include, for example, alkyl, alkenyl, alkynyl, halogen, hydroxyl, oxo, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkylene linker" is intended to include $C_1$, $C_2$, $C_3$, $C_4$, $C_5$ or $C_6$ straight chain (linear) saturated divalent aliphatic hydrocarbon groups and $C_2$, $C_3$, $C_4$, $C_5$ or $C_6$ branched saturated aliphatic hydrocarbon groups. For example, $C_{1-3}$ alkylene linker as used in describing $Q^1$ and $Q^2$ of Formula I herein is a $C_{1-3}$ alkylene intended to include $C_1$, $C_2$, and $C_3$ alkyl linker groups. These linker groups bind to the core Formula I and to $T^1$ or $T^2$. Examples of alkylene linker include, moieties having from one to six carbon atoms, such as, but not limited to, methyl, ethyl, n-propyl, i-propyl, n-butyl, s-butyl, i-butyl, n-pentyl, s-pentyl, or n-hexyl.

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_{2-6}$" or "$C_2$-$C_6$" includes alkenyl groups containing two to six carbon atoms. The term "$C_{3-6}$" or "$C_3$-$C_6$" includes alkenyl groups containing three to six carbon atoms.

Substituted alkenyl is alkenyl in which the designated substituents replace one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyl groups described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_{2-6}$" or "$C_2$-$C_6$" includes alkynyl groups containing two to six carbon atoms. The term "$C_{3-6}$" or "$C_3$-$C_6$" includes alkynyl groups containing three to six carbon atoms.

Substituted alkynyl is alkynyl in which the designated substituents replace one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and lacking a heteroatom in the ring structure. For example, a $C_{6-10}$aryl is intended to include a monocyclic, bicyclic or tricyclic ring having 6, 7, 8, 9, or 10 carbon atoms. Examples include phenyl, 1,2,3,4-tetrahydronaphthalenyl, naphthalene, etc.

"Heteroaryl" groups are aryl groups, as defined above, except having from one to four heteroatoms in the ring structure, and may also be referred to as "aryl heterocycles" or "heteroaromatics." For example, a 5 to 10-membered heteroaryl ring is intended to include a stable 5-, 6-, 7-, 8-, or 9-membered monocyclic or 5-, 6-, 7-, 8-, 9-, or 10-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen, sulfur, selenium, and boron. The nitrogen atom may be substituted or unsubstituted (i.e., N or NR wherein R is H or other substituents, as defined). The nitrogen and sulfur heteroatoms may optionally be oxidized (i.e., N→O and S(=O)$_p$, where p=1 or 2). It is to be noted that total number of S and O atoms in the aromatic heterocycle is not more than 1. Preferred heteroaryl groups herein include 5- or 6-membered monocyclic heteroaryl or 9- or 10-membered bicyclic heteroaryl.

Examples of heteroaryl groups include pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, indolinyl, indolyl, 3H-indolyl, isoindolyl, isoquinolinyl, pyridazinyl, pyridooxazolyl, pyridoimidazolyl, pyridothiazoyle, pyridinyl, pyrimidinyl, oxadiazolyl (e.g. 1,2,3-oxadiazolyl, 1,2,4-oxadiazolyl, 1,2,5-oxadiazolyl, 1,3,4-oxadiazolyl), pyrazolopyridinyl, benzimidazolyl, tetrahydrobenzimidazolyl, benzothiazolyl, benzofuranyl, dihydrobenzofuranyl, pteridinyl, purinyl, pyrazinyl, benzothiofuranyl, benztriazolyl, benztetrazolyl, benzisoxazolyl, benzisothiazolyl, benzothiophenyl, benzoxazolyl, azabenzimidazolyl, azabenzoxazolyl, azabenzothiazolyl, thiadiazolyl (e.g. 1,2,4-thiadiazolyl, 1,2,5-thiadiazolyl, 1,3,4-thiadiazolyl, 1,2,3-thiadiazolyl), triazinyl, triazolyl (e.g. 1,2,3-triazolyl, 1,2,4-triazolyl, 1,2,5-triazolyl, 1,3,4-triazolyl), benzoxazolinyl, benzimidazolinyl, indolizinyl, quinazolinyl, 4H-quinolizinyl, quinoxalinyl, benzodioxolyl, benzoxazolyl, benzoxadiazolyl, tetrahydrobenzoxazolyl (e.g. 4,5,6,7-tetrahydrobenzo[d]oxazolyl), tetrahydrobenzimidazolyl (e.g. 4,5,6,7-tetrahydro-1H-benzo[d]imidazolyl), quinolinyl, isoquinolinyl, tetrahydroquinolinyl (e.g. 1,2,3,4-tetrahydroquinolinyl), tetrahydroisoquinolinyl (e.g. 1,2,3,4-tetrahydroisoquinolinyl), naphthrydinyl, deazapurinyl, benzodihydropyranyl, imidazopyridinyl (e.g. imidazo[1,2-a]]pyridinyl), indazolyl, pyrazolopyrimidinyl (e.g. pyrazolo[1,5-a]pyrimidinyl), 5,6,7,8-tetrahydro-4H-cyclohepta[d]oxazolyl, oxazolopyrimidinyl (e.g. oxazolo[5,4-d]pyrimidinyl), oxazolopyridinyl (e.g. oxazolo[4,5-b]pyridinyl, oxazolo[5,4-b]pyridinyl, oxazolo[5,4-c]pyridinyl, oxazolo[4,5-c]pyridinyl), isobenzofuranyl, dihydroisobenzofuranyl, triazolopyridinyl, tetrahydrooxazoloazepinyl (e.g. 5,6,7,8-tetrahydro-4H-oxazolo[4,5-c]azepinyl), azocinyl, carbazolyl, 4aH-carbazolyl, carbolinyl, chromanyl, chromenyl, cinnolinyl, isoindolinyl, indolenyl, isatinonyl, isochromanyl, isoindazolyl, naphthyridinyl, thianthrenyl, thienothiazolyl, thienooxazolyl, thienoimidazolyl, xanthenyl, furazanyl, oxindolyl, phenanthridinyl, phenanthrolinyl, phenazinyl, phenothiazinyl, phenoxathinyl, phenoxazineyl, phthalazinyl, and the like.

Furthermore, the terms "aryl" and "heteroaryl" include multicyclic aryl and heteroaryl groups, e.g., tricyclic or bicyclic rings.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, oxo, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

The term "substituted," as used herein, means that any one or more hydrogen atoms on the designated atom is replaced with a selection from the indicated groups, provided that the designated atom's normal valency is not exceeded, and that the substitution results in a stable compound. When a moiety is indicated as substituted with one or more substituents, this typically indicates substitution with 1, 2, 3, 4, 5, or more, including 1 to 5, 1 to 4, 1 to 3, 1 to 2 or 1 substituents independently selected from an indicated group. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $X^1$) occurs more than one time in any constituent or formula for a compound, its definition at each occurrence is independent of its definition at every other occurrence. Thus, for example, if a group is shown to be substituted with 0-2 $X^1$ moieties, then the group may optionally be substituted with up to two $X^1$ moieties and $X^1$ at each occurrence is selected independently from the definition of $X^1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms. For example, $C_{1-6}$haloalkyl indicates a 1 to 6 carbon alkyl group (linear or branched) where one or more hydrogens is replaced with a halogen.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(=O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyrazolo[1,5-a]pyrimidin-7(4H)-ones and the corresponding pyrazolo[1,5-a]pyrimidin-7-ol, as shown below.

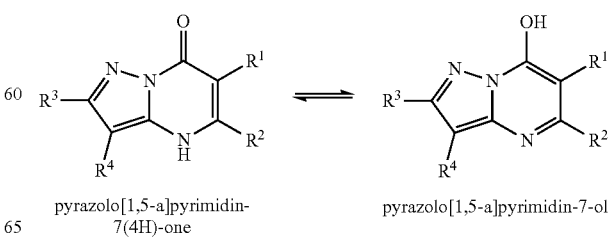

pyrazolo[1,5-a]pyrimidin-7(4H)-one     pyrazolo[1,5-a]pyrimidin-7-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

Synthesis of pyrazolopyrimidinone and triazolopyrimidinone Compounds

The present invention provides methods for the synthesis of the compounds of any Formula disclosed herein. The present invention also provides detailed methods for the synthesis of various disclosed compounds of the present invention according to the following schemes and further exemplified for specific compounds as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, solvate, hydrate, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

For example, compounds of the present invention can be prepared according to the processes illustrated below in Scheme 1, 2, 3, and 4.

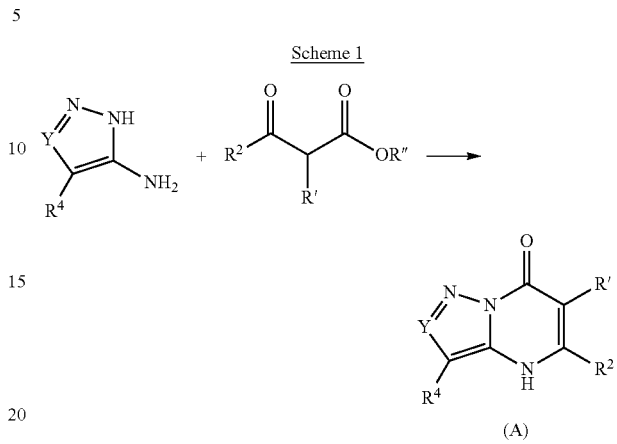

Scheme 1 shows the synthesis of a compound of Formula (A), which can be a compound of Formula (I), where Y can be CR$^3$ (Formula IA) or Y can be N (Formula IA'), R' is R$^1$, and R$^1$, R$^2$, R$^3$ and R$^4$ are within the definitions of Formula I (see e.g. Example 5), or can provide an intermediate that can be further reacted to provide compounds of Formula I (e.g. R' can be —C(=O)OMe, —CH$_2$C(=O)Me (see Examples 1 or 2), hydrogen (see Example 3 or 12). R" is e.g. methyl or ethyl. Substituted aminopyrazoles, or aminotriazoles, many of which are commercially available or can be made by reacting a beta-keto amide with an appropriately substituted hydrazide, or by using other chemistry known to one skilled in the art, can be condensed with an appropriately substituted beta-keto ester to give compounds of A, including compounds of Formula (I).

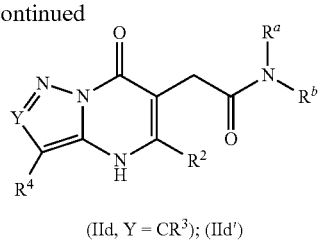

(IId, Y = CR³); (IId')

Scheme 2 shows the synthesis of pyrazolopyrimidinones of Formulas (IId) and triazolopyrimidinones of Formula (IId'), where Y, R², R⁴, Rᵃ and Rᵇ are within the definitions of Formula (I). An aminopyrazole or amino triazole can be condensed with an appropriate beta-keto ester, e.g., dimethyl 2-acetylsuccinate, to give an ester (e.g. R' of above scheme 1=CH₂C(=O)OMe, see Example 2) that is then saponified to produce an acid (compound B). The acid can then be coupled to an NRᵃRᵇ group to give compounds of Formula (IId) or (IId'). Compounds of Formulas (IIc) or (IIc') can be synthesized using a similar route, starting with a beta-keto ester such as dimethyl 2-acetylmalonate (e.g. scheme 1 where R'=C(=O)OMe, see Example 1).

Scheme 3 shows the synthesis of some pyrazolopyrimidinones of Formula (IIa) or triazolopyrimidinones of Formula (IIa'), where Y, R², R⁴, T¹ and X¹ are within the definitions of Formula (I). An aminopyrazole or aminotriazole can be condensed with an appropriate beta-keto ester to give compound C (e.g. scheme 1 where R' is H) an ester that is subsequently brominated (e.g. per Example 3, the corresponding iodo compound is prepared per Example 4). The T¹-X¹ group can then be introduced through a metal-catalyzed cross-coupling reaction with an M-T¹-X¹ group to give compounds of Formula (IIa) or (IIa'). Alternatively, the brominated intermediate can be converted to a metalated nucleophile, which can then react with an electrophilic T¹-X¹ group to form compounds of Formula (IIa) or (IIa'). "M" refers to metallic functional groups such as B(OH)₂, Sn(alkyl)₃, Si(alkyl)₃, MgBr, Li, CuLi, ZnCl, and the like. Specific reactions where R' is Br are found in Examples 3 and R' iodo in Examples 4, 10, and 12.

Scheme 3

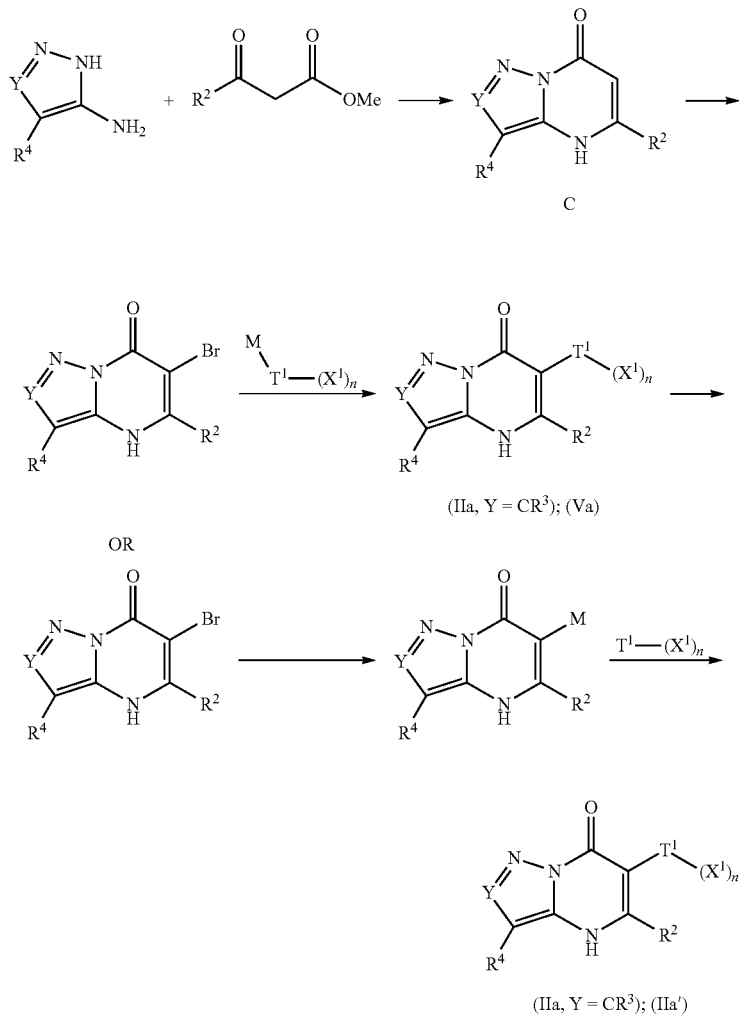

Scheme 4

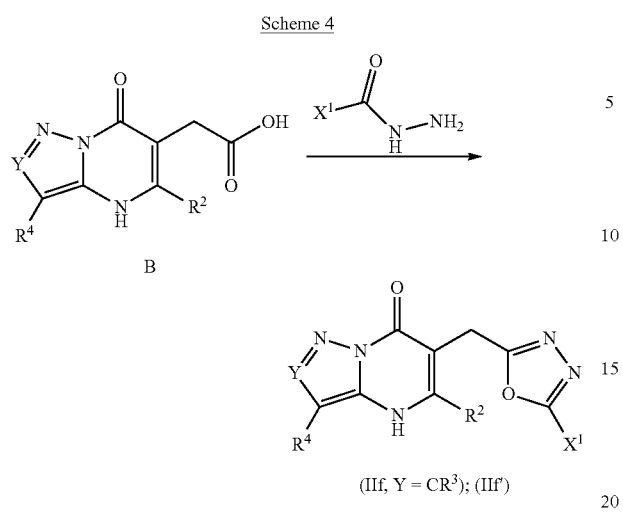

Scheme 4 shows the synthesis of compounds of Formula (IIf) and (IIf') from acid Compound B (see scheme 2). Compound B can be treated with an appropriate hydrazide, e.g., acetylhydrazide, to give compounds of Formula (IIf) or (IIf') (see Examples 2 and 17). Compounds of Formula (IIe) and (IIe') can be synthesized using a similar route, starting from the acid resulting from the reaction of 4-phenyl-3-(trifluoromethyl)-1H-pyrazol-5-amine with a beta-keto ester such as dimethyl 2-acetylmalonate (see Example 1 and 17). Additional methods of making compounds of Formula (I) are found in the Examples 1-19 below.

Compounds of the invention can also be used in the preparation of Proteolysis Targeting Chimeras (PROTACs), wherein the conjugates of the invention are conjugated to ligand that binds an E3 ubiquitin ligase via a suitable linker. For example, a compound of Formula I can be modified off of the $R^3$ or $R^4$ substituent position to provide a linker, which can be reacted to bind with a suitable ligand. Thus in one embodiment, a conjugate is provided comprising a compound of the invention that binds cGAS linked to a ligand of an E3 ubiquitin ligase, wherein the resulting conjugate binds to both the E3 ubiquitin ligase and cGAS. This results in the binding of ubiquitin to the cGAS protein by the E3 ubiquitin ligase. The resulting modified cGAS is then processed by the cell, resulting in degradation of the protein. Suitable ligands that bind E3 ubiquitin ligase, and suitable linkers, and methods of making such conjugates are well known to one skilled in the art. See, for example, Collins et al., Biochemical Journal 2017, 474:1127-1147; Bondeson, et al., Nature Chemical Biology 2015, 11:611-617; and Toure and Crews, Angew. Chem. Int. Ed. 2016, 55:2-10.

Thus, conjugates are provided comprising compounds of the invention linked to a suitable ligand. In one embodiment, compounds of Formula I can be modified by replacing or modifying the $R^3$ or $R^4$ substituent, e.g. in compounds of Formula IA, or by replacing or modifying the $R^4$ substituent in compounds of Formula IA', to provide a suitable substituent comprising a reactive group capable of binding to a suitable linker. In some embodiments, the reactive group comprises a suitable hydroxy or amine group (e.g. an $R^3$ or $R^4$ substituent or modification thereof comprising a terminal —OH, —$NH_2$, C(=O)$NH_2$, and the like) that is capable of reacting with a suitable linker. In one embodiment, compounds of Formula I can be modified by replacing or modifying the $R^3$ or $R^4$ substituent, e.g. in compounds of Formula IA, or by replacing or modifying the $R^4$ substituent in compounds of Formula IA', to provide a suitable substituent bound to a linker moiety, wherein said linker moiety comprises a reactive group capable of binding to a suitable ligand. In one embodiment, compounds of Formula I can be modified by replacing or modifying the $R^3$ or $R^4$ substituent, e.g. in compounds of Formula IA, or by replacing or modifying the $R^4$ substituent in compounds of Formula IA', to provide a suitable substituent bound to a linker moiety, wherein said linker moiety is bound to a suitable ligand. In one embodiment, the ligand binds to an E3 ubiquitin ligase. In some embodiments, the E3 ubiquitin ligase is MDM2, cIAP1, CRBN, or VHL. In one embodiment, a modified compound of the invention is a compound of Formula (Va), Formula (Vb), or Formula (Vc):

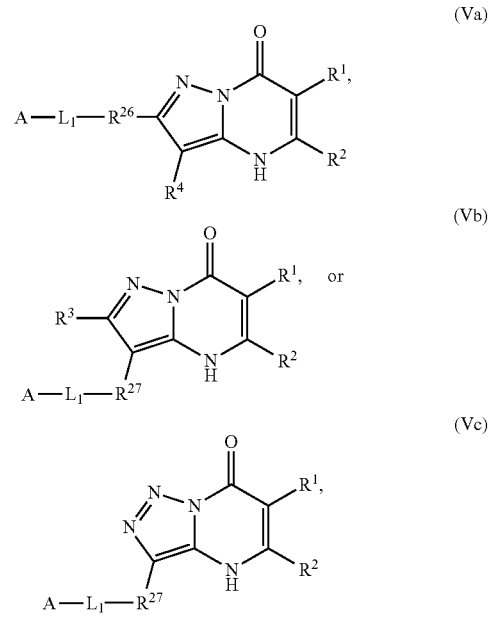

or a pharmaceutically acceptable salt, pharmaceutically acceptable solvate or pharmaceutically acceptable hydrate thereof. In these formulae, A is an E3 ubiquitin ligase ligand; Li is a suitable linker, $R^{26}$ is a suitable $R^3$ or modification or replacement of $R^3$ (as defined in Formula I), and $R^{27}$ is a suitable $R^4$ or modification or replacement of $R^4$ (as defined in Formula I); and $R^1$, $R^2$, $R^3$, and $R^4$ are as defined for compounds of Formula (I).

Methods

The phrase "cGAS/STING pathway-mediated condition," as used herein, comprises autoimmune, inflammatory, and neurodegenerative conditions. For example, the autoimmune disorder is selected from disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes. For example, the inflammatory disorder is selected from atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

Compound of the invention as described herein, can be useful in treating a variety of diseases, where the modulation of the cGAS/STING pathway can provide therapeutic benefit. In some aspects, a compound of the invention inhibits the cGAS/STING pathway, and can be useful in treating a disease selected from the group consisting of systemic inflammatory response syndrome (SIRS), sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI (STING-associated vasculopathy with onset in infancy), CANDLE (Chronic Atypical Neutrophilic Dermatosis with Lipodystrophy and Elevated Temperature) syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease. In some embodiments, compounds of the invention are useful in treating Aicardi-Goutieres Syndrome, X-linked reticulate pigmentary disorder, dermatomyositis, systemic lupus erythematosus, rheumatoid arthritis, multiple sclerosis, or Type I or Type II diabetes.

As used herein, "treating" or "treat" describes the management and care of a mammalian subject (e.g. human patient) for the purpose of combating a disease, condition, or disorder and includes the administration of a compound of the present invention, or a pharmaceutically acceptable salt, pharmaceutically acceptable solvate or pharmaceutically acceptable hydrate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, pharmaceutically acceptable solvate or pharmaceutically acceptable hydrate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as an autoimmune, inflammatory, or neurodegenerative disease, which can occur in multiple locations, is alleviated if the severity of the disease is decreased within at least one of multiple locations.

Compounds of the present invention can inhibit the cGAS/STING pathway and, accordingly, in one aspect of the invention, certain compounds disclosed herein are candidates for treating, or preventing certain conditions and diseases. The present invention provides methods for treating conditions and diseases wherein the course of the condition or disease can be influenced by the cGAS/STING pathway. The method includes administering to a subject in need of such treatment, a therapeutically effective amount of a compound of the present invention, or a pharmaceutically acceptable salt, metabolite, solvate, hydrate, or stereoisomer thereof.

The present invention provides a method of inhibiting the cGAS/STING pathway in a cell, comprising contacting the cell with one or more compounds or compositions of the present invention.

The present invention also provides a method of treating a cGAS/STING pathway-mediated condition, comprising administering to a patient in need thereof an effective amount of one or more compounds or compositions of the present invention. In some embodiments, the cGAS/STING pathway-mediated condition is an autoimmune, inflammatory, or neurodegenerative condition or cancer (see Rayburn, E. R. et al., Mol Cell Pharmacol. 2009; 1(1): 29-43 and Urbanska, A. M. et al., Cell Biochem Biophys. 2015 July; 72(3):757-69).

The present invention also provides a method of inhibiting type I interferon production mediated by the cGAS/STING pathway comprising: administering to the subject in need thereof a therapeutically effective amount of one or more compounds or compositions of the present invention. The cGAS/STING pathway of cytosolic DNA sensing as that phrase is used herein comprises the following proteins: SAMHD1, DNase II, STAT1, STAT2, TREX1, ENPP1, cGAS, STING, IRF3, IRF7, TBK1, IKK, and NF-κB. Such a method may be practiced in vitro, in a cell, or in an organism (e.g., in a human).

The present invention also provides a method of treating a type I interferon-mediated disease in a subject, comprising: administering to the subject in need thereof a therapeutically effective amount of one or more compounds or compositions of the present invention.

The present invention also provides a method of inhibiting cytokine production in a cell, comprising: contacting the cell with one or more compounds or compositions of the present invention.

The present invention also provides a method of treating a cytokine-mediated disease in a subject, comprising: administering to the subject in need thereof a therapeutically effective amount of one or more compounds or compositions of the present invention.

The present invention provides a method of treating an autoimmune disease in a subject, comprising administering to the subject in need thereof a therapeutically effective amount of one or more compounds or compositions of the present invention. In some embodiments, the autoimmune disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes.

The present invention provides a method of treating an inflammatory disease in a subject, comprising administering to the subject in need thereof a therapeutically effective amount of one or more compounds or compositions of the present invention. For example, the inflammatory disease can be atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

The present invention further provides a method of treating neurodegenerative diseases in a subject, comprising administering to the subject in need thereof a therapeutically effective amount of one or more compounds or compositions of the present invention. For example, the neurodegenerative disease can be Alzheimer's disease, Parkinson's disease, multiple sclerosis, IgM polyneuropathies, or myasthenia gravis.

The compounds of the invention can also be use in combination with additional agents for the treatment of autoimmune and inflammatory diseases. Janus Kinase inhibitors (Jak inhibitors) including a Jak1, Jak2, Jak3 or Tyk2 inhibitor, or compound that inhibits any combination thereof, including Jak1/2 inhibitors. Jak inhibitors can block cytokine-mediated signaling via the JAK-STAT pathway, and have been developed for the treatment of a variety of inflammatory and autoimmune diseases. For example, tofacitinib is an approved Jak1 and Jak3 inhibitor used for the treatment of rheumatoid arthritis, psoriatic arthritis and ulcerative colitis; baricitinib is a Jak1 and Jak2 inhibitor approved in Europe, and used in the treatment of rheumatoid arthritis; filgotinib is a Jak1 inhibitor being developed for the treatment of rheumatoid arthritis and Crohn's disease.

The present invention provides a method of treating a disease in a subject, comprising administering to the subject in need thereof a therapeutically effective amount of a compound of the invention in combination with a Janus Kinase (Jak) inhibitor, including a Jak1, Jak2, Jak3 or Tyk2 inhibitor, or compound that inhibits any combination thereof. In some embodiments, the Jak inhibitor is a Jak1/2 inhibitor. In some embodiments, the Jak inhibitor is selected from the group consisting of ruxolitinib, tofacitinib, oclacitinib, baricitinib, filgotinib, gandotinib, itacitinib, lestaurtinib, momelotinib, pacritinib, upadacitinib, peficitinib, fedratinib, decemotinib, cerdulatinib, tasocitinib, PF-04965842, PF-06651600, PF-06700841, PF-06263276, BMS-986165, BMS-911543, AZD1480, AZD4205, AT9283, CHZ868, and TD-1473. In one embodiment, the disease is selected from the group consisting of SIRS, sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI, CANDLE syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease. In some embodiments, compounds of the invention in combination with a Jak inhibitor are useful in treating Aicardi-Goutieres Syndrome, X-linked reticulate pigmentary disorder, dermatomyositis, systemic lupus erythematosus, rheumatoid arthritis, multiple sclerosis, or Type I or Type II diabetes.

The present invention further provides the use of one or more compounds or compositions of the present invention for inhibiting the cGAS/STING pathway in a cell.

The present invention further provides the use of one or more compounds or compositions of the present invention for the treatment of a cGAS/STING pathway-mediated condition.

The present invention further provides the use of one or more compounds or compositions of the present invention for inhibiting type I interferon production mediated by the cGAS/STING pathway in a cell.

The present invention further provides the use of one or more compounds or compositions of the present invention for the treatment of a type I interferon-mediated disease.

The present invention further provides the use of one or more compounds or compositions of the present invention for inhibiting cytokine production in a cell.

The present invention further provides the use of one or more compounds or compositions of the present invention for the treatment of a cGAS/STING pathway-mediated condition.

The present invention further provides the use of one or more compounds or compositions of the present invention for the treatment of an autoimmune disease. In some embodiments, the autoimmune disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes.

The present invention further provides the use of one or more compounds or compositions of the present invention for the treatment of an inflammatory disease. For example, the inflammatory disease can be atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

The present invention further provides the use of one or more compounds or compositions of the present invention for the treatment of a neurodegenerative disease. For example, the neurodegenerative disease can be Alzheimer's disease, Parkinson's disease, multiple sclerosis, IgM polyneuropathies, or myasthenia gravis.

The present invention further provides one or more compounds or compositions of the present invention for use in inhibiting the cGAS/STING pathway in a cell.

The present invention further provides one or more compounds or compositions of the present invention for use in the treatment of a cGAS/STING pathway-mediated condition.

The present invention further provides one or more compounds or compositions of the present invention for use in inhibiting type I interferon production mediated by the cGAS/STING pathway in a cell.

The present invention further provides one or more compounds or compositions of the present invention for use in the treatment of a type I interferon-mediated disease.

The present invention further provides one or more compounds or compositions of the present invention for use in inhibiting cytokine production in a cell.

The present invention further provides one or more compounds or compositions of the present invention for use in the treatment of a cGAS/STING pathway-mediated condition.

The present invention further provides one or more compounds or compositions of the present invention for use in the treatment of an autoimmune disease, such as those described herein.

The present invention further provides one or more compounds or compositions of the present invention for use in the treatment of an inflammatory disease, such as those described herein.

The present invention further provides one or more compounds or compositions of the present invention for use in the treatment of a neurodegenerative disease, such as those described herein.

Any of the one or more compounds or compositions for use described above may be for use in combination with a Janus Kinase (Jak) inhibitor, such as those described herein.

The present invention further provides the use of one or more compounds or compositions of the present invention in the manufacture of a medicament for inhibiting the cGAS/STING pathway in a cell.

The present invention further provides the use of one or more compounds or compositions of the present invention in the manufacture of a medicament for the treatment of a cGAS/STING pathway-mediated condition.

The present invention further provides the use of one or more compounds or compositions of the present invention in the manufacture of a medicament for inhibiting type I interferon production in a cell.

The present invention further provides the use of one or more compounds or compositions of the present invention in the manufacture of a medicament for the treatment of a type I interferon-mediated disease.

The present invention further provides the use of one or more compounds or compositions of the present invention in the manufacture of a medicament for inhibiting cytokine production in a cell.

The present invention further provides the use of one or more compounds or compositions of the present invention in the manufacture of a medicament for the treatment of a cytokine-mediated condition.

The present invention further provides the use of one or more compounds or compositions of the present invention in the manufacture of a medicament for the treatment of an autoimmune disease, such as those described herein.

The present invention further provides the use of one or more compounds or compositions of the present invention in the manufacture of a medicament for the treatment of an inflammatory disease, such as those described herein.

The present invention further provides the use of one or more compounds or compositions of the present invention in the manufacture of a medicament for the treatment of a neurodegenerative disease, such as those described herein.

The present invention further provides the use of one or more compounds or compositions of the present invention in combination with a Janus Kinase (Jak) inhibitor, including a Jak1, Jak2, Jak3 or Tyk2 inhibitor, or compound that inhibits any combination thereof, in the manufacture of a medicament for the treatment of a disease selected from the group consisting of SIRS, sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI, CANDLE syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease. In some embodiments, the Jak inhibitor is a Jak1/2 inhibitor. In some embodiments, the Jak inhibitor is selected from the group consisting of ruxolitinib, tofacitinib, oclacitinib, baricitinib, filgotinib, gandotinib, itacitinib, lestaurtinib, momelotinib, pacritinib, upadacitinib, peficitinib, fedratinib, decemotinib, cerdulatinib, tasocitinib, PF-04965842, PF-06651600, PF-06700841, PF-06263276, BMS-986165, BMS-911543, AZD1480, AZD4205, AT9283, CHZ868, and TD-1473.

cGAS inhibitory activity of any of the compounds disclosed herein can be determined by reacting the compound in a properly buffered environment with a DNA-activated cGAS in the presence of ATP and GTP. Antagonist activity can then be quantified by measuring the amount of ATP and/or GTP remaining after reaction is halted. Human cGAS sequence encoding amino acids 155-522 (DAAPGASKLRAVLEKLKLSRDDISTAAGMVKGVVDHLLLRLKCDSAFRGVGLLNT GSYYEHVKISAPNEFDVMFKLEVPRIQLEEYSNTRAYYFVKFKRNPKENPLSQFL EGE ILSASKMLSKFRKIIKEEINDIKDTDVIMKRKRGGSPAVTLLISEKISVDITLALESKSS WPASTQEGLRIQNWLSAKVRKQLRLKPFYLVPKHAKEGNGFQEETWRLSFSHIEKEI LNNHGKSKTCCENKEEKCCRKDCLKLMKYLLEQLKERFKDKKHLDKFSSYHVKTA FFHVCTQNPQDSQWDRKDLGLCFDNCVTYFLQCLRTEKLENYFIPEFNLFSSNLIDKR SKEFLTKQIEYERNNEFPVFDEF, SEQ ID No. 1) can be cloned into an expression plasmid to create a construct containing codes for the appropriate proteins and tags (e.g., hexahistidine tag, maltose binding protein fusion, and a cleavable linker) preceding the cGAS sequence. The protein can then be expressed and purified using standard techniques.

The cGAS/STING pathway inhibitory activity of any of the compounds disclosed herein can also be determined by measuring changes in the type I interferon signature resulting from administration of the compound(s).

Potential cGAS antagonists, e.g., the pyrazolopyrimidinone compounds disclosed herein, can be made to interact, in a properly buffered environment, with a DNA-activated cGAS in the presence of ATP and GTP. Antagonist activity can then be quantified by measuring the amount of ATP and/or GTP remaining after reaction is halted.

A cellular assay can be used to assess the compounds of the invention for their ability to inhibit the cGAS/STING pathway. Cells that express a luciferase-based reporter that is linked to IRF-3 activation are used to determine response as a function of compound concentration. Such an assay is described in Vincent et al., Nature Communications 2017, 8(1):750, doi: 10.1038/s41467-017-00833-9.

A cellular assay can be used to asses the compounds of the invention for their ability to inhibit cytokine production. Bone marrow macrophages harvested from mice can be used to determine response as a function of compound concentration.

Pharmaceutical Compositions

The present invention also provides pharmaceutical compositions comprising a compound of any Formula disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. The dose chosen should be sufficient to constitute effective treatment but not so high as to cause unacceptable side effects. The state of the disease condition and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In general, a compound of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the progression of the autoimmune, neurodegenerative, or inflammatory disease. Dosages can be in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, bisulfate, bitartric, boric, bromic, butyric, calcium, calcium edetic, camsylate, carbonic, chloric, citric, clavularic, dihydrochloric, edetic, ethane disulfonic, 1,2-ethane sulfonic, estolate, esylate, fumaric, glucoheptonic, gluconic, glutamic, glycolic, glycollyarsanilic, hexafluorophosphoric, hexylresorcinic, hydrabamic, hydrobromic, hydrochloric, hydroiodic, hydroxymaleic, hydroxynaphthoic, iodic, isethionic, lactic, lactobionic, lauryl sulfonic, maleic, malic, mandelic, methane sulfonic, methylbromic, methylnitric, napsylic, nitric, N-methylglucamine ammonium salt, 3-hydroxy-2-naphthoic, oleic, oxalic, pamoic, pantothenic, phenylacetic, phosphoric, polygalacturonic, propionic, salicyclic, stearic, subacetic, succinic, sulfamic, sulfanilic, sulfuric, sulfosalicylic, suramic, tannic, tartaric, toluene sulfonic, tosyl, triethiodic, trifluoroacetic, and valeric and the commonly occurring amine acids, e.g., glycine, alanine, phenylalanine, arginine, etc.

In addition to pharmaceutically acceptable salts, the compounds and pharmaceutically acceptable salts as disclosed herein can be "pharmaceutically acceptable solvates", or where the solvent is water, "pharmaceutically acceptable hydrates". For example, pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates or hydrates When a disclosed compound or its salt is named or depicted by structure, it is to be understood that the compound or salt, including solvates or hydrates thereof, may exist in crystalline forms, non-crystalline forms or a mixture thereof. The compound or salt, or solvates or hydrates thereof, may also exhibit polymorphism (i.e. the capacity to occur in different crystalline forms). These different crystalline forms are typically known as "polymorphs." It is to be understood that when named or depicted by structure, the disclosed compound, or solvates or hydrates thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used during the crystallization or recrystallization of the compounds described herein.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered by a route selected from the group consisting of enterally, orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

The present invention provides a kit comprising a compound capable of inhibiting the cGAS/STING pathway selected from one or more compounds of the present invention, or a pharmaceutically acceptable salt, pharmaceutically acceptable solvate or pharmaceutically acceptable hydrate thereof, and instructions for use in treating an autoimmune disease. In some embodiments, the autoimmune disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes.

The present invention provides a kit comprising a compound capable of inhibiting the cGAS/STING pathway selected from one or more compounds of the present invention, or a pharmaceutically acceptable salt, pharmaceutically acceptable solvate or pharmaceutically acceptable hydrate thereof, and instructions for use in treating an inflammatory disease. In some embodiments, the inflammatory disease can be atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

The present invention provides a kit comprising a compound capable of inhibiting the cGAS/STING pathway selected from one or more compounds of the present invention, or a pharmaceutically acceptable salt, pharmaceutically acceptable solvate or pharmaceutically acceptable hydrate thereof, and instructions for use in treating a neurodegenerative disease. In some embodiments, the neurodegenerative disease can be Alzheimer's disease, Parkinson's disease, multiple sclerosis, IgM polyneuropathies, or myasthenia gravis.

The present invention provides a kit comprising a compound capable of inhibiting type I interferon production selected from one or more compounds of the present invention, or a pharmaceutically acceptable salt, pharmaceutically acceptable solvate or pharmaceutically acceptable hydrate thereof, and instructions for use in treating an autoimmune disease. In some embodiments, the autoimmune disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes.

The present invention provides a kit comprising a compound capable of inhibiting type I interferon production selected from one or more compounds of the present invention, or a pharmaceutically acceptable salt, pharmaceutically acceptable solvate or pharmaceutically acceptable hydrate thereof, and instructions for use in treating an inflammatory disease. In some embodiments, the inflammatory disease can be atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

The present invention provides a kit comprising a compound capable of inhibiting type I interferon production selected from one or more compounds of the present invention, or a pharmaceutically acceptable salt, pharmaceutically acceptable solvate or pharmaceutically acceptable hydrate thereof, and instructions for use in treating a neurodegenerative disease. In some embodiments, the neurodegenerative disease can be Alzheimer's disease, Parkinson's disease, multiple sclerosis, IgM polyneuropathies, or myasthenia gravis.

The present invention provides a kit comprising a compound capable of inhibiting cytokine production selected from one or more compounds of the present invention, or a pharmaceutically acceptable salt, pharmaceutically acceptable solvate or pharmaceutically acceptable hydrate thereof, and instructions for use in treating an autoimmune disease. In some embodiments, the autoimmune disease can be a type I interferonopathy (e.g., Aicardi-Goutieres Syndrome, Sjögren's syndrome, Singleton-Merten Syndrome, proteasome-associated autoinflammatory syndrome, SAVI (STING-associated vasculopathy with onset in infancy), CANDLE syndrome, chilblain lupus erythematosus, systemic lupus erythematosus, spondyloenchondrodysplasia), rheumatoid arthritis, juvenile rheumatoid arthritis, idiopathic thrombocytopenic purpura, autoimmune myocarditis, thrombotic thrombocytopenic purpura, autoimmune thrombocytopenia, psoriasis, Type 1 diabetes, or Type 2 diabetes.

The present invention provides a kit comprising a compound capable of inhibiting cytokine production selected from one or more compounds of the present invention, or a pharmaceutically acceptable salt, pharmaceutically acceptable solvate or pharmaceutically acceptable hydrate thereof, and instructions for use in treating an inflammatory disease. In some embodiments, the inflammatory disease can be atherosclerosis, dermatomyositis, SIRS, sepsis, septic shock, celiac disease, interstitial cystitis, transplant rejection, inflammatory bowel disease (ulcerative colitis, Crohn's disease), age-related macular degeneration, IgA nephropathy, glomerulonephritis, vasculitis, polymyositis, or Wegener's disease.

The present invention provides a kit comprising a compound capable of inhibiting cytokine production selected from one or more compounds of the present invention, or a pharmaceutically acceptable salt, pharmaceutically acceptable solvate or pharmaceutically acceptable hydrate thereof, and instructions for use in treating a neurodegenerative disease. In some embodiments, the neurodegenerative disease can be Alzheimer's disease, Parkinson's disease, multiple sclerosis, IgM polyneuropathies, or myasthenia gravis.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

NMR spectra were recorded on a Bruker Avance II Ultra shield spectrometer (500 MHz). LCMS were acquired on a Waters Alliance 2695 with column heater LC system equipped with a Waters PDA 996 (210-300 nm) UV detector and a Waters ZQ 2000, ESI (ES+, 100-1200 amu) MS Detector. Mobile phases (Mobile phase A: Milli-Q H2O+10 mM Ammonium Formate pH: 3.8 (Am. F.), or Ammonium Bicarbonate pH: 10 (Am. B.), Mobile Phase B: CH3CN). LC conditions are: XBridge C18, 3.5 m, 4.6×30 mm; Iso 5% B for 0.5 min, 5% to 100% B in 5 minutes; hold 100% B for 2 minutes; flow rate: 3 mL/min. The methods described in the examples below can be readily modified by one skilled in the art. Compounds made similarly to the exemplified methods may include modifications of reaction conditions, such as any one or more of the reagent concentrations, solvents, reaction times, temperatures, work-up conditions, purification conditions, and the like to provide additional compounds of the invention as described herein.

Abbreviations and Acronyms. AcOH=acetic acid, Burgess reagent=1-Methoxy-N-triethylammoniosulfonyl-methanimidate, DCM=$CH_2Cl_2$=dichloromethane, DIPEA=N,N-Diisopropylethylamine, DMEDA=N,N'-Dimethylethylenediamine, DMF=Dimethylformamide, DMSO=Dimethyl sulfoxide, EtOH=ethanol, EtOAc=ethyl acetate, FBS=Fetal Bovine Serum, HATU (Hexafluorophosphate Azabenzotriazole Tetramethyl Uronium)=1-[Bis(dimethylamino)methylene]-1H-1,2,3-triazolo[4,5-b]pyridinium 3-oxide hexafluorophosphate, LAH=Lithium aluminum hydride, LTB=Lithium tert-butoxide, MeCN=acetonitrile, MeOH=methanol, NaOMe=Sodium methoxide, NBS=N-Bromosuccinimide, NIS=N-Iodosuccinimide, Pyr-SO$_3$=sulfur trioxide pyridine complex, Pd(dppf)Cl$_2$=[1,1'-bis(diphenylphosphino)ferrocene]dichloropalladium(ll), TEA=triethylamine, TFA=trifluoroacetic acid, THF=tetrahydrofuran, TEMPO=(2,2,6,6-Tetramethylpiperidin-1-yl)oxyl, Fe(acac)$_3$=Iron(III) acetylacetonate.

Example 1

Synthesis of N-(4-methoxyphenyl)-5-methyl-7-oxo-3-phenyl-2-(trifluoromethyl)-4,7-dihydropyrazolo[1,5-a]pyrimidine-6-carboxamide (A1001) was carried out in three steps as follows:

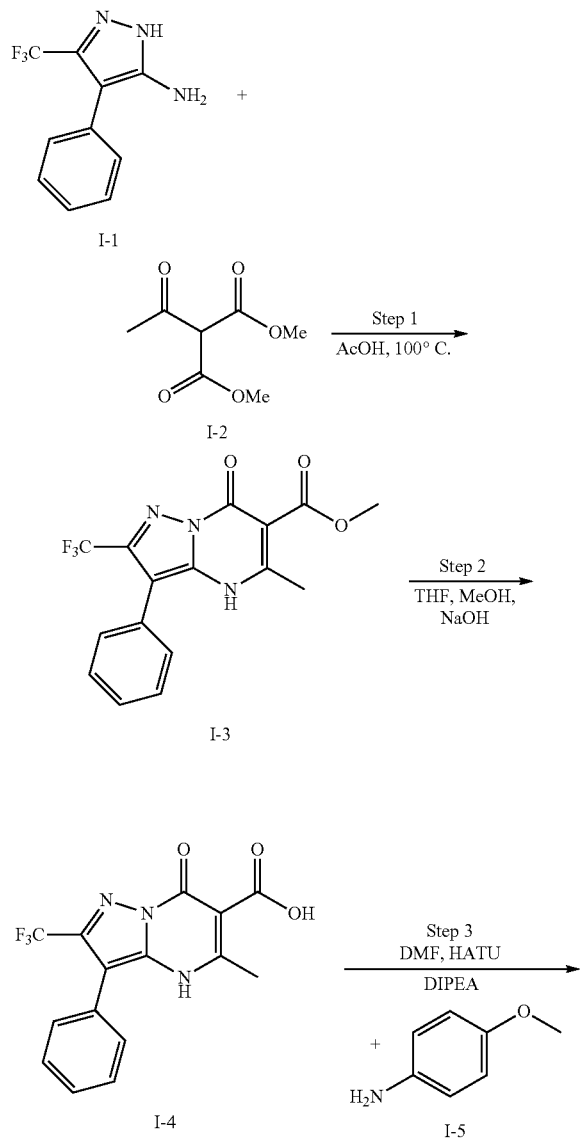

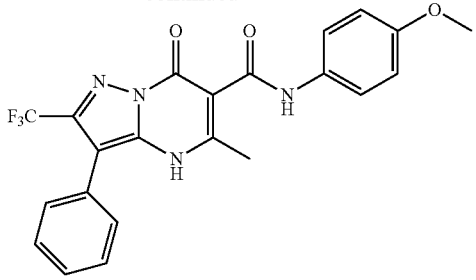

A1001

Step 1:
Synthesis of methyl 5-methyl-7-oxo-3-phenyl-2-(trifluoromethyl)-4,7-dihydropyrazolo[1,5-a]pyrimidine-6-carboxylate (I-3). To a stirred solution of 4-phenyl-3-(trifluoromethyl)-1H-pyrazol-5-amine (I-1, 2.00 g, 8.80 mmol) (WO 2012149157) in AcOH (10 mL) was added dimethyl 2-acetylmalonate (I-2, 1.3 eq, 1.99 g, 11.4 mmol) (JACS, 136(34), 12137-12160, 2014). The reaction mixture was heated at 100° C. for 30 min and concentrated in vacuo to dryness. The reaction mixture was triturated in EtOAc for 15 min. The solid was collected by filtration, rinsed with EtOAc, dried under high vacuum to afford the compound I-3 (1.60 g, 4.55 mmol, 52%) as a white solid which was used without further purification. $^1$H NMR (500 MHz, DMSO) δ 12.69 (s, 1H), 7.54-7.45 (m, 3H), 7.45-7.42 (m, 2H), 3.81 (s, 3H), 2.43 (s, 3H); MS (m/z): 325.0 [M+1]$^+$, 97.2%.

Step 2:
Synthesis of 5-methyl-7-oxo-3-phenyl-2-(trifluoromethyl)-4,7-dihydropyrazolo[1,5-a]pyrimidine-6-carboxylic acid (I-4). To a stirred solution of compound I-3 (1.60 g, 4.55 mmol) in a mixture of THF (25 mL) and MeOH (25 mL) was added a solution of sodium hydroxide 2M (18.2 mL, 36.4 mmol). The reaction mixture was stirred at r.t. for 17 h, heated at reflux for 2 h and concentrated to dryness. After addition of water and HCl 10%, the white slurry was stirred at r.t. for 10 min. The solid was collected by filtration, rinsed with water, dried under high vacuum to afford compound I-4 (1.42 g, 4.21 mmol, 92%) as a white solid which was used without further purification. $^1$H NMR (500 MHz, DMSO) 13.07 (s, 1H), 7.60-7.36 (m, 5H), 2.58 (s, 3H); MS (m/z): 337.9 [M+1]+, 96.3%.

Step 3:
Synthesis of N-(4-methoxyphenyl)-5-methyl-7-oxo-3-phenyl-2-(trifluoromethyl)-4,7-dihydropyrazolo[1,5-a]pyrimidine-6-carboxamide (A1001): To a stirred solution of 5-methyl-7-oxo-3-phenyl-2-(trifluoromethyl)-4,7-dihydropyrazolo[1,5-a]pyrimidine-6-carboxylic acid (I-4, 50 mg, 0.15 mmol) in DMF (1 mL) was added HATU (85 mg, 0.22 mmol), p-anisidine (I-5, 27.7 mg, 0.22 mmol) and DIPEA (78 μL, 0.44 mmol). The reaction mixture was stirred at r.t. for 18 h. After addition of EtOAc, water and HCl 10%, the layers were separated and the aqueous layer was extracted with EtOAc. The combined organics layers were washed with brine, dried over Na$_2$SO$_4$ and concentrated in vacuo. The residue was purified by reverse flash chromatography (KP-C18-H5 (Biotage LLC, Charlotte, N.C., USA), using a gradient 0 to 100% MeCN in 10 mM aqueous ammonium formate buffer) to afford compound A1001 (42 mg, 0.09 mmol, 64%) as a white solid after lyophilization. 1H NMR (500 MHz, DMSO) δ 12.66 (s, 1H), 11.19 (s, 1H), 7.63-7.55 (m, 2H), 7.49 (dt, J=15.3, 7.5 Hz, 4H), 7.40 (t, J=7.0 Hz, 1H), 6.94-6.87 (m, 2H), 3.74 (s, 3H), 2.56 (s, J=12.0 Hz, 3H). MS (m/z): 443.1 [M+1]$^+$, >99%.

Table 2 below provides additional compounds that can be synthesized similarly to the methods described in Steps 1-3 above, optionally substituting the listed compound for I-5, and/or substituting for I-1 and/or I-2 where indicated. Data for compounds synthesized is provided in columns 3-5.

TABLE 2

| Compound ID | Compound I-5 replacement | ¹H NMR | Purity (%) | MS (m/z) |
|---|---|---|---|---|
| A1002 | phenyl-NH₂ (aniline) | (500 MHz, DMSO) δ 12.69 (s, 1H), 10.95 (s, 1H), 7.71-7.64 (m, 2H), 7.55-7.41 (m, 5H), 7.39-7.30 (m, 2H), 7.11-7.04 (m, 1H), 2.54 (s, 3H). | 99.6 | 413.0 |
| A1003 | 1-phenylpiperazine | (500 MHz, DMSO) δ 12.55 (s, 1H), 7.54-7.34 (m, 5H), 7.27-7.19 (m, 2H), 7.00-6.91 (m, 2H), 6.86-6.76 (m, 1H), 3.95-3.80 (m, 1H), 3.75-3.63 (m, 1H), 3.59-3.43 (m, 2H), 3.30-3.18 (m, 2H), 3.17-3.08 (m, 1H), 3.02-2.93 (m, 1H), 2.25 (s, 3H). | 99.2 | 482.1 |
| A1004 | morpholine | (500 MHz, DMSO) δ 12.54 (s, 1H), 7.58-7.35 (m, 5H), 3.74-3.54 (m, 5H), 3.51-3.43 (m, 1H), 3.42-3.34 (m, 2H), 2.25 (s, 3H). | 96.5 | 407.0 |
| A1005 | 3-aminopyridine | (500 MHz, DMSO) δ 11.31 (s, 1H), 8.88 (s, 1H), 8.33 (s, 1H), 8.18 (d, J = 8.4 Hz, 1H), 7.53-7.47 (m, 4H), 7.47-7.40 (m, 2H), 2.56 (s, 3H). | 100.00 | 414.0 |
| A1006 | benzene-1,2-diamine | (500 MHz, DMSO) δ 10.51 (s, 1H), 7.52-7.40 (m, 7H), 6.92 (t, J = 7.5 Hz, 1H), 6.78 (d, J = 7.3 Hz, 1H), 6.61 (t, J = 7.4 Hz, 1H), 5.02 (s, 2H), 2.59 (s, 3H). | 96.9 | 428.1 |
| A1007 | 4-(trifluoromethyl)aniline | (500 MHz, DMSO) δ 12.78 (s, 1H), 11.04 (s, 1H), 7.91 (d, J = 8.5 Hz, 2H), 7.73 (d, J = 8.6 Hz, 2H), 7.57-7.44 (m, 5H), 2.53 (s, 3H). | 99.1 | 481.0 |
| A1008 | cyclopentylamine | (500 MHz, DMSO) δ 12.51 (s, 1H), 8.66 (br s, 1H), 7.53-7.48 (m, 2H), 7.44 (d, J = 7.4 Hz, 3H), 4.22-4.09 (m, 1H), 2.46 (s, 3H), 1.94-1.81 (m, 2H), 1.72-1.62 (m, 2H), 1.60-1.51 (m, 2H), 1.51-1.43 (m, 2H). | 100.0 | 405.1 |
| A1009 | pyrrolidine | (500 MHz, DMSO) δ 12.53 (s, 1H), 7.51-7.44 (m, 4H), 7.43-7.36 (m, 1H), 3.44 (t, 2H), 3.40-3.33 (m, 1H), 3.27-3.19 (m, J = 10.9, 6.3 Hz, 1H), 2.23 (s, 3H), 1.91-1.78 (m, 4H). | 100.0 | 391.0 |
| A1010 | cyclohexylamine | (500 MHz, DMSO) δ 12.52 (s, 1H), 8.58 (s, 1H), 7.53-7.48 (m, 2H), 7.48-7.42 (m, 3H), 3.80-3.67 (m, 1H), 2.46 (s, 3H), 1.87-1.79 (m, 2H), 1.74-1.65 (m, 2H), 1.60-1.50 (m, 1H), 1.39-1.14 (m, 5H). | 100.0 | 419.0 |

TABLE 2-continued

| Compound ID | Compound I-5 replacement | ¹H NMR | Purity (%) | MS (m/z) |
|---|---|---|---|---|
| A1011 | piperidine (NH) | (500 MHz, DMSO) δ 12.48 (s, 1H), 7.53-7.47 (m, 2H), 7.47-7.42 (m, 3H), 3.74-3.64 (m, 1H), 3.55-3.44 (m, 1H), 3.39-3.24 (m, 2H), 2.24 (s, 3H), 1.65-1.43 (m, 5H), 1.42-1.31 (m, 1H). | 98.9 | 405.0 |
| A1012 | 4-methylaniline | (500 MHz, DMSO) δ 12.68 (s, 1H), 11.01 (s, 1H), 7.56 (d, J = 8.4 Hz, 2H), 7.53-7.46 (m, 4H), 7.46-7.39 (m, 1H), 7.14 (d, J = 8.2 Hz, 2H), 2.54 (s, 3H), 2.28 (s, 3H). | 99.2 | 427.0 |
| A1013 | N-methylbenzylamine | (500 MHz, DMSO) δ 12.56 (s, 1H), 7.55-7.25 (m, 10H), 4.80-4.43 (m, 2H), 2.88 (d, J = 7.3 Hz, 3H), 2.27 (d, J = 24.4 Hz, 3H). | 100.0 | 441.1 |
| A1014 | trans-1,2-diaminocyclohexane | (500 MHz, DMSO) δ 9.40 (d, J = 8.5 Hz, 1H), 8.32 (s, 1H), 7.57 (d, J = 7.4 Hz, 2H), 7.45-7.37 (m, 2H), 7.32-7.22 (m, 1H), 3.88-3.76 (m, 1H), 2.96-2.82 (m, 1H), 2.03-1.95 (m, 1H), 1.93-1.86 (m, 1H), 1.72 (d, J = 4.6 Hz, 2H), 1.46-1.21 (m, 4H) | 100.0 | 434.1 |
| A1015 | 4-aminobenzonitrile | (500 MHz, DMSO) δ 12.79 (s, 1H), 11.22 (s, 1H), 7.91-7.84 (m, 2H), 7.84-7.78 (m, 2H), 7.56-7.49 (m, 2H), 7.49-7.42 (m, 3H), 2.53 (s, J = 6.7 Hz, 3H). | 99.7 | 437.7 |
| A1016 | 4-chloroaniline | (500 MHz, DMSO) δ 12.73 (s, 1H), 10.82 (s, 1H), 7.72 (d, J = 8.8 Hz, 2H), 7.56-7.50 (m, 2H), 7.47 (dd, J = 12.7, 7.0 Hz, 3H), 7.41 (d, J = 8.8 Hz, 2H), 2.50 (s, 3H). | 100.0 | 447.0 |
| A1017 | 2-aminopyridine | (500 MHz, DMSO) δ 12.57 (s, 1H), 8.29 (d, J = 8.4 Hz, 2H), 7.74 (t, J = 7.8 Hz, 1H), 7.57 (d, J = 7.5 Hz, 2H), 7.44 (dd, J = 10.6, 4.9 Hz, 2H), 7.32 (t, J = 7.4 Hz, 1H), 7.06-6.99 (m, 2H), 2.69 (s, 3H). | 100.0 | 414.0 |
| A1018 | 4-aminopyridazine | (500 MHz, DMSO) δ 12.72 (s, 1H), 12.50 (s, 1H), 9.36 (s, 1H), 9.03 (s, 1H), 8.10 (s, 1H), 7.55 (d, J = 7.5 Hz, 2H), 7.45 (t, J = 7.7 Hz, 2H), 7.35 (t, J = 7.4 Hz, 1H), 2.64 (s, 3H). | 96.8 | 415.0 |
| A1019 | 4-amino-3,5-dimethylisoxazole | (500 MHz, DMSO) δ 12.74 (s, 1H), 10.03 (s, 1H), 7.55-7.49 (m, 2H), 7.49-7.43 (m, 3H), 2.53 (s, 3H), 2.34 (s, 3H), 2.17 (s, 3H). | 100.0 | 432.1 |

TABLE 2-continued

| Compound ID | Compound I-5 replacement | ¹H NMR | Purity (%) | MS (m/z) |
|---|---|---|---|---|
| A1020 | 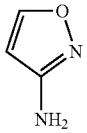 | (500 MHz, DMSO) δ 12.93 (s, 1H), 8.76 (d, J = 1.7 Hz, 1H), 7.57 (d, J = 7.5 Hz, 2H), 7.43 (dd, J = 10.6, 4.8 Hz, 2H), 7.31 (t, J = 7.4 Hz, 1H), 7.08 (d, J = 1.7 Hz, 1H), 3.17 (s, 1H), 2.67 (s, 3H). | 99.6 | 403.9 |
| A1021 | 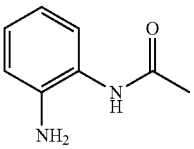 | (500 MHz, DMSO) δ 12.88 (s, 1H), 10.87 (s, 1H), 9.56 (s, 1H), 8.03 (d, J = 7.9 Hz, 1H), 7.54-7.41 (m, 6H), 7.21 (t, J = 7.7 Hz, 1H), 7.13 (t, J = 7.5 Hz, 1H), 2.68 (s, 3H), 2.14 (s, 3H). | 99.9 | 470.1 |
| A1022 |  | (500 MHz, DMSO) δ 12.88 (vbs, 1H), 11.40 (s, 1H), 9.10 (s, 1H), 8.20 (d, J = 7.8 Hz, 1H), 7.50 (d, J = 4.4 Hz, 4H), 7.45-7.41 (m, 1H), 7.37 (d, J = 7.9 Hz, 1H), 7.31 (t, J = 7.3 Hz, 1H), 7.15 (t, J = 7.0 Hz, 1H), 3.04 (s, 3H), 2.68 (s, 3H). | 95.6 | 506.0 |
| A1023 | 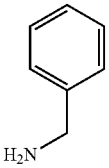 | (500 MHz, DMSO) δ 12.59 (s, 1H), 9.07 (s, 1H), 7.54-7.42 (m, 5H), 7.41-7.32 (m, 4H), 7.26 (t, J = 7.2 Hz, 1H), 4.49 (d, J = 5.9 Hz, 2H), 2.48 (s, 3H). | 98.2 | 427.1 |
| A1024 | 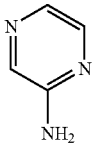 | (500 MHz, DMSO) δ 9.52 (s, 1H), 8.45-8.38 (m, 1H), 8.37-8.31 (m, 1H), 7.58-7.35 (m, 5H), 2.68 (s, 3H). | 96.9 | 415.0 |
| A1025 | 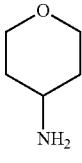 | (500 MHz, DMSO) δ 12.54 (s, 1H), 8.66 (s, 1H), 7.53-7.48 (m, 2H), 7.48-7.42 (m, 3H), 4.01-3.90 (m, 1H), 3.85 (dt, J = 11.5, 3.7 Hz, 2H), 3.42 (td, J = 11.4, 2.2 Hz, 2H), 2.46 (s, 3H), 1.86-1.76 (m, 2H), 1.54-1.41 (m, 2H). | 96.1 | 421.1 |
| A1026 | 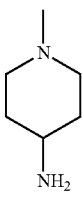 | (500 MHz, DMSO) δ 9.76 (s, 1H), 9.43 (s, 1H), 7.56 (d, J = 7.4 Hz, 2H), 7.47-7.34 (m, 2H), 7.34-7.22 (m, 1H), 4.08-3.87 (m, 1H), 3.56-3.34 (m, 2H), 3.21-3.00 (m, 2H), 2.80 (s, 3H), 2.57 (s, 3H), 2.18-2.01 (m, 2H), 1.84-1.56 (m, 2H). | 100.0 | 434.1 |
| A1027 | 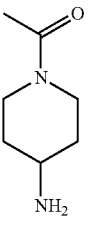 | (500 MHz, DMSO) δ 12.54 (s, 1H), 8.92-8.64 (m, 1H), 7.52-7.47 (m, 2H), 7.47-7.42 (m, 3H), 4.19-4.07 (m, 1H), 4.04-3.91 (m, 1H), 3.80-3.69 (m, 1H), 3.26-3.15 (m, 1H), 2.92-2.82 (m, 1H), 2.47 (s, 3H), 2.01 (s, 3H), 1.95-1.85 (m, 1H), 1.86-1.78 (m, 1H), 1.53-1.36 (m, 1H), 1.36-1.23 (m, 1H). | 96.9 | 462.1 |
| A1028 | 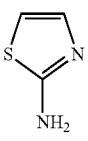 | (500 MHz, DMSO) δ 13.32 (s, 1H), 7.53 (d, J = 7.6 Hz, 2H), 7.47 (m, 3H), 7.38 (t, J = 7.5 Hz, 1H), 7.19 (d, J = 5.3 Hz, 2H), 2.68 (s, 3H). | 98.0 | 420.0 |

TABLE 2-continued

| Compound ID | Compound I-5 replacement | ¹H NMR | Purity (%) | MS (m/z) |
|---|---|---|---|---|
| A1029 | 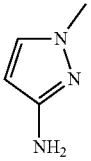 | (500 MHz, DMSO) δ 12.73 (s, 1H), 11.88 (s, 1H), 7.59-7.50 (m, 3H), 7.47 (t, J = 7.7 Hz, 2H), 7.38 (t, J = 7.3 Hz, 1H), 6.59 (s, 1H), 3.76 (s, 3H), 2.64 (s, 3H). | 100.0 | 417.1 |
| A1030 | 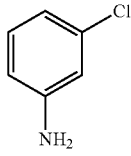 | (500 MHz, DMSO) δ 12.68 (s, 1H), 10.92 (s, 1H), 7.90 (t, J = 1.9 Hz, 1H), 7.48-7.37 (m, 6H), 7.31 (t, J = 8.1 Hz, 1H), 7.08 (dd, J = 8.0, 1.2 Hz, 1H), 2.45 (s, 3H). | 100.0 | 447.0 |
| A1031 | 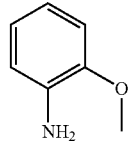 | (500 MHz, DMSO) δ 12.88 (s, 1H), 11.36 (s, 1H), 8.45-8.37 (m, 1H), 7.56-7.49 (m, 2H), 7.49-7.43 (m, 3H), 7.11-7.02 (m, 2H), 6.94 (ddd, J = 8.6, 6.8, 2.1 Hz, 1H), 3.91 (s, 3H), 2.75 (s, 3H). | 99.2 | 443.0 |
| A1032 | 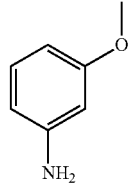 | (500 MHz, DMSO) δ 12.69 (s, 1H), 10.63 (s, 1H), 7.57-7.43 (m, 5H), 7.41 (t, J = 2.0 Hz, 1H), 7.25 (t, J = 8.1 Hz, 1H), 7.19 (d, J = 8.7 Hz, 1H), 6.68 (dd, J = 8.1, 1.7 Hz, 1H), 3.76 (s, 3H), 2.50 (s, 3H). | 95.4 | 443.1 |
| A1033 | 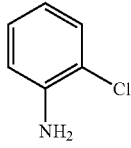 | (500 MHz, DMSO) δ 13.00 (s, 1H), 11.74 (s, 1H), 8.44 (d, J = 7.9 Hz, 1H), 7.56-7.44 (m, 6H), 7.39-7.33 (m, 1H), 7.16-7.11 (m, 1H), 2.76 (s, 3H) | 100.0 | 447.0 |
| A1034 | 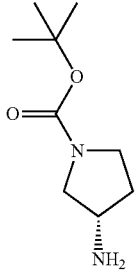 | (500 MHz, DMSO) δ 12.55 (s, 1H), 8.99 (s, 1H), 7.53-7.40 (m, 5H), 4.43-4.27 (m, 1H), 3.58-3.44 (m, 1H), 3.33 (d, J = 6.7 Hz, 2H), 3.23-3.08 (m, 1H), 2.45 (s, 3H), 2.14-2.03 (m, 1H), 1.91-1.75 (m, 1H), 1.41 (s, 9H). | 100.0 | 450.0 |
| A1035 | 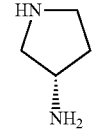 | (400 MHz, DMSO) δ 9.95 (d, J = 5.8 Hz, 1H), 8.86 (s, 2H), 7.57 (d, J = 7.4 Hz, 2H), 7.41 (t, J = 7.7 Hz, 2H), 7.28 (t, J = 7.4 Hz, 1H), 4.51-4.38 (m, 1H), 3.45-3.36 (m, 2H), 3.30-3.19 (m, 2H), 2.49 (s, 3H), 2.35-2.19 (m, 1H), 1.92 (td, J = 13.2, 6.7 Hz, 1H). | 99.7 | 406.0 |
| A1036 | 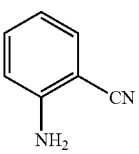 | (500 MHz, DMSO) δ 12.98 (br s, 1H), 11.94 (br s, 1H), 8.28 (s, 1H), 7.86-7.80 (m, 1H), 7.71 (t, J = 7.9 Hz, 1H), 7.54-7.48 (m, 4H), 7.48-7.42 (m, 1H), 7.29 (t, J = 7.8 Hz, 1H), 2.71 (s, 3H). | 100.0 | 438.2 |

TABLE 2-continued

| Compound ID | Compound I-5 replacement | ¹H NMR | Purity (%) | MS (m/z) |
|---|---|---|---|---|
| A1037 | 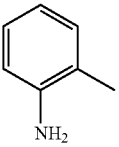 | (500 MHz, DMSO) δ 12.83 (s, 1H), 7.99 (d, J = 8.1 Hz, 1H), 7.56-7.43 (m, 5H), 7.25 (d, J = 7.1 Hz, 1H), 7.23-7.17 (m, 1H), 7.08-7.02 (m, 1H), 2.67 (s, 3H), 2.34 (s, 3H). | 99.6 | 427.3 |
| A1038 | 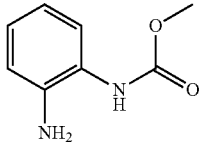 | (400 MHz, DMSO) δ 8.89 (s, 1H), 7.99 (s, 1H), 7.56-7.35 (m, 7H), 7.23-7.15 (m, 1H), 7.11 (t, J = 7.3 Hz, 1H), 3.67 (s, 3H), 2.66 (s, 3H). | 100.0 | 485.9 |
| A1039 | 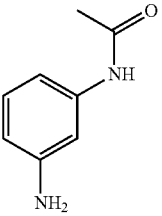 | (400 MHz, DMSO) δ 12.70 (s, 1H), 11.02 (s, 1H), 9.98 (s, 1H), 7.98 (s, 1H), 7.56-7.46 (m, 4H), 7.44 (s, 1H), 7.35 (d, J = 7.5 Hz, 2H), 7.23 (t, J = 8.0 Hz, 1H), 2.54 (d, J = 2.2 Hz, 3H), 2.04 (s, 3H). | 96.1 | 469.8 |
| A1040 | 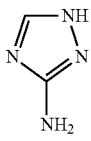 | (500 MHz, DMSO) δ 13.46 (s, 1H), 7.75 (s, 1H), 7.58-7.44 (m, 5H), 7.40 (s, 1H), 2.68 (s, 3H). | 100.0 | 404.1 |
| A1041 | 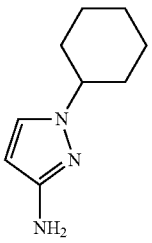 [SMILES: Nc1ccn(C2CCCCC2)n1] | (500 MHz, DMSO) δ 12.75 (s, 1H), 7.66 (d, J = 2.2 Hz, 1H), 7.55-7.43 (m, 5H), 6.58 (d, J = 2.3 Hz, 1H), 4.08-3.99 (m, 1H), 2.58 (s, 3H), 2.00 (d, J = 10.6 Hz, 2H), 1.81 (d, J = 13.5 Hz, 2H), 1.71-1.64 (m, 2H), 1.45-1.33 (m, 2H), 1.26-1.14 (m, 1H). | 100.0 | 485.2 |
| A1042 | 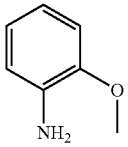<br>Also replace I-2 with<br>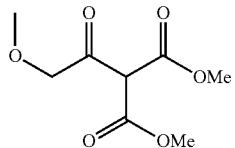 | (500 MHz, DMSO) δ 11.37 (s, 1H), 8.42-8.38 (m, 1H), 7.56-7.43 (m, 5H), 7.11-7.04 (m, 2H), 6.99-6.92 (m, 1H), 4.95 (s, 2H), 3.91 (s, 3H), 3.40 (s, 3H). | 100.0 | 473.2 |
| A1043 | 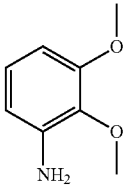 | (500 MHz, DMSO) δ 12.92 (s, 1H), 11.45 (s, 1H), 8.05 (dd, J = 8.3, 1.1 Hz, 1H), 7.56-7.51 (m, 2H), 7.50-7.45 (m, 3H), 7.05 (t, J = 8.3 Hz, 1H), 6.81 (dd, J = 8.4, 1.3 Hz, 1H), 3.84 (s, 3H), 3.83 (s, 3H), 2.76 (s, 3H). | 98.8 | 473.1 |

TABLE 2-continued

| Compound ID | Compound I-5 replacement | $^1$H NMR | Purity (%) | MS (m/z) |
|---|---|---|---|---|
| A1044 | (2-aminophenoxy cyclopentane) | (500 MHz, DMSO) δ 12.91 (s, 1H), 11.40 (s, 1H), 8.43 (d, J = 8.3 Hz, 1H), 7.55-7.44 (m, 5H), 7.08-7.00 (m, 2H), 6.93-6.88 (m, 1H), 4.98-4.90 (m, 1H), 2.02-1.93 (m, 2H), 1.92-1.82 (m, 4H), 1.67-1.58 (m, 2H). | 95.7 | 497.2 |
| A1045 | (3-amino-N-methylsulfonylaniline) | (500 MHz, DMSO) δ 12.70 (s, 1H), 11.02 (s, 1H), 9.76 (s, 1H), 7.61 (t, J = 2.0 Hz, 1H), 7.53-7.46 (m, 4H), 7.44 (d, J = 7.8 Hz, 2H), 7.28 (t, J = 8.1 Hz, 2H), 6.94 (dd, J = 8.1, 1.3 Hz, 1H), 3.00 (s, 3H), 2.53 (s, 3H). | 99.8 | 505.9 |
| A1046 | (3-amino-N,N-bis(methylsulfonyl)aniline) | (500 MHz, DMSO) δ 12.76 (s, 1H), 11.26 (s, 1H), 7.86 (s, 1H), 7.77 (d, J = 8.5 Hz, 1H), 7.59-7.37 (m, 6H), 7.23 (d, J = 7.9 Hz, 1H), 3.54 (s, 6H), 2.57 (s, 3H). | 100.0 | 584.0 |
| A1047 | (4-aminopyridine) | (400 MHz, DMSO) δ 12.58 (s, 1H), 8.42 (s, 3H), 7.65 (s, 2H), 7.57 (d, J = 7.4 Hz, 2H), 7.43 (t, J = 7.4 Hz, 2H), 7.31 (t, J = 7.2 Hz, 1H), 2.65 (s, 3H). | 99.4 | 414.0 |
| A1048 | (2-amino-4-isopropyloxazole) | (500 MHz, DMSO) δ 13.05 (s, 1H), 8.16 (s, 1H), 7.57 (d, J = 7.3 Hz, 2H), 7.50 (d, J = 1.2 Hz, 1H), 7.44-7.36 (m, 2H), 7.32-7.25 (m, 1H), 2.79-2.68 (m, 1H), 2.64 (s, 3H), 1.19 (d, J = 6.9 Hz, 6H). | 99.4 | 446.2 |
| A1049 | (2-(trifluoromethoxy)aniline) | (500 MHz, DMSO) δ 13.03 (s, 1H), 11.92 (s, 1H), 8.51 (d, J = 8.2 Hz, 1H), 7.55-7.36 (m, 7H), 7.20 (dt, J = 24.8, 9.1 Hz, 1H), 2.76 (s, 3H). | 99.6 | 497.2 |
| A1050 | (3-(trifluoromethoxy)aniline) | (500 MHz, DMSO) δ 12.76 (s, 1H), 11.30 (s, 1H), 7.95 (s, 1H), 7.54-7.41 (m, 7H), 7.08 (d, J = 8.9 Hz, 1H), 2.54 (d, J = 5.7 Hz, 3H). | 99.2 | 497.2 |
| A1051 | (2-(isopropylsulfonyl)aniline) | (500 MHz, DMSO) δ 12.11 (s, 1H), 8.41 (d, J = 7.5 Hz, 1H), 8.22 (s, 1H), 7.84 (dd, J = 8.0, 1.6 Hz, 1H), 7.68 (t, J = 7.1 Hz, 1H), 7.58 (d, J = 7.5 Hz, 2H), 7.44 (t, J = 7.7 Hz, 2H), 7.30 (dd, J = 15.4, 7.9 Hz, 2H), 3.67-3.60 (m, 1H), 2.63 (s, 3H), 1.21-1.18 (m, 6H). | 98.6 | 519.2 |

TABLE 2-continued

| Compound ID | Compound I-5 replacement | ¹H NMR | Purity (%) | MS (m/z) |
|---|---|---|---|---|
| A1052 | 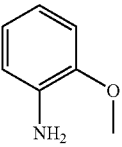<br>Also replace I-1 with<br>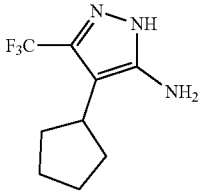 | (500 MHz, DMSO) δ 12.48 (s, 1H), 11.30 (s, 1H), 8.40 (d, J = 8.0 Hz, 1H), 7.11-7.02 (m, 2H), 6.98-6.90 (m, 1H), 3.89 (s, 3H), 3.41-3.28 (m, 1H), 2.81 (s, 3H), 2.01-1.89 (m, 2H), 1.87-1.60 (m, 6H). | 97.1 | 435.2 |
| A1053 | 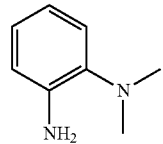 | (500 MHz, DMSO) δ 12.86 (s, 1H), 11.33 (s, 1H), 8.43-8.34 (m, 1H), 7.56-7.43 (m, 5H), 7.26-7.19 (m, 1H), 7.12-6.99 (m, 2H), 2.75 (s, 3H), 2.68 (s, 6H). | 99.7 | 456.2 |
| A1054 | 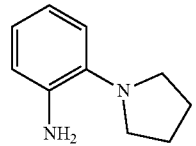 [SMILES: Nc1ccccc1N1CCCC1] | (500 MHz, DMSO) δ 8.08 (d, J = 8.2 Hz, 1H), 7.50 (d, J = 4.5 Hz, 4H), 7.46-7.38 (m, 1H), 7.08 (dd, J = 8.0, 1.4 Hz, 1H), 7.06-6.99 (m, 1H), 6.97-6.91 (m, 1H), 3.13-3.07 (m, 4H), 2.71 (s, 3H), 1.97-1.87 (m, 4H). | 99.7 | 482.3 |
| A1055 | 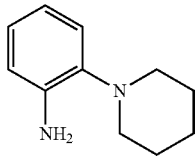 [SMILES: Nc1ccccc1N1CCCCC1] | (500 MHz, DMSO) δ 11.60 (s, 1H), 8.43 (dd, J = 7.9, 1.7 Hz, 1H), 7.54-7.46 (m, 4H), 7.45-7.38 (m, 1H), 7.18 (dd, J = 7.6, 1.7 Hz, 1H), 7.10-6.98 (m, 2H), 2.83-2.77 (m, 4H), 2.74 (s, 3H), 1.84-1.76 (m, 4H), 1.61-1.51 (m, 2H). | 100 | 496.3 |
| A1056 | 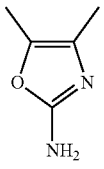 | (500 MHz, DMSO) δ 12.91 (s, 1H), 8.30 (s, 1H), 7.57 (d, J = 7.5 Hz, 2H), 7.44 (t, J = 7.7 Hz, 2H), 7.31 (t, J = 7.4 Hz, 1H), 2.63 (s, 3H), 2.21 (s, 3H), 1.99 (s, 3H). | 95.6 | 432.3 |
| A1057 | 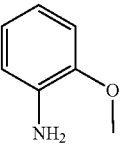<br>Also replace I-2 with<br>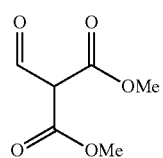 | (500 MHz, MeOD) δ 8.77 (s, 1H), 8.42 (dd, J = 8.0, 1.5 Hz, 1H), 7.59-7.43 (m, 5H), 7.15-7.04 (m, 2H), 7.02-6.90 (m, 1H), 4.01 (s, 3H). | 99.9 | 429.8 |
| A1058 | 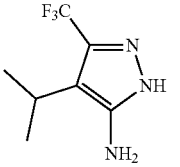 | (500 MHz, DMSO) δ 13.45 (s, 2H), 7.56-7.43 (m, 14H), 3.08-2.99 (m, 3H), 2.69 (s, 8H), 1.28 (d, J = 7.1 Hz, 6H). | 99.5 | 513.3 |

TABLE 2-continued

| Compound ID | Compound I-5 replacement | ¹H NMR | Purity (%) | MS (m/z) |
|---|---|---|---|---|
| A1059 | 2-aminophenyl phenylsulfonamide | (500 MHz, DMSO) δ 8.37-8.17 (m, 1H), 8.02-7.90 (m, 1H), 7.68 (d, J = 7.4 Hz, 2H), 7.61 (d, J = 7.8 Hz, 2H), 7.55-7.47 (m, 1H), 7.47-7.36 (m, 5H), 7.35-7.27 (m, 1H), 7.12-7.01 (m, 1H), 6.97-6.82 (m, 2H), 2.65 (s, 2H). | 96.1 | 568.0 |
| A1060 | 2-isopropoxyaniline | (500 MHz, DMSO) δ 12.89 (s, 1H), 11.41 (s, 1H), 8.42 (dd, J = 8.1, 1.5 Hz, 1H), 7.56-7.40 (m, 5H), 7.13-7.08 (m, 1H), 7.03 (td, J = 7.8, 1.6 Hz, 1H), 6.96-6.88 (m, 1H), 4.75-4.64 (m, 1H), 2.78 (s, 3H), 1.37 (s, 3H), 1.36 (s, 3H). | 99.2 | 471.2 |
| A1061 | 4-cyclopentyl-3-trifluoromethyl-5-amino-1H-pyrazole | (500 MHz, DMSO) δ 13.48 (s, 1H), 7.54-7.43 (m, 5H), 3.06-2.94 (m, 1H), 2.68 (s, 3H), 1.93-1.56 (m, 8H). | 98.1 | 539.3 |
| A1062 | 2,2-difluoro-1,3-benzodioxol-4-amine | (500 MHz, DMSO) δ 12.89 (s, 1H), 11.42 (s, 1H), 7.90 (d, J = 8.1 Hz, 1H), 7.60-7.42 (m, 5H), 7.25-7.13 (m, 2H), 2.65 (s, 3H). | 99.8 | 493.2 |
| A1063 | 4-methoxy-2-aminopyridine | (500 MHz, DMSO) δ 12.54 (s, 1H), 8.17-8.07 (m, 2H), 7.93 (d, J = 1.9 Hz, 1H), 7.57 (d, J = 7.4 Hz, 2H), 7.45 (dd, J = 10.6, 4.9 Hz, 2H), 7.33 (t, J = 7.4 Hz, 1H), 6.67 (dd, J = 5.8, 2.4 Hz, 1H), 3.86 (s, 3H), 2.69 (s, 3H). | 98.6 | 444.9 |
| A1064 | 6-methoxy-2-aminopyridine | (500 MHz, DMSO) δ 13.00-12.58 (m, 1H), 11.89-11.30 (m, 1H), 7.84 (d, J = 7.8 Hz, 1H), 7.70 (t, J = 7.9 Hz, 1H), 7.54-7.37 (m, 5H), 6.53 (d, J = 8.0 Hz, 1H), 3.85 (s, 3H), 2.65 (s, 3H). | 99.5 | 444.9 |
| A1065 | 1-isopropyl-3-amino-1H-pyrazole | (500 MHz, DMSO) δ 12.64 (s, 1H), 11.22 (s, 1H), 7.59 (d, J = 2.2 Hz, 1H), 7.48-7.35 (m, 5H), 6.51 (d, J = 2.3 Hz, 1H), 4.39-4.29 (m, 1H), 2.51 (s, 3H), 1.34 (s, 3H), 1.33 (s, 3H). | 99.3 | 445.2 |
| A1066 | 3-isopropoxyaniline | (500 MHz, DMSO) δ 12.70 (s, 1H), 10.61 (s, 1H), 7.56-7.51 (m, 2H), 7.50-7.44 (m, 3H), 7.40 (t, J = 2.1 Hz, 1H), 7.23 (t, J = 8.1 Hz, 1H), 7.16-7.13 (m, 1H), 6.66 (dd, J = 8.2, 1.8 Hz, 1H), 4.63-4.53 (m, 1H), 1.29 (s, 3H), 1.28 (s, 3H). | 99.5 | 471.2 |

TABLE 2-continued

| Compound ID | Compound I-5 replacement | ¹H NMR | Purity (%) | MS (m/z) |
|---|---|---|---|---|
| A1067 | 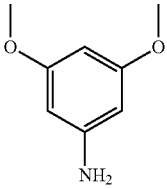 | (500 MHz, DMSO) δ 12.69 (s, 1H), 7.54-7.41 (m, 5H), 6.93 (d, J = 2.2 Hz, 2H), 6.25 (dd, J = 2.5, 2.2 Hz, 1H), 3.74 (s, 6H), 2.52 (s, 3H). | 95.5 | 473.8 |
| A1068 | 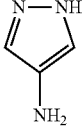 | (500 MHz, DMSO) δ 12.66 (s, 1H), 10.89 (s, 1H), 7.83 (s, 3H), 7.55-7.39 (m, 5H), 2.56 (s, 3H). | 99.4 | 403.2 |
| A1069 | 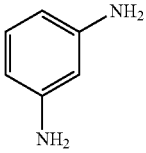 | (400 MHz, DMSO) δ 11.98 (s, 1H), 8.13 (s, 1H), 7.58 (d, J = 7.6 Hz, 2H), 7.42 (t, J = 7.5 Hz, 2H), 7.29 (t, J = 7.3 Hz, 1H), 7.06 (s, 1H), 6.92 (t, J = 7.8 Hz, 1H), 6.72 (d, J = 7.6 Hz, 1H), 6.22 (d, J = 8.0 Hz, 1H), 2.65 (s, 3H). | 98.4 | 428.0 |
| A1070 | 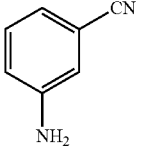 | (500 MHz, DMSO) δ 12.78 (s, 1H), 8.27 (s, 1H), 7.84 (d, J = 8.0 Hz, 1H), 7.59-7.47 (m, 6H), 7.46-7.40 (m, 1H), 2.57 (s, 3H). | 98.4 | 438.1 |
| A1071 | 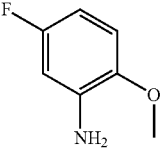 | (500 MHz, DMSO) δ 12.97 (s, 1H), 11.59 (s, 1H), 8.30 (dd, J = 11.3, 3.2 Hz, 1H), 7.56-7.45 (m, 5H), 7.09 (dd, J = 9.1, 5.2 Hz, 1H), 6.91-6.85 (m, 1H), 3.92 (s, 3H), 2.78 (s, 3H). | 100.0 | 461.1 |
| A1072 | 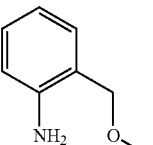 | (500 MHz, DMSO) δ 12.86 (s, 1H), 10.85 (s, 1H), 8.06 (d, J = 8.1 Hz, 1H), 7.56-7.45 (m, 5H), 7.39 (dd, J = 7.6, 1.3 Hz, 1H), 7.37-7.32 (m, 1H), 7.14 (td, J = 7.5, 1.0 Hz, 1H), 4.52 (s, 2H), 3.38 (s, 3H), 2.70 (s, 3H). | 100.0 | 425.1 |
| A1073 | 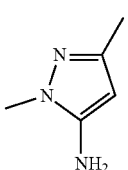 | (500 MHz, DMSO) δ 12.82 (s, 1H), 11.34 (s, 1H), 7.55-7.38 (m, 5H), 6.19 (s, 1H), 3.68 (s, 3H), 2.62 (s, 3H), 2.12 (s, 3H). | 99.8 | 431.9 |
| A1074 | 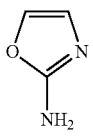 | (500 MHz, DMSO) δ 13.10 (s, 1H), 7.84 (s, 1H), 7.55 (d, J = 14.4 Hz, 2H), 7.44 (t, J = 7.7 Hz, 2H), 7.33 (t, J = 7.4 Hz, 1H), 7.07 (s, 1H), 2.65 (s, 3H). | 98.4 | 404.1 |
| A1075 | 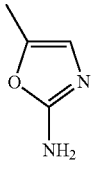 | (500 MHz, DMSO) δ 12.96 (s, 1H), 8.21 (s, 1H), 7.57 (d, J = 7.3 Hz, 2H), 7.46-7.41 (m, 2H), 7.34-7.29 (m, 1H), 6.68 (d, J = 1.3 Hz, 1H), 2.63 (s, 3H), 2.28 (s, 3H). | 96.4 | 418.1 |

| Compound ID | Compound I-5 replacement | $^1$H NMR | Purity (%) | MS (m/z) |
|---|---|---|---|---|
| A1076 | 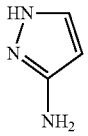 | (500 MHz, DMSO) δ 12.73 (s, 1H), 12.36 (s, 1H), 7.61 (s, 1H), 7.56-7.46 (m, 4H), 7.40 (t, J = 7.9 Hz, 1H), 6.62 (s, 1H), 2.63 (s, 3H). | 100.0 | 403.2 |
| A1077 | 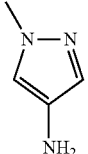 | (500 MHz, DMSO) δ 7.94 (s, 1H), 7.47 (d, J = 7.5 Hz, 2H), 7.43 (d, J = 0.6 Hz, 1H), 7.38 (t, J = 7.5 Hz, 2H), 7.31-7.25 (m, 1H), 3.74 (s, 3H), 2.53 (s, 3H). | | 417.1 |
| A1078 | 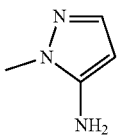 | (500 MHz, DMSO) δ 12.74 (s, 1H), 11.90 (br s, 1H), 7.54-7.46 (m, 4H), 7.44-7.38 (m, 1H), 7.34 (d, J = 1.8 Hz, 1H), 6.39 (d, J = 1.8 Hz, 1H), 3.77 (s, 3H), 2.65 (s, 3H). | | 417.1 |
| A1079 | 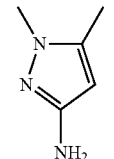 | (500 MHz, DMSO) δ 12.73 (s, 1H), 11.64 (br s, 1H), 7.54-7.45 (m, 4H), 7.42-7.36 (m, 1H), 6.43 (s, 1H), 3.64 (s, 3H), 2.62 (s, 3H), 2.24 (s, 3H). | | 431.2 |
| A1080 | 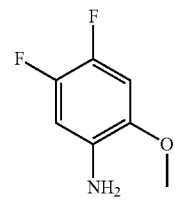 | (500 MHz, DMSO) δ 12.86 (s, 1H), 11.12 (s, 1H), 8.06 (dd, J = 13.1, 7.4 Hz, 1H), 7.49-7.36 (m, 5H), 7.24 (dd, J = 12.4, 7.9 Hz, 1H), 3.78 (s, 3H), 2.62 (s, 3H). | | 479.2 |
| A1081 | 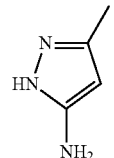 | (500 MHz, DMSO) δ 12.24 (s, 1H), 11.85 (s, 1H), 7.58 (d, J = 7.4 Hz, 2H), 7.47-7.39 (m, 2H), 7.33-7.26 (m, 1H), 6.41 (s, 1H), 5.90 (br s, 1H), 2.67 (s, 3H), 2.21 (s, 3H). | | 417.1 |
| A1082 | 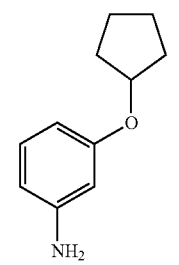 [SMILES: Nc1cccc(OC2CCCC2)c1] | (500 MHz, DMSO) δ 12.69 (s, 1H), 10.67 (s, 1H), 7.55-7.50 (m, 2H), 7.47 (t, J = 6.8 Hz, 3H), 7.39 (t, J = 2.1 Hz, 1H), 7.22 (t, J = 8.1 Hz, 1H), 7.13 (d, J = 9.0 Hz, 1H), 6.63 (dd, J = 8.2, 1.8 Hz, 1H), 4.84-4.73 (m, 1H), 1.97-1.86 (m, 2H), 1.77-1.66 (m, 4H), 1.65-1.54 (m, 2H). | | 497.2 |
| A1083 | 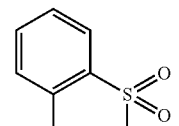 | (500 MHz, DMSO) δ 12.97 (s, 1H), 11.13 (s, 1H), 8.40 (d, J = 8.2 Hz, 1H), 7.94 (dd, J = 8.0, 1.5 Hz, 1H), 7.76 (t, J = 7.5 Hz, 1H), 7.55-7.45 (m, 5H), 7.40 (t, J = 7.7 Hz, 1H), 3.35 (s, 3H), 2.69 (s, 3H). | 96.6 | 491.2 |

TABLE 2-continued

| Compound ID | Compound I-5 replacement | ¹H NMR | Purity (%) | MS (m/z) |
|---|---|---|---|---|
| A1084 | 3-methylsulfonyl aniline | (500 MHz, DMSO) δ 12.76 (s, 1H), 11.10 (s, 1H), 8.41 (s, 1H), 7.90 (s, 1H), 7.64 (d, J = 5.0 Hz, 2H), 7.55-7.42 (m, 5H), 3.23 (s, 3H), 2.54 (s, 3H). | 99.7 | 491.2 |
| A1085 | 2-methoxycyclohexan-1-amine | (500 MHz, DMSO) δ 12.58 (s, 1H), 8.82 (s, 1H), 7.58-7.34 (m, 5H), 4.07-3.95 (m, 1H), 3.42-3.37 (m, 1H), 3.29 (s, 3H), 2.56 (s, 3H), 1.91-1.83 (m, 1H), 1.66-1.27 (m, 7H). | 98.9 | 449.2 |
| A1086 | 3-(benzyloxy)aniline | (500 MHz, MeOD) δ 7.53-7.44 (m, 8H), 7.37 (t, J = 7.5 Hz, 2H), 7.31 (t, J = 7.4 Hz, 1H), 7.25 (t, J = 8.1 Hz, 1H), 7.17 (d, J = 8.8 Hz, 1H), 6.78 (dd, J = 8.2, 2.4 Hz, 1H), 5.11 (s, 2H), 2.70 (s, 3H). | | 519.2 |
| A1087 | 2-methoxypyridin-4-amine | (500 MHz, DMSO) δ 11.06 (s, 1H), 8.06 (d, J = 5.0 Hz, 1H), 7.54-7.42 (m, 6H), 7.23 (s, 1H), 7.13 (d, J = 5.7 Hz, 1H), 3.84 (s, 3H), 2.50 (s, 3H). | 100 | 444.2 |
| A1088 | 6-methoxypyridin-3-amine | (500 MHz, DMSO) δ 12.72 (s, 1H), 10.97 (s, 1H), 8.45 (d, J = 2.6 Hz, 1H), 8.02 (dd, J = 8.9, 2.7 Hz, 1H), 7.54-7.41 (m, 5H), 6.84 (d, J = 8.8 Hz, 1H), 3.84 (s, 3H), 2.54 (s, 3H). | 100 | 444.1 |
| A1089 | 2-methoxycyclohexan-1-amine | (500 MHz, DMSO-d6) δ 12.53 (s, 1H), 7.47 (s, 4H), 7.41 (s, 1H), 3.86-3.73 (m, 1H), 3.29 (s, 3H), 3.17-3.06 (m, 1H), 2.52 (s, 3H), 2.03-1.86 (m, 2H), 1.70-1.55 (m, 2H), 1.37-1.20 (m, 4H). | 95.8 | 449.2 |
| A1090 | 3-amino-1-methyl-1H-pyrazole-4-carbonitrile | (500 MHz, DMSO) δ 12.38 (s, 1H), 8.31 (s, 1H), 8.20 (s, 1H), 7.51 (d, J = 7.6 Hz, 2H), 7.36 (t, J = 7.7 Hz, 2H), 7.24 (t, J = 7.4 Hz, 1H), 3.75 (s, 3H), 2.58 (s, 3H). | | 442.2 |
| A1091 | 2-aminocyclohexan-1-ol | (500 MHz, DMSO) δ 12.53 (s, 1H), 7.55-7.39 (m, 5H), 4.65 (s, 1H), 3.68-3.52 (m, 1H), 3.37-3.31 (m, 1H), 2.51 (s, 3H), 1.98-1.91 (m, 1H), 1.89-1.82 (m, 1H), 1.68-1.56 (m, 2H), 1.33-1.15 (m, 4H). | 97.1 | 435.2 |

TABLE 2-continued

| Compound ID | Compound I-5 replacement | $^1$H NMR | Purity (%) | MS (m/z) |
|---|---|---|---|---|
| A1092 | 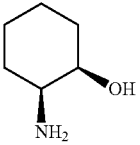 | (500 MHz, DMSO) δ 12.57 (s, 1H), 8.73 (s, 1H), 7.59-7.36 (m, 5H), 4.65 (s, 1H), 3.89-3.82 (m, 1H), 3.80-3.76 (m, 1H), 2.57 (s, 3H), 1.72-1.45 (m, 6H), 1.37-1.25 (m, 2H). | 97.8 | 435.3 |
| A1093 | 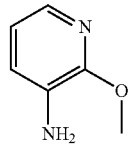 | (500 MHz, DMSO) δ 12.97 (s, 1H), 11.46 (s, 1H), 8.66 (dd, J = 7.8, 1.7 Hz, 1H), 7.87 (dd, J = 5.0, 1.7 Hz, 1H), 7.58-7.41 (m, 5H), 7.01-6.98 (m, 1H), 4.00 (s, 3H), 2.76 (s, 3H). | 99.0 | 444.1 |
| A1094 | 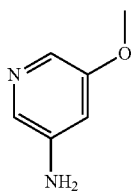 | (500 MHz, CD$_3$CN) δ 12.48 (s, 1H), 8.28 (d, J = 1.7 Hz, 1H), 7.97 (s, 1H), 7.94-7.92 (m, 1H), 7.88 (d, J = 2.5 Hz, 1H), 7.54 (d, J = 7.4 Hz, 2H), 7.39-7.35 (m, 2H), 7.30-7.25 (m, 1H), 3.80 (s, 3H), 2.67 (s, 3H). | 99.0 | 444.1 |
| A1095 | 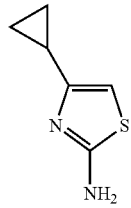 | (500 MHz, DMSO) δ 13.40 (s, 1H), 12.73 (s, 1H), 7.56 (s, 1H), 7.55 (s, 1H), 7.48-7.43 (m, 2H), 7.35 (t, J = 7.3 Hz, 1H), 6.71 (s, 1H), 2.68 (s, 3H), 2.02-1.95 (m, 1H), 0.88-0.76 (m, 4H). | 98.0 | 460.2 |
| A1096 | 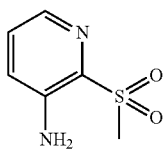 | (500 MHz, DMSO) δ 12.14 (s, 1H), 8.85 (dd, J = 8.5, 1.2 Hz, 1H), 8.39 (d, J = 3.3 Hz, 1H), 7.74-7.66 (m, 1H), 7.56 (s, 1H), 7.54 (s, 1H), 7.50-7.42 (m, 2H), 7.36 (t, J = 7.3 Hz, 1H), 3.40 (s, 3H), 2.70-2.60 (m, 3H). | 96.0 | 491.2 |
| A1097 | 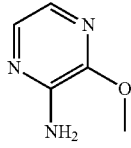 | (500 MHz, CD$_3$CN) δ 8.05 (s, 1H), 7.83 (d, J = 2.9 Hz, 1H), 7.73 (d, J = 3.0 Hz, 1H), 7.61 (d, J = 7.2 Hz, 1H), 7.46-7.41 (m, 2H), 7.30 (dd, J = 3.8, 2.7 Hz, 1H), 7.22 (dd, J = 2.7, 1.6 Hz, 1H), 7.01 (dd, J = 4.1, 1.6 Hz, 1H), 4.01 (s, 3H), 2.89 (s, 3H). | 95.6 | 445.2 |
| A1098 | 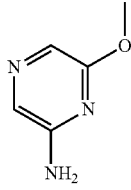 | (500 MHz, DMSO) δ 12.83 (s, 1H), 9.10 (s, 1H), 8.13 (s, 1H), 7.93 (s, 1H), 7.58 (s, 1H), 7.56 (s, 1H), 7.46-7.40 (m, 2H), 7.31 (t, J = 7.4 Hz, 1H), 3.91 (s, 3H), 2.69 (s, 3H). | 99.8 | 445.2 |
| A1099 | 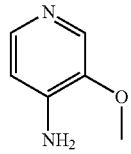 | (500 MHz, DMSO) δ 13.10 (s, 1H), 8.64 (s, 1H), 8.34 (s, 1H), 8.22 (s, 1H), 8.13 (s, 1H), 7.57 (s, 1H), 7.56 (s, 1H), 7.46-7.41 (m, 2H), 7.34-7.29 (m, 1H), 4.04 (s, 3H), 2.69 (s, 3H). | 99.2 | 444.3 |

TABLE 2-continued

| Compound ID | Compound I-5 replacement | ¹H NMR | Purity (%) | MS (m/z) |
|---|---|---|---|---|
| A1100 | | (500 MHz, DMSO) δ 12.74 (s, 1H), 8.14 (s, 1H), 7.93 (d, J = 5.2 Hz, 1H), 7.59 (s, 1H), 7.58 (s, 1H), 7.48-7.42 (m, 2H), 7.34 (t, J = 7.6 Hz, 1H), 7.18 (s, 1H), 3.95 (s, 3H), 2.69 (s, 3H). | 99.6 | 444.1 |
| A1101 | | (500 MHz, DMSO) δ 12.86 (s, 1H), 11.15 (s, 1H), 8.07 (t, J = 6.3 Hz, 1H), 7.51-7.44 (m, 5H), 6.96 (dd, J = 7.3, 0.8 Hz, 1H), 6.80 (t, J = 7.7 Hz, 1H), 4.64-4.60 (m, 2H), 3.27-3.22 (m, 2H), 2.70 (s, 3H). | 100 | 455.3 |
| A1102 | | (500 MHz, DMSO) δ 12.75 (s, 1H), 8.13 (s, 1H), 7.69 (s, 1H), 7.56-7.43 (m, 4H), 7.38 (s, 1H), 7.06 (t, J = 8.0 Hz, 1H), 6.49 (d, J = 7.8 Hz, 1H), 4.62-4.55 (m, 2H), 3.23-3.17 (m, 2H), 2.66 (s, 3H). | 100 | 455.2 |
| A1103 | | (500 MHz, DMSO) δ 12.87 (s, 1H), 9.67 (s, 1H), 8.40 (d, J = 5.4 Hz, 1H), 7.58 (s, 1H), 7.56 (s, 1H), 7.51 (d, J = 7.5 Hz, 1H), 7.45 (m, 3H), 7.33 (t, J = 7.4 Hz, 1H), 4.15 (s, 3H), 2.71 (s, 3H). | 97.9 | 444.2 |
| A1104 | | (500 MHz, DMSO) δ 12.79 (s, 1H), 8.31 (d, J = 5.6 Hz, 1H), 8.19 (s, 1H), 7.61-7.51 (m, 2H), 7.46-7.35 (m, 2H), 7.32-7.23 (m, 1H), 6.52 (d, J = 5.6 Hz, 1H), 3.92 (s, 3H), 2.63 (s, 3H). | 93.0 | 445.2 |
| A1105 | Also replace I-1 with 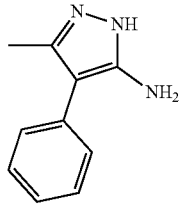 | (500 MHz, DMSO) δ 12.54-12.46 (m, 1H), 11.82-11.67 (m, 1H), 8.14 (t, J = 5.9 Hz, 1H), 7.86 (s, 1H), 7.53-7.46 (m, 4H), 7.41-7.36 (m, 1H), 6.74-6.71 (m, 1H), 3.85 (s, 3H), 2.71 (s, 3H), 2.33 (s, 3H) | 97.9 | 390.3 |

TABLE 2-continued

| Compound ID | Compound I-5 replacement | ¹H NMR | Purity (%) | MS (m/z) |
|---|---|---|---|---|
| A1106 | (2-aminophenyl methyl sulfone) Also replace I-1 with (3-amino-5-methyl-4-phenyl-1H-pyrazole) | (500 MHz, DMSO) δ 12.56 (s, 1H), 11.49-11.15 (m, 1H), 8.40 (d, J = 8.4 Hz, 1H), 7.92 (dd, J = 7.9, 1.5 Hz, 1H), 7.73 (t, J = 7.5 Hz, 1H), 7.55-7.48 (m, 4H), 7.36 (t, J = 7.5 Hz, 2H), 3.33 (s, 3H), 2.70 (s, 3H), 2.34 (s, 3H). | 100 | 437.25 |
| A1107 | (8-amino-chroman) | (500 MHz, DMSO) δ 11.91 (s, 1H), 8.26 (d, J = 6.6 Hz, 1H), 8.12 (s, 1H), 7.55-7.32 (m, 5H), 6.77-6.68 (m, 2H), 4.29-4.25 (m, 2H), 2.77-2.73 (m, 2H), 2.69 (s, 3H), 1.99-1.93 (m, 2H). | 99.3 | 469.3 |
| A1108 | (2-amino-5-(methylsulfonyl)pyridine) | (500 MHz, CD₃CN) δ 13.03 (s, 1H), 8.64 (d, J = 2.4 Hz, 1H), 8.44 (d, J = 8.9 Hz, 1H), 8.02 (dd, J = 8.9, 2.5 Hz, 1H), 7.92 (s, 1H), 7.48 (s, 1H), 7.46 (s, 1H), 7.33-7.29 (m, 2H), 7.21 (t, J = 7.4 Hz, 1H), 2.96 (s, 3H), 2.61 (s, 3H). | 92.4 | 491.2 |
| A1109 | (3-amino-4-(methylsulfonyl)pyridine) | (500 MHz, CD₃CN) δ 12.10 (s, 1H), 9.51 (s, 1H), 8.28 (d, J = 5.0 Hz, 1H), 7.86 (d, J = 17.0 Hz, 1H), 7.59 (d, J = 5.0 Hz, 1H), 7.36 (s, 1H), 7.35 (s, 1H), 7.25-7.19 (m, 2H), 7.13 (t, J = 7.4 Hz, 1H), 3.06 (s, 3H), 2.50 (s, 3H). | 96.7 | 492.2 |
| A1110 | (3-amino-6-methoxypyridazine) | (500 MHz, CD₃CN) δ 12.53 (s, 1H), 8.32 (s, 1H), 7.85 (s, 1H), 7.38 (s, 1H), 7.36 (s, 1H), 7.26-7.22 (m, 2H), 7.17-7.13 (m, 1H), 6.87 (d, J = 9.3 Hz, 1H), 3.83 (s, 3H), 2.55 (s, 3H). | 99.8 | 445.2 |
| A1111 | (propane sulfonamide) | (500 MHz, DMSO) δ 12.45 (s, 1H), 7.55-7.40 (m, 5H), 3.47 (dt, J = 15.5, 7.0 Hz, 2H), 2.57 (s, 3H), 1.76 (dt, J = 15.0, 7.5 Hz, 2H), 1.02 (t, J = 7.5 Hz, 3H). | 96.2 | 443.1 |
| A1112 | (benzyl sulfonamide) | (500 MHz, CDCl3) δ 12.41 (s, 1H), 7.53-7.41 (m, 5H), 7.40-7.36 (m, 5H), 4.83 (s, 2H), 2.65-2.60 (m, 3H). | 100 | 489.2 (M − H) |

TABLE 2-continued

| Compound ID | Compound I-5 replacement | ¹H NMR | Purity (%) | MS (m/z) |
|---|---|---|---|---|
| A1113 | (pyridine with S(=O)₂CH₃ and NH₂ substituents) | (500 MHz, DMSO) δ 12.48 (s, 1H), 8.93 (d, J = 1.9 Hz, 1H), 8.50 (dd, J = 8.6, 2.1 Hz, 1H), 8.12 (s, 1H), 8.01 (d, J = 8.6 Hz, 1H), 7.56-7.32 (m, 5H), 3.23 (s, 3H), 2.63 (s, 3H). | 99.6 | 492.0 |
| A1114 | (benzene with OMe and NHMe substituents) | (500 MHz, DMSO) δ 12.70 (s, 1H), 8.13 (s, 1H), 7.49 (s, 1H), 7.47 (s, 1H), 7.42-7.34 (m, 2H), 7.27 (s, 1H), 7.14 (s, 1H), 6.93 (s, 1H), 6.88 (d, J = 7.8 Hz, 1H), 6.71 (s, 1H), 3.65 (s, 3H), 3.31 (s, 3H), 2.13 (s, 3H). | 100.0 | 457.3 |
| A1115 | (pyrazole with N-CH₂CH₂OMe and NH₂ substituents) | (500 MHz, DMSO) δ 12.73 (s, 1H), 11.27 (s, 1H), 7.58 (d, J = 2.2 Hz, 1H), 7.51-7.40 (m, 5H), 6.56 (d, J = 2.2 Hz, 1H), 4.18-4.11 (m, 2H), 3.66-3.61 (m, 2H), 3.20 (s, 3H), 2.56 (s, 3H). | 99.6 | 461.1 |
| A1116 | (benzenesulfonamide) | (500 MHz, DMSO) δ 13.31 (s, 1H), 8.09-8.04 (m, 2H), 7.77 (t, J = 7.4 Hz, 1H), 7.70 (t, J = 7.6 Hz, 2H), 7.53 (dt, J = 15.2, 7.5 Hz, 4H), 7.44 (d, J = 7.2 Hz, 1H), 2.50 (s, 3H). | 98.5 | 477.1 |
| A1117 | (methanesulfonamide) | (500 MHz, DMSO) δ 8.34 (s, 1H), 7.55 (d, J = 7.7 Hz, 2H), 7.44 (dd, J = 10.6, 4.9 Hz, 2H), 7.33 (dd, J = 10.5, 4.3 Hz, 1H), 3.33 (s, 3H), 2.62 (s, 3H). | 97.0 | 413.1 (M − H) |
| A1118 | (pyrazole with N-CH₂CH₂OH and NH₂ substituents) | (500 MHz, DMSO) δ 12.04 (s, 1H), 8.13 (s, 1H), 7.57-7.29 (m, 6H), 6.57 (s, 1H), 4.86 (s, 1H), 4.03 (s, 2H), 3.71 (s, 2H), 2.64 (s, 3H). | 99.3 | 447.4 |

TABLE 2-continued

| Compound ID | Compound I-5 replacement | ¹H NMR | Purity (%) | MS (m/z) |
|---|---|---|---|---|
| A1119 | (structure: 2-aminophenyl sulfonamide of cyclohexane) | (500 MHz, DMSO) δ 12.25 (s, 1H), 8.26 (s, 1H), 7.77 (dd, J = 8.1, 1.4 Hz, 1H), 7.52 (d, J = 7.4 Hz, 2H), 7.41-7.33 (m, 2H), 7.30 (dd, J = 8.0, 1.5 Hz, 1H), 7.26-7.20 (m, 1H), 7.18-7.12 (m, 1H), 7.06-7.00 (m, 1H), 2.97-2.94 (m, 1H), 2.58 (s, 3H), 1.95 (d, J = 10.9 Hz, 2H), 1.56 (d, J = 13.1 Hz, 2H), 1.43 (d, J = 12.4 Hz, 1H), 1.31-1.19 (m, 2H), 1.13-1.03 (m, 2H), 1.02-0.93 (m, 1H). | 96.4 | 574.1 |
| A1120 | (structure: pyridine-2-sulfonamide) | (500 MHz, DMSO) δ 8.72 (dt, J = 4.7, 1.3 Hz, 1H), 8.15-8.13 (m, 2H), 7.70 (dd, J = 8.8, 4.6 Hz, 1H), 7.53 (d, J = 7.4 Hz, 2H), 7.43 (dd, J = 10.6, 4.9 Hz, 2H), 7.32 (t, J = 7.4 Hz, 1H), 2.43 (s, 3H). | 96.7 | 478.2 |
| A1121 | (structure: 2-methoxybenzenesulfonamide) | (500 MHz, DMSO) δ 7.91 (dd, J = 7.9, 1.7 Hz, 1H), 7.69-7.65 (m, 1H), 7.49-7.45 (m, 4H), 7.42 (s, 1H), 7.24 (d, J = 8.2 Hz, 1H), 7.19-7.13 (m, 1H), 3.86 (s, 3H), 2.45 (s, 3H). | 96.9 | 507.3 |
| A1122 | (structure: 3-methoxyaniline) Also replace I-1 with (structure: 3-methylthio-4-phenyl-1H-pyrazol-5-amine) | (500 MHz, DMSO) δ 12.34 (brs, 1H), 7.60-7.54 (m, 2H), 7.49 (t, J = 7.7 Hz, 2H), 7.42 (t, J = 2.1 Hz, 1H), 7.36 (t, J = 7.2 Hz, 1H), 7.27-7.22 (m, 1H), 7.21-7.17 (m, 1H), 3.77 (s, 3H), 2.58 (s, 3H), 2.58 (overlapping s, 3H). | 97.6 | 421.1 |
| A1123 | (structure: 3-methoxyaniline) Also replace I-1 with (structure: 3-cyclopropyl-4-phenyl-1H-pyrazol-5-amine) | (500 MHz, DMSO) δ 7.67-7.62 (m, 2H), 7.49 (t, J = 7.7 Hz, 2H), 7.42 (m, 1H), 7.37-7.32 (m, 1H), 7.25-7.20 (m, 1H), 7.15 (m, 1H), 6.63 (dd, J = 8.1, 1.0 Hz, 1H), 3.76 (s, 3H), 2.59 (s, 3H), 1.98-1.90 (m, 1H), 1.02-0.95 (m, 4H). | 98.2 | 415.2 |

TABLE 2-continued

| Compound ID | Compound I-5 replacement | ¹H NMR | Purity (%) | MS (m/z) |
|---|---|---|---|---|
| A1124 | cyclohexyl-SO₂NH₂ | (500 MHz, DMSO) δ 13.08 (s, 1H), 7.54 (d, J = 7.3 Hz, 2H), 7.46-7.41 (m, 2H), 7.34-7.30 (m, 1H), 3.51 (tt, J = 12.2, 3.5 Hz, 2H), 2.59 (s, 3H), 2.04 (d, J = 10.7 Hz, 2H), 1.82 (d, J = 13.2 Hz, 2H), 1.63 (d, J = 12.4 Hz, 1H), 1.48 (qd, J = 12.5, 3.3 Hz, 2H), 1.33-1.23 (m, 2H), 1.16 (dd, J = 25.3, 12.6 Hz, 1H). | 100 | 483.3 |
| A1125 | 3-methoxyphenyl-SO₂NH₂ | (500 MHz, DMSO) δ 13.78-13.56 (m, 1H), 8.15 (s, 1H), 7.57-7.50 (m, 4H), 7.47 (dd, J = 2.5, 1.2 Hz, 1H), 7.44-7.39 (m, 2H), 7.33-7.28 (m, 1H), 7.27-7.24 (m, 1H), 3.83 (s, 3H), 2.48 (s, 3H). | 97.1 | 507.3 |
| A1126 | 3-methoxyaniline; Also replace I-1 with methylsulfonyl-phenyl-pyrazol-amine | (500 MHz, DMSO) δ 12.72 (brs, 1H), 7.70 (brs, 2H), 7.43-7.47 (m, 3H), 7.35-7.41 (m, 1H), 7.22-7.25 (m, 1H), 7.16-7.18 (m, 1H), 6.62-6.67 (m, 1H), 3.77 (s, 3H), 3.35 (s, 3H), 2.60 (s, 3H), 2.55 (s, 3H). | 99.3 | 453.5 |
| A1127 | 2-chlorophenyl-SO₂NH₂ | (500 MHz, DMSO) δ 8.18 (dd, J = 7.9, 1.5 Hz, 1H), 7.69 (ddd, J = 13.0, 7.9, 6.4 Hz, 2H), 7.64-7.60 (m, 1H), 7.51 (d, J = 7.5 Hz, 2H), 7.44 (t, J = 7.7 Hz, 2H), 7.35 (d, J = 7.2 Hz, 1H), 2.45 (s, 3H). | 97.0 | 509.1 (M − H) |
| A1128 | 3-cyanophenyl-SO₂NH₂ | (500 MHz, DMSO) δ 8.43 (t, J = 1.5 Hz, 1H), 8.34-8.31 (m, 1H), 8.19 (d, J = 7.8 Hz, 1H), 7.86 (t, J = 7.9 Hz, 1H), 7.49 (d, J = 7.4 Hz, 2H), 7.45 (t, J = 7.6 Hz, 2H), 7.36 (s, 1H), 2.45 (s, 3H). | 94.0 | 500.1 (M − H) |
| A1129 | 3-bromo-5-methoxyaniline | (500 MHz, DMSO) δ 12.74 (s, 1H), 10.95 (s, 1H), 7.59 (t, J = 1.7 Hz, 1H), 7.54-7.49 (m, 2H), 7.48-7.44 (m, 3H), 7.24 (t, J = 2.0 Hz, 1H), 6.90-6.87 (m, 1H), 3.78 (s, 3H), 2.51 (s, 3H). | 99.4 | 520.0 and 522.0 |

TABLE 2-continued

| Compound ID | Compound I-5 replacement | ¹H NMR | Purity (%) | MS (m/z) |
|---|---|---|---|---|
| A1130 | 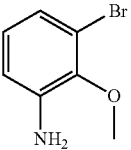 | (500 MHz, DMSO) δ 12.98 (s, 1H), 11.57 (s, 1H), 8.44 (d, J = 7.2 Hz, 1H), 7.56-7.44 (m, 5H), 7.33 (dd, J = 8.1, 1.3 Hz, 1H), 7.09 (t, J = 8.1 Hz, 1H), 3.88 (s, 3H), 2.76 (s, 3H). | 98.7 | 520.0 and 522.0 |
| A1131 | 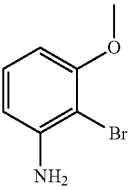 | (500 MHz, DMSO) δ 12.99 (s, 1H), 11.42 (s, 1H), 7.98 (d, J = 8.1 Hz, 1H), 7.56-7.44 (m, 5H), 7.35 (t, J = 8.3 Hz, 1H), 6.90 (dd, J = 8.3, 1.2 Hz, 1H), 3.88 (s, 3H), 2.76 (s, 3H). | 99.3 | 520.0 and 522.0 |
| A1132 | 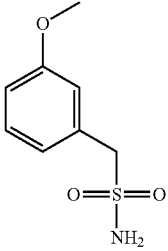 | (400 MHz, DMSO) δ 7.54 (d, J = 7.5 Hz, 2H), 7.44 (t, J = 7.6 Hz, 2H), 7.35 (d, J = 6.5 Hz, 1H), 7.26 (d, J = 7.8 Hz, 1H), 6.91 (d, J = 9.7 Hz, 3H), 4.77 (s, 2H), 3.67 (s, 3H), 2.66 (s, 3H). | 94.6 | 519.8 (M − H) |
| A1133 | 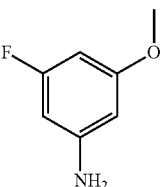 | (500 MHz, DMSO) δ 12.74 (s, 1H), 11.06 (s, 1H), 7.53-7.43 (m, 5H), 7.24 (dt, J = 11.2, 1.9 Hz, 1H), 7.06 (s, 1H), 6.56 (dt, J = 10.9, 2.3 Hz, 1H), 3.77 (s, 3H), 2.52 (s, 3H). | 96.9 | 461.2 |
| A1134 | 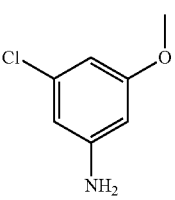 | (500 MHz, DMSO) δ 12.74 (s, 1H), 10.95 (s, 1H), 7.55-7.49 (m, 2H), 7.49-7.44 (m, 4H), 7.21 (t, J = 1.9 Hz, 1H), 6.76 (t, J = 2.0 Hz, 1H), 3.78 (s, 3H), 2.51 (s, 3H). | 99.5 | 477.2 |
| A1135 | 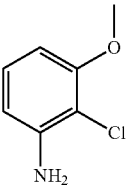 | (500 MHz, DMSO) δ 12.44-12.19 (m, 1H), 11.91 (s, 1H), 8.15-8.09 (m, 1H), 7.53-7.48 (m, 4H), 7.46-7.41 (m, 1H), 7.29 (t, J = 8.3 Hz, 1H), 6.89 (dd, J = 8.4, 1.1 Hz, 1H), 3.88 (s, 3H), 2.74 (s, 3H). | 99.4 | 477.2 |
| A1136 | 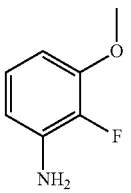 | (500 MHz, DMSO) δ 12.91 (s, 1H), 11.35 (s, 1H), 7.88 (t, J = 7.1 Hz, 1H), 7.55-7.43 (m, 5H), 7.13-7.07 (m, 1H), 6.93 (td, J = 8.3, 1.3 Hz, 1H), 3.86 (s, 3H), 2.68 (s, 3H). | 99.6 | 461.2 |

TABLE 2-continued
| Compound ID | Compound I-5 replacement | ¹H NMR | Purity (%) | MS (m/z) |
|---|---|---|---|---|
| A1137 | 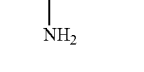 | (500 MHz, DMSO) δ 12.97 (s, 1H), 11.75 (s, 1H), 8.26 (d, J = 8.3 Hz, 1H), 7.55-7.42 (m, 5H), 7.09 (td, J = 8.4, 6.1 Hz, 1H), 6.97 (ddd, J = 11.0, 8.4, 1.4 Hz, 1H), 3.94 (s, 3H), 2.74 (s, 3H). | 99.8 | 461.2 |
| A1138 | 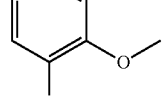 | (500 MHz, DMSO) δ 12.98 (s, 1H), 11.68 (s, 1H), 8.41 (dd, J = 7.9, 1.7 Hz, 1H), 7.57-7.42 (m, 5H), 7.22-7.10 (m, 2H), 3.90 (s, 3H), 2.76 (s, 3H). | 98.7 | 477.1 |
| A1139 | 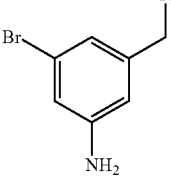 | (500 MHz, DMSO) δ 12.52 (s, 1H), 8.16-8.09 (m, 2H), 7.59-7.53 (m, 3H), 7.45-7.41 (m, 2H), 7.33-7.29 (m, 1H), 7.24 (s, 1H), 3.96-3.79 (m, 2H), 2.66 (s, 3H), 2.50 (s, 6H). | 95.4 | 548.0 550.0 |
| A1140 | $NH_3$ | (500 MHz, DMSO) δ 12.58 (s, 1H), 8.06 (s, 1H), 7.55-7.38 (m, 6H), 2.54 (s, 3H). | 99 | 337.6 |
| A1144 | 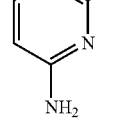<br>Also replace I-1 with<br>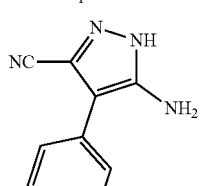 | (400 MHz, DMSO) δ 11.41 (s, 1H), 7.79-7.75 (m, 1H), 7.71-7.61 (m, 3H), 7.53-7.48 (m, 2H), 7.42-7.36 (m, 1H), 6.50-6.45 (m, 1H), 3.79 (s, 3H), 2.61 (s, 3H). | 95.2 | 401.2 |

Example 2

Synthesis of N-(2-aminophenyl)-2-(5-methyl-7-oxo-3-phenyl-2-(trifluoromethyl)-4,7-dihydropyrazolo[1,5-a]pyrimidin-6-yl)acetamide (B1001) was carried out in three steps as follows:

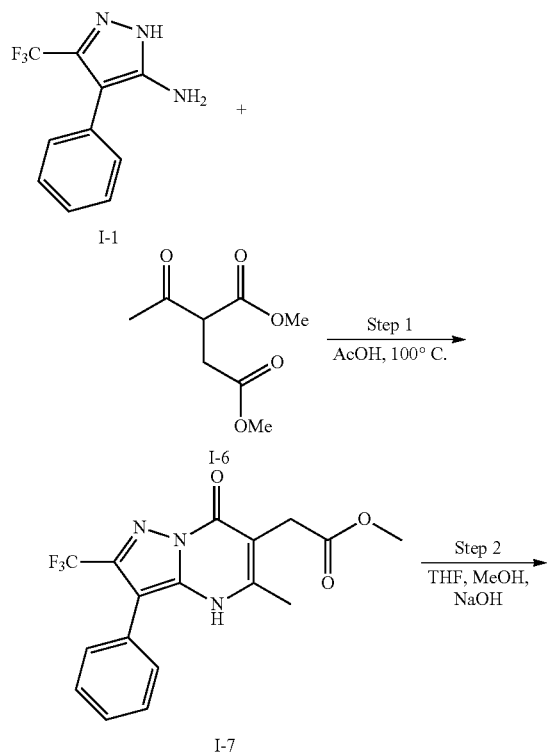

Step 1:

Synthesis of methyl 2-(5-methyl-7-oxo-3-phenyl-2-(trifluoromethyl)-4,7-dihydropyrazolo[1,5-a]pyrimidin-6-yl)acetate (I-7): To a stirred solution of 4-phenyl-3-(trifluoromethyl)-1H-pyrazol-5-amine (I-1, 2.00 g, 8.80 mmol) (WO 2012149157) in AcOH (15 mL) was added dimethyl 2-acetylsuccinate (I-6, 1.5 eq, 2.48 g, 13.2 mmol). The reaction mixture was heated at 100° C. for 5 h and concentrated to dryness. The reaction mixture was triturated in EtOAc for 15 min. The solid was collected by filtration, rinsed with EtOAc, and dried in vacuo to afford compound I-7 (2.38 g, 6.51 mmol, 74%) as a white solid which was used without further purification. $^1$H NMR (500 MHz, DMSO) δ 12.27 (s, 1H), 7.56-7.39 (m, 5H), 3.63 (s, 3H), 3.61 (s, 2H), 2.34 (s, 3H); MS (m/z): 365.9 [M+1]$^+$, 99.3%.

Step 2:

Synthesis of 2-(5-methyl-7-oxo-3-phenyl-2-(trifluoromethyl)-4,7-dihydropyrazolo[1,5-a]pyrimidin-6-yl)acetic acid (I-8): To a stirred solution of compound I-7, 2.38 g, 6.51 mmol) in a mixture of THF (15 mL) and MeOH (15 mL) was added a solution of sodium hydroxide 2M (15 mL, 30 mmol). The reaction mixture was stirred at r.t. for 1.5 h and concentrated to dryness. After addition of water (15 mL) and HCl 10% (15 mL), the white slurry was stirred at r.t. for 15 min. The solid was collected by filtration, rinsed with water, and dried in vacuo to afford compound I-8 (2.27 g, 6.46 mmol, 99%) as a white solid which was used without further purification. MS (m/z): 352.1 [M+1]$^+$, >99%.

Step 3:

Synthesis of N-(2-aminophenyl)-2-(5-methyl-7-oxo-3-phenyl-2-(trifluoromethyl)-4,7-dihydropyrazolo[1,5-a]pyrimidin-6-yl)acetamide (B1001): To a stirred solution of compound I-8 (130 mg, 0.37 mmol) in DMF (1.8 mL) was added HATU (185 mg, 0.48 mmol), o-phenylenediamine (I-9, 161 mg, 1.48 mmol) and TEA (104 µL, 0.74 mmol). The reaction mixture was stirred at r.t. for 18 h. After addition of EtOAc, water and NaHCO$_3$, the layers were separated and the aqueous layer was extracted with EtOAc. The combined organics layers were washed with brine, dried over Na$_2$SO$_4$ and concentrated in vacuo. The residue was purified by reverse flash chromatography (KP-C18-H5, using a gradient 0 to 100% MeCN in 10 mM aqueous ammonium formate buffer) to afford compound B1001 (122 mg, 0.27 mmol, 75%) as a beige solid after lyophilization. $^1$H NMR (500 MHz, DMSO) δ 12.24 (s, 1H), 9.20 (s, 1H), 7.53-7.50 (m, 2H), 7.47-7.43 (m, 3H), 7.10-7.07 (m, 1H), 6.93-6.88 (m, 1H), 6.72-6.69 (m, 1H), 6.52 (t, J=7.0 Hz, 1H), 4.86 (s, 2H), 3.63 (s, 2H), 2.40 (s, 3H); MS (m/z): 442.1 [M+1]+, 99.9%.

Table 3 below provides additional compounds that can be synthesized similarly to the methods described in Steps 1-3 above, substituting the listed compound for I-9. Data for compounds synthesized is provided in columns 3-5.

TABLE 3

| Compound ID | Compound I-9 replacement | ¹H NMR | Purity (%) | MS (m/z) |
|---|---|---|---|---|
| B1002 | 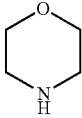 | (500 MHz, DMSO) δ 12.22 (s, 1H), 7.58-7.34 (m, 5H), 3.64 (s, 4H), 3.62 (s, 2H), 3.58-3.52 (m, 2H), 3.48-3.41 (m, 2H), 2.28 (s, 3H). | 100.0 | 421.0 |
| B1003 | 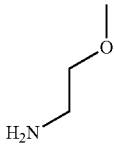 | (500 MHz, DMSO) δ 12.20 (s, 1H), 7.91 (t, J = 5.6 Hz, 1H), 7.62-7.32 (m, 5H), 3.40 (s, J = 15.2 Hz, 2H), 3.34-3.30 (m, 2H), 3.23 (s, 3H), 3.20 (q, J = 5.7 Hz, 2H), 2.29 (s, 3H). | 100.0 | 409.0 |
| B1004 | 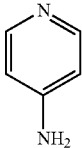 | (500 MHz, DMSO) δ 12.75 (s, 1H), 10.60 (s, 1H), 8.45 (s, 2H), 7.62 (d, J = 5.4 Hz, 2H), 7.57-7.40 (m, 5H), 3.71 (s, 2H), 2.38 (s, 3H). | 100.0 | 428.0 |
| B1005 | 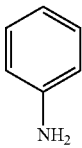 | (500 MHz, DMSO) δ 12.27 (s, 1H), 10.06 (s, 1H), 7.59 (dd, J = 8.6, 1.0 Hz, 2H), 7.52 (dd, J = 11.2, 4.4 Hz, 2H), 7.49-7.42 (m, 3H), 7.33-7.26 (m, 2H), 7.03 (t, J = 7.4 Hz, 1H), 3.65 (s, 2H), 2.37 (s, 3H). | 100.0 | 427.0 |
| B1006 | 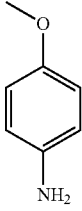 | (500 MHz, DMSO) δ 12.25 (s, 1H), 9.89 (s, 1H), 7.58-7.39 (m, 7H), 6.96-6.80 (m, 2H), 3.71 (s, 3H), 3.62 (s, 2H), 2.37 (s, 3H). | 99.7 | 457.0 |
| B1007 | 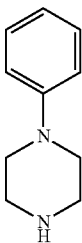 | (500 MHz, DMSO) δ 12.22 (s, 1H), 7.54-7.41 (m, 5H), 7.24 (dd, J = 8.7, 7.3 Hz, 2H), 6.98 (d, J = 7.9 Hz, 2H), 6.82 (t, J = 7.3 Hz, 1H), 3.84-3.75 (m, 2H), 3.68 (s, 2H), 3.65-3.57 (m, 2H), 3.27-3.20 (m, 2H), 3.15-3.07 (m, 2H), 2.30 (s, 3H). | 98.1 | 496.1 |
| B1008 | 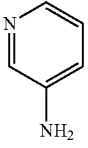 | (500 MHz, DMSO) δ 12.29 (s, 1H), 10.28 (s, 1H), 8.75 (d, J = 2.2 Hz, 1H), 8.26 (d, J = 3.6 Hz, 1H), 8.02 (ddd, J = 8.4, 2.5, 1.5 Hz, 1H), 7.55-7.40 (m, 5H), 7.34 (dd, J = 8.2, 4.5 Hz, 1H), 3.69 (s, 2H), 2.38 (s, 3H). | 99.1 | 428.0 |
| B1009 |  | (500 MHz, DMSO) δ 12.21 (s, 1H), 7.54-7.40 (m, 5H), 7.25-7.10 (m, 4H), 3.67-3.56 (m, 4H), 3.52-3.38 (m, 4H), 2.46-2.38 (m, 2H), 2.37-2.30 (m, 2H), 2.29 (s, 3H), 2.26 (s, 3H). | 96.1 | 524.1 |

TABLE 3-continued

| Compound ID | Compound I-9 replacement | ¹H NMR | Purity (%) | MS (m/z) |
|---|---|---|---|---|
| B1010 | 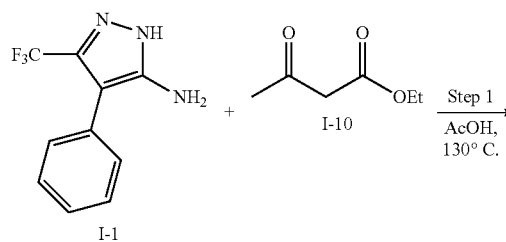 | (400 MHz, DMSO) δ 12.26 (s, 1H), 9.22 (s, 1H), 7.91 (d, J = 7.9 Hz, 1H), 7.55-7.40 (m, 5H), 7.10-7.00 (m, 2H), 6.92-6.84 (m, 1H), 3.84 (s, 3H), 3.71 (s, 2H), 2.39 (s, 3H). | 99.2 | 457.0 |
| B1011 | | (400 MHz, DMSO) δ 12.28 (s, 1H), 10.07 (s, 1H), 7.55-7.48 (m, 2H), 7.46 (t, J = 6.5 Hz, 3H), 7.32 (s, 1H), 7.20 (t, J = 8.1 Hz, 1H), 7.11 (d, J = 8.3 Hz, 1H), 6.62 (dd, J = 8.1, 1.9 Hz, 1H), 3.71 (s, 3H), 3.64 (s, 2H), 2.37 (s, 3H). | 99.7 | 457.0 |

Example 3

Synthesis of 5-methyl-3-phenyl-6-(pyridin-4-yl)-2-(trifluoromethyl)pyrazolo[1,5-a]pyrimidin-7(4H)-one (C1001) was carried out in three steps as follows:

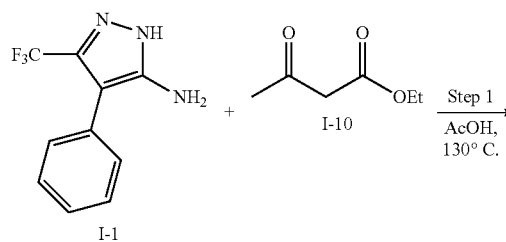

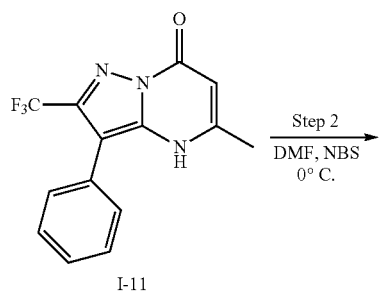

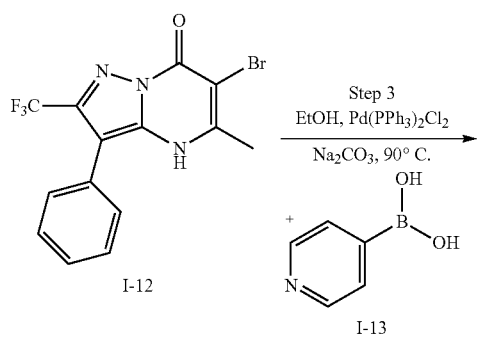

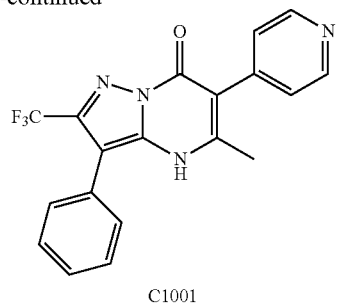

C1001

Step 1:

Synthesis of 5-methyl-3-phenyl-2-(trifluoromethyl)pyrazolo[1,5-a]pyrimidin-7(4H)-one (I-11): To a stirred solution of 4-phenyl-3-(trifluoromethyl)-1H-pyrazol-5-amine (I-1, 1.43 g, 6.29 mmol) (WO 2012149157) in AcOH (31.5 mL) was added ethyl acetoacetate (I-10, 1 eq, 796 µL, 6.29 mmol). The reaction mixture was heated at 130° C. for 1 h and concentrated to dryness. The reaction mixture was triturated in EtOAc for 15 min. The solid was collected by filtration, rinsed with EtOAc, and dried in vacuo to afford compound I-11 (1.04 g, 6.29 mmol, 56%) as a white solid which was used without further purification. ¹H NMR (500 MHz, DMSO) δ 12.27 (s, 1H), 7.52-7.44 (m, 3H), 7.43-6.7.40 (m, 2H), 5.79 (d, J=0.6 Hz, 1H), 2.30 (s, 3H); MS (m/z): 294.1 [M+1]+, 99.9%.

Step 2:

Synthesis of 6-bromo-5-methyl-3-phenyl-2-(trifluoromethyl)pyrazolo[1,5-a]pyrimidin-7(4H)-one (I-12): To a stirred suspension of compound I-11 (830 mg, 2.83 mmol) in DMF (9.4 mL) was added N-bromosuccinimide (509 mg, 2.83 mmol) at 0° C. The reaction mixture was stirred at r.t. for 30 min. After addition of water, the white slurry was stirred at r.t. for 10 min. The solid was collected by filtration, rinsed with water, and dried in vacuo to afford compound I-12 (921 mg, 2.47 mmol, 87%) as an off-white solid which was used without further purification. MS (m/z): 372.2-374.2 [M+1]+, 98.1%.

Step 3:

Synthesis of 5-methyl-3-phenyl-6-(pyridin-4-yl)-2-(trifluoromethyl)pyrazolo[1,5-a]pyrimidin-7(4H)-one (C1001): To a stirred solution of compound I-12 (100 mg, 0.26 mmol) in a mixture of degassed EtOH (4 mL) and water (1 mL) was added pyridine-4-boronic acid (I-13, 40 mg, 0.32 mmol), Pd(PPh$_3$)$_2$Cl$_2$ (19 mg, 0.02 mmol) and Na$_2$CO$_3$ (117 mg, 1.10 mmol). The reaction mixture was heated at 90° C. for 18 h. The reaction mixture was filtered through Celite, washed with MeOH and concentrated in vacuo. The residue was purified twice by reverse flash chromatography (KP-C18-H5, using a gradient 0 to 100% MeCN in 10 mM aqueous ammonium formate buffer) to afford compound C1001 (7.4 mg, 0.02 mmol, 7%) as a yellow solid after lyophilization. $^1$H NMR (500 MHz, DMSO) δ 12.61 (bs, 1H), 8.62 (s, 2H), 7.52-7.48 (m, 4H), 7.45-7.39 (m, 3H), 2.21 (s, 3H); MS (m/z): 371.2 [M+1]$^+$, 98.7%.

Table 4 below provides additional compounds that can be synthesized similarly to the methods described in Steps 1-3 above, substituting the listed compound for I-13. Data for compounds synthesized is provided in columns 3-5.

TABLE 4

| Compound ID | Compound I-13 replacement | $^1$H NMR | Purity (%) | MS (m/z) |
|---|---|---|---|---|
| C1002 | HO-B(OH)-(3-methylphenyl) | (500 MHz, DMSO) δ 12.35 (s, 1H), 7.53-7.44 (m, 5H), 7.32 (t, J = 7.5 Hz, 1H), 7.18 (d, J = 7.6 Hz, 1H), 7.13-7.08 (m, 2H), 2.35 (s, 3H), 2.15 (s, 3H). | 95.7 | 384.2 |
| C1003 | HO-B(OH)-(pyridin-3-yl) | (500 MHz, DMSO) δ 12.50 (bs, 1H), 8.56 (d, J = 10.9 Hz, 2H), 7.78 (d, J = 7.8 Hz, 1H), 7.54-7.45 (m, 6H), 2.21 (s, 3H). | 99.2 | 371.0 |
| C1004 | HO-B(OH)-(3-chlorophenyl) | (500 MHz, DMSO) δ 12.43 (s, 1H), 7.54-7.40 (m, 8H), 7.31 (dt, J = 7.4, 1.4 Hz, 1H), 2.18 (s, 3H). | 98.7 | 404.1 |
| C1006 | HO-B(OH)-(imidazo[1,2-a]pyridin-6-yl) | (500 MHz, DMSO) δ 8.53 (s, 1H), 7.99 (s, 1H), 7.66-7.61 (m, 2H), 7.52-7.47 (m, 4H), 7.44-7.40 (m, 1H), 7.21 (dd, J = 9.2, 1.4 Hz, 1H), 2.23 (s, 3H). | 98.4 | 410.2 |
| C1007 | HO-B(OH)-(quinolin-3-yl) | (500 MHz, DMSO) δ 12.57 (bs, 1H), 8.86 (s, 1H), 8.34 (d, J = 1.5 Hz, 1H), 8.07 (d, J = 8.4 Hz, 1H), 8.02 (d, J = 7.8 Hz, 1H), 7.83-7.77 (m, 1H), 7.65 (t, J = 7.4 Hz, 1H), 7.55-7.44 (m, 5H), 2.27 (s, 3H). | 99.9 | 421.1 |
| C1273 | HO-B(OH)-phenyl | (400 MHz, DMSO) δ 12.56 (s, 1H), 7.64-7.56 (m, 4H), 7.53-7.43 (m, 3H), 7.42-7.36 (m, 1H), 7.36-7.31 (m, 2H), 2.22 (s, 3H). | 95.9 | 327.1 |

Also replace I-1 with

TABLE 4-continued
| Compound ID | Compound I-13 replacement | ¹H NMR | Purity (%) | MS (m/z) |
|---|---|---|---|---|
| | 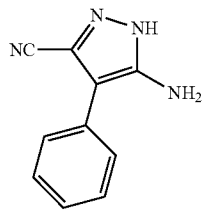 [SMILES: N#Cc1n[nH]c(N)c1-c1ccccc1] | | | |
| C1281 | 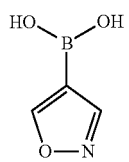 | (500 MHz, DMSO): δ 9.17 (s, 1H), 8.86 (s, 1H), 7.67 (d, J = 7.4 Hz, 2H), 7.58 (t, J = 7.7 Hz, 2H), 7.53-7.42 (m, 1H), 2.46 (s, 3H). | 100 | 318.1 |
| | Also replace I-1 with 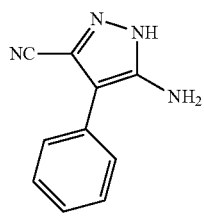 [SMILES: N#Cc1n[nH]c(N)c1-c1ccccc1] | | | |
| C1282 | 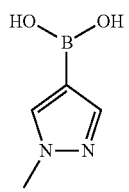 | (500 MHz, DMSO) δ 7.88 (s, 1H), 7.86-7.73 (m, 2H), 7.58 (s, 1H), 7.53-7.50 (m., 2H), 7.38 (s, 1H), 3.88 (s, 3H), 2.40 (s, 3H). | 100 | 329.1 (M − H) |
| | Also replace I-1 with 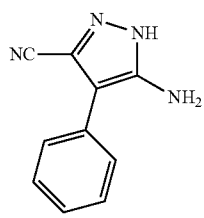 [SMILES: N#Cc1n[nH]c(N)c1-c1ccccc1] | | | |

Example 4

Synthesis of 6-(4-methoxybenzo[d]oxazol-2-yl)-5-methyl-3-phenyl-2-(trifluoromethyl)pyrazolo[1,5-a]pyrimidin-7(4H)-one (C1014) was carried out in two steps as follows:

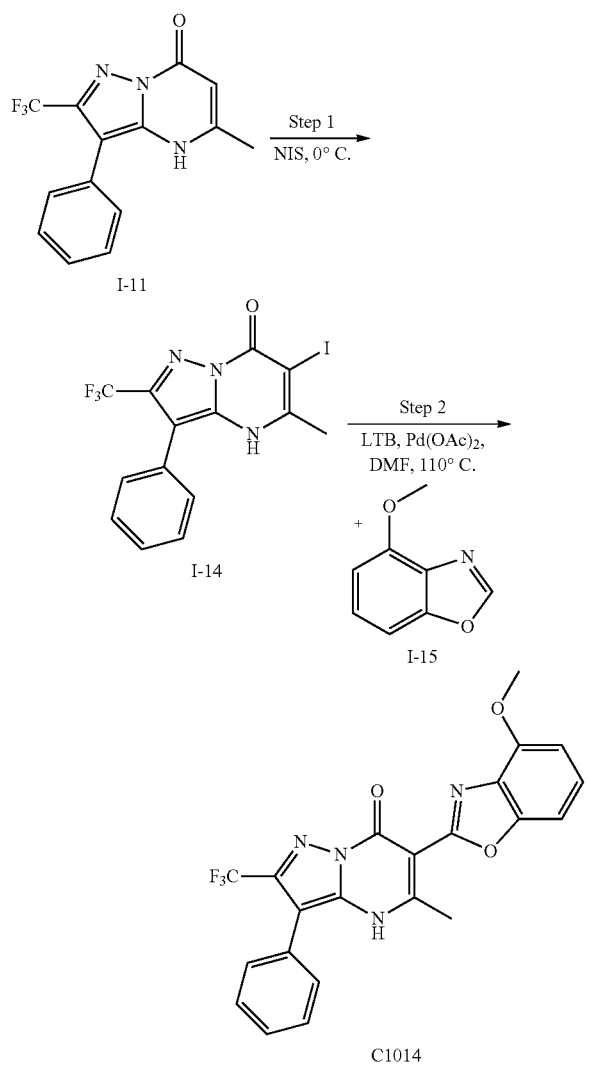

Step 1:
Synthesis of 6-iodo-5-methyl-3-phenyl-2-(trifluoromethyl)pyrazolo[1,5-a]pyrimidin-7(4H)-one (I-14): To a suspension of 5-methyl-3-phenyl-2-(trifluoromethyl)pyrazolo[1,5-a]pyrimidin-7(4H)-one (I-11, 450 mg, 1.53 mmol) was added N-iodosuccinimide (363 mg, 1.53 mmol) at 0° C. After 30 min, LCMS showed complete conversion. The reaction was poured into water. The precipitated solid was filtered, washed with dilute aquoues $Na_2S_2O_3$ followed by water. The solid was dried under high vacuum to afford the desired I-14. $^1$H NMR (500 MHz, DMSO) δ 12.75 (bs, 1H), 7.53-7.40 (m, 5H), 2.58 (s, 3H). MS (m/z): 420.0 [M+1]$^+$.

Step 2:
Synthesis of 6-(4-methoxybenzo[d]oxazol-2-yl)-5-methyl-3-phenyl-2-(trifluoromethyl)pyrazolo[1,5-a]pyrimidin-7(4H)-one (C1014): A mixture of 6-iodo-5-methyl-3-phenyl-2-(trifluoromethyl)pyrazolo[1,5-a]pyrimidin-7(4H)-one (I-14, 100 mg, 239 mol), 4-methoxybenzo[d]oxazole (I-15, 53.5 mg, 358 µmol), Lithium tert-butoxide (133 µL, 1.43 mmol) and palladium(ll) acetate (5.36 mg, 23.9 µmol) in DMF (1.50 mL) was degassed with nitrogen. The reaction mixture was heated at 110° C. for 16 h. The crude reaction mixture was filtered over celite and washed with ethyl acetate. The filtrate was evaporated and the residue was purified by reverse phase column chromatography using a gradient of 20-70% MeCN/H2O (0.1% ammonium formate buffer) to give compound C1014 (96.9% purity). $^1$H NMR (500 MHz, DMSO) δ 12.95 (s, 1H), 7.52-7.43 (m, 5H), 7.35 (d, J=4.6 Hz, 2H), 7.01-6.91 (m, 1H), 4.00 (s, 3H), 2.48 (s, 3H). MS (m/z): 441.2 [M+1]$^+$.

Table 5 below provides additional compounds that can be synthesized similarly to the methods described in Steps 1-2 above, optionally substituting the listed compound as indicated for I-15, and/or substituting for I-1 and/or I-10 where indicated to provide the suitable analog of I-11 (per Example 3). Data for compounds synthesized is provided in columns 3-5.

TABLE 5

| Compound ID | Compound I-15 replacement | $^1$H NMR | Purity (%) | MS (m/z) |
|---|---|---|---|---|
| C1011 | benzoxazole structure | (500 MHz, DMSO) δ 12.96 (s, 1H), 7.66 (d, J = 8.7 Hz, 1H), 7.57-7.28 (m, 6H), 7.03-6.98 (m, 1H), 3.84 (s, 3H), 2.44 (s, 3H). | 95.1 | 411.1 |

TABLE 5-continued

| Compound ID | Compound I-15 replacement | ¹H NMR | Purity (%) | MS (m/z) |
|---|---|---|---|---|
| C1012 | 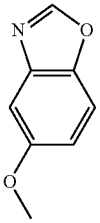 | (500 MHz, DMSO) δ 12.96 (s, 1H), 7.66 (d, J = 8.7 Hz, 1H), 7.57-7.28 (m, 6H), 7.03-6.98 (m, 1H), 3.84 (s, 3H). | 97.0 | 441.2 |
| C1022 | 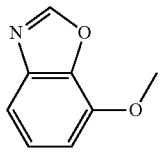 | (500 MHz, DMSO) δ 7.59 (d, J = 7.6 Hz, 2H), 7.45 (t, J = 7.7 Hz, 2H), 7.33 (d, J = 7.3 Hz, 2H), 7.28 (t, J = 8.0 Hz, 1H), 7.00 (d, J = 8.1 Hz, 1H), 3.99 (s, 3H), 2.38 (s, 3H). | 96.4 | 441.2 |
| C1028 | 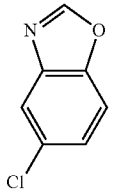 | (500 MHz, MeOD) δ 7.77 (s, 1H), 7.66 (sb, 1H), 7.52-7.40 (m, 6H), 2.59 (s, 3H). | 95.3 | 445.0 |
| C1030 | 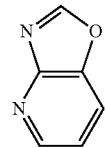 | (500 MHz, DMSO, Aromatic protons only) δ 8.45 (dd, J = 4.9, 1.4 Hz, 1H), 8.12 (dd, J = 8.0, 1.4 Hz, 1H), 7.60 (d, J = 7.7 Hz, 2H), 7.44 (t, J = 7.8 Hz, 2H), 7.37-7.28 (m, 2H). | 97.7 | 412.2 |
| C1037 | 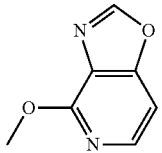 | (500 MHz, DMSO) δ 8.01 (d, J = 5.7 Hz, 1H), 7.49 (d, J = 13.6 Hz, 2H), 7.42-7.33 (m, 3H), 7.29-7.23 (m, 1H), 3.99 (s, 3H), 2.35 (s, 3H). | 96.4 | 442.2 |
| C1038 | 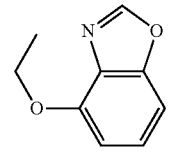 | (500 MHz, DMSO) δ 8.27 (s, 1H), 7.60 (d, J = 7.3 Hz, 2H), 7.46-7.38 (m, 2H), 7.33-7.17 (m, 3H), 6.91-6.83 (m, 1H), 4.35 (q, J = 7.0 Hz, 2H), 2.35 (s, 3H), 1.42 (t, J = 7.0 Hz, 3H). | 99.2 | 455.2 |
| C1039 | 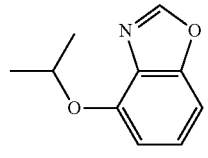 | (500 MHz, DMSO) δ 12.71 (s, 1H), 8.13 (s, 1H), 7.59 (d, J = 7.5 Hz, 2H), 7.44 (dd, J = 10.6, 4.8 Hz, 2H), 7.31 (t, J = 7.4 Hz, 1H), 7.27-7.21 (m, 2H), 6.87 (dd, J = 7.5, 1.5 Hz, 1H), 5.23-5.06 (m, 1H), 2.38 (s, 3H), 1.36 (d, J = 6.1 Hz, 6H). | 99.3 | 469.1 |
| C1040 | 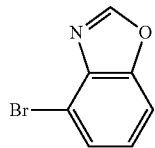 | (500 MHz, DMSO) δ 8.08 (s, 1H), 7.71 (dd, J = 8.1, 0.8 Hz, 1H), 7.60-7.54 (m, 3H), 7.44-7.40 (m, 2H), 7.31-7.26 (m, 2H), 2.44 (s, 3H). | 99.4 | 488.0 and 490.0 |

TABLE 5-continued

| Compound ID | Compound I-15 replacement | ¹H NMR | Purity (%) | MS (m/z) |
|---|---|---|---|---|
| C1041 | 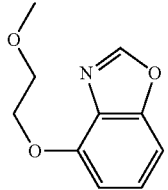 | (500 MHz, DMSO) δ 7.60 (d, J = 7.4 Hz, 2H), 7.42 (t, J = 7.8 Hz, 2H), 7.31-7.21 (m, 3H), 6.89 (d, J = 8.9 Hz, 1H), 4.47-4.41 (m, 2H), 3.78-3.72 (m, 2H), 3.34 (s, 3H), 2.35 (s, 3H). | 98.2 | 485.3 |
| C1042 | Replace I-1 with 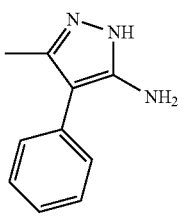 | (500 MHz, DMSO) δ 12.47 (brs, 1H), 7.52 (d, J = 4.5 Hz, 4H), 7.44-7.29 (m, 3H), 6.97 (dd, J = 7.0, 2.0 Hz, 1H), 4.01 (s, 3H), 2.48 (S, 3H), 2.33 (s, 3H). | 99.5 | 387.8 |
| C1043 | Replace I-1 with 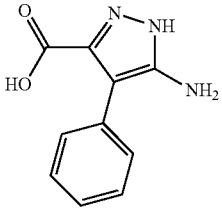 | (500 MHz, DMSO) δ 7.58 (d, J = 7.0 Hz, 2H), 7.39 (t, J = 7.4 Hz, 2H), 7.32-7.26 (m, 3H), 6.94-6.89 (m, 1H), 4.00 (s, 3H), 2.43 (s, 3H). | 98.0 | 417.3 |
| C1045 | 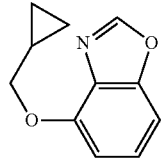 [SMILES: c1cc(OCC2CC2)c2ncoc2c1] | (500 MHz, DMSO) δ 7.60 (d, J = 7.7 Hz, 2H), 7.42 (t, J = 7.7 Hz, 2H), 7.30-7.20 (m, 3H), 6.86 (d, J = 7.8 Hz, 1H), 4.14 (d, J = 7.0 Hz, 2H), 2.35 (s, 3H), 1.33 (m, 1H), 0.60 (q, J = 5.5 Hz, 2H), 0.38 (t, J = 4.9 Hz, 2H). | 98.9 | 481.2 |
| C1046 | 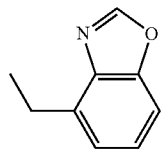 | (500 MHz, DMSO) δ 12.96 (brs, 1H), 7.59 (d, J = 8.0 Hz, 1H), 7.52 (m, 4H), 7.46 (dd, J = 8.9, 4.4 Hz, 1H), 7.40-7.31 (m, 1H), 7.24 (d, J = 7.3 Hz, 1H), 2.99 (q, J = 7.6 Hz, 2H), 1.34 (t, J = 7.6 Hz, 3H). | 98.7 | 439.1 |
| C1047 | 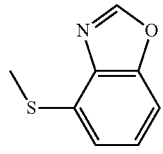 | (500 MHz, DMSO) δ 7.60 (d, J = 7.3 Hz, 2H), 7.48 (dd, J = 8.1, 0.8 Hz, 1H), 7.42 (t, J = 7.8 Hz, 2H), 7.32-7.27 (m, 2H), 7.17 (dd, J = 7.8, 0.8 Hz, 1H), 2.62 (s, 3H), 2.40 (s, 3H). | 94.8 | 457.1 |
| C1049 | Replace I-1 with 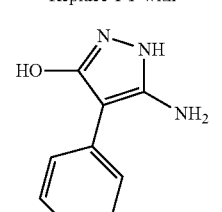 | (500 MHz, DMSO) δ 11.73-11.39 (m, 1H), 8.50-8.20 (s, 2H), 7.34-7.19 (m, 4H), 7.01 (s, 1H), 6.89 (t, J = 4.5 Hz, 1H), 4.00 (s, 3H), 2.45 (s, 3H) | 100 | 389.2 |

TABLE 5-continued

| Compound ID | Compound I-15 replacement | ¹H NMR | Purity (%) | MS (m/z) |
|---|---|---|---|---|
| C1050 | Replace I-1 with [pyrazole with F₂HC, NH₂, phenyl substituents] | (500 MHz, DMSO) δ 7.75 (dd, J = 8.3, 1.2 Hz, 2H), 7.36-7.30 (m, 2H), 7.22-7.12 (m, 3H), 7.06-6.92 (m, J = 53.9 Hz, 1H), 6.82 (dd, J = 6.8, 2.2 Hz, 1H), 3.93 (s, 3H), 2.33 (s, 3H). | 97.6 | 423.1 |
| C1051 | Replace I-1 with [pyrazole with NC, NH₂, phenyl substituents] | (DMSO, 500 MHz) δ 8.08 (dd, J = 8.3, 1.1 Hz, 2H), 7.49 (dd, J = 10.7, 5.0 Hz, 2H), 7.35-7.22 (m, 3H), 6.91 (dd, J = 5.1, 3.9 Hz, 1H), 4.01 (s, 3H), 2.45 (s, 3H). | 99.9 | 398.1 |
| C1053 | [4-hydroxybenzoxazole] | (500 MHz, DMSO) δ 7.60 (d, J = 7.3 Hz, 2H), 7.42 (t, J = 7.8 Hz, 2H), 7.30-7.26 (m, 1H), 7.15-7.07 (m, 2H), 6.71 (dd, J = 7.6, 1.4 Hz, 1H), 2.32 (s, 3H). | 96.7 | 427.2 |
| C1054 | [4-(methylsulfonyl)benzoxazole] | (500 MHz, DMSO) δ 8.42 (s, 2H), 8.08 (dd, J = 8.1, 1.0 Hz, 1H), 7.78 (dd, J = 7.8, 1.0 Hz, 1H), 7.60 (s, 1H), 7.51 (t, J = 8.0 Hz, 1H), 7.47-7.40 (m, 2H), 7.33-7.27 (m, 1H), 3.51 (s, 3H), 2.57 (s, 1.5H), 2.54 (s, 1.5H). | 97.5 | 489.2 |
| C1055 | [4-chlorobenzoxazole] | (500 MHz, DMSO) δ 13.02 (s, 1H), 7.75 (d, J = 8.0 Hz, 1H), 7.55 (d, J = 7.5 Hz, 2H), 7.48 (t, J = 7.7 Hz, 3H), 7.42-7.36 (m, 2H), 2.50 (s, 3H). | 96.0 | 441.2 |
| C1058 | [methoxy-oxazolopyridine] | (500 MHz, DMSO) δ 8.11 (d, J = 5.6 Hz, 1H), 7.59-7.52 (m, 2H), 7.51-7.43 (m, 3H), 7.42-7.34 (m, 1H), 4.07 (s, 3H), 2.46 (s, 3H). | 95.0 | 442.1 |
| C1060 | [4-methylbenzoxazole] | (500 MHz, DMSO) δ 12.96 (s, 1H), 7.58-7.48 (m, 5H), 7.45-7.39 (m, 1H), 7.30 (t, J = 7.8 Hz, 1H), 7.24-7.18 (m, 1H), 2.58 (s, 3H), 2.47 (s, 3H). | 99.7 | 425.2 |
| C1061 | [4-(2-aminoethoxy)benzoxazole] | (400 MHz, DMSO) δ 8.00 (s, 3H), 7.53-7.23 (m, 7H), 6.96 (s, 1H), 4.51 (m, 2H), 2.62 (s, 3H). | 94.6 | 470.0 |

TABLE 5-continued

| Compound ID | Compound I-15 replacement | ¹H NMR | Purity (%) | MS (m/z) |
|---|---|---|---|---|
| C1062 | (structure) | (400 MHz, DMSO) δ 8.20 (s, 2H), 7.60 (m, 2H), 7.45-7.38 (m, 2H), 7.28 (m, 3H), 6.90 (m, 1H), 4.32 (m, 2H), 2.35 (s, 3H), 1.84 (s, 3H). | 93.5 | 512.0 |
| C1063 | Replace I-1 with (structure) | (500 MHz, DMSO) δ 12.10 (brs, 1H), 7.65-7.53 (m, 2H), 7.50-7.43 (m, 2H), 6.94 (d, J = 6.9 Hz, 1H), 5.35 (brs, 2H), 4.00 (s, 3H), 2.80 (s, 3H). | 100 | 388.6 |
| C1064 | Replace I-1 with (structure) | (500 MHz, DMSO) δ 12.40 (s, 1H), 7.54-7.22 (m, 7H), 6.91-6.87 (m, 1H), 4.02 (s, 3H), 4.01 (s, 3H), 2.44 (s, 3H). | 95.5 | 403.1 |
| C1066 | (structure) | (500 MHz, DMSO) δ 8.26 (s, 1H), 7.60 (d, J = 7.3 Hz, 2H), 7.45-7.39 (m, 2H), 7.31-7.22 (m, 3H), 6.91 (dd, J = 8.0, 1.0 Hz, 1H), 4.36 (t, J = 5.6 Hz, 2H), 3.02 (s, 3H), 2.36 (s, 3H). | 96.2 | 548.1 |
| C1068 | Replace I-1 with (structure) | (500 MHz, DMSO) δ 12.92 (brs, 1H), 7.67 (m, 2H), 7.51-7.46 (m, 2H), 7.44-7.38 (m, 1H), 7.37-7.33 (m, 2H), 6.98-6.95 (m, 1H), 4.01 (s, 3H), 2.47 (s, 3H). | 100 | 451.1 |
| C1070 | (structure) | (500 MHz, DMSO) δ 7.63 (d, J = 7.3 Hz, 2H), 7.55 (dd, J = 7.9, 0.9 Hz, 1H), 7.44 (t, J = 7.8 Hz, 2H), 7.33-7.27 (m, 2H), 7.20 (t, J = 7.9 Hz, 1H), 6.94 (dd, J = 7.9, 0.8 Hz, 1H), 3.99 (s, 3H), 2.94 (s, 3H). | 95.4 | 457.1 |

TABLE 5-continued

| Compound ID | Compound I-15 replacement | ¹H NMR | Purity (%) | MS (m/z) |
|---|---|---|---|---|
| C1072 | Replace I-1 with [structure: 3-amino-4-phenyl-1H-pyrazol-5-yloxy acetic acid] | (400 MHz, DMSO) δ 8.57 (d, J = 7.8 Hz, 2H), 7.28-7.21 (m, 4H), 6.96 (t, J = 7.1 Hz, 1H), 6.90-6.85 (m, 1H), 4.94 (s, 2H), 3.99 (s, 3H), 2.42 (s, 3H). | 96.4 | 447.1 |
| C1073 | [structure: 4-(benzyloxy)benzoxazole] | (500 MHz, DMSO) δ 12.96 (s, 1H), 7.54-7.50 (m, 6H), 7.44-7.40 (m, 3H), 7.37-7.34 (m, 3H), 7.05 (d, J = 8.8 Hz, 1H), 5.42 (s, 2H), 2.48 (s, 3H). | 94.4 | 517.2 |
| C1074 | [structure: benzoxazole-7-carboxamide] | (500 MHz, DMSO) δ 8.64 (s, 1H), 7.94-7.90 (m, 1H), 7.86 (s, 1H), 7.61 (s, 1H), 7.60 (s, 1H), 7.46-7.40 (m, 4H), 7.33-7.29 (m, 2H), 2.55 (s, 3H). | 96.0 | 454.2 |
| C1075 | [structure: 7-cyanobenzoxazole] | (500 MHz, DMSO) δ 8.07 (dd, J = 8.1, 0.9 Hz, 1H), 7.80 (dd, J = 7.8, 0.9 Hz, 1H), 7.61 (s, 1H), 7.59 (s, 1H), 7.49-7.41 (m, 3H), 7.38-7.28 (m, 2H), 2.55 (s, 3H). | 94.0 | 436.2 (M − H) |
| C1076 | [structure: 7-fluorobenzoxazole] | (500 MHz, DMSO) δ 13.02 (s, 1H), 7.69 (d, J = 8.1 Hz, 1H), 7.55-7.44 (m, 6H), 7.32-7.27 (m, 1H), 2.55 (s, 3H). | 97.9 | 429.7 |
| C1077 | Replace I-10 with [structure: ethyl 4,4,4-trifluoro-3-oxobutanoate] | (500 MHz, DMSO) δ 7.60 (d, J = 7.4 Hz, 2H), 7.47 (t, J = 7.7 Hz, 2H), 7.38-7.29 (m, 3H), 6.94 (dd, J = 7.8, 1.1 Hz, 1H), 3.99 (s, 3H). | 97.3 | 495.1 |
| C1078 | [structure: 7-(dimethylamino)benzoxazole] | (400 MHz, DMSO) δ 7.50-7.41 (m, 4H), 7.41 (t, J = 7.0 Hz, 1H), 7.20 (t, J = 8.1 Hz, 1H), 7.05 (d, J = 8.0 Hz, 1H), 6.56 (d, J = 8.2 Hz, 1H), 3.19 (s, 6H), 2.46 (s, 3H). | 97.9 | 454.2 |
| C1079 | Replace I-10 with [structure: ethyl 3-oxopropanoate] | (400 MHz, DMSO) δ 8.71 (s, 1H), 7.59 (d, J = 6.3 Hz, 2H), 7.44 m, 2H), 7.29 (m, 2H), 7.19 (d, J = 5.6 Hz, 1H), 6.87 (d, J = 7.9 Hz, 1H), 3.98 (s, 3H). | 99.3 | 427.1 |

TABLE 5-continued

| Compound ID | Compound I-15 replacement | ¹H NMR | Purity (%) | MS (m/z) |
|---|---|---|---|---|
| C1080 | Replace I-1 with [tetrahydropyran-4-yloxy pyrazole with phenyl and NH₂ substituents] | (500 MHz, DMSO) δ 8.53 (dd, J = 8.5, 1.3 Hz, 2H), 8.24 (s, 1H), 7.27-7.21 (m, 4H), 7.00-6.94 (m, 1H), 6.88 (dd, J = 6.9, 2.1 Hz, 1H), 4.88-4.81 (m, 1H), 3.99 (s, 3H), 3.91 (dd, J = 11.1, 4.4 Hz, 2H), 2.41 (s, 3H), 1.55 (d, J = 9.1 Hz, 2H). | 100 | 473.3 |
| C1081 | [4-methoxy-7-bromo benzoxazole] | (500 MHz, DMSO) δ 12.72 (s, 1H), 7.60-7.54 (m, 2H), 7.53-7.43 (m, 3H), 7.39-7.33 (m, 1H), 6.93 (d, J = 8.0 Hz, 1H), 4.01 (s, 3H), 2.42 (s, 3H). | 96.1 | 518.9 520.6 |
| C1082 | [4-methoxy-6-bromo benzoxazole] | (400 MHz, DMSO) δ 13.08-12.91 (m, 1H), 7.57-7.52 (m, 3H), 7.51-7.45 (m, 2H), 7.43-7.39 (m, 1H), 7.37 (d, J = 8.6 Hz, 1H), 4.37 (s, 3H), 2.52 (s, 3H). | 100 | 519.0 521.1 |
| C1083 | Replace I-1 with [2-methoxyethoxy pyrazole with phenyl and NH₂ substituents] | (500 MHz, DMSO) δ 12.72 (s, 1H), 8.63-8.35 (m, 2H), 7.36-7.21 (m, 4H), 7.09-6.94 (m, 1H), 6.94-6.88 (m, 1H), 4.36 (t, J = 5.9 Hz, 2H), 3.99 (s, 3H), 3.48-3.43 (m, 2H), 3.16 (s, 3H), 2.43 (s, 3H). | 96.5 | 447.1 |
| C1086 | Replace I-1 with [CF₃-pyrazole with 2-methoxyphenyl and NH₂ substituents] | (500 MHz, DMSO) δ 12.82 (brs, 1H), 7.49 (t, J = 7.4 Hz, 1H), 7.41-7.32 (m, 3H), 7.17 (d, J = 8.3 Hz, 1H), 7.08 (t, J = 7.4 Hz, 1H), 6.98 (dd, J = 6.6, 2.3 Hz, 1H), 4.01 (s, 3H), 3.78 (s, 3H). | 99.8 | 471.1 |
| C1088 | [benzoxazol-4-yl dimethylcarbamate] | (500 MHz, DMSO) δ 12.87 (d, J = 132.8 Hz, 1H), 7.62 (d, J = 8.1 Hz, 1H), 7.57 (s, 1H), 7.56 (s, 1H), 7.51-7.45 (m, 2H), 7.41-7.35 (m, 2H), 7.15 (d, J = 8.0 Hz, 1H), 3.15 (s, 3H), 2.96 (s, 3H), 2.43 (s, 3H). | 99.9 | 498.2 |

TABLE 5-continued

| Compound ID | Compound I-15 replacement | ¹H NMR | Purity (%) | MS (m/z) |
|---|---|---|---|---|
| C1090 | Replace I-1 with 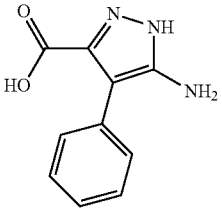 [SMILES: Nc1[nH]nc(C(=O)O)c1-c1ccccc1] And replace I-10 with 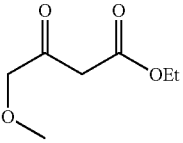 | (500 MHz, DMSO) δ 12.83 (s, 1H), 7.63 (d, J = 7.1 Hz, 7H), 7.39 (t, J = 7.7 Hz, 7H), 7.31-7.24 (m, J = 9.1, 5.4 Hz, 10H), 6.91 (dd, J = 6.3, 2.6 Hz, 4H), 4.53 (s, 7H), 4.01 (s, 10H), 3.09 (s, 10H). | 100 | 447.0 |
| C1091 | Replace I-1 with 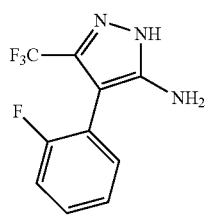 [SMILES: Nc1[nH]nc(C(F)(F)F)c1-c1ccccc1F] | (500 MHz, DMSO) δ 13.09 (brs, 1H), 7.58-7.50 (m, 2H), 7.40-7.32 (m, 4H), 6.98-6.96 (m, 1H), 4.01 (s, 3H), 2.48 (s, 3H). | 99.9 | 459.1 |
| C1092 | 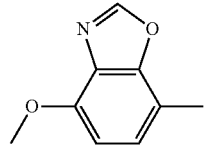 | (500 MHz, DMSO) δ 12.77 (s, 1H), 7.56 (d, J = 7.5 Hz, 2H), 7.46 (t, J = 7.7 Hz, 2H), 7.35 (t, J = 7.3 Hz, 1H), 7.10 (d, J = 8.3 Hz, 1H), 6.82 (d, J = 8.2 Hz, 1H), 3.96 (s, 3H), 2.42 (s, 3H), 2.38 (s, 3H). | 98.7 | 455.2 |
| C1093 | 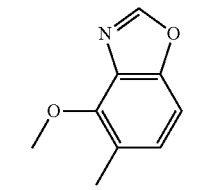 | (500 MHz, DMSO) δ 12.74 (s, 1H), 7.59 (d, J = 7.1 Hz, 2H), 7.44 (t, J = 7.3 Hz, 2H), 7.31 (m, 1H), 7.21 (d, J = 8.1 Hz, 1H), 7.12 (d, J = 8.1 Hz, 1H), 4.31 (s, 3H), 2.42 (s, 3H), 2.27 (s, 3H). | 97.1 | 455.2 |
| C1094 | 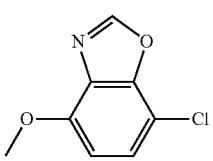 | (500 MHz, DMSO) δ 7.60 (d, J = 7.5 Hz, 2H), 7.42 (t, J = 7.8 Hz, 2H), 7.35 (d, J = 8.7 Hz, 1H), 7.29 (t, J = 7.4 Hz, 1H), 6.93 (d, J = 8.8 Hz, 1H), 4.00 (s, 3H), 2.37 (s, 3H). | 98.9 | 475.1 |
| C1095 | 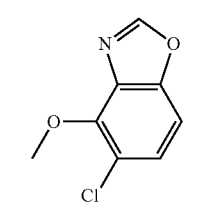 | (500 MHz, DMSO) δ 7.59 (d, J = 7.4 Hz, 2H), 7.42 (t, J = 7.8 Hz, 2H), 7.35 (s, 2H), 7.29 (t, J = 7.4 Hz, 1H), 4.37 (s, 3H), 2.45 (s, 3H). | 98.2 | 475.1 |

TABLE 5-continued

| Compound ID | Compound I-15 replacement | ¹H NMR | Purity (%) | MS (m/z) |
|---|---|---|---|---|
| C1096 | (structure: 4-methoxy-oxazolopyridine) | (500 MHz, DMSO) δ 8.75 (s, 1H), 8.27 (s, 1H), 7.59-7.52 (m, 2H), 7.51-7.44 (m, 2H), 7.42-7.35 (m, 1H), 4.15 (s, 3H), 2.55 (s, 3H). | 95.3 | 442.0 |
| C1097 | (structure: 4-(methylsulfinyl)benzoxazole) | (500 MHz, DMSO) δ 7.88 (dd, J = 8.0, 0.9 Hz, 1H), 7.64 (dd, J = 7.7, 1.0 Hz, 1H), 7.61-7.54 (m, 3H), 7.43 (t, J = 7.7 Hz, 2H), 7.30 (t, J = 7.4 Hz, 1H), 2.99 (s, 3H), 2.47 (s, 3H). | 99.8 | 473.0 |
| C1098 | (structure: 4-methoxy-6-methylbenzoxazole) | (500 MHz, DMSO) δ 7.55-7.48 (m, 5H), 7.17 (s, 1H), 6.81 (s, 1H), 3.98 (s, 3H), 2.48 (s, 3H), 2.46 (s, 3H) | 99.6 | 455.0 |
| C1099 | Replace I-10 with (structure: ethyl 4-(benzyloxy)-3-oxobutanoate) | (500 MHz, DMSO) δ 7.52-7.50 (m, 5H), 7.36-7.34 (m, 3H), 7.18-7.12 (m, 2H), 7.03 (d, J = 6.3 Hz, 2H), 6.96 (m, 1H), 4.70 (s, 2H), 4.36 (s, 2H), 4.01 (s, 3H). | 94.8 | 547.1 |
| C1100 | (structure: 4-methoxy-7-cyanobenzoxazole) | (500 MHz, DMSO) δ 7.79 (d, J = 8.6 Hz, 1H), 7.59 (d, J = 7.4 Hz, 2H), 7.43 (t, J = 7.8 Hz, 2H), 7.31-7.27 (m, 1H), 7.08 (d, J = 8.7 Hz, 1H), 4.10 (s, 3H), 2.42 (s, 3H). | 98.0 | 466.1 |
| C1105 | (structure: 4-methoxy-6-chlorobenzoxazole) | (500 MHz, DMSO) δ 7.59-7.56 (m, 1H), 7.54-7.50 (m, 4H), 7.48-4.42 (m, 1H), 7.05 (d, J = 1.6 Hz, 1H), 4.03 (s, 3H), 2.49 (s, 3H). | 95.9 | 475.0 |
| C1106 | (structure: N-methyl-oxazolopyridinone) | (500 MHz, DMSO) δ 7.68 (d, J = 7.3 Hz, 1H), 7.54-7.50 (m, 2H), 7.38-7.31 (m, 2H), 7.22 (t, J = 7.4 Hz, 1H), 6.77 (d, J = 7.3 Hz, 1H), 3.50 (s, 3H), 2.27 (s, 3H). | 95.6 | 442.0 |

TABLE 5-continued

| Compound ID | Compound I-15 replacement | ¹H NMR | Purity (%) | MS (m/z) |
|---|---|---|---|---|
| C1107 | Replace I-1 with 3-amino-4-(4-fluorophenyl)-5-(trifluoromethyl)-1H-pyrazole | (500 MHz, DMSO) δ 12.92 (brs, 1H), 7.56-7.53 (m, 2H), 7.40-7.36 (m, 4H), 6.99 (dd, J = 6.9, 2.1 Hz, 1H), 4.01 (s, 3H). | 100 | 458.9 |
| C1110 | 8-methoxy-[1,2,4]triazolo[1,5-a]pyridine | (500 MHz, DMSO) δ 8.30 (s, 1H), 7.66-7.54 (m, 2H), 7.47-7.39 (m, 2H), 7.35-7.26 (m, 1H), 7.16 (d, J = 8.1 Hz, 1H), 7.05 (d, J = 6.8 Hz, 1H), 4.04 (s, 3H), 1.96 (s, 3H). | 97.9 | 441.2 |
| C1111 | 1-(4-methoxybenzo[d]oxazol-7-yl)ethan-1-one | (500 MHz, DMSO) δ 7.86 (d, J = 8.9 Hz, 1H), 7.60-7.56 (m, 2H), 7.49-7.44 (m, 2H), 7.38-7.32 (m, 1H), 7.08-7.03 (m, 1H), 4.10 (s, 3H), 2.75 (s, 3H), 2.08 (s, 3H). | 100 | 482.9 |
| C1112 | 4-methoxybenzo[d]oxazole-6-carbonitrile | (500 MHz, DMSO) δ 13.15 (brs, 1H), 7.53-7.44 (m, 7H), 4.06 (s, 3H), 2.57 (s, 3H). | 96.5 | 466.1 |
| C1113 | 4-methoxybenzo[d]oxazole-7-carboxamide | (400 MHz, DMSO) δ 7.72 (d, J = 8.6 Hz, 1H), 7.57-7.54 (m, 2H), 7.41-7.35 (m, 2H), 7.27-7.22 (m, 1H), 6.95 (d, J = 8.7 Hz, 1H), 4.02 (s, 3H), 2.51 (s, 3H). | 97.5 | 484.2 |
| C1114 | Replace I-1 with 3-amino-4-(3-fluorophenyl)-5-(trifluoromethyl)-1H-pyrazole | (500 MHz, DMSO) δ 12.95 (brs, 1H), 7.61-7.56 (m, 1H), 7.40-7.32 (m, 5H), 6.99 (dd, J = 6.8, 2.2 Hz, 1H), 4.01 (s, 3H), 2.52 (s, 3H). | 100 | 459.8 |

TABLE 5-continued

| Compound ID | Compound I-15 replacement | ¹H NMR | Purity (%) | MS (m/z) |
| --- | --- | --- | --- | --- |
| C1115 | Replace I-1 with [structure: 3-amino-4-(4-methoxyphenyl)-5-(trifluoromethyl)-1H-pyrazole] | (500 MHz, DMSO) δ 12.89 (brs, 1H), 7.44-7.35 (m, 4H), 7.12-7.08 (m, 2H), 6.98 (dd, J = 6.6, 2.5 Hz, 1H), 4.02 (s, 3H), 3.84 (s, 3H), 2.51 (s, 3H) | 100 | 470.9 |
| C1116 | [structure: oxazolo-pyridinone] | (500 MHz, DMSO) δ 11.71 (s, 1H), 7.62-7.51 (m, 2H), 7.50-7.29 (m, 4H), 6.81 (d, J = 6.9 Hz, 1H), 2.38 (s, 3H). | 95.5 | 428.0 |
| C1117 | [structure: benzoxazol-7-yloxyacetic acid] | (500 MHz, DMSO) δ 12.96 (s, 1H), 7.60 (d, J = 7.5 Hz, 2H), 7.48-7.39 (m, 2H), 7.33-7.26 (m, 2H), 7.27-7.21 (m, 1H), 7.11-7.08 (m, 1H), 6.85-6.81 (m, 1H), 5.06 (s, 2H), 2.40 (s, 3H) | 99.9 | 485.1 |
| C1119 | Replace I-1 with [structure: 3-amino-4-(3,5-difluorophenyl)-5-(trifluoromethyl)-1H-pyrazole] | (500 MHz, DMSO) δ 7.43-7.39 (m, 2H), 7.30-7.27 (m, 2H), 7.15 (tt, J = 9.4, 2.6 Hz, 1H), 6.91 (dd, J = 5.8, 3.2 Hz, 1H), 4.01 (s, 3H), 2.41 (s, 3H). | 100 | 476.9 |
| C1120 | Replace I-1 with [structure: 3-amino-4-(3-methoxyphenyl)-5-(trifluoromethyl)-1H-pyrazole] | (500 MHz, DMSO) δ 12.94 (brs, 1H), 7.44 (t, J = 7.9 Hz, 1H), 7.40-7.34 (m, 2H), 7.07 (dd, J = 17.0, 9.2 Hz, 3H), 7.00-6.95 (m, 1H), 4.01 (s, 3H), 3.82 (s, 3H) | 100 | 470.9 |
| C1122 | [structure: 2-(oxazolopyridin-yloxy)acetamide] | (500 MHz, CD3CN) δ 12.52 (s, 1H), 8.31 (s, 1H), 7.84 (s, 1H), 7.36 (d, J = 7.4 Hz, 2H), 7.26-7.20 (m, 2H), 7.17-7.12 (m, 1H), 6.86 (d, J = 9.3 Hz, 1H), 3.82 (s, 3H), 2.54 (s, 3H) | 98.6 | 484.1 |

TABLE 5-continued

| Compound ID | Compound I-15 replacement | ¹H NMR | Purity (%) | MS (m/z) |
|---|---|---|---|---|
| C1123 | 4-methoxy-6-amino-benzoxazole structure | (500 MHz, DMSO) δ 7.56-7.47 (m, 4H), 7.44 (d, J = 6.7 Hz, 1H), 6.40 (d, J = 1.5 Hz, 1H), 6.23 (d, J = 1.6 Hz, 1H), 5.37 (brs, 1H), 3.90 (s, 3H), 2.40 (s, 3H) | 100 | 456.0 |
| C1125 | 4-methoxy-7-methylsulfonyl-benzoxazole structure | (500 MHz, DMSO) δ 7.68 (d, J = 8.7 Hz, 2H), 7.60 (d, J = 7.6 Hz, 4H), 7.43 (t, J = 7.7 Hz, 4H), 7.30 (t, J = 7.4 Hz, 2H), 7.10 (d, J = 8.7 Hz, 2H), 4.10 (s, 5H), 3.43 (s, 6H), 2.49 (s, 6H). | 97.8 | 519.0 |
| C1126 | 4-methoxy-benzoxazole-cyano structure | (400 MHz, DMSO) δ 7.70-7.64 (m, 1H), 7.58-7.54 (m, 2H), 7.52-7.43 (m, 3H), 7.39-7.29 (m, 1H), 4.51 (s, 3H), 2.52 (s, 3H). | 95 | 466.0 |
| C1127 | Replace I-1 with 3-CF₃-4-(pyridin-2-yl)-5-amino-1H-pyrazole | (500 MHz, DMSO) δ 8.73 (d, J = 4.2 Hz, 1H), 7.97 (t, J = 7.7 Hz, 1H), 7.90-7.85 (m, 1H), 7.46-7.31 (m, 3H), 6.98 (dt, J = 7.9, 4.5 Hz, 1H), 4.02 (s, 3H), 2.59 (s, 3H). | 98.4 | 442.0 |
| C1128 also C1135 (HCl salt) | 4-methoxy-6-aminomethyl-benzoxazole structure | (500 MHz, DMSO) δ 8.15 (s, 2H), 7.60 (d, J = 7.4 Hz, 2H), 7.47-7.40 (m, 3H), 7.35-7.24 (m, 1H), 7.05 (d, J = 1.2 Hz, 1H), 4.17 (s, 2H), 4.04 (s, 3H), 2.39 (s, 3H). | 98.9 | 469.9 |
| C1129 | Replace I-1 with 3-CF₃-4-(pyridin-3-yl)-5-amino-1H-pyrazole | (500 MHz, DMSO) δ 8.79 (brs, 1H), 8.60 (brs, 1H), 7.97 (d, J = 7.8 Hz, 1H), 7.54 (s, 1H), 7.33 (d, J = 5.3 Hz, 2H), 6.97-6.92 (m, 1H), 4.02 (s, 3H), 2.44 (s, 3H). | 98.3 | 441.9 |
| C1130 | 4-methoxy-benzoxazole-7-carboxylic acid structure | (500 MHz, MeOD) δ 8.00 (d, J = 8.7 Hz, 1H), 7.55-7.51 (m, 2H), 7.49-7.45 (m, 2H), 7.43-7.38 (m, 1H), 7.03 (d, J = 8.7 Hz, 1H), 4.13 (s, 3H), 2.48 (s, 3H). | 99.1 | 485.0 |

TABLE 5-continued

| Compound ID | Compound I-15 replacement | ¹H NMR | Purity (%) | MS (m/z) |
|---|---|---|---|---|
| C1133 | Replace I-1 with 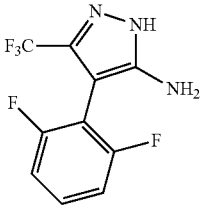 [SMILES: Nc1[nH]nc(C(F)(F)F)c1-c1c(F)cccc1F] | (500 MHz, DMSO) δ 13.12 (brs, 1H). 7.71-7.59 (m, 1H), 7.42-7.35 (m, 2H), 7.35-7.28 (m, 2H), 6.98 (dd, J = 6.5, 2.5 Hz, 1H). 4.01 (s, 3H), 2.53 (s, 3H) | 99.3 | 477.0 |
| C1134 | Replace I-10 with 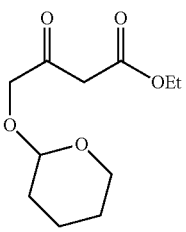 [SMILES: CCOC(=O)CC(=O)COC1CCCCO1] | (500 MHz, DMSO) δ 7.60 (d, J = 6.9 Hz, 2H), 7.44 (t, J = 7.3 Hz, 2H), 7.33-7.28 (m, 3H), 6.93-6.87 (m, 1H), 4.69 (m, 1H), 4.56 (m, 1H), 4.48 (m, 1H), 3.99 (s, 3H), 3.53 (t, J = 7.3 Hz, 1H), 3.24 (m, 1H), 1.37-1.12 (m, 5H), 1.07-0.99 (m, 1H). | 97.0 | 541.2 |
| C1137 | Replace I-10 with 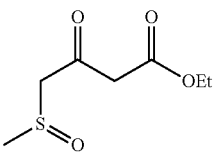 | (500 MHz, DMSO) δ 7.61 (d, J = 7.6 Hz, 2H), 7.44 (dd, J = 10.6, 4.9 Hz, 2H), 7.34-7.25 (m, 3H), 6.91 (dd, J = 7.6, 1.4 Hz, 1H), 4.43 (q, J = 12.6 Hz, 2H), 4.01 (s, 3H), 2.60 (s, 3H). | 97.4 | 503.0 |
| C1138 | Replace I-10 with 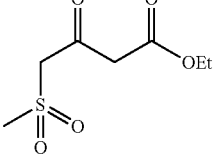 | (500 MHz, DMSO) δ 7.60 (d, J = 7.6 Hz, 2H), 7.43 (t, J = 7.7 Hz, 2H), 7.34-7.25 (m, 3H), 6.91 (dd, J = 7.5, 1.6 Hz, 1H), 4.95 (s, 2H), 4.01 (s, 3H), 3.07 (s, 3H). | 99.2 | 519.1 |
| C1140 | Replace I-10 with 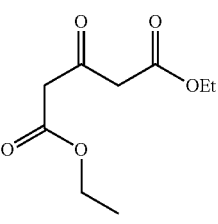 | (500 MHz, DMSO) δ 10.67 (s, 1H), 10.10 (s, 1H), 8.02 (s, 1H), 7.58-7.51 (m, 4H), 7.47 (t, J = 6.9 Hz, 1H), 7.28 (t, J = 8.4 Hz, 1H), 6.66-6.65 (m, 2H), 4.27 (q, J = 7.1 Hz, 2H), 3.70 (s, 3H), 1.29 (t, J = 7.1 Hz, 3H). | 97.3 | 513.1 |
| C1141 | 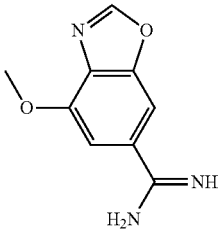 | (500 MHz, DMSO) δ 8.40 (brs, 2 H), 7.85 (d, J = 1.4 Hz, 1H), 7.60 (d, J = 7.3 Hz, 2H), 7.44 (t, J = 7.8 Hz, 2H), 7.36 (d, J = 1.4 Hz, 1H), 7.31 (t, J = 7.4 Hz, 1H), 4.10 (s, 3H), 2.49 (s, 2H). | 99.4 | 482.9 |

TABLE 5-continued

| Compound ID | Compound I-15 replacement | ¹H NMR | Purity (%) | MS (m/z) |
|---|---|---|---|---|
| C1144 | Replace I-10 with ethyl 3-oxobutanoate-derived group (acetoacetate ethyl ester) | 500 MHz, DMSO) δ 9.48 (s, 1H), 7.62 (d, J = 7.7 Hz, 2H), 7.43 (t, J = 7.7 Hz, 2H), 7.30 (t, J = 7.4 Hz, 1H), 7.18 (t, J = 8.3 Hz, 1H), 6.57 (dd, J = 8.2, 2.9 Hz, 2H), 3.66 (s, 3H), 2.54 (s, 3H). | 98.8 | 469.1 |
| C1147 | Replace I-10 with 3-oxoglutarate monoethyl ester group | (500 MHz, DMSO) δ 9.98 (s, 1H), 7.82 (s, 1H), 7.56 (d, J = 7.6 Hz, 2H), 7.51 (d, J = 7.6 Hz, 2H), 7.38 (s, 1H), 7.25 (t, J = 8.4 Hz, 1H), 6.64 (d, J = 8.3 Hz, 2H), 3.69 (s, 3H). | 98.4 | 485.1 |
| C1148 | Replace I-1 with 5-amino-3-(trifluoromethyl)-4-(2-cyanophenyl)-1H-pyrazole | (500 MHz, DMSO) δ 8.05-8.00 (m, 1H), 7.85-7.80 (m, 1H), 7.74-7.70 (m, 1H), 7.70-7.62 (m, 1H), 7.40-7.33 (m, 2H), 6.97-6.93 (m, 1H), 4.02 (s, 3H), 2.45 (s, 3H). | 99.2 | 466.0 |
| C1149 | 4-methoxybenzoxazole-6-carboxamide | (500 MHz, DMSO) δ 8.09 (s, 1H), 7.89 (s, 1H), 7.54-7.51 (m, 4H), 7.51-7.48 (m, 2H), 7.47-7.43 (m, 1H), 4.05 (s, 3H), 2.52 (s, 3H). | 100 | 484.2 |
| C1150 | 2-acetamido-7-methoxy-oxazolo[5,4-d]pyrimidine | (500 MHz, DMSO) δ 13.04-12.93 (m, 1H), 8.20 (s, 1H), 7.51 (d, J = 7.6 Hz, 2H), 7.39-7.34 (m, 2H), 7.24 (t, J = 7.4 Hz, 1H), 4.04 (s, 3H), 2.60 (s, 3H), 2.52 (s, 3H). | 97.4 | 500.0 |
| C1154 | 7-amino-4-methoxybenzoxazole | (500 MHz, DMSO) δ 7.61 (d, J = 7.4 Hz, 2H), 7.45-7.39 (m, 2H), 7.31-7.25 (m, 1H), 6.63 (d, J = 8.4 Hz, 1H), 6.52 (d, J = 8.4 Hz, 1H), 4.90 (s, 2H), 3.88 (s, 3H), 2.27 (s, 3H). | 98.2 | 456.0 |
| C1155 | 4-methoxybenzoxazole-6-carboxylic acid | (500 MHz, DMSO) δ 13.15 (brs, 1H), 7.88 (s, 1H), 7.55 (d, J = 7.4 Hz, 2H), 7.52-7.46 (m, 3H), 7.41 (d, J = 7.1 Hz, 1H), 4.06 (s, 3H). | 100 | 484.9 |

TABLE 5-continued

| Compound ID | Compound I-15 replacement | ¹H NMR | Purity (%) | MS (m/z) |
|---|---|---|---|---|
| C1156 | 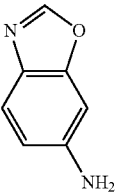 | (500 MHz, DMSO) δ 7.54 (d, J = 7.2 Hz, 2H), 7.49 (t, J = 7.6 Hz, 2H), 7.40 (d, J = 8.2 Hz, 2H), 6.81 (s, 1H), 6.64 (d, J = 8.3 Hz, 1H), 2.39 (s, 3H). | 94.6 | 424.1 |
| C1161 | 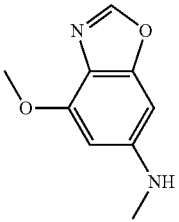 | (500 MHz, DMSO) δ 7.56 (d, J = 7.7 Hz, 2H), 7.45 (t, J = 7.6 Hz, 2H), 7.34 (s, 1H), 6.33 (d, J = 1.7 Hz, 1H), 6.18 (d, J = 1.7 Hz, 1H), 5.87 (s, 1H), 3.91 (s, 3H), 2.72 (s, 3H), 2.32 (s, 3H) | 100 | 470.0 |
| C1162 | 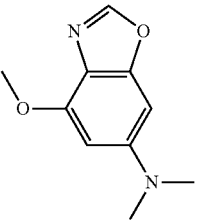 | (500 MHz, DMSO) δ 7.55 (d, J = 7.3 Hz, 2H), 7.48 (t, J = 7.4 Hz, 2H), 7.39 (s, 1H), 6.59 (s, 1H), 6.33 (s, 1H), 4.00 (s, 3H), 2.98 (s, 6H), 2.38 (s, 3H) | 99.7 | 484.0 |
| C1163 | 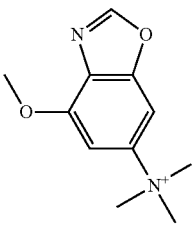<br>(formate salt) | (500 MHz, DMSO) δ 8.45 (s, 1H), 8.06 (d, J = 2.4 Hz, 1H), 7.60 (d, J = 7.4 Hz, 2H), 7.47 (d, J = 2.4 Hz, 1H), 7.46-7.39 (m, 2H), 7.35-7.25 (m, 1H), 4.15 (s, 3H), 3.69 (s, 9H), 2.45 (s, 3H) | 98.9 | 498.0 |
| C1164 | Replace I-1 with<br>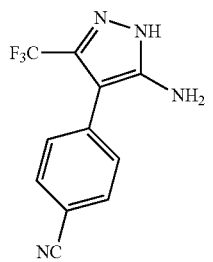 [SMILES: N#Cc1ccc(-c2c(C(F)(F)F)n[nH]c2N)cc1] | (500 MHz, DMSO) δ 7.90 (s, 4H), 7.30 (s, 1H). 7.29 (d, J = 2.0 Hz, 1H), 6.92 (dd, J = 5.4, 3.6 Hz, 1H). 4.01 (s, 3H), 2.40 (s, 3H) | 98.5 | 465.9 |
| C1166 | 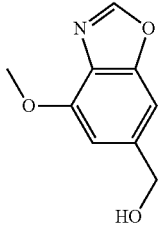 | (500 MHz, DMSO) δ 7.56 (d, J = 7.6 Hz, 2H), 7.48 (t, J = 7.6 Hz, 2H), 7.39 (s, 1H), 7.25 (s, 1H), 6.91 (s, 1H), 5.34 (s, 1H), 4.63 (s, 2H), 4.00 (s, 3H), 2.42 (s, 3H). | 399.2 | 99.7 |

TABLE 5-continued

| Compound ID | Compound I-15 replacement | ¹H NMR | Purity (%) | MS (m/z) |
|---|---|---|---|---|
| C1171 | Replace I-1 with 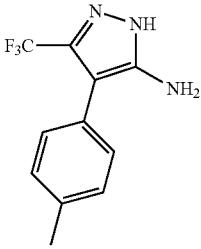 [SMILES: Cc1ccc(-c2c(C(F)(F)F)n[nH]c2N)cc1] | (500 MHz, DMSO) δ 12.91 (s, 1H), 7.40-7.37 (m, 4H), 7.37-7.33 (m, 2H), 6.98 (dd, J = 6.9, 2.2 Hz, 1H), 4.01 (s, 3H), 2.50 (s, 3H), 2.40 (s, 3H) | 100 | 455.1 |
| C1172 | Replace I-1 with 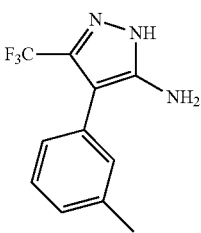 [SMILES: Cc1cccc(-c2c(C(F)(F)F)n[nH]c2N)c1] | (500 MHz, DMSO) δ 12.93 (s, 1H), 7.45-7.41 (m, 1H), 7.39-7.36 (m, 2H), 7.31 (d, J = 7.2 Hz, 2H), 7.27 (d, J = 7.7 Hz, 1H). 4.01 (s, 3H), 2.52 (s, 3H), 2.40 (s, 3H). | 100 | 455.1 |
| C1173 | Replace I-10 with 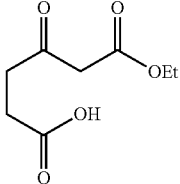 [SMILES: CCOC(=O)CC(=O)CCC(=O)O] | (500 MHz, DMSO) δ 12.02 (s, 1H), 7.66 (m, 2H), 7.46-7.39 (m, 2H), 7.29 (m, 3H), 6.93-6.89 (m, 1H), 4.01 (s, 3H), 2.96 (t, J = 6.5 Hz, 2H), 2.60 (t, J = 7.3 Hz, 2H). | 98.6 | 499.3 |
| C1174 | 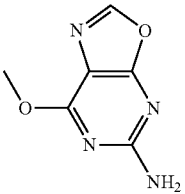 | (500 MHz, DMSO) δ 7.66-7.56 (m, J = 7.6 Hz, 2H), 7.46-7.38 (m, J = 7.4 Hz, 2H), 7.31-7.24 (m, 1H), 6.80 (s, 2H), 4.01 (s, 3H), 2.30 (s, 3H) | 95.7 | 457.9 |
| C1183 | Replace I-10 with 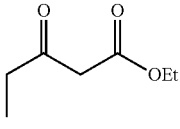 | (500 MHz, DMSO) δ 7.66 (d, J = 7.5 Hz, 2H), 7.42 (t, J = 7.8 Hz, 2H), 7.30-7.25 (m, 3H), 6.90 (dd, J = 5.6, 3.4 Hz, 1H), 4.00 (s, 3H), 2.66 (q, J = 7.5 Hz, 2H), 1.07 (t, J = 7.5 Hz, 3H). | 96.8 | 455.0 |
| C1191 | 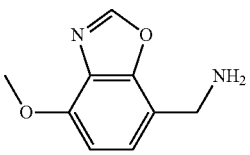 | (500 MHz, DMSO) δ 13.00 (s, 1H), 8.36 (s, 3H), 7.60-7.38 (m, 6H), 7.04 (d, J = 8.6 Hz, 1H), 4.26 (d, J = 5.5 Hz, 2H), 4.03 (s, 3H), 2.47 (s, 3H). | 98.6 | 470.1 |

TABLE 5-continued

| Compound ID | Compound I-15 replacement | ¹H NMR | Purity (%) | MS (m/z) |
|---|---|---|---|---|
| C1210 | Replace I-1 with [structure: 3-acetyl-5-amino-4-phenyl-1H-pyrazole] | (500 MHz, DMSO-d$_6$): δ ppm = 7.60 (d, J = 7.5 Hz, 2H), 7.33 (t, J = 7.5 Hz, 2H), 7.27-7.24 (m, 2H), 7.20 (t, J = 7.5 Hz, 1H), 7.10 (br s, 1H), 6.89 (dd, J = 6.0 Hz, 3.0 Hz, 1H), 4.00 (s, 3H), 2.63 (s, 3H), 2.35 (s, 3H). | 99.9 | 414.41 |
| C1224 | [structure: 4-methoxybenzoxazol-7-yl methanol] | (500 MHz, DMSO): δ 8.35 (s, 1H), 7.62 (d, J = 7.4 Hz, 2H), 7.45-7.41 (m 2H), 7.34-7.20 (m, 2H), 6.88 (d, J = 8.4 Hz, 1H). 4.71 (s, 2H), 3.99 (s, 3H), 2.33 (s, 3H). | 96.0 | 471.1 |
| C1228 | Replace I-1 with [structure: 5-amino-3-(cyclopropylethynyl)-4-phenyl-1H-pyrazole] | (500 MHz, DMSO-d$_6$): δ ppm = 8.05 (br s, 1H), 7.41 (t, J = 8.0 Hz, 2H), 7.27 (d, J = 4.5 Hz, 2H), 7.24-7.15 (m, 2H), 7.08 (br s, 1H), 6.99 (br s, 1H), 6.90 t, J = 4.5 Hz, 1H), 4.00 (s, 3H), 2.43 (s, 3H), 1.63-1.58 (m, 1H), 0.95-0.91 (m, 2H), 0.80-0.77 (m, 2H). | 99.9 | 436.46 |
| C1242 | Replace I-1 with [structure: 5-amino-3-cyclopropyl-4-phenyl-1H-pyrazole] | (500 MHz, DMSO-d$_6$): δ ppm = 7.63 (m, 2H), 7.51 (t, J = 7.5 Hz, 2H), 7.39-7.36 (m, 1H), 7.34-7.31 (m, 2H), 6.95 (dd, J = 7.0 Hz, 2.0 Hz, 1H), 4.00 (s, 3H), 2.45 (s, 3H), 1.97-1.89 (m, 1H), 1.00-0.93 (m, 4H) | 98.2 | 412.44 |
| C1283 | Replace I-1 with [structure: 5-amino-3-cyano-4-(3-fluorophenyl)-1H-pyrazole] | (500 MHz, DMSO) δ ppm = 8.03 (ddd, J = 11.0 Hz, 2.5 Hz, 1.5 Hz, 1H), 7.94-7.92 (m, 1H), 7.54-7.50 (m, 1H), 7.28 (dd, J = 4.5 Hz, 0.5 Hz, 2H), 7.13-7.09 (m, 1H), 6.91 (quint, J = 4.5 Hz, 1H), 4.00 (s, 3H), 2.45 (s, 3H). | 99.9 | 416.1 |

The compounds in Table 5A below were synthesized similarly to the methods described in Steps 1-2 above, optionally substituting the listed compound as indicated for I-15, and/or substituting for I-10 where indicated and substituting I-1 with

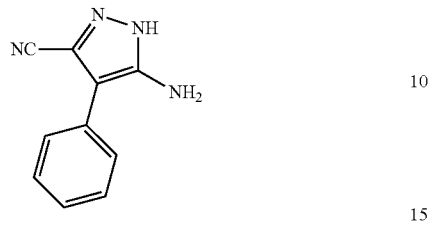

to provide the suitable analog of I-11 (per Example 3).

TABLE 5A

| Compound ID | Compound I-15 replacement | ¹H NMR | Purity (%) | MS (m/z) |
|---|---|---|---|---|
| C1118 | Replace I-10 with F₃C-C(O)-CH₂-C(O)-OEt | (500 MHz, DMSO) δ 8.05-8.00 (m, 2H), 7.56-7.50 (m, 2H), 7.39-7.29 (m, 3H), 6.95 (dd, J = 7.9, 0.8 Hz, 1H), 4.00 (s, 3H). | 99.5 | 452.2 |
| C1160 | 4-methoxy-6-chlorobenzoxazole | (500 MHz, DMSO) δ 8.01 (d, J = 7.0 Hz, 2H), 7.52-7.45 (m, 3H), 7.31 (t, J = 7.4 Hz, 1H), 6.99 (d, J = 1.7 Hz, 1H), 4.01 (s, 3H), 2.46 (s, 3H). | 98.2 | 431.9 |
| C1167 | 4-methoxyoxazolopyridine | (500 MHz, DMSO) δ 8.12-8.01 (m, 3H), 7.54-7.42 (m, 3H), 7.31 (t, J = 7.3 Hz, 1H), 2.49 (s, 3H). | 399.2 | 99.7 |
| C1175 | 4-methoxy-6-aminooxazolopyridine | (500 MHz, DMSO) δ 8.08 (d, J = 7.2 Hz, 2H), 7.48 (t, J = 7.8, Hz 2H), 7.29 (t, J = 7.4 Hz, 1H), 6.38 (d, J = 1.5 Hz, 1H), 6.20 (d, J = 1.5 Hz, 1H), 3.91 (s, 3H), 2.35 (s, 3H). | 95.3 | 413.0 |
| C1181 | 5-aminobenzoxazole | (500 MHz, DMSO) δ 8.38 (s, 2H), 8.07 (d, J = 7.3 Hz, 2H), 7.48 (t, J = 7.8 Hz, 2H), 7.35-7.19 (m, 2H), 6.85 (d, J = 1.8 Hz, 1H), 6.61 (dd, J = 8.6, 2.1 Hz, 1H), 2.40 (s, 3H). | 97.2 | 382.9 |
| C1188 | 4-ethylbenzoxazole | (500 MHz, DMSO) δ 13.16 (brs, 1H), 7.71 (d, J = 6.3 Hz, 2H), 7.62-7.57 (m, 3H), 7.49 (t, J = 7.3 Hz, 1H), 7.36 (t, J = 7.8 Hz, 1H), 7.26 (d, J = 7.5 Hz, 1H), 2.99 (q, J = 7.5 Hz, 2H), 2.57 (s, 3H), 1.34 (t, J = 7.6 Hz, 3H). | 100 | 396.1 |

TABLE 5A-continued

| Compound ID | Compound I-15 replacement | $^1$H NMR | Purity (%) | MS (m/z) |
|---|---|---|---|---|
| C1193 | 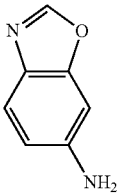 | (500 MHz, DMSO) 8.16-7.99 (m, 2H), 7.59-7.42 (m, 2H), 7.35 (d, J = 8.4 Hz, 1H), 7.34-7.23 (m, 1H), 6.78 (d, J = 1.7 Hz, 1H), 6.60 (dd, J = 8.4, 2.1 Hz, 1H), 5.23 (s, 2H), 2.35 (s, 3H). | 100 | 383.1 |
| C1202 | 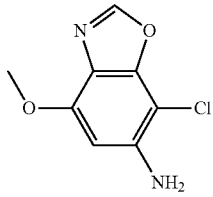 | (400 MHz, DMSO): δ 13.10 (brs, 1H): δ 7.68 (d, J = 7.3 Hz, 2H), 7.59 (t, J = 7.6 Hz, 2H), 7.50 (t, J =7.2 Hz, 1H), 6.47 (s, 1H), 5.67 (s, 2H), 3.92 (s, 3H), 2.48 (s, 3H). | 96.9 | 447.2 |
| C1203 | 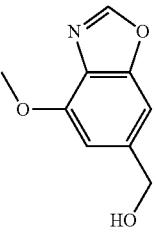 | (500 MHz, DMSO): δ 7.75 (m, 2H), 7.58 (t, J = 7.6 Hz, 2H), 7.49-7.45 (m, 1H), 7.29 (s, 1H), 6.94 (s, 1H), 4.64 (s, 2H), 4.01 (s, 3H). | 94.9 | 428.0 |
| C1204 | 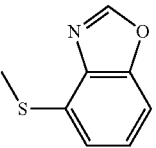 | (500 MHz, DMSO-d6): δ ppm = 8.36 (br s, 1H), 8.08-8.05 (m, 2H), 7.49-7.46 (m, 3H), 7.32 (d, J = 7.5Hz, 1H), 7.31-7.28 (m, 1H), 7.18 (dd, J = 7.5 Hz, 0.5Hz, 1H), 2.63 (s, 3H), 2.47 (s, 3H). | 97.0 | 413.46 |
| C1205 | 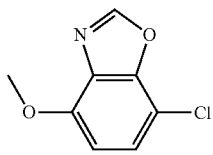 | (500 MHz, DMSO-d6): δ ppm = 8.34 (br s, 1H), 8.07-8.04 (m, 2H), 7.48 (t, J = 8.0 Hz, 2H), 7.36 (d, J = 9.0 Hz, 1H), 7.32-7.28 (m, 1H), 6.94 (d, J = 9.0 Hz, 1H), 4.00 (s, 3H), 2.45 (s, 3H). | 95.7 | 431.84 |
| C1206 | 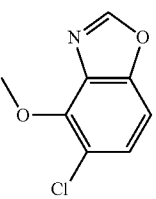 | (500 MHz, DMSO-d6): δ ppm = 8.13 (s, 1H), 8.02 (d, J = 7.5 Hz, 2H), 7.51-7.48 (m, 2H), 7.39-7.35 (m, 2H), 7.32 (t, J = 7.5 Hz, 1H), 4.38 (s, 3H), 2.53 (s, 3H). | 96.8 | 431.84 |
| C1218 | 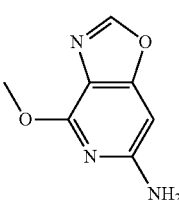 | (500 MHz, DMSO) δ 8.10-8.02 (m, J = 8.3, 1.1 Hz, 2H), 7.51-7.42 (m, J = 7.8 Hz, 2H), 7.29 (t, J = 7.4 Hz, 1H), 6.22 (s, 1H), 5.89 (s, 2H), 3.95 (s, 3H), 2.34 (s, 3H). | 98 | 414.1 |
| C1222 | 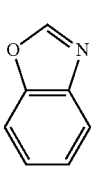 | (500 MHz, DMSO): δ 8.11-8.04 (m, 2H), 7.77-7.72 (m, 1H), 7.72-7.69 (m, 1H), 7.52-7.45 (m, 2H), 7.39-7.33 (m, 2H), 7.33-7.27 (m, 1H), 7.08 (s, 1H), 2.47 (s, 3H). | 97.0 | 368.0 |

TABLE 5A-continued

| Compound ID | Compound I-15 replacement | ¹H NMR | Purity (%) | MS (m/z) |
|---|---|---|---|---|
| C1223 | 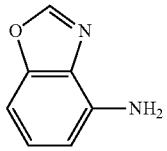 | (500 MHz, DMSO): δ 7.85-7.78 (m, 2H), 7.56 (t, J = 7.7 Hz, 2H), 7.48-7.42 (m, 1H), 7.08 (t, J = 8.0 Hz, 1H), 6.85 (d, J = 7.9 Hz, 1H), 6.56 (d, J = 7.9 Hz, 1H), 5.66 (brs, 1H), 2.49 (s, 3H). | 94.0 | 383.1 |
| C1230 | 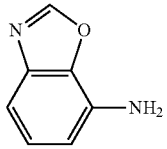 | (400 MHz, DMSO): δ 8.07 (d, J = 7.5Hz, 2H), 7.49 (t, J = 7.8 Hz, 2H), 7.30 (t, J = 7.4 Hz, 1H), 7.07-7.00 (m, 1H), 6.96-6.90 (m, 1H), 6.61 (d, J = 7.8 Hz, 1H), 5.43 (s, 2H), 2.37 (s, 3H). | 95.6 | 383.1 |
| C1240 | 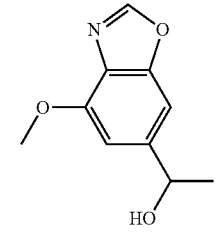 | (500 MHz, DMSO): δ 8.09-8.07 (m, 2H), 7.50-7.47 (m, 2H), 7.31-7.28 (m, 1H), 7.23 (s, 1H), 6.91 (s, 1H), 5.28 (d, J = 4.3 Hz, 1H), 4.87-4.81 (m, 1H), 4.01 (s, 3H), 2.42 (s, 3H), 1.40 (d, J = 6.4 Hz, 3H). | 97.6 | 442.1 |
| C1250 | 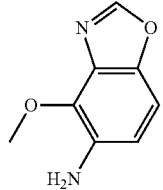 | (400 MHz, DMSO): δ 8.08 (d, J = 7.3 Hz, 2H), 7.48 (t, J = 7.8 Hz, 2H), 7.30 (t, J = 7.4 Hz, 1H), 7.07 (d, J = 8.5 Hz, 1H), 6.72 (d, J = 8.5 Hz, 1H), 4.66 (s, 2H), 4.20 (s, 3H), 2.46 (s, 3H). | 97.1 | 413.1 |
| C1271 | 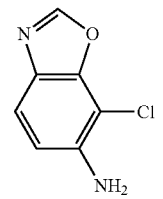 [SMILES: Nc1ccc2ncoc2c1Cl] | (500 MHz, DMSO) δ 8.08 (dd, J = 8.4, 1.2 Hz, 2H), 7.48 (t, J = 7.8 Hz, 2H), 7.39 (d, J = 8.5 Hz, 1H), 7.29 (t, J = 7.4 Hz, 1H), 6.82 (d, J = 8.5 Hz, 1H), 5.53 (s, 2H), 2.37 (s, 3H). | 100 | 417.2 |
| C1272 | 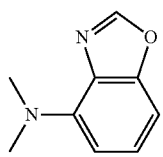 | (400 MHz, DMSO) δ 7.73 (d, J = 6.3 Hz, 2H), 7.58 (t, J = 7.6 Hz, 2H), 7.48 (t, J = 7.4 Hz, 1H), 7.24 (t, J = 8.1 Hz, 1H), 7.07 (d, J = 7.9 Hz, 1H), 6.59 (d, J = 8.0 Hz, 1H), 3.21 (s, 6H), 2.55 (s, 3H). | 94.5 | 411.2 |
| C1274 | 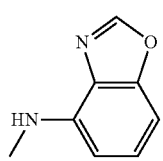 | (500 MHz, DMSO) δ 8.01 (d, J = 7.2 Hz, 2H), 7.50 (t, J = 7.8 Hz, 2H), 7.33 (t, J = 7.3 Hz, 1H), 7.14 (t, J = 8.0 Hz, 1H), 6.85 (d, J = 7.9 Hz, 1H), 6.40 (d, J = 7.9 Hz, 1H), 6.00 (s, 1H), 2.88 (s, 3H), 2.42 (s, 3H). | 100 | 397.2 |

TABLE 5A-continued

| Compound ID | Compound I-15 replacement | 1H NMR | Purity (%) | MS (m/z) |
|---|---|---|---|---|
| C1275 | 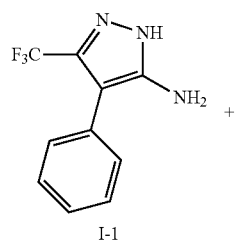 1p;6p | (500 MHz, MeOD) δ 8.87 (s, 1H), 8.42-8.37 (m, 1H), 8.35 (s, 2H), 7.86 (dd, J = 8.4, 1.2 Hz, 1H), 7.66 (s, 1H), 7.41-7.36 (m, 1H), 7.27-7.23 (m, 1H), 2.55 (s, 3H). | 94.1 | 369.2 |
| C1277 | 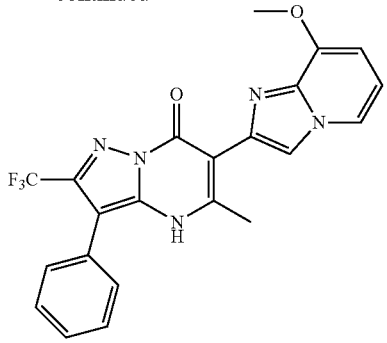 | (500 MHz, DMSO) δ 8.07 (dd, J = 8.4, 1.2 Hz, 2H), 7.47 (dd, J = 11.1, 4.6 Hz, 2H), 7.32-7.26 (m, 3H), 7.15 (dd, J = 6.1, 2.9 Hz, 1H), 4.15-4.11 (m, 1H), 2.42 (s, 3H), 0.86-0.77 (m, 4H). | 97.2 | 424.2 |

Example 5

Synthesis of 6-(8-methoxyimidazo[1,2-a]pyridin-2-yl)-5-methyl-3-phenyl-2-(trifluoromethyl)pyrazolo[1,5-a]pyrimidin-7(4H)-one (C1044) was carried out in one step as follows:

Step 1:

To a solution of 4-phenyl-3-(trifluoromethyl)-1H-pyrazol-5-amine (I-1, 55.0 mg, 242 μmol) and ethyl 2-(8-methoxyimidazo[1,2-a]pyridin-2-yl)-3-oxobutanoate (I-16, 73.6 mg, 266 μmol) in dioxane (807 μL) was added TFA (403 μL) and the reaction mixture was heated at 50° C. for 6 h. LCMS shows reaction was completed. The volatiles were removed in vacuo. The crude material was purified by Reverse Phase chromatography on a Companion Combiflash using 10 g C18 column with a gradient elution of 20-50% MeCN/H₂O (0.1% ammonium formate buffer) over 15 min and a flow rate of 30 mL/min. The clean fractions were combined and lyophilized to afford the compound C1044. $^1$HNMR (500 MHz, DMSO) δ 12.46 (s, 1H), 8.31 (s, 1H), 8.26 (d, J=6.6 Hz, 1H), 7.55-7.48 (m, 4H), 7.46 (s, 1H), 6.85 (s, 1H), 6.70 (s, 1H), 3.97 (s, 3H), 2.71-2.60 (m, 3H). MS (m/z): 440.2 [M+1]⁺, 98.1%.

Table 6 below provides additional compounds that can be synthesized similarly to the methods described in the above step, substituting the listed compound as indicated for I-16, as well as substituting for I-1 where indicated. Data for compounds synthesized is provided in columns 3-5.

TABLE 6

| Compound ID | Compound I-16 replacement | ¹H NMR | Purity (%) | MS (m/z) |
|---|---|---|---|---|
| C1017 | | (500 MHz, DMSO) δ 7.58 (d, J = 7.6 Hz, 1H), 7.42 (t, J = 7.7 Hz, 2H), 7.29 (t, J = 7.4 Hz, 1H), 2.64-2.57 (m, 4H), 2.39 (s, 3H), 1.84-1.78 (m, 4H). | 98.6 | 414.2 |
| C1019 | | (500 MHz, DMSO) δ 12.76 (s, 1H), 12.45 (s, 1H), 8.18 (dd, J = 8.0, 1.3 Hz, 1H), 7.91-7.78 (m, 1H), 7.70 (d, J = 7.9 Hz, 1H), 7.60-7.42 (m, 6H), 2.44 (s, 3H). | 99.1 | 438.2 |
| C1021 | | (500 MHz, MeOD) δ 7.63 (s, 2H), 6.71 (d, J = 7.5 Hz, 2H), 6.62 (t, J = 7.6 Hz, 2H), 6.54 (t, J = 7.4 Hz, 1H), 1.53 (s, 3H), 1.50 (s, 6H). | 99.0 | 388.1 |
| C1023 | | (500 MHz, DMSO) δ 7.52-7.51 (m, 2H), 7.45 (t, J = 7.7 Hz, 2H), 7.36 (t, J = 7.4 Hz, 1H), 4.32-4.24 (m, 1H), 2.34 (s, 3H), 1.34 (d, J = 6.7 Hz, 6H). | 98.9 | 420.2 |
| C1024 | | (500 MHz, DMSO) 12.66 (s, 1H), 7.61 (t, J = 8.2 Hz, 1H), 7.48-7.40 (m, 4H), 7.38-7.28 (m, 1H), 7.10 (s, 1H), 6.96-6.91 (m, 1H), 3.81 (s, 3H), 2.48-2.44 (m, 3H). | 98.9 | 468.1 |
| C1025 | | (500 MHz, DMSO) δ 12.74 (s, 1H), 12.41 (s, 1H), 7.73 (dd, J = 8.0 1.3 Hz, 1H), 7.58-7.54 (m, 2H), 7.53-7.46 (m, 4H), 7.41 (dd, J = 8.2, 1.2 Hz, 1H), 3.91 (s, 3H), 2.40 (s, 3H). | 99.1 | 468.2 |

TABLE 6-continued

| Compound ID | Compound I-16 replacement | ¹H NMR | Purity (%) | MS (m/z) |
| --- | --- | --- | --- | --- |
| C1026 | | (500 MHz, DMSO) δ 13.43 (s, 1H), 12.52 (s, 1H), 7.58-7.46 (m, 5H), 7.10 (d, J = 8.1 Hz, 1H), 7.02 (t, J = 7.8 Hz, 1H), 6.86 (d, J = 7.4 Hz, 1H), 3.99 (s, 3H), 2.22 (s, 3H). | 98.7 | 440.1 |
| C1029 | | (500 MHz, DMSO) δ 12.62 (s, 2H), 7.56-7.47 (m, 10H), 4.28 (d, J = 1.4 Hz, 4H), 3.20 (s, 6H). | 99.1 | 645.2 |
| C1057 | | (500 MHz, DMSO) δ 12.45 (br s, 1H), 8.05 (s, 1H), 7.51-7.13 (m, 7H), 6.46 (s, 1H), 4.10 (s, 3H), 2.56 (s, 3H). | 97.7 | 440.2 |
| C1168 | | (500 MHz, DMSO) δ 12.53 (s, 1H), 7.90 (d, J = 7.6 Hz, 1H), 7.77-7.69 (m, 1H), 7.61 (t, J = 7.5 Hz, 1H), 7.56-7.46 (m, 3H), 7.44 (d, J = 6.7 Hz, 2H), 6.88 (s, 1H), 3.57 (s, 3H). | 426.0 | 97.4 |
| C1211 | Also replace I-1 with | (500 MHz, DMSO-d₆): δ ppm = 8.30 (br s, 1H), 8.22-8.20 (m, 2H), 7.39 (t, J = 8.0 Hz, 2H), 7.27-7.23 (m, 2H), 7.19-7.16 (m, 1H), 6.88 (dd. J = 5.5 Hz, 3.0 Hz, 1H. 4.38 (s, 1H), 4.00 (s, 3H), 2.42 (s, 3H) | 97.1 | 396.41 |

TABLE 6-continued

| Compound ID | Compound I-16 replacement | ¹H NMR | Purity (%) | MS (m/z) |
|---|---|---|---|---|
| C1215 | (structure: 8-methoxyimidazo[1,2-a]pyridine with CH2OH and ethyl acetoacetate substituent) | (500 MHz, DMSO) δ 12.54 (s, 1H), 8.23-7.98 (m, 1H), 7.62-7.47 (m, 4H), 7.46-7.33 (m, 1H), 7.04-6.84 (m, 1H), 6.83-6.61 (m, 1H), 5.23-4.98 (m, 1H), 4.65 (d, J = 4.8 Hz, 2H), 3.96 (s, 3H), 2.25 (s, 3H). | 98.06 | 470.0 |
| C1233 | (structure: 4-methoxybenzoxazole with ethyl ester and cyclohexenyl-COOEt ketone) | (500 MHz, DMSO) δ 7.62 (d, J = 7.5 Hz, 2H), 7.42 (t, J = 7.8 Hz, 2H), 7.31-7.22 (m, 3H), 6.88 (dd, J = 6.9, 2.2 Hz, 1H), 5.51 (s, 1H), 4.04-3.94 (m, 5H), 2.37-2.34 (m, 1H), 2.06-1.88 (m, 2H) 1.55-1.47 (m, 1H), 1.26 (t, J = 6.9 Hz, 3H), 1.17-1.05 (m, 3H). | 96.6 | 579.2 |
| C1234 | (structure: 4-methoxybenzoxazole with ethyl ester and cyclohexenyl-COOH ketone) | (500 MHz, DMSO) δ 12.99 (s, 1H), 12.15 (s, 1H), 7.53-7.48 (m, 4H), 7.33-7.30 (m, 3H), 6.99-6.91 (m, 1H), 5.89 (s, 1H), 4.00 (s, 3H), 2.30-1.85 (m, 4H), 1.45-1.40 (m, 1H), 1.25-1.22 (m, 2H). | 96.2 | 551.2 |
| C1236 | (structure: 4-methoxybenzoxazole with ethyl ester and cyclopentyl-CH2OH ketone) | (500 MHz, DMSO) δ 7.74-7.72 (m, 2H), 7.44-7.39 (m, 2H), 7.30-7.23 (m, 3H), 6.92-6.90 (m, 1H), 4.36-4.32 (m, 1H), 4.02-4.01 (m, 3H), 3.26-3.16 (m, 2H), 1.96-1.84 (m, 3H), 1.71-1.66 (m, 1H), 1.57-1.51 (m, 2H), 1.47-1.41 (m, 1H). | 98.3 | 525.3 |

TABLE 6-continued

| Compound ID | Compound I-16 replacement | ¹H NMR | Purity (%) | MS (m/z) |
|---|---|---|---|---|
| C1237 | MeO-benzoxazole-CH(C(O)OEt)-C(O)-cyclohexyl-COOH | (500 MHz, DMSO) δ 12.27 (s, 1H), 12.03 (s, 1H), 7.74-7.29 (m, 7H), 6.94 (s, 1H), 4.03 (s, 3H), 2.78-2.72 (m, 1H), 2.14-2.03 (m, 1H), 1.94-1.80 (m, 4H), 1.73-1.68 (m, 2H), 1.23-1.16 (m, 2H). (Isomer 1) | 99.6 | 553.2 |
| C1238 | MeO-benzoxazole-CH(C(O)OEt)-C(O)-cyclohexyl-COOH | (500 MHz, DMSO) δ 12.73 (s, 1H), 11.99 (s, 1H), 7.74-7.69 (m, 2H), 7.53-7.41 (m, 5H), 6.92-6.88 (m, 1H), 4.03 (s, 3H), 2.87-2.79 (m, 1H), 2.47-2.41 (m, 1H), 2.12-2.04 (m, 2H), 1.73-1.70 (m, 2H), 1.67-1.55 (m, 2H), 1.40-1.29 (m, 2H). (Isomer 2) | 98.7 | 553.2 |
| C1239 | MeO-benzoxazole-CH(C(O)OEt)-C(O)-cyclopentyl-COOH | (500 MHz, DMSO) δ 7.73 (d, J = 7.4 Hz, 2H), 7.44-7.38 (m, 2H), 7.34-7.21 (m, 3H), 6.91 (dd, J = 5.0 4.0 Hz, 1H), 4.01 (s, 3H), 2.67-2.60 (m, 1H), 2.53-2.51 (m, 1H), 2.09-2.04 (m, 2H), 1.98-1.85 (m, 2H), 1.79-1.67 (m, 2H). | 99.5 | 539.2 |
| C1241 | MeO-benzoxazole-CH(C(O)OEt)-C(O)-CH3; Also replace I-1 with | (500 MHz, DMS0-d₆): δ ppm = 8.87 (br s, 0.5H), 8.34 (br s, 0.5H), 7.58 (d, J = 7.5 Hz, 2H), 7.41 (t, J = 7.5 Hz, 2H), 7.27-7.22 (m, 3H), 7.12 (br s, 1H), 6.88 (dd, J = 6.0 Hz 2.5 Hz, 1H), 6.81 (dd, J = 17.5Hz, 11.0Hz, 1H), 6.00 (dd, J = 17.5 Hz, 2.0Hz, 1H), 5.34 (dd, J = 11.0 Hz, 2.0Hz, 1H), 400 (s, 3H), 2.37 (s, 3H) | 97.5 | 398.42 |

TABLE 6-continued

| Compound ID | Compound I-16 replacement | ¹H NMR | Purity (%) | MS (m/z) |
|---|---|---|---|---|
| | 3-vinyl-4-phenyl-1H-pyrazol-5-amine structure | | | |
| C1247 | 2-(5-oxo-4,5-dihydro-1,3,4-oxadiazol-2-yl)-3-oxobutanoate structure | (500 MHz, DMSO) δ 12.94 (bs, 1H), 12.49 (s, 1H), 7.52-7.40 (m, 5H), 2.39 (s, 3H). | 97.1 | 378.1 |
| C1252 | 2-(7-methoxybenzo[d]oxazol-2-yl)-3-(cyclobutyl-COOH)-oxopropanoate structure | (500 MHz, DMSO) δ 7.74 (d, J = 7.7 Hz, 2H), 7.44-7.41 (m, 2H), 7.32-7.24 (m, 3H), 6.92-6.89 (m, 1H), 4.03-4.01 (m, 3H), 3.83-3.66 (m, 1H), 2.97-2.83 (m, 1H), 2.42-2.36 (m, 2H), 2.13-2.10 (m, 2H). | 98.6 | 525.2 |
| C1264 | 2-benzyl-3-oxobutanoate structure<br>Also replace I-1 with<br>3-(trifluoromethyl)-4-cyclopropyl-1H-pyrazol-5-amine structure | (500 MHz, DMSO) δ 11.94 (s, 1H), 7.28-7.19 (m, 4H), 7.19-7.13 (m, 1H), 3.87 (s, 2H), 2.40 (s, 3H), 1.72-1.65 (m, 1H), 0.97-0.91 (m, 2H), 0.61-0.56 (m, 2H). | 99.6 | 348.1 |
| C1265 | 2-phenyl-3-oxobutanoate structure<br>Also replace I-1 with | (500 MHz, DMSO) δ 12.13 (s, 1H), 7.45 (ddd, J = 7.6, 4.5, 1.2 Hz, 2H), 7.40-7.35 (m, 1H), 7.33-7.29 (m, 2H), 2.25 (s, 3H), 1.77-1.69 (m, 1H), 1.01-0.95 (m, 2H), 0.65-0.59 (m, 2H). | 99.6 | 334.2 |

TABLE 6-continued
| Compound ID | Compound I-16 replacement | ¹H NMR | Purity (%) | MS (m/z) |
|---|---|---|---|---|
| | 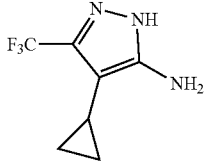 | | | |
| C1266 | 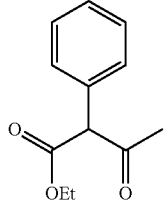 Also replace I-1 with 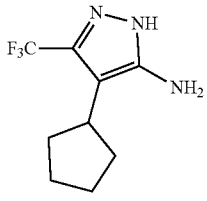 | (500 MHz, DMSO-$d_6$) δ 11.94 (s, 1H), 7.47-7.42 (m, 2H), 7.39-7.35 (m, 1H), 7.33-7.29 (m, 2H), 2.23 (s, 3H), 1.98-1.90 (m, 2H), 1.83 (dt, J = 9.3, 6.6 Hz, 2H), 1.71 (ddd, J = 26.5, 11.7, 6.7 Hz, 4H). | 100 | 334.2 |
| C1267 | 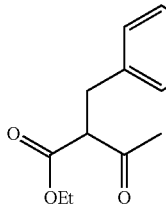 Also replace I-1 with 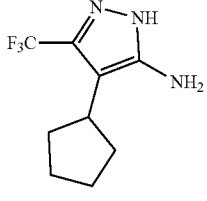 | (500 MHz, DMSO-$d_6$) δ 11.78 (s, 1H), 7.27-7.21 (m, 4H), 7.19-7.14 (m, 1H), 3.87 (s, 2H), 3.30-3.21 (m, 1H), 2.39 (s, 3H), 1.96-1.87 (m, 2H), 1.86-1.77 (m, 2H), 1.74-1.60 (m, 4H). | 100 | 376.2 |
| C1268 | 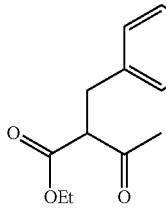 Also replace I-1 with 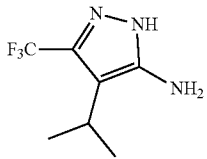 | (500 MHz, DMSO-$d_6$) δ 11.77 (s, 1H), 7.28-7.21 (m, 4H), 7.19-7.14 (m, 1H), 3.87 (s, 2H), 3.35-3.27 (m, 1H), 2.39 (s, 3H), 1.29 (d, J = 7.1 Hz, 6H). | 99.5 | 350.2 |

TABLE 6-continued

| Compound ID | Compound I-16 replacement | ¹H NMR | Purity (%) | MS (m/z) |
|---|---|---|---|---|
| C1269 | 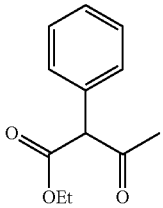 Also replace I-1 with 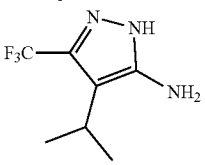 | (500 MHz, DMSO-$d_6$) δ 11.94 (s, 1H), 7.46-7.42 (m, 2H), 7.39-7.35 (m, 1H), 7.33-7.29 (m, 2H), 3.40-3.32 (m, 1H), 2.24 (s, 3H), 1.32 (d, J = 7.1 Hz, 6H). | 99.9 | 336.1 |
| C1280 | 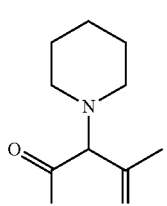 Also replace I-1 with 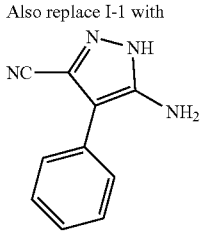 | (500 MHz, DMSO) δ 8.14 (s, 1H), 7.98-7.84 (m, 2H), 7.46 (t, J = 7.7 Hz, 2H), 7.30 (t, J = 7.1 Hz, 1H), 2.79-2.58 (m, 2H), 2.37 (s, 3H), 1.82-1.43 (m, 6H), 1.32-1.15 (m, 2H). | 97.7 | 334.2 |

Example 6

Synthesis of 5-methyl-3-phenyl-6-(1-phenyl-1H-benzo[d]imidazol-2-yl)-2-(trifluoromethyl)pyrazolo[1,5-a]pyrimidin-7(4H)-one (C1229) was carried out in two steps as follows:

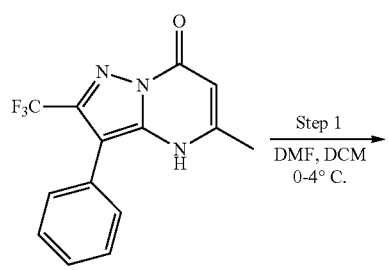

I-11

Step 1
DMF, DCM
0-4° C.

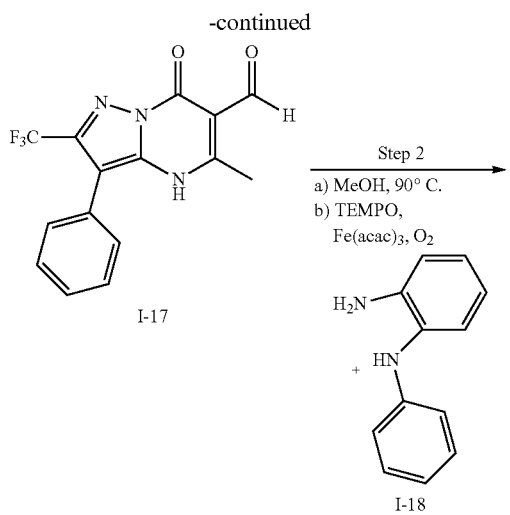

I-17

Step 2
a) MeOH, 90° C.
b) TEMPO, Fe(acac)₃, O₂

I-18

-continued

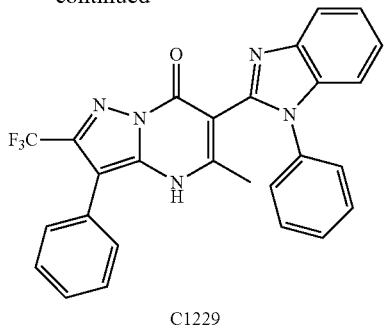

C1229

Step 1:

Synthesis of 5-methyl-7-oxo-3-phenyl-2-(trifluoromethyl)-4,7-dihydropyrazolo[1,5-a]pyrimidine-6-carbaldehyde (I-17): A suspension of 5-methyl-3-phenyl-2-(trifluoromethyl)pyrazolo[1,5-a]pyrimidin-7(4H)-one (I-11, 1.00 g, 3.41 mmol) in dry DMF (3.40 mL), is pre-cooled to 0-4° C. using an ice/water bath. In a separate flask, oxalyl chloride (383 μL, 4.43 mmol) is dissolved in DCM (3.41 mL) and cooled to 0-4° C. using an ice/water bath. To this solution is added DMF (343 μL, 4.43 mmol) and the resulting mixture is added dropwise to the suspension of compound I-11. The reaction mixture is stirred at 0-4° C. and gradually warmed to room temperature. After overnight at room temperature, the reaction mixture is poured into a mixture of ice and 1M NaOH aqueous solution. EtOAc is then added and layers are separated. The organic layer is washed with brine, dried over anhydrous $Na_2SO_4$, filtered and concentrated in vacuo. The crude oil was purified by normal phase chromatography ($SiO_2$, using a gradient of 0 to 20% MeOH in DCM) to afford the compound I-17. MS (m/z): 322.0 $[M+1]^+$, 92.25%.

Step 2:

Synthesis of 5-methyl-3-phenyl-6-(1-phenyl-1H-benzo[d]imidazol-2-yl)-2-(trifluoromethyl)pyrazolo[1,5-a]pyrimidin-7(4H)-one (C1229): To a stirred solution of compound I-17 (50 mg, 0.156 mmol) in MeOH (1 mL) was added N-phenylbenzene-1,2-diamine (I-18, 28.7 mg, 0.156 mmol). The reaction mixture was placed in a preheated oil bath at 90° C. overnight. After this time, reaction mixture was cooled to room temperature and TEMPO (2.5 mg, 0.016 mmol), followed by iron(III) acetylacetonate (11 mg, 0.031 mmol) were added. $O_2$ was bubbled into the dark solution for 5 min and the resulting mixture was heated at 40° C. for 2 h. After this time, the reaction mixture was concentrated in vacuo to dryness. The residue was purified by reverse flash chromatography (KP-C18-H5, using a gradient 0 to 100 $MeCN/H_2O$ (0.1% ammonium formate buffer) to afford compound C1229 after lyophilization. $^1$H NMR (500 MHz, DMSO) δ 12.68 (s, 1H), 7.74 (d, J=6.9 Hz, 1H), 7.55-7.33 (m, 10H), 7.32-7.11 (m, 3H), 2.21 (s, 3H); MS (m/z): 486.1 $[M+1]^+$, 99.4%.

Table 7 below provides additional compounds that can be synthesized similarly to the methods described in steps 1-2 above, substituting the listed compound as indicated for I-18, as well as substituting for I-1 (per Example 3) where indicated to give the suitable I-11 analog. Data for compounds synthesized is provided in columns 3-5.

TABLE 7

| Compound ID | Compound I-18 replacement | $^1$H NMR | Purity (%) | MS (m/z) |
|---|---|---|---|---|
| C1005 | [H₂N, NH₂ on benzene] | (500 MHz, DMSO) δ 12.99 (bs, 1H), 7.66 (bs, 2H), 7.60 (d, J = 7.5 Hz, 2H), 7.45 (t, J = 7.5 Hz, 2H), 7.34 (t, J = 7.6 Hz, 1H), 7.25 (bs, 2H), 2.75 (s, 3H). | 96.4 | 410.1 |
| C1008 | [H₂N, NH₂, NH₂ on benzene] | (500 MHz, DMSO) δ 8.32 (s, 2H), 7.63 (d, J = 7.4 Hz, 2H), 7.46-7.38 (m, 2H), 7.32-7.23 (m, 1H), 6.83-6.76 (m, 2H), 6.35-6.26 (m, 1H), 2.79 (s, 3H). | 97.7 | 425.1 |
| C1009 | [H₂N, NH₂, NHAc on benzene] | (500 MHz, DMSO) δ 12.92 (s, 1H), 12.07 (s, 1H), 7.97 (s, 1H), 7.54 (d, J = 7.4 Hz, 2H), 7.48 (t, J = 7.7Hz, 2H), 7.38 (t, J = 7.4 Hz, 1H), 7.18 (dt, J = 15.7, 7.9 Hz, 2H), 2.72 (s, 3H), 2.60 (s, 3H). | 95.1 | 467.1 |
| C1016 | [H₂N, NH₂, OMe on benzene] | (500 MHz, DMSO) δ 12.89 (s, 2H), 7.61 (d, J = 7.6 Hz, 2H), 7.50 (d, J = 8.7 Hz, 1H), 7.44 (t, J =7.7 Hz, 72H), .31 (t, J = 7.4 Hz, 1H), 7.18 (d, J = 2.3 Hz, 1H), 6.81 (d, J = 6.5 Hz, 1H), 3.80 (s, 3H), 2.76 (s, 3H). | 96.5 | 440.3 |

TABLE 7-continued

| Compound ID | Compound I-18 replacement | ¹H NMR | Purity (%) | MS (m/z) |
|---|---|---|---|---|
| C1018 | 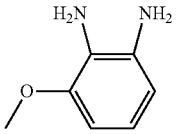 | (500 MHz, DMSO) δ 7.56 (d, J = 7.5 Hz, 2H), 7.49 (t, J = 7.5 Hz, 2H), 7.43-7.36 (m, 1H), 7.29 (s, 2H) 6.92 (br s, 1H), 4.01 (s, 3H), 2.60 (s, 3H). | 99.3 | 440.2 |
| C1020 | 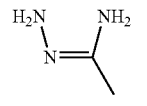 | (500 MHz, DMSO) δ 12.82 (brs, 1H), 7.49 (t, J = 7.4 Hz, 1H), 7.41-7.32 (m, 3H), 7.17 (d, J = 8.3 Hz, 1H), 7.08 (t, J = 7.4 Hz, 1H), 6.98 (dd, J = 6.6, 2.3 Hz, 1H), 4.01 (s, 3H), 3.78 (s, 3H). | 92.3 | 375.2 |
| C1065 | 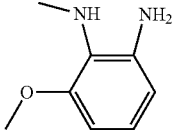 | (500 MHz, DMSO) δ 7.63 (d, J = 8.1 Hz, 2H), 7.42 (t, J = 7.0 Hz, 2H), 7.33-7.26 (m, 1H), 7.21 (d, J = 7.8 Hz, 1H), 7.09-7.05 (m, 1H), 6.80-6.74 (m, 1H), 3.94 (s, 3H), 3.80 (s, 3H), 2.11 (s, 3H). | 94.1 | 454.2 |
| C1087 | 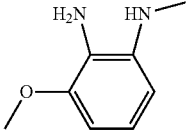 | (500 MHz, DMSO) δ 7.62 (d, J = 6.3 Hz, 2H), 7.48-7.40 (m, 2H), 7.31 (s, 1H), 7.15 (s, 2H), 6.73 (s, 1H), 3.97 (s, 3H), 3.60 (s, 3H), 2.16 (s, 3H). | 99.4 | 454.1 |
| C1176 | 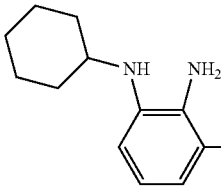 | (500 MHz, DMSO) δ 12.72 (br s, 1H), 7.58 (d, J = 7.6 Hz, 2H), 7.53-7.43 (m, 2H), 7.43-7.32 (m, 2H), 7.25-7.12 (m, 1H), 6.88-6.68 (m, 1H), 4.18-4.03 (m, 1H), 3.95 (s, 3H), 2.27-2.14 (m, 3H), 2.11 (s, 3H), 1.83 (d, J = 10.9 Hz, 1H), 1.76 (d, J = 9.5 Hz, 1H), 1.72-1.56 (m, 2H), 1.41-1.18 (m, 3H). | 98.05 | 522.0 |
| C1189 | 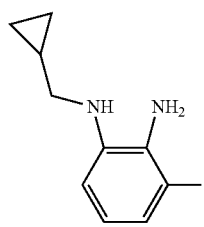 | (500 MHz, DMSO) δ 8.25 (s, 1H), 7.64 (d, J = 7.3 Hz, 2H), 7.42 (t, J = 7.8 Hz, 2H), 7.31-7.24 (m, 1H), 7.22-7.16 (m, 1H), 7.12 (t, J = 8.0 Hz, 1H), 6.70 (d, J = 7.2 Hz, 1H), 4.07-3.98 (m, 1H), 3.96 (s, 3H), 3.86-3.74 (m, 1H), 2.11 (s, 3H), 1.10-1.01 (m, 1H), 0.41-0.30 (m, 2H), 0.30-0.22 (m, 1H), 0.13-0.03 (m, 1H) | 99.37 | 494.0 |
| C1190 | 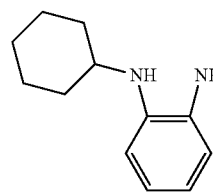 | (500 MHz, DMSO) δ 12.74 (s, 1H), 8.09-7.86 (m, 1H), 7.77-7.64 (m, 1H), 7.61-7.47 (m, 4H), 7.46-7.20 (m, 3H), 4.29-4.12 (m, 1H), 2.33-2.09 (m, 6H), 1.92-1.80 (m, 1H), 1.82-1.70 (m, 2H), 1.69-1.53 (m, 1H), 1.47-1.17 (m, 3H). | 99.69 | 492.1 |
| C1200 | 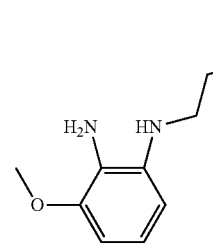 | (500 MHz, DMSO) δ 12.81 (s, 1H), 7.76-7.11 (m, 7H), 7.03-6.63 (m, 1H), 4.57-4.10 (m, 2H), 3.98 (s, 3H), 3.73-3.55 (m, 1H), 3.53-3.41 (m, 1H), 3.08 (s, 3H), 2.20 (s, 3H). | 99.9 | 498.0 |

TABLE 7-continued
| Compound ID | Compound I-18 replacement | ¹H NMR | Purity (%) | MS (m/z) |
|---|---|---|---|---|
| C1201 | 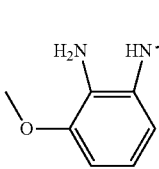 | (500 MHz, DMSO) δ 12.77 (s, 1H), 7.72-7.13 (m, 7H), 7.04-6.63 (m, 1H), 4.89-4.64 (m, 1H), 4.40-4.04 (m, 2H), 3.98 (s, 3H), 3.73-3.49 (m, 2H), 2.22 (s, 3H). | 98.48 | 484.0 |
| C1221 | 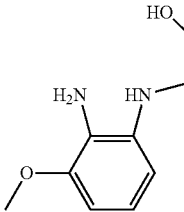 | (500 MHz, DMSO) δ 13.13 (s, 2H), 7.55 (d, J = 7.5 Hz, 2H), 7.52-7.44 (m, 2H), 7.43-7.33 (m, 1H), 7.26-7.05 (m, 2H), 6.87-6.69 (m, 1H), 5.17-4.72 (m. 2H), 3.97 (s, 3H) 2.20 (s, 3H). | 99.9 | 498.1 |
| C1231 | 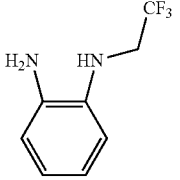 | (500 MHz, DMSO) δ 12.83 (s, 1H), 7.80-7.68 (m, 2H), 7.63-7.44 (m, 5H), 7.43-7.24 (m, 2H), 5.53-5.29 (m, 1H), 5.15-4.91 (m, 1H), 2.22 (s, 3H). | 98.47 | 492.1 |
| C1235 | 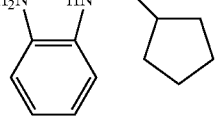 | (500 MHz, DMSO) δ 7.86-7.76 (m, 1H), 7.71 (d, J = 7.8 Hz, 1H), 7.61-7.55 (m, 2H), 7.53-7.45 (m, 2H), 7.44-7.29 (m, 3H), 4.30-4.22 (m, 1H), 4.14-4.03 (m, 1H), 2.39-2.29 (m, 1H), 2.22 (s, 3H), 1.61-1.33 (m, 6H), 1.22-0.99 (m, 2H). | 96.92 | 492.2 |
| C1276 | 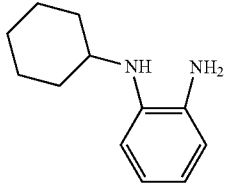 [SMILES: Nc1ccccc1NC1CCCCC1] Also replace I-1 with 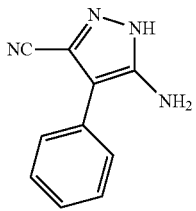 | (500 MHz, DMSO) δ 8.36-7.75 (m, 4H), 7.72-7.26 (m, 5H), 4.29 (br s, 1H), 4.19-3.81 (m, 3H), 2.32-2.19 (m, 4H), 1.89-1.74 (m, 2H), 1.68-1.59 (m, 1H), 1.45-1.22 (m, 3H). | 100 | 449.2 |
| C1278 | 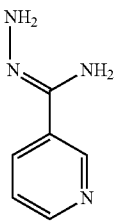 | (500 MHz, DMSO) δ 8.40 (s, 1H), 7.81-7.56 (m, 2H), 7.47 (s, 1H), 6.75-6.45 (m, 5H), 1.88 (s, 3H). | 97.2 | 438.1 |

TABLE 7-continued

| Compound ID | Compound I-18 replacement | ¹H NMR | Purity (%) | MS (m/z) |
|---|---|---|---|---|
| C1279 | 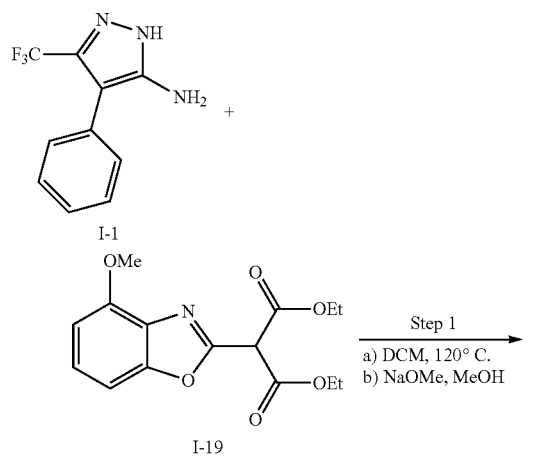 Also replace I-1 with | (500 MHz, MeOD) δ 7.85-7.81 (m, 2H), 7.41-7.33 (m, 3H), 7.25 (t, J = 7.5 Hz, 1H), 7.13 (d, J = 1.8 Hz, 1H), 6.77 (dd, J = 8.7, 1.9 Hz, 1H), 4.11-4.02 (m, 1H), 2.25-2.19 (m, 2H), 2.13 (s, 3H), 1.84-1.68 (m, 4H), 1.34-1.22 (m, 4H). | 95.2 | 464.3 |

Example 7

Synthesis of 5-chloro-6-(4-methoxybenzo[d]oxazol-2-yl)-3-phenyl-2-(trifluoromethyl)pyrazolo[1,5-a]pyrimidin-7(4H)-one (C1071) and 5-methoxy-6-(4-methoxybenzo[d]oxazol-2-yl)-3-phenyl-2-(trifluoromethyl)pyrazolo[1,5-a]pyrimidin-7(4H)-one (C1084) were carried out in two and three steps, respectively, as follows:

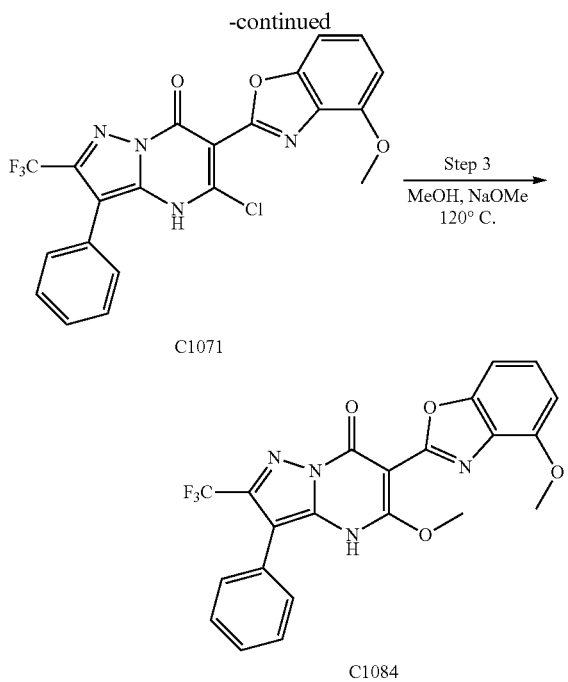

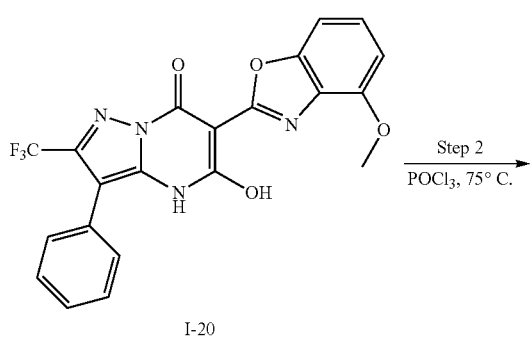

Step 1:

Synthesis of 5-hydroxy-6-(4-methoxybenzo[d]oxazol-2-yl)-3-phenyl-2-(trifluoromethyl)pyrazolo[1,5-a]pyrimidin-7(4H)-one (I-20): A mixture of 4-phenyl-3-(trifluoromethyl)-1H-pyrazol-5-amine (I-1, 1.68 g, 7.40 mmol) and 2-(4-methoxybenzo[d]oxazol-2-yl)malonate (I-19, 2.50 g, 8.14 mmol) were dissolved in DCM (5 mL). The reaction mixture was concentrated in vacuo and the residue was heated at 120° C. for 2 h. LCMS showed complete reaction and the crude mixture was dissolved in MeOH (5 mL), and sodium methoxide in MeOH (30 mmol) was added and the reaction was stirred at r.t. for 3 h. The reaction was quenched with AcOH, and concentrated in vacuo. The desired compound was crashed out after adding water. The resulting white solid was filtered and dried in vacuo to afford compound I-20. MS (m/z): 443.0 [M+1]⁺.

Step 2:

Synthesis of 5-chloro-6-(4-methoxybenzo[d]oxazol-2-yl)-3-phenyl-2-(trifluoromethyl)pyrazolo[1,5-a]pyrimidin-7(4H)-one (C1071): Compound I-20 (2.0 g, 4.52 mmol) was dissolved in POCl$_3$ (10 mL) and heated at 75° C. for 4 h in a sealed tube. The excess POCl$_3$ was removed in vacuo and the crude material was purified directly on normal phase flash chromatography (Hexanes:EtOAc, 100:10 to 0:100) to obtain compound C1071. MS (m/z): 460.8 [M+1]$^+$.

Step 3:

Synthesis of 5-methoxy-6-(4-methoxybenzo[d]oxazol-2-yl)-3-phenyl-2-(trifluoromethyl)pyrazolo[1,5-a]pyrimidin-7(4H)-one (C1084): Sodium methoxide (0.05 mL of 25% in MeOH, 0.217 mmol) was added to a solution of compound C1071 (10 mg, 0.0217 mmol) dissolved in MeOH (1.0 mL, alternatively DMF can be used here depending on the desired compound) with stirring, then heated at 120° C. for 1 h. The reaction mixture was quenched with sat. NH$_4$Cl, diluted with EtOAc (5 mL), and the two phases were separated. The organic layer was washed with Sat. NH$_4$Cl, then brine and dried over Na$_2$SO$_4$. The mixture was concentrated in vacuo and purified by reverse phase chromatography using MeCN/H2O (0.1% ammonium formate buffer) as the eluent to afford compound C1084. $^1$H NMR (500 MHz, DMSO) δ 7.66 (d, J=7.5 Hz, 2H), 7.44 (t, J=7.8 Hz, 2H), 7.29 (m, 3H), 6.98-6.94 (m, 1H), 4.00 (s, 3H), 3.83 (s, 3H). MS (m/z): 457.1 [M+1]$^+$, 96.0%.

Table 8 below provides additional compounds that can be synthesized similarly to the methods described in step 3 above, substituting the listed compound for NaOMe in Step 3. Data for compounds synthesized is provided in columns 3-5.

Example 8

Synthesis of N-(2-hydroxycyclohexyl)-5-methyl-7-oxo-3-phenyl-2-(trifluoromethyl)-4,7-dihydropyrazolo[1,5-a]pyrimidine-6-carboxamide (A11141), 5-methyl-7-oxo-N-(2-oxocyclohexyl)-3-phenyl-2-(trifluoromethyl)-4,7-dihydropyrazolo[1,5-a]pyrimidine-6-carboxamide (A1142), and 5-methyl-3-phenyl-6-(4,5,6,7-tetrahydrobenzo[d]oxazol-2-yl)-2-(trifluoromethyl)pyrazolo[1,5-a]pyrimidin-7(4H)-one (C1015) were carried out in one, two and three steps, respectively, as follows:

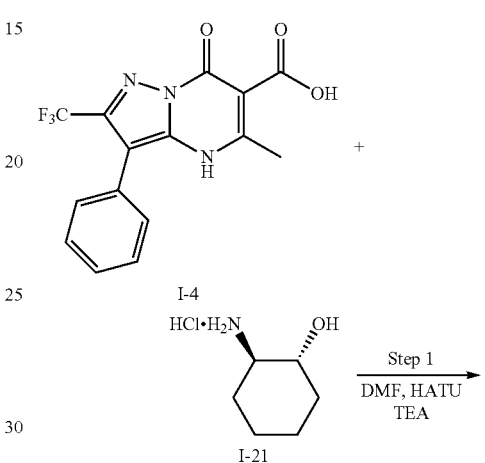

TABLE 8

| Compound ID | NaOMe replacement | $^1$H NMR | Purity (%) | MS (m/z) |
| --- | --- | --- | --- | --- |
| C1067 | ONa-CH$_2$CH$_2$-N(CH$_3$)$_2$ | (400 MHz, DMSO) δ 7.63 (d, J = 7.8 Hz, 2H), 7.43 (t, J = 7.6 Hz, 2H), 7.32-7.23 (m, 3H), 6.92 (d, J = 7.5 Hz, 1H), 4.56 (t, J = 5.1 Hz, 2H), 3.99 (s, 3H), 3.18 (s, 2H), 2.67 (s, 6H). | 96.6 | 514.9 |
| C1085 | NH$_3$ | (500 MHz, DMSO) δ 8.15 (s, 1H), 7.58 (d, J = 7.3 Hz, 2H), 7.37 (t, J = 7.8 Hz, 2H), 7.27-7.19 (m, 2H), 7.15 (d, J = 8.1 Hz, 1H), 6.86 (d, J = 7.6 Hz, 1H), 3.96 (s, 3H). | 94.0 | 442.0 |
| C1121 | NaSMe | (500 MHz, DMSO) δ 7.72 (d, J = 7.5 Hz, 2H), 7.43 (t, J = 7.8 Hz, 2H), 7.29-7.24 (m, 3H), 6.90-6.88 (m, 1H), 4.02 (s, 3H), 2.37 (s, 3H). | 97.8 | 472.9 |
| C1257 | 3-hydroxycarbonyl piperidine | (500 MHz, DMSO) δ 7.73 (d, J = 7.7 Hz, 2H), 7.37 (t, J = 7.8 Hz, 2H), 7.26-7.18 (m, 3H), 6.86 (dd, J = 6.5, 2.4 Hz, 1H), 3.98 (s, 3H), 3.82 (d, J = 11.2 Hz, 1H), 2.75-2.68 (m, 1H), 2.62 (d, J = 11.9 Hz, 1H), 1.89-1.84 (m, 1H), 1.44-1.36 (m, 3H). | 99.9 | 554.2 |
| C1258 | morpholine | 500 MHz, DMSO) δ 7.67 (d, J = 7.5 Hz, 2H), 7.40 (t, J = 7.8 Hz, 2H), 7.26-7.21 (m, 3H), 6.88 (dd, J = 7.0, 2.0 Hz, 1H), 3.99 (s, 3H), 3.50-3.46 (m, 4H), 3.06-3.02 (m, 4H). | 99.9 | 512.2 |

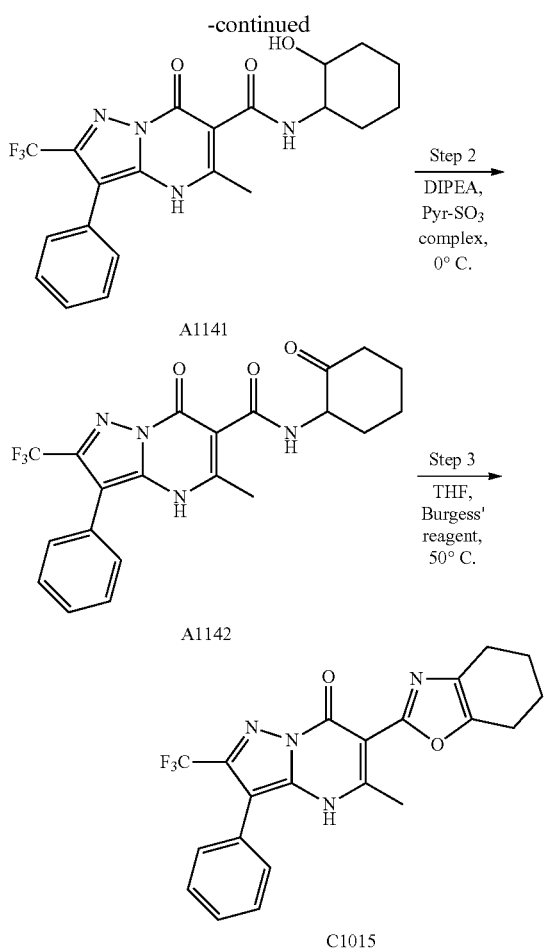

A1141

A1142

C1015

Step 1:

Synthesis of N-(2-hydroxycyclohexyl)-5-methyl-7-oxo-3-phenyl-2-(trifluoromethyl)-4,7-dihydropyrazolo[1,5-a]pyrimidine-6-carboxamide (A1141): To a mixture of 5-methyl-7-oxo-3-phenyl-2-(trifluoromethyl)-4,7-dihydropyrazolo[1,5-a]pyrimidine-6-carboxylic acid (I-4, 50.0 mg, 148 μmol), trans-2-aminocyclohexanol hydrochloride (I-21, 45.0 mg, 297 μmol), HATU (58.1 mg, 148 μmol) in DMF (740 μL) was added TEA (83.5 μL, 593 μmol) and the solution was stirred at r.t. for 24 h. Afterwards, the reaction mixture was purified directly on a reverse flash chromatography (KP-C18-H5, using a gradient 0 to 100% MeCN in 10 mM aqueous ammonium formate buffer) to afford compound A1141 as a white solid after lyophilization. $^1$H NMR (500 MHz, DMSO) δ 12.53 (s, 1H), 7.55-7.39 (m, 5H), 4.65 (s, 1H), 3.68-3.52 (m, 1H), 3.37-3.31 (m, 1H), 2.51 (s, 3H), 1.98-1.91 (m, 1H), 1.89-1.82 (m, 1H), 1.68-1.56 (m, 2H), 1.33-1.15 (m, 4H); MS (m/z): 435.3 [M+1]$^+$.

Step 2:

Synthesis of 5-methyl-7-oxo-N-(2-oxocyclohexyl)-3-phenyl-2-(trifluoromethyl)-4,7-dihydropyrazolo[1,5-a]pyrimidine-6-carboxamide (A1142): To a solution of compound A1141 (50.0 mg, 115 μmol) in DIPEA (241 μL, 1.37 mmol) was added sulfur trioxide pyridine complex (220 mg, 1.38 mmol) followed by DIPEA (241 μL, 1.37 mmol) at 0° C. The reaction was gradually warmed to r.t. overnight. After 18 h, the reaction mixture was diluted with 1N HCl (10 mL) and extracted with EtOAc (3×10 mL). The organic fraction was washed with brine (10 mL), dried over Na$_2$SO$_4$, filtered and concentrated in vacuo. The crude reaction mixture was directly subjected to purification via reverse flash chromatography (KP-C18-H5, using a gradient 0 to 100% MeCN in 10 mM aqueous ammonium formate buffer) to afford compound A1142 (22.5 mg, 45%) as a white solid after lyophilization. $^1$H NMR (500 MHz, DMSO) δ 12.71 (s, 1H), 7.55 (d, J=7.2 Hz, 2H), 7.43 (t, J=7.6 Hz, 2H), 7.31 (s, 1H), 4.60 (dt, J=12.3, 6.2 Hz, 1H), 2.59 (s, 3H), 2.47-2.38 (m, 2H), 2.38-2.28 (m, 1H), 2.08-1.99 (m, 1H), 1.87-1.73 (m, 2H), 1.62 (s, 1H), 1.50-1.39 (m, 1H). MS (m/z): 433.1 [M+1]$^+$, 96.9%.

Step 3:

Synthesis of 5-methyl-3-phenyl-6-(4,5,6,7-tetrahydrobenzo[d]oxazol-2-yl)-2-(trifluoromethyl)pyrazolo[1,5-a]pyrimidin-7(4H)-one (C1015): To a 10 mL flask containing compound A1142 (21.5 mg, 49.7 μmol) in THF (2.50 mL) was added Burgess reagent (30.6 mg, 124 μmol). The resulting solution was stirred overnight at 50° C. Additional Burgess reagent (61.4 mg, 249 μmol) was added and stirred until full consumption of starting material. Afterwards, the crude solution was directly subjected to purification via reverse flash chromatography (KP-C18-H5, using a gradient 0 to 100% MeCN in 10 mM aqueous ammonium formate buffer) to afford compound C1015 after lyophilization. $^1$H NMR (500 MHz, DMSO) δ 8.41 (s, 2H), 7.58 (d, J=7.4 Hz, 2H), 7.43-7.37 (m, 2H), 7.29-7.23 (m, 1H), 2.67-2.60 (m, 2H), 2.50-2.46 (m, 2H), 2.18 (s, 3H), 1.87-1.74 (m, 4H). MS (m/z): 415.2 [M+1]$^+$, 97.9%.

Table 9 below provides additional compounds that can be synthesized similarly to the methods described in steps 1-3 above, optionally substituting the listed compound for I-21, and/or substituting for I-1 and/or I-2 (see Example 1) where indicated to provide the suitable analog of for I-4. Data for compounds synthesized is provided in columns 3-5.

TABLE 9

| Compound ID | Compound I-21 replacement | $^1$H NMR | Purity (%) | MS (m/z) |
|---|---|---|---|---|
| C1010 | H$_2$N—⟨⟩—OH (cyclopentyl) | (500 MHz, DMSO) δ 7.55-7.40 (m, 5H), 7.02 (s, 1H), 3.24-3.16 (m, 1H), 2.38-2.29 (m, 3H), 2.05-1.95 (m, 2H), 1.76-1.59 (m, 6H). | 95.5 | 429.9 |

TABLE 9-continued

| Compound ID | Compound I-21 replacement | ¹H NMR | Purity (%) | MS (m/z) |
|---|---|---|---|---|
| C1013 | 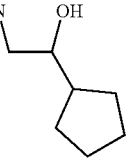 Also replace I-2 with 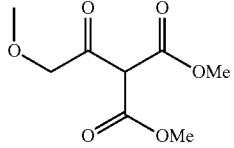 | (500 MHz, DMSO) δ 7.53 (d, J = 7.7 Hz, 2H), 7.35 (t, J = 7.7 Hz, 2H), 7.21 (t, J = 7.5 Hz, 1H), 6.78 (s, 1H), 4.20 (s, 2H), 3.09 (s, 1H), 3.02 (s, 3H), 1.97-1.87 (m, 2H), 1.70-1.49 (m, 6H). | 100 | 459.2 |
| C1027 | 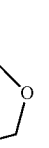 | (500 MHz, DMSO) δ 12.73 (s, 1H), 7.52 (d, J = 7.4 Hz, 2H), 7.47 (t, J = 7.6 Hz, 2H), 7.39 (d, J = 7.3 Hz, 1H), 7.03 (s, 1H), 3.98 (dd, J = 10.9, 2.9 Hz, 1H), 3.80 (dt, J = 11.7, 3.7 Hz, 1H), 3.48-3.40 (m, 2H), 3.05-2.97 (m, 1H), 2.28 (s, 3H), 2.12-2.04 (m, 1H), 1.79-1.59 (m, 3H). | 97.7 | 445.1 |
| C1032 | 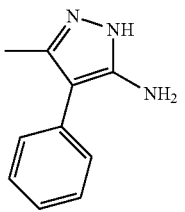 | (500 MHz, DMSO) δ 7.68 (d, J = 6.5 Hz, 2H), 7.41 (t, J = 7.7 Hz, 2H), 7.23 (d, J = 7.5 Hz, 1H), 2.67-2.61 (m, 2H), 2.50-2.47 (m, 2H), 2.39 (s, 3H), 2.26 (s, 3H), 1.88-1.75 (m, 4H). | 99.2 | 361.2 |
| C1033 | 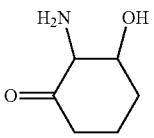 | (500 MHz, DMSO) δ 7.54-7.36 (m, 5H), 3.05 J = 6.2 Hz, 2H), 2.55-2.51 (m, 2H), 2.36 (s, 3H), 2.21-2.13 (m, 2H). | 96.8 | 429.2 |
| C1034 | Replace I-1 with 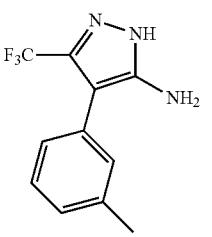 | (500 MHz, DMSO) δ 12.74 (brs, 1H), 7.35-7.30 (m, 3H), 7.18-7.17 (m, 1H), 2.66-2.64 (m, 2H), 2.36 (s, 3H), 2.28 (brs, 2H), 1.88-1.75 (m, 4H). | 100 | 429.2 |
| C1035 | Replace I-1 with 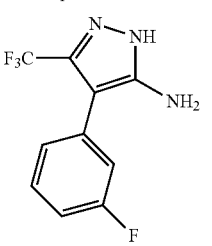 | (500 MHz, DMSO) δ 12.77 (brs, 1H), 7.50-7.46 (m, 3H), 7.15-7.08 (m, 1H), 3.18 (d, J = 5.1 Hz, 2H), 2.69-2.62 (m, 2H), 2.22 (s, 3H), 1.87-1.76 (m, 4H). | 97.0 | 433.4 |

TABLE 9-continued

| Compound ID | Compound I-21 replacement | ¹H NMR | Purity (%) | MS (m/z) |
|---|---|---|---|---|
| C1036 | Replace I-1 with 3-trifluoromethyl-4-(pyridin-3-yl)-1H-pyrazol-5-amine | (500 MHz, DMSO) δ 8.80 (s, 1H), 8.46 (d, J = 3.6 Hz, 1H), 7.97 (d, J = 8.0 Hz, 1H), 7.45 (dd, J = 7.9, 4.7 Hz, 1H), 2.64 (m, 2H), 2.20 (s, 3H), 1.88-1.76 (m, 4H), 1.27-1.21 (m, 2H). | 98.9 | 416.6 |
| C1048 | 2-amino-3-methoxycyclohexan-1-ol | (500 MHz, DMSO) δ 12.67 (s, 1H), 7.49 (d, J = 7.5 Hz, 2H), 7.37 (t, J = 7.7 Hz, 2H), 7.26 (t, J = 7.1 Hz, 1H), 4.20 J = 3.5 Hz, 1H), 3.34 3H), (s, 3H), 2.64 (ddd, J = 16.5, 5.7, 3.4 Hz, 1H), 2.59-2.50 (m, 1H), 2.19 (s, 3H), 1.94-1.80 (m, 2H), 1.80-1.64 (m, 2H). | 99.6 | 445.3 |
| C1052 | 3-amino-cyclohexane-1,2-diol | (500 MHz, DMSO) δ 7.59 (d, J = 7.4 Hz, 2H), 7.42-7.37 (m, 2H), 7.28-7.23 (m, 1H), 5.02 (d, J = 5.6 Hz, 1H), 4.56 (d, J = 4.6 Hz, 1H), 2.70-2.62 (m, 1H), 2.60-2.56 (m, 1H), 2.20 (s, 3H), 2.03-1.95 (m, 1H), 1.85-1.72 (m, 3H). | 98.0 | 431.2 |
| C1059 | 3-amino-4-hydroxyazepan-2-one | (400 MHz, DMSO) δ 7.89 (s, 1H), 7.54 (d, J = 7.5 Hz, 2H), 7.45 (t, J = 7.5 Hz, 2H), 7.36 (t, J = 7.1 Hz, 1H), 3.25 (dd, J = 9.1, 5.6 Hz, 2H), 3.03 (t, J = 6.5 Hz, 2H), 2.32 (s, 3H), 1.99 (dd, J = 14.4, 6.0 Hz, 2H). | 95.1 | 444.2 |
| C1101 | ethyl 2-amino-3-hydroxypropanoate | (500 MHz, DMSO) δ 12.93 (s, 1H), 8.89 (s, 1H), 7.52 (m, 2H), 7.47 (m, 2H), 7.38 (m, 1H), 4.31 (q, J = 7.1 Hz, 2H), 2.33 (s, 3H), 1.31 (t, J = 7.1 Hz, 3H). | 99.0 | 433.0 |
| C1102 | 2,3-diamino-3-hydroxypropanamide | (500 MHz, DMSO) δ 8.52 (s, 1H), 7.63-7.56 (m, 2H), 7.41 (t, J = 6.8 Hz, 2H), 7.28 (t, J = 6.8 Hz, 1H), 7.07 (bs, 2H), 2.25 (s, 3H). | 98.9 | 404.1 |
| C1104 | 2-aminopropane-1,3-diol | (500 MHz, DMSO) δ 7.91 (s, 1H), 7.55 (d, J = 7.5 Hz, 2H), 7.44 (t, J = 7.6 Hz, 2H), 7.32 (s, 1H), 5.17 (s, 1H), 4.42 (d, J = 4.7 Hz, 2H), 2.25 (s, 3H). | 98.5 | 391.1 |
| C1108 | 2-amino-3-methoxypropan-1-ol | (500 MHz, DMSO) δ 7.58 (d, J = 7.5 Hz, 2H), 7.43-7.36 (m, 2H), 7.29-7.24 (m, 1H), 4.34 (d, J = 0.6 Hz, 2H), 3.31 (s, 3H), 2.20 (s, 3H). | 99.7 | 405.1 |

TABLE 9-continued

| Compound ID | Compound I-21 replacement | ¹H NMR | Purity (%) | MS (m/z) |
|---|---|---|---|---|
| C1169 | H₂N, OH, HO₂C, cyclohexyl | (500 MHz, DMSO) δ 12.84 (s, 1H), 7.54 (d, J = 7.5 Hz, 2H), 7.48-7.40 (m, 2H), 7.40-7.28 (m, 1H), 3.48-3.41 (m, 1H), 2.26 (s, 3H), 1.90-1.76 (m, 4H), 1.69 (d, J = 12.3 Hz, 1H), 1.59-1.48 (m, 2H), 1.40-1.22 (m, 3H). | 100 | 487.0 |
| C1170 | H₂N-CH₂-CH₂-OH | (500 MHz, DMSO) δ 8.12 (s, 1H), 7.56 (d, J = 7.7 Hz, 2H), 7.47-7.41 (m, 2H), 7.34-7.25 (m, 2H), 2.23 (s, 3H). | 100 | 361.0 |
| C1143 | H₂N, OH, iPr, OH | (400 MHz, DMSO-d6) δ 7.50-7.40 (m, 4H), 7.39-7.31 (m, 1H), 4.96 (s, 1H), 4.35 (s, 2H), 3.24-3.14 (m, 1H), 2.25 (s, 3H), 1.21 (d, J = 6.9 Hz, 6H). | 97.1 | 433.1 |
| C1153 | H₂N, OH, iPr, OMe | (500 MHz, MeOD) δ 7.51 (d, J = 7.2 Hz, 2H), 7.47-7.42 (m, 2H), (7.39-7.35 m, 1H), 4.43 (s, 2H), 3.39 (s, 3H), 3.28-3.21 (m, 1H), 2.32 3(s, H), 1.34 (d, J = 6.9 Hz, 6H). | 99.3 | 447.1 |
| C1157 | H₂N, OH, cyclohexyl, OH | (500 MHz, MeOD) δ 7.51 (d, J =7.2 Hz, 2H), 7.46-7.41 (m, 2H), 7.39-7.34 (m, 1H), 4.55 (s, 2H), 2.92 (dddd, J = 12.0, 12.0, 3.5, 3.5 Hz, 1H), 2.33 (s, 3H), 1.98-1.90 (m, 2H), 1.90-1.83 (m, 2H), 1.79-1.72 (m, 1H), 1.71-1.60 (m, 2H), 1.51-1.39 (m, 2H), 1.38-1.26 (m, 1H). | 100 | 473.1 |
| C1158 | H₂N, OH, cyclohexyl, OMe | (400 MHz, MeOD) δ 7.53-7.48 (m, 2H), 7.44-7.38 (m, 2H), 7.36-7.31 (m, 1H), 4.71 (s, 2H), 3.82 (s, 3H), 3.04 (tt, J = 11.9, 3.4 Hz, 1H), 2.37 (s, 3H), 2.00-1.91 (m, 2H), 1.91-1.82 (m, 2H), 1.80-1.71 (m, 1H), 1.69-1.58 (m, 2H), 1.52-1.39 (m, 2H), 1.37-1.26 (m, 1H). | 99.6 | 487.2 |
| C1165 | H₂N, OH, HO₂C | (500 MHz, MeOD) δ 8.44 (s, 1H), 7.54-7.37 (m, 5H), 2.46 (s, 3H). | 95.2 | 405.0 |
| C1260 | H₂N, OH, iPr  Replace I-1 with 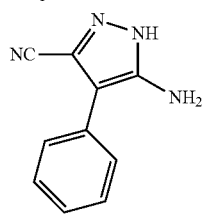 | | | |

TABLE 9-continued

| Compound ID | Compound I-21 replacement | 1H NMR | Purity (%) | MS (m/z) |
|---|---|---|---|---|
| C1270 | <br>Replace I-1 with | (500 MHz, DMSO) δ 8.26 (s, 1H), 7.69 (s, 2H), 7.57 (t, J = 7.6 Hz, 2H), 7.47 (t, J = 7.3 Hz, 1H), 7.41 (s, 1H), 2.41 (s, 3H). | 97.7 | 318.1 |

Example 9

Synthesis of (S)—N-(1-hydroxy-3-methoxypropan-2-yl)-5-methyl-7-oxo-3-phenyl-2-(trifluoromethyl)-4,7-dihydropyrazolo[1,5-a]pyrimidine-6-carboxamide (A1143), and (R)-6-(4-(methoxymethyl)-4,5-dihydrooxazol-2-yl)-5-methyl-3-phenyl-2-(trifluoromethyl)pyrazolo[1,5-a]pyrimidin-7(4H)-one (C1184) were carried out in one and two steps, respectively, as follows:

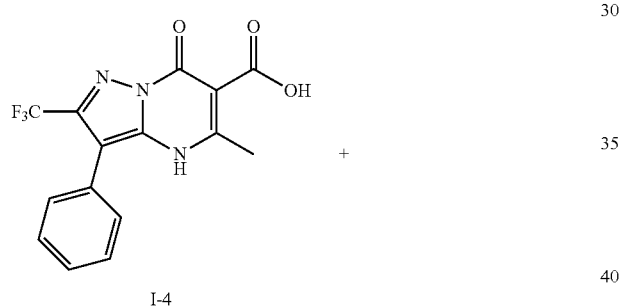

I-4

+

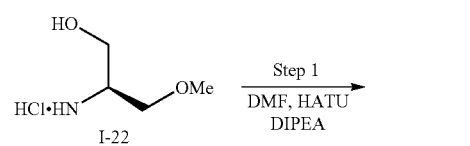

I-22

→ Step 1
DMF, HATU
DIPEA

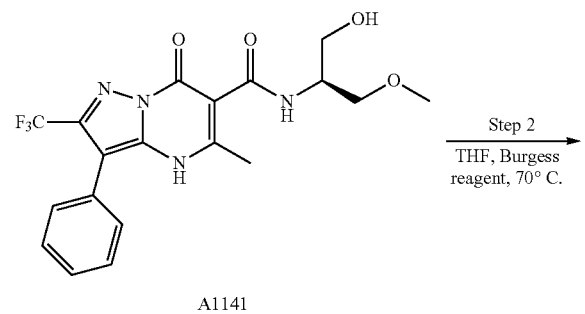

A1141

→ Step 2
THF, Burgess reagent, 70° C.

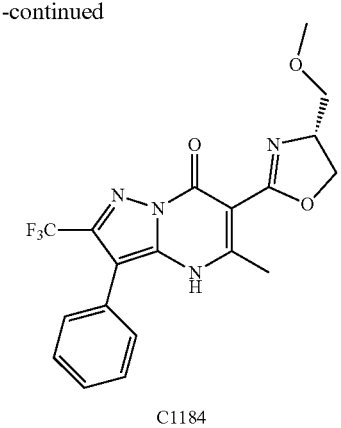

C1184

Step 1:
Synthesis of (S)—N-(1-hydroxy-3-methoxypropan-2-yl)-5-methyl-7-oxo-3-phenyl-2-(trifluoromethyl)-4,7-dihydropyrazolo[1,5-a]pyrimidine-6-carboxamide (A1143): A solution of 5-methyl-7-oxo-3-phenyl-2-(trifluoromethyl)-4,7-dihydropyrazolo[1,5-a]pyrimidine-6-carboxylic acid (I-4, see Example 1, 1.00 g, 2.97 mmol), HATU (4.51 g, 11.9 mmol) and N,N-diisopropylethylamine (2.61 mL, 14.8 mmol) in DMF (319 µL) was stirred for 30 min. L-serine methyl ether hydrochloride (I-22, 840 mg, 5.93 mmol) was added. The resulting solution was stirred at r.t. for 1 h. 1N HCl was added and the mixture was extracted with EtOAc (3×20 mL). The organic layer was washed with sat NH$_4$Cl (10 mL), then brine (10 mL) and dried over Na$_2$SO$_4$, filtered and concentrated to afford compound A1143. MS (m/z): 425.0 [M+1]$^+$.

Step 2:
Synthesis of (R)-6-(4-(methoxymethyl)-4,5-dihydrooxazol-2-yl)-5-methyl-3-phenyl-2-(trifluoromethyl)pyrazolo[1,5-a]pyrimidin-7(4H)-one (C1184): To a 10 mL flask containing compound A1143 (30.0 mg, 70.7 µmol) in THF (1.18 mL) was added Burgess reagent (20.9 mg, 84.8 µmol). The resulting solution was stirred overnight at 70° C. Afterwards, the reaction mixture was diluted in saturated ammonium chloride (10 mL) and extracted with EtOAc (3×20 mL). The organic phase was washed with brine (10 mL), dried over Na$_2$SO$_4$, filtered and concentrated. The product was stored in a minimal amount of EtOAc overnight. The precipitate that formed was filtered and washed with EtOAc, followed by drying to afford compound C1184. $^1$H NMR (500 MHz, DMSO) δ 11.20 (s, 1H), 7.57-7.51 (m, 2H), 7.51-7.42 (m, 2H), 7.41-7.31 (m, 1H), 4.96-4.89 (m, 1H), 5.00-4.87 (m, 1H), 4.75 (dd, J=8.8, 6.0 Hz, 1H), 4.56-4.50 (m, 1H), 3.69 (dd, J=10.1, 3.9 Hz, 1H), 3.57 (dd, J=10.2, 3.5 Hz, 1H), 3.32 (s, 3H), 2.52 (s, 3H). MS (m/z): 407.1 [M+1]$^+$, 100%.

Table 10 below provides additional compounds that can be synthesized similarly to the methods described in steps 1-2 above, substituting the listed compound for I-22. Data for compounds synthesized is provided in columns 3-5.

TABLE 10

| Compound ID | Compound I-22 replacement | $^1$H NMR | Purity (%) | MS (m/z) |
|---|---|---|---|---|
| C1187 | HO-CH(NH$_2$)-C(=O)-O-CH$_3$ | (400 MHz, DMSO) δ 11.43 (s, 1H), 7.55-7.50 (m, 2H), 7.49-7.42 (m, 2H), 7.40-7.34 (m, 1H), 5.10-4.97 (m, 3H), 3.76 (s, 3H), 2.51-2.50 (m, 3H) | 95.6 | 421.0 |
| C1192 | HO-CH(NH$_2$)-C(=O)-OH | (400 MHz, DMSO-d6) δ 11.34 (s, 1H), 7.55-7.50 (m, 2H), 7.50-7.43 (m, 2H), 7.41-7.33 (m, 1H), 5.15-5.01 (m, 2H), 4.97 (dd, J = 10.6, 5.4 Hz, 1H), 2.53 (s, 3H). | 99.3 | 407.1 |
| C1213 | HO-CH(CH$_3$)-CH(NH$_2$)-C(=O)-OH | (500 MHz. DMSO) δ 7.53 (d, J = 7.4 Hz, 2H), 7.47-7.42 (m, 2H), 7.37-7.32 (m, 1H), 5.48-5.38 (m, 1H) 5.00 (d, J = 9.7 Hz, 1H), 3.76 (s, 3H), 2.49 (s, 3H), 1.41 (d. J = 6.5 Hz, 3H). | 98.0 | 435.0 |
| C1216 | HO-CH(CH$_3$)-CH(NH$_2$)-C(=O)-OH | (400 MHz, DMSO) δ 7.54 (d, J = 7.4 Hz, 2H), 7.44 (t, J = 7.6 Hz, 2H), 7.33 (t, J = 7.4 Hz, 1H), 5.42-5.05 (m, 1H), 4.64-4.12 (m, 1H), 2 48 (s, 3H), 1.59-1.42 (m, 3H). | 100 | 421.0 |

Example 10

Synthesis of 5-methyl-6-(1-oxoisoindolin-2-yl)-3-phenyl-2-(trifluoromethyl)pyrazolo[1,5-a]pyrimidin-7(4H)-one (C1214) was carried out in one step as follows:

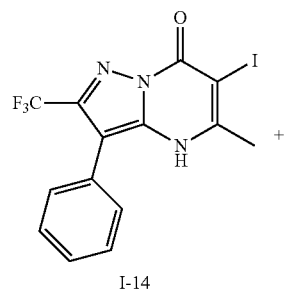

I-14

+

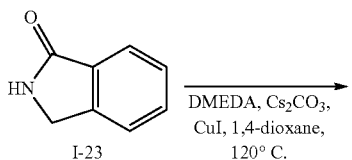

I-23 → DMEDA, Cs$_2$CO$_3$, CuI, 1,4-dioxane, 120° C.

-continued

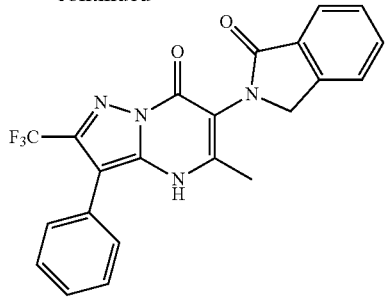

C1214

Step 1:

To a sealed tube was added 1-isoindolinone (I-23, 32.4 mg, 239 μmol), N,N-dimethylethylenediamine (27.0 μL, 239 μmol), Cs$_2$CO$_3$ (236 mg, 716 μmol), copper iodide (22.7 mg, 119 μmol), and was flushed with nitrogen. Afterwards, 1,4-dioxane (2.39 mL) and 6-iodo-5-methyl-3-phenyl-2-(trifluoromethyl)pyrazolo[1,5-a]pyrimidin-7(4H)-one (I-14, 100 mg, 239 μmol) were added. The mixture was bubbled with nitrogen for 5 min. The reaction was then heated at 120° C. overnight. The crude mixture was concentrated in vacuo, then subjected to purification via reverse flash chromatography (KP-C18-H5, using a gradient 0 to 100% MeCN in 10 mM aqueous ammonium formate buffer) to afford compound C1214 as a white solid after lyophilization. ¹H NMR (500 MHz, DMSO) δ 12.69 (s, 1H), 7.79 (d, J=7.5 Hz, 1H), 7.72-7.66 (m, 2H), 7.60-7.54 (m, 1H), 7.54-7.47 (m, 4H), 7.45-7.39 (m, 1H), 4.89 (d, J=17.2 Hz, 1H), 4.60 (d, J=17.2 Hz, 1H), 2.24 (s, 3H); MS (m/z): 425.1 [M+1]⁺, 99.7%.

Table 11 below provides additional compounds that can be synthesized similarly to the methods described in the above step, substituting the listed compound for I-23. Data for compounds synthesized is provided in columns 3-5.

TABLE 11

| Compound ID | Compound I-23 replacement | ¹H NMR | Purity (%) | MS (m/z) |
|---|---|---|---|---|
| C1217 | 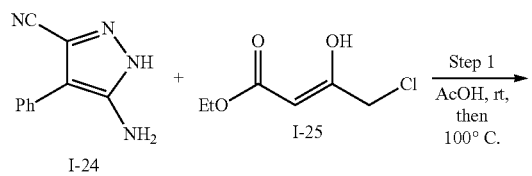 | (400 MHz, DMSO) δ 7.55 (d, J = 7.4 Hz, 2H), 7.49-7.41 (m, 2H), 7.38-7.31 (m, 1H), 7.26 (d, J = 8.0 Hz, 1H), 6.91 (s, 1H), 6.86 (d, J = 8.0 Hz, 1H), 5.32 (brs, 2H), 4.70 (d, J = 15.5 Hz, 1H), 4.34 (d, J = 15.6 Hz, 1H), 2.15 (s, 3H). | 98.9 | 440.0 |
| C1220 | 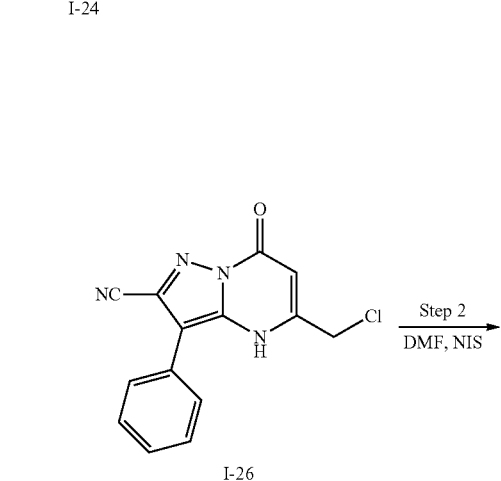 | (500 MHz, DMSO) δ 12.68 (s, 1H), 7.58-7.45 (m, 5H), 7.44-7.35 (m, 2H), 7.30 (d, J = 8.1 Hz, 1H), 4.75 (d, J = 17.3 Hz, 1H), 4.52 (d, J = 17.4 Hz, 1H), 3.93 (s, 3H), 2.22 (s, 3H). | 98.9 | 455.1 |

Example 11

Synthesis of 5-((2-hydroxyethoxy)methyl)-6-(4-methoxybenzo[d]oxazol-2-yl)-7-oxo-3-phenyl-4,7-dihydropyrazolo[1,5-a]pyrimidine-2-carbonitrile (C1248) was carried out in four steps as follows:

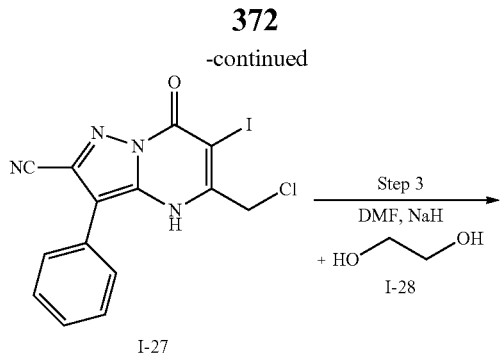

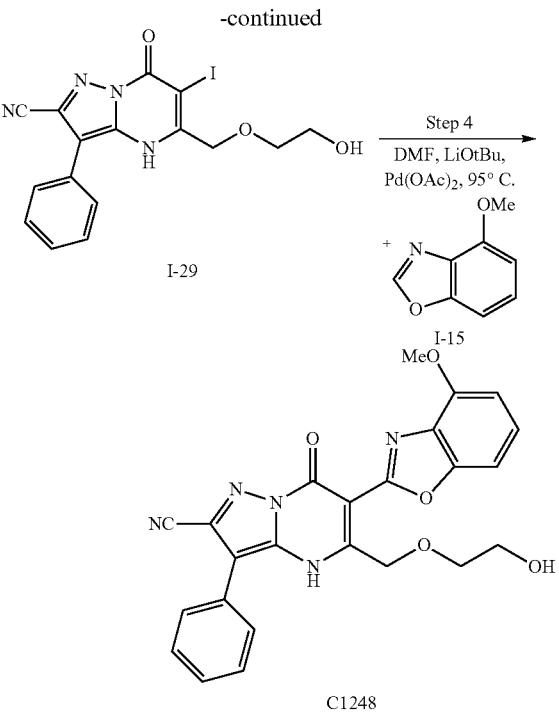

Step 1:
Synthesis of 5-(chloromethyl)-7-oxo-3-phenyl-4,7-dihydropyrazolo[1,5-a]pyrimidine-2-carbonitrile (I-26): Ethyl 4-Chloroacetoacetate (I-25, 927 μL, 6.51 mmol) was added to a solution of 5-amino-4-phenyl-1H-pyrazole-3-carbonitrile (I-24, 1.00 g, 4.34 mmol) in AcOH (4.93 mL). The solution was stirred at r.t. for 15 min and then heated at 100° C. for 1 h. After cooling, the white suspension was filtered and the resulting solid was washed with Et$_2$O (×3) to provide the compound I-26 as a beige solid. MS (m/z): [M+H]$^+$ 285.0.

Step 2:

Synthesis of 5-(chloromethyl)-6-iodo-7-oxo-3-phenyl-4,7-dihydropyrazolo[1,5-a]pyrimidine-2-carbonitrile (I-27): In a 20 mL microwave-vial was added compound I-26 (500 mg, 1.76 mmol) in DMF (11.7 mL). N-iodosuccinimide (489 mg, 2.11 mmol) was then added in one portion. The reaction was stirred at r.t. for 20 min. The reaction was quenched with water and transferred in a separation funnel. The organic layer was separated and the aqueous layer was extracted (×2) with EtOAc. The combined organic layers were successively washed with aqueous thiosulfate solution (5%) and brine, dried over sodium sulfate, filtered and concentrated in vacuo. The product was triturated with a 1:1 mixture of diethyl ether:hexanes to afford compound I-27 as a light brown solid. MS (m/z): [M+H]$^+$ 410.9.

Step 3:

Synthesis of 5-((2-hydroxyethoxy)methyl)-6-iodo-7-oxo-3-phenyl-4,7-dihydropyrazolo[1,5-a]pyrimidine-2-carbonitrile (I-29): In a 10 mL flame-dried-microwave-vial was added sodium hydride (60% in mineral oil) (7.1 mg, 0.49 mmol) in dry DMF (0.7 mL). Then, ethylene glycol (I-28, 25.1 μL, 0.45 mmol) was added. The mixture was stirred at r.t. for 5 min and compound I-27 (80.0 mg, 0.20 mmol) in DMF (0.7 mL) was added dropwise. The reaction was stirred at r.t. for 18 h then quenched with ammonium chloride. The organic layers were separated and the aqueous layer was extracted (2×) with EtOAc. The organic layers were combined, washed with brine, dried over sodium sulfate, filtered and concentrated in vacuo to provide a brownish oil. This crude material was recrystallized from DCM/diethyl ether, filtered and washed with diethyl ether (3×) to afford compound I-29 as a yellow solid. MS (m/z): [M+H]$^+$ 437.0.

Step 4:

Synthesis of 5-((2-hydroxyethoxy)methyl)-6-(4-methoxybenzo[d]oxazol-2-yl)-7-oxo-3-phenyl-4,7-dihydropyrazolo[1,5-a]pyrimidine-2-carbonitrile (C1248): In a 10 mL flame-dried-microwave-vial were successively added compound I-29 (50.0 mg, 0.12 mmol), 4-methoxybenzo[d]oxazole (I-15, 26.6 mg, 0.17 mmol), lithium tert-butoxide (47.3 mg, 0.57 mmol) and palladium(II) acetate (2.63 mg, 10 mol %) in dry DMF (0.40 mL). Then, the reaction mixture was degassed with argon and heated at 95° C. for 12 h. The reaction was cooled to r.t. and poured in a separation funnel containing ammonium chloride and EtOAc. The organic layers was separated and the aqueous layer was extracted (2×) with EtOAc. The organic layers were combined, washed with brine, dried over sodium sulfate, filtered and concentrated in vacuum. This crude product was purified by flash column chromatography (40 g, SiO$_2$ column gradient 0 to 10% MeOH in DCM) to afford the title product. $^1$H NMR (500 MHz, DMSO): δ 8.08 (dd, J=8.3, 1.1 Hz, 2H), 7.53-7.46 (m, 3H), 7.33-7.28 (m, 1H), 7.27 (dd, J=6.6, 2.7 Hz, 2H), 6.92-6.87 (m, 1H), 4.63 (s, 1H), 4.00 (s, 3H), 3.31-3.26 (m, 2H), 3.20 (t, J=5.4 Hz, 2H). MS (m/z): [M+H]$^+$ 458.0; purity>97%.

Table 12 below provides additional compounds that can be synthesized similarly to the methods described in the above steps 1-4, optionally substituting the listed compound for I-15, and/or substituting for I-24 and/or I-28 where indicated. Data for compounds synthesized is provided in columns 3-5.

TABLE 12

| Compound ID | Compound I-15 replacement | $^1$H NMR | Purity (%) | MS (m/z) |
|---|---|---|---|---|
| C1056 | Replace I-24 with I-1<br>Replace I-28 with CH$_3$OH | (400 MHz, DMSO) δ 12.69 (s, 1H), 7.56 (d, J = 6.2 Hz, 2H), 7.40 (t, J = 7.6 Hz, 2H), 7.32-7.19 (m, 3H), 6.88-6.82 (m, 1H), 4.45 (s, 2H), 3.95 (s, 3H), 3.01 (s, 3H). | 99.6 | 471.2 |
| C1103 | Replace I-24 with I-1<br>Replace I-28 with H$_2$O | (500 MHz, DMSO) δ 7.61 (d, J = 7.5 Hz, 2H), 7.45 (t, J = 7.8 Hz, 2H), 7.28-7.24 (m, 3H), 6.90 (d, J = 6.9 Hz, 1H), 5.21 (t, J = 5.0 Hz, 1H), 4.57 (d, J = 5.2 Hz, 2H), 3.99 (s, 3H). | 99.3 | 456.9 |
| C1109 | Replace I-24 with I-1<br>Replace I-28 with NH(CH$_3$)$_2$ | (500 MHz, CD3CN) δ 7.65 (d, J = 7.5 Hz, 2H), 7.46 (t, J = 7.7 Hz, 2H), 7.38-7.34 (m, 1H), 7.33-7.26 (m, 2H), 6.92 (dd, J = 7.5 1.1 Hz, 1H), 4.33 (s, 2H), 4.03 (s, 3H), 2.91 (s, 6H) | 99.0 | 484.2 |
| C1136 | Replace I-24 with I-1<br>Replace I-28 with CH$_3$SH | (500 MHz, DMSO) δ 7.62 (d, J = 7.6 Hz, 2H), 7.43 (t, J = 7.7 Hz, 2H), 7.34-7.21 (m, 3H), 6.89 (d, J = 7.4 Hz, 1H), 4.01 (s, 3H), 3.92 (s, 2H), 1.95 (s, 3H). | 99.0 | 487.1 |
| C1139 | Replace I-28 with CH$_3$OH | (500 MHz, DMSO) δ 8.08 (d, J = 8.4 Hz, 2H), 7.49 (t, J = 7.8 Hz, 2H), 7.34-7.25 (m, 3H), 6.94-6.87 (m, 1H), 4.56 (s, 2H), 4.00 (s, 3H), 3.10 (s, 3H). | 95.6 | 428.2 |

TABLE 12-continued

| Compound ID | Compound I-15 replacement | 1H NMR | Purity (%) | MS (m/z) |
|---|---|---|---|---|
| C1145 | 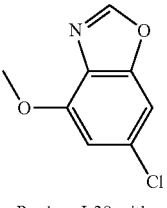<br>Replace I-28 with CH3OH | (500 MHz, DMSO) δ 8.04 (d, J = 8.0 Hz, 2H), 7.52-7.46 (m, 3H), 7.32 (t, J = 7.5 Hz, 1H), 6.99 (d, J = 1.7 Hz, 1H), 4.55 (s, 2H), 4.01 (s, 3H), 3.09 (s, 3H). | 97.3 | 462.0 |
| C1146 | Replace I-24 with I-1<br>Replace I-28 with<br>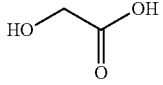 | (400 MHz, DMSO) δ 7.59 (d, J = 7.6 Hz, 1H), 7.52 (d, J = 5.4 Hz, 1H), 7.39 (t, J = 7.6 Hz, 2H), 7.27-7.21 (m, 3H), 6.85 (d, J = 7.6 Hz, 1H), 5.31 (s, 2H), 3.97 (s, 3H), 3.91 (d, J = 6.2 Hz, 2H). | 96.2 | 515.1 |
| C1151 | Replace I-24 with I-1<br>Replace I-28 with<br>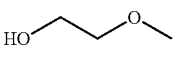 | (500 MHz, DMSO) δ 7.62 (d, J = 7.4 Hz, 2H), 7.43 (t, J = 7.8 Hz, 2H), 7.32-7.23 (m, 3H), 6.89 (dd, J = 6.3, 2.8 Hz, 1H), 4.54 (s, 2H), 4.00 (s, 3H), 3.09 (dd, J = 5.6 4.3 Hz, 2H), 2.99 (s, 3H). | 100 | 515.2 |
| C1152 | Replace I-24 with I-1<br>Replace I-28 with<br>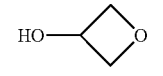 | (500 MHz, DMSO) δ 7.60 (d, J = 7.6 Hz, 2H), 7.43 (t, J = 7.7 Hz, 2H), 7.33-7.25 (m, 3H), 6.90 (dd, J = 6.7, 2.3 Hz, 1H), 4.54 (s, 2H), 4.46 (p, J = 5.7 Hz, 1H), 4.36 (t, J = 6.8 Hz, 2H), 4.10 (dd, J = 7.0, 5.7 Hz, 2H), 4.00 (s, 3H). | 99.7 | 513.1 |
| C1159 | Replace I-24 with I-1<br>Replace I-28 with<br>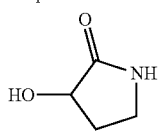 | (500 MHz, DMSO) δ 7.64 (d, J = 7.4 Hz, 2H), 7.62 (s, 1H), 7.44 (t, J = 7.8 Hz, 2H), 7.33-7.25 (m, 3H), 6.90 (dd, J = 6.6, 2.4 Hz, 1H), 4.80 (dd, J = 43.7, 12.0 Hz, 2H), 4.00 (s, 3H), 3.83-3.78 (m, 1H), 2.92-2.86 (m, 2H), 1.84-1.76 (m, 1H), 1.41 (m, 1H). | 99.1 | 540.2 |
| C1177 | Replace I-24 with I-1<br>Replace I-28 with<br>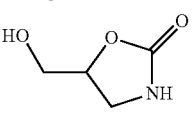 | (500 MHz, DMSO) δ 8.27 (s, 1H), 7.68 (d, J = 7.5 Hz, 2H), 7.43 (t, J = 7.8 Hz, 2H), 7.33-7.22 (m, 3H), 6.90 (dd, J = 7.7, 1.2 Hz, 1H), 5.01 (t, J = 5.8 Hz, 1H), 4.66-4.51 (m, 2H), 4.40 (dd, J = 9.1, 6.5 Hz, 1H), 4.0 (s, 3H), 3.75 (t, J = 8.6 Hz, 1H), 3.45-3.38 (m, 2H). | 99.9 | 556.3 |
| C1180 | Replace I-24 with I-1<br>Replace I-28 with<br>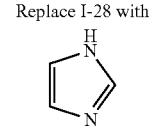 | (400 MHz, DMSO) δ 7.63-7.53 (m, 3H), 7.37 (t, J = 7.4 Hz, 2H), 7.31-7.22 (m, 3H), 7.11 (s, 1H), 6.92 (d, J = 6.4 Hz, 1H), 6.81 (s, 1H), 5.38 (s, 2H), 4.02 (s, 3H). | 99.0 | 507.0 |
| C1182 | Replace I-24 with I-1<br>Replace I-28 with<br>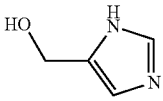 | (500 MHz, CD3CN) δ 7.64 (d, J = 7.9Hz, 2H), 7.47 (t, J = 7.6 Hz,2H), 7.37 (t, J = 7.3 Hz, 1H), 7.31-7.18(m, 3H), 7.03 (s, 1H), 6.88 (d, J = 8.0 Hz, 1H), 6.70 (s, 1H),4.69 (s, 2H), 4.36 (s, 2H), 4.01 (s, 3H). | 97.9 | 537.0 |

TABLE 12-continued

| Compound ID | Compound I-15 replacement | ¹H NMR | Purity (%) | MS (m/z) |
|---|---|---|---|---|
| C1198 | Replace I-24 with I-1 Replace I-28 with 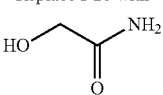 | (500 MHz, DMSO) δ 7.72 (s, 1H), 7.56 (d, J = 7.5 Hz, 2H), 7.41 (t, J = 7.7 Hz, 2H), 7.30-7.25 (m, 2H), 6.90 (t, J = 7.1 Hz, 1H), 6.69-6.66 (m, 2H), 4.93 (s, 2H), 4.39 (s, 2H), 3.71 (s, 3H). | 98.95 | 514.0 |
| C1199 | Replace I-24 with I-1 Replace I-28 with 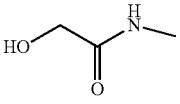 | (500 MHz, DMSO) δ 8.97 (s, 1H), 7.57 (d, J = 7.2 Hz, 2H), 7.43-7.40 (m, 2H), 7.31-7.28 (m, 1H), 6.93 (t, J = 8.3 Hz, 1H), 6.75-6.69 (m, 2H), 4.96 (s, 2H), 4.48 (s, 2H), 3.72 (s, 3H), 2.75 (d, J = 4.6 Hz, 3H). | 98.54 | 528.1 |
| C1225 | Replace I-24 with I-1 Replace I-28 with 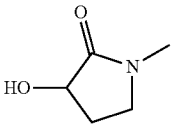 | (500 MHz, DMSO) δ 7.63 (d, J = 7.4 Hz, 2H), 7.43 (t, J = 7.8 Hz, 2H), 7.32-7.24 (m, 3H), 6.89 (dd, J = 6.1, 2.9 Hz, 1H), 4.79 (q, J = 12.0 Hz, 2H), 4.00 (s, 3H), 3.90-3.86 (m, 1H), 3.01-2.94 (m, 2H), 2.57 (s, 3H), 1.83-1.76 (m, 1H), 1.38-1.34 (m, 1H). | 97.8 | 554.3 |
| C1226 | Replace I-24 with I-1 | (500 MHz, DMSO) δ 7.60 (d, J = 7.6 Hz, 2H), 7.45 (t, J = 7.6 Hz,2H), 7.36-7.26 (m, 3H), 6.92-6.89 (m, 1H), 4.59 (s 2H), 4.00 (s,3H), 3.28-3.25 (m, 2H), 3.21-3.17 (m, 2H). | 98.3 | 501.2 |
| C1227 |  Replace I-28 with CH₃OH | (400 MHz, DMSO) δ 8.07 (d, J = 7.2 Hz, 2H), 7.48 (t, J = 7.8 Hz, 2H), 7.30 (t, J = 7.4 Hz, 1H), 6.21 (s, 1H), 5.86 (s, 2H), 4.47 (s, 2H), 3.94 (s, 3H), 3.11 (s, 3H). | 99.7 | 444.2 |
| C1232 | Replace I-24 with I-1 Replace I-28 with 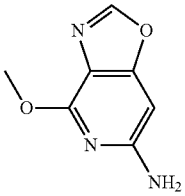 | (500 MHz, DMSO) δ 7.57 (d, J = 6.7 Hz, 2H), 7.47 (t, J = 7.3 Hz, 2H), 7.42-7.28 (m, 3H), 6.95-6.90 (m, 1H), 5.92 (tt, J = 54.8,3.5 Hz, 1H), 4.75 (s, 2H), 4.00 (s,3H), 3.65 (td, J = 15.1, 3.7 Hz, 2H). | 99.8 | 521.2 |
| C1243 | Replace I-28 with 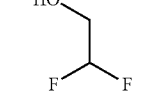 | (500 MHz, DMSO): δ 8.11-8.06 (m, 2H), 7.50-7.45 (m, 2H), 7.32-7.28 (m, 1H), 7.28-7.26 (m, 2H), 707 (s, 1H), 6.92-6.88 (m, 1H), 4.62 (s, 2H), 4.00 (s, 3H), 3.40-3.37 (m, 2H), 3.14 (dd, J = 5.6, 4.3 Hz, 2H), 3.02 (s, 3H) | 99 | 471.2 |
| C1246 | 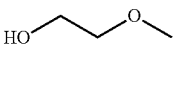 Replace I-28 with CH₃OH | (500 MHz, DMSO) δ 8.09-8.02 (m, 3H), 7.52-7.46 (m, 2H), 7.44 (d, J = 5.7 Hz, 1H), 7.33-7.30 (m, 1H), 4.56 (s, 2H), 4.06 (s, 3H), 3.08 (s, 3H). | 99.6 | 429.1 |

TABLE 12-continued

| Compound ID | Compound I-15 replacement | ¹H NMR | Purity (%) | MS (m/z) |
|---|---|---|---|---|
| C1251 | Replace I-28 with [structure: hydroxymethyl oxazolidinone] | (500 MHz, DMSO): δ 8.09 (dd, J = 8.4, 1.2 Hz, 2H), 7.51-7.44 (m, 2H), 7.33-7.24 (m, 3H), 6.91 (dd, J = 7.3, 1.7 Hz, 1H), 5.08 (t, J = 5.7 Hz, 1H), 4.70 (d, J = 17.6 Hz, 1H), 4.58 (d, J = 17.6 Hz, 1H), 4.54-4.47 (m, 1H), 4.01 (s, 3H), 3.78 (t, J = 8.7 Hz, 1H), 3.53 (td, J = 5.6, 2.2 Hz, 2H), 3.44 (dd, J= 8.3, 6.7 Hz, 1H). | 99 | 513.2 |
| C1259 | Replace I-28 with [structure: 3-hydroxyoxetane] | (500 MHz, DMSO): δ 8.05 (d, J = 7.3 Hz, 2H), 7.49 (t J = 7.8 Hz, 2H), 7.34-7.26 (m, 3H), 6.94-6.89 (m, 1H), 4.61 (s, 2H), 4.55-4.49 (m, 1H), 4.41 (t, J = 6.8 Hz, 2H), 4.14 (dd, J = 7.1, 5.7 Hz, 2H), 4.00 (s, 3H). | 99 | 470.2 |
| C1261 | [structure: 4-(2,2-difluoroethoxy)benzoxazole]<br>Replace I-28 with CH₃OH | | | |
| C1262 | [structure: 4-(2,2,2-trifluoroethoxy)benzoxazole]<br>Replace I-28 with CH₃OH | | | |
| C1263 | [structure: trifluoromethyl-oxazolopyridine]<br>Replace I-28 with HO–CH₂CH₂–O–CH₃ | | | |

Example 12

Synthesis of 6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1131) and 6-(4-methoxybenzo[d]oxazol-2-yl)-N-(2-methoxyethyl)-7-oxo-3-phenyl-2-(trifluoromethyl)-4,7-dihydropyrazolo[1,5-a]pyrimidine-5-carboxamide (C1142) were carried out in three and four steps, respectively, as follows:

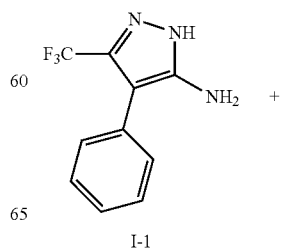

I-1

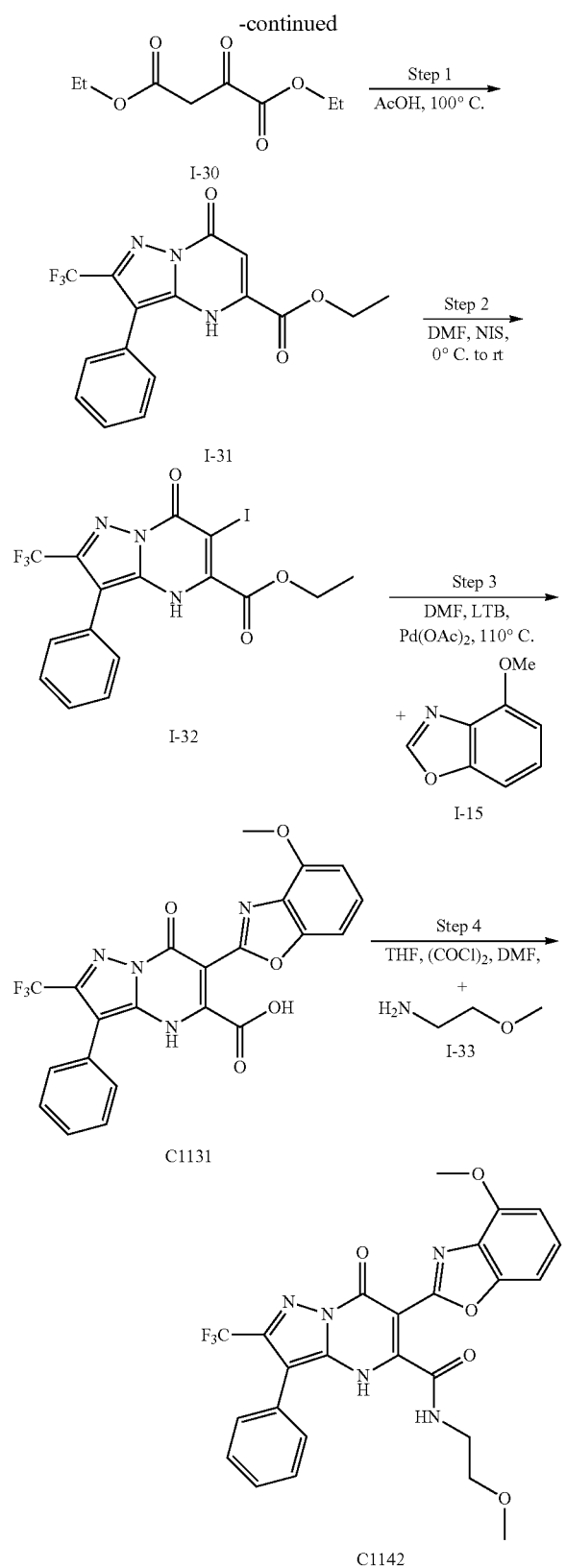

pyrazol-5-amine (I-1, 1.0 g, 4.48 mmol) in AcOH (5 mL) was added diethyl oxalacetate (I-30, 0.98 g, 5.2 mmol). The reaction mixture was heated at 100° C. for 120 min. The acetic acid was removed in vacuo. Et$_2$O/Hex 1.1 (5 mL) was added and stirred at r.t. for 5 min. The mixture was filtered, washed with Et$_2$O/Hex 1:1 (2×30 mL) and dried in vacuo to afford the compound I-31 as a white solid. MS (m/z): 352.1 [M+1]$^+$, 100%.

Step 2:

Synthesis of ethyl 6-iodo-7-oxo-3-phenyl-2-(trifluoromethyl)-4,7-dihydropyrazolo[1,5-a]pyrimidine-5-carboxylate (I-32): To a stirred solution of compound I-31 (1.2 g, 3.36 mmol) in DMF (11.2 mL) cooled at 0° C. (white suspension) was added N-iodosuccinimide (0.87 g, 3.52 mmol), then warmed to r.t. After 1 h, LCMS showed complete conversion. The reaction mixture was poured onto dil Na$_2$S$_2$O$_3$ (30 mL). The precipitated solid was filtered, washed with dil NaHCO$_3$ and dried in vacuo to give compound I-32 as a white solid. MS (m/z): 477.9 [M+1]$^+$.

Step 3:

Synthesis of 6-(4-methoxybenzo[d]oxazol-2-yl)-7-oxo-3-phenyl-2-(trifluoromethyl)-4,7-dihydropyrazolo[1,5-a]pyrimidine-5-carboxylic acid (C1131): Compound I-32 (300 mg, 629 μmol), 4-methoxybenzo[d]oxazole (I-15, 1.5 eq, 141 mg, 943 mol), Lithium tert-butoxide (292 μL, 3.14 mmol), palladium(II) acetate (14.3 mg, 62.9 mol) were added in DMF (2 mL). The reaction was degassed with nitrogen then heated at 110° C. for 4 h. The reaction was cooled to r.t. and the product was crashed out with 1N HCl and then filtered. The solid obtained was purified by reverse phase chromatography 0-100% MeCN/H$_2$O (0.1% ammonium bicarbonate buffer) and lyophilized to give compound C1131 as a white solid. $^1$H NMR (500 MHz, DMSO) δ 7.60 (d, J=7.6 Hz, 2H), 7.42 (t, J=7.7 Hz, 2H), 7.30 (t, J=7.4 Hz, 1H), 7.24-7.21 (m, 2H) 6.89-6.84 (m, 1H), 3.98 (s, 3H); MS (m/z): 471.1/427.1 [M+1]$^+$, 100%.

Step 4:

Synthesis of 6-(4-methoxybenzo[d]oxazol-2-yl)-N-(2-methoxyethyl)-7-oxo-3-phenyl-2-(trifluoromethyl)-4,7-dihydropyrazolo[1,5-a]pyrimidine-5-carboxamide (C1142): A solution of compound C1131 (25.0 mg 53.2 μmol) in THF (500 μL) was cooled to 0° C. oxalyl chloride (13.8 μL, 159 μmol) was added followed by one drop of DMF and the reaction was stirred for 0.5 h. The reaction mixture was concentrated, THF (500 μL) was added and concentrated again. THF (500 μL) was added and the mixture cooled to 0° C. 2-Methoxyethylamine (I-33, 5.60 μL, 79.7 μmol) was added and the reaction was stirred overnight. The volatiles were removed in vacuo and the residue purified by reverse phase chromatography 0-100% MeCN/H$_2$O (0.1% ammonium bicarbonate buffer) and lyophilized to give compound C1142. $^1$H NMR (500 MHz, DMSO) δ 8.25 (t, J=5.8 Hz, 1H), 7.67 (d, J=7.4 z, 2H), 7.46 (t, J=7.8 Hz, 2H), 7.33 (t, J=7.4 Hz, 1H), 7.29-7.21 (m, 2H), 6.90 (dd, J=7.8, 1.2 Hz, 1H), 3.99 (s, 3H), 3.37 (t, J=6.0 Hz, 2H), 3.28-3.24 (m, 2H), 3.24 (s, 3H); MS (m/z): 527.9 [M+1]$^+$, 96%.

Table 13 below provides additional compounds that can be synthesized similarly to the methods described in the above steps 1-4, substituting the listed compound for I-33, or substituting I-24 for I-1 where indicated. Data for compounds synthesized is provided in columns 3-5.

Step 1:

Synthesis of ethyl 7-oxo-3-phenyl-2-(trifluoromethyl)-4,7-dihydropyrazolo[1,5-a]pyrimidine-5-carboxylate (I-31): To a stirred solution of 4-phenyl-3-(trifluoromethyl)-1H-

TABLE 13

| Compound ID | Compound I-33 replacement | ¹H NMR | Purity (%) | MS (m/z) |
|---|---|---|---|---|
| C1132 | NH₃ | (500 MHz, DMSO) δ 7.61 (d, J = 7.5 Hz, 2H), 7.55 (br s, 1H), 7.40-7.35 (m, 2H), 7.27-7.21 (m, 2H), 7.17-7.16 (m, 1H), 6.98 (br s, 2H), 6.81 (dd, J = 7.5, 1.6 Hz, 1H), 3.91 (s, 3H) | 100 | 470.0 |
| C1178 | H₂N⁓OH | (500 MHz, DMSO) δ 8.22 (t, J = 5.5 Hz, 1H), 7.66 (d, J = 7.5 Hz, 2H), 7.45 (t, J = 7.8 Hz, 2H), 7.32 (t, J = 7.4 Hz, 1H), 7.24 (dt, J = 8.1, 7.5 Hz, 2H), 6.89 (dd, J = 7.9, 1.2 Hz, 1H), 4.67 (t, J = 5.4 Hz, 1H), 3.98 (s, 3H), 3.41 (q, J = 6.0 Hz, 2H), 3.17 (q, J = 6.2 Hz, 2H). | 96.0 | 513.13 |
| C1179 | HN(CH₃)CH₂CH₂OCH₃ | (500 MHz, DMSO) (mixture of rotamers): δ 7.56 (d, J = 7.5 Hz, 2H), 7.46-7.41 (m, 2H), 7.34-7.29 (m, 1H), 7.23 (dd, J = 13.3, 7.4 Hz, 1H), 6.91-6.84 (m, 1H), 4.03 (s, 1.34H), 3.98 (s, 1.66H), 3.58-3.51 (m, 2H), 3.49-3.43 (m, 2H), 3.23 (s, 1.80H), 3.15 (s, 1.20H), 2.95 (s, 1.66H), 2.92 (s, 1.30H). | 98.03 | 541.16 |
| C1185 | H₂N-oxetanyl | (500 MHz, DMSO) δ 8.90 (d, J = 6.7 Hz, 1H), 7.65 (d, J = 7.4 Hz, 2H), 7.48-7.42 (m, 2H), 7.34-7.30 (m, 1H), 7.24 (d, J = 7.1 Hz, 2H), 6.88 (dd, J = 7.1, 1.9 Hz, 1H), 4.82-4.75 (m, 1H), 4.67-4.62 (m, 2H), 4.53 (t, J = 6.5 Hz, 2H), 3.96 (s, 3H). | 95.7 | 525.13 |
| C1186 | piperidine (NH) | (500 MHz, DMSO) δ 7.55 (d, J = 7.5 Hz, 2H), 7.45 (dd, J = 10.6, 4.9 Hz, 2H), 7.33 (t, J = 7.4 Hz, 1H), 7.28-7.22 (m, 2H), 6.92-6.85 (m, 1H), 3.99 (s, 3H), 3.53-3.41 (m, 4H), 1.62-1.46 (m, J = 24.3 Hz, 6H). | 98.2 | 537.16 |
| C1194 | H₂N-tetrahydropyranyl | (500 MHz, DMSO) δ 8.41-8.33 (m, 1H), 7.58 (d, J = 7.8 Hz, 2H), 7.52 (d, J = 7.4 Hz, 1H), 7.48 (t, J = 7.6 Hz, 2H), 7.40-7.36 (m, 1H), 7.31-7.24 (m, 2H), 6.93-6.89 (m, 1H), 3.97 (s, 3H), 3.77-3.71 (m, 3H), 3.30 (td, J = 11.4, 2.1 Hz, 3H), 1.71-1.63 (m, 2H), 1.42 -1.33 (m, 2H). | 99 | 553.16 |
| C1195 | H₂N-CH₂-C(=O)-OH | (500 MHz, MeOD) δ 7.66 (d, J = 7.4 Hz, 2H), 7.46 (t, J = 7.7 Hz, 2H), 7.37 (t, J = 7.5 Hz, 1H), 7.32 (t, J = 8.2 Hz, 1H), 7.27-7.17 (m, 1H), 6.92 (d, J = 8.0 Hz, 1H), 4.03 (s, 3H), 4.00 (s, 2H). | 96.3 | 527.11 |
| C1196 | H₂N-CH(CH₃)-CH₂OH | (500 MHz, DMSO) δ 8.17-8.06 (m, 1H), 7.66-7.60 (m, 2H), 7.46 (t, J = 7.7 Hz, 2H), 7.34 (t, J = 7.4 Hz, 1H), 7.31-7.21 (m, 2H), 6.90 (d, J = 8.6 Hz, 1H), 3.98 (s, 3H), 3.72 (dt, J = 12.8, 6.4 Hz, 1H), 3.24 (dd, J = 10.6, 6.2 Hz, 3H), 1.02 (d, J = 6.7 Hz, 3H). | 99 | 527.14 |

TABLE 13-continued

| Compound ID | Compound I-33 replacement | $^1$H NMR | Purity (%) | MS (m/z) |
|---|---|---|---|---|
| C1197 | 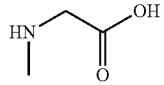 | (500 MHz, DMSO) mixture of rotamers δ 12.63 (s, 1H), 7.60-7.52 (m, 2H), 7.44 (dd, J = 16.3, 7.9 Hz, 2H), 7.33 (dt, J = 11.2, 7.4 Hz, 1H), 7.29-7.19 (m, 2H), 6.87 (d, J = 7.4 Hz, 1H), 4.11 (s, 0.92H), 4.07 (s, 1.14H), 4.06-3.98 (m, 3H), 2.99 (s, 1.74H), 2.96 (s, 1.43H). | 99 | 541.12 |
| C1207 | 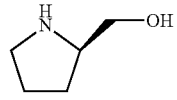 | (500 MHz, DMSO): δ 7.54 (dd, J = 12.3, 7.5 Hz, 2H), 7.46 (dd, J = 15.2, 7.6 Hz, 2H), 7.35 (dd, J = 15.9, 8.2 Hz, 1H), 7.31-7.22 (m, 2H), 6.90 (t, J = 7.3 Hz, 1H), 3.98 (s, 3H), 3.95-3.89 (m, 1H), 3.64 (dd, J = 10.6, 4.1 Hz, 1H), 3.56-3.52 (m, 2H), 3.24 (ddd, J = 8.9, 8.4, 2.7 Hz, 1H), 1.98-1.79 (m, 4H). | 95.1 | 553.2 |
| C1208 | 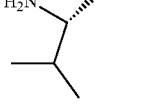 | (500 MHz, DMSO) δ 8.13 (d, J = 9.4 Hz, 1H), 7.68 (d, J = 7.6 Hz, 2H), 7.45 (dd, J = 10.6, 4.8 Hz, 2H), 7.34 (t, J = 7.4 Hz, 1H), 7.28 (t, J = 8.1 Hz, 1H), 7.26-7.20 (m, 1H), 6.90 (d, J = 8.8 Hz, 1H), 3.98 (s, 3H), 3.54-3.48 (m, 1H), 3.43 (dd, J = 11.0, 4.9 Hz, 1H), 3.34 (dd, J = 10.9, 5.7 Hz, 1H), 1.94-1.82 (m, 1H), 0.81 (dd, J = 6.8, 3.0 Hz, 6H). | 97.9 | 555.17 |
| C1209 | 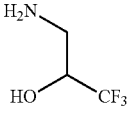 | (500 MHz, DMSO): δ 8.47 (d, J = 5.8 Hz, 1H), 7.65 (d, J = 7.4 Hz, 2H), 7.49-7.43 (m, 1H), 7.37-7.32 (m, 1H), 7.30-7.21 (m, 2H), 6.90 (dd, J = 7.9, 1.1 Hz, 1H), 4.17-4.10 (m, 1H), 3.97 (s, 3H), 3.50 (ddd, J = 13.6, 6.6, 4.3 Hz, 1H), 3.20 (ddd, J = 14.3, 8.2, 5.9 Hz, 1H). | 95.4 | 581.1 |
| C1212 | 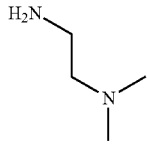 | (500 MHz, DMSO) δ 8.27 (t, J = 5.6 Hz, 1H), 7.68 (d, J = 7.6 Hz, 2H), 7.45 (t, J = 7.7 Hz, 2H), 7.32 (t, J = 7.4 Hz, 1H), 7.28-7.21 (m, 2H), 6.89 (d, J = 7.2 Hz, 1H), 3.98 (s, 3H), 3.19 (dd, J = 12.3, 6.3 Hz, 2H), 2.37 (t, J = 6.3 Hz, 2H), 2.18 (s, 6H). | 99 | 540.2 |
| C1219 | 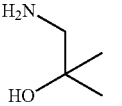 | (500 MHz, DMSO) δ 8.28-8.20 (m, 1H), 7.68 (d, J = 7.5 Hz, 2H), 7.45 (t, J = 7.7 Hz, 2H), 7.34 (t, J = 7.4 Hz, 1H), 7.27 (t, J = 8.1 Hz, 1H), 7.22 (d, J = 8.1 Hz, 1H), 6.90 (dd, J = 8.1, 0.8 Hz, 1H), 3.98 (s, 3H), 3.05 (d, J = 6.1 Hz, 2H), 1.04 (s, 6H). | 98.14 | 541.2 |
| C1244 | 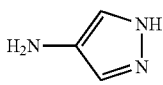 | (500 MHz, DMSO) δ 10.21 (s, 1H), 7.64-7.59 (m, 4H), 7.43-7.37 (m, 3H), 7.30-7.24 (m, 1H), 7.21-7.17 (m, 2H), 6.83-6.79 (m, 1H), 3.92 (s, 1H), 3.86 (s, 3H). | 97.2 | 536.3 |
| C1245 | 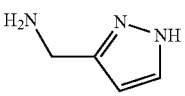 | (500 MHz, DMSO) δ 8.60 (s, 1H), 7.68-7.63 (m, 2H), 7.53 (s, 1H), 7.32-7.19 (m, 3H), 7.16 (s, 1H), 7.06 (s, 1H), 6.96 (s, 1H), 6.89-6.86 (m, 1H), 6.19-6.17 (m, 1H), 4.32-4.26 (m, 2H), 3.97 (s, 3H). | 95.2 | 550.2 |
| C1249 | Replace I-1 with I-24 Isolate after Step 3 | (500 MHz, DMSO) δ 8.09 (d, J = 7.3 Hz, 2H), 7.46 (t, J = 7.8 Hz, 2H), 7.30-7.18 (m, 3H), 6.86 (dd, J = 7.0, 2.0 Hz, 1H), 3.98 (s, 3H). | | 428.0 |

TABLE 13-continued

| Compound ID | Compound I-33 replacement | 1H NMR | Purity (%) | MS (m/z) |
|---|---|---|---|---|
| C1256 | H2N-pyrazole | (500 MHz, DMSO) δ 10.31 (s, 1H), 8.38 (s, 2H), 7.67-7.65 (m, 2H), 7.52-7.50 (m, 1H), 7.48-7.44 (m, 2H), 7.35-7.31 (m, 1H), 7.22-7.20 (m, 1H), 6.88-6.85 (m, 1H), 6.32-6.30 (m, 1H), 3.93 (s, 3H), 3.71 (s, 3H) | 95 | 550.2 |

Example 13

Synthesis of 6-(4-methoxybenzo[d]oxazol-2-yl)-7-oxo-3-phenyl-2-(trifluoromethyl)-4,7-dihydropyrazolo[1,5-a]pyrimidine-5-carbonitrile (C1089) was carried out in one step as follows:

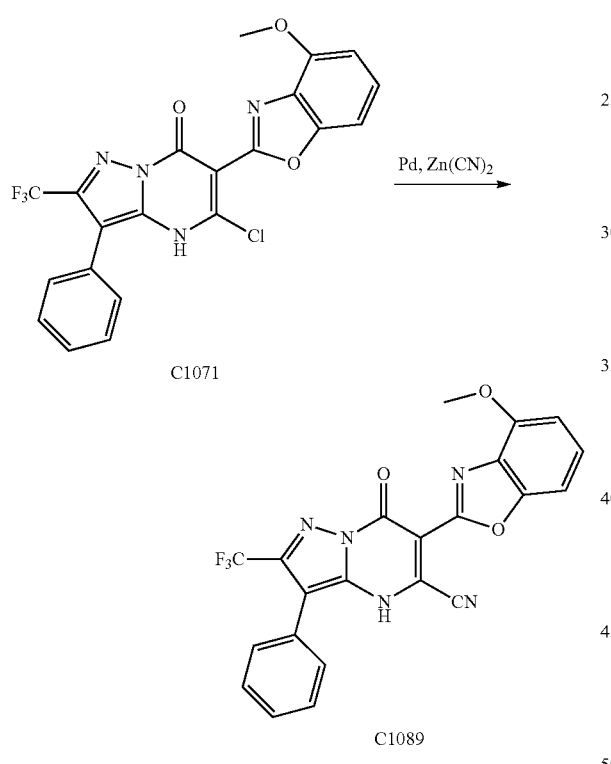

Step 1:

Compound C1071 (see Example 7, Step 2, 20.0 mg, 0.0434 mmol), Pd(TFA)₂ (1.44 mg, 0.00434 mmol), Zinc cyanide (5.20 mg, 0.0434 mmol), TrixPhos (3.53 mg, 0.00868 mmol), Zn (0.203 µL, 0.0217 mmol) were charged successively to a glass tube equipped with a magnetic stir bar and Teflon screw-cap. The tube was evacuated and back-filled with nitrogen. DMAC (anhydrous, 99.8%, 3 mL) was added via syringe and the resulting reaction mixture was degassed. The reaction mixture was then heated at 110° C. for 14 hours. The reaction mixture was then cooled to room temperature, diluted with MeCN, filtered through Celite. The solvent was evaporated and the crude material was purified by semi-prep HPLC-MS using MeCN and 10 mM aqueous AmForm buffer as eluent to afford compound C1089 (8.00 mg, 41%). ¹H NMR (500 MHz, DMSO) δ 8.27 (s, 1H), 7.57 (d, J=7.3 Hz, 2H), 7.48 (t, J=7.7 Hz, 2H), 7.37-7.32 (m, 3H), 6.94 (dd, J=7.3, 1.7 Hz, 1H), 4.04 (s, 3H). LCMS m/z: [M+H]⁺=452.2; 5-100% MeCN/H₂O (0.1% AMF buffer) over 7 min.

Example 14

Synthesis of 5-amino-6-(4-methoxybenzo[d]oxazol-2-yl)-3-phenyl-2-(trifluoromethyl)pyrazolo[1,5-a]pyrimidin-7(4H)-one (C1085) was carried out in one step as follows:

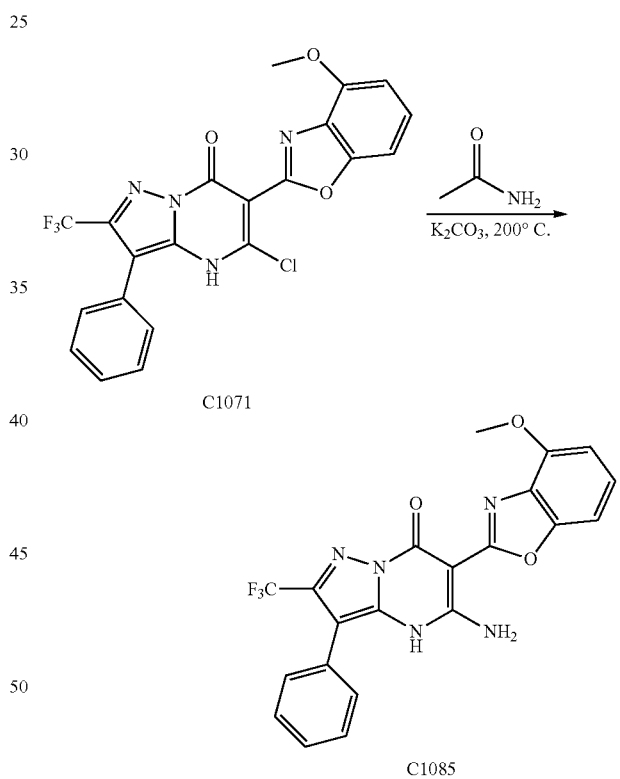

Step 1:

A mixture of acetamide (51.8 mg, 868 µmol), C1071 (see Example 7, Step 2, 10.0 mg, 21.7 µmol), and K₂CO₃ (51.8 mg, 109 µmol) was heated at 200° C. for 2 h. The reaction mixture was dissolved in 1 mL DMSO and purified by reverse flash chromatography (KP-C18-H5 reverse phase column using MeCN and 10 mM aqueous AmForm buffer as eluent) to afford C1085 (2 mg, 21%). ¹H NMR (500 MHz, DMSO) δ 8.15 (s, 1H), 7.58 (d, J=7.3 Hz, 2H), 7.37 (t, J=7.8 Hz, 2H), 7.27-7.19 (m, 2H), 7.15 (d, J=8.1 Hz, 1H), 6.86 (d, J=7.6 Hz, 1H), 3.96 (s, 3H). LCMS m/z: [M+H]⁺=442.0; 5-100% MeCN/H₂O (0.1% AMF buffer) over 7 min.

Example 15

Synthesis of 6-(4-methoxybenzo[d]oxazol-2-yl)-5-(1-methyl-1H-pyrazol-4-yl)-3-phenyl-2-(trifluoromethyl)pyrazolo[1,5-a]pyrimidin-7(4H)-one (C1255) was carried out in one step as follows:

Example 16

Compounds 6-(4-methoxybenzo[d]oxazol-2-yl)-5-(3-methylisoxazol-4-yl)-3-phenyl-2-(trifluoromethyl)pyrazolo[1,5-a]pyrimidin-7(4H)-one (C1253) and 6-(4-methoxybenzo[d]oxazol-2-yl)-3-phenyl-5-(1H-pyrazol-4-yl)-2-(triluoromethyl)pyrazolo[1,5-a]pyrimidin-7(4H)-one (C1254)

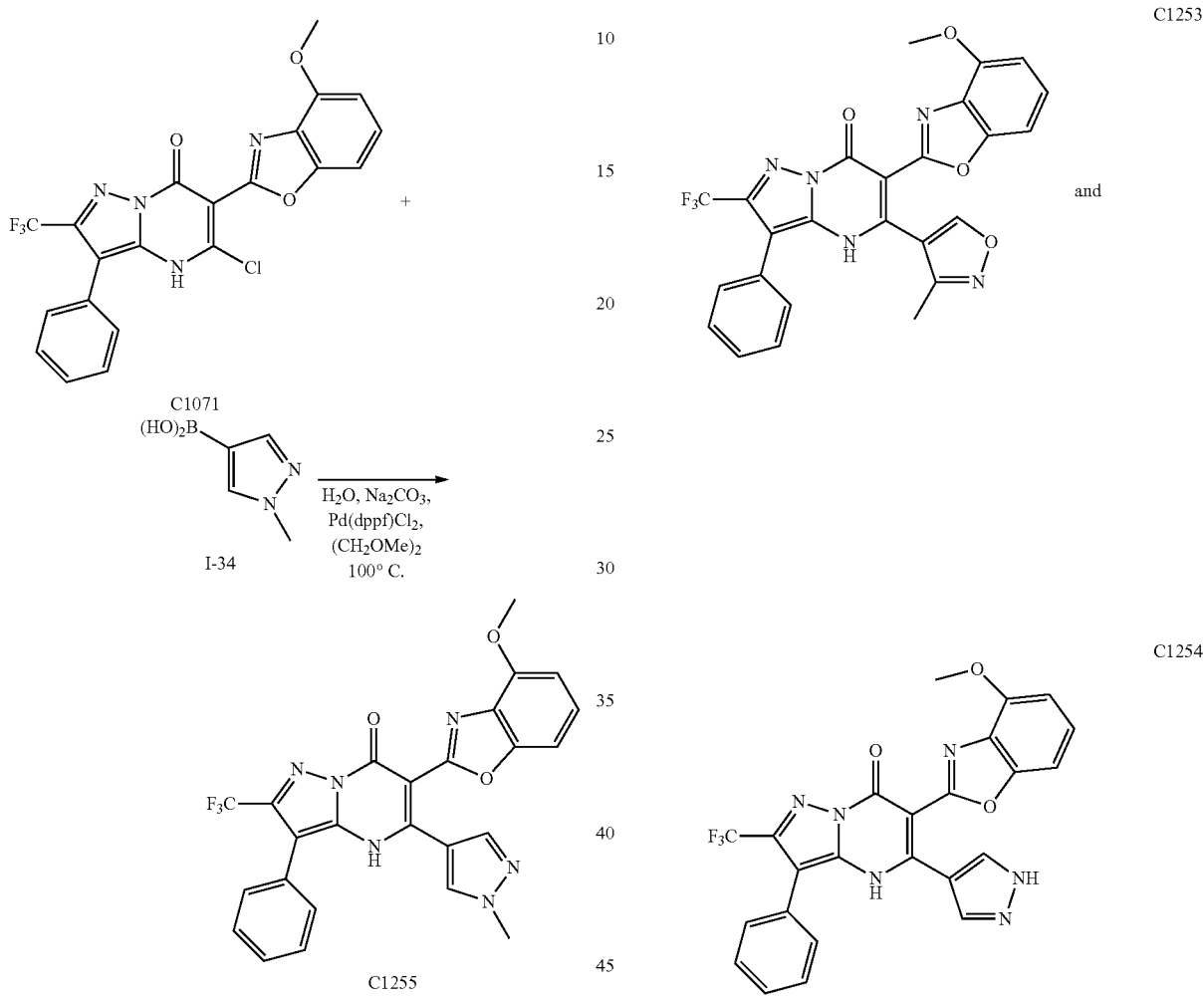

Step 1:

A mixture of compound C1071 (see Example 7, Step 2, 30.0 mg, 62.9 µmol, see Example 7), (1-methyl-1H-pyrazol-4-yl)boronic acid (I-34, 12.5 mg, 94.4 µmol), sodium carbonate (13.3 mg, 126 µmol) and [1,1'-bis(diphenylphosphino)ferrocene]dichloropalladium(ll) (30.6 mg, 37.4 µmol) in water (110 µL) and dimethoxyethane (220 µL) was degassed by bubbling under nitrogen for 5 min. The reaction was stirred overnight at 110° C. The crude mixture was concentrated in vacuo, then purified via reverse phase chromatography (KP-C18-H5, using a gradient 0 to 100% MeCN in 10 mM aqueous AmForm buffer) to afford compound C1255 after lyophilization. $^1$H NMR (500 MHz, DMSO-d6) δ 7.94 (s, 1H), 7.56 (d, J=7.3 Hz, 2H), 7.53-7.46 (m, 2H), 7.45-7.35 (m, 2H), 7.31 (d, J=7.6 Hz, 1H), 7.05 (s, 1H), 6.98 (d, J=7.7 Hz, 1H), 3.98 (s, 3H), 3.76 (s, 3H); MS (m/z): 507.3 [M+1]$^+$.

and were prepared similarly to the above method, replacing I-34 with

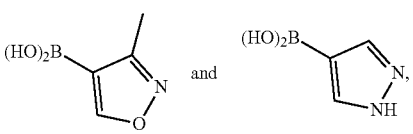

respectively.

Example 16

Synthesis of 5-(dimethylphosphoryl)-6-(4-methoxybenzo[d]oxazol-2-yl)-3-phenyl-2-(trifluoromethyl)pyrazolo[1,5-a]pyrimidin-7(4)-one (C1284) was carried out in one step as follows:

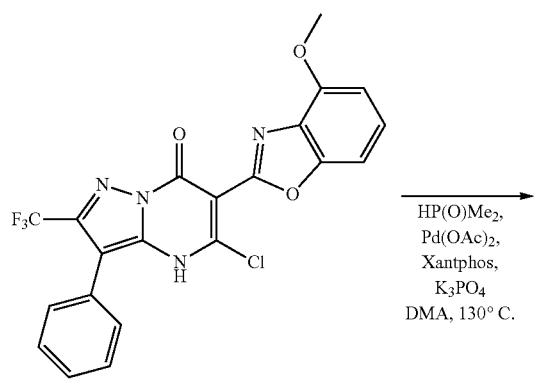

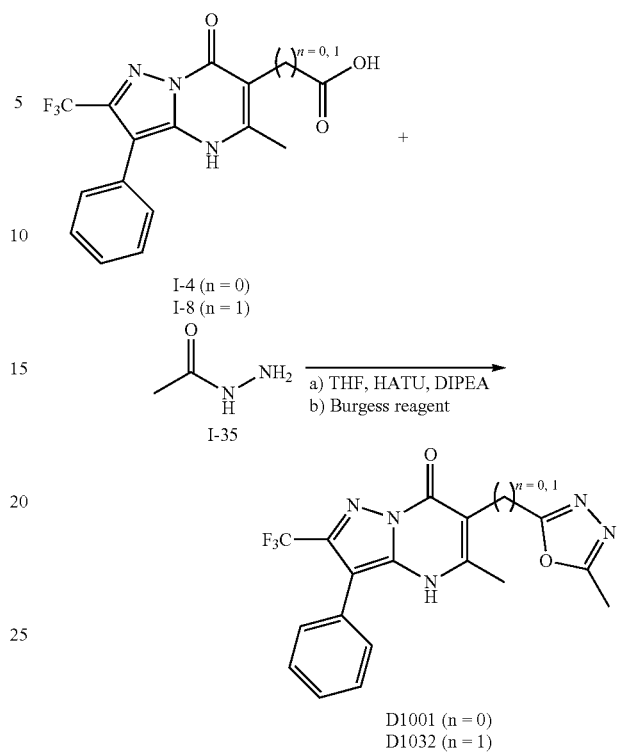

I-4 (n = 0)
I-8 (n = 1)

I-35 a) THF, HATU, DIPEA
b) Burgess reagent

D1001 (n = 0)
D1032 (n = 1)

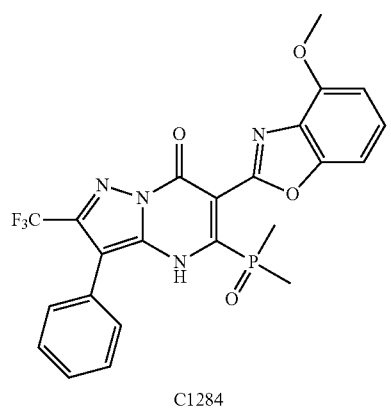

C1284

Step 1:

A mixture of compound C1071 (see Example 7, Step 2, 20.0 mg, 0.043 mmol), dimethylphosphine oxide (10.0 mg, 0.130 mmol), Pd(OAc)$_2$ (1.48 mg, 0.00651 mmol), Xantphos (7.69 mg, 0.013 mmol), and K$_3$PO$_4$ (27.6 mg, 0.130 mmol) in DMF (500 µL) was degassed with N$_2$. The reaction mixture was then heated at 130° C. for 3 h after which it was filtered over celite and washed with MeOH. The filtrate was evaporated in vacuo and the resulting material was purified by reverse phase HPLC (AmF/MeCN) to afford Compound C1284. $^1$H NMR (500 MHz, DMSO) δ 7.69 (d, J=7.5 Hz, 2H), 7.44 (t, J=7.7 Hz, 2H), 7.32-7.23 (m, 3H), 6.89 (d, J=7.4 Hz, 1H), 4.00 (s, 3H), 1.69 (s, 3H), 1.67 (s, 3H); MS (m/z): 503.1 [M+1]$^+$, 100%.

Example 17

Synthesis of 5-methyl-6-(5-methyl-1,3,4-oxadiazol-2-yl)-3-phenyl-2-(trifluoromethyl)pyrazolo[1,5-a]pyrimidin-7(4H)-one (D1001) or 5-methyl-6-((5-methyl-1,3,4-oxadiazol-2-yl)methyl)-3-phenyl-2-(trifluoromethyl)pyrazol[1,5-a]pyrimidin-7(4H)-one (D1032) was carried out in one step as follows:

Step 1:

Preparation of 5-methyl-6-((5-methyl-1,3,4-oxadiazol-2-yl)methyl)-3-phenyl-2-(trifluoromethyl)pyrazolo[1,5-a]pyrimidin-7(4H)-one (D1032): To a stirred suspension of 2-(5-methyl-7-oxo-3-phenyl-2-(trifluoromethyl)-4,7-dihydropyrazolo[1,5-a]pyrimidin-6-yl)acetic acid (I-8, 70 mg, 0.2 mmol, see Example 2) in THF (2 mL) was added HATU (76 mg, 0.2 mmol), acetylhydrazine (I-35, 15 mg, 0.2 mmol) and DIPEA (70 µL, 0.40 mmol). The reaction mixture was stirred at r.t. for 18 h. After addition of Burgess reagent (124 mg, 0.50 mmol), the reaction mixture was stirred at r.t. for 2 days. More Burgess reagent (124 mg, 0.50 mmol) was added and the reaction mixture was heated at 40° C. for 3 h and concentrated. The residue was purified by reverse flash chromatography (KP-C18-H5, using a gradient 0 to 100% MeCN in 10 mM aqueous ammonium formate buffer) to afford compound D1032 (122 mg, 0.27 mmol, 75%) as a white solid after lyophilization. $^1$H NMR (500 MHz, DMSO) δ 12.36 (s, 1H), 7.53-7.42 (m, 5H), 4.11 (s, 2H), 2.44 (s, 3H), 2.41 (s, 3H); MS (m/z): 390.0 [M+1]$^+$, 99.9%.

Step 1: 5-methyl-6-(5-methyl-1,3,4-oxadiazol-2-yl)-3-phenyl-2-(trifluoromethyl)pyrazolo[1,5-a]pyrimidin-7(4H)-one (D1001) was prepared following this method starting from compound I-4 (see Example 1). $^1$H NMR (500 MHz, DMSO) δ 7.54 (d, J=7.4 Hz, 2H), 7.45 (t, J=7.7 Hz, 2H), 7.35 (t, J=7.4 Hz, 1H), 2.55 (s, 3H), 2.31 (s, 3H); MS (m/z): 376.1 [M+1]$^+$, 99.0%.

Table 14 below provides additional compounds that can be synthesized similarly to the methods described in the above step from I-4 unless indicated otherwise by substituting the listed compound for I-35, and/or replacing I-1 and/or I-2 where indicated to provide the suitable analog of I-4 (per Example 1). Data for compounds synthesized is provided in columns 3-5.

TABLE 14

| Compound ID | Compound I-35 replacement | ¹H NMR | Purity (%) | MS (m/z) |
|---|---|---|---|---|
| D1002 | 4-methoxybenzohydrazide | (500 MHz, DMSO) δ 13.05 (s, 1H), 7.98 (d, J = 8.6 Hz, 2H), 7.55-7.42 (m, 5H), 7.18 (d, J = 8.7 Hz, 2H), 3.87 (s, 3H), 2.48 (s, 3H). | 97.3 | 468.1 |
| D1003 | cyclopentanecarbohydrazide | (500 MHz, DMSO) δ 7.55 (d, J = 7.5 Hz, 2H), 7.44 (t, J = 7.7 Hz, 2H), 7.33 (t, J = 7.4 Hz, 1H), 3.43-3.36 (m, 1H), 2.29 (s, 3H), 2.12-2.04 (m, 2H), 1.90-1.83 (m, 2H), 1.78-1.62 (m, 4H). | 97.8 | 430.2 |
| D1004 | cyclohexanecarbohydrazide | (500 MHz, DMSO) δ 12.96 (bs, 1H), 7.53 (d, J = 7.4 Hz, 2H), 7.46 (dd, J = 10.5, 4.9 Hz, 2H), 7.37 (t, J = 7.3 Hz, 1H), 3.01 (tt, J = 10.9. 3.6 Hz, 1H), 2.32 (s, 3H), 2.08-2.01 (m, 2H), 1.80-1.73 (m, 2H), 1.69-1.53 (m, 3H), 1.46-1.37 (m, 2H), 1.34-1.24 (m, 1H). | 99.9 | 444.2 |
| D1005 | isobutyrohydrazide | (500 MHz, DMSO) δ 7.52-7.46 (m, 4H) 7.41 (t, J = 6.7 Hz, 1H), 3.29-3.22 (m, 1H), 2.36 (s, 3H), 1.35 (d, J = 6.9 Hz, 6H). | 97.3 | 404.1 |
| D1006 | cyclohexanecarbothiohydrazide — Forms (thiadiazole) | (500 MHz, DMSO) δ 12.99 (s, 1H), 7.57-7.41 (m, 5H), 3.21-3.15 (m, 1H), 2.81 (s, 3H), 2.13-2.06 (m, 2H), 1.84-1.77 (m, 2H), 1.74-1.67 (m, 1H), 1.58 (ddd, J = 24.2. 12.5, 3.2 Hz, 2H), 1.44 (ddt, J = 25.3, 12.6, 3.3 Hz, 2H), 1.35-1.25 (m, 1H). | 100 | 460.2 |
| D1007 | furan-2-carbohydrazide | (500 MHz, DMSO) δ 8.06 (dd, J = 1.7, 0.7 Hz, 1H), 7.59 (d, J = 7.5 Hz, 2H), 7.46-7.39 (m, 2H), 7.34-7.25 (m, 2H), 6.81 (dd, J = 3.5, 1.8 Hz, 1H), 2.35 (s, 3H). | 99.4 | 428.0 |
| D1008 | 3,3,3-trifluoro-2-hydroxy-2-methylpropanehydrazide | 1H NMR (500 MHz, DMSO) δ 13.08 (s, 1H), 7.67 (s, 1H), 7.52-7.40 (m, J = 25.2 Hz, 5H), 2.37 (s, 3H), 1.84 (s, 3H). | 96.3 | 474.1 |

TABLE 14-continued

| Compound ID | Compound I-35 replacement | ¹H NMR | Purity (%) | MS (m/z) |
|---|---|---|---|---|
| D1009 | morpholine carbohydrazide | (500 MHz, DMSO) δ 7.51 (d, J = 7.3 Hz. 2H), 7.46 (t, J = 7.6 Hz, 2H), 7.38 (t, J = 7.3 Hz, 1H), 3.76-3.70 (m, 4H), 3.44-3.39 (m, 4H), 2.32 (s, 3H). | 97.9 | 447.2 |
| D1011 | benzohydrazide | 1H NMR (500 MHz, DMSO) δ 13.07 (s, 1H), 8.11-7.98 (m, 2H), 7.73-7.60 (m, 3H), 7.59-7.42 (m, 5H), 2.54 (s, 3H). | 99.2 | 438.2 |
| D1012 | tetrahydrofuran-2-carbohydrazide | 1H NMR (500 MHz, DMSO) δ 13.02 (s, 1H), 7.52-7.40 (m, 5H), 5.22 (dd, J = 7.7, 5.5 Hz, 1H), 3.96-3.81 (m, 2H), 2.40 (s, 3H), 2.38-2.23 (m, 2H), 2.13-1.97 (m, 2H). | 99.5 | 432.2 |
| D1013 | tetrahydrofuran-3-carbohydrazide | 1H NMR (500 MHz, DMSO) δ 13.00 (s, 1H), 7.54-7.40 (m, 5H), 4.11-3.98 (m, 1H), 3.97-3.75 (m, 4H), 2.43-2.32 (m, 4H), 2.28-2.20 (m, 1H). | 96.3 | 432.2 |
| D1014 | pyrrolidine carbohydrazide | (500 MHz, DMSO) δ 12.85 (bs, 1H), 7.55-7.44 (m, 4H), 7.37 (t, J = 7.2 Hz, 1H), 3.43 (bs, 4H), 2.29 (s, 3H), 1.96 (s, 4H). | 99.4 | 431.9 |
| D1015 | tetrahydropyran-3-carbohydrazide | (500 MHz, DMSO) δ 12.99 (s, 1H), 7.61-7.39 (m, 5H), 4.07 (dd, J = 11.1, 2.9 Hz, 1H), 3.82-3.74 (m, 1H), 3.71-3.64 (m, 1H), 3.55-3.45 (m, 1H), 3.29-3.20 (m, 1H), 2.42 (s, 3H), 2.20-2.10 (m, 1H), 1.99-1.86 (m, 1H), 1.77-1.70 (m, 1H), 1.68-1.55 (m, 1H). | 97.7 | 446.2 |
| D1016 | tetrahydropyran-4-carbohydrazide | (500 MHz, DMSO) δ 13.23-12.65 (m, 1H), 7.56-7.28 (m, 5H), 3.99-3.78 (m, 2H), 3.54-3.44 (m, 2H), 2.36 (d, J = 16.9 Hz, 3H), 2.07-1.96 (m, 2H), 1.86-1.67 (m, 2H). | 97.4 | 446.2 |

TABLE 14-continued
| Compound ID | Compound I-35 replacement | ¹H NMR | Purity (%) | MS (m/z) |
|---|---|---|---|---|
| D1017 | 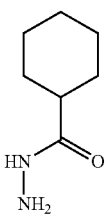 Also replace I-1 with 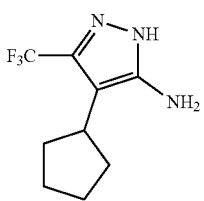 | (500 MHz, DMSO) 3.29-3.19 (m, 1H), 3.03-2.96 (m, 1H), 2.45-2.31 (m, 3H), 2.07-2.00 (m, 2H), 1.92-1.80 (m, 5H), 1.79-1.71 (m, 2H), 1.69-1.52 (m, 5H), 1.46-1.36 (m, 2H), 1.33-1.22 (m, 2H). | 95.0 | 436.2 |
| D1018 | 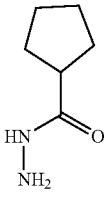 Also replace I-2 with 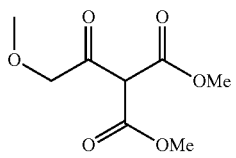 | ¹H NMR (500 MHz, DMSO) δ 7.58 (d, J = 7.4 Hz, 2H), 7.45-7.40 (m, 2H), 7.33-7.28 (m, 1H), 4.31 (s, 2H), 3.41-3.35 (m, 1H), 3.07 (s, 3H), 2.11-2.03 (m, 2H), 1.90-1.81 (m, 2H), 1.78-1.62 (m, 4H). | 96.5 | 460.2 |
| D1019 | 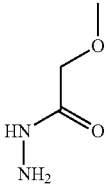 | (500 MHz, DMSO) δ 12.95 (s, 1H), 7.52-7.30 (m, 5H), 4.67 (s, 2H), 3.33 (s, 3H), 2.37 (s, 3H). | 95.1 | 406.1 |
| D1020 | 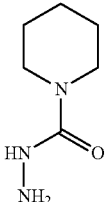 | (500 MHz, DMSO) δ 12.89 (s, 1H), 7.54-7.45 (m, 5H), 3.44 (bs, 4H), 2.40 (s, 3H), 1.61 (bs, 6H). | 99.3 | 445.2 |
| D1021 Iso-1 | 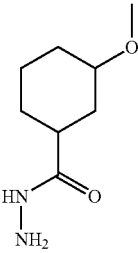 | (500 MHz, DMSO) δ 8.28 (s, 1H), 7.57 (d, J = 7.5 Hz, 2H), 7.41 (t, J = 7.7 Hz, 2H), 7.28 (t, J = 6.9 Hz, 1H), 3.28 (s, 3H), 3.06-2.97 (m, 1H), 2.41 (d, J = 15.4 Hz, 1H), 2.24 (s, 3H), 2.04 (d, J = 11.8 Hz, 2H), 1.88-1.78 (m, 1H), 1.48-1.31 (m, 3H), 1.17-1.07 (m, 1H). (Isomer 1) | 99.1 | 747.1 |

TABLE 14-continued

| Compound ID | Compound I-35 replacement | ¹H NMR | Purity (%) | MS (m/z) |
|---|---|---|---|---|
| D1021 Iso-2 | | (Also isolated Isomer 2) | | |
| D1022 | | (500 MHz, DMSO) δ 12.88 (s, 1H), 7.53-7.46 (m, 4H), 7.45-7.39 (m, 1H), 3.98-3.90 (m, 1H), 3.56-3.49 (m, 1H), 3.46-3.39 (m, 1H), 2.35 (s, 3H), 2.18-2.08 (m, 1H), 2.06-1.98 (m, 1H), 1.96-1.87 (m, 1H), 1.69-1.62 (m, 1H), 1.26 (d, J = 6.3 Hz, 3H). | | 445.2 |
| D1023 | | (500 MHz, CDCl3) δ 7.27-7.06 (m, 5H), 2.68 (s, 3H), 2.27-2.17 (m, 2H), 1.84-1.69 (m, 6H), 1.49 (s, 3H). | 99.6 | 444.2 |
| D1024 | | (500 MHz, CDCl3) δ 7.31 (s, 1H), 7.17 (d, J = 25.4 Hz, 4H), 4.72 (dd, J = 10.2, 2.7 Hz, 1H), 4.02 (d, J = 11.3 Hz, 1H), 3.56 (t, J = 10.6 Hz, 1H), 2.78 (s, 3H), 2.11-1.90 (m, 3H), 1.61 (m, 3H). | 98.9 | 446.2 |
| D1025 | | (500 MHz, DMSO) δ 13.00 (s, 1H), 7.58-7.32 (m, J = 16.0 Hz, 5H), 4.07 (dd, J = 11.1, 2.8 Hz, 1H), 3.81-3.75 (m, 1H), 3.69 (dd, J = 11.1, 8.6 Hz, 1H), 3.55-3.45 (m, 1H), 3.29-3.20 (m, 1H), 2.37 (dd, J = 6.6, 4.7 Hz, 3H), 2.18 (dd, J = 13.1, 5.3 Hz, 1H), 1.97-1.87 (m, 1H), 1.74 (dd, J = 9.0, 4.6 Hz, 1H), 1.69-1.59 (m, 1H). | 98.3 | 446.2 |
| D1026 | | (500 MHz, DMSO) δ 13.00 (s, 1H), 7.60-7.38 (m, 5H), 4.07 (dd, J = 11.1, 2.9 Hz, 1H), 3.83-3.75 (m, 1H), 3.69 (dd, J = 11.2, 8.5 Hz, 1H), 3.55-3.48 (m, 1H), 3.30-3.23 (m, 1H), 2.42 (s, 3H), 2.22-2.11 (m, 1H), 1.99-1.87 (m, 1H), 1.74 (dd, J = 8.8, 4.4 Hz, 1H), 1.70-1.58 (m, 1H). | 99.5 | 446.2 |

TABLE 14-continued

| Compound ID | Compound I-35 replacement | ¹H NMR | Purity (%) | MS (m/z) |
|---|---|---|---|---|
| D1027 | (piperidine with 3-OMe, N-C(O)NHNH₂) | (500 MHz, DMSO) δ 12.82 (s, 1H), 7.46 (d, J = 7.4 Hz, 2H), 7.39 (t, J = 7.7 Hz, 2H), 7.29 (t, J = 7.6 Hz, 1H), 3.54 (d, J = 10.5 Hz, 1H), 3.39-3.27 (m, 5H), 3.22 (s, 3H), 2.22 (s, 3H), 1.84-1.77 (m, 1H), 1.77-1.69 (m, 1H), 1.55-1.47 (m, 1H), 1.43 (m, 1H). | | 475.2 |
| D1028 | (Ph, OMe, CF₃ bearing C(O)NHNH₂) | (500 MHz, DMSO) δ 8.15 (s, 1H), 7.60-7.51 (m, 7H), 7.42 (t, J = 7.7 Hz, 2H), 7.29 (t, J = 7.4 Hz, 1H), 3.44 (s, 3H), 2.35 (s, 3H). | 95.5 | 550.2 |
| D1029 | (Ph, CF₃, OMe bearing C(O)NHNH₂, opposite stereochem) | (500 MHz, DMSO) δ 8.13 (s, 1H), 7.59-7.39 (m, 10H), 3.45 (s, 3H), 2.35 (s, 3H). | 98.9 | 550.2 |
| D1030 | (tetrahydropyran-3-yl C(O)NHNH₂) Also replace I-1 with (3-methyl-4-phenyl-1H-pyrazol-5-amine) | (500 MHz, DMSO) δ 12.52 (s, 1H), 7.62-7.54 (m, 2H), 7.46 (t, J = 7.3 Hz, 2H), 7.34-7.28 (m, 1H), 4.06 (dd, J = 11.3, 3.8 Hz, 1H), 3.82-3.76 (m, 1H), 3.67 (dd, J = 11.1, 8.7 Hz, 1H), 3.52-3.46 (m, 1H), 3.27-3.20 (m, 1H), 2.38-2.31 (m, 6H), 2.20-2.13 (m, 1H), 1.96-1.86 (m, 1H), 1.78-1.70 (m, 1H), 1.68-1.60 (m, 1H). | 98.9 | 392.2 |
| D1031 | (N-Boc piperidine-3-C(O)NHNH₂) | (500 MHz, DMSO) δ 13.00 (s, 1H), 7.54-7.44 (m, 5H), 4.10-4.03 (m, 1H), 3.73-3.66 (m, 1H), 3.21-3.14 (m, 1H), 3.07 (t, J = 10.4 Hz, 1H), 2.41 (s, 3H), 2.19-2.11 (m, 1H), 1.88-1.76 (m, 3H), 1.56-1.47 (m, 1H), 1.39 (s, 9H). | 98.5 | 545.4 |

TABLE 14-continued

| Compound ID | Compound I-35 replacement | ¹H NMR | Purity (%) | MS (m/z) |
|---|---|---|---|---|
| D1033 | 4-methoxyphenyl-C(O)NHNH₂ (Also replace I-4 with I-8) | (500 MHz, DMSO) δ 12.38 (s, 1H), 7.91-7.87 (m, 2H), 7.53-7.43 (m, 5H), 7.14-7.10 (m, 2H), 4.23 (s, 2H), 3.84 (s, 3H), 2.47 (s, 3H). | 99.9 | 482.1 |
| D1034 | cyclopentyl-C(O)NHNH₂ (Also replace I-4 with I-8) | (400 MHz, DMSO) δ 12.37 (s, 1H), 7.54-7.48 (m, 2H), 7.48-7.42 (m, 3H), 4.11 (s, 2H), 3.33-3.22 (m, 1H), 2.40 (s, 3H), 2.08-1.95 (m, 2H), 1.85-1.55 (m, 6H). | 98.9 | 444.0 |
| D1035 | cyclohexyl-C(O)NHNH₂ (Also replace I-4 with I-8) | (400 MHz, DMSO) δ 12.37 (s, 1H), 7.55-7.42 (m, 5H), 4.11 (s, 2H), 2.89 (tt, J = 10.9, 3.7 Hz, 1H), 2.41 (s, 3H), 2.01-1.90 (m, 2H), 1.78-1.67 (m, 2H), 1.67-1.58 (m, 1H), 1.54-1.42 (m, 2H), 1.42-1.17 (m, 3H). | 99.4 | 458.0 |
| D1036 | piperidin-3-yl-C(O)NHNH₂ | (500 MHz, DMSO) δ 8.82-8.50 (m, 2H), 7.57 (d, J = 7.4 Hz, 2H), 7.44-7.38 (m, 2H), 7.31-7.26 (m, 1H), 3.67-3.62 (m, 1H), 3.49-3.41 (m, 1H), 3.28-3.24 (m, 2H), 3.03-2.94 (m, 1H), 2.29 (s, 3H), 2.22-2.16 (m, 1H), 1.92-1.73 (m, 3H). | 99.5 | 445.2 |
| D1037 | 3-methoxypyrrolidin-1-yl-C(O)NHNH₂ | (500 MHz, DMSO) δ 7.55 (d, J = 7.6 Hz, 2H), 7.45 (t, J = 7.7 Hz, 2H), 7.35 (t, J = 7.4 Hz, 1H), 4.12-4.08 (m, 1H), 3.59-3.41 (m, 4H), 3.28 (s, 3H), 2.27 (s, 3H), 2.11-2.05 (m, 2H). | 100 | 461.3 |
| D1038 | 1-(trifluoromethyl)cyclopropyl-C(O)NHNH₂ | (500 MHz, DMSO) δ 7.53-7.45 (m, 4H), 7.40 (t, J = 7.1 Hz, 1H), 2.39 (s, 3H), 1.73-1.61 (m, 4H). | 98.8 | 470.1 |

TABLE 14-continued

| Compound ID | Compound I-35 replacement | ¹H NMR | Purity (%) | MS (m/z) |
| --- | --- | --- | --- | --- |
| D1039 | morpholine-3-carbohydrazide with N-Cbz | (500 MHz, CDCl₃) δ 7.39-7.11 (m, 10H), 5.43 (d, J = 34.8 Hz, 1H), 5.17 (d, J = 34.7 Hz, 2H), 4.43 (d, J = 9.8 Hz, 1H), 3.91 (m, 3H), 3.60 (m, 2H), 2.69 (s, 3H). | 98.4 | 581.2 |
| D1040 | piperidine-3-carbohydrazide with N-SO₂Me | (500 MHz, DMSO) δ 13.00 (s, 1H), 7.55-7.41 (m, 5H), 3.82 (dd, J = 11.6, 3.3 Hz, 1H), 3.50-3.43 (m, 1H), 3.17 (dd, J = 11.6, 9.7 Hz, 1H), 2.92 (s, 3H), 2.37 (s, 3H), 2.19-2.12 (m, 1H), 1.91-1.84 (m, 1H), 1.82-1.73 (m, 1H), 1.72-1.62 (m, 1H). | 97.8 | 523.3 |
| D1041 | piperidine-3-carbohydrazide with N-acetyl | Mixture of rotamers: (500 MHz, DMSO) δ 12.98 (s, 1H), 7.54-7.45 (m, 4H), 7.42-7.36 (m, 1H), 4.48 (d, J = 10.1 Hz, 0.5H), 3.94 (dd, J = 13.8, 3.4 Hz, 0.5H), 3.78-3.71 (m, 1H), 3.66 (dd, J = 13.7, 8.0 Hz, 0.5H), 3.23-3.17 (m, 1H), 3.12-3.01 (m, 1H), 2.35 (s, 3H), 2.23-2.08 (m, 1H), 2.07-2.00 (m, 3H), 1.96-1.89 (m, 0.5H), 1.88-1.81 (m, 1H), 1.72-1.45 (m, 2H). | 99.5 | 487.2 |
| D1042 | morpholine-3-carbohydrazide | (500 MHz, DMSO) δ 8.13 (s, 1H), 7.57 (d, J = 7.5 Hz, 2H), 7.43 (t, J = 7.6 Hz, 2H), 7.31 (m, 1H), 6.52 (s, 1H), 4.15 (m, 1H), 3.91-3.79 (m, 32H), 3.71-3.63 (m, 1H), 3.19 (m, 1H), 3.07 (m, 1H), 2.30 (s, 3H). | 98.4 | 447.1 |
| D1043 | N-cyclohexyl-N-methyl carbohydrazide | (500 MHz, DMSO) δ 12.88 (s, 1H), 7.53-7.48 (m, 4H), 7.47-7.41 (m, 1H), 3.75-3.63 (m, 1H), 2.95 (s, 3H), 2.36 (s, 3H), 1.85-1.72 (m, 4H), 1.66-1.52 (m, 3H), 1.38-1.27 (m, 2H), 1.20-1.07 (m, 1H). | 100 | 473.3 |
| D1044 | piperidine-4-carbohydrazide with N-Boc | (500 MHz, DMSO) δ 12.98 (s, 1H), 7.54-7.43 (m, 5H), 3.93 (d, J = 13.1 Hz, 2H), 3.30-3.24 (m, 1H), 3.06-2.97 (m, 2H), 2.41 (s, 3H), 2.05 (dd, J = 13.1, 3.1 Hz, 2H), 1.69-1.60 (m, 2H), 1.42 (s, 9H). | 98.3 | 543.5 (M − H) |

TABLE 14-continued

| Compound ID | Compound I-35 replacement | ¹H NMR | Purity (%) | MS (m/z) |
|---|---|---|---|---|
| D1045 | piperidine-2-carbohydrazide, N-Boc | (500 MHz, DMSO) δ 13.10-12.93 (m, 1H), 7.52-7.41 (m, 5H), 5.61-5.52 (m, 1H), 4.70-4.58 (m, 1H), 4.17-4.09 (m, 1H), 3.94 (d, J = 13.2 Hz, 1H), 2.41 (s, 3H), 2.20 (d, J = 13.9 Hz, 1H), 1.91-1.83 (s, 1H), 1.72-1.58 (m, 3H), 1.42 (s, 9H). | 95.7 | 543.4 (M − H) |
| D1046 | 3-methoxycyclohexane-1-carbohydrazide | (500 MHz, DMSO) δ 8.34 (s, 1H), 7.58 (d, J = 7.2 Hz, 2H), 7.45-7.36 (m, 2H), 7.30-7.21 (m, 1H), 3.19 (s, 3H), 2.99-2.96 (m, 1H), 2.21 (s, 3H), 2.17-2.15 (m, 1H), 2.10-2.08 (m, 3H), 1.98-1.95 (m, 1H), 1.81-1.74 (m, 1H), 1.72-1.68 (m, 1H), 1.35-1.33 (m, 2H). | 99.1 | 474.3 |
| D1047 | 4-(methylsulfonyl)morpholine-3-carbohydrazide | (500 MHz, DMSO) δ 8.20 (s, 1H), 7.58 (d, J = 7.3 Hz, 2H), 7.45-7.39 (m, 2H), 7.31-7.25 (m, 1H), 5.23 (s, 1H), 4.24 (d, J = 11.2 Hz, 1H), 3.92 (d, J = 11.6 Hz, 1H), 3.86 (dd, J = 12.0, 3.4 Hz, 1H), 3.61-3.47 (m, 3H), 3.07 (s, 3H), 2.33 (s, 3H). | 98.9 | 525.3 |
| D1048 | 2-methoxy-2-methylpropanehydrazide | (500 MHz, CDCl₃) δ 7.19 (m, 5H), 3.23 (s, 3H), 2.73 (s, 3H), 1.72 (s, 6H). | 98.6 | 434.2 |
| D1049 | 2-methoxycyclopentane-1-carbohydrazide | (500 MHz, DMSO) δ 12.97 (s, 1H), 7.46-7.53 (m, 5H), 4.07 (dt, J = 6.3, 4.2 Hz, 1H), 3.43-3.37 (m, 1H), 3.27 (s, 3H), 2.42 (s, 3H), 2.22-2.19 (m, 1H), 1.97-1.86 (m, 2H), 1.80-1.66 (m, 3H). | 99.8 | 460.3 |
| D1050 | 4-acetylmorpholine-3-carbohydrazide | (500 MHz, DMSO) δ 8.26 (s, 1H), 7.58 (d, J = 7.4 Hz, 2H), 7.42 (t, J = 7.7 Hz, 2H), 7.28 (t, J = 7.4 Hz, 1H), 5.68 (d, J = 2.9 Hz, 0.6H), 5.48 (s, 0.4H, 4.26-4.35 (m, 1H), 4.14 (d, J = 2.9 Hz, 0.5H) 3.89-3.75 (m, 1.5H), 3.91-3.80 (m, 1.5H), 3.78-3.74 (m, 1H), 3.61-3.51 (m, 2H), 2.87-2.92 (m, 0.5H), 2.30 (s, 1H), 2.26 (s, 2H), 2.13 (3H). | 98.1 | 489.3 |
| D1051 | 4-methyltetrahydro-2H-pyran-4-carbohydrazide | (500 MHz, DMSO) δ 12.97 (s, 1H), 7.49 (dd, J = 10.3, 2.8 Hz, 4H), 7.46-7.41 (m, 1H), 4.06-4.00 (m, 1H), 3.71-3.66 (m, 1H), 3.61-3.58 (m, 1H), 3.57-3.48 (m, 2H), 2.38 (s, 3H), 2.32-2.26 (m, 1H), 1.80-1.70 (m, 2H), 1.62 (m, 1H), 1.30 (s, 3H). | 95.6 | 460.2 |

TABLE 14-continued

| Compound ID | Compound I-35 replacement | ¹H NMR | Purity (%) | MS (m/z) |
|---|---|---|---|---|
| D1052 | (piperidine-4-carbohydrazide) | (500 MHz, DMSO) δ 7.51 (d, J = 7.3 Hz, 2H), 7.38-7.32 (m, 2H), 7.24-7.18 (m, 1H), 3.33-3.27 (m, 3H), 2.98 (td, J = 12.5, 3.0 Hz, 2H), 2.21 (s, 3H), 2.13 (dd, J = 14.2, 3.3 Hz, 2H), 1.89-1.80 (m, 2H). | 100 | 445.2 |
| D1053 | (1-(methylsulfonyl)piperidine-4-carbohydrazide) | (500 MHz, DMSO) δ 13.00 (s, 1H), 7.54-7.42 (m, 5H), 3.60 (td, J = 8.7, 3.7 Hz, 2H), 3.27-3.21 (m, 1H), 2.98 (td, J = 12.1, 2.7 Hz, 2H), 2.91 (s, 3H), 2.41 (s, 3H), 2.19 (dd, J = 13.5, 3.5 Hz, 2H), 1.88-1.78 (m, 2H). | 98.4 | 523.2 |
| D1054 | (1-acetylpiperidine-4-carbohydrazide) | (500 MHz, DMSO) δ 7.56 (d, J = 7.6 Hz, 2H), 7.44-7.40 (m, 2H), 7.31-7.27 (m, 1H), 4.32-4.25 (m, 1H), 3.88-3.82 (m, 1H), 3.28-3.25 (m, 2H), 2.91-2.83 (m, 1H), 2.30 (s, 3H), 2.12-2.05 (m, 2H), 2.03 (s, 3H), 1.79-1.70 (m, 1H), 1.64-1.55 (m, 1H). | 99.3 | 487.2 |
| D1055 | (1-methoxycyclopentane-1-carbohydrazide) | (500 MHz, DMSO) δ 13.02 (s, 1H), 7.56-7.42 (m, 5H), 3.12 (s, 3H), 2.44 (s, 3H), 2.21-2.11 (m, 4H), 1.84-1.69 (m, 4H). | 99.3 | 460.3 |
| D1056 | (1-(methylsulfonyl)piperidine-2-carbohydrazide) | (500 MHz, DMSO) δ 7.55 (d, J = 7.5 Hz, 2H), 7.45 (t, J = 7.7 Hz, 2H), 7.33 (t, J = 7.3 Hz, 1H), 5.39 (d, J = 3.7 Hz, 1H), 3.69-3.63 (m, 1H), 3.09 (td, J = 12.8, 2.4 Hz, 1H), 3.03 (s, 3H), 2.37 (s, 3H), 2.23-2.17 (m, 1H), 1.98-1.89 (m, 1H), 1.75-1.69 (m, 2H), 1.67-1.46 (m, 2H). | 100 | 523.2 |
| D1057 | (1-acetylpiperidine-2-carbohydrazide) | (500 MHz, DMSO) (mixture of rotamers) δ 7.58 (d, J = 7.2 Hz, 2H), 7.44-7.40 (m, 2H), 7.31-7.27 (m, 1H), 6.01-5.96 (m, 1H), 5.60-5.55 (m, 1H), 4.44-4.37 (m, 1H), 3.87-3.80 (m, 1H), 3.25-3.18 (m, 1H), 2.30-2.23 (m, 3H), 2.17-2.10 (m, 3H), 1.81-1.64 (m, 2H), 1.52 (m, 2H). | 100 | 487.3 |

TABLE 14-continued

| Compound ID | Compound I-35 replacement | $^1$H NMR | Purity (%) | MS (m/z) |
|---|---|---|---|---|
| D1058 | | (500 MHz, DMSO) δ 8.25 (s, 1H), 7.57 (d, J = 7.5 Hz, 1H), 7.41 (t, J = 7.7 Hz, 1H), 7.28 (t, J = 7.4 Hz, 1H), 4.28-3.66 (m, 6H), 3.43-3.40 (m, 2H), 2.51-2.48 (m, 3H), 2.46-2.42 (m, 2H), 2.24 (s, 3H) | 96 | 460.1 |
| D1059 | | (500 MHz, DMSO) δ 8.20 (s, 1H), 7.64-7.60 (m, 2H), 7.48-7.43 (m, 2H), 7.36-7.28 (m, 1H), 3.97 (s, 1H), 3.53-3.50 (m, 1H), 3.44-3.40 (m, 3H), 3.28 (s, 3H), 2.31-2.22 (m, 3H), 2.03-1.88 (m, 4H) | 99 | 475.2 |
| D1060 | | (500 MHz, DMSO) δ 12.87 (s, 1H), 7.54-7.46 (m, 4H), 4.20-4.10 (m, 1H), 3.78-3.65 (m, 2H), 3.55-3.49 (m, 1H), 3.26 (s, 3H), 3.25-3.23 (m, 1H), 3.19 (d, J = 1.9 Hz, 1H), 2.38 (s, 3H), 1.74-1.51 (m, 6H) | 98.8 | 489.2 |
| D1061 | | (500 MHz, DMSO) δ 10.94 (s, 1H), 8.48-8.44 (m, 1H), 8.37-8.28 (m, 2H), 8.14 (d, J = 8.6 Hz, 1H), 7.51 (s, 2H), 7.41-7.31 (m, 3H), 3.32 (s, 3H) | 95 | 483.1 |
| D1062 | | (500 MHz, DMSO) δ 7.58 (d, J = 7.3 Hz, 2H), 7.44-7.40 (m, 2H), 7.31-7.27 (m, 1H), 3.31 (s, 2H), 2.65-2.63 (m, 1H), 2.38-2.36 (m, 1H), 2.29 (s, 3H), 2.09 (s, 2H), 2.03-1.99 (m, 1H), 1.93-1.88 (m, 2H), 1.83-1.77 (m, 2H). | 99.7 | 445.2 |
| D1063 | | (500 MHz, DMSO) δ 9.12 (s, 1H), 8.71 (d, J = 4.3 Hz, 1H), 8.30 (d, J = 8.0 Hz, 1H), 7.60-7.56 (m, 1H), 7.52-7.48 (m, 2H), 7.36-7.32 (m, 2H), 7.21 (d, J = 7.3 Hz, 1H), 4.93 (s, 1H), 1.14 (s, 3H) | 98.7 | 439.1 |

TABLE 14-continued

| Compound ID | Compound I-35 replacement | ¹H NMR | Purity (%) | MS (m/z) |
|---|---|---|---|---|
| D1064 | | (500 MHz, DMSO) δ 8.39 (d, J = 3.4 Hz, 1H), 8.28 (d, J = 7.2 Hz, 1H), 7.54-7.49 (m, 2H), 7.45-7.40 (m, 2H), 7.32 (t, J = 7.3 Hz, 1H), 7.23-7.18 (m, 1H), 3.97 (s, 3H), 2.36 (s, 3H) | 98.4 | 468.9 |
| D1065 | | (500 MHz, DMSO) δ 9.12 (s, 1H), 7.59 (d, J = 7.4 Hz, 2H), 7.45-7.41 (m, 2H), 7.32-7.28 (m, 1H), 3.43 (s, 1H), 3.29-3.20 (m, 1H), 2.94 (s, 3H), 2.76 (s, 3H), 2.29 (s, 3H), 2.11-1.93 (m, 3H), 1.62-1.45 (m, 2H), 1.31-1.21 (m, 1H) | 96.8 | 473.1 |
| D1066 | | (500 MHz, DMSO) δ 8.47 (s, 1H), 8.07 (s, 1H), 7.50 (d, J = 7.6 Hz, 2H), 7.43-7.30 (m, J = 7.6 Hz, 2H), 7.25 (t, J = 7.3 Hz, 1H), 2.28 (s, 3H). (ammonium salt) | 99.7 | 405.0 |
| D1067 | | (500 MHz, DMSO) δ 8.19-8.14 (m, 1H), 7.69 (d, J = 5.3 Hz, 1H), 7.60 (d, J = 7.4 Hz, 2H), 7.45-7.40 (m, 2H), 7.30 (t, J = 7.4 Hz, 1H), 7.09 (s, 2H), 6.42 (t, J = 6.6 Hz, 1H), 2.32 (s, 3H) | 99.1 | 455.0 |
| D1068 | | (500 MHz, DMSO) δ 12.91 (s, 1H), 7.54-7.45 (m, 5H), 3.98-3.89 (m, 4H), 3.38-3.34 (m, 4H), 2.45 (s, 3H) | 97.9 | 495.0 |
| D1069 | | (500 MHz, DMSO) δ 7.93-7.73 (m, 2H), 7.53-7.38 (m, 3H), 4.13 (s, 1H), 3.81-3.73 (m, 1H), 3.69-3.63 (m, 1H), 3.20-3.14 (m, 1H), 2.88 (s, 2H), 2.51 (s, 3H), 2.50-2.49 (m, 1H), 2.38 (s, 2H), 2.17-2.07 (m, 1H), 1.93-1.81 (m, 1H), 1.72 (s, 1H), 1.67-1.61 (m, 2H), 1.53 (s, 1H), 1.29-1.09 (m, 1H) | 97 | 486.2 (M − H) |
| D1070 | | (500 MHz, DMSO) δ 11.14 (s, 1H), 10.44 (s, 1H), 8.79 (s, 1H), 7.55-7.51 (m, 2H), 7.49-7.44 (m, 2H), 7.40-7.34 (m, 1H), 3.92 (d, J = 14.3 Hz, 2H), 3.76 (t, J = 9.3 Hz, 1H), 3.25-3.20 (m, 1H), 3.07 (t, J = 12.7 Hz, 1H), 2.55 (s, 3H), 1.84 (s, 2H), 1.73 (s, 1H), 1.46 (d, J = 8.2 Hz, 2H), 1.24 (s, 1H). | 99.5 | 474.1 |

TABLE 14-continued

| Compound ID | Compound I-35 replacement | ¹H NMR | Purity (%) | MS (m/z) |
|---|---|---|---|---|
| D1071 | [structure: HN(NH₂)-C(=O)-CN] Final step followed by primary amide dehydration | (500 MHz, DMSO) δ 13.53-12.91 (brs, 1H), 7.52 (s, 5H), 2.59 (s, 3H). | 100 | 387.0 |
| D1072 | [structure: tetrahydropyrimidine with C(=O)NHNH₂] | (500 MHz, DMSO) δ 13.53-12.91 (m, 1H), 7.52 (s, 5H), 2.59 (s, 3H). | 99.1 | 443.9 |
| D1073 | [structure: piperidine N-C(=O)NHNH₂ with ethyl-NH-SO₂Me substituent] | (500 MHz, DMSO) δ 12.90 (s, 1H), 7.54-7.48 (m, 4H), 7.43 (s, 1H), 7.04-6.98 (m, 1H), 4.12 (s, 1H), 3.77-3.72 (m, 1H), 3.23-3.16 (m, 1H), 3.04-2.92 (m, 2H), 2.89 (s, 3H), 2.37 (s, 3H), 2.04-1.95 (m, 1H), 1.86-1.78 (m, 1H), 1.70-1.62 (m, 4H), 1.52 (s, 1H), 1.25 (s, 1H) | 98.7 | 566.1 |
| D1074 | [structure: H₂N-C(=NH)-C(=O)-NH-NH₂] | (500 MHz, DMSO) δ 9.78 (s, 3H), 7.63-7.53 (m, 2H), 7.48-7.39 (m, 2H), 7.36-7.23 (m, 1H), 2.40 (s, 3H). | 97.9 | 404.1 |
| D1075 | [structure: H₂N-C(=O)-NH-NH₂ semicarbazide] | (500 MHz, DMSO) δ 12.85 (s, 1H), 7.56-7.35 (m, 5H), 7.13 (s, 2H), 2.39 (s, 3H). | 97.9 | 377.1 |
| D1076 | [structure: 4-methoxypyrimidine-2-C(=O)NHNH₂] | (500 MHz, DMSO) δ 13.03 (s, 1H), 8.77 (d, J = 5.8 Hz, 1H), 7.56-7.45 (m, 5H), 7.19 (d, J = 5.8 Hz, 1H), 4.06 (s, 3H), 2.50 (s, 3H) | 98.4 | 470.0 |
| D1077 | [structure: H₂N-C(=NH)-NH-C(=O)-NH-NH₂] | (500 MHz, DMSO) δ 7.59 (d, J = 7.4 Hz, 2H), 7.41 (t, J = 7.7 Hz, 2H), 7.27 (t, J = 7.4 Hz, 1H), 6.87 (br s, 4H), 2.19 (s, 3H). | 96.1 | 419.0 |

TABLE 14-continued

| Compound ID | Compound I-35 replacement | ¹H NMR | Purity (%) | MS (m/z) |
|---|---|---|---|---|
| D1078 | HO-pyrimidine-C(O)NHNH₂ | (500 MHz, DMSO) δ 13.12 (s, 1H), 8.56 (s, 1H), 7.62-7.57 (m, 2H), 7.46-7.41 (m, 2H), 7.33-7.28 (m, 1H), 6.79 (s, 1H), 2.38 (s, 3H) | 99.8 | 456.1 |
| D1079 | 3-H₂N-phenyl-C(O)NHNH₂ | (500 MHz, DMSO) δ 8.35 (s, 1H), 7.62-7.59 (m, 2H), 7.45-7.41 (m, 2H), 7.32-7.26 (m, 2H), 7.17-7.14 (m, 1H), 7.07-6.97 (m, 1H), 6.79-6.75 (m, 1H), 5.49 (s, 2H), 2.34 (s, 3H) | 96.2 | 453.1 |
| D1080 | 2-H₂N-cyclohexyl-C(O)NHNH₂ | (500 MHz, DMSO) δ 7.59-7.56 (m, 2H), 7.44-7.38 (m, 2H), 7.31-7.25 (m, 1H), 3.04 (s, 1H), 2.86-2.81 (m, 1H), 2.54 (s, 1H), 2.29 (s, 3H), 2.08-1.91 (m, 3H), 1.74 (s, 2H), 1.62-1.48 (m, 1H), 1.39-1.22 (m, 4H) | 97.9 | 495.0 |
| D1081 | 4-H₂N-phenyl-C(O)NHNH₂ | (500 MHz, DMSO) δ 8.48 (s, 1H), 7.70-7.65 (m, 2H), 7.62-7.58 (m, 2H), 7.45-7.41 (m, 2H), 7.31-7.27 (m, 1H), 6.71-6.67 (m, 2H), 5.85 (s, 2H), 2.30 (s, 3H) | 95.8 | 453.1 |
| D1082 | 2-H₂N-phenyl-C(O)NHNH₂ | (500 MHz, DMSO) δ 8.20 (s, 1H), 7.67-7.63 (m, 1H), 7.56 (d, J = 7.4 Hz, 2H), 7.41-7.37 (m, 2H), 7.28-7.19 (m, 2H), 6.90-6.85 (m, 1H), 6.70 (s, 2H), 6.68-6.62 (m, 1H), 2.33 (s, 3H) | 98.2 | 453.1 |
| D1083 | 3-(aminomethyl)piperidine-1-C(O)NHNH₂ | (500 MHz, DMSO) δ 7.60-7.57 (m, 2H), 7.44-7.40 (m, 2H), 7.31-7.26 (m, 1H), 3.95-3.91 (m, 1H), 3.80-3.72 (m, 2H), 3.22-3.14 (m, 1H), 3.11-3.03 (m, 1H), 2.92-2.76 (m, 4H), 2.55 (s, 1H), 2.22 (s, 3H), 1.97-1.84 (m, 2H), 1.31-1.21 (m, 1H), 1.13-1.04 (m, 1H) | 95.6 | 474.1 |

TABLE 14-continued
| Compound ID | Compound I-35 replacement | ¹H NMR | Purity (%) | MS (m/z) |
|---|---|---|---|---|
| D1084 | 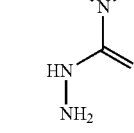 | (500 MHz, DMSO) δ 7.74 (s, 1H), 7.61-7.57 (m, 2H), 7.44-7.40 (m, 2H), 7.31-7.27 (m, 1H), 3.92-3.70 (m, 2H), 3.62-3.56 (m, 1H), 3.29-3.18 (m, 3H), 2.24 (s, 3H), 2.01-1.93 (m, 1H), 1.89-1.82 (m, 1H), 1.68-1.56 (m, 2H), 1.28-1.07 (m, 1H) | 98.1 | 460.1 |
| D1085 | 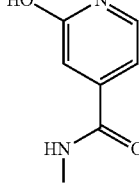 | (500 MHz, DMSO) δ 11.98 (s, 1H), 7.65-7.60 (m, 1H), 7.60-7.55 (m, 2H), 7.48-7.43 (m, 2H), 7.36-7.31 (m, 1H), 6.88-6.85 (m, 1H), 6.77-6.70 (m, 1H), 2.55 (s, 1H), 2.44 (s, 3H) | 97.4 | 455.1 |
| D1086 | 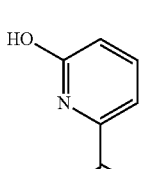 | (500 MHz, DMSO) δ 13.08 (s, 1H), 7.93-7.83 (m, 1H), 7.68-7.54 (m, 3H), 7.52-7.45 (m, 2H), 7.39 (s, 1H), 6.86-6.82 (m, 1H), 4.02 (s, 1H), 2.43 (s, 3H) | 96.2 | 455.1 |
| D1087 | 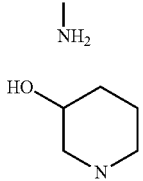 | (500 MHz, DMSO) δ 7.53-7.41 (m, 5H), 5.01 (s, 1H), 3.76-3.68 (m, 1H), 3.67-3.53 (m, 2H), 3.28-3.23 (m, 1H), 3.22-3.13 (m, 1H), 3.04-2.96 (m, 1H), 2.35 (s, 3H), 1.92-1.77 (m, 2H), 1.58-1.37 (m, 2H). | 97.0 | 461.1 |
| D1088 | 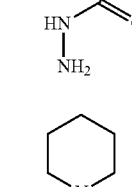
Also replace I-1 with
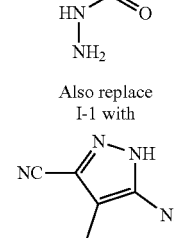
Also replace I-2 with
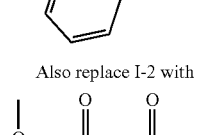 | | | |

TABLE 14-continued

| Compound ID | Compound I-35 replacement | ¹H NMR | Purity (%) | MS (m/z) |
|---|---|---|---|---|
| D1089 | 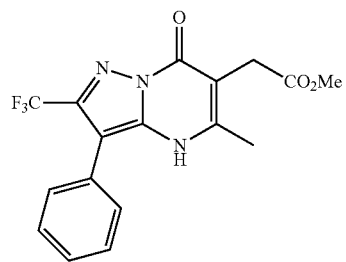 Also replace I-1 with | (500 MHz, DMSO) δ 8.00 (d, J = 7.0 Hz, 2H), 7.51-7.46 (m, 2H), 7.33-7.29 (m, 1H), 2.94 (s, 2H) 2.54 (s, 2H), 2.33 (s, 3H), 2.08-2.01 (m, 2H), 1.78-1.74 (m, 2H), 1.62-1.54 (m, 2H), 1.44-1.38 (m, 2H) | 96.8 | 401.3 |

Example 18

Synthesis of 6-(2-aminoethyl)-5-methyl-3-phenyl-2-(trifluoromethyl)pyrazolo[1,5-a]pyrimidin-7(4H)-one (B1012) and N-(2-(5-methyl-7-oxo-3-phenyl-2-(trifluoromethyl)-4,7-dihydropyrazolo[1,5-a]pyrimidin-6-yl)ethyl)acetamide (B1013) was carried out in four and five steps, respectively, as follows:

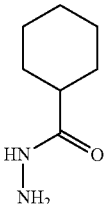

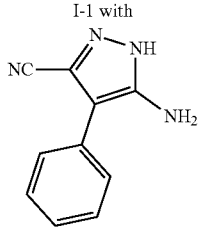

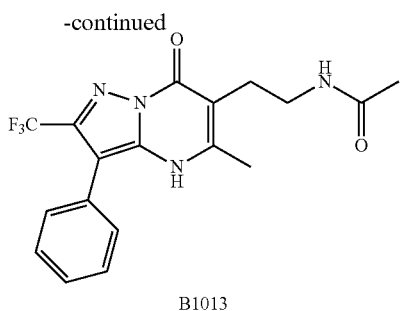

B1013

Step 1:

Synthesis of 6-(2-hydroxyethyl)-5-methyl-3-phenyl-2-(trifluoromethyl)pyrazolo[1,5-a]pyrimidin-7(4H)-one (I-36): Lithium aluminum hydride (457 µL, 12.4 mmol) was added to a white suspension of methyl 2-(5-methyl-7-oxo-3-phenyl-2-(trifluoromethyl)-4,7-dihydropyrazolo[1,5-a]pyrimidin-6-yl)acetate (I-7, 2.27 g, 6.21 mmol, see Example 2) in THF (60 mL). The solution was stirred at r.t. for 1.5 h. NaOH 2M (12 mL) was added and stirred at r.t. for 30 min. the mixture was filtered, washed with THF (2×15 mL), and the filtrate concentrated in vacuo. The crude material was purified by reverse phase chromatography (KP-C18-H5, 30 g, 0 to 100% MeCN in water 10 mM ammonium formate over 20 column volumes) to afford the compound I-36. $^1$HNMR (500 MHz, DMSO) δ 12.09 (s, 1H), 7.55-7.20 (m, 5H), 4.61 (t, J=5.6 Hz, 1H), 3.50 (dd, J=12.6, 6.8 Hz, 2H), 2.67 (t, J=6.9 Hz, 2H), 2.37 (s, 3H); MS (m/z): 338.0 [M+1]$^+$.

Step 2:

Synthesis of 2-(5-methyl-7-oxo-3-phenyl-2-(trifluoromethyl)-4,7-dihydropyrazolo[1,5-a]pyrimidin-6-yl)ethyl methanesulfonate (I-37): Methanesulfonyl chloride (127 µL, 1.63 mmol) was added to a solution of I-36 (500 mg, 1.48 mmol) and triethylamine (417 µL, 2.96 mmol) in THF (30 mL) at 0° C. The solution was stirred at 0° C. for 1.5 h. EtOAc (75 mL), water (50 mL) and HCl 10% (3 mL) were added and the layers were separated. The aqueous layer was extracted with EtOAc (2×50 mL). The combined organic layers were washed with brine (50 mL), dried over Na$_2$SO$_4$ and concentrated in vacuo. The solid was triturated with DCM (20 mL) for 15 min, filtered, washed with DCM (2×5 mL) and dried in vacuo to afford the compound I-37. $^1$HNMR (500 MHz, DMSO) δ 12.19 (s, 1H), 7.53-7.44 (m, 3H), 7.44-7.40 (m, 2H), 4.32 (t, J=6.7 Hz, 2H), 3.17 (s, 3H), 2.94 (t, J=6.7 Hz, 2H), 2.40 (s 3H). MS (m/z): 416.0 [M+1]$^+$.

Step 3:

Synthesis of 6-(2-azidoethyl)-5-methyl-3-phenyl-2-(trifluoromethyl)pyrazolo[1,5-a]pyrimidin-7(4H)-one (I-38): Sodium azide (37.7 µL, 578 mol) was added to a solution of I-37 (200 mg, 481 µmol) in DMF (3.00 mL). The solution was stirred at r.t. for 1 h. EtOAc (25 mL), water (25 mL) and 10% HCl (1 mL) were added and the layers were separated. The aqueous layer was extracted with EtOAc (2×25 mL). The combined organic layers were washed with brine (25 mL), dried over Na$_2$SO$_4$ and concentrated in vacuo to afford compound I-38. $^1$HNMR (400 MHz, DMSO) δ 12.19 (s, 1H), 7.54-7.38 (m, 5H), 3.47 (t, J=7.1 Hz, 2H), 2.79 (t, J=7.1 Hz, 2H), 2.41 (s, 3H). MS (m/z): 363.2 [M+1]$^+$.

Step 4:

Synthesis of 6-(2-aminoethyl)-5-methyl-3-phenyl-2-(trifluoromethyl)pyrazolo[1,5-a]pyrimidin-7(4H)-one (B1012): A mixture of I-38 (162 mg, 447 µmol), palladium on carbon 10% loading (200 mg, 188 µmol) in MeOH (10 mL) was hydrogenated under an atmosphere of hydrogen for 18 h. The mixture was filtered through celite, washed with MeOH (2×10 mL) and concentrated in vacuo to afford compound B1012. $^1$HNMR (400 MHz, DMSO) δ 7.76 (s, 2H), 7.58 (d, J=7.5 Hz, 2H), 7.38 (t, J=7.7 Hz, 2H), 7.23 (t, J=7.4 Hz, 1H), 2.93 (t, J=7.1 Hz, 2H), 2.80 (t, J=7.2 Hz, 2H), 2.26 (d, J=6.9 Hz, 3H).

Step 5:

Synthesis of N-(2-(5-methyl-7-oxo-3-phenyl-2-(trifluoromethyl)-4,7-dihydropyrazolo[1,5-a]pyrimidin-6-yl)ethyl)acetamide (B1013): Acetyl chloride (I-39, 10.3 µL, 143 µmol) was added to a solution of B1012 (40.0 mg, 119 µmol) and N,N-diisopropylethylamine (62.2 µL, 357 µmol) in DMF (2.00 mL). The yellow solution was stirred at r.t. for 17 h. EtOAc (25 mL), water (25 mL) and 10% HCl (1 mL) were added and the layers were separated. The aqueous layer was extracted with EtOAc (2×25 mL). The combined organic layers were washed with brine (25 mL), dried over Na$_2$SO$_4$ and concentrated in vazuo. Purification by reverse phase chromatography (KP-C18-H5, 12 g, 0 to 100% MeCN in water 10 mM ammonium formate over 40 column volumes) afforded compound B1013. $^1$HNMR (500 MHz, DMSO) δ 12.08 (s, 1H), 7.93 (t, J=5.8 Hz, 1H), 7.53-7.48 (m, 2H), 7.48-7.39 (m, 3H), 3.17 (dd, J=13.5 Hz, 6.5 Hz, 2H), 2.62 (t, J=7.1 Hz, 2H), 2.34 (s, 3H), 1.77 (s, 3H). MS (m/z): 379.1 [M+1]$^+$.

N-(2-(5-methyl-7-oxo-3-phenyl-2-(trifluoromethyl)-4,7-dihydropyrazolo[1,5-a]pyrimidin-6-yl)ethyl) benzamide (B1014)

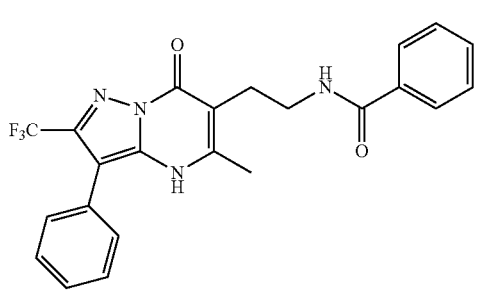

B1014 was prepared similarly, replacing I-39 with benzoyl chloride in Step 5.

6-(2-((3-methoxyphenyl)amino)ethyl)-5-methyl-3-phenyl-2-(trifluoromethyl)pyrazolo[1,5-a]pyrimidin-7(4H)-one (B1015)

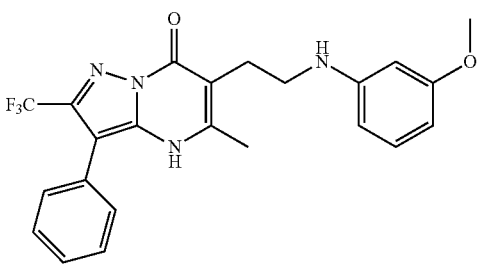

B1015 was prepared from compound I-38 (from Step 2 above) in one step as follows:

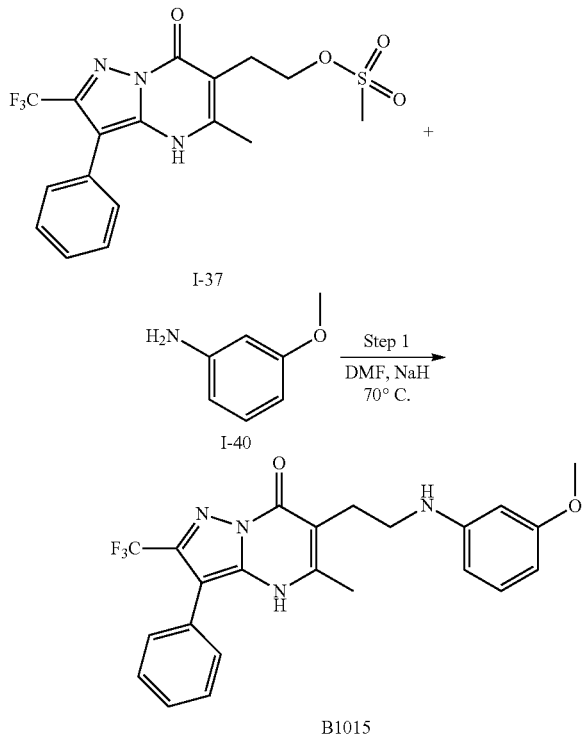

I-37

I-40

B1015

Step 1:

Sodium hydride (3.76 mg, 156 µmol) was added to a solution of I-37 (50.0 mg, 120 µmol) and m-anisidine (I-40, 17.1 µL, 144 µmol) in DMF (1.00 mL). The solution was heated at 70° C. for 45 min. EtOAc (25 mL), water (25 mL), and 10% HCl (1 mL) were added and the layers were separated. The aqueous layer was extracted with EtOAc (2×25 mL). The combined organic layers were washed with brine (25 mL), dried over $Na_2SO_4$ and concentrated in vacuo. Purification by reverse phase chromatography (KP-C18-H5, 12 g, 0 to 100% MeCN in water 10 mM ammonium formate over 20 column volumes) to afford Compound B1015. $^1$HNMR (400 MHz, DMSO) δ 8.17 (s, 1H), 7.54 (d, J=7.6 Hz, 2H), 7.40 (t, J=7.6 Hz, 2H), 7.28 (t, J=7.5 Hz, 1H), 6.94 (t, J=8.2 Hz, 1H), 6.23-6.15 (m, 2H), 6.10-6.03 (m, 1H), 5.79 (s, 1H), 3.67 (s, 3H), 3.15-3.05 (m, 2H), 2.75 (t, J=7.2 Hz, 2H), 2.27 (s, 3H). MS (m/z): 443.1 [M+1]$^+$.

Example 19: Synthesis of Triazolopyrimidinone Analogs

Triazolopyrimidinone analogs of the pyrazolopyrimidine compounds described in the above Examples 1-18, e.g. compounds of Formula Ia, can be prepared following similar methods, where the starting aminopyrazole, e.g. compound I-1 and similar starting materials used in Examples 1-18 can be replaced with the corresponding aminotriazole to provide the desired compounds. For example, 6-(4-methoxybenzo[d]oxazol-2-yl)-5-methyl-3-phenyl-[1,2,3]triazolo[1,5-a]pyrimidin-7(4H)-one (E1001) was prepared following the procedure of Example 4, starting with 4-phenyl-1H-1,2,3-triazol-5-amine (I-41) in place of 4-phenyl-3-(trifluoromethyl)-1H-pyrazol-5-amine (I-1) in Step 1 of Example 3
Step 1:

Synthesis of 5-methyl-3-phenyl-[1,2,3]triazolo[1,5-a]pyrimidin-7(4H)-one (I-42): 4-phenyl-1H-1,2,3-triazol-5-amine (I-41) was reacted with ethyl acetoacetate (I-10) according to the methods described in Step 1 of Example 3 to provide the desired compound I-42.

Step 2:

Synthesis of 6-iodo-5-methyl-3-phenyl-[1,2,3]triazolo[1,5-a]pyrimidin-7(4H)-one (I-43): Compound I-42 was reacted according to the methods described in Step 1 of Example 4 to provide the desired compound I-43.

Step 3:

Synthesis of 6-(4-methoxybenzo[d]oxazol-2-yl)-5-methyl-3-phenyl-[1,2,3]triazolo[1,5-a]pyrimidin-7(4H)-one (E1001): Compound I-43 was reacted with 4-methoxybenzo[d]oxazole (I-15) according to the methods described in Step 2 of Example 4 to provide the desired compound E1001. $^1$HNMR (500 MHz, DMSO) δ 8.40-8.33 (m, 3H), 7.48-7.41 (m, 2H), 7.30-7.26 (m, 2H), 7.23 (t, J=7.4 Hz, 1H), 6.94-6.89 (m, 1H), 4.02 (s, 3H), 2.49 (s, 3H). MS (m/z): 374.1 [M+1]$^+$, 94%.

Example 20: cGAS Biochemical Activity Assay

Human cGAS sequence encoding amino acids 155-522 was cloned into a pET (EMD Millipore) based expression plasmid. The resulting construct contained a tandem N-terminal hexahistidine tag, maltose binding protein fusion followed by a tobacco etch virus protease cleavable linker preceding cGAS amino acids 155-522.

Construct sequence: Amino acids 155-522. Human cGAS
SEQ. ID No. 1
DAAPGASKLRAVLEKLKLSRDDISTAAGMVKGVVDHLLLRLKCDSAFRGVG

LLNTGSYYEHVKISAPNEFDVMFKLEVPRIQLEEYSNTRAYYFVKFKRNPK

ENPLSQFLEGEILSASKMLSKFRKIIKEEINDIKDTDVIMKRKRGGSPAVT

LLISEKISVDITLALESKSSWPASTQEGLRIQNWLSAKVRKQLRLKPFYLV

PKHAKEGNGFQEETWRLSFSHIEKEILNNHGKSKTCCENKEEKCCRKDCLK

LMKYLLEQLKERFKDKKHLDKFSSYHVKTAFFHVCTQNPQDSQWDRKDLGL

CFDNCVTYFLQCLRTEKLENYFIPEFNLFSSNLIDKRSKEFLTKQIEYERN

NEFPVFDEF,

Protein was expressed and purified from *E. coli* BL21 DE3 Rosetta 2 (EMD Millipore) cells using standard techniques. Cells were grown in 2× yeast extract tryptone medium and expression was initiated via the addition of isopropyl β-D-1-thiogalactopyranoside. Expression proceeded overnight at 18° C. Cells were harvested by centrifugation and subsequently lysed via sonication. Insoluble fraction was removed by centrifugation. Maltose binding protein (MBP) fusion proteins were purified on a dextrin sepharose column (GE Healthcare) and the MBP tag was removed using tobacco etch virus protease overnight during dialysis. Protein was further purified on a heparin column (GE Healthcare) and eluted using a NaCl gradient. Column fraction were pooled and further purified on a Superdex 75 gel filtration column (GE Healthcare). Protein was quantified using 280 nm absorbance. Protein was then flash frozen in liquid nitrogen and stored at −80° C. until use.

Potential antagonists were diluted in 100% dimethyl sulfoxide and added to the reaction. Final dimethyl sulfoxide concentration was 5%. The compounds were tested from 1 µM with either 3- or 4-fold serial dilutions down to 0.000051 or 0.000004 µM respectively.

Two complementary DNA oligos (IDT DNA) were annealed by slow cooling from 95° C. The resulting double stranded DNA was used to activate cGAS.

Top strand oligo:
SEQ. ID No. 2
5'-TACAGATCTACTAGTGATCTATGACTGATCTGTACATGATCTACA-3'

Bottom strand oligo:
SEQ. ID No. 3
3'-TGTAGATCATGTACAGATCAGTCATAGATCACTAGTAGATCTGTA-3'

Reactions were performed at 37° C. for 1.25 hours. Reaction buffer: 20 mM Tris HCl pH 9, 100 mM NaCl, 5 mM $MgCl_2$, 0.1 mg/ml bovine gamma globulin, 250 µM adenosine triphosphate, 100 µM guanosine triphosphate, 0.5 mM Tris(2-carboxyethyl)phosphine hydrochloride, 1 µM double stranded DNA and 300 nM purified cGAS protein.

Reactions were stopped and ATP levels in the reaction were measured using a luciferase based assay. Promega Kinase-Glo Max Assay. Luminescence was measured on a plate reader (Molecular Devices). Values were normalized to control wells lacking compound.

Table 15 below provides $IC_{50}$ data for certain compounds of the invention on cGAS. "A" indicates an $IC_{50}$ value between less than 20 µM, "B" indicates an $IC_{50}$ value between 20 and 250 µM, and "C" indicates an $IC_{50}$ above the upper limit of the assay (250 µM), or where an $IC_{50}$ value could not be generated from the data.

TABLE 15

| Compound ID | cGAS $IC_{50}$ (µM) |
| --- | --- |
| A1001 | B |
| A1002 | A |
| A1003 | C |
| A1004 | C |
| A1005 | B |
| A1006 | A |
| A1007 | B |
| A1008 | B |
| A1009 | C |
| A1010 | B |
| A1011 | C |
| A1012 | B |
| A1013 | C |
| A1014 | B |
| A1015 | B |
| A1016 | B |
| A1017 | A |
| A1018 | B |
| A1019 | C |
| A1020 | B |
| A1021 | B |
| A1022 | A |
| A1023 | B |
| A1024 | A |
| A1025 | B |
| A1026 | B |
| A1027 | B |
| A1028 | A |
| A1029 | A |
| A1030 | A |
| A1031 | A |
| A1032 | A |
| A1033 | B |
| A1034 | C |
| A1035 | C |
| A1036 | B |
| A1037 | B |
| A1038 | B |
| A1039 | B |
| A1040 | B |

TABLE 15-continued

| Compound ID | cGAS $IC_{50}$ (µM) |
| --- | --- |
| A1041 | B |
| A1042 | B |
| A1043 | B |
| A1044 | B |
| A1045 | A |
| A1046 | B |
| A1047 | B |
| A1048 | B |
| A1049 | B |
| A1050 | B |
| A1051 | A |
| A1052 | B |
| A1053 | B |
| A1054 | B |
| A1055 | B |
| A1056 | A |
| A1057 | B |
| A1058 | B |
| A1059 | A |
| A1060 | B |
| A1061 | B |
| A1062 | A |
| A1063 | A |
| A1064 | A |
| A1065 | A |
| A1066 | A |
| A1067 | A |
| A1068 | B |
| A1069 | A |
| A1070 | A |
| A1071 | B |
| A1072 | B |
| A1073 | B |
| A1074 | A |
| A1075 | A |
| A1076 | A |
| A1077 | A |
| A1078 | B |
| A1079 | A |
| A1080 | B |
| A1081 | A |
| A1082 | A |
| A1083 | A |
| A1084 | A |
| A1085 | B |
| A1086 | A |
| A1087 | B |
| A1088 | B |
| A1089 | A |
| A1090 | A |
| A1091 | B |
| A1092 | B |
| A1093 | B |
| A1094 | A |
| A1095 | A |
| A1096 | A |
| A1097 | B |
| A1098 | B |
| A1099 | B |
| A1100 | A |
| A1101 | A |
| A1102 | A |
| A1103 | B |
| A1104 | A |
| A1105 | A |
| A1106 | A |
| A1107 | A |
| A1108 | B |
| A1109 | B |
| A1110 | A |
| A1111 | A |
| A1112 | A |
| A1113 | B |
| A1114 | C |
| A1115 | B |
| A1116 | A |
| A1117 | B |

TABLE 15-continued

| Compound ID | cGAS IC$_{50}$ (μM) |
|---|---|
| A1118 | B |
| A1119 | B |
| A1120 | A |
| A1121 | A |
| A1122 | B |
| A1123 | C |
| A1124 | A |
| A1125 | A |
| A1126 | C |
| A1127 | A |
| A1128 | A |
| A1129 | A |
| A1130 | B |
| A1131 | B |
| A1132 | A |
| A1133 | A |
| A1134 | A |
| A1135 | A |
| A1136 | A |
| A1137 | B |
| A1138 | B |
| A1139 | A |
| A1140 | B |
| B1001 | B |
| B1002 | C |
| B1003 | C |
| B1004 | B |
| B1005 | B |
| B1006 | B |
| B1007 | C |
| B1008 | B |
| B1009 | C |
| B1010 | B |
| B1011 | B |
| B1013 | B |
| B1014 | B |
| B1015 | A |
| C1001 | B |
| C1002 | B |
| C1003 | B |
| C1004 | B |
| C1005 | B |
| C1006 | C |
| C1007 | B |
| C1008 | B |
| C1009 | A |
| C1010 | C |
| C1011 | C |
| C1012 | C |
| C1013 | C |
| C1014 | A |
| C1015 | C |
| C1016 | A |
| C1017 | A |
| C1018 | A |
| C1019 | A |
| C1020 | B |
| C1021 | B |
| C1022 | A |
| C1023 | A |
| C1024 | A |
| C1025 | A |
| C1026 | B |
| C1027 | A |
| C1028 | C |
| C1029 | B |
| C1030 | A |
| C1032 | A |
| C1033 | A |
| C1034 | C |
| C1035 | C |
| C1036 | C |
| C1037 | A |
| C1038 | A |
| C1039 | A |
| C1040 | A |
| C1041 | A |
| C1042 | A |
| C1043 | C |
| C1044 | A |
| C1045 | A |
| C1046 | A |
| C1047 | A |
| C1048 | A |
| C1049 | B |
| C1050 | A |
| C1051 | A |
| C1052 | A |
| C1053 | A |
| C1054 | B |
| C1055 | A |
| C1056 | A |
| C1057 | A |
| C1058 | A |
| C1059 | A |
| C1060 | A |
| C1061 | B |
| C1062 | A |
| C1063 | C |
| C1064 | B |
| C1065 | B |
| C1066 | A |
| C1067 | C |
| C1068 | B |
| C1070 | A |
| C1071 | A |
| C1072 | B |
| C1073 | A |
| C1074 | B |
| C1075 | A |
| C1076 | A |
| C1077 | A |
| C1078 | A |
| C1079 | C |
| C1080 | B |
| C1081 | A |
| C1082 | A |
| C1083 | C |
| C1084 | A |
| C1085 | A |
| C1086 | C |
| C1087 | B |
| C1088 | A |
| C1089 | A |
| C1090 | B |
| C1091 | A |
| C1092 | A |
| C1093 | A |
| C1094 | A |
| C1095 | A |
| C1096 | A |
| C1097 | A |
| C1098 | A |
| C1099 | A |
| C1100 | A |
| C1101 | A |
| C1102 | B |
| C1103 | A |
| C1104 | A |
| C1105 | A |
| C1106 | A |
| C1107 | C |
| C1108 | A |
| C1109 | A |
| C1110 | B |
| C1111 | A |
| C1112 | B |
| C1113 | A |
| C1114 | A |
| C1115 | B |
| C1116 | A |
| C1117 | A |
| C1118 | A |
| C1119 | A |

TABLE 15-continued

| Compound ID | cGAS IC$_{50}$ (μM) |
|---|---|
| C1120 | B |
| C1121 | A |
| C1122 | A |
| C1123 | A |
| C1125 | A |
| C1126 | A |
| C1127 | B |
| C1128 | C |
| C1129 | B |
| C1130 | A |
| C1131 | A |
| C1132 | A |
| C1133 | B |
| C1134 | A |
| C1135 | A[1] |
| C1136 | A |
| C1137 | A |
| C1138 | A |
| C1139 | A |
| C1140 | B |
| C1141 | A |
| C1142 | A |
| C1143 | A |
| C1144 | B |
| C1145 | A |
| C1146 | A |
| C1147 | B |
| C1148 | B |
| C1149 | A |
| C1150 | B |
| C1151 | A |
| C1152 | A |
| C1153 | A |
| C1154 | A |
| C1155 | A |
| C1156 | A |
| C1157 | A |
| C1158 | C |
| C1159 | A |
| C1160 | A |
| C1161 | A |
| C1162 | A |
| C1163 | A |
| C1164 | C |
| C1165 | A |
| C1166 | A |
| C1167 | A |
| C1168 | B |
| C1169 | A |
| C1170 | A |
| C1171 | B |
| C1172 | A |
| C1173 | A |
| C1174 | A |
| C1175 | A |
| C1176 | B |
| C1177 | A |
| C1178 | A |
| C1179 | B |
| C1180 | A |
| C1181 | A |
| C1182 | A |
| C1183 | A |
| C1184 | A |
| C1185 | A |
| C1186 | B |
| C1187 | A |
| C1188 | A |
| C1189 | B |
| C1190 | B |
| C1191 | C |
| C1192 | A |
| C1193 | A |
| C1194 | A |
| C1195 | A |
| C1196 | A |
| C1197 | B |
| C1198 | B |
| C1199 | B |
| C1200 | B |
| C1201 | B |
| C1202 | A |
| C1203 | A |
| C1204 | A |
| C1205 | A |
| C1206 | A |
| C1207 | B |
| C1208 | B |
| C1209 | A |
| C1210 | A |
| C1211 | A |
| C1212 | B |
| C1213 | A |
| C1214 | B |
| C1215 | B |
| C1216 | A |
| C1217 | B |
| C1218 | A |
| C1219 | A |
| C1220 | B |
| C1221 | B |
| C1222 | A |
| C1223 | A |
| C1224 | A |
| C1225 | A |
| C1226 | A |
| C1227 | A |
| C1228 | B |
| C1229 | B |
| C1230 | A |
| C1231 | B |
| C1232 | A |
| C1233 | A |
| C1234 | A |
| C1235 | B |
| C1236 | A |
| C1237 | B |
| C1238 | B |
| C1239 | A |
| C1240 | A |
| C1241 | A |
| C1242 | C |
| C1243 | A |
| C1244 | A |
| C1245 | A |
| C1246 | A |
| C1247 | A |
| C1248 | A |
| C1249 | A |
| C1250 | A |
| C1251 | A |
| C1252 | A |
| C1253 | A |
| C1254 | A |
| C1255 | A |
| C1256 | A |
| C1257 | A |
| C1258 | A |
| C1259 | A |
| C1264 | C |
| C1265 | C |
| C1266 | C |
| C1267 | C |
| C1268 | C |
| C1269 | C |
| C1270 | A |
| C1271 | A |
| C1272 | A |
| C1273 | A |
| C1274 | A |
| C1275 | A |
| C1276 | A |
| C1277 | A |
| C1284 | A |

TABLE 15-continued

| Compound ID | cGAS IC$_{50}$ (µM) |
|---|---|
| D1001 | B |
| D1002 | C |
| D1003 | A |
| D1004 | A |
| D1005 | B |
| D1006 | A |
| D1007 | C |
| D1008 | B |
| D1009 | B |
| D1011 | C |
| D1012 | A |
| D1013 | B |
| D1014 | A |
| D1015 | B |
| D1016 | A |
| D1017 | C |
| D1018 | A |
| D1019 | A |
| D1020 | A |
| D1021 | A |
| D1021 Iso-1 | |
| D1021 Iso-2 | A |
| D1022 | A |
| D1023 | A |
| D1024 | A |
| D1025 | A |
| D1026 | A |
| D1027 | A |
| D1028 | A |
| D1029 | A |
| D1030 | A |
| D1031 | B |
| D1032 | B |
| D1033 | B |
| D1034 | B |
| D1035 | B |
| D1036 | B |
| D1037 | A |
| D1038 | A |
| D1039 | B |
| D1040 | A |
| D1041 | B |
| D1042 | B |
| D1043 | C |
| D1044 | B |
| D1045 | B |
| D1046 Iso-1 | A |
| D1046 Iso-2 | A |
| D1046 Iso-3 | A |
| D1047 | A |
| D1048 | B |
| D1049 Iso-1 | A |
| D1049 Iso-2 | A |
| D1050 | B |
| D1051 | B |
| D1052 | B |
| D1053 | B |
| D1054 | B |
| D1055 | A |
| D1056 | A |
| D1057 | A |
| D1058 | B |
| D1059 | B |
| D1060 | B |
| D1061 | B |
| D1062 | A |
| D1063 | B |
| D1064 | C |
| D1065 | B |
| D1066 | A |
| D1067 | A |
| D1068 | B |
| D1069 | B |
| D1070 | A |
| D1071 | A |
| D1072 | A |
| D1073 | A |
| D1074 | A |
| D1075 | B |
| D1076 | B |
| D1077 | A |
| D1078 | A |
| D1079 | C |
| D1080 | C |
| D1081 | C |
| D1082 | B |
| D1083 | B |
| D1084 | A |
| D1085 | A |
| D1086 | A |
| D1087 | B |
| D1089 | A |
| E1001 | A |

[1]HCl salt of the insoluble free base (C1128)

Example 21: THP1 Cell-Based cGAS/STING Pathway Activity Assay

A cellular assay can be used to assess the compounds of the invention for their ability to inhibit the cGAS/STING pathway. Cells that express a luciferase-based reporter that is linked to IRF-3 activation are used to determine response as a function of compound concentration. Such an assay is described in Vincent et al., Nature Communications 2017, 8(1):750, doi: 10.1038/s41467-017-00833-9. Compounds of the invention were assessed using similar assay methods in a THP1 cell assay to generate IC$_{50}$ values as provided in the following Table 16. In this table, activity level "A" indicates an IC$_{50}$ value less than 20 µM, "B" indicates an IC$_{50}$ value between 20 and 100 µM, and "C" indicates an IC$_{50}$ value above the upper limit of the assay (100 µM), or where an IC$_{50}$ value could not be generated from the data.

TABLE 16

| Compound ID | THP-1 IC$_{50}$ (µM) |
|---|---|
| A1002 | B |
| A1006 | C |
| A1023 | B |
| A1028 | B |
| A1029 | B |
| A1031 | C |
| A1032 | A |
| A1033 | B |
| A1048 | B |
| A1051 | B |
| A1056 | B |
| A1059 | A |
| A1062 | A |
| A1063 | B |
| A1064 | B |
| A1065 | B |
| A1066 | A |
| A1067 | C |
| A1068 | C |
| A1069 | B |
| A1070 | A |
| A1072 | B |
| A1073 | C |

TABLE 16-continued

| Compound ID | THP-1 IC$_{50}$ ($\mu$M) |
|---|---|
| A1074 | C |
| A1075 | B |
| A1076 | B |
| A1077 | C |
| A1079 | C |
| A1081 | B |
| A1082 | A |
| A1083 | C |
| A1084 | B |
| A1088 | B |
| A1089 | C |
| A1095 | A |
| A1096 | B |
| A1099 | C |
| A1100 | B |
| A1101 | A |
| A1102 | C |
| A1104 | B |
| A1106 | C |
| A1107 | A |
| A1110 | C |
| A1111 | C |
| A1112 | B |
| A1113 | C |
| A1115 | C |
| A1116 | B |
| A1117 | C |
| A1118 | C |
| A1120 | C |
| A1121 | C |
| A1124 | C |
| A1125 | B |
| A1127 | B |
| A1128 | C |
| A1129 | B |
| A1132 | B |
| A1134 | A |
| A1135 | A |
| A1136 | B |
| A1139 | A |
| B1010 | B |
| B1011 | B |
| C1005 | C |
| C1008 | C |
| C1009 | B |
| C1010 | A |
| C1011 | A |
| C1012 | A |
| C1013 | A |
| C1014 | A |
| C1015 | A |
| C1016 | A |
| C1017 | B |
| C1018 | C |
| C1019 | B |
| C1020 | C |
| C1022 | B |
| C1023 | C |
| C1024 | B |
| C1025 | C |
| C1026 | A |
| C1027 | B |
| C1030 | C |
| C1032 | B |
| C1033 | C |
| C1037 | A |
| C1038 | A |
| C1039 | C |
| C1040 | A |
| C1041 | A |
| C1042 | A |
| C1045 | A |
| C1046 | A |
| C1047 | A |
| C1048 | B |
| C1050 | A |
| C1051 | B |

TABLE 16-continued

| Compound ID | THP-1 IC$_{50}$ ($\mu$M) |
|---|---|
| C1052 | B |
| C1053 | B |
| C1054 | C |
| C1055 | A |
| C1056 | A |
| C1057 | C |
| C1058 | C |
| C1059 | C |
| C1060 | A |
| C1061 | B |
| C1062 | C |
| C1064 | A |
| C1065 | C |
| C1066 | C |
| C1070 | A |
| C1071 | A |
| C1073 | A |
| C1074 | C |
| C1075 | C |
| C1076 | A |
| C1077 | A |
| C1078 | A |
| C1079 | A |
| C1081 | A |
| C1082 | A |
| C1084 | A |
| C1085 | C |
| C1088 | B |
| C1089 | A |
| C1091 | A |
| C1092 | C |
| C1093 | B |
| C1094 | A |
| C1095 | C |
| C1096 | C |
| C1097 | C |
| C1098 | A |
| C1099 | A |
| C1100 | B |
| C1101 | B |
| C1103 | B |
| C1104 | C |
| C1105 | A |
| C1106 | B |
| C1107 | A |
| C1108 | C |
| C1109 | C |
| C1111 | A |
| C1112 | C |
| C1113 | A |
| C1114 | A |
| C1116 | C |
| C1117 | C |
| C1118 | A |
| C1119 | A |
| C1121 | A |
| C1122 | B |
| C1123 | B |
| C1125 | B |
| C1126 | B |
| C1130 | B |
| C1131 | C |
| C1132 | C |
| C1134 | A |
| C1135 | C |
| C1136 | A |
| C1137 | C |
| C1138 | C |
| C1139 | A |
| C1141 | C |
| C1143 | C |
| C1145 | A |
| C1146 | C |
| C1149 | B |
| C1151 | A |
| C1152 | B |
| C1153 | B |

TABLE 16-continued

| Compound ID | THP-1 IC$_{50}$ (μM) |
|---|---|
| C1154 | A |
| C1155 | B |
| C1156 | B |
| C1157 | A |
| C1159 | C |
| C1160 | C |
| C1161 | A |
| C1162 | A |
| C1163 | C |
| C1165 | C |
| C1166 | B |
| C1167 | A |
| C1169 | B |
| C1170 | C |
| C1173 | B |
| C1174 | C |
| C1175 | B |
| C1177 | B |
| C1178 | A |
| C1180 | C |
| C1181 | C |
| C1182 | C |
| C1183 | A |
| C1184 | C |
| C1185 | B |
| C1187 | C |
| C1188 | A |
| C1193 | C |
| C1194 | C |
| C1195 | C |
| C1202 | B |
| C1203 | C |
| C1204 | C |
| C1205 | C |
| C1206 | C |
| C1209 | C |
| C1211 | C |
| C1213 | B |
| C1216 | C |
| C1218 | C |
| C1219 | C |
| C1222 | B |
| C1223 | B |
| C1224 | C |
| C1226 | B |
| C1227 | C |
| C1229 | A |
| C1230 | C |
| C1231 | A |
| C1232 | B |
| C1233 | A |
| C1234 | C |
| C1240 | A |
| C1241 | A |
| C1243 | A |
| C1244 | A |
| C1245 | C |
| C1246 | C |
| C1248 | C |
| C1249 | C |
| C1250 | C |
| C1251 | C |
| C1252 | C |
| C1253 | B |
| C1254 | C |
| C1255 | C |
| C1256 | C |
| C1257 | C |
| C1258 | A |
| C1259 | C |
| C1269 | B |
| C1271 | C |
| C1272 | A |
| C1273 | A |
| C1274 | C |
| C1275 | C |
| D1004 | C |
| D1007 | B |
| D1008 | C |
| D1012 | C |
| D1014 | C |
| D1015 | C |
| D1016 | C |
| D1018 | B |
| D1019 | C |
| D1020 | C |
| D1021 | B |
| D1021 Iso-1 | C |
| D1021 Iso-2 | |
| D1022 | C |
| D1023 | C |
| D1024 | C |
| D1025 | B |
| D1026 | C |
| D1027 | C |
| D1028 | C |
| D1029 | C |
| D1030 | C |
| D1038 | A |
| D1040 | C |
| D1041 | C |
| D1042 | C |
| D1046 | A |
| D1046 Iso-1 | |
| D1046 Iso-3 | C |
| D1047 | C |
| D1048 | C |
| D1049 | C |
| D1049 Iso-2 | |
| D1050 | C |
| D1051 | C |
| D1055 | B |
| D1056 | C |
| D1057 | B |
| D1062 | C |
| D1070 | C |
| D1071 | A |
| D1072 | C |
| D1077 | C |
| D1078 | C |
| D1085 | C |
| D1086 | C |

Example 22: Inhibition of Cytokine Secretion by Trex1-Knockout (KO) Bone Marrow-Derived Macrophages (BMMs)

The inhibition of secreted cytokine was measured in bone marrow-derived macrophages (BMMs) from diseased mice to evaluate the potency of compounds of the invention as described herein. Mice lacking the gene for Trex1 protein (trex1−/− or Trex1-KO) exhibit cGAS/STING pathway-dependent autoimmune and autoinflammatory disease manifestations, including enhanced cytokine secretion by cells. To derive bone marrow macrophages, marrow extracted from the femurs and tibias were harvested from Trex1-KO mice was cultured in growth media supplemented with macrophage colony-stimulating factor (M-CSF). Differentiated BMM were harvested and frozen for subsequent experimentation. For treatment with compound C1089 (see Example 13), a frozen stock of Trex1-KO BMM was thawed and 1×10$^5$ cells were plated in 96 well format. BMMs were treated with a dilution series of C1089 and incubated overnight at 37° C. 5% CO$_2$, at which point cellular supernatants were harvested and stored at −80° C. for subsequent analysis. The media used for this dilution series was without FBS. Remaining cells were evaluated for viability using Cell Titer Glo 2.0 kit according to the manufacturer instructions. BMM supernatants were evaluated for the secreted cytokine normal T cell expressed and secreted (RANTES/CCL5) or for secreted cytokine monocyte chemoattractant protein 1 (MCP-1/CCL2) using cytometric bead array mouse Flex Set kits (BD Biosciences). Cytokine concentration was calculated from a standard curve and normalized to vehicle (DMSO) treated cells.

FIG. 1 shows that C1089 can significantly inhibit cytokine secretion by diseased Trex1-KO BMM (RANTES/CCL5 $IC_{50}$=1.251 µM, MCP-1/CCL2 $IC_{50}$=6.973 µM). Additionally, BMM were 100% viable at these concentrations, indicating that inhibition is not simply due to cellular cytotoxicity. Additional compounds were assessed by this assay.

Table 17 below provides $IC_{50}$ data for certain compounds of the invention for inhibition of RANTES expression. "A" indicates an $IC_{50}$ value less than 5 µM, "B" indicates an $IC_{50}$ value between 5 and 20 µM, and "C" indicates where an $IC_{50}$ value could not be calculated from the data. ND indicates no data for that cytokine. In this table, column M refers to MCP-1 and column R refers to RANTES.

TABLE 17

| Compound ID | BMM $IC_{50}$ (µM) | |
|---|---|---|
|  | M | R |
| A1052 | C | ND |
| A1059 | C | ND |
| A1082 | C | C |
| A1095 | C | C |
| A1129 | B | C |
| A1134 | A | A |
| A1139 | C | C |
| C1008 | C | ND |
| C1014 | C | ND |
| C1029 | C | C |
| C1045 | C | B |
| C1047 | B | A |
| C1053 | C | C |
| C1055 | C | C |
| C1056 | C | ND |
| C1071 | C | C |
| C1073 | C | C |
| C1074 | C | C |
| C1077 | C | C |
| C1081 | B | B |
| C1082 | C | C |
| C1091 | C | C |
| C1092 | C | C |
| C1094 | C | A |
| C1098 | B | A |
| C1099 | C | C |
| C1105 | B | A |
| C1113 | A | C |
| C1114 | B | C |
| C1117 | C | C |
| C1118 | C | A |
| C1119 | C | C |
| C1121 | A | C |
| C1123 | C | C |
| C1126 | C | C |
| C1134 | B | C |
| C1136 | B | C |
| C1139 | B | B |
| C1140 | C | C |
| C1145 | C | C |
| C1147 | C | C |
| C1151 | C | B |
| C1154 | C | C |
| C1160 | C | C |
| C1167 | C | C |
| C1169 | C | C |
| C1173 | C | C |
| C1175 | C | C |
| C1176 | C | C |
| C1190 | C | C |
| C1205 | C | C |
| C1233 | C | C |
| C1236 | C | C |
| D1018 | C | C |
| D1028 | C | C |
| D1071 | B | A |

INCORPORATION BY REFERENCE

The disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (I):

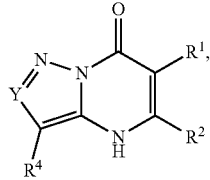

or a pharmaceutically acceptable salt, pharmaceutically acceptable solvate or pharmaceutically acceptable hydrate thereof, wherein Y is —$CR^3$= or —N=;

$R^1$ is $Q^1$-$T^1$-$(X)_n$;

$Q^1$ is a bond or $C_{1-3}$alkylene, wherein the $C_{1-3}$alkylene group is optionally substituted with one or more substituents independently selected from the group consisting of halo, $C_{1-6}$alkyl, $C_{2-6}$alkenyl, $C_{2-6}$alkynyl, cyano, $C_{1-6}$haloalkyl, —$OR^{w2}$, and —$NR^{w2}R^{x2}$;

$T^1$ is $C_{3-8}$cycloalkyl, $C_{6-10}$aryl, 3- to 12-membered heterocycloalkyl, 5- to 10-membered heteroaryl, —C(=O)$C_{0-3}$alkylene-$C_{3-8}$cycloalkyl, —C(=O)—$C_{0-3}$alkylene-$C_{6-10}$aryl, —C(=O)—$C_{0-3}$alkylene-3 to 12-membered heterocycloalkyl, —C(=O)—$C_{0-3}$alkylene-5 to 10-membered heteroaryl, —$NR^aR^b$, —S(=O)$_2R^a$, —$NR^aC(=O)R^a$, —$NR^aC(=O)NR^aR^b$, —$NR^aC(=O)OR^a$, —$NR^aS(=O)_2R^a$, —C(=O)$NR^aS(=O)_2R^a$, —$NR^aS(=O)_2NR^aR^b$, —C(=O)$NR^aR^b$, or —S(=O)$_2NR^aR^b$;

each $X^1$ is independently selected from the group consisting of halo, cyano, oxo, $C_{0-3}$alkylene-C(=O)$R^c$, $C_{0-3}$alkylene-$OR^c$, $C_{0-3}$alkylene-C(=O)$OR^c$, $C_{0-3}$alkylene-OC(=O)$R^c$, $C_{0-3}$alkylene-$NR^cR^d$, $C_{0-3}$alkylene-$N^+R^cR^dR^{d'}$, $C_{0-3}$alkylene-S(=O)$_mR^c$, $C_{0-3}$alkylene-$NR^cC(=O)R^c$, $C_{0-3}$alkylene-$NR^cC(=O)NR^cR^d$, $C_{0-3}$alkylene-OC(=O)$NR^cR^d$, $C_{0-3}$alkylene-$NR^cC(=O)OR^c$, $C_{0-3}$alkylene-$NR^cS(=O)_2R^c$, $C_{0-3}$alkylene-C(=O)$NR^cS(=O)_2R^c$, $C_{0-3}$alkylene-$NR^cS(=O)_2NR^cR^d$, $C_{0-3}$alkylene-C(=O)$NR^cR^d$, $C_{0-3}$alkylene-S(=O)$_2NR^cR^d$, $C_{0-3}$alkylene-C(=$NR^c$)$NR^cR^d$, $C_{0-3}$alkylene-$NR^cC(=NR)NR^cR^d$, and $R^{S1}$, in which $R^{S1}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S1}$ is optionally substituted with one or more substituents independently selected from the group consisting of halo, cyano, nitro, oxo, $C_{1-6}$alkyl, $C_{2-6}$alkenyl, $C_{2-6}$alkynyl, $C_{1-6}$haloalkyl, $C_{0-3}$alkylene-$NR^eR^f$, $C_{0-3}$alkylene-$OR^e$, $C_{0-3}$alkylene-$NR^eC(=O)R^e$, $C_{0-3}$alkylene-$NR^eC(=O)OR^e$, $C_{0-3}$alkylene-$NR^eC(=O)NR^eR^f$, $C_{0-3}$alkylene-OC(=O)$R^e$, $C_{0-3}$alkylene-C(=O)$OR^e$, $C_{0-3}$alkylene-C(=O)$NR^eR^f$, $C_{0-3}$alkylene-C(=O)$R^e$, $C_{0-3}$alkylene-S(=O)$_mR^e$, $C_{0-3}$alkylene-S(=O)$_2NR^eR^f$, $C_{0-3}$alkylene-$NR^eS(=O)_2R^e$, $C_{0-3}$alkylene-C(=O)$NR^eS(=O)_2R^e$, $C_{0-3}$alkylene-$NR^eS(=O)_2NR^eR^f$, and $R^{S2}$, in which $R^{S2}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl, and each $R^{S2}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^w$, and —$NR^wR^x$;

$R^2$ is $Q^2$-$T^2$-$(X^2)_p$;

$Q^2$ is a bond or $C_{1-3}$alkylene, wherein the $C_{1-3}$alkylene group is optionally substituted with one or more substituents independently selected from the group consisting of halo, $C_{1-6}$alkyl, $C_{2-6}$alkenyl, $C_{2-6}$alkynyl, cyano, $C_{1-6}$haloalkyl, —$OR^{w3}$, and —$NR^{w3}R^{x3}$;

$T^2$ is H, halo, cyano, $C_{1-6}$alkyl, $C_{2-6}$alkenyl, $C_{2-6}$alkynyl, $C_{3-8}$cycloalkyl, $C_{6-10}$aryl, 3- to 12-membered heterocycloalkyl, 5- to 10-membered heteroaryl, —C(=O)—$C_{0-3}$alkylene-$C_{3-8}$cycloalkyl, —C(=O)—$C_{0-3}$alkylene-$C_{6-10}$aryl, —C(=O)—$C_{0-3}$ alkylene-3- to 12-membered heterocycloalkyl, —C(=O)—$C_{0-3}$alkylene-5- to 10-membered heteroaryl, —$OR^z$, —S(=O)$_mR^k$, —P(=O)$R^{kk}R^{mm}$, —$NR^kR^m$, —C(=O)$OR^k$, or —C(=O)$NR^kR^m$;

each $X^2$ is independently selected from the group consisting of halo, cyano, oxo, $C_{0-3}$alkylene-$OR^n$, $C_{0-3}$alkylene-S(=O)$_mR^n$, $C_{0-3}$alkylene-$NR^nR^o$, $C_{0-3}$alkylene-C(=O)$NR^nR^o$, $C_{0-3}$alkylene-C(=O)$OR^n$, and $R^{S3}$, in which $R^{S3}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and $R^{S3}$ is optionally substituted with one or more substituents independently selected from the group consisting of halo, oxo, cyano, $C_{0-3}$alkylene-$OR^p$, $C_{0-3}$alkylene-S(=O)$_mR^p$, $C_{0-3}$alkylene-$NR^pR^q$, $C_{0-3}$alkylene-C(=O)$NR^pR^q$, $C_{0-3}$alkylene-$C_{0-3}$alkylene-C(=O)$OR^p$, $C_{1-6}$alkyl, $C_{2-6}$alkenyl, $C_{2-6}$alkynyl, $C_{1-6}$haloalkyl, and $R^{S4}$, in which $R^{S4}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S4}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w4}$, and —$NR^{w4}R^{x4}$;

R$^3$ is C$_{1-3}$alkyl, C$_{1-3}$haloalkyl, C$_{2-3}$alkenyl, C$_{2-3}$alkynyl, C$_{3-6}$cycloalkyl, —CN, —OR$^r$, —C(=O)R$^r$, —S(=O)$_m$R$^r$, NR$^r$R$^t$, or —C(=O)OR$^r$, wherein C$_{1-3}$alkyl, C$_{2-3}$alkenyl and C$_{2-3}$alkynyl are optionally substituted with one C$_{3-6}$cycloalkyl;

R$^4$ is C$_{1-6}$alkyl, C$_{1-6}$haloalkyl, S(=O)$_m$R$^n$, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl, wherein C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl are optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, OR$^{w5}$, and NR$^{w5}$R$^{x5}$;

each of R$^a$ and R$^b$, independently, is H or R$^{S5}$, in which R$^{S5}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and R$^{S5}$ is optionally substituted with one or more substituents independently selected from the group consisting of halo, cyano, oxo, C$_{1-6}$haloalkyl, C$_{0-3}$alkylene-OR$^{c2}$, C$_{0-3}$alkylene-C(=O)R$^{c2}$, C$_{0-3}$alkylene-C(=O)OR$^{c2}$, C$_{0-3}$alkylene-OC(=O)R$^{c2}$, C$_{0-3}$alkylene-C(=O)NR$^{c2}$R$^{d2}$, C$_{0-3}$alkylene-S(=O)$_m$R$^{c2}$, C$_{0-3}$alkylene-S(=O)$_2$NR$^{c2}$R$^{d2}$, C$_{0-3}$alkylene-NR$^{c2}$R$^{d2}$, C$_{0-3}$alkylene-NR$^{c2}$C(=O)R$^{c2}$, C$_{0-3}$alkylene-NR$^{c2}$C(=O)OR$^{c2}$, C$_{0-3}$alkylene-NR$^{c2}$C(=O)NR$^{c2}$R$^{d2}$, C$_{0-3}$alkylene-NR$^{c2}$S(=O)$_2$R$^{c2}$, C$_{0-3}$alkylene-C(=O)NR$^2$S(=O)$_2$R$^{c2}$, C$_{0-3}$alkylene-NR$^{c2}$S(=O)$_2$NR$^{c2}$R$^{d2}$, C$_{0-3}$alkylene-N(S(=O)$_2$R$^{c2}$)$_2$, and R$^{S6}$, in which R$^{S6}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S6}$ is optionally substituted with one or more substituents independently selected from the group consisting of halo, cyano, oxo, C$_{1-6}$alkyl, C$_{2-6}$alkenyl, C$_{2-6}$alkynyl, C$_{1-6}$haloalkyl, C$_{0-3}$alkylene-NR$^{e2}$R$^{f2}$, C$_{0-3}$alkylene-OR$^{e2}$, C$_{0-3}$alkylene-NR$^{e2}$C(=O)R$^{e2}$, C$_{0-3}$alkylene-NR$^{e2}$C(=O)OR$^{e2}$, C$_{0-3}$alkylene-NR$^{e2}$C(=O)NR$^{e2}$R$^{f2}$, C$_{0-3}$alkylene-OC(=O)R$^{e2}$, C$_{0-3}$alkylene-C(=O)OR$^{e2}$, C$_{0-3}$alkylene-C(=O)NR$^{e2}$R$^{f2}$, C$_{0-3}$alkylene-C(=O)R$^{e2}$, C$_{0-3}$alkylene-S(=O)$_m$R$^{e2}$, C$_{0-3}$alkylene-S(=O)$_2$NR$^{e2}$R$^{f2}$, C$_{0-3}$alkylene-NR$^{e2}$S(=O)$_2$R$^{e2}$, C$_{0-3}$alkylene-C(=O)NR$^{e2}$S(=O)$_2$R$^{e2}$, C$_{0-3}$alkylene-NR$^{e2}$S(=O)$_2$NR$^{e2}$R$^{f2}$, and R$^{S7}$, in which R$^{S7}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S7}$ is optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, —OR$^{w6}$, and —NR$^{w6}$R$^{x6}$;

each of R$^c$, R$^{c2}$, R$^d$, R$^{d'}$, and R$^{d2}$, independently, is H or R$^{S8}$, in which R$^{S8}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S8}$ is optionally substituted with one or more substituents independently selected from the group consisting of halo, cyano, oxo, C$_{1-6}$alkyl, C$_{2-6}$alkenyl, C$_{2-6}$alkynyl, C$_{1-6}$haloalkyl, C$_{0-3}$alkylene-NR$^{e3}$R$^{f3}$, C$_{0-3}$alkylene-OR$^{e3}$, C$_{0-3}$alkylene-C(=O)OR$^{e3}$, C$_{0-3}$alkylene-C(=O)NR$^{e3}$R$^{f3}$, C$_{0-3}$alkylene-C(=O)R$^{e3}$, C$_{0-3}$alkylene-S(=O)$_m$R$^{e3}$, C$_{0-3}$alkylene-S(=O)$_2$NR$^{e3}$R$^{f3}$, C$_{0-3}$alkylene-NR$^{f3}$C(=O)R$^{e3}$, C$_{0-3}$alkylene-NR$^{f3}$S(=O)$_m$R$^{e3}$, and R$^{S9}$, in which R$^{S9}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, C$_{0-3}$alkylene-5- to 10-membered heteroaryl;

and each R$^{S9}$ is optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, —OR$^{w7}$, and —NR$^{w7}$R$^{x7}$;

each of R$^e$, R$^{e2}$, R$^{e3}$, R$^f$, R$^{f2}$, and R$^{f3}$, independently, is H or R$^{S10}$, in which R$^{S10}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S10}$ is optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, —OR$^{w8}$, and —NR$^{w8}$R$^{x8}$;

each of R$^{kk}$, and R$^{mm}$, is independently selected from the group consisting of R$^k$, —OR$^k$, and —NR$^k$R$^m$;

each of R$^k$, and R$^m$, independently, is H or R$^z$, in which R$^z$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^z$ is optionally substituted with one or more substituents independently selected from the group consisting of halo, cyano, oxo, C$_{1-6}$alkyl, C$_{2-6}$alkenyl, C$_{2-6}$alkynyl, C$_{1-6}$haloalkyl, C$_{0-3}$alkylene-NR$^{n2}$R$^{o2}$, C$_{0-3}$alkylene-OR$^{n2}$, C$_{0-3}$alkylene-C(=O)OR$^{n2}$, C$_{0-3}$alkylene-C(=O)NR$^{n2}$R$^{o2}$, C$_{0-3}$alkylene-C(=O)R$^{n2}$, C$_{0-3}$alkylene-S(=O)$_m$R$^{n2}$, C$_{0-3}$alkylene-S(=O)$_2$NR$^{n2}$R$^{o2}$, and R$^{S11}$, in which R$^{S11}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

and each R$^{S11}$ is optionally substituted with one or more substituents independently selected from the group consisting of halo, oxo, cyano, C$_{0-3}$alkylene-OR$^{p2}$, C$_{0-3}$alkylene-S(=O)$_m$R$^{p2}$, C$_{0-3}$alkylene-NR$^{p2}$R$^{q2}$, C$_{0-3}$alkylene-C(=O)NR$^{p2}$R$^{q2}$, C$_{0-3}$alkylene-C$_{0-3}$alkylene-C(=O)OR$^{p2}$, C$_{1-6}$alkyl, C$_{2-6}$alkenyl, C$_{2-6}$alkynyl, C$_{1-6}$haloalkyl, and R$^{S12}$, in which R$^{S12}$ is C$_{0-3}$alkylene-C$_{3-8}$cycloalkyl, C$_{0-3}$alkylene-C$_{6-10}$aryl, C$_{0-3}$alkylene-3- to 12-membered heterocycloalkyl, or C$_{0-3}$alkylene-5- to 10-membered heteroaryl;

each R$^{S12}$ is optionally substituted with one or more substituents independently selected from the group consisting of halo, oxo, C$_{1-6}$alkyl, C$_{2-6}$alkenyl, C$_{2-6}$alkynyl, cyano, C$_{1-6}$haloalkyl, —OR$^{w9}$, and —NR$^{w9}$R$^{x9}$;

each of R$^n$, R$^{n2}$, R$^o$, and R$^{o2}$, independently, is H or R$^{S13}$, in which R$^{S13}$ is C$_{1-6}$alkyl, C$_{2-6}$alkenyl, C$_{2-6}$alkynyl, C$_{0-3}$alkylene-C$_{3-8}$cycloalkyl, C$_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S13}$ is optionally substituted with one or more substituents independently selected from the group consisting of halo, oxo, cyano, $C_{0-3}$alkylene-$OR^{p3}$, $C_{0-3}$alkylene-S(=O)$_m$$R^{p3}$, $C_{0-3}$alkylene-$NR^{p3}R^{q3}$, $C_{0-3}$alkylene-C(=O)$NR^{p3}R^{q3}$, $C_{0-3}$alkylene-C(=O)$OR^{p3}$, $C_{1-6}$alkyl, $C_{2-6}$alkenyl, $C_{2-6}$alkynyl, $C_{1-6}$haloalkyl, and $R^{S14}$, in which $R^{S14}$ is $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S14}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w10}$, and —$NR^{w10}R^{x10}$;

each of $R^p$, $R^{p2}$, $R^{p3}$, $R^q$, $R^{q2}$, and $R^{q3}$, independently, is H or $R^{S15}$, in which $R^{S15}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

each $R^{S15}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —$OR^{w11}$, and —$NR^{w11}R^{x11}$;

each of $R^r$, $R^t$, and $R^u$, independently, is H or $R^{S16}$, in which $R^{S16}$ is $C_{1-6}$alkyl, $C_{2-6}$alkenyl, $C_{2-6}$alkynyl, $C_{0-3}$alkylene-$C_{3-8}$cycloalkyl, $C_{0-3}$alkylene-$C_{6-10}$aryl, $C_{0-3}$alkylene-3- to 12-membered heterocycloalkyl, or $C_{0-3}$alkylene-5- to 10-membered heteroaryl;

and each $R^{S16}$ is optionally substituted with one or more substituents independently selected from the group consisting of halo, oxo, $C_{1-6}$alkyl, $C_{2-6}$alkenyl, $C_{2-6}$alkynyl, cyano, $C_{1-6}$haloalkyl, —C(=O)$OR^{w12}$, —$OR^{w12}$, and —$NR^{w12}R^{x12}$;

each $R^w$, $R^{w2}$, $R^{w3}$, $R^{w4}$, $R^{w5}$, $R^{w6}$, $R^{w7}$, $R^{w8}$, $R^{w9}$, $R^{w10}$, $R^{w11}$, $R^{w12}$, $R^x$, $R^{x2}$, $R^{x3}$, $R^{x4}$, $R^{x5}$, $R^{x6}$, $R^{x7}$, $R^{x8}$, $R^{x9}$, $R^{x10}$, $R^{x11}$, and $R^{x12}$, independently, is H, $C_{1-6}$alkyl, $C_{2-6}$alkenyl, $C_{2-6}$alkynyl or $C_{1-6}$haloalkyl;

each of n and p independently is 0, 1, 2, 3, 4, or 5, wherein when $T^2$ is H, p is 0; and m is 0, 1, or 2;

with the proviso that, for compounds where Y is —$CR^3$=:

a) when $R^1$ is unsubstituted phenyl, $R^2$ is methyl and $R^3$ is methyl, $R^4$ is not ethyl, unsubstituted phenyl, or unsubstituted pyridine;

b) when $R^1$ is unsubstituted cyclohexyl, $R^2$ is methyl and $R^3$ is methyl, $R^4$ is not unsubstituted pyridine;

c) when $R^1$ is unsubstituted cyclopentyl, $R^2$ is methyl and $R^3$ is methyl, $R^4$ is not ethyl or unsubstituted pyridine, d) when $R^2$ is methyl, $R^3$ is methyl and $R^4$ is 3,4-diethoxy-phenyl, $R^1$ is not unsubstituted 1-pyrrolidine, unsubstituted 1-piperidine, 4-methyl-1-piperidine, 4-(phenylmethyl)-1-piperidine, unsubstituted 2-1,2,3,4-tetrahydro-isoquinoline, unsubstituted morpholine, or NHCH$_2$CH$_2$-3-indole;

e) when $R^1$ is unsubstituted CH$_2$-phenyl, $R^2$ is methyl and $R^3$ is methyl, $R^4$ is not ethyl, trifluoromethyl, 1-methyl-piperidin-4-yl, unsubstituted pyridine, unsubstituted phenyl, phenyl mono-substituted with 4-F, 4-Cl, 2-methoxy or 4-methoxy, or phenyl disubstituted with 3,4-methoxy;

f) when $R^2$ is methyl, $R^3$ is methyl and $R^4$ is unsubstituted pyridine, $R^1$ is not CH$_2$-phenyl wherein the phenyl is substituted with 4-CN, 4-NO$_2$, 4-F or 2-F;

g) when $R^2$ is methyl, $R^3$ is methyl and $R^4$ is ethyl, $R^1$ is not CH$_2$-phenyl wherein the phenyl is substituted with 4-CN or 4-NO$_2$;

h) when $R^2$ is methyl, $R^3$ is methyl and $R^4$ is 4-methoxy-phenyl, $R^1$ is not CH$_2$-phenyl wherein the phenyl is substituted with 2-Cl, 3-Cl, 4-Br, 2-methyl or 4-methyl;

i) when $R^2$ is methyl, $R^3$ is methyl and $R^4$ is unsubstituted phenyl, $R^1$ is not CH$_2$-phenyl wherein the phenyl is substituted with 2-Cl, 3-Cl, 4-Cl, 4-Br, 2-methyl, 3-methyl, 4-methyl, 4-isopropyl or 4-tert-butyl; or $R^1$ is not unsubstituted CH$_2$-1-naphthylene or unsubstituted CH$_2$-pyridine;

j) when $R^2$ is methyl, $R^1$ is methyl and $R^4$ is 4-Cl-phenyl, $R^1$ is not CH$_2$-phenyl wherein the phenyl is substituted with 2-Cl, 4-Cl or 4-isopropyl;

k) when $R^1$ is unsubstituted CH$_2$-phenyl, $R^2$ is methyl and $R^3$ is trifluoromethyl, $R^4$ is not unsubstituted phenyl or phenyl substituted with 2-Cl or 4-Cl;

l) the compound is not wherein $R^1$ is CH$_2$-4-Br-phenyl, $R^2$ is methyl, $R^3$ is ethyl and $R^4$ is unsubstituted phenyl;

m) when $R^2$ is methyl, $R^3$ is methyl and $R^4$ is unsubstituted phenyl, $R^1$ is not CH$_2$CH$_2$C(=O)NH-phenyl wherein the phenyl ring is unsubstituted or is substituted at the 4-position with Cl, methyl or methoxy;

n) when $R^2$ is methyl or ethyl, $R^3$ is methyl and $R^4$ is unsubstituted phenyl, $R^1$ is not substituted pyrazolo[1,5-a]pyrimidin-7-yl;

o) when $R^2$ is H, $R^3$ is isopropyl and $R^4$ is methyl, $R^1$ is not unsubstituted pyrazole; and p) the compound is not wherein $R^1$ is unsubstituted CH$_2$-phenyl, $R^2$ is H, $R^3$ is methyl and $R^4$ is unsubstituted phenyl; and with the proviso that, for compounds where Y is —N=, the compound is not wherein $R^1$ is unsubstituted phenyl, $R^2$ is H and $R^4$ is 2-fluoro-phenyl.

2. The compound of claim 1, wherein the compound is of Formula (IA):

(IA)

[Structure: pyrazolo-pyrimidinone core with substituents $R^1$, $R^2$, $R^3$, $R^4$]

or a pharmaceutically acceptable salt, pharmaceutically acceptable solvate or pharmaceutically acceptable hydrate thereof.

3. The compound of claim 1, wherein $Q^1$ is a bond and $T^1$ is $C_{6-10}$aryl, 3- to 12-membered heterocycloalkyl, or 5- to 10-membered heteroaryl, and n is 0, 1, 2, 3 or 4.

4. The compound of claim 1, wherein $Q^1$ is a bond or —CH$_2$— and $T^1$ is $C_{3-8}$cycloalkyl, $C_{6-10}$aryl, 3- to 12-membered heterocycloalkyl, 5- to 10-membered heteroaryl, or —C(=O)$NR^aR^b$.

5. The compound of claim 1, wherein Q¹ is a bond or —CH₂—, T¹ is —C(=O)NRᵃRᵇ and n is 0.

6. The compound of claim 1, wherein T¹ is a 9- or 10-membered bicyclic heteroaryl.

7. The compound of claim 1, wherein one of Rᵃ and Rᵇ is H or methyl.

8. The compound of claim 1, wherein one of Rᵃ and Rᵇ independently is an optionally substituted heteroaryl selected from the group consisting of pyridinyl, pyrazinyl, pyridazinyl, pyrimidinyl, indolyl, indazolyl, benzimidazolyl, imidazopyridinyl, quinolinyl, isoquinolinyl, quinazolinyl, oxazolyl, isoxazolyl, thiazolyl, isothiazolyl, benzoxazolyl, oxadiazolyl, triazolyl, imidazolyl, furan, and thiophenyl, and the other is hydrogen or methyl.

9. The compound of claim 1, wherein R² is Q²-T²-(X²)ₚ, Q² is a bond, T² is H, halo, cyano, C₁₋₆alkyl, C₁₋₆haloalkyl, C₂₋₆alkenyl, or C₂₋₆alkynyl, and each X² independently is halo or —OC₁₋₆alkyl.

10. The compound of claim 1, wherein R² is H, cyano, methyl or methoxymethyl.

11. The compound of claim 1, wherein R³ is C₁₋₆alkyl, C₁₋₃haloalkyl, —CN, —S(=O)₂C₁₋₃alkyl or —C(=O)OC₁₋₃alkyl.

12. The compound of claim 1, wherein R³ is —CN, C₁₋₃alkyl, C₁₋₃haloalkyl or —C(=O)OC₁₋₃alkyl.

13. The compound of claim 1, wherein R³ is —CN or —CF₃.

14. The compound of claim 1, wherein R⁴ is C₁₋₃alkyl, C₁₋₃haloalkyl, —S(=O)₂C₁₋₃alkyl, C₃₋₈cycloalkyl, C₆₋₁₀aryl, 3- to 12-membered heterocycloalkyl, or 5- to 10-membered heteroaryl, wherein C₃₋₈cycloalkyl, C₆₋₁₀aryl, 3- to 12-membered heterocycloalkyl, or 5- to 10-membered heteroaryl are optionally substituted with 1-3 substituents selected from the group consisting of halo, oxo, C₁₋₆alkyl, C₂₋₆alkenyl, C₂₋₆alkynyl, cyano, C₁₋₆haloalkyl, —ORʷ⁵, and —NRʷ⁵Rˣ⁵.

15. The compound of claim 1, wherein R⁴ is C₃₋₈cycloalkyl or C₆₋₁₀aryl, wherein C₃₋₈cycloalkyl and C₆₋₁₀aryl are optionally substituted with 1-3 substituents selected from the group consisting of halo, oxo, C₁₋₆alkyl, C₂₋₆alkenyl, C₂₋₆alkynyl, cyano, C₁₋₆haloalkyl, —ORʷ⁵, and —NRʷ⁵Rˣ⁵, wherein Rʷ⁵ and Rˣ⁵ are independently H, C₁₋₆alkyl or C₁₋₆haloalkyl.

16. The compound of claim 1, wherein R⁴ is phenyl optionally substituted with 1-3 substituents selected from the group consisting of halo, oxo, C₁₋₆alkyl, C₂₋₆alkenyl, C₂₋₆alkynyl, cyano, C₁₋₆haloalkyl, —ORʷ⁵, and —NRʷ⁵Rˣ⁵, wherein Rʷ⁵ and Rˣ⁵ are independently H, C₁₋₆alkyl or C₁₋₆haloalkyl.

17. The compound of claim 1, wherein T¹ is an aryl or heteroaryl.

18. The compound of claim 1, wherein T¹ is a 5- or 6-membered monocyclic heteroaryl or 9- or 10-membered bicyclic heteroaryl.

19. The compound of claim 1, wherein T¹ is pyridinyl, pyrazinyl, pyridazinyl, pyrimidinyl, indolyl, indolinyl, isoindolyl, isoindolinyl, indazolyl, pyrazolopyridinyl, pyrazolopyrimidinyl, oxazolopyrimidinyl, oxazolopyridinyl, imidazopyridinyl, benzimidazolyl, tetrahydrobenzimidazolyl, benzofuranyl, dihydrobenzofuranyl, isobenzofuranyl, dihydroisobenzofuranyl, triazolopyridinyl, benzothiazolyl, azabenzimidazolyl, azabenzoxazolyl, azabenzothiazolyl, imidazopyridinyl, quinolinyl, isoquinolinyl, quinazolinyl, oxazolyl, isoxazolyl, thiazolyl, isothiazolyl, benzoxazolyl, benzodioxolyl, chromanyl, tetrahydrooxazoloazepinyl, tetrahydrobenzoxazolyl, oxadiazolyl, thiadiazolyl, pyrazolyl, triazolyl, imidazolyl, furanyl, or thiophenyl.

20. The compound of claim 1, wherein T¹ is 3- to 12-membered heterocycloalkyl.

21. The compound of claim 20, wherein T¹ is piperazine, piperidine, quinuclidine, or morpholine.

22. The compound of claim 1, wherein the compound is of Formula (Ib):

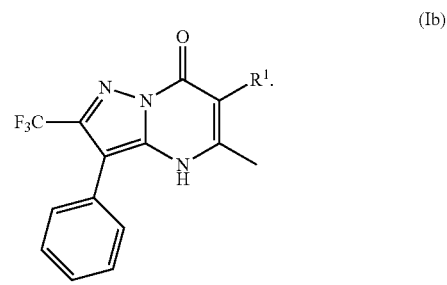

(Ib)

23. The compound of claim 1, wherein the compound is of Formula (IIa):

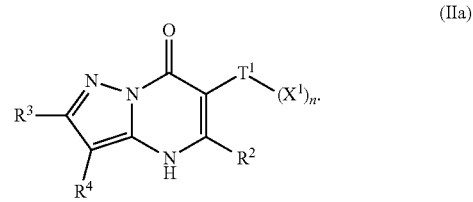

(IIa)

24. A compound of Formula (III):

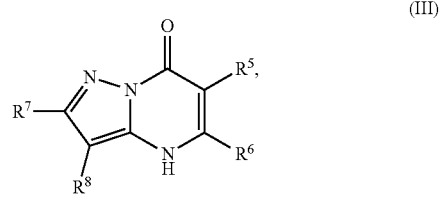

(III)

or a pharmaceutically acceptable salt, pharmaceutically acceptable solvate or pharmaceutically acceptable hydrate thereof, wherein R⁵ is selected from the group consisting of —C(=O)NR⁹R¹⁰; —CH₂C(=O)NR¹¹R¹²; —CH₂CH₂NR¹³R¹⁴; —CH₂-phenyl; —CH₂-5-membered monocyclic heteroaryl optionally substituted with one C₁₋₃alkyl, monocyclic C₅₋₆cycloalkyl, or phenyl, wherein phenyl is optionally substituted with one —OC₁₋₃alkyl; phenyl optionally substituted with one halo or C₁₋₃alkyl; a 5- or 6-membered monocyclic heterocycloalkyl optionally substituted with 1, 2, or 3 R¹⁵; a 5- or 6-membered monocylic heteroaryl optionally substituted with 1, 2, or 3 R¹⁶; and 9- or 10-membered bicyclic heteroaryl optionally substituted with 1, 2, 3, or 4 R¹⁷;

R⁹ and R¹⁰ are independently selected from the group consisting of H; C₁₋₃alkyl optionally substituted with 1 or 2 substituents independently selected from the group consisting of —OH and —OC₁₋₃alkyl; —CH₂phenyl; —S(=O)₂R¹⁸; C₅₋₆cycloalkyl optionally substituted with one —NH₂, oxo, —OH, or —$OC_{1-3}$alkyl; phenyl optionally substituted with 1, 2, or 3 $R^{19}$; a 5- or 6-membered monocyclic heterocycloalkyl optionally substituted with one —$C_{1-3}$alkyl, —$C(=O)C_{1-3}$alkyl, or —$C(=O)OC_{1-6}$alkyl; a 5- or 6-membered monocyclic heteroaryl optionally substituted with 1, 2, or 3 $R^{20}$; and a 9- or 10-membered bicyclic heteroaryl optionally substituted with 1 or 2 halo; or $R^9$ and $R^{10}$ combine with the nitrogen to which they are bound to form an N-linked 5- or 6-membered monocyclic heterocycloalkyl optionally substituted with one phenyl;

$R^{11}$ and $R^{12}$ are independently selected from the group consisting of H; $C_{1-3}$alkyl optionally substituted with one —OH or —$OC_{1-3}$alkyl; phenyl optionally substituted with one —$NH_2$ or —$OC_{1-3}$alkyl; and a 5- or 6-membered monocyclic heteroaryl; or $R^{11}$ and $R^{12}$ combine with the nitrogen to which they are bound to form an N-linked 5- or 6-membered monocyclic heterocycloalkyl optionally substituted with one $C_{1-3}$alkyl, phenyl or —$CH_2$-phenyl, wherein the phenyl ring of phenyl or —$CH_2$-phenyl is optionally substituted with one $C_{1-3}$alkyl;

$R^{13}$ and $R^{14}$ are independently selected from the group consisting of H; —$C(=O)C_{1-3}$alkyl; —$C(=O)$phenyl; and phenyl optionally substituted with one —$OC_{1-3}$alkyl;

each $R^{15}$ is independently selected from the group consisting of oxo; —$C(=O)OH$; —$C(=O)OC_{1-3}$alkyl; and $C_{1-3}$alkyl optionally substituted with one —OH or —$OC_{1-3}$alkyl;

each $R^{16}$ is independently selected from the group consisting of —CN; —$C(=O)OH$; —$C(=O)OC_{1-3}$alkyl; —$C(=O)NH_2$; —$C(=O)NHC_{1-3}$alkyl; —$C(=O)N(C_{1-3}$alkyl$)_2$; —$C(=NH)NH_2$; —$NHC(=NH)NH_2$; —$NH_2$; —$NHC_{1-3}$alkyl; —$N(C_{1-3}$alkyl$)_2$; —$NHC_{3-6}$cycoalkyl; —$N(C_{1-3}$alkyl)$C_{3-6}$cycloalkyl; $C_{1-3}$alkyl optionally substituted with one —OH, —$OC_{1-3}$alkyl, or 5- or 6-membered monocyclic heterocycloalkyl, wherein the monocyclic heterocycloalkyl is optionally substituted with —$C_{1-3}$alkyl; $C_{1-3}$haloalkyl optionally substituted with 1 or 2 substituents independently selected from the group consisting of —OH and phenyl; —$C_{3-6}$cycloalkyl optionally substituted with one —$NH_2$, $C_{1-3}$alkyl, $C_{1-3}$haloalkyl, or —$OC_{1-3}$alkyl; phenyl optionally substituted with one —OH, —$OC_{1-3}$alkyl, —$NO_2$, —$NH_2$, —$NHC_{1-3}$alkyl, or —$N(C_{1-3}$alkyl$)_2$; 5- or 6-membered monocyclic heterocycloalkyl optionally substituted with 1 or 2 substituents independently selected from the group consisting of oxo, —OH, —$NH_2$, —$OC_{1-3}$alkyl, —$C(=O)C_{1-3}$alkyl, —$S(=O)_2C_{1-3}$alkyl, —$C(=O)OC_{1-6}$alkyl, —$C(=O)OCH_2$phenyl, and $C_{1-3}$alkyl, wherein $C_{1-3}$alkyl is optionally substituted with one —$NH_2$, —$NHS(=O)_2C_{1-3}$alkyl, —OH, or —$OC_{1-3}$alkyl; and 5- or 6-membered monocyclic heteroaryl optionally substituted with one —OH or —$OC_{1-3}$alkyl;

each $R^{17}$ is independently selected from the group consisting of oxo; halo; —OH; —CN; —$NH_2$; —$NHC_{1-3}$alkyl; —$N(C_{1-3}$alkyl$)_2$; —$N^+(C_{1-3}$alkyl$)_3$; —$NHC(=O)C_{1-3}$alkyl; —$C(=O)C_{1-3}$alkyl; —$S(=O)_mC_{1-3}$alkyl; —$C(=O)OH$; —$C(=O)OC_{1-6}$alkyl; —$C(=O)NH_2$; —$C(=O)NHC_{1-3}$alkyl; —$C(=O)N(C_{1-3}$alkyl$)_2$; —$OC(=O)NHC_{1-3}$alkyl; —$OC(=O)N(C_{1-3}$alkyl$)_2$; —$C(=NH)NH_2$; —$C(=NH)NHC_{1-3}$alkyl; —$C(=NH)N(C_{1-3}$alkyl$)_2$; —$OC_{1-3}$haloalkyl; $C_{1-3}$haloalkyl; monocyclic $C_{3-6}$cycloalkyl; $C_{1-3}$alkyl optionally substituted with one monocyclic $C_{3-6}$cycloalkyl, —OH, —$OC_{1-3}$alkyl, —$C(=O)OH$, —$C(=O)OC_{1-3}$alkyl, —$NH_2$, —$NHC_{1-3}$alkyl, or —$N(C_{1-3}$alkyl$)_2$; —$OC_{1-3}$alkyl optionally substituted with one monocyclic $C_{3-6}$cycloalkyl, phenyl, —OH, —$OC_{1-3}$alkyl, —$C(=O)OH$, —$C(=O)OC_{1-3}$alkyl, —$C(=O)NH_2$, —$C(=O)NHC_{1-3}$alkyl, —$C(=O)N(C_{1-3}$alkyl$)_2$, —$NH_2$, —$NHC_{1-3}$alkyl, —$N(C_{1-3}$alkyl$)_2$, —$NHC(=O)C_{1-3}$alkyl, or —$NHS(=O)_2C_{1-3}$alkyl; and phenyl optionally substituted with one halo, —CN, $C_{1-3}$alkyl, $C_{1-3}$haloalkyl, —$OC_{1-3}$alkyl, —$NH_2$, —$NHC_{1-3}$alkyl or —$N(C_{1-3}$alkyl$)_2$;

$R^{18}$ is selected from the group consisting of $C_{1-3}$alkyl; monocyclic $C_{3-6}$cycloalkyl; a 5- or 6-membered monocyclic heteroaryl; phenyl; and —$CH_2$phenyl; wherein the phenyl ring of phenyl or —$CH_2$phenyl is optionally substituted with one halo, —CN, or —$OC_{1-3}$alkyl;

each $R^{19}$ is independently selected from the group consisting of halo; —CN; —$NH_2$; —$NHC_{1-3}$alkyl; —$N(C_{1-3}$alkyl$)_2$; —$NHC(=O)C_{1-3}$alkyl; —$NHS(=O)_2C_{1-3}$alkyl; —$N(S(=O)_2C_{1-3}$alkyl$)_2$; —$NHS(=O)_2C_{3-6}$cycloalkyl; —$NHS(=O)_2$phenyl; —$NHC(=O)OH$; —$NHC(=O)OC_{1-3}$alkyl; —$S(=O)_2C_{1-3}$alkyl; —$OC_{1-3}$alkyl optionally substituted with one phenyl; $C_{1-3}$haloalkyl; —$OC_{1-3}$haloalkyl; monocyclic $C_{3-6}$cycloalkyl; a 5- or 6-membered monocyclic heterocycloalkyl; and $C_{1-3}$alkyl optionally substituted with one monocyclic $C_{3-6}$cycloalkyl, —OH, —$OC_{1-3}$alkyl, —$NH_2$, —$NHC_{1-3}$alkyl, or —$N(C_{1-3}$alkyl$)_2$;

each $R^2$ is independently selected from the group consisting of —CN; —$OC_{1-3}$alkyl; —$S(=O)_2C_{1-3}$alkyl; $C_{1-3}$haloalkyl; and $C_{1-3}$alkyl optionally substituted with one —OH or —$OC_{1-3}$alkyl; and monocyclic $C_{3-6}$cycloalkyl;

$R^6$ is selected from the group consisting of H; halo; —CN; —$NH_2$; —$C(=O)OH$; —$C(=O)OC_{1-3}$alkyl; —$C(=O)C_{1-3}$alkyl; —$S(=O)_mC_{1-3}$alkyl; —$P(=O)(C_{1-3}$alkyl$)_2$; —$C(=O)NR^{21}R^{22}$; $C_{1-3}$haloalkyl; —$OC_{1-3}$alkyl optionally substituted with one —OH, —$OC_{1-3}$alkyl, —$NH_2$, —$NHC_{1-3}$alkyl, or —$N(C_{1-3}$alkyl$)_2$; $C_{1-3}$alkyl optionally substituted with one —$NH_2$, —$NHC_{1-3}$alkyl, —$N(C_{1-3}$alkyl$)_2$, —$C(=O)OH$, —$C(=O)OC_{1-3}$alkyl, —$S(=O)_mC_{1-3}$alkyl, —$C(=O)C_{1-3}$alkyl, —$OR^{23}$, or 5- or 6-membered monocyclic heteroaryl, wherein monocyclic heteroaryl is optionally substituted with 1 or 2 $C_{1-3}$alkyl; monocyclic $C_{3-6}$cycloalkyl optionally substituted with one —$C(=O)OH$, —$C(=O)OC_{1-3}$alkyl or $C_{1-3}$alkyl, wherein $C_{1-3}$alkyl is optionally substituted with one —OH or —$OC_{1-3}$alkyl; a 5- or 6-membered monocyclic heterocycloalkyl optionally substituted with one —$C(=O)OH$, or —$C(=O)OC_{1-3}$alkyl; and a 5- or 6-membered heteroaryl optionally substituted with 1 or 2 $C_{1-3}$alkyl;

$R^{21}$ and $R^{22}$ are independently selected from the group consisting of H; $C_{1-6}$alkyl optionally substituted with one —OH, —$OC_{1-3}$alkyl, —$C(=O)OH$, —$C(=O)OC_{1-3}$alkyl, —$NH_2$, —$NHC_{1-3}$alkyl, —$N(C_{1-3}$alkyl$)_2$, or 5- or 6-membered monocyclic heteroaryl; $C_{1-3}$haloalkyl optionally substituted with one —OH or —$OC_{1-3}$alkyl; a 5- or 6-membered monocyclic heteroaryl optionally substituted with 1 or 2 $C_{1-3}$alkyl; and a 4- to 6-membered monocyclic heterocycloalkyl; or $R^{21}$ and $R^{22}$ combine with the nitrogen to which they are bound to form an N-linked 5- or 6-membered monocyclic heterocycloalkyl optionally substituted with one —C(=O)OH, —C(=O)O$C_{1-3}$alkyl, or $C_{1-3}$alkyl, wherein $C_{1-3}$alkyl is optionally substituted with one —OH or —O$C_{1-3}$alkyl;

$R^{23}$ is selected from the group consisting of H; $C_{1-3}$haloalkyl; $C_{1-3}$alkyl optionally substituted with one —OH, —O$C_{1-3}$alkyl, —C(=O)OH, —C(=O)O$C_{1-3}$alkyl, —C(=O)NH$_2$, —C(=O)NH$C_{1-3}$alkyl, —C(=O)N($C_{1-3}$alkyl)$_2$, phenyl, 5- or 6-membered monocyclic heteroaryl, or 5- or 6-membered monocyclic heterocycloalkyl, wherein monocyclic heterocycloalkyl is optionally substituted with 1 or 2 oxo or $C_{1-3}$alkyl; a 4-, 5-, or 6-membered monocyclic heterocycloalkyl optionally substituted with 1 or 2 substituents independently selected from the group consisting of oxo and $C_{1-3}$alkyl; and a 5- or 6-membered monocyclic heteroaryl;

$R^7$ is selected from the group consisting of —CN; —OH; —C(=O)OH; —C(=O)O$C_{1-3}$alkyl; —C(=O)$C_{1-3}$alkyl; —S(=O)$_m$$C_{1-3}$alkyl; —NH$_2$; —NH$C_{1-3}$alkyl; —N($C_{1-3}$alkyl)$_2$; $C_{1-3}$alkyl optionally substituted with one monocyclic $C_{3-6}$cycloalkyl; $C_{1-3}$haloalkyl; $C_{2-3}$alkenyl optionally substituted with one monocyclic $C_{3-6}$cycloalkyl; $C_{2-3}$alkynyl optionally substituted with one monocyclic $C_{3-6}$cycloalkyl; monocyclic $C_{3-6}$cycloalkyl; —O-5- or 6-membered monocyclic heterocycloalkyl; and —O$C_{1-3}$alkyl optionally substituted with one —OH, —O$C_{1-3}$alkyl, —C(=O)OH, or —C(=O)O$C_{1-3}$alkyl; and $R^8$ is selected from the group consisting of $C_{1-3}$alkyl; $C_{1-3}$haloalkyl; monocyclic $C_{3-6}$cycloalkyl; phenyl optionally substituted with 1, 2, or 3 substituents independently selected from the group consisting of —CN, halo, $C_{1-3}$alkyl, $C_{1-3}$haloalkyl, —O$C_{1-3}$alkyl and —O$C_{1-3}$haloalkyl; and pyridinyl optionally substituted with 1, 2, or 3 substituents independently selected from the group consisting of —CN, halo, $C_{1-3}$alkyl, $C_{1-3}$haloalkyl, —O$C_{1-3}$alkyl and —O$C_{1-3}$haloalkyl, with the proviso that:
a) when $R^5$ is unsubstituted phenyl, $R^6$ is methyl and $R^7$ is methyl, $R^8$ is not ethyl, unsubstituted phenyl, or unsubstituted pyridine;
b) when $R^5$ is unsubstituted cyclohexyl, $R^6$ is methyl and $R^7$ is methyl, $R^8$ is not unsubstituted pyridine;
c) when $R^5$ is unsubstituted cyclopentyl, $R^6$ is methyl and $R^7$ is methyl, $R^8$ is not ethyl or unsubstituted pyridine,
d) when $R^6$ is methyl, $R^7$ is methyl and $R^8$ is 3,4-diethoxy-phenyl, $R^5$ is not unsubstituted 1-pyrrolidine, unsubstituted 1-piperidine, 4-methyl-1-piperidine, unsubstituted 2-1,2,3,4-tetrahydro-isoquinoline, or unsubstituted morpholine;
e) when $R^5$ is unsubstituted $CH_2$-phenyl, $R^6$ is methyl and $R^7$ is methyl, $R^8$ is not ethyl, trifluoromethyl, unsubstituted pyridine, unsubstituted phenyl, phenyl mono-substituted with 4-F, 4-Cl, 2-methoxy or 4-methoxy, or phenyl disubstituted with 3,4-methoxy;
f) when $R^5$ is unsubstituted $CH_2$-phenyl, $R^6$ is methyl and $R^7$ is trifluoromethyl, $R^8$ is not unsubstituted phenyl or phenyl substituted with 2-Cl or 4-Cl;
g) when $R^6$ is methyl, $R^7$ is methyl and $R^8$ is unsubstituted phenyl, $R^5$ is not $CH_2CH_2C(=O)NH$-phenyl wherein the phenyl ring is unsubstituted or is substituted at the 4-position with Cl, methyl or methoxy;
h) when $R^6$ is methyl or ethyl, $R^7$ is methyl and $R^8$ is unsubstituted phenyl, $R^5$ is not substituted pyrazolo[1,5-a]pyrimidin-7-yl;
i) when $R^6$ is H, $R^7$ is isopropyl and $R^8$ is methyl, $R^5$ is not unsubstituted pyrazole; and
j) the compound is not wherein $R^5$ is unsubstituted $CH_2$-phenyl, $R^6$ is H, $R^7$ is methyl and $R^8$ is unsubstituted phenyl.

25. The compound of claim 24, wherein $R^5$ is a 9- or 10-membered bicyclic heteroaryl optionally substituted with 1, 2, 3, or 4 $R^{17}$.

26. The compound of claim 24, wherein the compound is of Formula (IIIa):

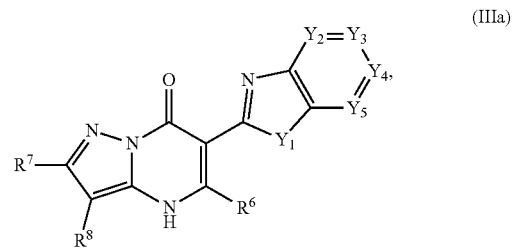

(IIIa)

or a pharmaceutically acceptable salt, pharmaceutically acceptable solvate or pharmaceutically acceptable hydrate thereof, wherein $Y_1$ is —O—, —NH—, —NR$^{24}$—, or —S—, and $Y_2$, $Y_3$, $Y_4$, and $Y_5$ are —N= or —CR$^{25}$=, provided that 0, 1 or 2 of $Y_2$, $Y_3$, $Y_4$, and $Y_5$ are —N=; wherein $R^{24}$ is selected from the group consisting of $C_{1-3}$haloalkyl; monocyclic $C_{3-6}$cycloalkyl; $C_{1-3}$alkyl optionally substituted with one monocyclic $C_{3-6}$cycloalkyl, —OH, —O$C_{1-3}$alkyl, —C(=O)OH, —C(=O)O$C_{1-3}$alkyl, —NH$_2$, —NH$C_{1-3}$ alkyl, or —N($C_{1-3}$alkyl)$_2$; and phenyl optionally substituted with one halo, —CN, $C_{1-3}$alkyl, $C_{1-3}$haloalkyl, —O$C_{1-3}$alkyl, —NH$_2$, —NH$C_{1-3}$alkyl or —N($C_{1-3}$ alkyl)$_2$; and wherein $R^{25}$ is H or $R^{17}$, provided that 0, 1, 2 or 3 of $Y_2$, $Y_3$, $Y_4$, and $Y_5$ are —CR$^{25}$= wherein $R^{25}$ is $R^{17}$.

27. The compound of claim 1, wherein the compound is selected from the group consisting of a compound as recited in Table 1A or Table 1B.

28. A pharmaceutical composition comprising the compound of claim 1, or a pharmaceutically acceptable salt, pharmaceutically acceptable solvate or pharmaceutically acceptable hydrate thereof, together with a pharmaceutically acceptable diluent or carrier.

29. A method of inhibiting the cGAS/STING pathway in a cell, comprising contacting the cell with the compound of claim 1, or a pharmaceutically acceptable salt, pharmaceutically acceptable solvate or pharmaceutically acceptable hydrate thereof.

30. A method of inhibiting cytokine production in a cell, comprising contacting the cell with the compound of claim 1, or pharmaceutically acceptable salt, pharmaceutically acceptable solvate or pharmaceutically acceptable hydrate thereof.

31. A method of treating a cGAS/STING pathway-mediated condition, selected from an autoimmune, inflammatory, or neurodegenerative condition comprising administering to a subject in need thereof an effective amount of a compound of claim 1, or a pharmaceutically acceptable salt, pharmaceutically acceptable solvate or pharmaceutically acceptable hydrate thereof.

32. A method of treating a disease in a subject, comprising administering to the subject in need thereof a therapeutically effective amount of the compound of claim 1, or a pharmaceutically acceptable salt, pharmaceutically acceptable solvate or pharmaceutically acceptable hydrate thereof, wherein the disease is selected from the group consisting of systemic inflammatory response syndrome (SIRS), sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI (STING-associated vasculopathy with onset in infancy), CANDLE (Chronic Atypical Neutrophilic Dermatosis with Lipodystrophy and Elevated Temperature) syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease.

33. A method of treating a disease in a subject, comprising administering to the subject in need thereof a therapeutically effective amount of the compound of claim 1, including any pharmaceutically acceptable salt, pharmaceutically acceptable solvate or pharmaceutically acceptable hydrate thereof, in combination with a Janus Kinase (Jak) inhibitor, wherein the disease is selected from the group consisting of systemic inflammatory response syndrome (SIRS), sepsis, septic shock, atherosclerosis, celiac disease, dermatomyositis, scleroderma, interstitial cystitis, transplant rejection (e.g. graft-versus-host disease), Aicardi-Goutieres Syndrome, Hutchison Guilford progeria syndrome, Singleton-Merten Syndrome, proteasome-associated autoinflammatory syndrome, SAVI (STING-associated vasculopathy with onset in infancy), CANDLE (Chronic Atypical Neutrophilic Dermatosis with Lipodystrophy and Elevated Temperature) syndrome, chilblain lupus erythematosus, systemic lupus erythematosus, rheumatoid arthritis, juvenile rheumatoid arthritis, Wegener's disease, inflammatory bowel disease (e.g. ulcerative colitis, Crohn's disease), idiopathic thrombocytopenic purpura, thrombotic thrombocytopenic purpura, autoimmune thrombocytopenia, multiple sclerosis, psoriasis, IgA nephropathy, IgM polyneuropathies, glomerulonephritis, autoimmune myocarditis, myasthenia gravis, vasculitis, Type 1 diabetes, Type 2 diabetes, Sjorgen's syndrome, X-linked reticulate pigmentary disorder, polymyositis, spondyloenchondrodysplasia, age-related macular degeneration, Alzheimer's disease and Parkinson's disease.

34. The pharmaceutical composition of claim 28, further comprising a Janus Kinase inhibitor.

35. A kit comprising a compound of claim 1, or a pharmaceutically acceptable salt, pharmaceutically acceptable solvate or pharmaceutically acceptable hydrate thereof, and a Janus Kinase inhibitor.

\* \* \* \* \*

UNITED STATES PATENT AND TRADEMARK OFFICE
CERTIFICATE OF CORRECTION

PATENT NO. : 10,738,056 B2  
APPLICATION NO. : 16/131221  
DATED : August 11, 2020  
INVENTOR(S) : Chudi Obioma Ndubaku et al.

Page 1 of 1

It is certified that error appears in the above-identified patent and that said Letters Patent is hereby corrected as shown below:

In the Specification

Column 1, Line 7 (approx.), delete "No." and insert -- Nos. --, therefor.

In the Claims

Column 443, Line 30, in Claim 1, delete "-(X)n;" and insert -- -($X^1$)n; --, therefor.

Column 443, Line 58, in Claim 1, delete "(=NR)NRcRd," and insert -- (=$NR^c$)$NR^cR^d$, --, therefor.

Column 445, Line 34, in Claim 1, delete "NR2S" and insert -- $NRc^{c2}$S --, therefor.

Column 448, Line 20, in Claim 1, delete "R1" and insert -- $R^3$ --, therefor.

Column 449, Line 8, in Claim 8, delete "Rbindependently" and insert -- $R^b$ independently --, therefor.

Column 449, Line 21, in Claim 11, delete "C1-6alkyl," and insert -- $C_{1-3}$alkyl, --, therefor.

Column 450, Line 58, in Claim 24, delete "monocylic" and insert -- monocyclic --, therefor.

Column 451, Line 37, in Claim 24, delete "—NHC3-6cycoalkyl;" and insert -- —$NHC_{3-6}$cycloalkyl; --, therefor.

Column 452, Line 36, in Claim 24, delete "R2" and insert -- $R^{20}$ --, therefor.

Column 455, Line 28 (approx.), in Claim 32, delete "Sjorgen's" and insert -- Sjogren's --, therefor.

Column 456, Line 23, in Claim 33, delete "Sjorgen's" and insert -- Sjogren's --, therefor.

Signed and Sealed this  
Thirteenth Day of October, 2020

Andrei Iancu  
*Director of the United States Patent and Trademark Office*